United States Patent [19]
Grogan et al.

[11] Patent Number: 5,326,476
[45] Date of Patent: Jul. 5, 1994

[54] METHOD AND APPARATUS FOR KIDNEY DIALYSIS USING MACHINE WITH PROGRAMMABLE MEMORY

[75] Inventors: Jeffrey B. Grogan, West Linn, Oreg.; Thore Falkvall, Helsingborg, Sweden; Harley D. Johnson, Portland, Oreg.; Thomas D. Kelly, Portland, Oreg.; Alan G. Wolfe, Portland, Oreg.

[73] Assignee: Althin Medical, Inc., Miami, Fla.

[21] Appl. No.: 975,523

[22] Filed: Nov. 12, 1992

Related U.S. Application Data

[63] Continuation-in-part of Ser. No. 688,174, Apr. 19, 1991, Pat. No. 5,247,434.

[51] Int. Cl.⁵ .............................................. B01D 61/32
[52] U.S. Cl. .............................. 210/646; 210/321.65; 210/929; 364/188; 364/413.07; 395/140; 395/924
[58] Field of Search .............. 364/188, 413.01, 413.02, 364/413.07, 502, 510, 190; 210/87, 143, 321.65, 321.71, 645, 646, 647, 729, 929; 422/48; 604/5, 65, 66; 364/190; 395/140, 155, 157, 924

[56] References Cited

U.S. PATENT DOCUMENTS

| | | | |
|---|---|---|---|
| 4,217,642 | 8/1980 | Dam et al. | 395/140 |
| 4,370,983 | 2/1983 | Lichtenstein | 210/929 |
| 4,582,598 | 4/1986 | Bilstad et al. | 210/321.65 |
| 4,756,706 | 7/1988 | Kerns et al. | 604/66 |
| 4,898,578 | 2/1990 | Rubalcaba | 364/188 |
| 4,974,599 | 12/1990 | Suzuki | 128/696 |
| 4,990,258 | 2/1991 | Bjare et al. | 210/321.65 |

Primary Examiner—Joseph W. Drodge
Attorney, Agent, or Firm—Klarquist Sparkman Campbell Leigh & Whinston

[57] ABSTRACT

Methods are disclosed for providing certain operational instructions to a hemodialysis machine. The hemodialysis machine possesses a programmable memory and a capability of operating according to a time-varying parameter such as variable ultrafiltration. According to the methods, the machine operator enters into the memory a desired time period, a target cumulative value of the time-varying parameter, such as target UF volume, and a proposed time-varying profile of the time-varying parameter that is representable as a plot of coordinates in a region defined by an ordinate of values of the parameter and a time-based abscissa, wherein the plot defines a profile cumulative value of the parameter. If the profile cumulative value is not equal to the target cumulative value, then the proposed time-varying profile is changed along the ordinate so that the profile cumulative value is made equal to the target cumulative value. The machine then operates according to the changed profile to enable the apparatus to achieve, while operating, the entered target cumulative value within the time period.

7 Claims, 11 Drawing Sheets

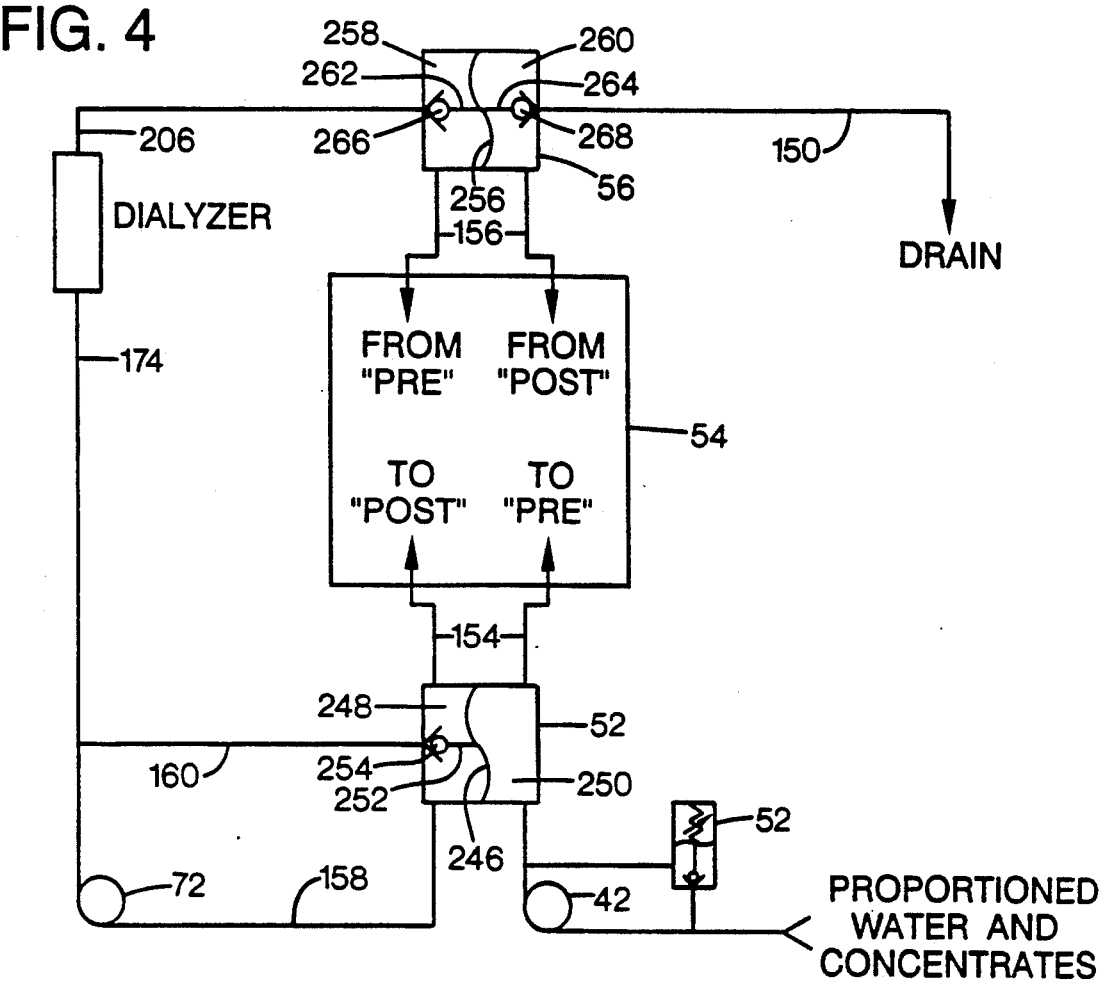
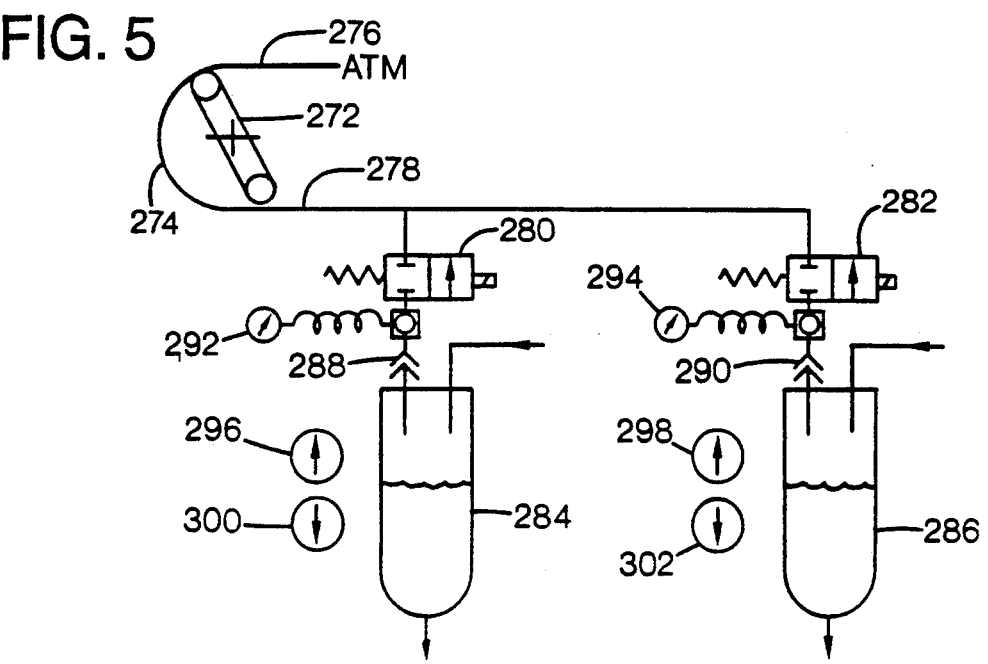

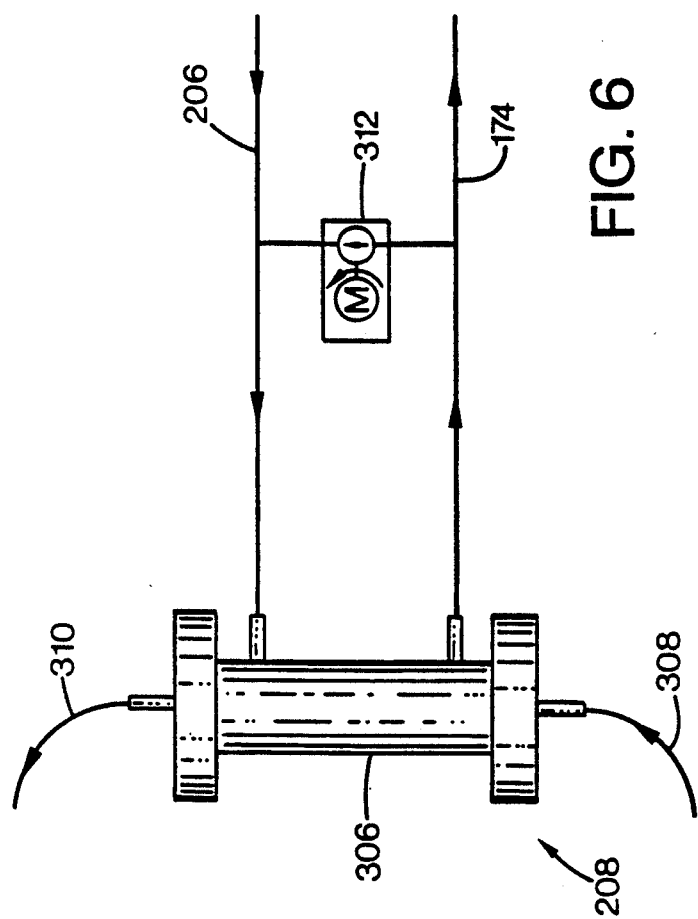

METHOD AND APPARATUS FOR KIDNEY DIALYSIS USING MACHINE WITH PROGRAMMABLE MEMORY

CROSS-REFERENCE TO RELATED APPLICATION

This application is a continuation-in-part of co-pending U.S. patent application Ser. No. 07/688,174 filed Apr. 12, 1991, now U.S. Pat. No. 5,247,434.

FIELD OF THE INVENTION

The present invention relates to improvements in kidney dialysis machines.

BACKGROUND OF THE INVENTION

Kidney dialysis machines are well known in the art and are illustrated, for example, in U.S. Pat. Nos. 3,598,727, 4,172,033, 4,267,040, and 4,769,134.

While machines according to the prior art provide a number of advantageous features, they nonetheless have certain limitations. The present invention seeks to overcome certain drawbacks of the prior art and to provide new features not heretofore available.

A discussion of the features and advantages of the present invention is deferred to the following detailed description, which proceeds with reference to the accompanying drawings.

BRIEF DESCRIPTION OF THE DRAWINGS

FIG. 4 is a schematic diagram showing the interconnection of input and output pressure equalizers into the hydraulic flow path of the present invention.

FIG. 5 is a schematic diagram of the automated drip-chamber level adjusters of the present invention.

FIG. 6 is a schematic diagram of a preferred embodiment of a means for increasing dialysate flow velocity through the dialyzer without increasing the dialysate flow rate.

DETAILED DESCRIPTION

Hydraulic Circuit

Figure 1A:
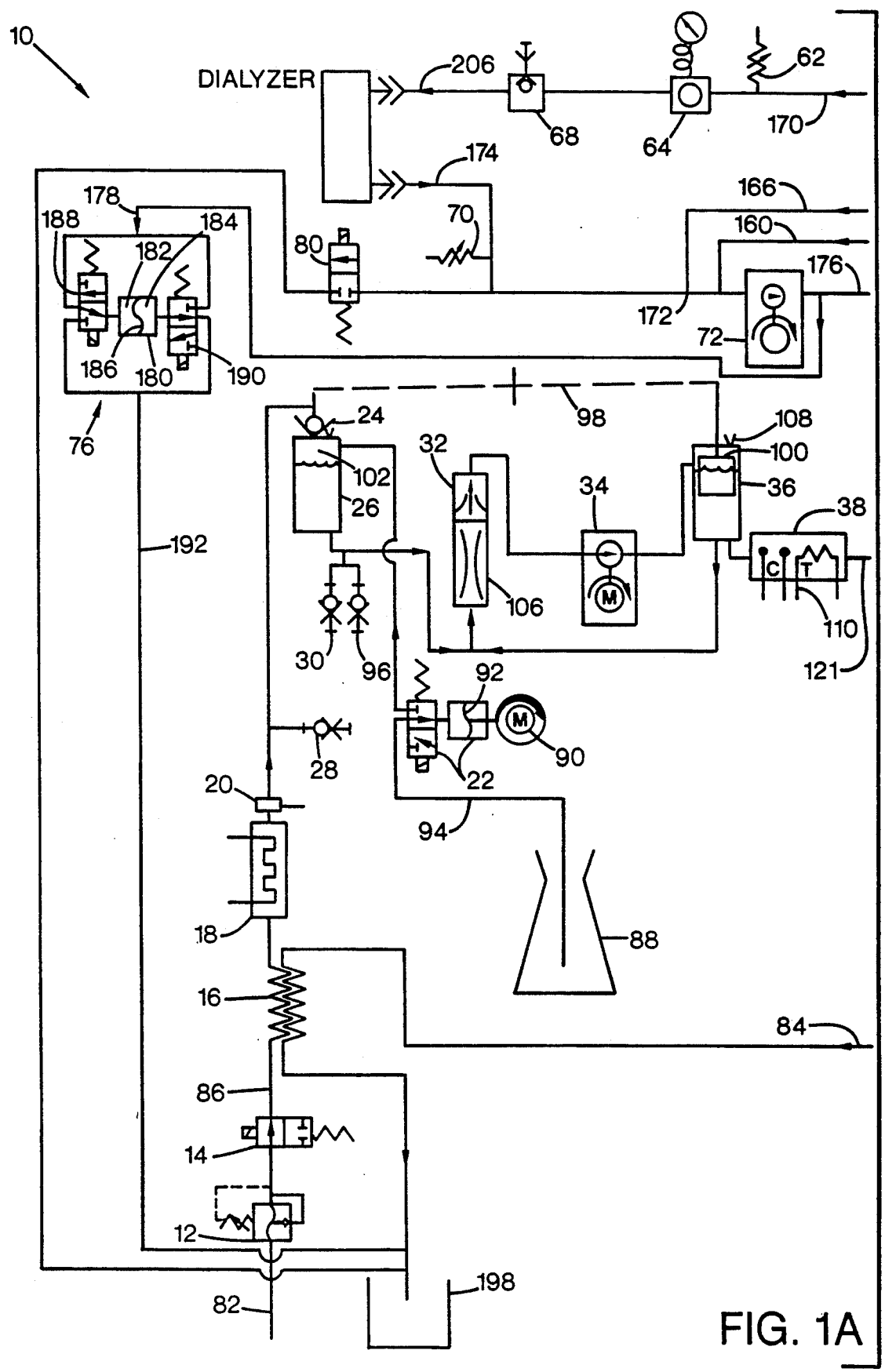
FIG. 1 is a schematic hydraulic diagram of a preferred embodiment of a kidney dialysis machine according to the present invention.
Figure 1B:
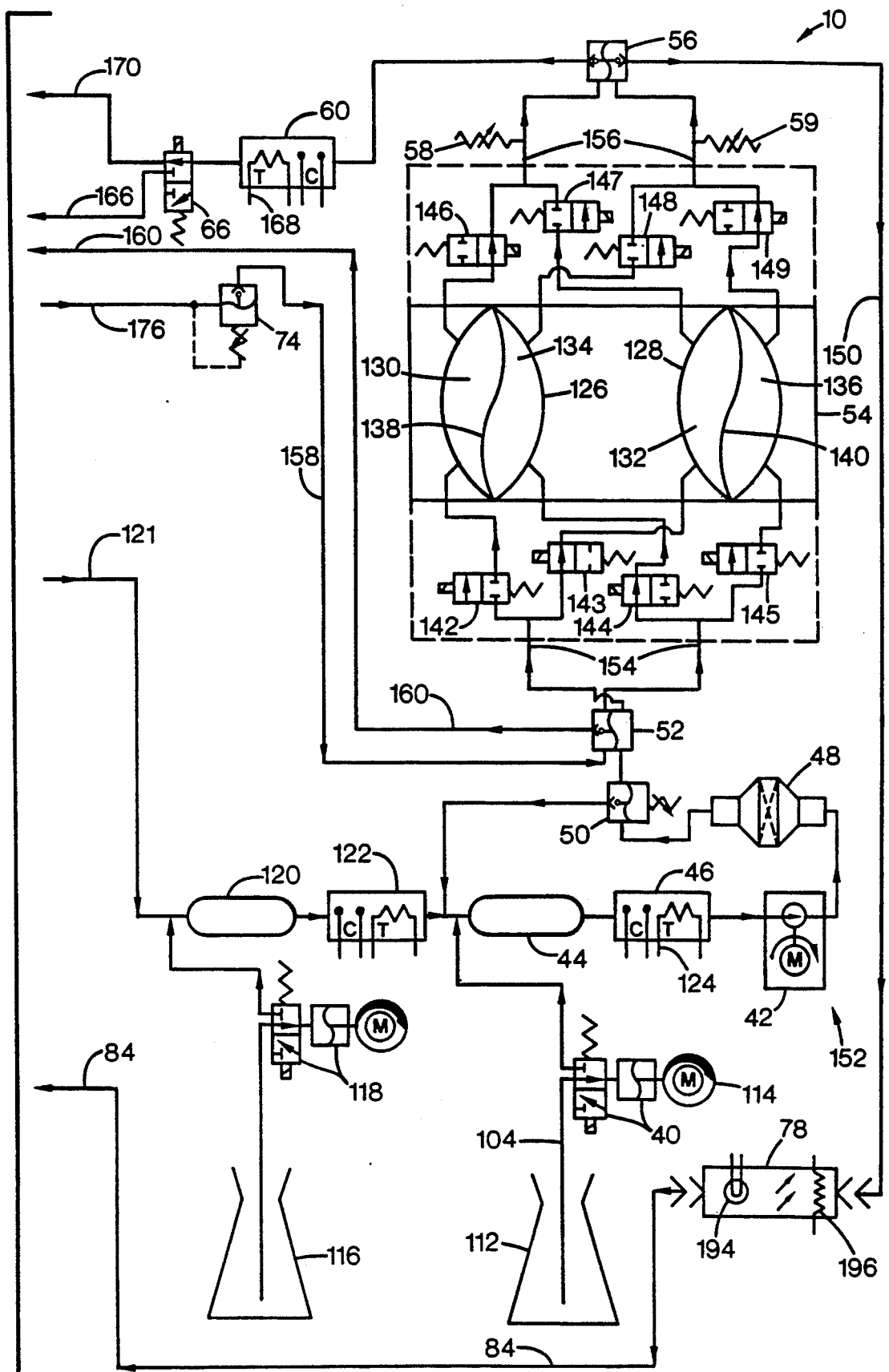

A hydraulic circuit 10 representing a preferred embodiment of an improved hemodialysis machine according to the present invention is illustrated in FIG. 1. The hydraulic circuit 10 is comprised of the following principal components: an incoming water pressure regulator 12, a water on/off valve 14, a heat exchanger 16, a heater 18, a safety thermostat 20, an "A" concentrate pump 22, a supply valve 24, an air gap chamber 26, an "A" rinse fitting 28, a "B" rinse fitting 30, a deaeration sprayer 32, an air removal pump 34, a vented air trap 36, an "A" conductivity probe 38, a "B" concentrate pump 40, a supply pump 42, a "B" mix chamber 44, a "B" conductivity probe 46, a dialysate filter 48, a supply regulator 50, an input pressure equalizer 52, a flow equalizer 54, an output pressure equalizer 56, end-of-stroke sensors 59, a dialysate conductivity probe 60, a pre-dialyzer flow sensor 62, a dialysate pressure transducer 64, a bypass valve 66, a dialysate sample port 68, a post-dialyzer flow sensor 70, a dialysate pressure pump 72, a UF removal regulator 74, a UF flow meter 76, a blood-leak detector 78, and a rinse valve 80. The aforementioned components are interconnected as shown in FIG. 1.

The incoming water pressure regulator 12 is coupled to a pressurized water source 82 and reduces and stabilizes the water supply pressure to a level of about 20 psig.

The water on/off valve 14 opens when machine power is on, thereby allowing water to flow from the source 82 into the hydraulic circuit 10. When the machine power is off, the water on/off valve 14 is closed.

The heat exchanger 16 transfers heat from "spent" or effluent dialysate, passing through conduit 84, to the cooler incoming water passing through conduit 86 as these two liquids pass countercurrently through separate but adjacent compartments in the heat exchanger 16. In this way, the incoming water is warmed, which reduces the amount of heat energy that must be supplied to the water by the heater 18.

The heater 18 further warms the incoming water to a suitable temperature for hemodialysis, which is about 38° C. A typical heater 18 is a resistance type known in the art, rated at about 1500 watts. The heater 18 includes a downstream thermistor 20 or analogous temperature-sensing device. A thermistor as known in the art is essentially a temperature-sensitive resistor which experiences a change in electrical resistance that is inversely proportional to a corresponding change in temperature. The thermistor 20 is coupled to the machine's microprocessor (not shown in FIG. 1) which utilizes signals from the thermistor for turning the heater 18 on and off as required to maintain the water temperature at the proper level.

The "A" concentrate pump 22 propels either "acid" or "acetate" concentrate as known in the art from a container thereof 88 into the air gap chamber 26. The "A" concentrate pump 22 is a fixed-volume cam-driven pump. A stepper motor 90 calibratable to rotate a precise number of rotations per minute is preferably used to drive the "A" concentrate pump 22. The stepper motor includes a shaft (not shown) to which is mounted a cam (not shown) which engages a flexible diaphragm 92, thereby delivering a known volume of "A" concentrate per each rotation of the cam. An optical sensor (not shown) on the cam monitors the angular rotation of the cam for processing by the microprocessor (not shown). The microprocessor, using information pertaining to dialysate flow rate and concentrate parameters entered by the machine operator using a touch screen (described in detail hereinbelow), calculates the amount of concentrate necessary to achieve a correct ratio of water and "A" concentrate for hemodialysis therapy.

The microprocessor thereby adjusts the angular velocity of the stepper motor shaft.

An "A" concentrate line 94 is used to deliver "A" concentrate from the supply 88 thereof to the "A" concentrate pump 22. When rinsing the machine, the "A" concentrate line 94 is coupled to the "A" rinse fitting 28 which serves as a source of rinse water for the "A" concentrate line.

When disinfecting the machine, the "A" concentrate line 94 is coupled to a disinfect fitting 96 which enables the "A" concentrate pump 22 to deliver a chemical disinfectant to the "A" concentrate line 94.

Heated water enters the air gap chamber 26 through the supply valve 24. The supply valve 24 is actuated by a lever 98. The lever 98 is coupled to a float 100 inside the air trap 36. Thus, the float 100 controls water flow into the hydraulic circuit 10 by opening the supply valve 24 when the water level supporting the float drops and by closing the supply valve 24 when the water level in the air trap 36 rises.

The air gap 102 in the chamber 26 is at atmospheric pressure. The air gap 102 helps prevent incoming water from flowing backward (upstream) in the event of a pressure drop in the water supply 82.

A proximity sensor (not shown in FIG. 1 but described in further detail hereinbelow) is built into the "A" rinse fitting 28. The proximity sensor senses when the "A" concentrate line 94 is coupled to the "A" rinse fitting 28 and when it is not, thereby serving as an important safety interlock feature which prevents unsafe operation of the machine.

The "B" rinse fitting 30 supplies water for rinsing the "B" concentrate line 104. During rinse, the "B" concentrate line 104 is coupled to the "B" rinse fitting 30. During acetate dialysis, the "B" concentrate line 104 is also coupled to the "B" rinse fitting 30 for recirculation of acetate dialysate solution therethrough.

The "B" rinse fitting 30 is also provided with a proximity sensor (not shown in FIG. 1 but described in further detail hereinbelow) similar to that provided with the "A" rinse fitting 28.

The hydraulic circuit includes components operable to remove dissolved gases from the liquid passing therethrough. Otherwise, if the liquid were not deaerated, dissolved gases therein could adversely affect the course of a dialysis treatment, including the accuracy at which the machine performs ultrafiltration of the patient. To facilitate deaeration, liquid flows through the air-removal sprayer 32 at a rate of about 1500 mL/min at a subatmospheric pressure (about 500 mmHg). The reduced pressure is attained by aspirating the liquid via the air-removal pump 34 through a flow restrictor 106 upstream of the air-removal sprayer 32. The air-removal sprayer 32 breaks the liquid into small droplets as it is subjected to the subatmospheric pressure, which favors the formation of air bubbles.

The air trap 36 vents air bubbles liberated from the liquid by the deaeration sprayer 32 through a vent opening 108 open to the atmosphere. The air trap also contains the float 100 discussed hereinabove.

The "A" conductivity probe 38 measures the electrical conductivity of the mixture of water and "A" concentrate. Conductivity is an accurate way to ascertain whether the "A" concentrate solution has been correctly proportioned. The conductivity measured at the "A" conductivity probe 38 can vary depending upon the ionic strength and electrolytic profile of the "A" concentrate. Since conductivity will be affected by temperature, the "A" conductivity probe 38 is also provided with a thermistor 110. The thermistor 110 is coupled to the microprocessor (not shown) which performs the necessary temperature compensation.

The "B" concentrate pump 40 delivers bicarbonate concentrate from a supply thereof 112 and is operable only during bicarbonate dialysis therapy. The "B" concentrate pump 40 is a fixed-volume cam-driven pump similar to the "A" concentrate pump 22. The "B" concentrate pump 40 is driven by a stepper motor 114. As with the "A" concentrate pump, the angular velocity of the stepper motor shaft is monitored by an optical sensor. The optical sensor is connected to the machine's microprocessor which calculates the amount of "B" concentrate necessary to achieve a correct dialysate composition for safe hemodialysis therapy and correspondingly controls the angular velocity of the cam. The "B" concentrate pump 40 will automatically compensate for changes in dialysate flow rate in the event that said flow rate is changed during a dialysis treatment by increasing or decreasing the pump rate.

FIG. 1 also shows an optional third concentrate supply 116, a third fixed-volume cam-driven concentrate pump 118 operable in the same manner as the "A" and "B" concentrate pumps 22, 40, a corresponding mixing chamber 120 and conductivity probe 122.

The "B" mix chamber 44 provides thorough mixing of the "B" concentrate with the proportioned mixture of "A" concentrate and water to form dialysate before the dialysate enters the "B" conductivity probe 46.

The "B" conductivity probe 46 monitors dialysate conductivity. Electronic circuitry (not shown) coupled to the "B" conductivity probe 46 subtracts the conductivity measured at the "A" conductivity probe 38 from the conductivity measured at the "B" conductivity probe 46. During acetate dialysis, the difference in these conductivity readings should be zero. Since conductivity measurements are affected by temperature, a thermistor 124 is included with the "B" conductivity probe 46 to provide temperature compensation of the "B" conductivity reading. The thermistor 124 also comprises a portion of a redundant high temperature alarm subsystem.

Before describing the hydraulic circuit any further, it is appropriate to briefly describe the flow equalizer 54. The flow equalizer 54 comprises a first chamber 126 and a second chamber 128 of substantially equal volume. Each chamber 126, 128 is comprised of two compartments, one termed a "pre-dialyzer" or "pre" compartment 130, 132 and the other a "post-dialyzer" or "post" compartment 134, 136. Each pair of opposing "pre" and "post" chambers is separated by a flexible diaphragm 138, 140. Solenoid-actuated valves 142–149 control the filling and emptying of each compartment. In general, each compartment 130, 132, 134, 136 is completely filled before its contents are discharged. Also, the "pre" compartments 130, 132 are alternately filled and discharged and the "post" compartments 134, 136 are alternately filled and discharged. Also, filling a "pre" compartment 130, 132 causes a corresponding discharge of an opposing "post" compartment 134, 136, respectively. The "pre" compartments 130, 132 alternately fill from the supply pump 42 and alternately discharge to the dialyzer. The "post" compartments 134, 136 alternately fill with "spent" dialysate returning from the dialyzer and discharge the spent dialysate to a drain line 150. For example, dialysate from the supply pump 42 enters the "pre" compartment 132, thereby displacing the diaphragm 140 in FIG. 1 to the right, causing the "post" compartment 136 to empty. Simultaneously, "post" compartment 134 fills while "pre" compartment 130 empties.

The flow equalizer 54 operates via a four-phase cycle. In the first phase, valves 142, 145, 147, and 148 turn on, thereby filling the "pre" compartment 130 with fresh dialysate and displacing the diaphragm 138 to the right in FIG. 1. Such displacement of the diaphragm 138 expels "spent" dialysate contained in the "post" compartment 134, which has a volume equal to the volume in the "pre" compartment 130, to pass to the drain line 150. At the same time, effluent dialysate from the dialyzer enters the "post" compartment 136, thereby forcing the diaphragm 140 to be displaced to the left in FIG. 1 to expel an equal volume of fresh dialysate from the "pre" compartment 132 to the dialyzer. In the second phase, all the solenoid valves 142-149 turn off for a short period of time (about 125 msec). This brief shut-off eliminates adverse affects on ultrafiltration accuracy that would otherwise result if at least two of said valves were open at the same time. In the third phase, solenoid valves 143, 144, 146, and 149 are energized, causing the "post" compartment 134 to fill with effluent dialysate from the dialyzer, thereby expelling fresh dialysate from "pre" compartment 130 to the dialyzer. Also, the "pre" compartment 132 simultaneously fills with fresh dialysate from the supply pump 42, thereby expelling effluent dialysate from the remaining "post" compartment 136 to the drain line 150. In the fourth phase, all the solenoid valves 142-149 are again turned off for about 125 msec.

Since the volumes of opposing "pre" and "post" compartments 130, 134 and 132, 136 are equal, the flow equalizer 54 volumetrically balances the flow of dialysate to and from the dialyzer. A further benefit of such volumetric equality is that dialysate flow to the dialyzer can be accurately measured over a wide range of flow rates.

The supply pump 42 has two functions: (a) to supply an adequate dialysate flow volume and pressure to fill the flow equalizer compartments with dialysate, and (b) to create a flow of dialysate through a loop 152 comprised of the dialysate filter 48, the supply regulator 50, the "B" mix chamber 44, and the "B" conductivity probe 46. The supply pump 42 delivers dialysate at a maximum regulated pressure of 12.5 psig and at a flow rate approximately 50 mL/min higher than the dialysate flow rate set by the operator using the touch screen.

The dialysate filter 48 is used to occlude downstream passage of particulate foreign material into the flow equalizer 54. The supply regulator 50 is adjusted to an output pressure of approximately 16 psig. Whenever the "pre" and "post" compartments of the flow equalizer 54 reach the end of a fill cycle during phases 1 or 3, pressure builds up in the loop 152. As the pressure increases to about 16 psig, the supply regulator 50 opens sufficiently to pass the dialysate output of the supply pump 42 through the loop 152 until the next phase 1 or 3.

The input pressure equalizer 52 equilibrates hydraulic pressures at the inlets 155 of the flow equalizer 54 so that the compartments 130, 132, 134, 136 fill at the same rate. Likewise, the output pressure equalizer 56 equilibrates hydraulic pressures at the outlets 156 of the flow equalizer 54. The input and output pressure equalizers are discussed in greater detail hereinbelow.

The input pressure equalizer 52 also automatically equilibrates the pressure of the dialysate flowing through the downstream lines 158, 160 with the pressure of dialysate at the flow equalizer inlets 154. Whenever the pressure at the flow equalizer inlets 154 exceeds the pressure generated by the dialysate pressure pump 72, the input pressure equalizer 52 restricts the flow of dialysate in lines 158, 160. Such equilibration of pressures allows both chambers 126, 128 in the flow equalizer 54 to be filled at identical rates.

End-of-stroke sensors 162, 164 are provided at the outlets 156 of the output pressure equalizer. The end-of-stroke sensors 162, 164 verify when the flow equalizer compartments have reached the end of a fill cycle (end of stroke). When the compartments are full, the end-of-stroke sensors 162, 164 send a no-flow signal to the machine's microprocessor, indicating that the compartments are full.

The dialysate conductivity probe 60 measures the conductivity of the dialysate before it enters the dialyzer. The machine's microprocessor compares the measured conductivity with an expected conductivity value (discussed in detail hereinbelow) based upon concentrate formulation information entered by the operator using the touch screen. If the measured dialysate conductivity is excessively above or below the expected conductivity value, the machine's microprocessor activates a conductivity alarm. Also, the bypass valve 66 is triggered during a conductivity alarm to divert dialysate away from the dialyzer through conduit 166.

The dialysate conductivity probe 60 includes a thermistor 168 which allows temperature compensation of the conductivity reading. The electronic signal from the thermistor 168 is also utilized to provide a dialysate temperature display on the machine's touch screen as well as primary high and low temperature alarm limits. The dialysate conductivity as measured by the conductivity probe 60 is also displayed on the machine's touch screen.

The dialysate flow sensor 62 includes a self-heating variable thermistor as well as a reference thermistor (not shown in FIG. 1, but discussed in detail hereinbelow). The dialysate flow sensor 62 is used mainly as a bypass monitor. Whenever the machine is in bypass, the resulting lack of dialysate flow past the flow sensor 62 serves as a verification that the bypass valve 66 is functioning correctly.

The dialysate pressure transducer 64 senses dialysate pressure and converts the pressure reading into an analog signal proportional to the dialysate pressure. The analog signal is utilized by the machine's microprocessor as the basis for a dialysate pressure display on the touch screen, pressure alarms, and other dialysate control functions (not shown in FIG. 1).

The bypass valve 66 protects the hemodialysis patient in the event of a temperature or conductivity alarm by diverting dialysate flow away from the dialyzer. The bypass valve 66 is a three-way solenoid valve which, when triggered, occludes the conduit 170 leading to the dialyzer and shunts the dialysate flow through conduit 166 to a location 172 downstream of the dialyzer.

The dialysate sample port 68 is an appliance which allows the operator to obtain a sample of the dialysate using a syringe for independent testing.

A second dialysate flow sensor 70 is located in the post-dialyzer ("venous") line 174. The second flow sensor 70 is constructed similarly to the first flow sensor 62 and is discussed in detail hereinbelow. The second flow sensor 70 is utilized for checking the accuracy of the machine's ultrafiltration capability.

The dialysate pressure pump 72 is situated downstream of the dialyzer. An accompanying recirculation loop comprising lines 158, 160 conducts effluent dialysate to the inlet pressure equalizer 52. The recirculation loop 158, 160 thereby helps equilibrate pressure differences that might otherwise be transmitted to the flow equalizer 54 and also serves as a source of hydraulic pressure sufficient to fill the UF flow meter 76 when demanded thereby.

The dialysate pressure pump 72 circulates dialysate at a constant flow rate of 1500 mL/min through the recirculation loop 158, 160 without affecting the overall dialysate flow rate through the hydraulic circuit 10. As a result, the dialysate pressure pump 72 is usable to adjust pressure differences across the dialyzer membrane.

As long as the dialysate pressure pump 72 receives an adequate volume of dialysate for pumping, the flow dynamics of dialysate through the hydraulic circuit 10 are unaffected. However, should liquid be removed from the recirculation loop 158, 160, the dialysate pressure pump will attempt to replace that lost volume by demanding more volume from the dialyzer. Since the flow equalizer 54 maintains volumetric constancy of dialysate passing to and from the dialyzer, the only fluid available to replace any fluid lost from the loop 158, 160 must come from the dialyzer itself. Hence, by precisely controlling the amount of liquid removed from the recirculation loop 158, 160 (using the UF flow meter 76), the operator can precisely control the amount of liquid that must be removed from the hemodialysis patient via the dialyzer.

Since the dialysate pumped by the dialysate pressure pump 72 has a partially restricted flow, a sufficient pressure is thereby provided at the input of the UF removal regulator 74. The UF removal regulator 74 regulates hydraulic pressure at the input 178 of the UF flow meter 76.

The UF flow meter 76 is comprised of a chamber 180 separated into two subcompartments 182, 184 via a diaphragm 186. Each subcompartment 182, 184 has a corresponding valve 188, 190, respectively, associated therewith. Either subcompartment 182, 184 of the UF flow meter 76 can only fill when the corresponding valve 188, 190 is opened. Whenever a first subcompartment 182 is filling, the opposing second compartment 184 is emptying its contents to a drain line 192. The rate of UF removal through the UF flow meter 76 is governed by the rate at which the corresponding valves 188, 190 are alternately opened and closed.

Whenever liquid leaves the recirculation loop 158, 160 through the UF flow meter 76, correspondingly less liquid is recirculated through the recirculation loop 158, 160. This causes a corresponding "starvation" at the input 172 of the dialysate pressure pump 72 which generates a corresponding decrease in dialysate pressure in the dialyzer. The decreased dialysate pressure causes a volume of liquid to be removed from the patient that is equal to the volume of liquid removed from the recirculation loop 158, 160 via the UF flow meter 76. These volumes will be equal so long as the dialyzer has an ultrafiltration capability sufficient to remove said volume from the patient at the desired rate.

Effluent dialysate expelled from the flow equalizer 54 passes through and is monitored for the presence of blood by the blood-leak detector 78. The blood-leak detector 78, discussed in further detail hereinbelow, comprises a light source 194 and a photocell 196 which monitors light transmitted through the effluent dialysate solution passing therethrough. If blood leaks through the dialyzer membrane from the patient into the dialysate, the dialysate passing through the blood-leak detector 78 will absorb a portion of the light passing therethrough. The corresponding decrease in the amount of light reaching the photocell 196, if the decrease is excessive, triggers a blood-leak alarm by the machine.

Effluent dialysate from the blood-leak detector 78 is routed through conduit 84 to the heat exchanger 16, then to a drain 198.

The rinse valve 80 allows the UF flow meter 76 to remove rinse water from the recirculation loop 158, 160 at a rate of about 4 L/h. Such rinsing ensures an adequate flushing of the recirculation loop 158, 160 and UF flow meter 76. However, since liquid is removed from the loop 158, 160 at a relatively high rate during rinse, the rinse valve 80 also allows an equivalent volume of liquid to be added back to the loop 158, 160.

User Interface

In the preferred embodiment, a touch screen user interface is employed. Appendix B contains various details concerning the user interface according to the present invention.

Touch screens are known in the art and are commercially available from a number of sources, including Elographics West of San Diego, Calif. The use of touch screens in user interface applications for medical equipment is also known, as shown for example in U.S. Pat. Nos. 4,974,599 and 4,898,578, the disclosures of which are incorporated herein by reference.

In the prior art, as illustrated by the above-referenced patents, touch screens have been used in conjunction with computers, and CRTs to provide a control panel that can be changed under computer control. The means by which a computer, a CRT, and a touch screen can be cooperatively operated in this fashion is well known and does not, per se, form a part of this invention.

Figure 7:
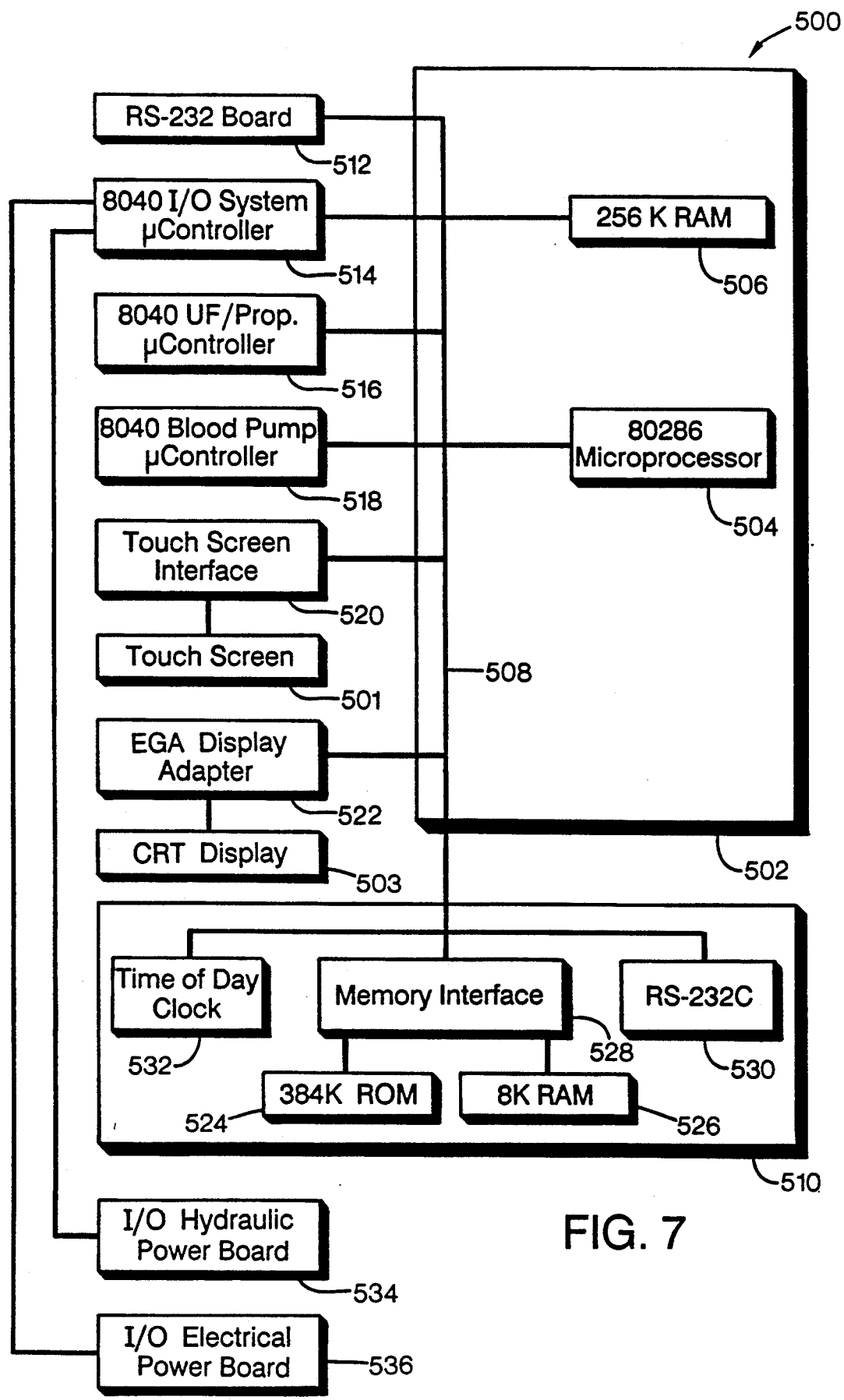
FIG. 7 shows a block diagram of a computer system used in the preferred embodiment.

FIG. 7 shows a block diagram of the computer system 500 that is used to control the touch screen 501, CRT display 503, and other components of the apparatus. This computer is programmed in the language 'C' in a conventional manner to accomplish the dialogue and other functions subsequently described.

Figure 8:
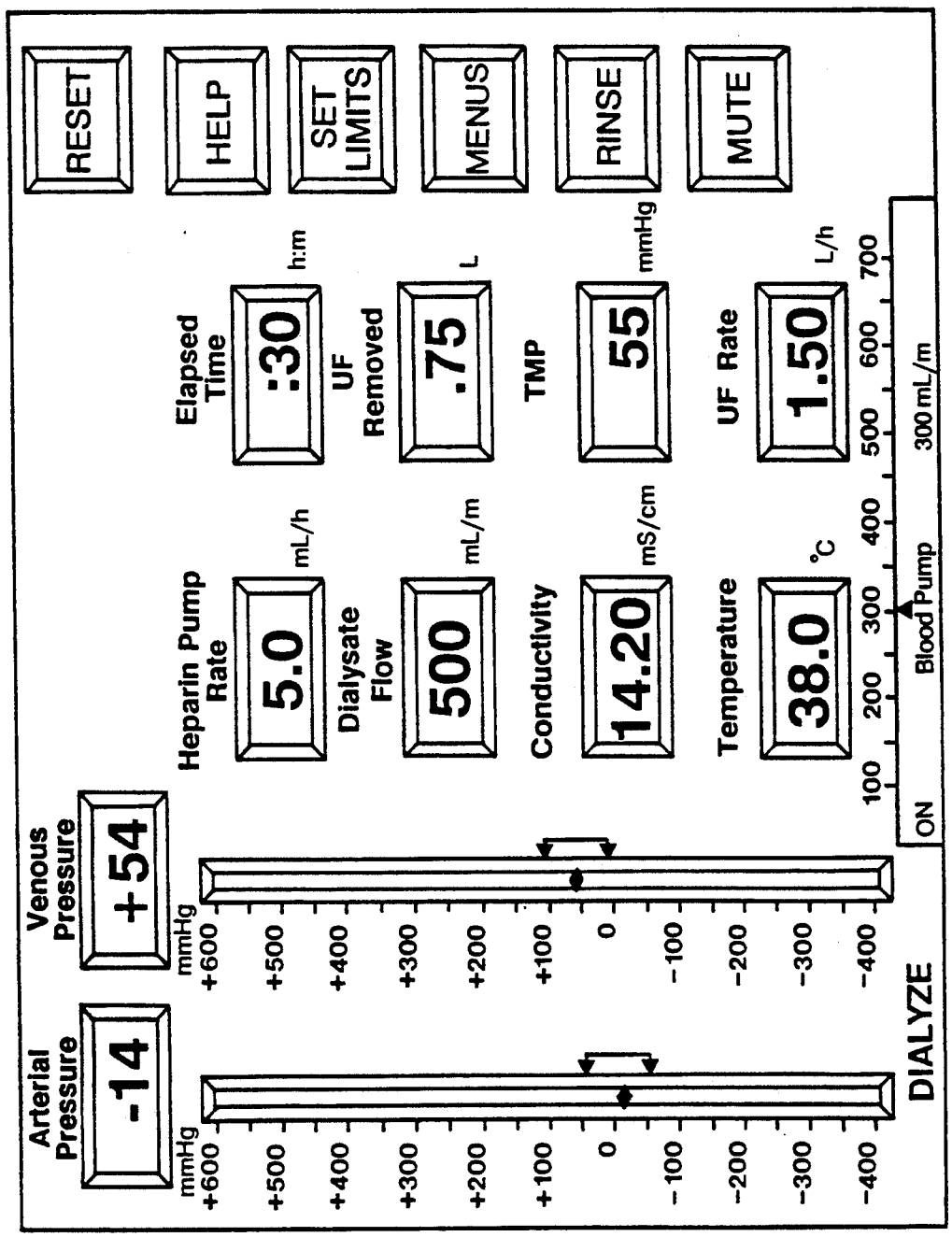
FIG. 8 shows a touch screen display used in the preferred embodiment.

FIG. 8 shows the touch screen display that is usually presented to the operator of the system of FIG. 7. As can be seen, the primary treatment parameters are displayed. These include the heparin pump rate, the dialysate flow rate, the dialysate conductivity, the dialysate temperature, the elapsed treatment time, the total ultrafiltrate removed, the transmembrane pressure, and the ultrafiltration rate. Also displayed are the patient's arterial and venous blood pressure (both in column of mercury form and in numeric form). A linear indicator at the bottom of the screen indicates the blood pump flow rate. A space at the top of the screen is reserved for alarm and help messages. These elements of the display are detailed more fully in Appendix A beginning at page Reference 1.

Most of these display elements are in a bordered box. The border serves as a visual alarm indicator and changes color and flashes if a corresponding alarm limit is violated.

A number of buttons are displayed on the right hand side of the display. The first is a RESET button and is used to reset alarm conditions after an alarm condition is corrected. HELP guides the user through a variety of help messages. SET LIMITS sets the alarm limits for various parameters including arterial pressure, venous pressure and TMP. MENUS replaces the buttons on the right hand side of the display with additional buttons corresponding to additional control functions, while maintaining the displayed parameters elsewhere on the screen. RINSE initiates the rinse mode, provided the interlocks are met. MUTE silences most audio alarms for 100 seconds. Additional buttons can appear in this part of the screen and are detailed in the Reference Section of Appendix A. Button locations are reprogrammable and can have multiple legends associated with them. Also, their positions on the touch screen can be varied by reprogramming.

Figure 9:
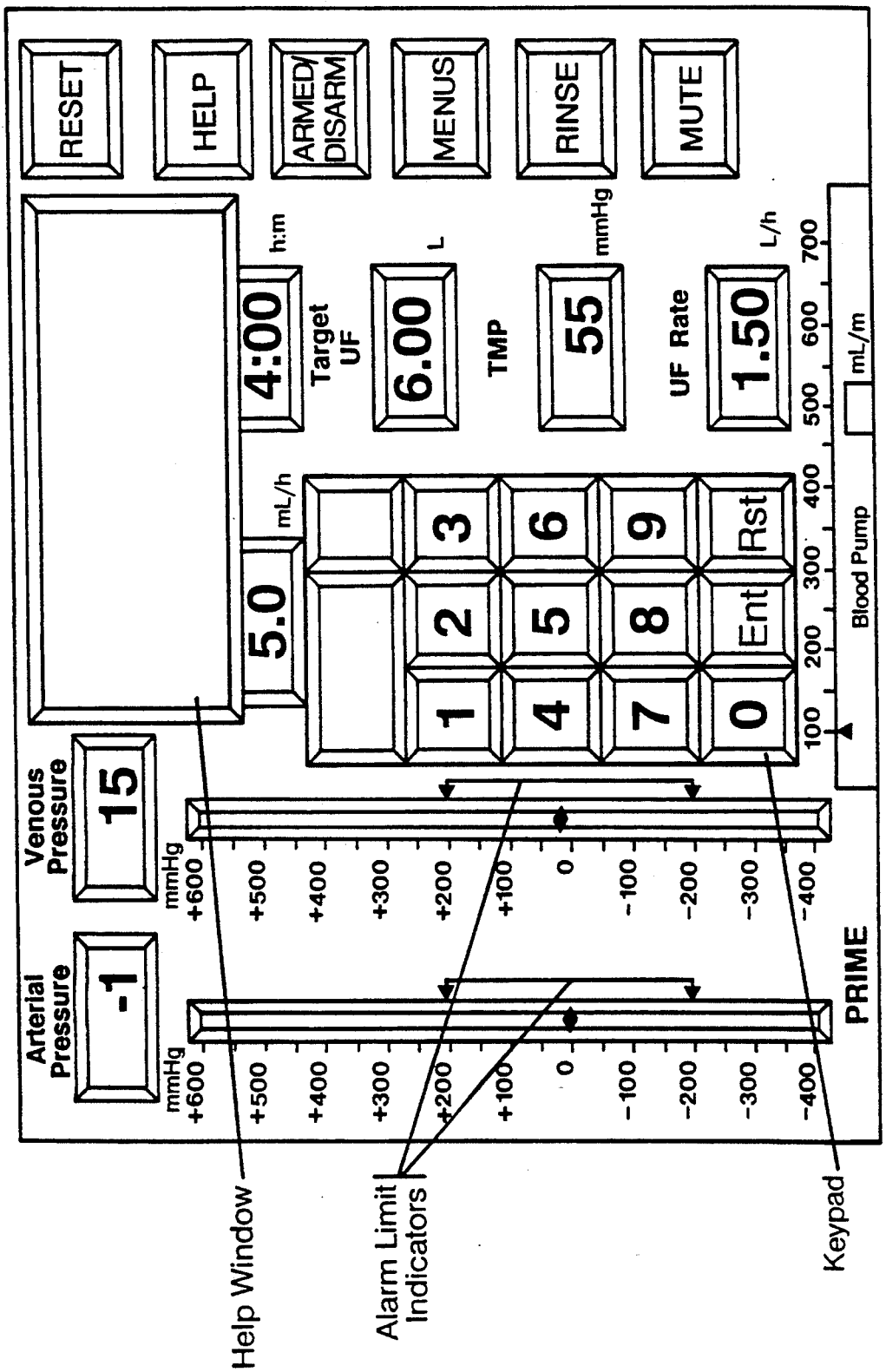
FIG. 9 shows the touch screen of FIG. 8 with a calculator window for data entry.

If it is desired to change one of the displayed parameters, such as the heparin pump rate, the operator simply touches the corresponding indicator. A calculator-like keyboard then pops up in a window superimposed on the display, as shown in FIG. 9. On this keyboard, the user can enter the new value for the selected parameter. Once the desired parameter is entered in this fashion, the operator presses ENTER on the calculator display and the calculator display disappears. The revised parameter is substituted in the corresponding indicator (with its border highlighted) and the user is prompted, through a button that appears at the lower right hand side of the screen, to verify the entered change. If the VERIFY button is not touched shortly after displayed, the VERIFY button disappears and the machine continues with its previous parameter. If timely verified, the change takes effect. In the preferred embodiment, the user has between one and five seconds to verify the parameter.

Some parameters are not susceptible to representation by a single number displayed in a parameter window. Exemplary are parameters that are programmed to change over time (so-called profiled parameters). In this class are the sodium concentration of the dialysate solution, the bicarbonate concentration of the dialysate solution, kT/V, and the ultrafiltration rate.

Figure 10:
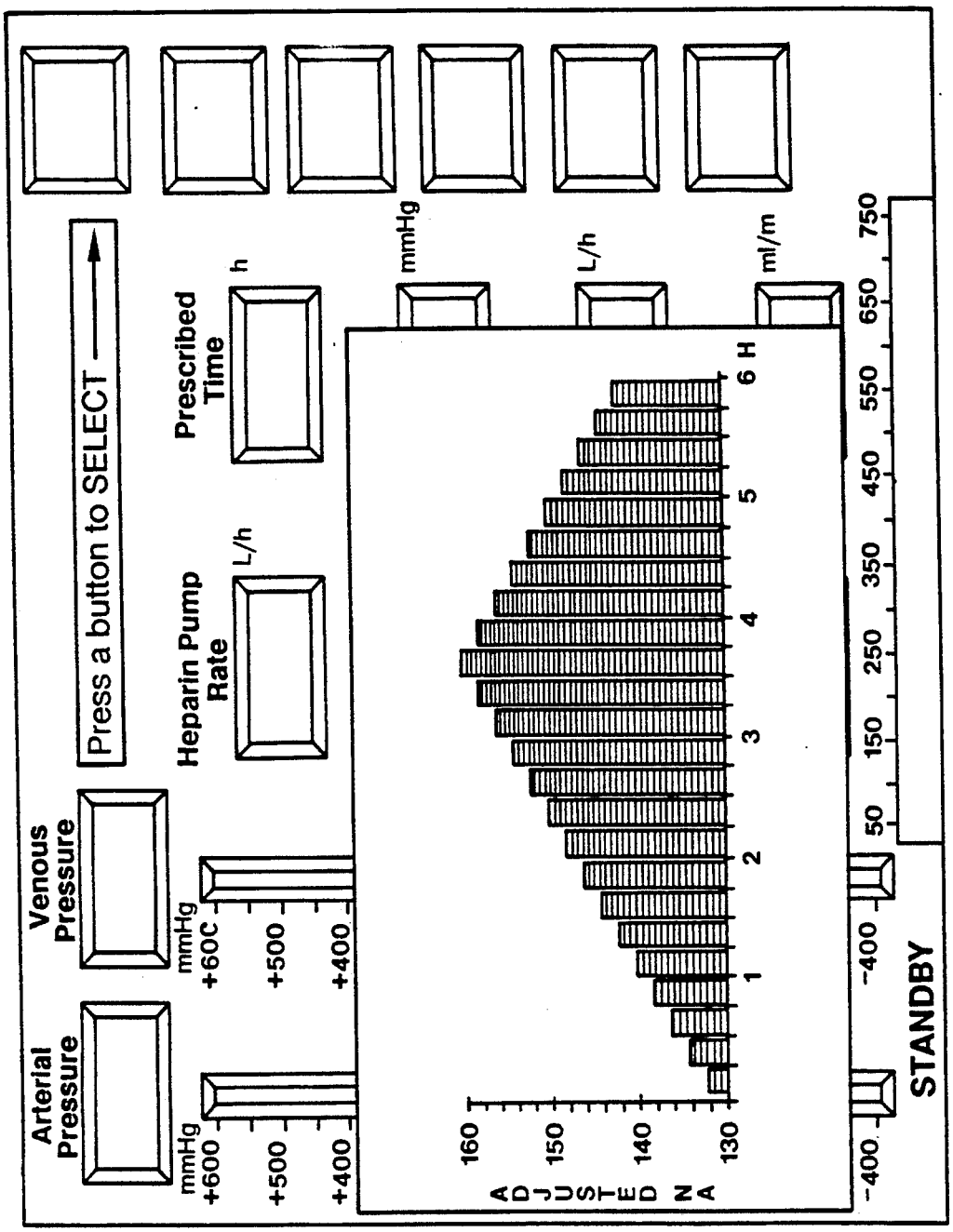
FIG. 10 shows a profile entry screen used in the preferred embodiment.

In the preferred embodiment, such profiled parameters are selectably displayed in the form of bar graphs on the display screen. Using sodium as an example, the Y-axis represents sodium concentrations in the range of 130-160 mEq/L. The X-axis represents the treatment period, broken down into fifteen minute intervals. Such a display is shown in FIG. 10.

The use of bar graphs to display profiled parameters is known in the art. The prior art fails, however, to provide a convenient manner by which data characterizing the profile curve may be entered into the machine. Typically, such data entry has been accomplished through a keypad on which data for each discrete time period is entered. However, this approach requires dozens of key presses and provides numerous opportunities for error.

In the preferred embodiment, in contrast, profiled parameters are entered by simply tracing the desired profile curve on the touch screen.

Figure 11:
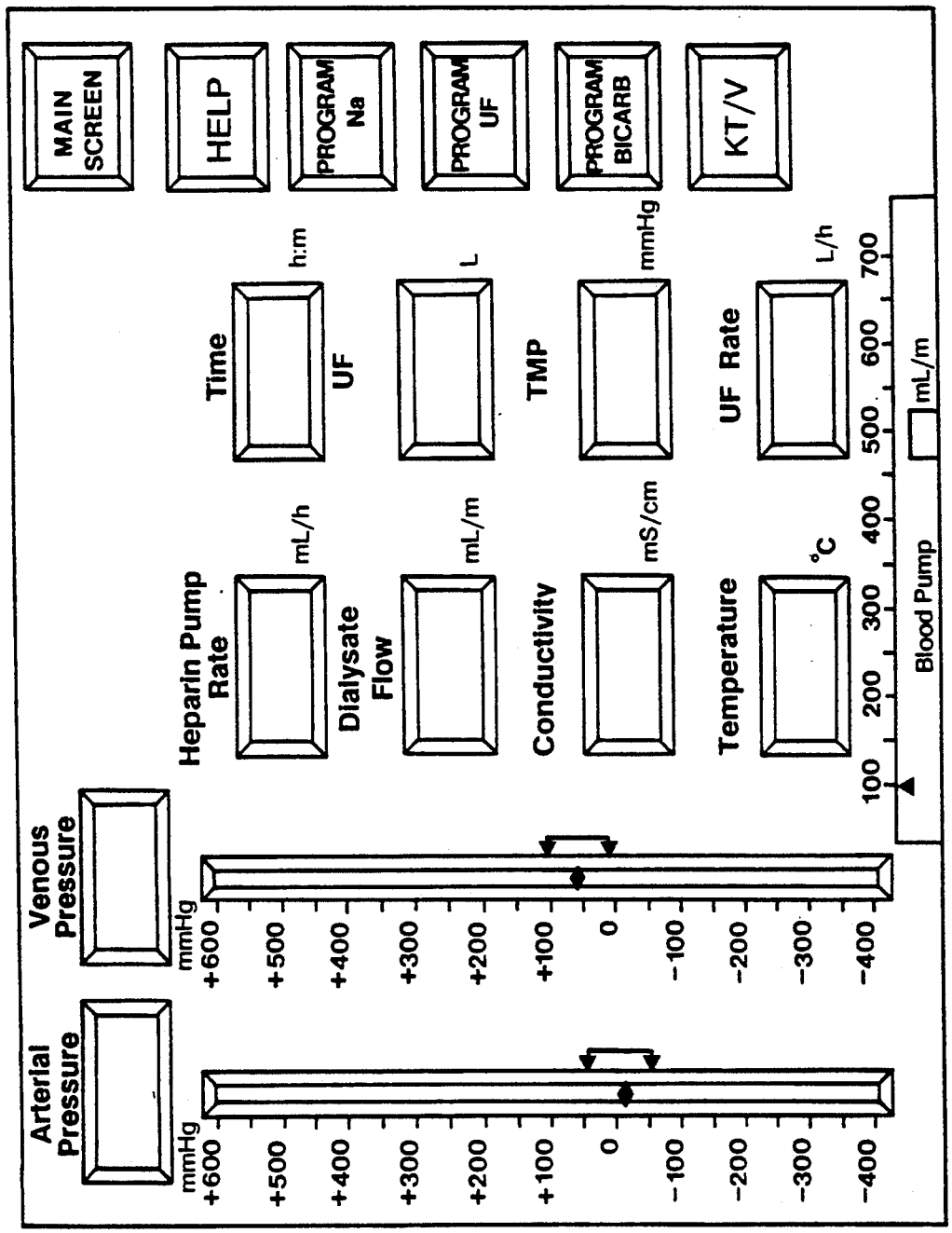
FIG. 11 shows a programming screen used in the preferred embodiment.

In more detail, programming of profiled parameters is performed as follows:

From the main touch screen display of FIG. 8, the user presses MENUS. The programming screen of FIG. 11 then appears, which includes along its right hand side buttons corresponding to the programming of sodium, bicarbonate, kT/V, and ultrafiltration. The parameter desired to be programmed is then selected by touching the corresponding button.

In response to this touch, the screen of FIG. 10 appears. If a profile has already been programmed, it is displayed in bar graph fashion on this screen. Otherwise, the graph is empty.

Before permitting the user to program the sodium profile, the machine first solicits the sodium value of the sodium concentrate being used. This data is entered on a pop-up keypad. If the treatment time was not earlier programmed, the machine also solicits this data by means of a pop-up keypad.

The user then traces the desired profile curve on the touch screen, and the computer virtually simultaneously displays a series of bars corresponding to the traced curve.

Alternatively, the user can touch the screen at discrete points on the desired profile curve. To program a linear increase in sodium from 140 to 160 mEq/L, for example, the user would touch the graph at 140 at the ordinate corresponding to the beginning of the treatment interval, and 160 at the ordinate corresponding to the end of the treatment interval. The computer would then fit a linearly increasing series of bars between these points.

Discrete touches can also be used to program stepped profiles. If the first hour of treatment is to be at 150 mEq/L and the second hour is to be at 135 mEq/L, the user would first touch the screen at 150 at the ordinate corresponding to the beginning of the first hour. At the ordinate corresponding to the end of the first hour, the user would press at two locations. First at 150 (to cause the computer to fill in the intervening period with bars corresponding to 150), and again at 135. Finally, the user would touch the screen at 135 at the ordinate corresponding to the end of the second hour. The computer would then fill in the second hour with bars corresponding to 135.

After the desired profile curve has been entered, the ENTER button is pressed to set the program in the machine.

In the preferred embodiment, the computer "snaps" the height of each bar to one of a series of discrete values. In the case of sodium, these discrete values are spaced in 1 mEq/L steps.

Displayed on the screen during this programming operation is a numeric data window in which the numeric counterpart to a particular bar may be displayed. When the curve is first traced, the computer displays in this window the numerical parameter corresponding to each bar as it is defined. After the profile has been programmed, the numeric counterpart to any bar can be displayed by first touching a LOCK button that locks the curve, and then touching the bar in question.

After the profile has been set, the user may wish to alter it in certain respects. One way, of course, is to simply repeat the above-described programming procedure. Another is to adjust the height of a particular bar. This can be accomplished in one of two ways. The first is simply to touch the bar to be altered. The height of the bar tracks movement of the user's finger. The second way of adjustment is to first select a bar to be adjusted by repeatedly touching (or pressing and holding) a Right Arrow button until the desired bar is highlighted. (The Right Arrow button causes highlighting to scroll through the bars, left to right, and cycles back to the left-most bar after the right-most bar. The highlighting indicates the bar that is selected.) The numeric parameter corresponding to the selected bar is displayed in the numeric data window. This value can then be adjusted by Up and Down arrow keys that cause the displayed parameter to increase and decrease, respectively. In the preferred embodiment, the Up and Down arrow keys cause the sodium parameter to change in steps of 0.1 mEq/L, one-tenth the resolution provided in the original data entry procedure. A similar ratio holds with other parameters programmed in this fashion. Again, the ENTER button is pressed to complete the programming operation.

As with other parameters, profiled parameters must also be Verified before they take effect.

After the above-detailed data profiling operations are completed, data corresponding to the programmed profile is stored in the computer's memory. Periodically, such as once every fifteen minutes, a timed interrupt in the system's software program causes the computer to poll this memory for the value of the programmed parameter for the next time interval (here fifteen minutes). The physical parameter is adjusted accordingly using conventional adjustment mechanisms.

Once treatment has begun, the system only permits bar graph-bars corresponding to upcoming time intervals to be programmed. Bars corresponding to past time intervals reflect treatment history and cannot be changed. To readily distinguish past from future, the bars corresponding to each are displayed in different colors.

Additional details on sodium programming, as well as details of bicarbonate and ultrafiltration programming, are contained in Appendix D.

In all aspects of the interface, the user is guided from one touch to the next by a feature of the preferred embodiment wherein the button that the user is most likely to press next is highlighted. For example, when the machine is in Rinse mode and is nearing completion of these operations, the Self-Test button is highlighted, indicating that this is the next likely operation. Similarly, when the Self-Test operation is nearing completion, the Prime button is highlighted. By this arrangement, even novice users are easily guided through the machine's various phases of operations.

In addition to the above-described user interface, communications with the dialysis machine can also be effected by an RS-232C serial data interface 530 and by a data card (See Appendix E).

Data cards (also known as memory cards or RAM cards) are known in the art, as represented by U.S. Pat. Nos. 4,450,024, 4,575,127, 4,617,216, 4,648,189, 4,683,371, 4,745,268, 4,795,898, 4,816,654, 4,827,512, 4,829,169, and 4,896,027, the disclosures of which are incorporated herein by reference. In the preferred embodiment, a data card can be used both to load treatment parameters into the machine and to download logged patient parameters from the machine for therapy analysis.

Among the treatment parameters that can be provided to the machine by a data card are the ultrafiltration profile, the sodium profile, the bicarbonate profile, the blood pump flow rate, the treatment time, the desired ultrafiltration removal volume, the dialysate flow rate, the dialysate temperature, the blood pressure measurement schedule and alarms, and the heparin prescription.

Among the patient parameters that are logged by the machine and that can be downloaded to a memory card for later therapy analysis are: temporal data relating to dialysate temperature and conductivity (both of which are typically measured at several points in the fluid circuit), venous, arterial, dialysate, systolic and diastolic pressures, blood flow rate, total blood processed, ultrafiltration rate, total ultrafiltrate removed, the ultrafiltrate goal, and the machine states.

Additionally, the data card can convey to the machine certain codes that, when read by the machine, initiate special operations. These operations include calibration mode, technician mode, enabling the blood pressure monitoring function, modifying the parameters transmitted over the serial port for diagnostics, and others.

The card used in the preferred embodiment is commercially available from Micro Chip Technologies under the trademark ENVOY and provides 32K of data storage in EEPROM form. Similar cards are also available from Datakey.

When a card containing treatment parameters is read by the machine, the stored parameters do not immediately take effect. Instead, each is displayed on the screen and the operator is asked, through prompts that appear on the screen, to verify each individually. If a parameter is not verified, that aspect of machine operation is left unchanged. In the preferred embodiment, the parameters loaded from a memory card are displayed in their respective parameter windows and each is highlighted in sequence, with the system soliciting verification of the parameter in the highlighted window. In alternative embodiments, a plurality of parameters are be displayed for verification as a group.

Returning now to FIG. 7, the computer system 500 that controls the user interface and other aspects of machine operations is built around an IBM-AT compatible motherboard 502 that includes an Intel 80286 microprocessor 504 and 256K of RAM 506 interconnected by an AT bus 508. Into expansion slots in this motherboard plug seven additional boards: a memory board 510, an RS-232 board 512 (which is dedicated to controlling a patient blood pressure monitor), an Input/Output system controller board 514, an ultrafiltration/proportioning system controller board 516, a blood pump system controller board 518, a touch screen interface board 520, and an EGA display adapter board 522.

The computer system has five primary responsibilities: (1) user interface (i e, through the CRT display and the touch screen); (2) state machine control (i.e., rinse, prime, dialyze, etc.); (3) microcontroller communications; (4) conducting of self-tests; and (5) calibrations. These functions are carried out by the AT-computer in conjunction with the above-listed expansion boards.

Turning now to a more detailed description of each component, the memory board 510 contains the firmware for the 80286 microprocessor. The memory board can hold up to 384K of read only memory (ROM) 524 and 8K of nonvolatile static random access memory (RAM) 526. Also included on the memory board is a memory interface 528, an RS-232C interface 530, and a time of day clock 532. The interface 528 is conventional and simply handles the addressing of memories 524 and 526 The RS-232C interface is for general purpose use (as opposed to the RS-232 interface 512 that is dedicated to use with a blood pressure monitor) and is typically used to remotely provide programming instructions to, and to interrogate patient treatment data from, the machine. The time of day clock 532 is used, inter alia, to time/date stamp patient data as it is acquired and to provide a time of day reference by which automated machine operations (such as unattended warm-up) may be controlled.

The host control program is written in the 'C' programming language. This code is compiled, linked and loaded into the ROM 524. The purpose of the host control program is to:

Gather data from the Input/Output, Blood Pump and Ultrafiltration controller sub-systems, and output control functions to the various controller sub-systems;

Input data from the user interface touch screen;

Monitor the data for violation of alarm limits and usage operating conditions, and to set the appropriate program alarm condition indicators;

Evaluate the data to determine the current operating state of the control program, i.e., Standby, Rinse, Self-Test, Prime, and Dialyze; and Update the display data to the CRT portion of the user interface.

The RAM memory 526 is used to store calibration and machine parameters.

In order for the memory board to operate without conflict with the host AT-motherboard, the motherboard must be modified by disabling the data buffers above address 256K. The memory controller's ROM space is mapped into the address space from 256K to 640K, with the portion between 256K and 312K being mapped also to address range 832K to 888K. The code at this upper address range is configured as a BIOS extension, which results in the ROM being given control by the motherboard's BIOS software following power-on initialization. Unlike the standard BIOS extensions, the host code does not return to the BIOS after being given control.

The RS-232 board 512 permits computerized remote control of a patient blood pressure monitor. Suitable blood pressure monitors that are adapted for RS-232 control are available from Spacelabs of Hillsboro, Oreg.

The touch screen interface board 520 is commercially available as part number E271-400 from Elographics and is designed to operate with the E272-12 touch panel 501 that is used in the preferred embodiment. The function of the interface board 520 is to translate signals returned from the touch screen into a data format suitable for use by the 80286 microprocessor 504. Terminate and stay resident software for driving the interface board 520 is available from Elographics.

The EGA display adapter card 522 is conventional and provides RGB signals to the CRT display 503.

The three microcontroller subsystems (the blood pump system 518, the ultrafiltration/proportioning system 516, and the I/O system 514) are particularly detailed in the following discussion.

Blood Pump System

The blood pump controller 518 is built using an Intel 8040 microcontroller and is responsible for controlling or monitoring five subsystems. They are (1) the blood pump; (2) the blood pressure measurement (arterial, venous and expansion chamber); (3) heparin delivery; (4) level adjust; and (5) ambient temperature. The blood pump controller operates in conjunction with a blood pump power board (not shown) that controllably provides operating power to devices controlled by the blood pump controller.

In still more detail, the primary operation of the blood pump controller 518 is to supply power to the blood pump motor such that the pump head will turn and pump at a rate selected by the operator.

The blood pump controller system consists of the following major components:

| Description | Location |
| --- | --- |
| User parameter entry | Host controller |
| Software Speed Error Control | Blood Pmp Controller |
| Hardware Speed Error Control | BP Power Board |
| Optical speed sensor | On motor shaft |
| Motor Power Driver Circuitry | BP Power Board |

The operator enters the desired blood pump rate information on the video screen (CRT) touch panel. The host controller (80286 microprocessor) converts this information to the appropriate motor rate which it then sends to the Blood Pump controller (8040) on the Blood Pump Controller board. The 8040 controller converts the motor rate information to an analog level, which is fed to a motor speed control IC (LM2917-8) on the Blood Pump Power board.

An optical speed sensor is mounted on the rear shaft of the blood pump motor, with an LED being positioned on one side of the shaft, and a photo transistor on the opposite side. The shaft has two holes drilled through it, with each hole being perpendicular to the shaft and to each other. This results in four optical pulses received per shaft revolution.

This tachometer signal is monitored by both the LM2917-8 and the 8040 controller. The LM2917-8 provides quick responding speed control by comparing the motor speed with the desired speed information from the 8040. The result of this comparison is an error signal which provides an input to the motor power driver circuit.

The motor power driver provides a +24 V pulse width modulated drive to the motor at a frequency of approximately 30 KHz. This drive is current limit protected, to prevent damage in the event of a stalled motor.

The 8040 compares the tachometer motor speed information with the desired speed commanded by the 80286 and corrects the level provided to the LM2917-8 accordingly. In this way the 8040 guarantees the ultimate accuracy of the pump, with the LM2917-8 circuit not requiring any calibration. In addition, the 8040 can monitor for control problems, such as under speed or over speed, which may result from failures in the LM2917-8 or motor drive circuitry.

The 8040 also monitors the motor speed independent of the tachometer signal using the motor's back EMF. Periodically (every 0.5 second) the motor drive is turned off for approximately 6 millisecond and the voltage at the motor terminals is measured. Though this does not result in as precise an indication as the tachometer signal, gross failures can be determined, such as when the tachometer signal is lost.

Blood Pressure Measurement

The blood pressure measurements include the venous, arterial and expansion chamber (for Single Needle treatment) pressures. All three measurement systems include identical hardware. Each pressure is sensed by a SenSym SCX15 gauge sensing pressure transducer mounted to the Blood Pump Power board. Each transducer is connected to a differential amplifier designed to provide a measurement range from −400 to +600 mmHg. The output of each amplifier drives an A/D input channel of the Blood Pump Control system, at which point it is converted to a 10 bit digital value. The calibration of each of the pressure inputs is handled entirely in software, requiring that the design of each amplifier guarantee that its output remain within the A/D input range of 0 to +5 V over the input pressure range and over all component tolerances.

Heparin Delivery

Heparin delivery is accomplished by stepping a stepper motor which rotates the pinion of a rack and pinion mechanism. The pinion moves the rack, and the mechanical fixture is such that the plunger of the heparin syringe moves the same distance. The stepper motor is controlled by the 8040 microcontroller located on the Blood Pump Controller board 518. When the operator enters a desired heparin rate in milliliters per hour (mL/h) via the front panel touch screen, the host 80286 microprocessor converts this information to the appropriate motor step rate and passes it to the Blood Pump microcontroller. The Blood Pump microcontroller outputs a motor step rate logic signal to the Blood Pump Power board where the heparin motor power drive circuitry energizes the appropriate stepper motor coil.

The motor step rate logic signal from the Blood Pump microcontroller 518 is also input to the I/O Controller board 8040 microcontroller 514. The I/O microcontroller monitors this signal to determine if the heparin motor is going the appropriate speed. If it determines that an overspeed condition exists, it disables the heparin motor via a disable line that goes to the Blood Pump Power board.

There are two optical sensors to provide information about the state of the heparin pump. The disengage sensor detects when the front panel syringe holder arm is in the disengage position. The end-of-stroke sensor detects when the pinion is raised up on the rack, which occurs when the gear teeth are not meshed. This is an indication of an overpressure condition. The Blood Pump microcontroller monitors the state of these sensors and passes the information to the host 80286 microprocessor.

Level Adjust

The level adjust system allows the operator to change the blood level in the arterial and venous drip chambers. A level up and level down button exists for each drip chamber. The 8040 microcontroller on the Blood Pump Controller board 518 monitors the button positions. When a button is pressed, a valve selects that drip chamber and power is supplied to the motor such that the pump head of a peristaltic pump rotates to apply a positive or negative pressure to the drip chamber. The software logic only accepts one button press at a time. If two buttons are pressed simultaneously, both are ignored.

The motor drive circuitry is located on the Blood Pump Power Board. The motor may be driven in the forward or reverse direction. A direction signal from the Blood Pump Controller Board, along with a pulse width modulated motor rate signal controls two bipolar half bridge motor drivers. Both half bridge motor drivers receive the same motor rate signal, while the motor direction signal is high at one and low at the other to determine the direction the motor runs. The half bridge drivers provide a 24 V pulse width modulated drive voltage of approximately 30 KHz to the motor.

Other details of the level adjusts are described hereinbelow.

Ambient Temperature Control

The purpose of the cabinet cooling system is to keep the internal temperature of the cabinet lower than the 50° C. maximum temperature at which the electronic components are guaranteed to operate. (Most electronic components are rated to operate at 60° C., the exception is the solid state relay used for heater control.) A fan is located at the base of the cabinet and exhausts the warm cabinet air. An intake vent for the ambient room temperature is located below the CRT on the back of the machine.

The cabinet cooling system consists of the following major components:

| Description | Location |
| --- | --- |
| Cabinet Fan | Base of cabinet |
| Blood Pump Temperature IC | Blood Pump Power Board |
| Misc I/O Temperature IC | Misc I/O Electronics Pwr Bd. |
| Software Fan Control | Host controller |
| Cabinet Fan Drive | Blood Pump Power Board |

The two LM35DZ temperature ICs are located on the Blood Pump and Misc I/O Electronics power boards. This IC outputs a voltage linear with temperature in °C. (10.0 mV/°C.). These temperature readings are input to the fan control software.

The fan control software always responds to the higher of the two temperatures. Typical values are as follows. At 46° C. the fan turns on in the low speed mode and at 48° C. it turns on in the high speed mode. There is a 2° C. of hysteresis at these threshold temperatures, i.e., the fan returns to low speed at 46° C. and turns off at 44° C. In addition, at 60° C. a cabinet temperature alarm occurs that results in the machine shutdown state.

The fan power driver is located on the Blood Pump Power board. A motor rate signal from the Blood Pump Controller board determines the duty cycle of a 30 KHz pulse width modulated signal. This signal is input into a passive filter to provide a DC signal to the motor.

UF/Proportioning Control System

The ultrafiltration/proportioning (UF/PROP) controller 516 is built using an Intel 8040 microcontroller and is responsible for controlling the systems associated with ultrafiltration and dialysate preparation. This controller operates in conjunction with an ultrafiltration/proportioning power card (not shown) that controllably provides operating power to devices controlled by the ultrafiltration/proportioning controller. Six subsystems are controlled or monitored by the UF/Proportioning controller 516. They are:
  a. Temperature Control
  b. Proportioning Control
  c. Flow Control
  d. UF Removal Control
  e. Conductivity Monitoring
  f. Temperature Monitoring

Temperature Control

The UF/PROP system 516 controls the dialysate temperature by enabling a zero voltage crossing solid state relay, which provides the power to a 1500 W heater (item 18 in FIG. 1), with a 5 Hz pulse width modulated digital signal (heater-enable signal). The duty cycle of the heater-enable signal is updated every 0.5 seconds with the sum of the past duty cycle and a temperature error correction value. The correction value is proportional to the difference between the desired temperature (stored by the host) and the measured control temperature (measured immediately down stream of the heater housing).

The host-determined desired temperature is calculated using the user-entered desired temperature and the stable "B" conductivity probe (item 46 in FIG. 1) temperature. If the stable "B" conductivity probe temperature is different from the user-entered desired temperature by more than 0.05° C., then the control temperature threshold sent to the UF/PROP controller is updated so that the "B" conductivity probe temperature will equal the user-entered desired temperature. In this way, the dialysate temperature at the "B" conductivity probe will be adjusted so that flow rate and ambient temperature effects on the "B" conductivity probe temperature (and the primary temperature, displayed on the video screen) will be compensated. This control temperature adjustment is performed a maximum of every 5 minutes.

Proportioning Control

The UF/PROP system 516 controls the concentrate(s) to water proportioning ratios by controlling the dialysate flow rate, the "A" concentrate flow rate, and the "B" concentrate flow rate.

The "A" and "B" concentrate pumps (items 22 and 40, respectively, in FIG. 1) are stepper-motor driven (each by a cam/follower) diaphragm pumps which deliver a calibrated volume of concentrate per stepper motor revolution. Their flow rates are controlled by controlling the speed of the stepper motors. The concentrate pumps are unidirectional and utilize the proper actuation of a three-way valve for their intake and output pumping strokes. The intake stroke is synchronized by a signal that is generated by an optical interrupter sensor which senses a pin mounted on the cam of the pump assembly. Further details pertaining to the "A" and "B" concentrate pumps are described hereinbelow.

The UF/PROP controller 516 utilizes the fact that the stepper motors require 200 motor steps per revolution (between each synchronization pulse) to check the concentrate pumps for stepping errors. If late or early synchronization pulses are received then the associated error conditions are reported on the screen during the Technician Mode of the machine (further details provided hereinbelow).

During the Rinse Mode, the host determines the concentrate treatment mode based on the "A" and "B" rinse port interlock information (further details provided hereinbelow). If the "B" concentrate line (FIG. 1, item 104) is not coupled to the "B" rinse port (FIG. 1, item 30), a bicarbonate treatment is initiated by setting the proportioning ratios and the conductivity alarm limits appropriately. Conversely, if the "B" concentrate line is coupled to the "B" rinse port, an acetate treatment is initiated (further details provided hereinbelow). Using the dialysate flow rate and the proportioning ratios, the host determines the associated concentrate flow rates and stores the two concentrate pump speeds in the UF/PROP controller. The proportioning mode (for acetate or bicarbonate dialysis) cannot be changed in the Prime or Dialyze Modes.

The control of the dialysate flow rate is described in the following Flow Control section of the UF/PROP controller description.

Flow Control

The UF/PROP system 516 controls the dialysate flow rate by controlling the time between the switching of the flow equalizer (FIG. 1, item 54) valves (provided that all the fluid within the flow equalizer chambers has been exchanged).

The average flow equalizer volume is calibrated (measured) during the Calibration Mode. The time between the switching of the flow equalizer valves (FIG. 1, items 142-149) is scaled by the host (according to the calibration constant) and stored in the UF/PROP controller so that the user entered desired dialysate flow rate is achieved.

To guarantee the complete fluid transfer to/from the flow equalizer chambers (FIG. 1, items 126, 128) two flow sensors (FIG. 1, items 58, 59; described in further details hereinbelow) are located within the fluid path to detect the absence of dialysate flow. The time at which both sensors detect no flow has been defined as end of stroke. The end-of-stroke time has been defined as the time between the moment an end of stroke was sensed and the desired flow equalizer valve switch time. Since the supply pump speed controls the instantaneous dialysate flow rate, the UF/PROP controller servos the supply pump speed in order to maintain a consistent end-of-stroke time.

Since the flow equalizer volume is calibrated and the end-of-stroke time is controlled, the UF/PROP system 516 can accurately control the dialysate flow rate to the user-entered value.

UF Removal Control

The UF/PROP system 516 controls the UF removal rate by controlling the time between the switching of the UF flow meter valves (FIG. 1, items 142-149). The UF/PROP system controls the accumulated UF volume by counting the number of UF flow meter strokes.

Since the UF flow meter volume is calibrated (measured) in the Calibration Mode, the rate which the host (80286 microprocessor) passes to the UF/PROP controller (number of seconds between valve switches) is scaled so that the user-entered UF removal rate is achieved.

In the same way, the user-entered UF removal volume is scaled by the UF flow meter's stroke volume to a number of UF meter strokes. The host passes the number of UF meter strokes to the UF/PROP controller. The UF/PROP controller will then switch the UF flow meter valves and decrement the stroke number, at the desired rate, as long as the stroke number is greater than zero. The host can then calculate the UF removal volume accumulated by subtracting the number of UF flow meter strokes remaining, scaled by the stroke volume, from the operator-entered desired UF removal volume. The accumulated volume is displayed during the Dialyze Mode. This value remains during the Rinse Mode and is cleared upon the entry of the Self Test Mode.

In Rinse, the UF removal rate is 3.6 L/h and the video screen indicates no UF volume accumulated. During the Self Test Mode, no UF removal occurs except during specific self tests performed by the machine (no UF volume is accumulated). In the Prime Mode, the UF removal rate is set by the operator and is no greater than 0.5 L/h (no UF volume is accumulated). During the Dialyze Mode, the UF removal rate is set by the operator and is limited to between 0.1 and 4.00 L/h. For UF removal to occur in the Dialyze Mode the following conditions must be met:
1. A target UF volume and a UF rate have been entered (or treatment time and target UF volume have been entered and a machine-calculated UF rate is used).
2. The blood pump is pumping.
3. The target UF volume has not been reached.

Conductivity Monitoring

Conductivity is used as a measurement of the electrolyte composition of the dialysate. Conductivity is usually defined as the ability of a solution to pass electrical current. The conductivity of dialysate will vary due to the temperature and the electrolyte composition of the dialysate.

The UF/PROP system measures conductivity at two locations (conductivity probes) in the hydraulic circuit using alternating-current resistance measurements between each of the conductivity probes' electrode pairs. The two flow path locations are at the "A" conductivity probe (FIG. 1, item 38) and the "B" conductivity probe (FIG. 1, item 46).

One electrode of each of the probes is stimulated with a 1 kHz ac voltage while the other is held at virtual ground (current sense electrode). Two voltages are produced by the resistance measurement circuit. The ratio of the voltages is proportional to the resistance of the respective probe. The resistance of the probes has been modeled as a function of temperature and conductivity. Since each of the conductivity probes contains a thermistor, the temperature at each of the probes is known. Using the model that was derived for the probes, the temperature measured at the probes, and the resistance measured at the probes the conductivity is calculated.

Each conductivity probe is calibrated during the Calibration Mode, at which time the resistance of each probe is measured at a known conductivity and temperature (by the use of an external reference meter) for the scaling of the probe's base resistance in the relationship described previously.

The UF/PROP system 516 generates alarms from the measured conductivities at the "A" and "B" probes. Since these conductivity alarms are used to verify the proportioning ratios, the alarms are generated by testing the "A" conductivity and the "B" portion of the total conductivity ("B" portion="B" conductivity—"A" conductivity). The alarm limits are determined from the concentrate treatment mode and are stored in the UF/PROP controller by the host. Therefore only during a bicarbonate dialysis treatment would the host store a non-zero expected "B" conductivity portion.

The host determines the concentrate treatment mode during the Rinse Mode by reading the "A" and "B" rinse port interlock information. If the "B" concentrate line is not on the "B" rinse port, a bicarbonate treatment is initiated by setting the proportioning ratios and the conductivity alarm limits appropriately. Conversely, if the "B" concentrate line is coupled to the "B" rinse port, an acetate treatment is initiated. Upon exiting the Rinse Mode the concentrate treatment mode is set for the remainder of the dialysis treatment (concentrate treatment mode is only adjusted in the Rinse Mode).

Temperature Monitoring

The UF/PROP system 516 measures the dialysate temperature at three locations in the fluid path. The first location is directly after the heater (FIG. 1, item 18) and this thermistor, the heater thermistor (FIG. 1, item 20), is used for the primary temperature control feedback. The next two thermistors (FIG. 1, items 110 and 124) are contained in the "A" and "B" conductivity probes (FIG. 1, items 38 and 46, respectively). These temperatures are used to temperature-compensate the "A" and "B" conductivity measurements. The "B" conductivity temperature is also used to generate a backup high temperature alarm.

The temperature measurement circuit used throughout the machine consists of a voltage divider with a Thevenin Equivalent circuit of 3062$\Omega$ in series with a 7.55 V supply. The voltage divider circuit when connected to the thermistor used in the temperature measurement system referenced to ground produces the voltage to temperature relationship of $$T(°C.) = (3.77V - Vtemp)(12.73)(°C./V) + 37° C.$$

The tolerance on the component parameters used in the temperature measurement system can be as great as 10%, therefore the temperature-to-voltage relationship must be calibrated. Calibration of the temperature measurements is a two-point calibration done at 30° and 40° C. The calibration procedure results in a calibration constant for both the slope and the offset for each temperature probe/circuit.

In the UF/PROP controller the voltage described above as Vtemp is measured for the three temperature probes in its system on a scheduled basis (every 0.2 seconds for the "A" and "B" temperatures and every 1 second for the heater temperature).

The temperature that is displayed on the video screen is measured at the primary ("dialysate") conductivity probe, located just before the bypass valve (see FIG. 1), by the I/O controller.

Input/Output Control System

Nine subsystems are controlled or monitored by the I/O control system 514. They are:
Air detector
Blood leak detector
Dialysate pressure monitor
Heparin pump overspeed monitor
Bypass system and flow sensor
Conductivity monitor
Temperature monitor
Line clamp
Power fail alarm

Air Detector

The air detector assembly utilizes a set of 2 MHz piezo crystals. One crystal functions as an ultrasonic transmitter and the second crystal functions as a receiver. The transmitter and receiver are housed in separate but identical assemblies. There is a distance of 0.20 inch between these assemblies into which the venous blood line is placed during dialysis. The emitter is driven by a 2 MHz squarewave that is derived from a crystal oscillator located on an I/O Electrical Power board 536 that is connected to the I/O controller 514 by a ribbon cable. When there is fluid in the blood line between the crystal assemblies, the 2 MHz signal is coupled to the detector assembly. The return signal from the detector assembly is amplified and rectified by two independent circuits also located on the I/O Electrical Power board 536. These dc output levels are monitored using two different methods. The first method is the software generated alarm and the second is the hardware generated alarm.

Software Alarm Detection (Primary Alarm)

One output is fed from the I/O Electrical Power board 536 to an A to D converter and read by the 8040 microcontroller on the I/O Controller board 514. This value is averaged over a 400 msec time period and reduced by multiplying it by 15/16 and subtracting 50 mV (for noise immunity). This new value is then converted back to an analog level to be used as an alarm limit. This software generated limit is compared to the rectified dc signal from the detector. The output state of this comparator is monitored by the on-board 8040. When the unaveraged signal falls below the software generated limit for longer than a calibratable time period, an alarm occurs. Sensitivity of the software alarm is 10 microlitres at 300 mL/min blood flow.

Hardware Alarm Detection (Secondary Alarm)

The hardware alarm is redundant to the software generated alarm. This alarm uses two comparators on the I/O Electrical Power board 536. One comparator looks for a minimum dc level from the rectified detector signal which guarantees the presence of fluid in the venous tubing. The second comparator is ac-coupled to react to a large air bubble in the tubing. Sensitivity of this detector is approximately 300 microlitres at 300 mL/min blood flow. Both comparator outputs are wire OR'd together so that either comparator will generate an alarm.

Blood Leak Detector

The detector assembly consists of a high-efficiency green LED and a photocell. These components are installed into a housing through which spent dialysate passes. Both of these components connect to the I/O Hydraulic Power board. The LED is connected to a voltage-to-current converter on an I/O Hydraulic Power board 534 (which is also connected to the I/O controller 514 by a ribbon cable). The input to this circuitry comes from the I/O Controller board 514. The photocell is tied to the +5 V reference supply through a 750 k ohm resistor. This provides a voltage divider which is monitored on the I/O Controller board.

The current through the LED is adjustable and controlled via a D to A output from the I/O Controller board. The light intensity of the LED is adjusted to illuminate the photocell to a point where its resistance is below the alarm threshold. During a blood leak, the presence of blood in the housing attenuates the light striking the photocell which causes an increase in both the photocell resistance and voltage. The increase in voltage (monitored by the microcontroller on the I/O controller board) results in a blood-leak alarm.

Further details on the blood-leak detector are provided hereinbelow.

Dialysate Pressure Monitor

The dialysate pressure is sensed by a resistive bridge pressure transducer (FIG. 1, item 64) located just upstream of the dialyzer. The transducer is connected to a differential amplifier circuit on the I/O Hydraulics Power board 534 designed to provide a measurement from −400 to +500 mmHg. The differential amplifier circuit also has an offset input that comes from a software calibratable variable, DAC_OFFSET. The output of the amplifier drives an A/D input channel of the I/O Controller system, at which point it is converted to a 10 bit digital value. The calibration of the pressure input is handled entirely in the software, requiring that the design of the amplifier guarantee that the output remains within the A/D input range of 0 to +5 V over the input pressure range and over all component tolerances.

Heparin Pump Overspeed Monitor

To ensure that the heparin pump does not exceed its set speed, the I/O controller board software monitors a clock signal from the Blood Pump Controller board that is equivalent to ¼th the heparin pump step rate. In the event that a heparin pump overspeed occurs, the I/O controller board disables the heparin pump via a hardware line that goes to the Blood Pump Power board and notifies the host of the alarm.

To determine if the heparin pump is running at the correct speed, the time required for ten clock signals to occur is measured (and stored in variable HEPTIMER) and compared against a minimum time period that is set by the host (HP_P_MIN). If the measured period is less than the host set limit, a normal-speed alarm occurs. The host is notified of the normal-speed alarm and the heparin pump is disabled via the hardware line to the Blood Pump Power board.

When the heparin pump rate changes, the host resets the minimum time period, HP_P_MIN, and the I/O controller waits for the first clock signal to restart the timer (this first clock is not counted as one of the ten). In this way, the alarm logic is resynchronized with the heparin pump stepper motor.

The I/O controller board 514 also monitors the total amount of heparin delivered in the high-speed bolus mode. When it receives clock signals at a rate faster than a predetermined speed, it assumes the pump is operating in the high-speed mode. It has a high-speed counter, H_SPD_CNTR, that is set by the host. If more high-speed counts occur than are in the counter, a high speed alarm occurs. The host is notified of the high-speed alarm and the heparin pump is disabled via the hardware line to the Blood Pump Power board.

Bypass System and Flow Sensor

The bypass mode is initiated when a primary dialysate alarm is detected by the I/O Controller board, when a redundant dialysate alarm is detected by the UF/PROP Controller board 516, when the host requests bypass, or when the manual bypass button is pushed.

The bypass valve (FIG. 1, item 66) is in the bypass position when deenergized. It is driven from the nominal +24 V supply with a straight on/off transistor control on the I/O Hydraulics Power board.

To verify that there is not a failure in the bypass system, a flow sensor (FIG. 1, item 62) located upstream of the dialyzer and just downstream of the bypass valve checks for flow. If flow exists during bypass, a Bypass Fail Alarm is triggered and the machine is put in the safe, nonfunctional, Shutdown state. If there is no flow when not in the bypass mode, a No Flow alarm is generated. (Further details on the flow sensor are provided hereinbelow.)

This flow sensor consists of two thermistors. The first is a reference thermistor used to determine the fluid temperature. The second thermistor uses thermal dilution to sense the fluid flow. The voltage outputs from the thermistors on the I/O Hydraulics Power board 534 drive A/D input channels on the I/O Controller board where they are converted to 10 bit digital values. A software algorithm in the I/O Controller code uses these inputs to determine the flow condition. The design of the voltage divider guarantees that the output remains within the A/D input range of 0 to +5 V over the input temperature/flow range and over all component tolerances.

Conductivity Monitoring

The dialysate conductivity probe (FIG. 1, item 60) comprises two stainless steel probes inserted into the flow path just prior to the dialyzer. The drive signal for the conductivity probes is a capacitive-coupled square-wave generated on the I/O Hydraulic board 534. This signal is sent to the conductivity probe and a monitor circuit. Both the monitor circuit and the return signal are rectified and filtered. These dc values are routed to I/O Controller board 514 along with the temperature signal.

On the I/O controller board, the temperature, conductivity, and conductivity reference signals are input to an A-to-D converter that is monitored by the on-board 8040 microcontroller. The microcontroller calculates the temperature-compensated conductivity. This value is then displayed on the CRT as the conductivity in milliSiemens per centimeter (mS/cm).

Temperature Monitoring

The thermistor (FIG. 1, item 168) installed in the dialysate conductivity probe (FIG. 1, item 60) changes its resistance in response to changes in temperature. The values for dialysate conductivity and temperature measured at this probe are displayed on the CRT and are used to generate the primary alarms for patient safety. If either value is outside preset alarm limits, a bypass condition and an audio alarm occur.

The thermistor is wired to a resistor divider network on the I/O hydraulic board. The output of this divider network is sent to the Miscellaneous I/O controller board 514 where it is monitored by the on-board 8040 microcontroller via an A-to-D converter network. From this information, the controller calculates the temperature using offset and gain parameters stored in the host from the calibration. Calibration of the temperature measurement is a two-point procedure done at 30° and 40° C.

Line Clamp

The line clamp opens with a solenoid and clamps with a spring return. When the solenoid is not energized, the spring pushes the plunger away from the solenoid. This causes the plunger to clamp the blood tubing. When the solenoid is energized, it pulls the plunger in with enough force to overcome the spring force. This unclamps the blood tubing. In the event of a power failure, the solenoid is de-energized causing the blood line to be clamped.

The solenoid is controlled by the line clamp board. On the line clamp board is a pulse-width modulated current controller. This circuit applies sufficient current to the line clamp solenoid to pull in the plunger. After pull in, the controller ramps the current down to a level capable of holding the line clamp open. This cut-back in current reduces the temperature of the solenoid, resulting in a more reliable device. Also located on the line clamp board, is a quick-release circuit which helps dissipate the power stored in the solenoid. The result of this circuitry is a quicker and more repeatable clamp time over the life of the machine.

Control for the line clamp comes from the Miscellaneous I/O controller board 514 via the I/O power board 536. The control signal for clamp and unclamp is optically coupled on the line clamp board. This provides electrical isolation between the high voltage used to operate the line clamp and the low voltage used for the control signals from the microprocessor.

Power Fail Alarm

The power-fail alarm circuitry is located on the Misc I/O Electrical Power board 536, and includes a CMOS power state flip flop powered by a 1 Farad (F) capacitor. The flip flop, which can be toggled by either the front panel power button or the 80286 system controller, provides the following functions:

Whenever power is not supplied to the machine (i.e., when the +5 V supply is off) and the flip flop is in the on state, power is supplied from the 1 F capacitor to the audio alarm device. Whenever power is supplied to the machine, the flip flop's output state is ready by the 80286, which provides indication of the intended machine power state. Also, when the flip flop is in the on state, power is supplied to the front panel power switch LED.

The first function listed above results in the power fail alarm. The alarm occurs either if the machine loses power while it is running, or if the front panel power button is pressed "on" when there is no power supplied to the machine. The alarm can be silenced by toggling the flip flop off via pressing "off" the front panel power button.

Additional details of the preferred computer system 500 are provided, inter alia, in Appendix C.

Reference is made herein to seven appendices (A–G) which form part of the specification hereof and which further detail certain aspects of the preferred embodiment.

Bypass valve Flow Sensor

Figure 2:
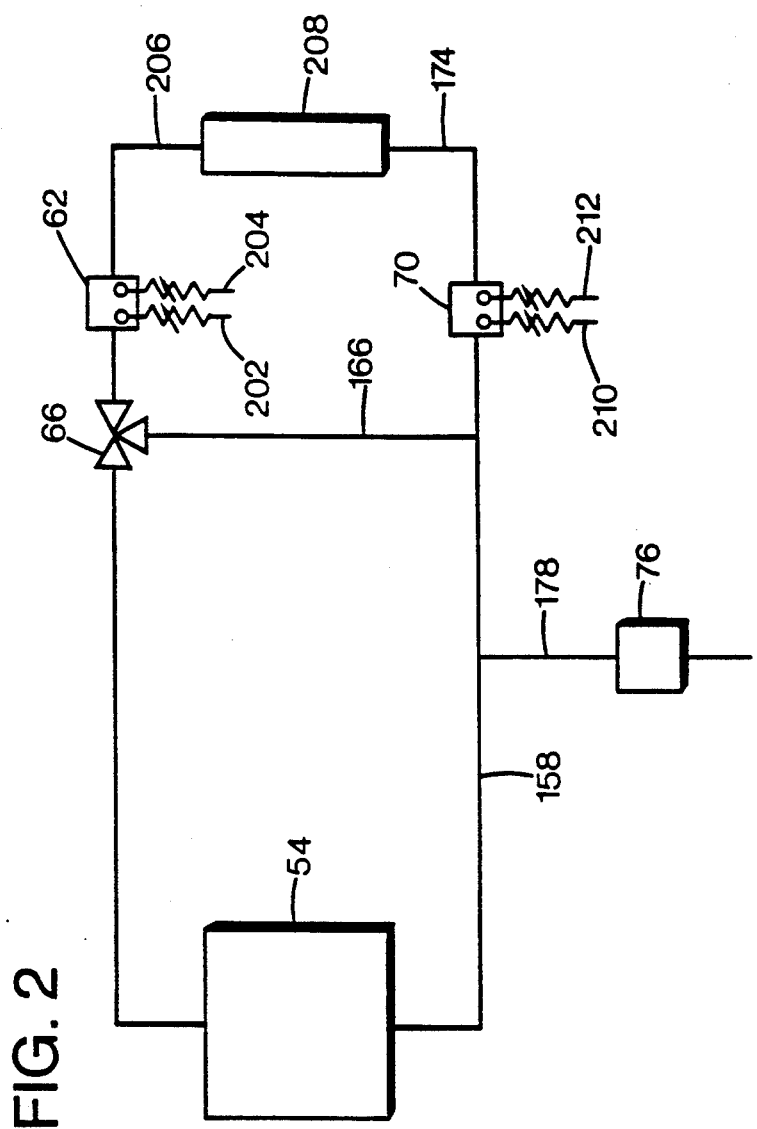
FIG. 2 is a schematic diagram showing flow path locations and components of a pre-dialyzer flow sensor and a post-dialyzer flow sensor according to the present invention.

The dialysis machine of the present invention includes a bypass valve flow sensor which is utilized to confirm that dialysate flow to the dialyzer is completely interrupted during bypass. The bypass valve flow sensor comprises a first thermistor 202 and a second thermistor 204, as shown schematically in FIG. 2. FIG. 2 also shows in simplified schematic form the flow equalizer 54, the bypass valve 166, and a dialyzer 208. The first and second thermistors 202, 204 are of a negative-temperature-coefficient (NTC) type known in the art. The first, or "sensing," thermistor 202 is energized with a 20 mA constant current while the second, or "reference," thermistor 204 is driven with a negligibly small current.

The electrical resistance of both thermistors 202, 204 is measured using electronic circuitry (not shown). The resistance R(T) of each thermistor 202, 204 at a given temperature T is determined by the following relationship:

$$R(T) = (K_1) \cdot \exp(-K_2 \cdot T)$$

where $K_1$ and $K_2$ are constants. Hence, the thermistor resistance is a function of its temperature.

Since the electrical power input to the reference thermistor 204 is negligibly small, the temperature of the reference thermistor 204 will be substantially equal to that of the liquid surrounding it, whether flowing or not, at all times. The sensing thermistor 202, on the other hand, is powered by a substantial constant current. Hence, the sensing thermistor 202 will undergo appreciable self-heating. During conditions of no dialysate flow past the thermistors 202, 204, such as during bypass, the temperature of the reference thermistor 204 will be equal to the temperature of the dialysate surrounding the reference thermistor 204. However, the no-flow temperature of the sensing thermistor 202, as a result of self-heating, will be substantially greater than the temperature of the reference thermistor 204. During conditions when dialysate is flowing past the thermistors 202, 204, the temperature of the reference thermistor 204 will, again, be equal to the temperature of the dialysate. The temperature of the sensing thermistor 202, while greater than that of the reference thermistor 204, will be somewhat lower than the temperature thereof would otherwise be during no-flow conditions. This is because dialysate flowing past the sensing thermistor 202 will conduct a portion of the self-heating energy away from the thermistor 202, thereby lowering the temperature of the thermistor 202. The bypass flow sensor can detect flow as low as about 3 mL/min.

Since the sensing thermistor 202 is driven with a constant-current source, the amount of power input into the thermistor 202 is limited according to the relationship $P=I^2R$. As a result, the ultimate self-heating temperature achievable by the sensing thermistor 202 will self-limit, thereby protecting the sensing thermistor 202 from a damaging thermal runaway condition.

The two thermistors 202, 204 are calibrated by measuring the electrical resistance across them individually under conditions of no dialysate flow at both 30° and 40° C. A mathematical relationship is utilized during calibration which equates the resistance of the sensing thermistor 202 and the resistance of the reference thermistor 204 at any temperature between 30° and 40° C. If Rh(t) represents the sensing thermistor resistance at T=t, and Rr(t) represents the reference thermistor resistance at T=t, then, at no dialysate flow, Rh(t)=A·Rr(t)+B, where A and B are calibration constants determined by the equations shown below (since Rh(30), Rh(40), Rr(30), and Rr(40) are measured during calibration):

$$Rh(30)=A\cdot Rr(30)+S$$

$$Rh(40)=A\cdot Rr(40)+S$$

Hence, if the thermistor resistances are equal, then the electronic circuitry (not shown) coupled to the thermistors 202, 204 recognizes such equal resistance as indicating a "no dialysate flow" condition. However, if the resistances of the first and second thermistors 202, 204 are not equal, which occurs when any dialysate flow (greater than about 3 mL/min) is passing by the first and second thermistors 202, 204, the electronic circuitry recognizes a "dialysate flow" condition. Therefore, whenever the machine is in bypass, if the electronic circuitry senses that the resistances across the first and second thermistors 202, 204 is unequal, indicating flow, the machine will trigger an alarm condition to notify the operator of failure of the bypass valve 66.

The advantage of the bypass valve flow sensor 62 as described hereinabove is that it enables the dialysate bypass valve 66 to be tested functionally, i.e., via a determination of whether or not the bypass valve 66 actually shut off the flow of dialysate to the dialyzer 208. This is the first known use of such a flow sensor in a hemodialysis machine. Other bypass valve sensors known in the relevant art merely test whether or not, for example, the bypass valve has been energized. One example of such a mechanism is a sensor that determines whether or not a solenoid controlling the valve has shifted position in response to application of current thereto. In the present invention, in contrast, the bypass valve flow sensor verifies that the bypass valve 66 has actually seated properly.

Further details and engineering data pertaining to the bypass valve flow sensor can be found in Appendix A, pp. ET 52–ET 57 ("Flow Sensing"), FF 75 ("Bypass Fail Alarm"), Hydraulic Theory 9 ("Flow Sensor" and "Bypass Valve"), EC 13 ("Bypass Fail Detection"), and EA 11 ("Bypass System and Flow Sensor").

No-Ultrafiltration-During-Bypass Sensor

This feature, shown schematically as item 70 in FIGS. 1 and 2, utilizes a first and a second thermistor 210, 212 in a manner similar to the bypass valve flow sensor 62 discussed above. The first and second thermistors 210, 212 are exposed to dialysate flowing through conduit 174 just downstream of the dialyzer 208 but upstream of the bypass line 166.

This feature 70 is utilized during automatic testing of machine functions, as controlled by the machine's microprocessor. During such a test, dialysate flow is bypassed from the dialyzer 208. The flow equalizer 54 volumetrically matches the volume of dialysate that would ordinarily enter the dialysate compartment (not shown) of the dialyzer 208 with the volume of dialysate exiting the dialyzer 208. During bypass, the volume of dialysate passing through the bypass valve 66 and bypass line 166 is equal to the volume passing back through the flow equalizer 54 via line 158. Since the UF line 178 is occluded by the UF flow meter 76, any dialysate flow past the first and second thermistors 210, 212 in either direction must be due to dialysate flow passing through the dialyzer membrane (not shown) into the blood compartment (not shown) thereof or from the blood compartment thereof into the dialysate compartment thereof. If such flow is detected, the machine triggers an operator alarm.

Further details and engineering data pertaining to the no-UF-during-bypass sensor can be found in Appendix A, pp. ET 52–ET 57 ("Flow Sensing"), and Hydraulic Theory 10 ("Flow Sensor").

Automatic Testing of Ultrafiltration Function

This feature is utilized during automatic testing of machine functions that occurs before the machine is used for patient treatment. This automatic test is controlled by the machine's microprocessor along with other self-test routines. One example of when ultrafiltration-function testing is automatically engaged is when the machine is in rinse and producing dialysate without any prevailing dialysate alarms such as temperature and conductivity. A complete self-test routine begins when the operator touches the "test" button on the touch screen before beginning a dialysis treatment. (See Appendix A, pp. Operation 3 (Step 10).)

In order to test the ultrafiltration function, the dialysate lines 174, 206 (FIGS. 1 and 2) must be connected together, enabling dialysate to circulate therethrough without having to use a dialyzer. Because a dialyzer is not used, the flow equalizer 54 discharges a volume of dialysate into line 206 that is substantially equal to the volume of dialysate passing through line 174. Hence, a volumetrically closed loop is formed wherein dialysate exits the flow equalizer 54 through the outlets 156 thereof, passes through lines 206 and 174 coupled together, and reenters the flow equalizer 54 through the inlets 154 thereof. Included in this closed loop is the UF flow meter 76. The UF flow meter 76 permits a discrete volume of fluid to be removed from the closed loop. Also included in the closed loop is the dialysate pressure transducer 64.

To perform the test, the UF flow meter 76 removes about 3 mL of dialysate from the closed loop. This removal of 3 mL is sufficient to lower the dialysate pressure measured at the transducer 64 by about 200 to 300 mmHg. If there are no leaks in the closed loop, this lowered pressure will remain substantially constant. The machine will monitor the depressed dialysate pressure for about 30 seconds during which the pressure must remain within a ±50 mmHg limit of the initial low value. If the pressure rises and passes a limit, the machine will trigger an operator alarm.

Further pertinent details concerning this feature and the UF flow meter can be found in Appendix A, pp. EA 7 ("UF Removal Control"), EC 25–EC 26 ("UF Protective System"), EC 29–EC 30 ("UF Test"), M 6 ("Flow Equalizer"), M 9 ("UF Removal Flowmeter"), M 17–M 19 ("Dialysate Flow Control System Performance"), and Hydraulic Theory 7 ("Flow Equalizer").

Automatic Setting of Proportioning Mode Based Upon Connection of Concentrate Lines As described hereinabove, the concentrate rinse fittings, e.g., the "A" and "B" rinse fittings 28, 30, respectively (FIG. 1), are equipped with proximity sensors which sense whether or not the corresponding concentrate lines 94, 104, respectively, are connected thereto. Such information regarding whether or not a concentrate line is coupled to a corresponding rinse fitting is utilized by the machine's microprocessor to set the correct proportioning mode, e.g., acetate or bicarbonate dialysis.

For example, during the machine's "dialyze" mode, if the machine's microprocessor receives a signal indicating that the "B" concentrate line 104 is coupled to the "B" rinse fitting 30, the machine will operate only the "A" concentrate pump 22. If the "B" concentrate line 104 is not coupled to the "B" rinse fitting 30, the machine will operate both the "A" and "B" concentrate pumps 22, 40, respectively. See Appendix A, pp. EA 5–EA 6 ("Proportioning Control"), and EA 7–EA 8 ("Conductivity Monitoring").

Such connections of the "A" and "B" concentrate lines 94, 104 also dictate the proportioning ratio of "A" concentrate. During acetate dialysis, the volumetric ratio of "A" concentrate to dialysate is 1:35. During bicarbonate dialysis with Drake Willock brand concentrates, for example, the volumetric ratio of "A" concentrate to dialysate is 1:36.83. Hence, the machine automatically adjusts the pumping rate of the "A" concentrate pump 22 in response to whether or not the "B" concentrate line 104 is coupled to the "B" rinse fitting 30.

Figure 3A:
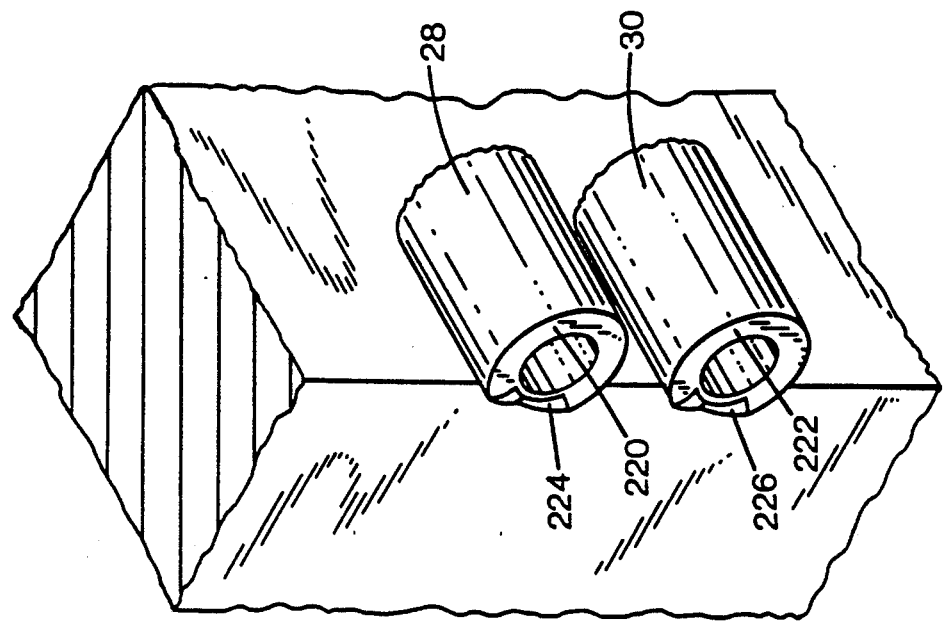
FIGS. 3A and 3B are isometric and schematic diagrams, respectively, of a concentrate-line proximity sensor comprising a portion of the automatic proportioning mode setting feature of the present invention.
Figure 3B:
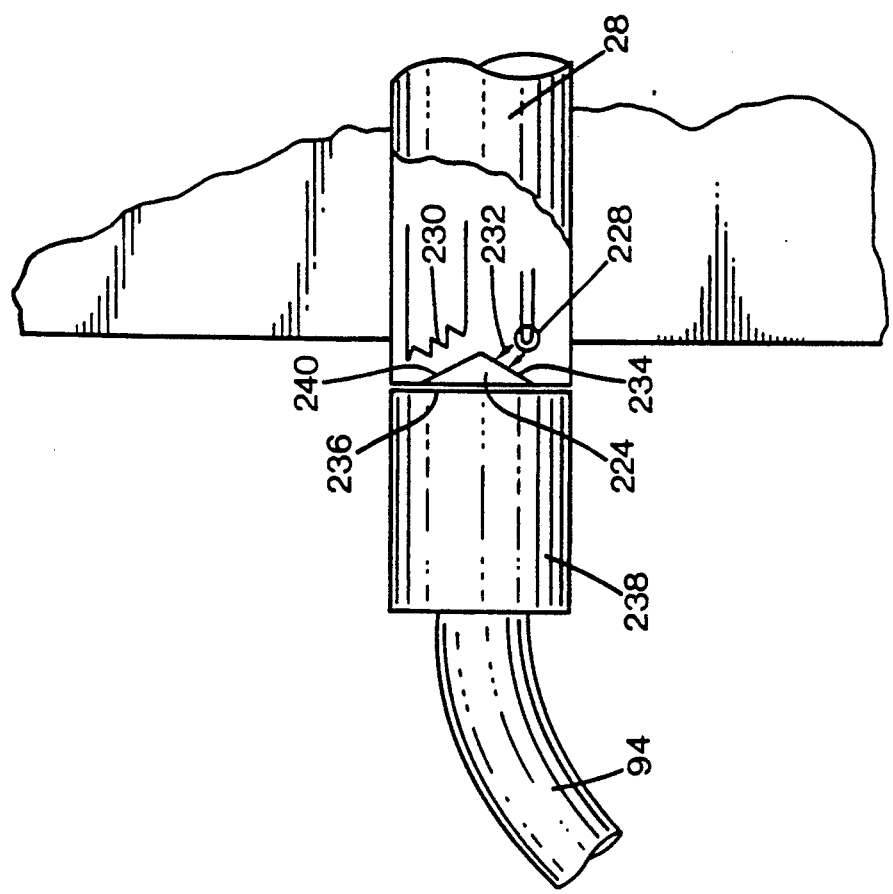

The proximity sensors are shown in FIGS. 3A and 3B. FIG. 3A is an isometric depiction of, for example, the "A" and "B" rinse fittings 28, 30 situated on the right side 218 of the machine. (See Appendix A, pp. Components & Functions 11). On the annular surface 220, 222 of each rinse fitting is an angled depression 224, 226, respectively. As depicted in the right-side elevational view of the "A" rinse fitting 28 shown in FIG. 3B, beneath the angled depression 224 is a light-emitting diode (LED) 228 (shown schematically). A photosensor 230 of a type known in the art is also situated beneath the angled depression 224. The LED 228 is energized with a pulsatile signal in the kilohertz range (so as to not be fooled by 60 Hz illumination). The LED 228 and photosensor 230 are oriented such that light 232 from the LED 228 passes through a first face 234 of the angled depression 224, is reflected off an annular surface 236 of a connector 238 on the end of the "A" concentrate line 94, passes through a second face 240 of the angled depression 224 to be sensed by the photosensor 230.

So long as the photosensor 230 receives reflected light from the LED 228, the machine's microprocessor circuitry (not shown) "interprets" such a condition as indicating that the "A" concentrate line 94 is coupled to the "A" rinse fitting 28. If the light 232 does not reflect so as to impinge the LED 230, the microprocessor circuitry "interprets" such a condition as indicating that the "A" concentrate line 94 is not coupled to the "A" rinse fitting 28 but is coupled to, e.g., a supply of "A" concentrate.

Prediction of Dialysate Conductivity

The software controlling the operation of the machine's microprocessor includes a routine for predicting correct dialysate conductivity. Such predictions automatically reflect the particular brand of concentrate being used, since different groups of concentrate brands require different proportioning to yield a dialysate having a correct ionic strength and electrolytic profile.

Various groups of concentrates are currently marketed. These include: (1) bicarbonate concentrates manufactured by Cobe (utilizable for variable sodium and variable bicarbonate dialysis and intended to be diluted at a ratio of 1 part "A" concentrate to 1.43 parts "B" concentrate to 45 parts dialysate); (2) bicarbonate concentrates manufactured by Drake Willock (utilizable for variable sodium dialysis only and intended to be diluted at a ratio of 1 part "A" concentrate to 1.83 parts "B" concentrate to 36.83 parts dialysate); and (3) acetate concentrates intended to be diluted at a ratio of 1 part acetate concentrate to 35 parts dialysate. The machine is "instructed" or programmed by a technician as to which brand of concentrate is being used. Such programming is done using the touch screen with the machine in the "calibration" mode. See, e.g., Appendix A, pp. Preventive Maintenance 8, Calibration Screen #1, item 17.

The software utilizes a different algorithm for each group of concentrates and for acetate or bicarbonate dialysis using concentrates within any single group, to calculate a baseline "calculated" conductivity value. Each algorithm requires that certain data be entered by the operator using the touch screen. For example, for bicarbonate dialysis, the machine will "ask" the operator to enter baseline (i.e., not adjusted up or down relative to a standard, or non-variable, proportioning ratio) values for sodium and bicarbonate ion concentrations. Assuming proper proportioning of the concentrates, the machine will determine a "calculated" dialysate conductivity. Before beginning a dialysis treatment, when the machine is proportioning concentrate and producing dialysate at the proper temperature, the touch screen will display an "actual" dialysate conductivity value as measured by the dialysate conductivity probe 60 (FIG. 1) and "ask" the operator to verify the correctness of that value against the value stated to be correct by the concentrate manufacturer on the concentrate label. See Appendix A, pp. Operation 3. If the operator responds that the displayed conductivity value is correct, the machine will compare the displayed "actual" value with the "calculated" value. If the "calculated" value is different from the displayed value, the machine will regard the displayed baseline value as correct since the operator "told" the machine that the displayed value is correct. The machine will also calculate the ratio of the displayed baseline value over the calculated baseline value and will multiply any subsequently determined calculated value during the dialysis treatment by the ratio to obtain new "expected" conductivity values. For example, for variable sodium dialysis, the operator will program the variable sodium profile to be delivered to a patient over the course of the upcoming dialysis treatment. Whenever the machine changes the sodium concentration during the course of treatment as programmed by the operator, which accordingly changes the dialysate conductivity, the machine will redetermine a "calculated" conductivity value and apply said ratio to determine a new "expected" conductivity value. These expected conductivity values are used by the machine to calculate and set upper and lower conductivity alarm limits at ±5% of the initial or adjusted "expected" conductivity value.

For Cobe brand bicarbonate concentrates, the calculated baseline dialysate conductivity is determined by the following algorithm:

calculated conductivity in
mS/cm=$[-0.036+3.7\times 10^{-5}([Na^+]-130)][HCO_3^-]+[14.37+0.101([Na^+]-130)]$ where the operator enters the baseline concentrations of sodium and bicarbonate using the touch screen.

For Drake Willock brand bicarbonate concentrates, the calculated baseline conductivity of bicarbonate dialysate is determined by the following algorithm:

calculated conductivity in
mS/cm=$0.1038[Na^+]-0.54$ where the operator enters the baseline concentration of sodium using the touch screen.

For all brands of acetate concentrates, the calculated baseline conductivity of acetate dialysate is determined by the following algorithm:

calculated conductivity in
mS/cm=$0.0895[Na^+]+1.41$ where the operator enters the baseline concentration of sodium using the touch screen.

For bicarbonate dialysis, the machine will also automatically set alarm limits around the conductivity measured at the "A" conductivity probe 38 (FIG. 1) in a similar manner. (During acetate dialysis, the conductivity at the "A" conductivity probe 38 is equal to the conductivity at the dialysate conductivity probe 60, so setting of alarm limits around the conductivity at the "A" conductivity probe is not necessary.) For bicarbonate dialysis, the machine "assumes" that the "A" concentrate is being proportioned properly (at the correct proportioning ratio), based upon the operator having verified that the displayed dialysate conductivity value is correct. The machine determines a baseline "calculated" conductivity at the "A" conductivity probe based on baseline sodium and bicarbonate concentrate information provided by the operator via the touch screen. The machine then calculates a ratio of the actual conductivity as measured at the "A" conductivity probe 38 over the calculated conductivity at the "A" conductivity probe. Then, whenever the machine changes the sodium concentration during the course of a dialysis treatment as programmed by the operator, the machine will determine a new calculated conductivity value and apply said ratio to determine a new "expected" conductivity value at the "A" conductivity probe.

For Cobe brand bicarbonate concentrates, the calculated baseline conductivity at the "A" conductivity probe is determined by the following algorithm:

calculated conductivity in
mS/cm=$[-0.110+9.7\times 10^{-5}([Na^+]-130)][HCO_3^-]+[15.04+0.105([Na^+]-130)]$ where the operator enters the baseline sodium and bicarbonate concentrations using the touch screen.

For Drake Willock brand bicarbonate concentrates, the calculated baseline conductivity at the "A" conductivity probe is determined by the following algorithm:

calculated conductivity in
mS/cm=$0.1114[Na^+]-5.90$ where the operator enters the baseline sodium concentration using the touch screen.

Further information on this feature is in Appendix A, pp. ET 23–ET 28 ("UF/Proportioning System"), and EC 34 ("Conductivity Verify Test").

Controlling Flow Equalizer End-Of-Stroke Time

As discussed hereinabove, the flow equalizer 54 (FIG. 1) operates via a four-phase cycle. In the first and third phases, "pre" compartments 130, 132 and "post" compartments 134, 136 alternately fill and discharge their contents. In the second and fourth phases, the valves 142–149 controlling liquid ingress and egress from the "pre" and "post" chambers are all in the off position for about 125 msec. During these brief second and fourth phases, therefore, no dialysate is flowing to the dialyzer.

Preferably, at the beginning of the second and fourth phases, the diaphragms 138, 140 will have already reached end of stroke. Further preferably, the diaphragms 138, 140 will have reached end of stroke at the same instant.

End of stroke is the moment when, for example, the "post" compartment 134 has reached a completely full condition during a phase after starting from a completely empty condition at the start of the phase. In accordance with the above, it is preferable, for example, that the filling of the "post" compartment 134 reach end of stroke at the same instant as filling of the "pre" compartment 132 during a phase and that filling of the "post" compartment 136 reach end of stroke at the same instant as filling of the "pre" compartment 130 during a different phase. Such simultaneous reaching of end of stroke eliminates ultrafiltration inaccuracies that otherwise could result if the "pre" and "post" compartments (e.g., 130 and 136) being, say, filled during a phase are not filled at exactly the same rate.

Since valves 143, 144, 146, and 149 all turn on at the same instant that valves 142, 145, 147, and 148 turn off, and vice versa, and since each pair of compartments 130, 134 and 132, 136 have exactly the same volume, it is possible to have pairs of compartments (130, 136, and 134, 132) reach end of stroke at the same instant. However, assuming that each chamber 126, 128 has exactly the same flow restriction therethrough, achieving simultaneous end of stroke requires at least that pressures at the inlets 154 be matched and that pressures at the outlets 156 be matched.

To achieve such pressure matching, the inlets 154 are provided with an input pressure equalizer 52 and the outlets 156 are provided with an output pressure equalizer 56, as shown in FIG. 4. The input pressure equalizer 52 is comprised of a flexible diaphragm 246 separating first and second enclosed cavities 248, 250. A stem 252 is attached to the center of the diaphragm 246 and terminates with a flow-restricting element 254. The output pressure equalizer 56 is likewise comprised of a flexible diaphragm 256 separating first and second enclosed cavities 258, 260. Extending from the center of the diaphragm 256 on both sides thereof are stems 262, 264, each terminating with a flow-restricting element 266, 268.

Dialysate from the supply pump 42 flows unimpeded through the second cavity 250 on into a "pre" compartment of the flow equalizer 54. The first cavity 248 passes dialysate from the dialyzer to a "post" compartment of the flow equalizer 54. The first cavity 248 is also part of a loop including the dialysate pressure pump 72. This hydraulic configuration has been found to maintain identical pressures and therefore identical flow rates at the inlets 154 of the flow equalizer 54.

With respect to the output pressure equalizer 56, when the pressure is equal in both cavities 258, 260, the flow rates through each is identical. When the pressure, say, in the first cavity 258 exceeds that in the second cavity 260, the flow-restricting element 268 impedes flow into line 150, thereby increasing the pressure in the second cavity 260. This hydraulic configuration has been found to maintain identical pressures and therefore identical flow rates at the outlets 156 of the flow equalizer 54.

Therefore, since pressures and flow rates are identical as described above, both diaphragms 138, 140 (FIG. 1) come to end of stroke at the same time.

The time required to attain end of stroke can also be controlled. The dialysate flow rate is set by the operator using the touch screen. This flow rate determines the shift frequency of the valves 142-149. The higher the dialysate flow rate, the more frequently the valves 142-149 shift. However, a machine malfunction or occlusion of a hydraulic line could cause an excessive end-of-stroke time for one or both diaphragms 138, 140.

As discussed hereinabove, flow sensors 162, 164 (FIG. 1) are provided at the outlets 156 of the flow equalizer 54 for verifying when the diaphragms 138, 140 have reached end of stroke. When a diaphragm 138 or 140 has reached end of stroke, the corresponding flow sensor 162 or 164, respectively, sends a no-flow signal to the microprocessor. The flow sensors 162, 164 are each comprised of a reference and sensing thermistor (not shown) and work in a manner similar to the bypass valve flow sensor 62 and sensor 70 discussed hereinabove.

If the valves 142-149 receive a signal from the microprocessor to shift before the flow sensors 162, 164 have detected end of stroke, the valves are prevented by the microprocessor from shifting until the end-of-stroke signal(s) are received by the microprocessor. In the event of an excessively long end-of-stroke time, the microprocessor triggers an increase in the pumping rate, of the supply pump 42 to speed up the time to end of stroke.

Controlling the end-of-stroke time not only increases the UF removal accuracy of the machine but also keeps dialysate flowing through the dialyzer as much as possible to maintain the desired osmotic gradient therein, and ensures accurate proportioning and mixing of concentrates with water to form dialysate.

Further details on this feature can be found in Appendix A, pp. EA 6 ("Flow Control"), ET 28-ET 32 ("Dialysate Flow Control"), M 17-M 19 ("Dialysate Flow Control System Performance"), and Hydraulic Theory 6-8 ("Input Pressure Equalizer," "Flow Equalizer," "Output Pressure Equalizer," "End of Stroke Sensors").

Timed Mode Initiate From Power-Off

The microprocessor programming as described herein can be conventionally implemented to accomplish a timed mode initiation from a power-off condition. As is known in the art, machine disinfection, rinsing, and "coming up" on concentrate and temperature to produce dialysate in a condition to begin treatment are burdensome tasks that typically must be performed before the start of a treatment day. In large clinics having multiple dialysis machines, performing these tasks manually can require a substantial expenditure of time and other personnel resources.

The electronics of the machine are continuously powered, even when the machine is "off," unless the mains switch has been turned off or unless the machine's power cord is unplugged. As a result, the programming is readily adapted to include use of the key pad display on the touch screen by the operator to enter the desired time at which certain designated machine functions are automatically initiated. These functions include disinfection (such as heat-cleaning), rinsing, and beginning the production of dialysate at the desired temperature and ionic strength for dialysis treatment.

Preservation of Machine Parameters During Brief Power-Off

The hemodialysis machine of the present invention is provided with a battery back-up which preserves certain operational parameters previously entered by the operator in the event of a temporary power interruption (less than about 20 minutes). Upon restoration of power, the machine is in the stand-by mode.

All of the following parameters are saved in static RAM every 30 seconds or upon any major change in machine state. Upon restoration of power after less than 20 minutes after the last "time stamp" (time at which parameters were saved) by the machine, the following parameters are restored:

Temperature correction
Accumulated UF volume removed

Desired UF removal volume
UF removal rate
UF override flag
Current machine state
Previous machine state
Self-test pass/fail flag
Time stamp
Prescribed dialysis time
Elapsed treatment time
Prescribed or elapsed treatment time display flag
Manual or calculated UF rate display flag
Heparin pump rate
Accumulated blood
Accumulated heparin
Alarm window limits for conductivity, temperature, prescribed treatment time, heparin, etc.
Profile settings for variable sodium and bicarbonate Upon restoration of power, the "dialyze" mode can be restored by the operator touching the appropriate "button" on the touch screen.

Drip-Chamber Level Adjusters

As is known in the art, hemodialysis treatment requires use of an extracorporeal blood-line set. Blood-line sets are available from a number of manufacturers in a variety of different configurations. Virtually all blood-line sets have at least a venous drip chamber. Usually, an arterial drip chamber is also included. The drip chambers serve several functions, including providing a means for removing air and foam from the extracorporeal blood before the blood is returned to the patient, and providing convenient sites at which extracorporeal arterial and venous blood pressure can be measured.

A portion of the extracorporeal blood-line set, including drip chambers, is normally fitted to the front of a hemodialysis machine in an orderly and convenient arrangement using special clips and the like. See Appendix A, pp. Components & Functions 4–5. Each drip chamber typically includes a short tubing segment terminated with a female fitting of a type known in the art as a Luer fitting. The female Luer is adapted for connection to a male Luer fitting on or near the front of the machine (see Appendix A, pp. Components & Functions 2–3), thereby providing the requisite connection of the drip chamber to a pressure-measuring component in the machine.

Drip chambers must be provided with a means for adjusting the blood level therein, particularly to ensure that the blood level does not drop so low in the drip chamber that air becomes re-entrained in the blood. Dialysis machines as currently known in the art require that the operator manually rotate one or more knobs on the machine to rotate a peristaltic pump coupled to the corresponding drip chamber. Such a manual operation has proven to be a cumbersome annoying task, especially since the peristaltic pumps can be difficult to rotate.

The machine of the present invention overcomes this problem by providing, as shown schematically in FIG. 5, an electrically driven reversible positive-displacement pump such as a peristaltic pump 272 which replaces the hand-operated peristaltic pumps found on conventional hemodialysis machines. The peristaltic pump 272 is fitted with flexible tubing 274, one end 276 of which is open to the atmosphere. The opposite end 278 is coupled in parallel to an "arterial" valve 280 and a "venous" valve 282 coupled to an arterial drip chamber 284 and a venous drip chamber 286, respectively. The valves 280, 282 are preferably solenoid valves of a type known in the art. Each drip chamber 284, 286 is coupled via a corresponding Luer fitting 288, 290 to the corresponding valve 280, 282. Included upstream of each Luer fitting 288, 290 is a pressure-measuring device 292, 294, such as a pressure transducer, which communicates with the microprocessor (not shown).

On the front of the machine are arterial and venous "up" buttons 296, 298, respectively, and arterial and venous "down" buttons 300, 302, respectively, which control operation of the corresponding valves 280, 282 and the peristaltic pump 272. See Appendix A, pp. Components & Functions 2–3. For example, pressing the arterial "up" button 296 opens valve 280 and initiates rotation of the peristaltic pump 272 so as to raise the blood level in the arterial drip chamber 284. Pressing the arterial "down" button 300 opens valve 280 and initiates an opposite rotation of the peristaltic pump 272 so as to lower the blood level in the arterial drip chamber 284. The venous "up" and "down" buttons 298, 302 operate in the same way to control the blood level in the venous drip chamber 286.

Further details pertaining to this feature are in Appendix A, pp. EA 4 ("Level Adjust"), ET 11–ET 12 ("Level Adjust"), and M 2–M 3 ("Level Adjusters").

Increasing Dialysate Flow Velocity Through the Dialyzer Without Increasing Dialysate Flow Rate Most hemodialyzers currently in use are hollow-fiber types which generally have a more compact shape than parallel-plate or coil dialyzers used previously. Hollow-fiber dialyzers as known in the art typically comprise a bundle of fine hollow fibers, each fiber made of a semipermeable membrane material, encased in an outer cylindrical shell. The shell defines a space surrounding the fibers termed the "dialysate compartment" through which flows the dialysate prepared by a dialysis machine. The patient's blood is conducted through the lumens of the hollow fibers, propelled by a blood pump on the dialysis machine.

Clearance of metabolic solutes from the blood through the fiber membrane to the dialysate depends on a number of factors, including the osmotic gradient across the semipermeable membranes. The osmotic gradient is dependent on a number of factors including ionic strength and ionic profile of the dialysate, dialysate flow rate through the dialysate compartment, and flow dynamics of the dialysate as it flows through the dialysate compartment.

It is important that the dialysate flow rate be high enough to expose the fibers to a sufficient supply of fresh dialysate to effect satisfactory clearance of toxic solutes from the patient's blood at a satisfactory rate. Any dead spaces or areas of blockage in the dialysate compartment which are not exposed to a continuous supply of fresh dialysate will adversely affect clearance. Such dead spaces can be reduced by merely increasing the dialysate flow rate. However, increasing the dialysate flow rate also increases the rate at which expensive dialysate concentrates are consumed. Therefore, it is advantageous, especially with large dialyzers, to increase dialysate flow velocity through the dialysate compartment without necessitating a corresponding increase in net dialysate flow through the dialysate compartment.

An embodiment of the dialysis machine of the present invention solves this problem by incorporating a dialysate recirculation pump parallel with the dialyzer as shown schematically in FIG. 6.

FIG. 6 depicts a typical hollow-fiber dialyzer 208 having an outer shell 306 defining a dialysate compartment. Extracorporeal blood is pumped by the machine's blood pump (not shown) through an arterial blood line 308 from the patient (not shown), through the hollow fibers (not shown) of the dialyzer 208, then returned through a venous blood line 310 to the patient. FIG. 6 also shows the "arterial" dialysate line 206 and "venous" dialysate line 174 (see also FIG. 1). A dialysate recirculation pump 312, such as an electrically driven gear pump, is coupled to the dialysate lines 206, 174 parallel with the dialyzer 208. The pump 312 can be driven with a variable-speed controller to adjust the pumping rate of the pump 312 relative to the flow rate of the dialysate as delivered by the dialysis machine (not shown).

By recirculating a portion of the "spent" dialysate from the "venous" dialysate line 174 to the "arterial" dialysate line 206 for repassage through the dialysate compartment 306, the flow velocity of the dialysate through the dialysate compartment can be increased without making a corresponding increase in dialysate flow. Hence, it is possible with this feature to improve clearances with a particular dialyzer without increasing the consumption of expensive dialysate concentrates.

Blood-Leak Detector

Virtually all dialysis machines in current use employ a blood-leak detector to monitor dialysate flowing from the dialyzer for the presence of blood that might have leaked from the blood compartment into the dialysate compartment of the dialyzer.

Most dialysis machines currently in use are capable of delivering only a fixed rate of dialysate flow, usually 500 mL/min. The blood-leak detectors on those machines operate with a detection sensitivity that is set at a fixed level and not changed during the course of treating a patient or even a series of patients. At a dialysate flow rate of 500 mL/min, many conventional blood-leak detectors are set to detect blood having a 25% hematocrit flowing at 0.35 mL/min into the dialysate.

The dialysis machine of the present invention is capable of delivering dialysate at flow rates ranging from 500 to 1000 mL/min, adjustable in 100 mL/min increments. At various dialysate flow rates, a fixed leak rate of blood from the patient will be diluted a different amount by the dialysate. Therefore, a blood-leak detector having a fixed sensitivity level enabling it to detect a small blood leak in dialysate flowing at 500 mL/min may not be able to detect the same blood leak in dialysate flowing at 1000 mL/min.

The dialysis machine of the present invention is provided with a blood-leak detector 78 employing a green LED 194 and a photosensor 196 (FIG. 1). (A green LED is used because of the strong absorbance of green light by red blood, yielding a greater contrast in the blood-leak detector between the presence and absence of blood.) The blood-leak detector has a sensitivity that is automatically adjusted in a proportional manner to sense a given leak rate of blood into dialysate having any dialysate flow rate between the 500 to 1000 mL/min adjustability range. Such automatic adjustment of the blood-leak detector sensitivity is performed by the microprocessor in response to the operator selecting a desired dialysate flow rate. The microprocessor adjusts the blood-leak detector sensitivity by altering the illumination level of the LED 194.

Further details on this feature can be found in Appendix A, pp. EA 10 ("Blood Leak Detector") EC 20 ("Blood Leak Detector"), EC 29 ("Blood Leak Detector Test"), and ET 46–ET 52 ("Blood Leak Detector").

Calibration Scheduler and Data Logger And Warning Message Logger

The dialysis machine of the present invention has a technician-activatable "calibration" mode and is programmed to permit entry of calibration data, dates on which certain calibrations or adjustments are performed, and dates on which a particular dialysis center may desire to have certain calibrations or adjustments performed. Appendix A, pp. Preventive Maintenance 8-9. The machine also automatically logs warning messages that can be of substantial help to a technician servicing the machine.

The calibration mode can be activated by turning on an internal calibration switch, as described in Appendix A, pp. Preventive Maintenance 7-8. When the calibrations are completed, the machine is returned to the operational mode by turning off the internal calibration switch, as described in Appendix A, pp. Preventive Maintenance 8, and restarting the machine using the mains power switch. Upon entering the calibration mode, the touch screen displays tables of various calibrations and makes provision for the operator to enter data or dates pertaining to any of the listed calibrations. These tables are illustrated in Appendix A, pp. Preventive Maintenance 8-9. Representative calibration instructions, including how to enter data, are provided in Appendix A, pp. Preventive Maintenance 9-20.

The machine includes a number of component monitors which are used by the microprocessor to note and "record" incidents wherein the respective components experience an operational anomaly of interest to a machine technician. For example, the "A" and "B" proportioning pumps 22, 40 (FIG. 1) are each driven with a stepper motor 90, 114, respectively. The stepper motors 90, 114 utilize 200 "steps" per revolution of the motor shaft. Appendix A, pp. EA 5–EA 6 ("Proportioning Control"). The stepper motors 90, 114 are provided with optical encoders by which the machine's microprocessor not only accurately monitors and controls the rate of concentrate delivery, but also monitors stepper motor operation. If the stepper motor experiences one full rotation per 190 "steps," the microprocessor will "note" and log this anomaly, even if no adverse effect on dialysate conductivity resulted therefrom. A list of warning messages is provided below. In the list, system names above groups of messages are for reference only. Messages having parentheses indicate software functions. While actual failure of such functions would not be expected to occur during machine operation, the messages were useful while debugging the software. Messages having particular value to the technician, especially for troubleshooting mechanical malfunctions, are denoted with an asterisk.

| BLOOD PUMP SYSTEM | |
|---|---|
| "illegal qlen in BP_XMIT" | |
| "Blood Pump Low Speed" | * |
| "BP Control Shutdown" | * |
| "BP Command Error" | * |
| "Blood Pump Overspeed Alarm" | * |
| "Bld Pmp Overspeed Alarm" | * |

| -continued | |
|---|---|
| "Illegal index in bp_xmit()" | |
| "Illegal index in bp_input()" | |
| "long timer error" | |
| UF/PROP SYSTEM | |
| "Too much time between EOS signals" | * |
| "Early EOS detection" | * |
| "UF SHUTDOWN" | * |
| "UF Command Error" | * |
| "UF Time scheduled Event Error" | * |
| "Unidentified Error in MISC_ERRFLG" | * |
| "A Pump Noise" | * |
| "A Pump Missed Steps" | * |
| "B Pump Noise" | * |
| "B Pump Missed Steps" | * |
| "C Pump Noise" | * (for three pump system) |
| "C Pump Missed Steps" | * |
| "A temperature probe error" | * |
| "B temperature probe error" | * |
| IO SYSTEM | |
| "illegal qlen in IO_XMIT" | |
| "IO_XMIT: bad stat chnge % d, % d" | |
| "Illegal io_xmit() index" | |
| "Illegal index in io_input()" | |
| "Illegal index in ioport_xmit()" | |
| IOPORT SYSTEM | |
| "No 8255 . . . port terminated" | * |
| "Set_pwr_state: hw_ver = 1" | |
| "Set_pwr_state: hw_ver = 2" | |
| "Set _power_state: Can't power on" | * |
| "Set_power_state: Can't power off" | * |
| "Converse: illegal return from uccom()" | |
| "Switch failure in reset_port() function" | |
| "Command buffer full in add_cmd()" | |
| "Unrecognizable command in make_cmd()" | |
| "Illegal number of data bytes in make_cmd()" | |
| "Illegal number of data bytes in make_cmd()" | |

UF Profiling

The UF profiling feature according to the present invention provides the operator with a method for programming a UF profile that can vary over time during a dialysis treatment to achieve a target UF removal volume. This feature is similar to variable sodium and variable bicarbonate features discussed hereinabove.

Specifications of the UF profiling feature are set forth in Appendix F.

A detailed description of the user interface pertaining to the UF profiling feature is set forth in Appendix G.

Having described and illustrated the principles of our invention with reference to a preferred embodiment, it will be apparent that the invention can be modified in arrangement and detail without departing from such principles. Accordingly, we claim as our invention all such embodiments as may come within the scope and spirit of the following claims and equivalents thereto.

Drake Willock™ System 1000
Dialysate Delivery System

510(k) Notification

APPENDIX A

APPLICATION OF GROGAN ET AL.

Althin CD Medical, Inc.

Portland, Oregon

CD Medical, Inc.
A Subsidiary of THE DOW CHEMICAL COMPANY

January 16, 1991

Food and Drug Administration
Bureau of Medical Devices & Diagnostic Products
Document Mail Center (HFZ-401)
1390 Piccard Drive
Rockville, MD 20850

Gentlemen:

Attached is a Premarket Notification [510(k)] concerning the marketing of the Drake Willock™ System 1000 dialysate delivery system.

If you have any questions, please feel free to contact Tom Kelley at (800) 547-5534 or (503) 659-3355.

Sincerely,

Gordon W. Robertson
Director of Quality Assurance,
Regulatory and Medical Affairs cc: T. Kelley
    A. Lewis
    M. Meyers ™Trademark Althin CD Medical, Inc.

---

DEPARTMENT OF HEALTH AND HUMAN SERVICES          Public Health Service

Food and Drug Administration
Center for Devices and
Radiological Health
Office of Device Evaluation
Document Mail Center (HFZ-401)
1390 Piccard Drive
Rockville, Maryland 20850

RECEIVED JAN 3 1 1991

JANUARY 18, 1991

CD MEDICAL, INC.
ATTN: GORDON V. ROBERTSON
14600 N.W. 60TH AVENUE
MIAMI LAKES, FL 33014

510(k) Number: K910215
Received:      01-17-91
Product:       DRAKE WILLOCK
               SYSTEM 1000
               DIALYSATE DELIVERY S We have received the Premarket Notification you submitted in accordance with Section 510(k) of the Federal Food, Drug, and Cosmetic Act (Act) for the above referenced product. We have assigned your submission a unique 510(k) number that is cited above. Please refer prominently to this 510(k) number in any future correspondence that relates to this submission. We will notify you when the processing of your premarket notification has been completed or if any additional information is required.

The Safe Medical Devices Act of 1990, signed on November 28, states that you may not place this device into commercial distribution until you receive a letter from FDA allowing you to do so. As in the past, we intend to complete our review as quickly as possible. Generally we do so within 90 days. However, the complexity of a submission or a requirement for additional information may occasionally cause the review to extend beyond 90 days. Thus, if you have not received a written decision or been contacted within 90 days of our receipt date you may want to check with FDA to determine the status of your submission.

This legislation also requires anyone who asserts that a device is substantially equivalent to a class III device to: (1) certify that they have conducted a reasonable search of all information known, or otherwise available, about the generic type of device; and (2) provide a summary description of the types of safety and effectiveness problems associated with the type of device and a citation to the literature, or other sources of information, upon which they have based the description. The description should be sufficiently comprehensive to demonstrate that an applicant is fully aware of the types of problems to which the device is susceptible. If you have not provided this certification and description (with citations) in your premarket notification, please provide it as soon as possible. We cannot complete the review of your submission until you do so.

Please note that the Safe Medical Devices Act of 1990 may have additional requirements affecting your device. You will be informed of these requirements as they become effective.

Please remember that all correspondence concerning your submission MUST be sent to the Document Mail Center (HFZ-401) at the above letterhead address. Correspondence sent to any address other than the Document Mail Center will not be considered as part of your official premarket notification submission. Because of equipment and personnel limitations we cannot accept telefaxed material as part of your official premarket notification submission, unless specifically requested of you by an FDA official.

If you have procedural or policy questions, please contact the Division of Small Manufacturers Assistance at (301) 443-6597 or their toll-free number (800) 638-2041, or contact me at (301) 427-1190.

Sincerely yours,

Robert I. Chissler
Chief, Premarket Notification Section
Office of Device Evaluation
Center for Devices and
 Radiological Health

Drake Willock™ System 1000 Dialysate Delivery System

510(k) Notification

Althin CD Medical, Inc.

Portland, Oregon

Summary

Althin CD Medical, Inc. (formerly CD Medical, Inc.) has developed a single patient delivery system that enhances some of the specifications of the currently commercially available Drake Willock™ 480 High Flow Single Patient Delivery System. The specification enhancements include automatic testing of essential monitors and alarm functions prior to dialysis, increased capability in dialysate and blood flow rates, and additional approved concentrate types and fluid pathway disinfects. These enhancements are consistent with the Fresenius A-2008E and the Cobe Centry 3 also currently commercially available.

Althin CD Medical, Inc. views certain parts of this notification as being confidential and, therefore, should not be divulged to the public. These parts are marked accordingly.

Althin CD Medical, Inc. feels that this enhanced delivery system matches existing patient care in hemodialysis. The company requests through this 510(k) Notification that the Commissioner determines the Drake Willock System 1000 Dialysate Delivery System to be substantially equivalent to other dialysis delivery systems currently commercially available.

™ Trademark of Althin CD Medical, Inc.

1. Product Name:

Classification Name:
    Hemodialysis Delivery System

Common Name:
    Single Patient Dialysate Delivery System

Trade Name:
    Drake Willock System 1000 Dialysate Delivery System

Project Name:
    Prior to the adoption of the trade name the delivery system was named SATRN.

2. Registration Number:

Althin CD Medical, Inc., Portland, Oregon - 3019627
    Althin CD Medical, Inc., Miami Lakes, Florida - 1042431

3. Product Class:

The June 20, 1977 Gastroenterology - Urology Panel Classification Device List indicates that single patient Dialysate Delivery Systems were recommended for Classification in Class II - Performance Standards.

4. Action Taken to Comply with Section 514 - Performance Standards:

At this time, no Performance Standard for single patient Dialysate Delivery Systems has been adopted by the FDA. The product meets the provisions of the General Controls.

5. Labeling:

a. Preliminary component identification labels are shown in Exhibit 1.

b. Preliminary draft of the operator's manual is shown in Exhibit 2.

c. Preliminary draft of the maintenance manual is shown in Exhibit 4.

6. Product Description and Statement of Equivalence:

a. Description of Dialysate Delivery System

The Drake Willock System 1000 Single Patient Dialysate Delivery System is a dialysate proportioning system for hemodialysis. The system fulfills the following functions:
    1) mixes concentrate with water in the appropriate proportions to produce dialysate,
    2) delivers dialysate at the appropriate temperature and ionic concentration to the dialyzer,
    3) removes the appropriate amount of liquid from the patient's blood, and
    4) along with the dialyzer and blood pump acts as a total artificial kidney.

b. Description of Drake Willock System 1000 Dialysate Delivery System:

The following information describes the methods and components utilized by the System 1000 Dialysate Delivery System to accomplish these functions:

1) Dialysate preparation:

The System 1000 Dialysate Delivery System volumetrically controls the proportion of water and concentrate(s) that are mixed to form dialysate.

"A" concentrate pump
  The "A" concentrate pump delivers a fixed volume of acid or acetate concentrate per pump stroke to the supply manifold. The ratio of acid concentrate to water to bicarbonate concentrate or acetate concentrate to water is controlled by the varying the relative number of pump strokes per minute.
Supply manifold
  The supply manifold has four main functions; e.g., control of incoming water flow, mixing of water and "A" concentrate, air removal, and measurement of the "A" concentrate – water conductivity.
"B" concentrate pump
  For bicarbonate dialysis, the "B" concentrate pump delivers a fixed volume of bicarbonate concentrate per pump stroke to the "B" mix point.
"B" mix chamber
  Mixes the dialysate solution before it is monitored by the "B" conductivity probe.
"B" conductivity probe
  Measures the conductivity of the dialysate downstream of the "B" mixpoint.

2) Delivering dialysate to the dialyzer:

The System 1000 Dialysate Delivery System heats dialysate to the appropriate temperature and delivers it to the dialyzer.

Heat exchanger
  Transfers heat from the used dialysate to the incoming water for energy efficiency.
Water heater
  Warms the incoming water to the appropriate temperature for dialysis.
Temperature control thermistor
  Senses the water temperature as part of the heater control circuit.
Air removal sprayer and pump
  Cause dissolved air in the water to form into air bubbles later vented at the air trap.
Air trap
  Traps air bubbles formed in the dialysate and vents them to atmosphere.
Dialysate conductivity and temperature probe
  Senses the conductivity and temperature of the dialysate before it enters the dialyzer.
Temperature window
  Displays the temperature of the dialysate.
Conductivity window
  Displays the conductivity of the dialysate.

3) Removing liquid from the patient's blood (ultrafiltration):

The System 1000 Dialysate Delivery System volumetrically controls the removal of liquid from the patient's blood. By controlling exactly how much dialysate is going to and returning from the dialyzer, accurate fluid removal is achieved.

Flow equalizer
  Balances (matches) the flow of dialysate to and from the dialyzer.
Pressure equalizers
  Balance the pressures in the flow equalizer so that the flow equalizer chambers fill and empty at the same rate.
Dialysate pressure pump
  Controls the pressure in the dialysate compartment of the dialyzer, which affects the rate at which liquid is drawn from the blood compartment.
UF removal regulator
  Regulates the pressure in the UF flow meter circuit causing the positive pressure used to fill the flow meter chambers.
UF flow meter
  Removes a precise volume of spent dialysate from the post dialyzer circuit which inturn causes a like amount of liquid to be removed from the dialyzer blood compartment.

4) Along with the dialyzer and blood pump, acts as a total artificial kidney.

The System 1000 Dialysate Delivery System controls the flow of the extracorporeal blood to the dialyzer then back to the patient.

Blood pump
    Controls the extracorporeal blood flow.
Dialyzer
    Interfaces the blood and dialysate, allowing dialysis and ultrafiltration to take place.

c. Specifications of the System 1000 Delivery System

Physical Characteristics
    Cabinet dimensions:
        Height .................................................................................................................. 60 in
        Width ................................................................................................................... 17 in
        Depth .................................................................................................................. 16 in
    Base dimension:
        Width ................................................................................................................... 17 in
        Depth .................................................................................................................. 27 in
    I.V. pole height ........................................................................................................ 60 to 78 in
    Power cord length .................................................................................................. 10 ft
    Water line and drain line length ............................................................................ 10 ft Performance Characteristics
    Dialysate Circuit:
        Dialysate flow rate:
            Range................................................................................. 500 to 1000 ml/min
                (adjustable in 100 ml/min increments)
            Accuracy ............................................................................±3% of range
        Dialysate temperature:
            Range ................................................................................ 35 to 39°C
            Display:
                Range ....................................................................... 20 to 42°C
                Accuracy ................................................................±0.3°C of range
            Alarm limits (fixed):
                Primary low ..............................................................35 ±0.5°C
                Primary high ............................................................ 40 ±0.5°C
                Redundant high ..................................................... 41 ±0.5°C
        Dialysate conductivity:
            Display:
                Range................................................................................7 to 17 mS/cm
                Accuracy ....................................................................±0.2 mS/cm
            Alarm limits:
                Primary ....................................................±5% of the indicated conductivity
                      when the conductivity was verified during Self Test
                Backup low (fixed)............................................................................. 12 mS/cm
                Backup high (fixed) ........................................................................... 16 mS/cm
                Redundant.................................. ±10% of desired A and B probe conductivites
        Dialysate proportioning:
            Ratio:
                Default value:
                      Acetate ...............................34 parts water to 1 part acetate concentrate
                      Bicarbonate ..........34 parts water to 1 part acid concentrate to 1.8 parts
                                                        bicarbonate concentrate
                Optional values (technician settable):
                    "F" type bicarbonate .............................32.77 parts water to 1 part acid
                                concentrate to 1.23 parts bicarbonate concentrate
                    "C" type bicarbonate..............................42.6 parts water to 1 part acid
                                concentrate to 1.4 parts bicarbonate concentrate
            Accuracy ................................................................................................................±2%

Patient Monitoring:
        Venous pressure display:
            Range...................................................................................−400 to +600 mmHg
            Accuracy ........................................................................±20 mmHg or 10% of reading
                                                       (whichever is greater)
            Alarm limits............................................................................... Automatically set
            Minimum low alarm limit (dialyze mode) ......................................... +10 mmHg Arterial pressure display:
  Range ..................................................................... −400 to +600 mmHg
  Accuracy ..................................................... ±20 mmHg or 10% of reading
    (whichever is greater)
  Alarm limits ........................................................................ Automatically set
Transmembrane pressure display:
  Range ..................................................................... −100 to +600 mmHg
  Accuracy ..................................................... ±20 mmHg or 10% of reading
    (whichever is greater)
  Alarm limits ........................................................................ Automatically set
Blood leak detector sensitivity (fixed) .................................................. 35 mg Hb/L
  (at 500 mL/min dialysate flow rate)
Air detector sensitivity:
  Primary ............................ air bubbles exceeding 10 μl in venous blood line
  Redundant ..................... air bubbles exceeding 300 μl in venous blood line Volumetric Ultrafiltration Control:
  Rate range ................................................................................ 0.1 to 4 L/h
UF accuracy:
  System ........................................................................................ ±50 ml/h
  Display ................................................................................. ±1% full scale Blood pump:
  Flow rate range ............................................................... 100 to 700 ml/min
  Speed accuracy ............................................... ±10% of indicated reading
    (excluding tubing variations)
  Pump segment selection:
    Inside diameter .............................................. 1/4-in, 6-mm, 7-mm or 8-mm
    Wall thickness ............................................ 0.8 to 1.65 mm (0.03 to 0.065 in)
Heparin pump:
  Infusion rate range .............................................................. 0.5 to 5.5 ml/h
  Accuracy ............................................................................................. ±5%
    (excluding syringe variations)
  Syringe:
    Size ................................................................................. 10 or 20 ml (cc)
    Type .......................................... B-D Plastipak, Monojet, Terumo or equivalent
      (Calibrated to specific syringe type.)

Electrical Characteristics:
  The System 1000 Single Patient Delivery System is available in 110, 120, 220, and 240 V 50 or 60 Hz configurations. Each nominal voltage has a tolerance of ±10%. The electrical requirements described below illustrate the most common configuration:
  Voltage, nominal .................................................................................... 120 V
  Frequency ............................................................................................. 60 Hz
  Current required .................................................................................... 15 A
  Current leakage (maximum):
    Dialysate to ground ........................................................................ 100 μA
    Chassis to ground .......................................................................... 100 μA Environmental Characteristics
  Water requirements:
    The incoming water must be of adequate quality or treated to comply with the attending physician's directives. The water supply between the water treatment unit and the dialysis machine must be made of materials that do not contaminate the treated water supply and that allow for chemical disinfection of the plumbing. It is recommended that water meet the AAMI standard for water used in hemodialysis and have zero detectable iron.
    Pressure (at the flow rate of 1000 ml/min):
      Minimum .............................................................................. 10 psig (0.7 bar)
      Maximum ............................................................................. 100 psig (7 bar)
    Temperature:
      Minimum ....................................................................................... 6°C
      Maximum ...................................................................................... 32°C
    Flow rate (minimum):
      Standard flows (500 to 600 ml/min) ............................................ 600 ml/min
      Rapid dialysis (>600 ml/min) ..................................................... 1000 ml/min
  Drain requirements:
    Vented; Adequate air gap
    Flow capacity, minimum ..................................................................... 1.5 L/min
    Drain height, maximum above floor .................................................. 56 cm (22 in)
  Power dissipation to environment:
    Approximately ......................................................................................... 250 W Operating environment:
Temperature ......................................................................18 to 40°C (64 to 104°F)
Humidity, relative (non-condensing) ..........................................................10 to 95%

All listed specifications are nominal.

d. Copy of the laboratory report is shown in Exhibit 3.

e. Product equivalence

The Drake Willock System 1000 Dialysate Delivery System is substantially equivalent to the following other products which are currently in commercial distribution:

1)  Drake Willock 480 High Flow Dialysate Delivery System - Althin CD Medical, Inc., Portland, Oregon.

2)  Fresenius A-2008 D - distributed by Fresenius USA, Concord, California

3)  Cobe Centry 3 - Cobe Laboratories, Inc., Lakewood, Colorado.

Features comparison matrices of the different systems is shown is Tables 1 and 2. From this comparison, equivalent system functionality is clearly demonstrated.

Table 1

| | Drake Willock System 1000 | Drake Willock 480 High Flow | Fresenius 2008E | Cobe Centry 3 | Braun Secura |
|---|---|---|---|---|---|
| UF Control | 0.1 to 4 L/h | 0.0 to 2.4 L/h | 0.0 to 2 L/h | 0.0 to 2.4 L/h | 0.05 to 2.0 L/h |
| Volumetric | Yes | Yes | Yes | Yes | Volumetric Measurment/ TMP Control |
| Programmable | Yes | No | Yes | Yes | Yes |
| UF Removed Display | Yes | Bag Level | Yes | Yes | Yes |
| Proportioning | Volumetric | Volumetric | Volumetric | Servo | Servo |
| Sodium Range | 130 to 160 mEq/L | 130 to 150 mEq/L | 130 to 155 mEq/L | 130 to 160 mEq/L | ? |
| Bicarbonate | 28 to 42 mEq/L | Fixed | ±8 mEq/L | 25 to 40 mEq/L | Bicarb is an option |
| Programmable Na | Yes | No | Yes | Yes | Yes |
| Programmable Bic | Yes | No | Yes | Yes | No |
| Dialysate Flow Rate | 500 to 1000 mL/min | 500/750 mL/min | 500 to 800 mL/min | 250 to 600 mL/min | 500 mL/min (300 to 600 mL/min internal adjustment) |
| Blood Flow Rate | 100 to 700 mL/min | To 650 mL/min | To 600 mL/min With 8 mm segment | 50 to 500 mL/min | 0 to 400 mL/min |
| Heparin Pump | 0.5 to 5.5 mL/h | 0.5 to 5.5 mL/h | 0.6 to 10 mL/h | 0.5 to 5.5 mL/h | 0.5 to 5.5 mL/h |
| Syringe size | 10 to 20 mL | 20 to 30 mL | 10 to 20 mL or 30 to 50 mL | 10 to 20 mL | Peristaltic Pump |
| Level Adjust | Powered Art., Ven. | Yes | Powered (Venous only) | None | None |
| KUF Limit | No | No | No | No | 40 mL/h/mmHg |
| Disinfection | Heat/Chemical | Chemical | Heat/Chemical | Chemical | Heat/Chemical |
| Pressure Reading | | | | | |
| Arterial | +600 to −400 mmHg | +400 to −300 mmHg | +300 to −300 mmHg | +400 to −200 mmHg | +400 to −250 mmHg |
| Venous | +600 to −400 mmHg | +400 to −300 mmHg | +500 to −100 mmHg | +400 to −200 mmHg | +350 to 20 mmHg |
| TMP | Yes | No | Yes | Yes | Yes |

Table 1
continued

|  | Drake Willock System 1000 | Drake Willock 480 High Flow | Fresenius 2008E | Cobe Centry 3 | Braun Secura |
|---|---|---|---|---|---|
| Display | 12" CRT High Resolution | Analog Meters | LEDs, Bargraphs | 9" CRT Low Resolution | 9" CRT Low Resolution |
| Color CRT | Possible option | N/A | N/A | ? | ? |
| Control System | Touch Screen | Knobs and Switches | Membrane Switches | Membrane Switches | Membrane Switches |
| RS232 | Yes | No | Yes | Yes | Optional |
| Memory Card | Yes | No | No | No | No |
| Auto Alarm Test Mode | Yes | No | No | Yes | Yes |
| Blood Lines Easy Installation | Yes | No | No | Yes | No |
| Cabinet Cleanable | Easy to clean | Crack and Crevices | Crack and Crevices | Easy to Clean | Crack and Crevices |
| Easy to access | Yes | No | Hydraulics are difficult to access | No | Must unstack some components |
| Single Needle Option | Double Pump | 8810 Double Pump | Double Pump | Single Pump | Double Pump |
| Dialysate Filtering Option | Yes | No | Yes | No | No |
| Blood Pressure Monitoring Option | Yes | No | Yes | Yes | ? |
| Built-In Dialyzer Clamp | Yes | No | No | Yes | No |
| Calibration Mechanical | Simple | Complex | Complex | Complex | Complex |

Table 2

System 1000 Dialysis Delivery System

Product Description:

A hemodialysis delivery system, which will provide dialysate at the prescribed temperature and ionic concentration to be used for hemodialysis treatment. It has the ability to monitor machine, dialysate and blood circuit functions during dialysis. The machine uses volumetric proportioning, volumetric ultrafiltration and digital electronics. The machine and treatment parameters are displayed on a CRT (video monitor). The operator control is done through an interactive touch screen which makes the machine very easy to clean and use.

The machine has an automated self test prior to the start of each dialysis, this ensures that all of the essential monitoring and alarm functions of the machine are tested before each patient treatment. The automatic self test eliminates the risk that a busy clinician will forget to perform the required machine checks prior to each treatment.

To enhance treatment quality assurance, the machine records essential treatment data such as actual treatment time. This actual treatment time clock stops when alarms interrupt dialysis by stopping the blood pump or bypassing the dialysate around the dialyzer. One of the major problems with the dialysis treatments given today is the non-delivery of the prescription (e.g.; the patient is taken off treatment 5 minutes early, repeated alarms stop the blood pump or divert the dialysate to drain stopping the treatment). The data report allows the operator of the machine to know the precise time spent on dialysis enabling the clinician to determine if the dialysis prescription was delivered.

Performance Characteristics

Dialysate Circuit:

- Dialysate flow rate .................................. 500 to 1000 mL/min
  (adjustable in 100 mL/min increments)
- Accuracy .................................................. ± 3% of range Dialysate temperature:

- Range .................................................. 35 to 39°C
  (adjustable in 0.1°C increments, more precise adjustment)
- Display range .......................................... 20 to 42°C
- Display accuracy ..................................... ±0.3°C Temperature Alarm Limits (fixed)

- Primary high .......................................... 40 ±0.5°C
- Primary low ........................................... 35 ±0.5°C
- Redundant high ..................................... 41 ±0.5°C Note: The risk of a technician miscalibrating the alarm limits is eliminated since the temperature alarm limits are fixed at a physiologically safe range. The redundant temperature alarm uses a separate temperature probe and alarm circuitry for added safety.

Temperature Alarm Response
- Dialysate bypasses dialyzer
- Audio alarm sounds
- Main alarm lamp flashes
- Window around temperature display flashes
- Elasped time of dialysis timer stops (provides a more accurate indication of the treatment delivered to the patient).
- Machine status window displays ALARM
- The alarm automatically is cleared when the temperature is at least 0.1°C into the permissible temperature window.

Proportioning Ratio:
Default value:
- Acetate .......................... 34 parts water to 1 part acetate concentrate
- Bicarbonate . 34 parts water to 1 part acid concentrate to 1.8 parts bicarbonate concentrate Optional values (technician settable):
- "F" type bicarbonate ............... 32.77 parts water to 1 part acid concentrate to 1.23 parts bicarbonate concentrate
- "C" type bicarbonate ......... 42.6 parts water to 1 part acid concentrate to 1.4 parts bicarbonate concentrate
- Accuracy .................................................. ±2%

480 High Flow Dialysis Delivery System

Product Description:

The 480 High Flow provides dialysate at the prescribed temperature and ionic concentration to be used for hemodialysis treatment. It has the ability to monitor machine, dialysate and blood circuit functions during dialysis. The machine is based on volumetric proportioning, volumetric ultrafiltration and analog electronics. The machine and treatment parameters are displayed on a analog gauges and meters. The operator control is done through switches and knobs located on the front of the machine.

Performance Characteristics

Dialysate Circuit:

- Dialysate flow rate ................................ 500 or 750 ±50 mL/min
  (selectable)

Dialysate temperature:

- Range .................................................. ±1.5°C from midpoint
  (adjustable on the front panel)
- Meter range .......................................... 34 to 42°C
- Meter accuracy ..................................... ±0.5°C Alarm limit adjustability range (by technician):
- Primary high ......................................... 37.5 to 41.5°C
- Primary low .......................................... 34.5 to 38.5°C
- Backup high .......................................... 41°C Temperature Alarm Response
- Dialysate bypasses dialyzer
- Audio alarm sounds
- Main alarm lamp flashes
- Temperature alarm lamp flashes
- The alarm automatically is cleared when the temperature is at least 0.1°C into the permissible temperature window.

Proportioning Ratio

- Acetate ................. 34 parts water to 1 part acetate concentrate
- Bicarbonate ......... 34 parts of water to 1 part acid concentrate to 1.8 parts bicarbonate concentrate
- Proportioning accuracy ............................................. +2 to -4%

Note: The bicarbonate concentrate used must contain 59 mEq/L of sodium.

Conductivity:
 Monitor range .................................................7 to 17 mS/cm
  Accuracy......................................................±0.2 mS/cm
 Alarm limits
  Primary ................................................................±5%
  Note: The alarm limits set automatically before dialysis begins eliminating the risk that the operator could inadvertently fail to set the alarm limits.
  Backup high (fixed)............................................16 mS/cm
  Backup low (fixed) .............................................12 mS/cm
  Redundant.........±10 % of the desired "A" and "B" probe conductivities
  Note: Redundant conductivity alarm uses a separate conductivity probe and alarm circuitry.
 Conductivity Alarm Response
 • Dialysate bypassed
 • Audio alarm sounds
 • Main alarm lamp flashes
 • Window around conductivity display flashes
 • Elasped time of dialysis timer stops (provides a more accurate indication of the treatment delivered to the patient).
 • Machine status window displays ALARM
 • The alarm automatically is cleared when the conductivity is at least 0.1 mS/cm into the permissible conductivity window.

Programmable Sodium
 Sodium Variability........................................ 130 to 160 mEq/L Programmable Bicarbonate
 Bicarbonate Variablity .................................... 28 to 42 mEq/L No Water Supply Alarm......................Creates an alarm when the water supply is off for 30 seconds Alarm Response
 • Audio alarm
 • Visual alarm Bypass Fail Alarm ..........Alarms if the bypass valve fails to divert the flow of dialysate away from the dialyzer during a conductivity or temperature alarm Alarm Response
 • Shuts down flow equalizer stopping flow to the dialyzer
 • Audio alarm
 • Visual alarm
 • Flashing error message Volumetric Ultrafiltration Control
 Ultrafiltration rate range .........................................0.1 to 4 L/h
 • Automatically calculated by setting Prescribed Time of Dialysis and Target Fluid Loss or Manually set with UF rate adjust
 • Ultrafiltrate Removed display shows total fluid removed during the treatment
 • UF System checked dynamically during the Self Test state, will not allow operator to dialyze patient if the system is inaccurate. This eliminates the risk that the operator will fail to check the UF system before the machine is used.

UF accuracy
 System .................................................................. ±40 mL/h
 UF removed monitor...........................................±1% full scale
 This variable is programmable.

Prescribed Time of dialysis display
 Operator sets the Prescribed Time of dialysis. When machine enters Dialyze Mode display changes to Elasped Time of dialysis which records the actual treatment time.

Elasped Time of dialysis does not count time when the blood pump is off or when the dialysate bypasses the dialyzer ensuring that the prescribed dialysis time is reached and improving treatment quality assurance.

Patient Monitoring:
 Venous pressure gauge range ....................−400 to +600 mmHg
  Accuracy ...................±20 mmHg or 10% of reading (whichever is greater)
 Arterial pressure gauge range ......................−400 to +600 mmHg
  Accuracy ...................±20 mmHg or 10% of reading (whichever is greater)

Conductivity:
 Meter range ..................................... 12 to 16 mS/cm
  Accuracy......................................................±0.2 mS/cm
 Alarm limits adjustability range:
  Primary low ......................................... 12 to 13.6 mS/cm
  Primary high .......................................... 13 to 16 mS/cm
  Note: The primary limits must be set an operator prior to dialyzing patient.
  Backup high .....................................................15.7 mS/cm
  Backup low ......................................................12.4 mS/cm Conductivity Alarm Response
 • Dialysate bypassed
 • Audio alarm sounds
 • Main alarm lamp flashes
 • Conductivity alarm lamp flashes
 • The alarm automatically is cleared when the conductivity is at least 0.1 mS/cm into the permissible conductivity window.

No Water Supply Alarm......................Creates an alarm when the water supply is off Alarm Response
 • Audio alarm
 • Visual alarm Volumetric Ultrafiltration Control:
 Ultrafiltration rate range...................... 0.1 to 2.5 L/h
 • Manually set with UF flow control knob
 • Ultrafiltrate Collection Bag will collect a volumetric equivalent to the patients ultrafiltrate.
 • Manual check of the UF balancing system is required before dialysis. The risk of the manual check is that occasionally operator's forget to perform the check.

UF accuracy
 System .................................................................. ±60 mL/h
 UFR flowmeter ................................................... ±2% full scale
 UF Collection Bag ............................................. ±2% full scale Patient Monitoring:
 Venous pressure gauge range.......................−300 to +400 mmHg
  Accuracy ...................±20 mmHg or 10% of reading (whichever is greater)
 Arterial pressure gauge range ......................−300 to +400 mmHg
  Accuracy ...................±20 mmHg or 10% of reading (whichever is greater)

- Pressure monitor accuracy and alarms are automatically tested in the self test mode.
- The arterial and venous alarm limits automatically set 10 seconds after the blood pump has started preventing the risk that a machine operator would forget to set the alarms.
- Minimum venous alarm limit (Dialyze mode) +10 mmHg Transmembrane pressure range:

TMP Monitor .............................................. 600 to −100 mmHg

Accuracy .............. ±20 mmHg or 10% of monitor reading
(whichever is greater)

Note: One minute after the treatment begins the alarm limits form a window ±35 mmHg from the desired TMP. The machine will not allow a limit to set which is greater than +500 mmHg or less than −80mmHg, so the machine will alarm to alert the operator if pressures are present in the hydraulics which could damage the dialyzer membrane.

Blood leak detector sensitivity (fixed):
(at 500 mL/min dialysate flow rate)

Nominal sensitivity ........................................ 35 mg Hb/L

- Automatically tested in the Self Test mode

Air detector sensitivity ...................... air bubbles exceeding 10 μL
in the venous blood line Redundant air detector sensitivity ........................ air bubbles exceeding 300 μL in the venous blood line

- Disarm limited to 5 minutes in the Prime mode. Air detector *cannot* be disarmed in the Dialyze mode, ensuring that the extracorporeal blood line will always be monitored for air bubbles whenever a patient is on the machine.
- Air detector function is verified in the Self Test mode.

Blood pump:

Flow rate range ........................................ 100 to 700 mL/min

Speed accuracy............ ±10% of indicated reading, excluding tubing variations Pump segment selection:

Inside diameter .................. 1/4-in, 6-mm, 7-mm or 8-mm

Wall thickness............................ 0.8 to 1.65 mm (0.03 to 0.065 in)

- Pump stops when the cover is open.
- Blood pump shuts down in overspeed condition
- Blood pump underspeed alarm
- Blood pump stop alarm
- Built in handle to return blood in case of power failure.
- Elasped Time of Dialysis does not count time when the blood pump is off Heparin pump:

Infusion rate range (B-D Plastipak, Monoject, Terumo syringe or equivalent, calibrated to specific syringe type)

10 mL (cc) syringe ...................... 0.5 to 5.5 mL/h 20 mL (cc) syringe ...................... 0.5 to 5.5 mL/h Accuracy (not including syringe variations)

Pump........................................................................ ±5%
- End of stroke alarm
- Overspeed alarm
- Overpressure alarm Heparin Pump Alarm Response
- Audio alarm
- Visual alarm
- Heparin pump shuts off
- Operator alerted to specific heparin pump alarm condition Drip chamber level adjustment
- Powered level adjust
- For arterial and venous drip chambers Dialyzer connector interlock
- The machine knows if the dialysate lines are not on the dialyzer.
- Prevents the machine from going into rinse if the dialysate connectors are not connected to the rinse block.

- Arterial and venous alarm limits are manually set by the operator.

Dialysate pressure range .............................. −400 to +400 mmHg

Dialysate pressure meter range .................... −440 to +400 mmHg

Accuracy .................. ±20 mmHg or 10% of meter reading
(whichever is greater)

Note: Dialysate pressure alarm limits manually set by operator.

Blood leak detector sensitivity (adjustable):
(at 500 mL/min dialysate flow rate)

Minimum sensitivity ........................................ 70 mg Hb/L
Nominal sensitivity .......................................... 35 mg Hb/L Air detector sensitivity ...................... air bubbles exceeding 10 μL
in the venous blood line

- Air detector can be disarmed in any mode.

Blood pump:

Flow rate range ........................................ 100 to 650 mL/min

Speed accuracy............ ±10% of indicated reading, excluding tubing variations Pump segment selection:

Inside diameter .................. 1/4-in, 6-mm, 7-mm or 8-mm

Wall thickness............................ 0.8 to 1.65 mm (0.03 to 0.065 in)

- Pump stops when the cover is open.
- Blood pump shuts down in overspeed condition
- Blood pump stop alarm
- Built in handle to return blood in case of power failure.

Heparin pump:

Infusion rate range (B-D Plastipak™ syringe or equivalent)

30 mL (cc) syringe ...................... 0.5 to 5.5 mL/h 20 mL (cc) syringe ...................... 0.4 to 4.4 mL/h Accuracy (B-D Plastipak syringe or equivalent)

Pump........................................................................ ±5%
- End of stroke alarm
- Overspeed alarm
- Overpressure alarm Heparin Pump Alarm Response
- Audio alarm
- Visual alarm
- Heparin pump shuts off Drip chamber level adjustment
- Manual level adjust
- For arterial and venous drip chambers Approved Disinfectants
- Household bleach (5.25% Sodium Hypochlorite)
- 37% Formaldehyde
- Actril
- Nephrex
- Heat Hour meter Dialysis Treatment Data Report Provides precise treatment data on the following variables enhancing treatment Quality Control.
- Prescribed time of dialysis
- Remaining time of dialysis
- Elasped time of dialysis (only records dialysis time with dialysate flow to the dialyzer and the blood pump on).
- Target UF
- UF removed
- Total blood processed
- Total heparin infused
- Current date and time
- If the operator set a manual or calculated UF rate Self Test Mode - The self test mode tests the critical safety and operating systems of the System 1000 machine prior to dialysis. If the machine does not pass a successful self test the machine will not be able to dialyze a patient. The following systems are checked during a self test:
- Conductivity alarms
- Temperature alarms
- Air detector
- Blood leak detector
- UF system integrity
- Arterial and venous pressure monitoring and alarm system
- Audible alarm
- Main alarm lamp

Physical Characteristics

Cabinet dimensions:

| | |
|---|---|
| Height | 60 in |
| Width | 17 in |
| Depth | 16 in |

Base dimension:

| | |
|---|---|
| Width | 17 in |
| Depth | 27 in |
| IV pole height | 60 to 78 in |
| Power cord length | 10 ft |
| Water line and drain line length | 10 ft |

Required Environmental Conditions

Water requirements:

The incoming water must be treated to comply with the attending physician's directives. The water supply system between the water treatment unit and the delivery system must be made of materials that do not contaminate the treated water supply and that will allow for chemical disinfection of the plumbing system. It is recommended that treated water meet the AAMI Standard for water used in hemodialysis and have zero detectable iron.

Water pressure (at the flow rate of 1000 mL/min)

| | |
|---|---|
| Minimum | 10 psig (0.7 bar) |
| Maximum | 100 psig (7 bar) |

Incoming water temperature

| | |
|---|---|
| Minimum | 6°C |
| Maximum | 32°C |

Incoming water flow rate minimum

| | |
|---|---|
| Standard flows (500 to 600 mL/min) | 600 mL/min |
| Rapid dialysis (>600 mL/min) | 1000 mL/min |

Drain requirements:

Vented; Adequate air gap

| | |
|---|---|
| Flow capacity, minimum | 1.5 L/min |
| Drain height, maximum above floor | 56 cm (22 in) |

Power dissipation to environment:

| | |
|---|---|
| Approximately | 250 W |

Approved Disinfectants
- Household bleach (5.25% Sodium Hypochlorite)
- 37% Formaldehyde

Physical Characteristics

Cabinet dimensions:

| | |
|---|---|
| Height | 47 in |
| Width | 21 in* |
| Depth | 13 in |

* IV pole adds 3 1/2 inches to width

Base dimension:

| | |
|---|---|
| Width | 19 in |
| Depth | 27 in |
| IV pole height | 48 to 71 in |
| Power cord length | 10 ft |
| Water line and drain line length | 10 ft |

Required Environmental Conditions

Water requirements:

The incoming water must be treated to comply with the attending physician's directives. The water supply system between the water treatment unit and the delivery system must be made of materials that do not contaminate the treated water supply and that will allow for chemical disinfection of the plumbing system. It is recommended that treated water meet the AAMI Standard for water used in hemodialysis and have zero detectable iron.

Water pressure (at the flow rate of 750 mL/min)

| | |
|---|---|
| Minimum | 20 psig (1.4 bar) |
| Maximum | 100 psig (7 bar) |

Incoming water temperature

| | |
|---|---|
| Minimum | 4°C |
| Maximum | 32°C |

Incoming water flow rate minimum ......... 750 mL/min

Drain requirements:

Vented; Adequate air gap

| | |
|---|---|
| Flow capacity, minimum | 2.8 L/min (0.26 gal/min) |
| Drain height, maximum above floor | 46 cm (18 in) |

Power dissipation to environment:

| | |
|---|---|
| Approximately | 250 W |

Operating environment:
  Temperature ................................. 18 to 40°C (64 to 104°F)
  Humidity, relative (non-condensing) ........................ 10 to 95%
Electrical power operation ........................... 120 Vac ±10%, 60 Hz
  Current required ............................................. 15 A
  System current leakage ............................................ <100 μA
Memory of essential treatment parameters in power failure Operating environment:
  Temperature ................................. 18 to 40°C (64 to 104°F)
  Humidity, relative (non-condensing) ........................ 10 to 95%
Electrical power operation ........................... 120 Vac ±10%, 60 Hz
  Current required ............................................. 12 A
  System current leakage ............................................ <100 μA Drake Willock System 1000 fluid path

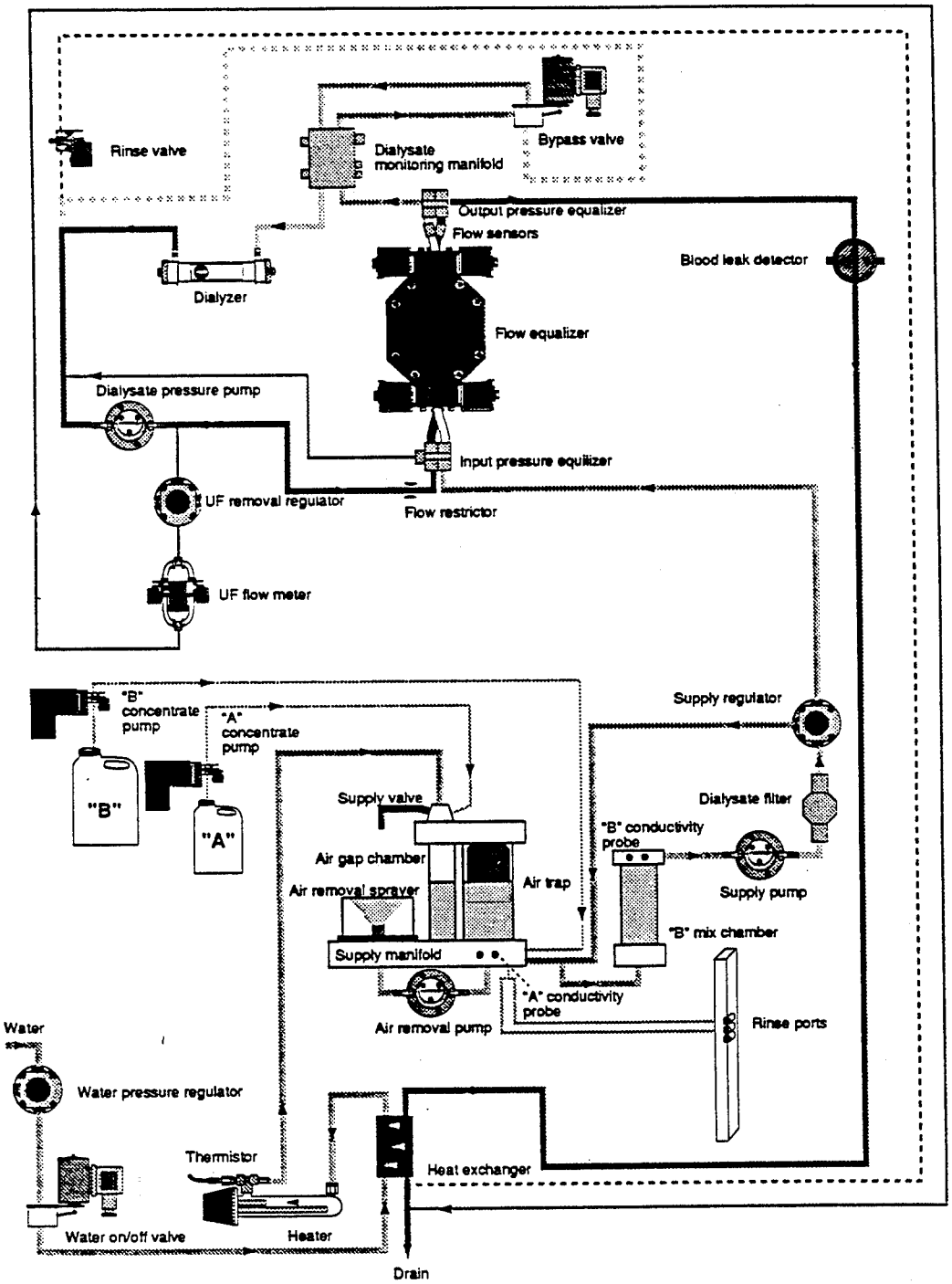

Drake Willock™ 480 High Flow fluid path
part 1 of 2
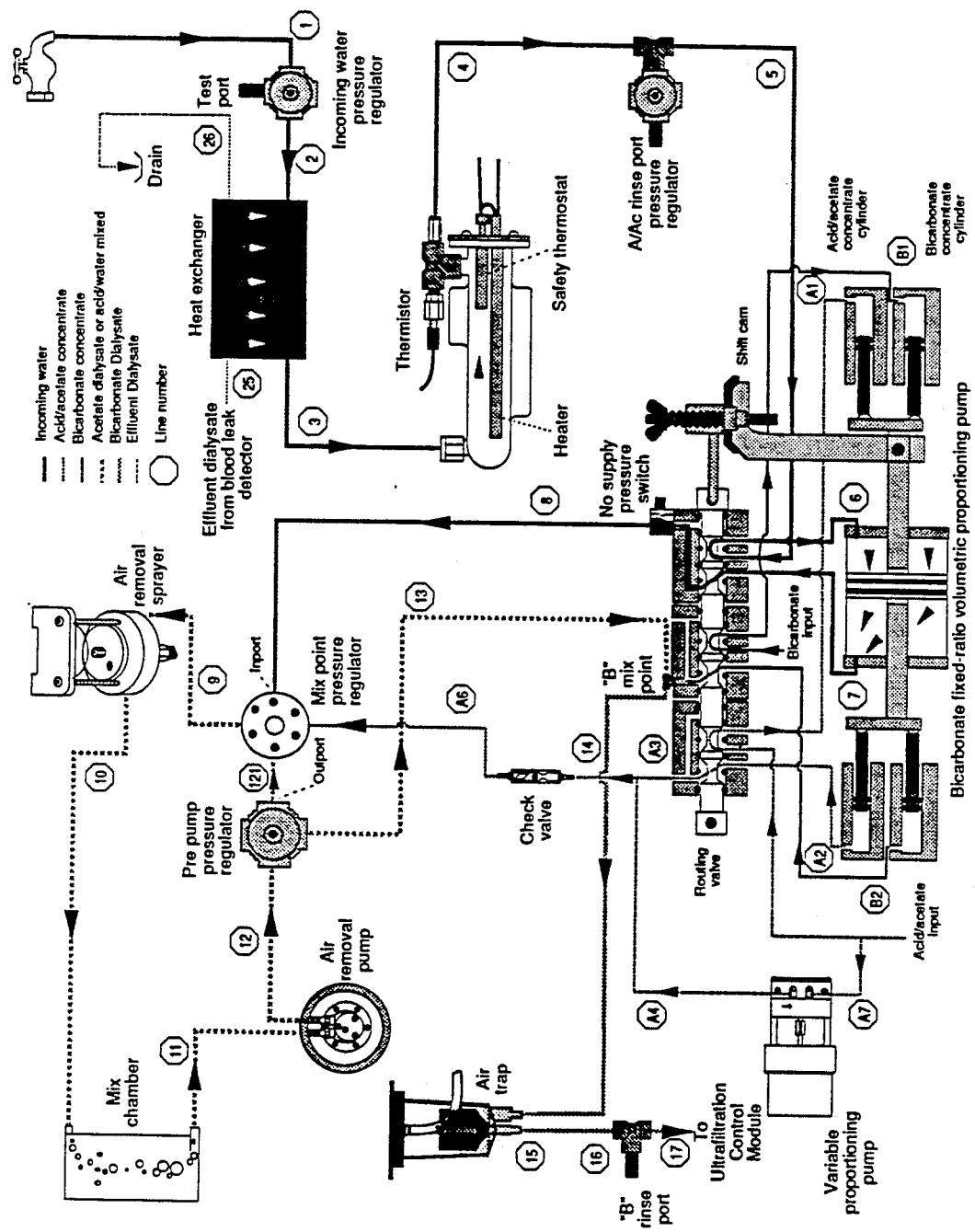

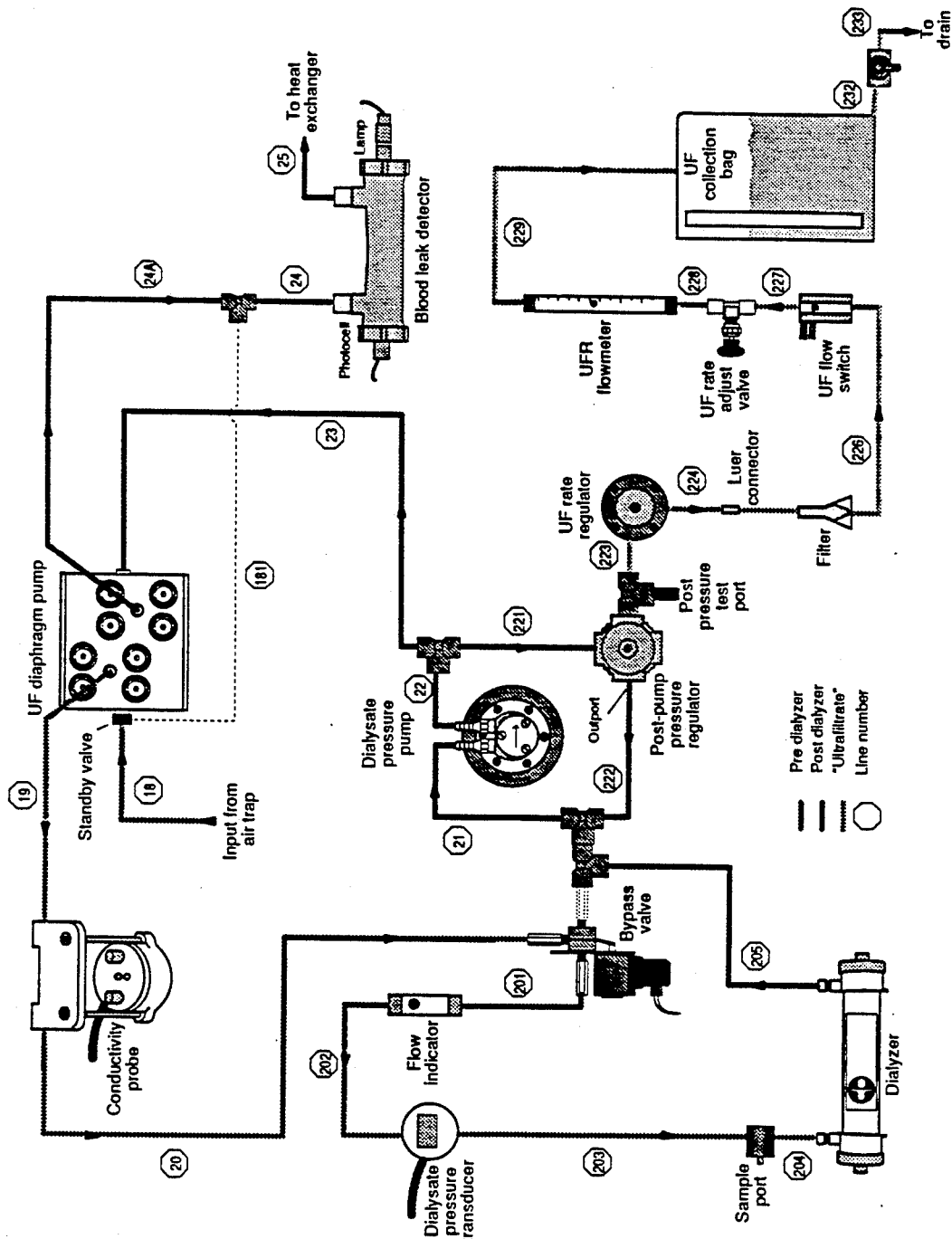
Drake Willock™ 480 High Flow fluid path
part 2 of 2

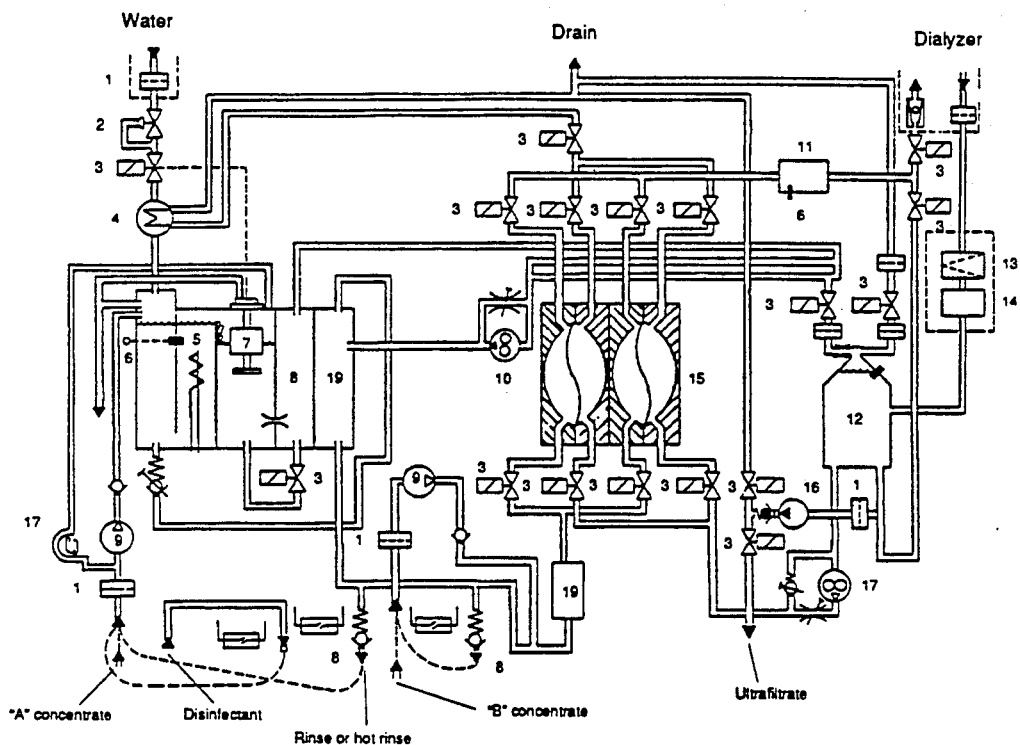
Fresenius Fluid Path
1. Filter
2. Pressure regulator
3. Valve
4. Heat exchanger
5. Heater
6. Temperature sensor
7. Float switch
8. Air removal chamber
9. Concentrate pump
10. Air removal pump
11. Conductivity sensor
12. Air separator
13. Blood leak detector
14. Pressure transducer
15. Balancing chamber
16. UF pump
17. Pump
18. Rinse port
19. Mix chamber

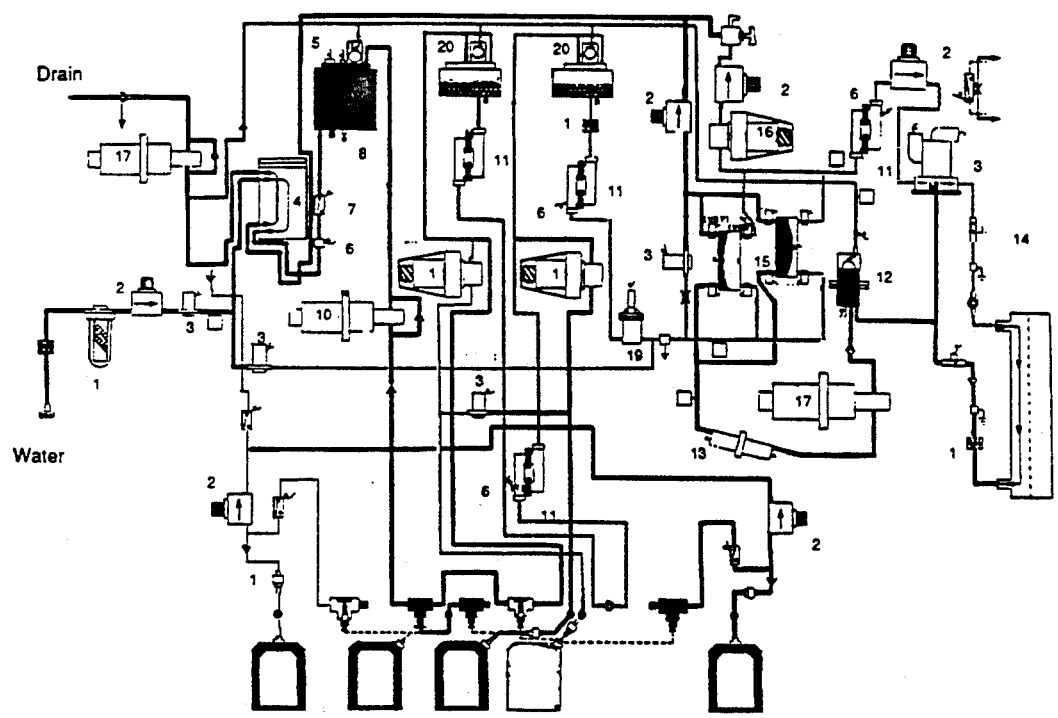
Cobe Centry 3 Fluid Path
1. Filter
2. Pressure regulator
3. Valve
4. Heat exchanger
5. Heater
6. Temperature sensor
7. Flow switch
8. Air removal chamber
9. Concentrate pump
10. Air removal pump
11. Conductivity sensor
12. Air separator
13. Blood leak detector
14. Pressure transducer
15. Balancing chamber
16. UF pump
17. Pump
18. Rinse port
19. pH sensor
20. Mix chamber Exhibit 1
Component Identification Labels
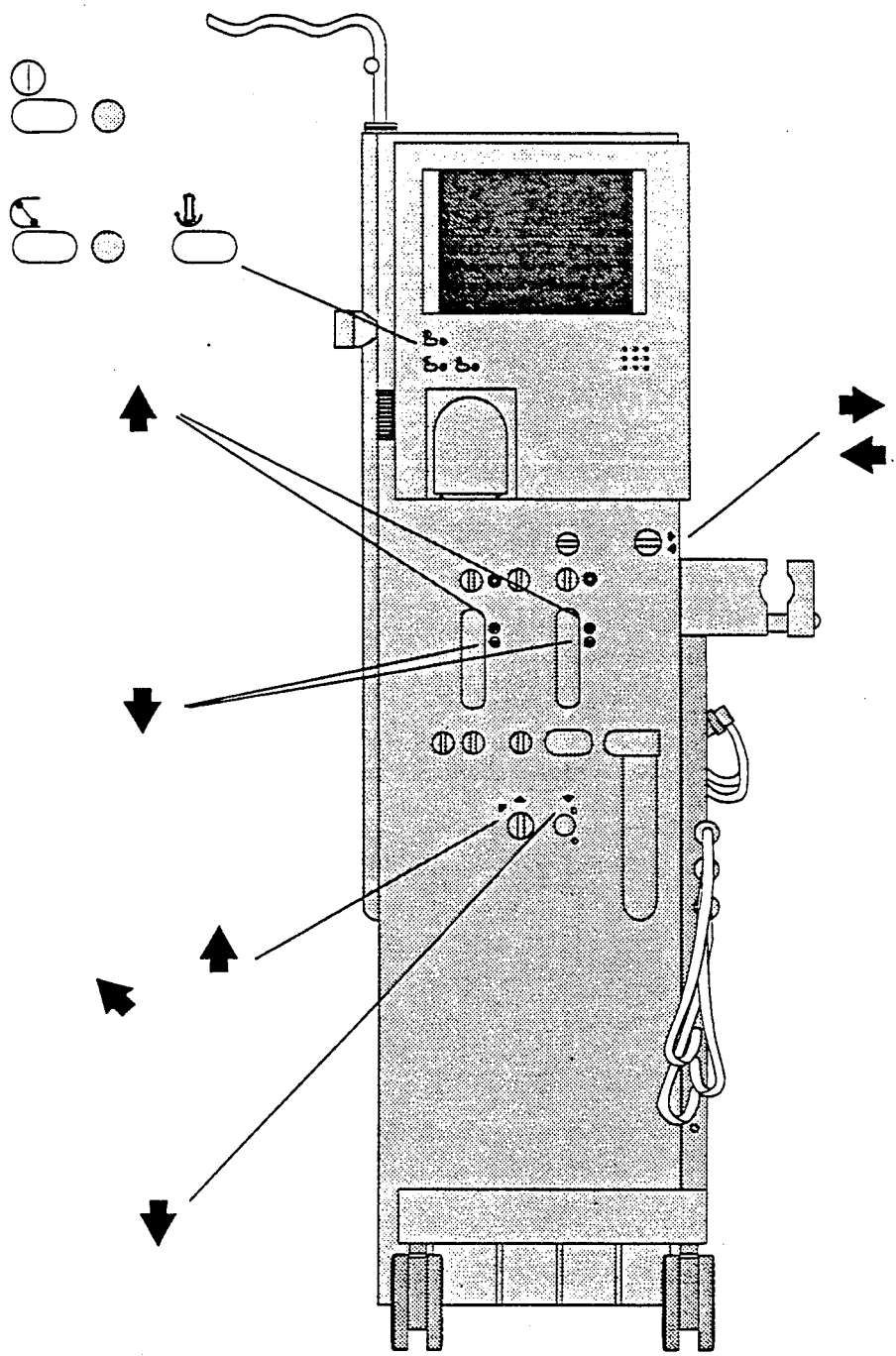

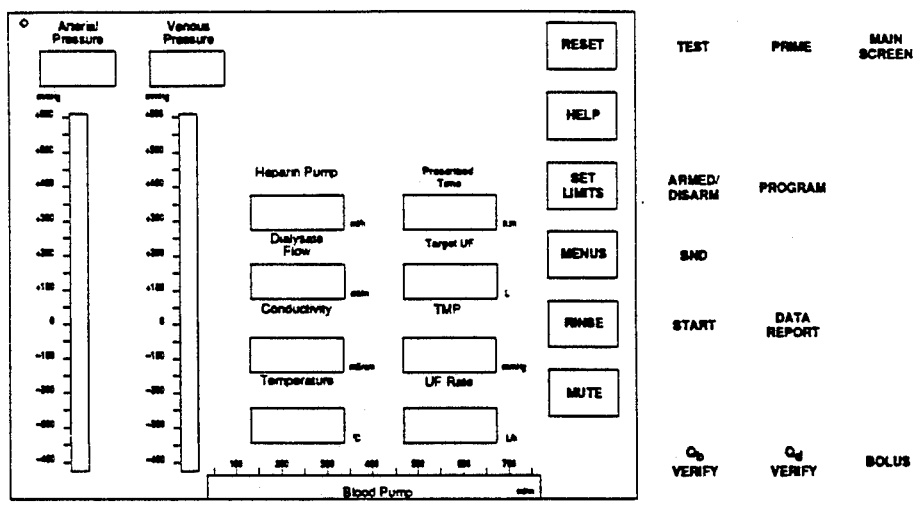
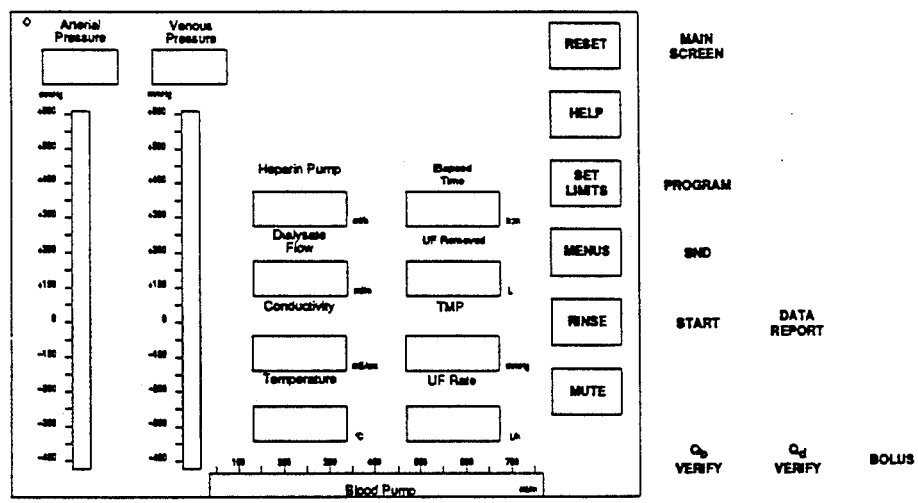

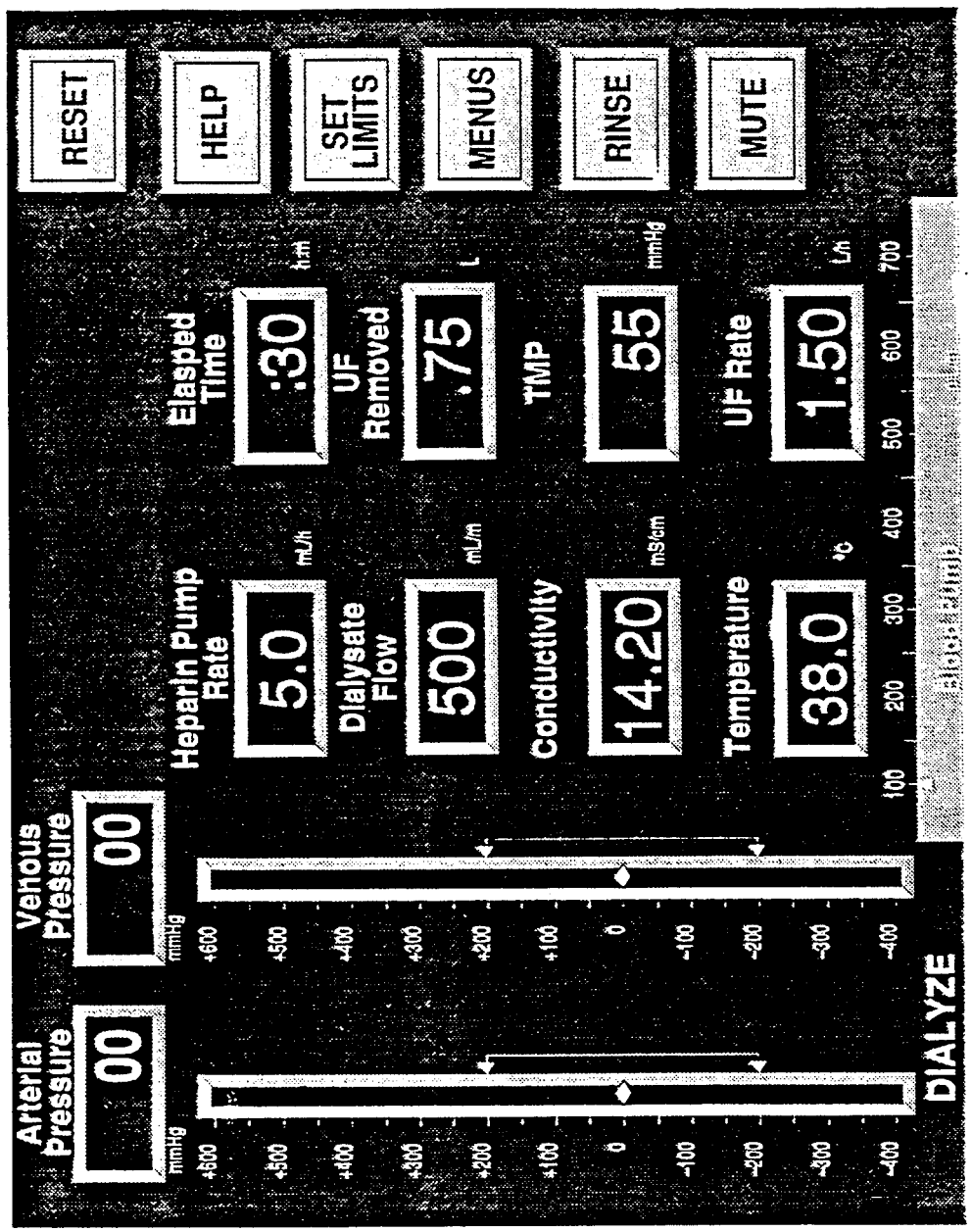

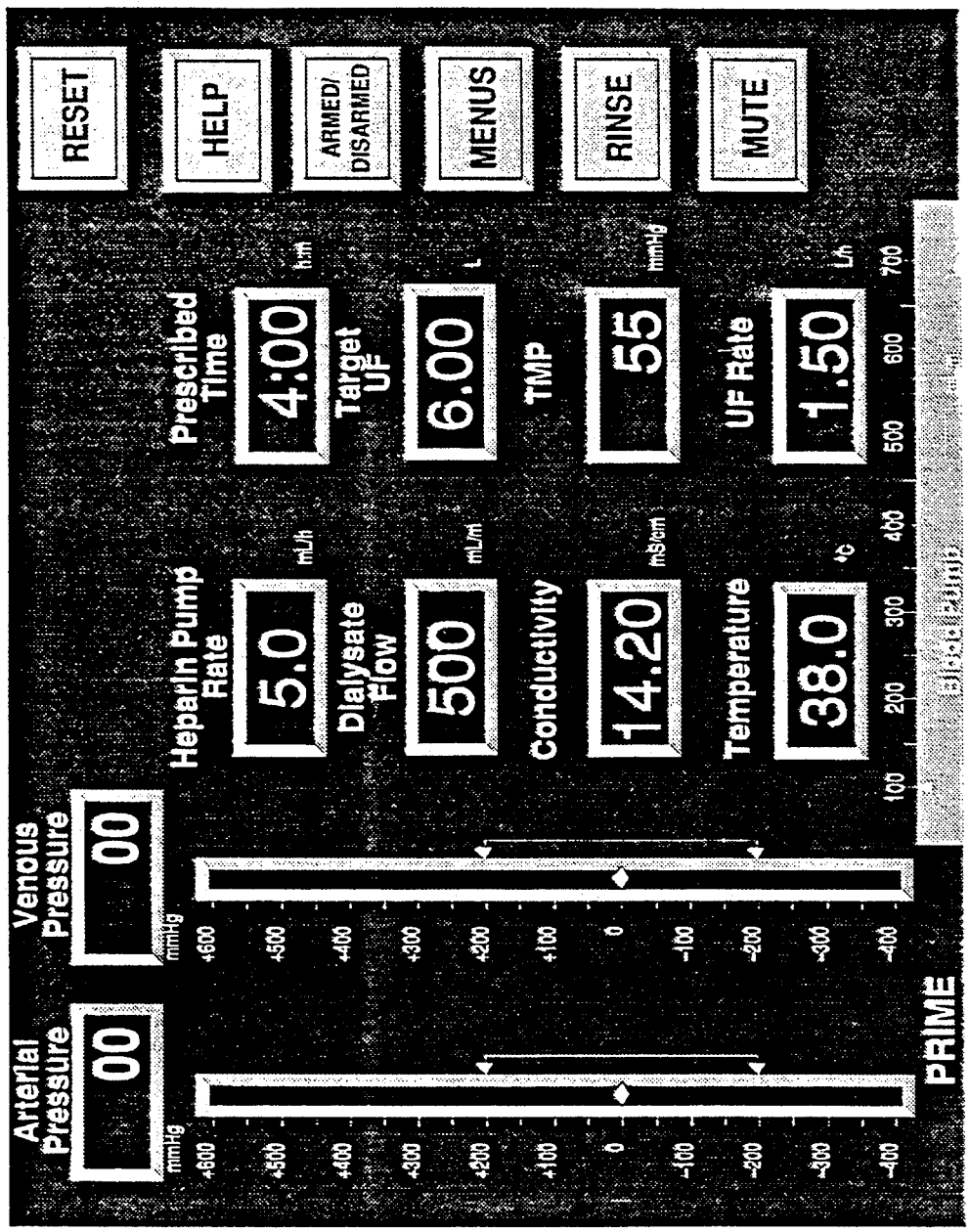

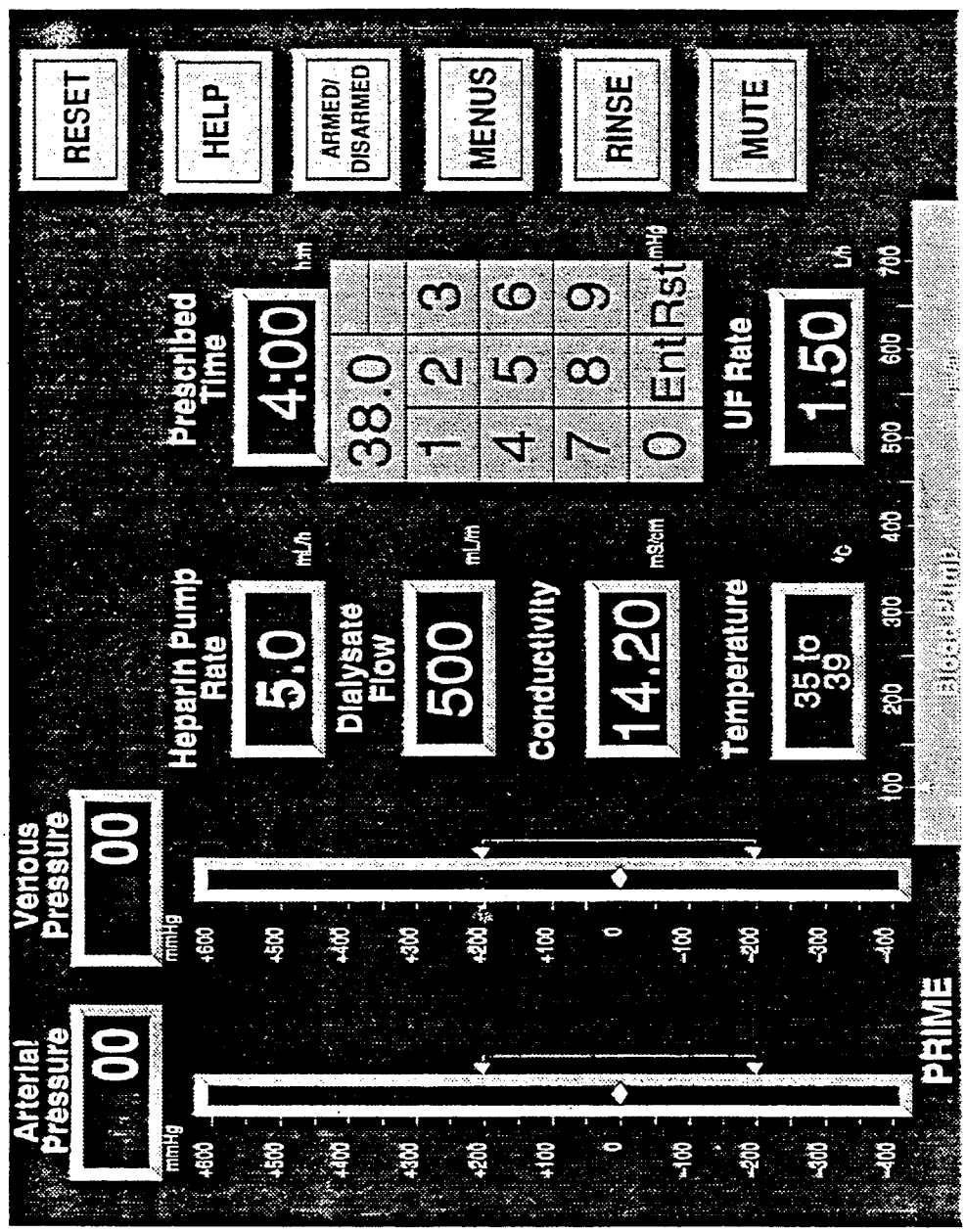

Exhibit 2
Preliminary Draft System 1000 Operator's Manual
Drake Willock System 1000 Single Patient Delivery System Operator's Manual
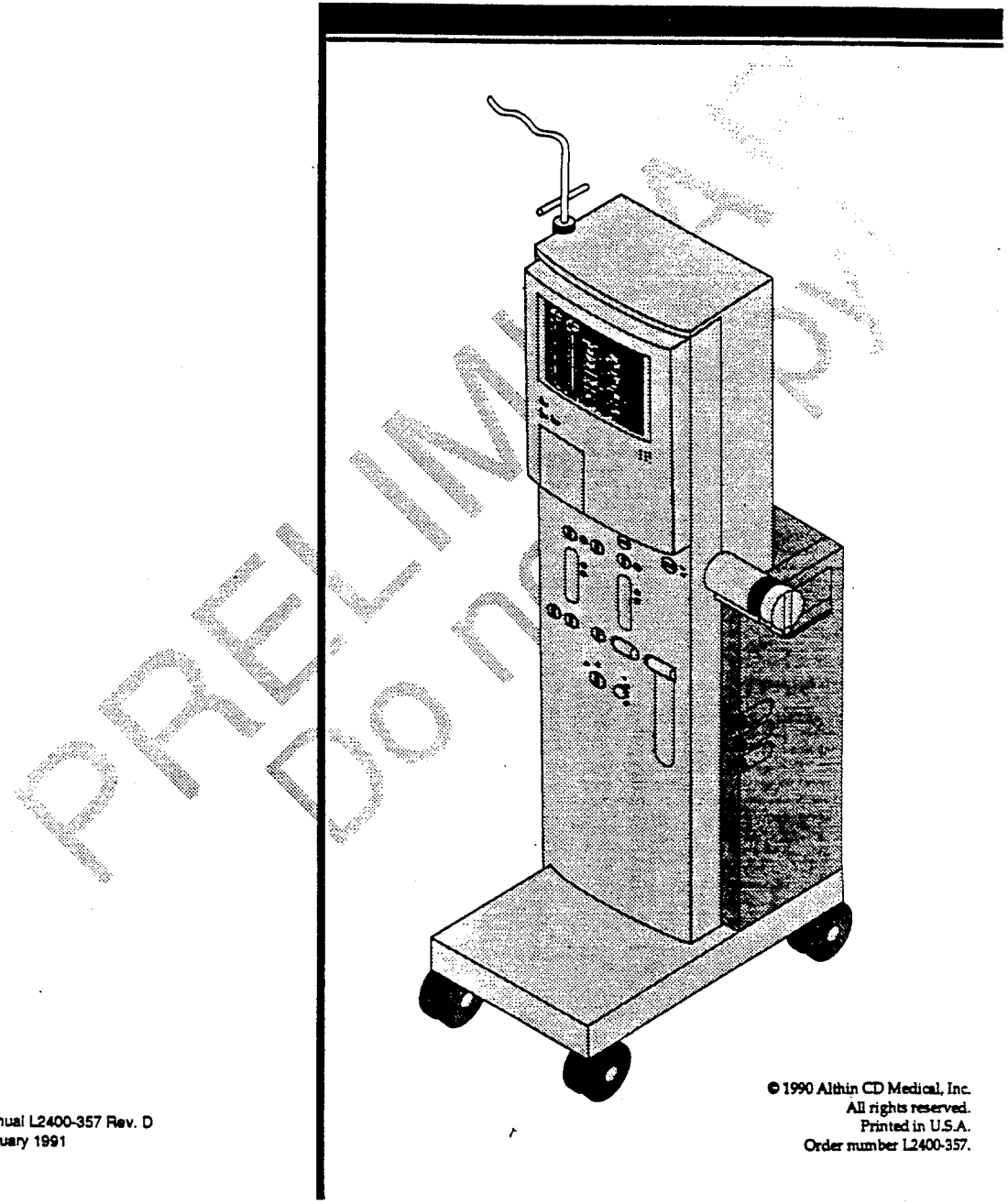
Manual L2400-357 Rev. D
January 1991
© 1990 Althin CD Medical, Inc.
All rights reserved.
Printed in U.S.A.
Order number L2400-357.

WARNING
This device is manufactured and intended for use only as prescribed by a physician. Modification, alteration, or lack of maintenance procedures as described in the labeling, may adversely affect the safety and efficacy of this device. The manufacturer is not responsible for malfunctions that compromise patient safety as a result of alteration, neglect, or misuse.

Replacement parts may vary from those shown in this manual. Should you have questions on those parts please contact Althin CD Medical, Inc.

The actual appearance of the machine may vary from the illustrations in this manual.

This publication may not be reproduced, stored in a retrieval system, or transmitted in whole or in part, in any form or by any means, electronic, mechanical, photocopying, recording, or otherwise, without the prior written permission of Althin CD Medical, Inc ™ Trademark of Althin CD Medical, Inc.
Drake Willock is a trademark of Althin CD Medical, Inc

——————————————————— The Althin Group ———————————————————

Althin CD Medical, Inc.          Phone              Telefax
Drake Willock Division           503-659-3355       503-652-0225
13520 S.E. Pheasant Court        800-547-5534
Portland, Oregon 97222

Table of Contents

Introduction
- Product Description .................................................................. 1
- Prerequisites ............................................................................ 1
- Indications .............................................................................. 1
- Contraindications .................................................................... 1
- Product Improvement Policy ................................................... 2
- Technical Support .................................................................... 2
- Operator's Manual ................................................................... 2

Safety Summary
- Advisories ............................................................................... 1
- Cautions .................................................................................. 1
- Warnings ................................................................................. 1
- Warning and Notes Regarding Concentrates ........................... 2
- Notes Regarding Water ............................................................ 2
- Notes About Blood Flow and Ultrafiltration Rate .................... 3

Components & Functions
- Front ....................................................................................... 2
- Video Screen and Touch Panel ................................................ 6
- Right Side ............................................................................. 10
- Back ...................................................................................... 14

Alarms

Theory
- Ultrafiltration .......................................................................... 2
- Venous and Arterial Pressure Monitors ................................... 4
- Heparin Pump ......................................................................... 4
- Dialysate ................................................................................. 5
- Treatment Data ....................................................................... 5
- Keypad .................................................................................... 6

Operation

Supplies ..................................................................... 1
Pre-Setup .................................................................. 1
Rinse Machine (Before Dialysis) ........................... 2
Start Dialysis ............................................................ 4
Discontinue Dialysis ............................................... 5
Prepare Machine for Another Patient .................. 5
Rinse Machine (After Dialysis) ............................. 5

Special Operation

Control Ultrafiltration ............................................ 1
Heparin ..................................................................... 2
Blood Pump .............................................................. 3
Alarm Limits ............................................................ 3
Dialysate Flow Rate ................................................ 4
Dialysate Temperature ........................................... 4
Help Window ........................................................... 5
Data Report .............................................................. 5
Disinfect Machine Fluid Pathway ......................... 5
Clean and Disinfect Machine External Surfaces ... 8
Keypad ...................................................................... 9
Blood Lines ............................................................. 12

Problem Solving

Patient ...................................................................... 1
Blood Pump .............................................................. 1
Self Test .................................................................... 2
Pulse Spot ................................................................. 2
Air Detector ............................................................. 2
Blood Leak Detector ............................................... 2
Air in Dialysate Circuit .......................................... 3
Ultrafiltration .......................................................... 3
Rinse ......................................................................... 3
Conductivity ............................................................ 4
Power Off Alarm ..................................................... 4

Reference

Monitor Windows .................................................... 2
Buttons ..................................................................... 4
Blood Pump Display ............................................... 8
Arterial and Venous Pressure Display
and Alarm Limit Indicators ................................... 8

Appendix

Glossary
Machine Modes
Data Report Worksheet
UF Control Worksheet
Conversion Chart
Formaldehyde Warning Card
Checklist

Introduction

Product Description

The Drake Willock ™ System 1000 Machine is a single-patient hemodialysis delivery system, which will provide dialysate at the prescribed temperature and ionic concentration to be used for hemodialysis treatment. It will have the ability to monitor machine, dialysate and blood circuit functions during dialysis. The machine is based on volumetric proportioning, volumetric ultrafiltration and digital electronics. The machine and treatment parameters are displayed on a CRT (video monitor). The operator control is done through a interactive touch screen which also makes the machine very easy to clean and use.

The machine has an automated self test prior to the start of each dialysis, this ensures that all of the essential monitoring and alarm functions of the machine are tested before each patient treatment. The automatic self test eliminates the risk that a busy clinician will forget to perform the required machine checks prior to each treatment.

One of the major problems with the dialysis treatments given today is the non-delivery of the prescription (e.g.; the patient is taken off treatment 5 minutes early, repeated alarms stop the blood pump or divert the dialysate to drain stopping the treatment). To enhance treatment quality assurance, the machine records essential treatment data such as treatment time. This treatment time clock stops when alarms interrupt dialysis by stopping the blood pump or bypassing the dialysate around the dialyzer. The data report allows the operator of the machine to know the precise time spent on dialysis enabling the clinician to determine if the dialysis prescription was delivered.

Prerequisites

The operator must:

- be proficient in the clinical application of hemodialysis and knowledgeable about the relevant physiology.
- be thoroughly trained and certified by the attending physician in the medical skills and knowledge required to operate this device and in providing the necessary patient treatment(s) normally associated with hemodialysis therapy.
- be thoroughly familiar with the contents of this manual and other operator's manuals that deal with the host machine and accessory devices that may be used with this device.
- be fully qualified and trained in the operation of this machine and able to distinguish normal from aberrant device behavior.

The System 1000 Single Patient Delivery System must:

- be in good working order and certified as such by the attending physician.
- be operated only in accordance with the machine specifications listed by Althin CD Medical, Inc. and with the operating instructions contained within the System 1000 System Operator's Manual and machine labeling. The attending physician is responsible for any changes to the procedures.

Indications

The System 1000 Single Patient Delivery System is indicated for use when a parallel flow dialyzer is chosen for use in chronic or acute hemodialysis treatments.

Contraindications

The System 1000 Single Patient Delivery System is not designed, sold or intended for any use except as indicated above. Furthermore, it is not intended to be used outside of the device specifications or limitations.

The System 1000 Single Patient Delivery System is not intended to be a substitute for the monitoring of the patient or of the patient's extracorporeal blood circuit by qualified personnel.

Product Improvement Policy

Drake Willock dialysis equipment was designed and built to the performance requirements stated in the product specifications.

It is the corporate policy to perform continuous product improvement research that often results in modifications to enhance patient safety or treatment effectiveness without incurring any obligation to make the same or similar changes to all equipment previously built and/or sold. When such improvements occur we will, from time to time, inform the owners of Drake Willock dialysis equipment and offer any available upgrades at reasonable prices. These upgrades, however, should not be construed as corrections of deficiencies, as the equipment met all the original product specifications when delivered.

Any product which, in the opinion of Althin CD Medical, Inc. proves not to have met product specifications will be remedied by us.

Should pre-owned Althin CD Medical equipment be purchased and reconditioned, the equipment should not be used until testing and analysis demonstrate that the equipment meets the original or upgraded specifications.

Technical Support

Althin CD Medical, Inc. offers technical support, technical training, consultation and machine service upon request. Contact your local Althin CD Medical service representative for additional information.

Operator's Manual

This manual provides the qualified operator with information necessary for the safe and efficacious operation of the System 1000 Single Patient Delivery System. The following summary of each section will give the operator an idea of where information is located in this manual.

Introduction

The "Introduction" section gives the operator general information about the machine, its prerequisites, indications and contraindications.

Safety Summary

The "Safety Summary" section contains many of the general safety statements about the machine and its operation.

Components & Functions

The "Components & Functions" section familiarizes the operator with the names and use of the external controls and features.

Alarms

The "Alarms" section contains a summary of the machine alarms, visual and audible indicators and machine responses.

Machine Modes

The "Machine Modes" section contains a summary of the machine modes, visual indicators and machine actions.

Theory

The "Theory" section explains the basic operation of the machine.

Operation

The "Operation" section contains the recommended basic operation procedure for the machine.

Special Operations

The "Special Operations" section contains the detailed operational steps needed to use the specialized features of the machine.

Problem Solving

The "Problem Solving" section contains possible treatment problems and the recommended machine related operator actions.

Reference

The "Reference" section describes in detail the use of the control panel buttons and windows.

Appendix

The "Appendix" contains a glossary, the machine specifications and a UF control worksheet.

Safety Summary

This summary does not contain all the safety statements in this manual. Other advisories, cautions and warnings are included within the manual text.

Advisories

An ADVISORY is a statement identifying conditions or practices that could result in misapplication of the therapy.

Cautions

A CAUTION is a statement identifying conditions or practices that could result in equipment or other property damage.

Warnings

A WARNING is a statement identifying conditions or practices that could result in personal injury or loss of life.

WARNING: Do:
- read and follow the operator's manual prior to operating this machine.
- keep this and other associated manuals readily available for use by new operators or qualified service personnel.
- use the proper power cord.
- make sure that the wheels are unlocked before attempting to move the machine.
- perform regular maintenance as described in the maintenance manual to ensure patient safety.
- keep your fingers out of the line clamp.

WARNING: Do Not:
- under any circumstances perform any testing or maintenance of this machine while dialysis is in progress.
- cut or remove the grounding contact from the plug.
- use any adapter device on the power cord for the purpose of plugging into a non-grounded power source.
- use an extension cord.
- remove covers or panels when the machine is connected to a power source.
- operate the machine without covers and panels properly installed.
- remove any caution, warning or other descriptive labels from the machine.
- operate this machine in an explosive environment or near flammable anesthetics.
- do not use the IV pole to move the machine.

Warnings and Notes Regarding Concentrates

1. It is important to know the expected conductivity of the dialysate made from the particular concentrates(s) being used.
2. If concentrates are prepared from dry chemicals, be sure the chemicals are thoroughly dissolved before using the concentrates. Make sure that the water used to prepare the concentrate at least conforms to the AAMI standards for water used in hemodialysis. It is recommended that the water be especially low in contaminants and pyrogenic material.
3. Use good quality concentrates, the better quality concentrates often dissolve faster and are easier to mix. The potential for precipitate formation is reduced with concentrates that mix correctly. Significant variations in quality have been reported in concentrates from different major manufacturers.

WARNING:
1. Make sure the correct concentrate is used for the dialysis and that the concentrate containers connected to the machine contain an adequate amount of concentrate(s) for the entire dialysis, including setup and shutdown.
2. Do not dialyze using acid concentrate alone.
3. Make sure that the concentrate containers are labeled regarding contents.
4. For correct proportioning, the concentrate lines must be connected to the correct machine fitting and/or concentrate containers.

Notes Regarding Water

The water supply entering the system should at least conform to the AAMI standards for water used in hemodialysis. It is recommended that the water be especially low in contaminants and pyrogenic material. This recommendation also applies to any concentrates used with the system, particularly bicarbonate concentrates which many facilities mix themselves. It is the responsibility of the attending physician in the clinic to evaluate the purity of the water supply and concentrates against any potential risk to the patient under the intended conditions of dialysis.

Components & Functions

This section of the manual identifies the components and describes their functions. The operator should become thoroughly familiar with this section prior to operating the machine.

Note: Words in bold CAPITAL LETTERS denote specific labels on the machine.

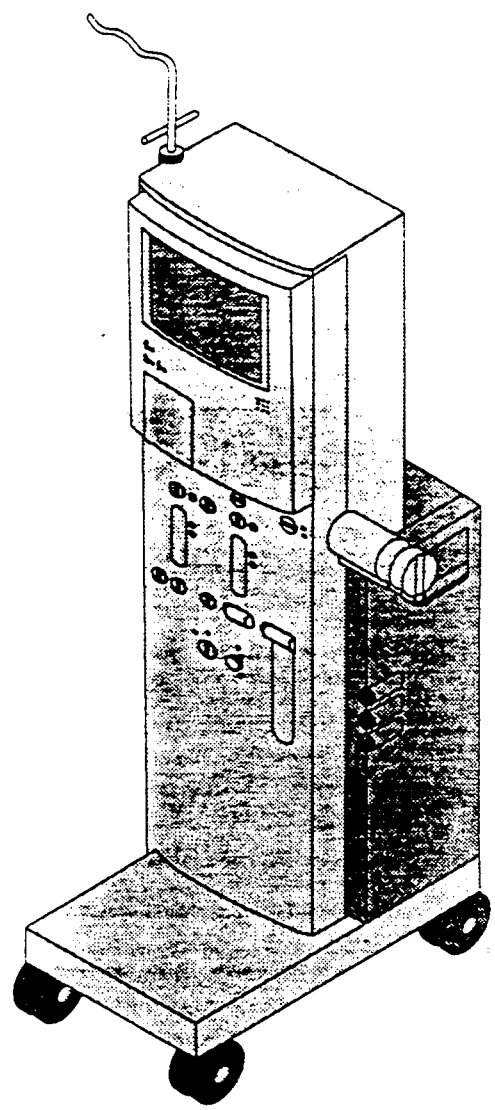

Front

Main alarm lamp

Flashes when operator input or assistance is needed at the machine. Flashes during the machine alarms (Alarm Mode), the Standby Mode, the Prime Mode and the Rinse Mode when the conductivity and temperature are within the normal operating range (i.e., between the high and low alarm limits)

Video screen and touch panel

> Display machine functions and controls. The operator controls operating parameters of the machine by touching specific areas of the screen.

IV pole knob

> Adjusts the height of the IV pole.

Blood pump

> Controls the extracorporeal blood flow.

Pressure luers

> Accept the pressure monitoring line from the drip chambers.

Level adjust buttons

> Raise or lower the liquid level in the drip chamber.

Air detector

> Detects the presence of air in the venous blood line.

Line clamp

> Clamps the venous blood line during an extracorporeal alarm and during a power failure.

Dialyzer holder

> Holds the dialyzer. The dialyzer holder rotates to facilitate dialyzer priming.

Heparin pump

> Infuses an operator-adjustable amount of heparin into the extracorporeal circuit over a period of time or by a bolus. The heparin pump stops when the blood pump is stopped.
>
> Uses a 10 or 20 ml capacity syringe. The syringe the machine is calibrated for is listed in the data report.
>
> The heparin pump may be turned off by setting the heparin pump rate to 0 ml/h.
>
> The heparin pump stops during an extracorporeal alarm or when the blood pump is turned off manually.

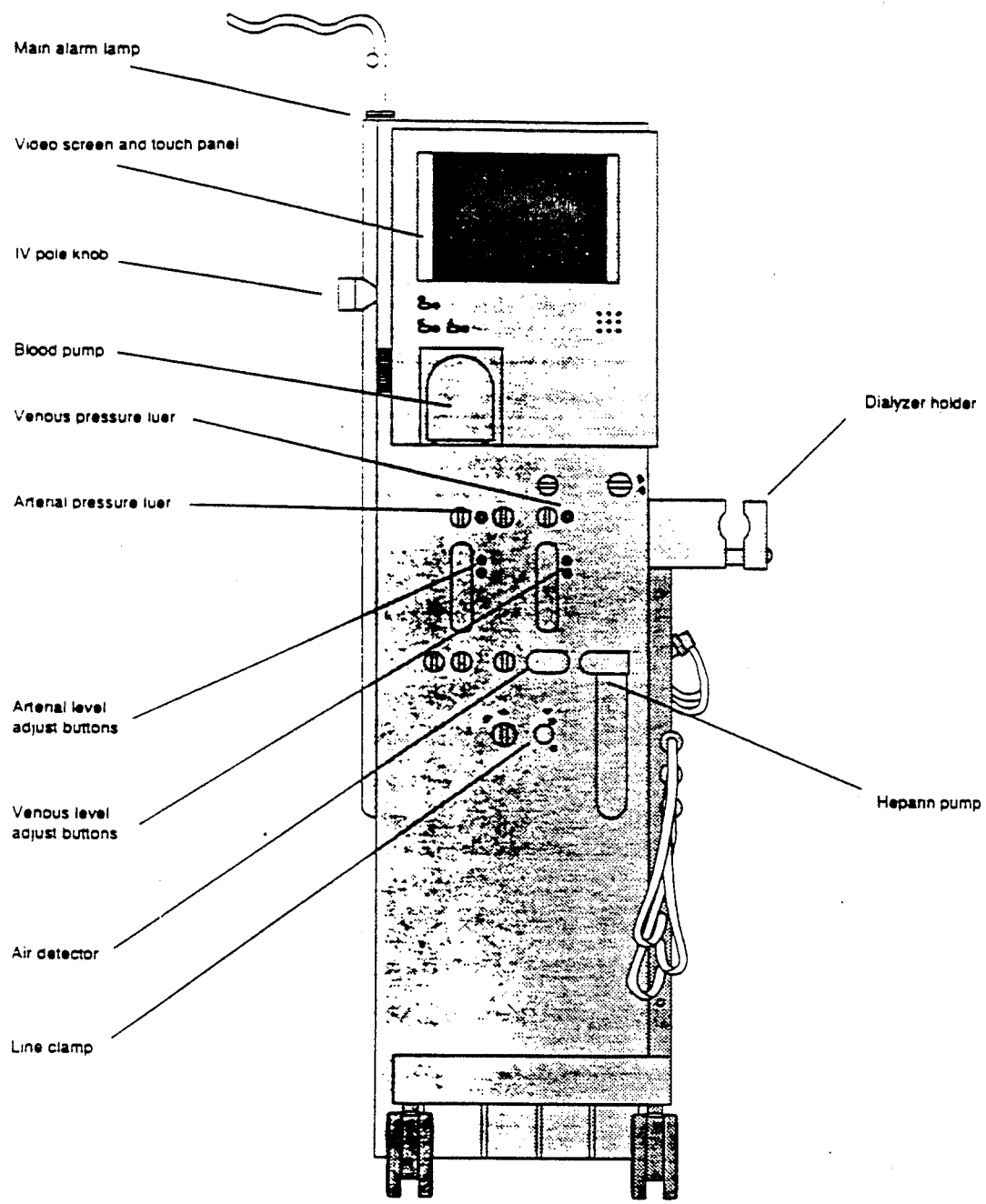

Power switch and lamp
: Turns the machine on and off. The lamp lights when power is on.

Blood pump switch and lamp
: Turns the blood pump on and off. The lamp lights when power is on.

Manual bypass switch and lamp
: During dialysis, stops the flow of dialysate through the dialysate lines for sequential ultrafiltration.

During setup and shutdown, stops the flow of dialysate through the dialysate lines for connection to the dialyzer or machine.

The lamp flashes when the machine is in manual bypass.

If the manual bypass button has been pressed, while in the Rinse Mode, the machine will remain in manual bypass for approximately 1 minute. At the end of the minute, the flow resumes in the "dialyzer circuit" and the manual bypass lamp goes off.

Blood line clips

Hold the blood lines in an orderly arrangement

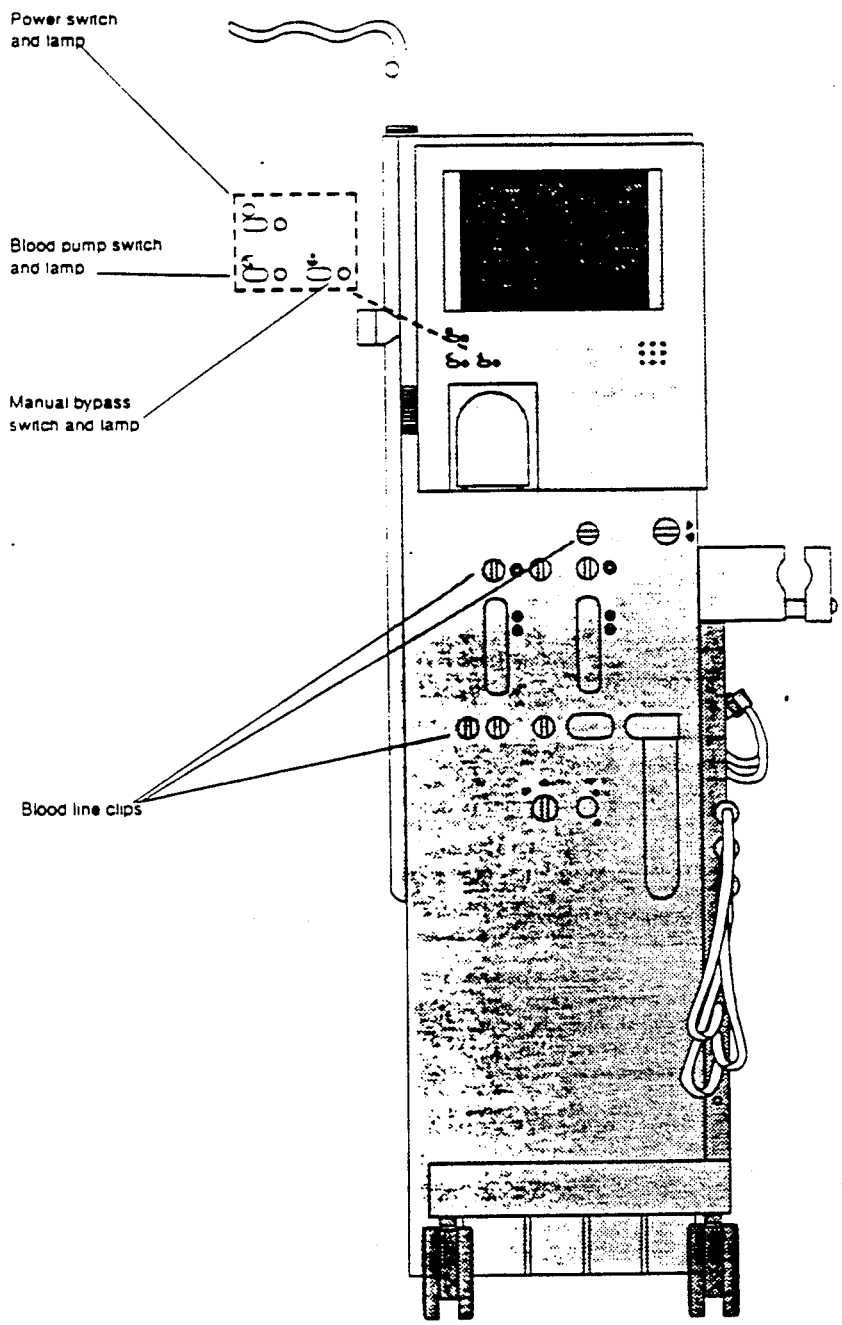

Video Screen and Touch Panel

Buttons

Touch sensitive areas used by the operator to control machine operation.

The function and displayed name of individual buttons may change with the machine operating mode.

Some buttons appear only when they are needed. Refer to the "Reference" section for detailed information.

Pulse spot

Flashes to indicate that the screen (control panel) is active.

Bulletin window

Displays messages about unusual operational or machine errors, such as the blood pump stop alarm.

Instructions window

Displays messages to assist the operator in operating the machine.

Alarm window

Displays alarms, that are not monitored elsewhere on the screen. Also displays some operator messages.

Alarms displayed in this window include blood leak, air detector, bypass fail and no dialysate flow. Operator messages displayed in this window include rinse interlock information.

Machine status area

Displays the operating mode and/or machine status such as POWER ON, STANDBY, RINSE, SELF TEST, PRIME, DIALYZE, ALARM and SHUTDOWN.

Monitor windows

Display the value of the monitored function. The monitor windows, except ARTERIAL PRESSURE and VENOUS PRESSURE, also are touch sensitive areas used by the operator to control machine operation.

Blood pump display

Indicates the blood pump speed and whether the blood pump is on or off.

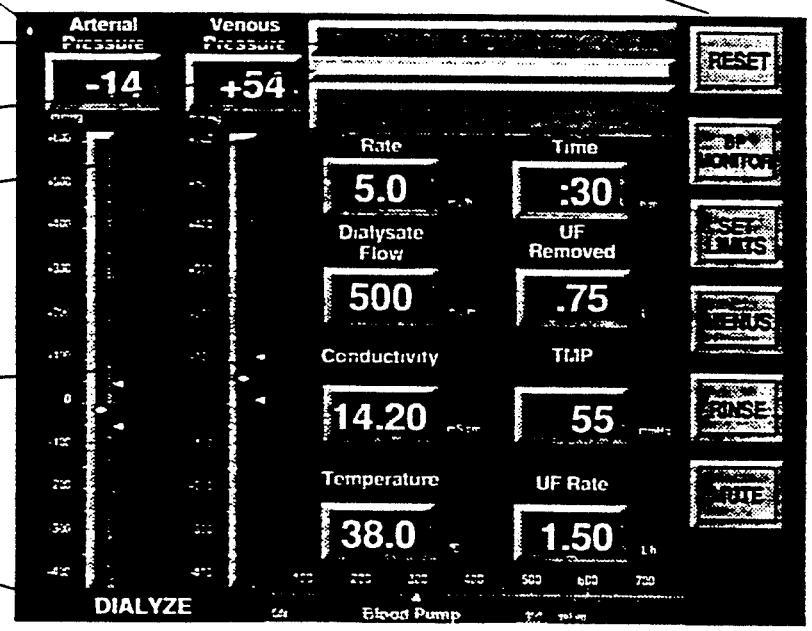

Main Screen

Alarm indicators

Flash to indicate which alarm has occurred. When a monitor is in alarm, a flashing pointer appears beside the monitor window, and the alarm window flashes. For air detector and blood leak alarms, the alarm message appears in the alarm window and the alarm window flashes.

Arterial and venous pressure alarm limit indicators

Are pointers indicating the upper and lower arterial and venous pressure alarm limits.

Help window

Displays a brief statement of the use of available buttons.

Keypad

Is used by the operator to input data into the machine to set the prescribed treatment time, target fluid loss, manual UF rate, heparin pump rate, and dialysate temperature.

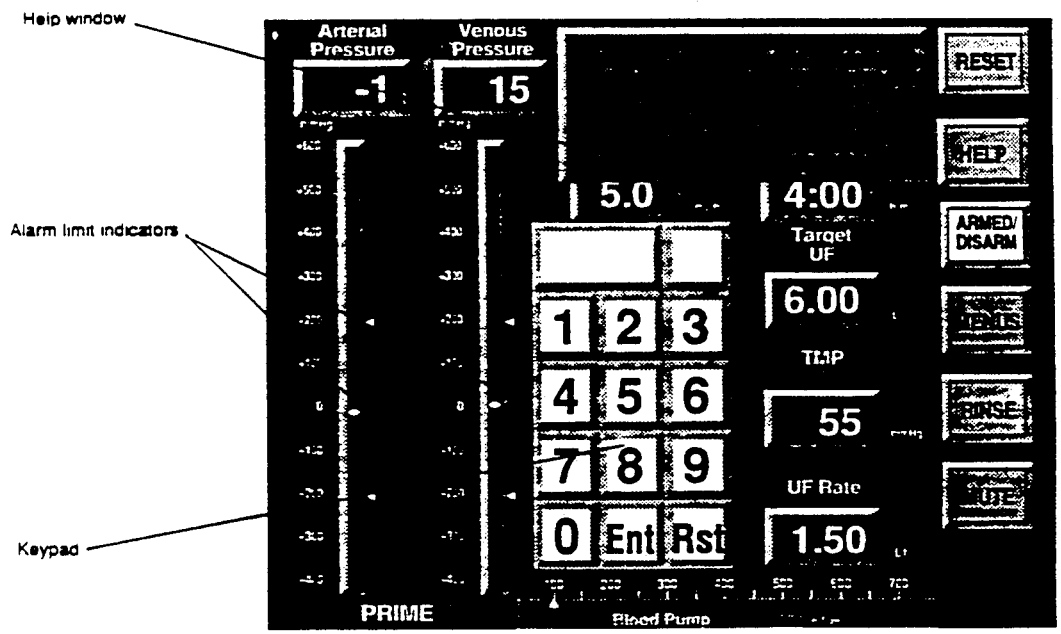

Main Screen

Right Side

Acid/acetate rinse port (pink/red)

During rinse and storage, accepts the acid/acetate concentrate line connector (pink).

The acid/acetate rinse port and concentrate line fitting are keyed and color-coded to prevent accidental insertion bicarbonate concentrate or chemical disinfect line connectors.

Acid/acetate concentrate line (with pink/red connector)

During acetate dialysis, delivers acetate concentrate from the acetate concentrate jug to the machine.

During bicarbonate dialysis, delivers acid concentrate from the acid concentrate jug to the machine.

During rinse and storage, is connected to the acid/acetate rinse port (pink).

During chemical disinfect, is connected to the disinfect port (yellow).

Bicarbonate concentrate line (with blue connector)

>During bicarbonate dialysis, delivers bicarbonate concentrate from the bicarbonate concentrate jug to the machine.

>During acetate dialysis, rinse, storage and chemical disinfect, is connected to the bicarbonate rinse port (blue).

Bicarbonate rinse port (blue)

>During rinse, chemical disinfection and acetate dialysis; accepts the bicarbonate concentrate line connector (blue).

>Is keyed and color coded to prevent accidental insertion of the acid/acetate concentrate or disinfectant line connector.

Disinfect line (with yellow connector)

>During chemical disinfect, delivers disinfectant from the disinfectant container to the machine.

>During acetate dialysis, bicarbonate dialysis and rinse, is connected to the disinfect port (yellow).

Disinfect rinse port (yellow)

>During chemical disinfection, accepts the acid/acetate concentrate line (pink).

>During rinse and dialysis, accepts the disinfectant line (yellow).

Dialysate line connector holders (rinse block)

>Accepts the dialysate line connectors when the machine is stored, rinsed, cleaned or disinfected.

Dialysate lines and connectors

>Attach to the dialyzer dialysate inlet and outlet port during dialysis to deliver fresh dialysate and remove used dialysate. The connectors are color-coded to indicate the dialysate flow direction and aid in connection to the dialyzer. The blue connector is connected to the line that delivers fresh dialysate to the dialyzer. The red connector is connected to the line that takes used dialysate from the dialyzer.

Handle

>Is used to push or position the machine.

Dialysate line sample port (post dialyzer)

>Permits sampling of the dialysate leaving the dialyzer.

Ultrafiltrate line

>May be disconnected and placed in a graduated cylinder for verification of ultrafiltrate removed.

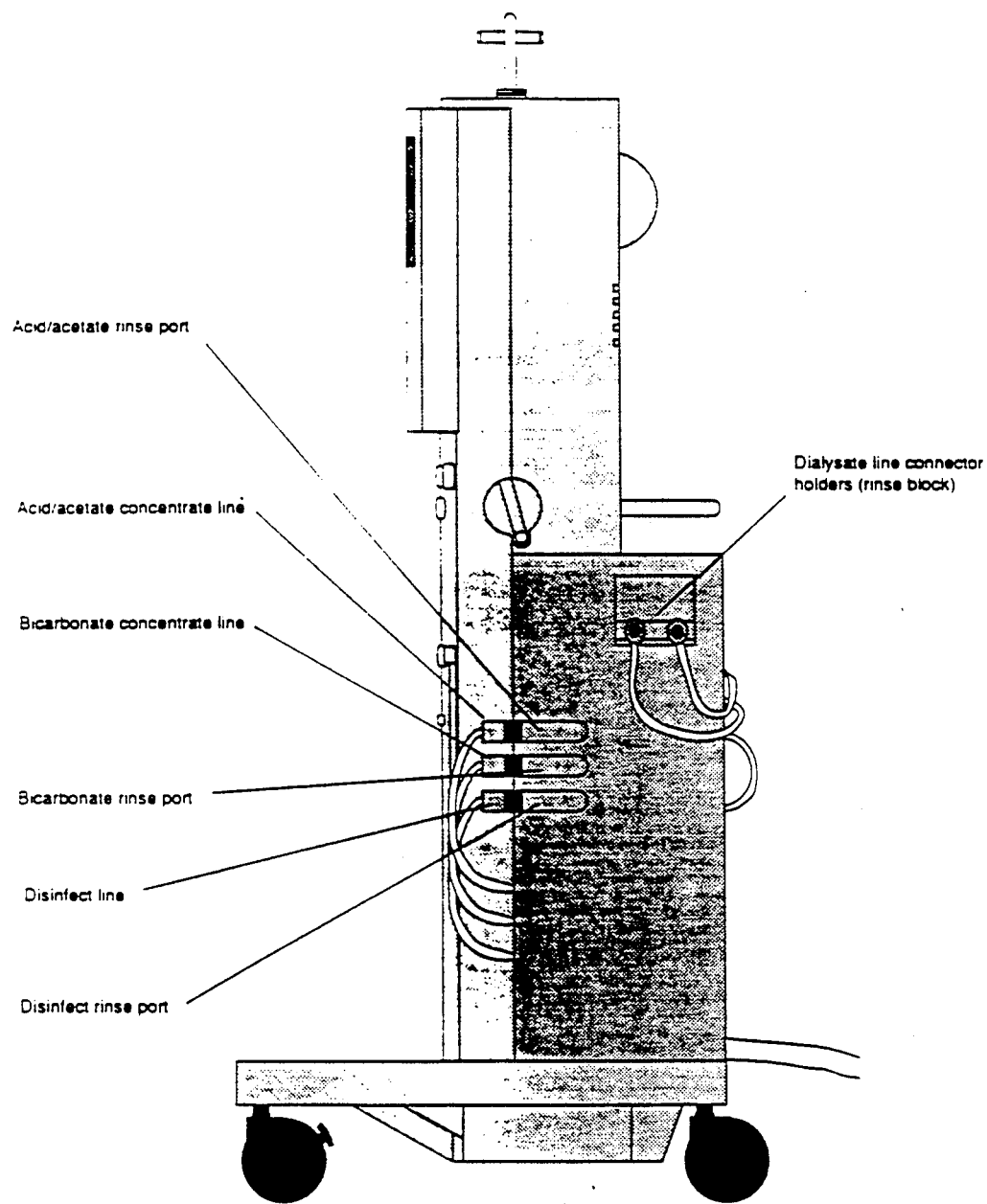

Back

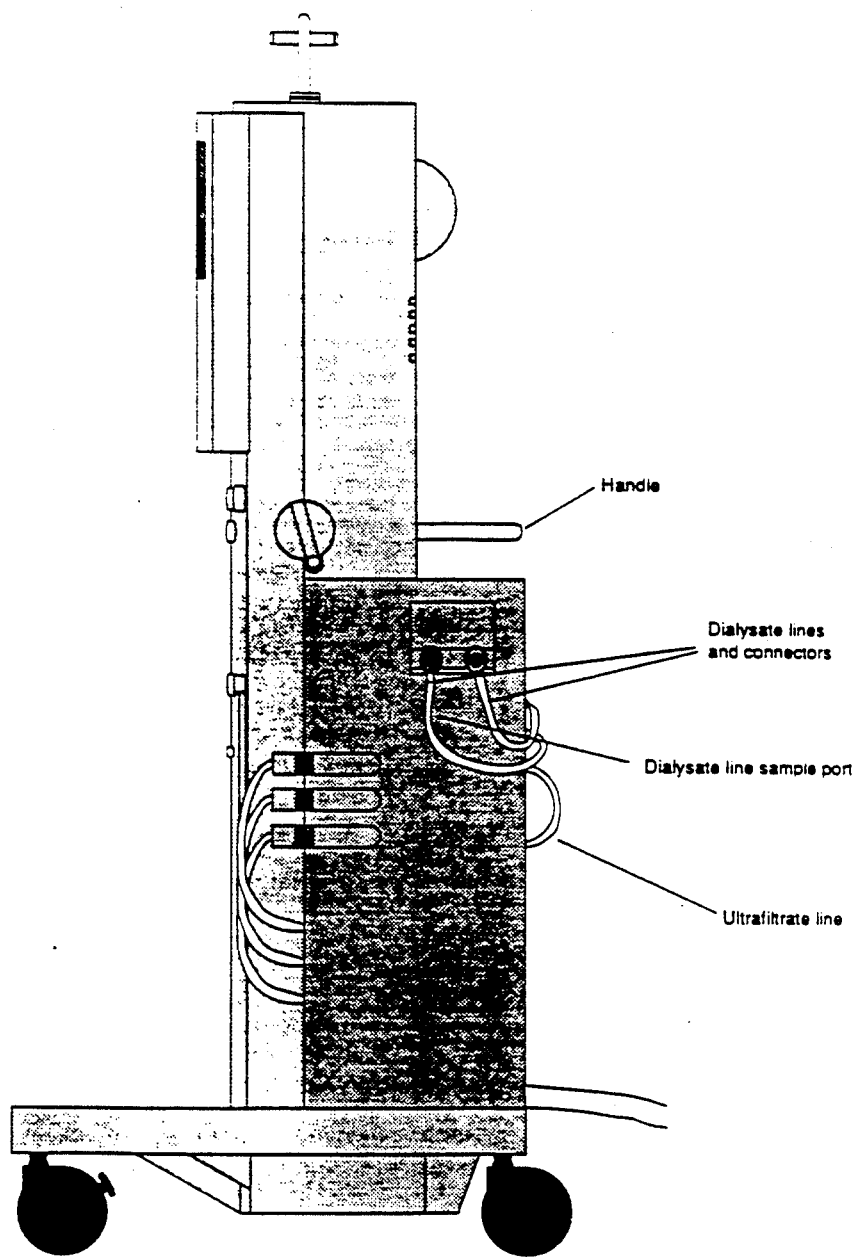

Hour meter

Records and displays the elapsed time the machine has operated.

Blood leak detector

Monitors the post dialyzer dialysate for blood.

RS232 connector

Provides a means for connection of the machine to a computer or computerized system.

Mains power switch

Turns the mains power to the machine on and off. Turn this switch off at the end of the day.

Power cord receptacle

Accepts the power cord. The other end of the cord plugs into an appropriate (hospital grade) wall outlet.

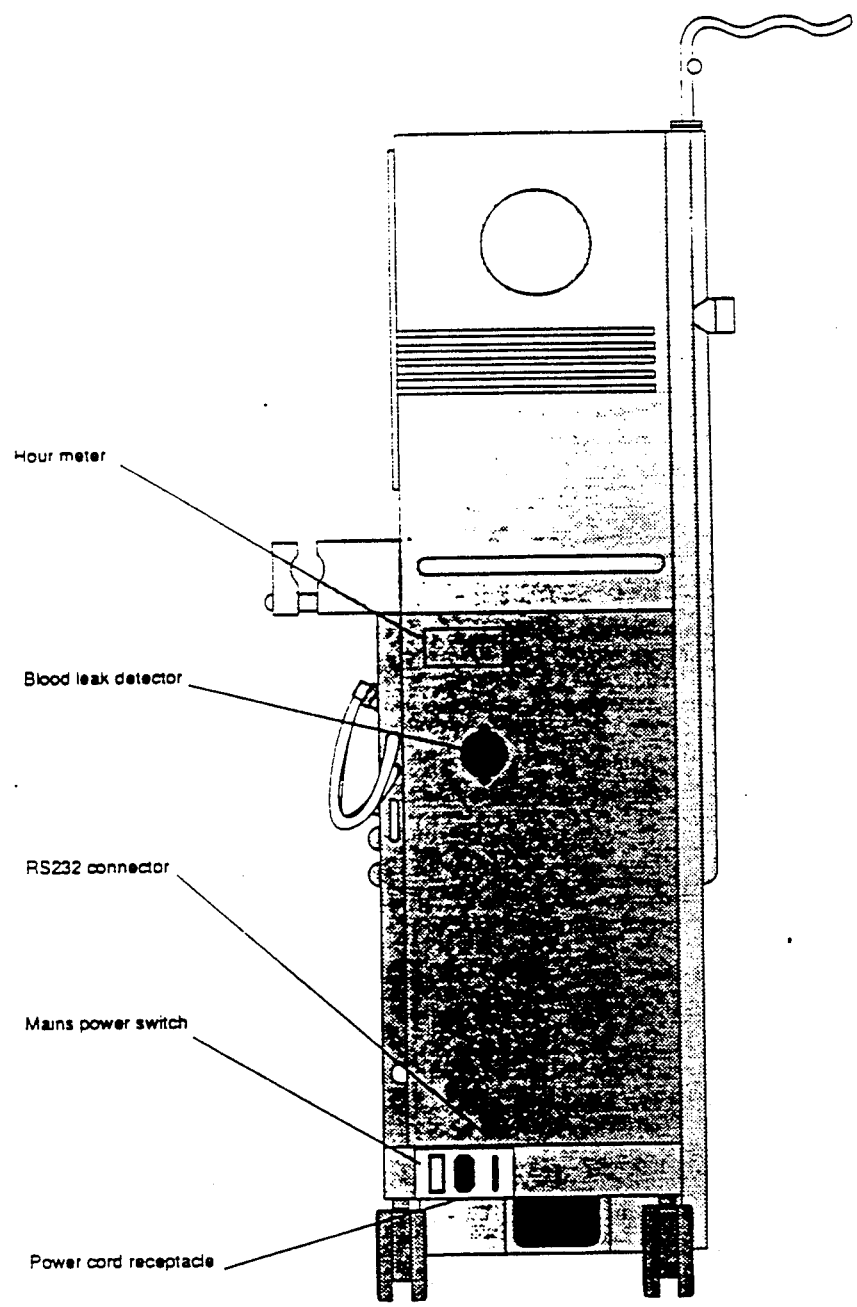

Alarm Matrix

| | Monitor/alarm | Visual indication | Audible indication | Silence available? | Reset required? | Machine action |
|---|---|---|---|---|---|---|
| AIR DETECTED | air detector | displayed in flashing alarm window main alarm lamp flashes | sounds | yes | yes | blood pump stopped<br>heparin pump stopped<br>line clamp clamped<br>UF rate 0 L/h (off)<br>elapsed time stopped |
| BLOOD LEAK DETECTED | blood leak detector | displayed in flashing alarm window main alarm lamp flashes | sounds | yes | yes | blood pump stopped<br>heparin pump stopped<br>line clamp clamped<br>UF rate 0 L/h (off)<br>elapsed time stopped |
| NO DIALYSATE FLOW | no supply | displayed in flashing alarm window main alarm lamp flashes | sounds | yes | no | no control function |
| ▲ | venous pressure | alarm indicator flashes main alarm lamp flashes | sounds | yes | yes | blood pump stopped<br>line clamp clamped<br>UF rate 0 L/h (off)<br>elapsed time stopped |
| ▲ | arterial pressure | alarm indicator flashes main alarm lamp flashes ALARM | sounds | yes | yes | blood pump stopped<br>line clamp clamped<br>UF rate 0 L/h (off)<br>elapsed time stopped |
| ▲ | conductivity (primary) | alarm indicator flashes main alarm lamp flashes ALARM | sounds | yes | no | bypass |
| ▲ | backup conductivity | alarm indicator flashes main alarm lamp flashes BACKUP | sounds | yes | no | bypass |
| ▲ | temperature (primary) | alarm indicator flashes main alarm lamp flashes ALARM | sounds | yes | no | bypass |
| ▲ | backup temperature | alarm indicator flashes main alarm lamp flashes BACKUP | sounds | yes | no | bypass |
| ▲ | transmembrane pressure | alarm indicator flashes main alarm lamp flashes | sounds | yes | no | no control function |

| Monitor/alarm | Visual Indication | Audible Indication | Silence available? | Reset required? | Machine action |
|---|---|---|---|---|---|
| heparin pump overspeed | alarm indicator flashes main alarm lamp flashes OVERSPEED | sounds | yes | yes | shuts off heparin pump |
| heparin pump overpressure | alarm indicator flashes main alarm lamp flashes OVERPRESSURE | sounds | yes | no | shuts off heparin pump |
| UF removed (target UF obtained) | alarm indicator flashes main alarm lamp flashes | sounds (5 rapid beeps) | yes | no | UF rate 0 L/h (off) |
| Elapsed time (prescribed time met) | alarm indicator flashes main alarm lamp flashes | sounds (5 rapid beeps) | yes | no | UF rate 0 L/h (off) |
| power off | control panel and all lamps off | sounds | yes | no | no control function |
| BYPASS HAS FAILED bypass | displayed in bulletin window main alarm lamp flashes | sounds | yes | call service technician | machine shutdown occurs instructs operator to turn off power. |
| BLOOD PUMP STOP ALARM blood pump stop | displayed in bulletin window main alarm lamp flashes | sounds | yes | no | no control function |

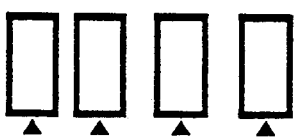

Theory

The System 1000 is a dialysis delivery system that combines the functions necessary for a dialysis treatment with volumetric ultrafiltration control, bicarbonate dialysis and sequential ultrafiltration.

The normal progression of the machine operation for a dialysis treatment is Power On, Standby, Rinse, Self Test, Prime, and Dialyze. After dialysis (and the patient disconnected), the treatment data is recorded, the fluid path is rinsed, and the fluid path is disinfected as required.

*Standby Mode*

When turned on, the machine powers up and enters the Standby Mode. Although this is a "safe" mode (the blood pump will not operate and the dialyzer circuit is bypassed), the machine is waiting for instruction from the operator.

*Rinse Mode*

Rinse is initiated by touching the RINSE then RINSE VERIFY buttons. Rinse is provided to heat the dialysate, introduce chemicals into the machine (either dialysate concentrates or disinfectants) or rinse chemicals from the machine. The audio alarm is muted except for power fail and no dialysate flow alarms. The line clamp remains open and the blood pump will operate as long as the dialyzer connectors are on the rinse block. This gives the operator the option of priming the blood side of the dialyzer during Rinse. The air detector and blood leak detector alarm machine functions are automatically disabled. The arterial pressure alarm limits are automatically set to −400 and +600 mmHg. The venous pressure alarm limits are automatically set ±200 mmHg around the pressure indicated 10 seconds after the blood pump starts, stops or the blood pump rate is changed.

After rinsing the fluid path with water, the concentrate(s) is/are connected to the machine. When the conductivity and temperature are within normal operating range and stable, the operator initiates the Self Test routine by touching the SELF TEST button.

*Self Test Mode*

During Self Test, the machine automatically performs the machine related pre-dialysis "operator tests." The essential alarms, monitors and functions are checked during rinse, such as the conductivity alarms, UF system, arterial and venous pressure monitoring systems, etc. At the beginning of Self Test, the operator is prompted to verify that the arterial and venous pressure luers are plugged, an audio alarm occurs, and the main alarm lamp flashes. A few minutes later, at the end of Self Test the operator is again prompted: IS CONDUCTIVITY CORRECT? At this time the operator verifies the conductivity by withdrawing a sample of dialysate from the dialyzer circuit sample port and performing an independent conductivity check with an external meter. The primary conductivity alarm limits are automatically set by the machine to ±5% of the indicated conductivity value when the YES button is touched to verify the dialysate conductivity.

*Prime Mode*

Upon successful completion of the Self Test, the operator initiates the Prime Mode by touching the PRIME button. During Prime, the extracorporeal alarm may be disarmed by the operator to allow the removal of air from the dialysate and blood sides of the dialyzer. The machine will remain in disarm for approximately 5 minutes, permitting priming of the blood lines and dialyzer. While the alarms are disarmed, the arterial pressure alarm limits are −400 and +600 mmHg, the venous pressure alarm limits are ±200 around the indicated venous pressure 10 seconds after the blood pump is turned on, off or the rate changed. The air and blood leak detector machine responses are disabled (except for the visual indicator).

While the extracorporeal alarms are armed, the alarms are active and the arterial and venous pressure alarm limits are ±50 mmHg around the indicated pressure 10 seconds after the blood pump is turned on or off or the rate is changed. The operator sets the prescribed dialysis time and the target fluid loss in the Prime Mode. However the manual UF rate set in Prime (0.01 to 0.5 L/h) will override the calculated UF rate until the START button is touched and the treatment is begun.

*Dialyze Mode*

The START button is touched to start the Dialyze Mode. The patient is connected and the dialysis treatment is performed in the Dialyze Mode. The machine automatically calculates the UF rate from the operator set PRESCRIBED TIME and TARGET UF. The ELAPSED TIME and the UF REMOVED are recorded and displayed. The alarms are functional. The arterial alarm limits open, for approximately 10 seconds, to −400 and +600 when the blood pump is started or the blood pump rate is changed. The venous alarm limits open, for approximately 10 seconds, to ±200 mmHg around the indicated pressure. After the 10 seconds, the alarm limits automatically set to ±50 mmHg of the indicated pressure. The minimum low venous alarm limit is +10 mmHg. When the blood pump is manually turned off, the arterial and venous alarm limits automatically open. The TMP alarm limits open to ±200 mmHg around the indicated TMP, for approximately 90 seconds, when the blood pump is started, the blood pump rate is changed or the UF rate is changed. After the 90 seconds, the alarm limits automatically set to ±35 mmHg of the indicated TMP. The minimum low TMP alarm limit is −80 mmHg. The maximum high TMP alarm limit is +500 mmHg. The arterial and venous alarm limits may be manually set to ±50 mmHg and the TMP alarm limits may be manually set to ±35 mmHg of the indicated pressures by touching the SET LIMITS button.

When the target fluid loss is reached, the main alarm lamp flashes, the audio alarm sounds five quick beeps, the UF REMOVED alarm indicator flashes and the UF rate goes to 0 L/h.

After the treatment is completed and the patient disconnected from the dialyzer and blood lines, the treatment data should be recorded from the data report prior to entering the Rinse Mode. While the dialyzer connectors are on the rinse block, the Rinse Mode is initiated. The machine may now be prepared for another patient or rinsed with water in preparation for disinfection and shutdown.

Ultrafiltration

The System 1000 accurately controls fluid removal. A volumetric flow equalizer controls and balances dialysate to and from the dialyzer. The volume of fresh dialysate measured and delivered to the dialyzer by the pre side of the flow equalizer is equal to the volume of used dialysate removed from the dialyzer by the post side of the flow equalizer.

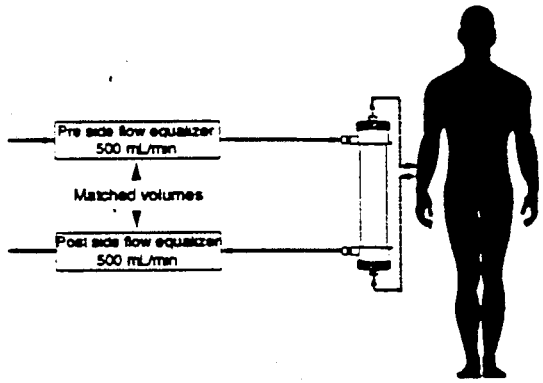

Between the balanced pre and post flow equalizers are two openings. One is the dialyzer membrane surface, the other is the UF flow meter. The UF flow meter is controlled by the electronics to meter a measured amount of used dialysate from the dialysate compartment. The fluid measured by the UF flow meter causes an identical amount of fluid to be pulled from the blood side of the dialyzer. Since the flow equalizer balances the dialysate flowing to and from the dialyzer, the fluid going through the UF flow meter is equivalent to the ultrafiltrate removed from the patient.

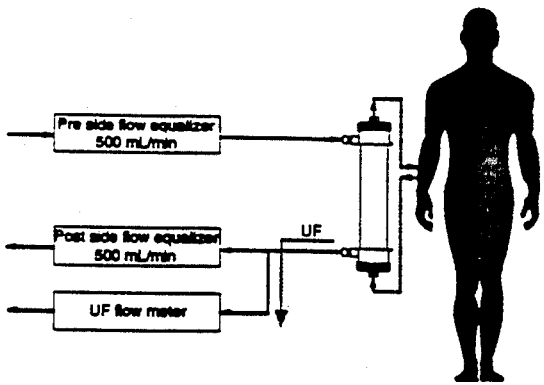

The flow through the UF flow meter is displayed in the UF RATE window and the data report screen. The fluid that passes through the UF flow meter is not entirely ultrafiltrate. It is volumetrically equivalent to the patient's ultrafiltrate. The total volume of fluid removed from the patient is continuously displayed throughout the treatment in the UF REMOVED window.

Ultrafiltration control steps:

*How to enter a UF rate.*

1. During Prime, the operator enters the prescribed treatment time (in hours and minutes) in the PRESCRIBED TIME window and the desired fluid to be removed (in liters) in the TARGET UF window.

2. The machine automatically calculates the hourly UF rate.

Note:
The manual UF rate controls the machine in the Prime Mode. Once the Dialyze Mode is started the calculated UF rate is displayed and controls the machine.

3. The desired volume of fluid is removed from the patient's blood.

4. The total volume of fluid removed (in liters) is displayed continuously in the UF REMOVED window.

The operator may manually override the calculated UF rate by manually entering the desired UF rate once dialysis has started.

Venous and Arterial Pressure Monitors

The monitors indicate pressures in the extracorporeal drip chambers. Whenever the pressure indicator goes outside of the alarm limit window for more than 3 seconds the monitor goes into alarm.

During a venous or arterial blood pressure alarm, the main alarm lamp flashes, the appropriate alarm indicator flashes, the audio alarm sounds, the blood pump stops, the line clamp occludes the venous blood line and the UF rate automatically goes to 0 L/h.

Connected to the venous and arterial luer connectors is an automatic level adjust pump, this pump is used to raise or lower the level of blood in the extracorporeal blood line drip chambers. In Dialyze when the level adjust pump is used, the arterial and venous pressure alarm limits automatically open for approximately 10 seconds. After the 10 seconds they automatically reset to ±50 mmHg of the indicated pressures.

During the standby and rinse modes, the arterial pressure alarm limits are wide open; i.e., -400 to +600 mmHg. The venous pressure alarm limits are set ±200 mmHg around the indicated venous pressure at the beginning of the rinse mode or 10 seconds after the blood pump rate is changed.

During the prime mode (with the extracorporeal alarms armed) and the dialyze mode; when the blood pump is started, manually turned off or rate changed, the arterial pressure alarm limits open to -400 to +600 mmHg and the venous pressure alarm limits open to ±200 mmHg around the appropriate indicated pressure. After 10 seconds the arterial and venous alarm limits close to ±50 mmHg around the respective pressure with the low venous alarm limit being no less than +10 mmHg.

Heparin Pump

The heparin pump is a syringe pump that infuses heparin into the blood flow circuit at an operator-adjustable rate during the prime and dialyze modes. It operates only when the blood pump is on. The heparin pump alarms when the motor is infusing heparin faster than the setting on the device. It also alarms when the heparin syringe is empty or the motor is stalled.

Install the heparin syringe during the prime mode. The heparin pump rate may be set during the Prime or Dialyze Modes. The heparin pump rate may be set from 0 to 5.5 ml/h. Entering a non-zero heparin rate turns on the pump. Entering a zero rate turns off the pump. The words ON and OFF will appear above the HEPARIN PUMP window appropriately.

A heparin bolus may be given by touching the HEPARIN PUMP window then the BOLUS button. The bolus volume is displayed on the BOLUS button. The bolus volume may be calibrated and is displayed on the data report and bolus button.

The heparin pump may set by a qualified service technician to be used with either 10 or 20 ml capacity syringes. The type of syringe for which the machine is calibrated, is indicated in the data report.

Dialysate

Dialysate Flow Rate

The dialysate flow rate may be set from 500 to 1000 ml/min in 100 ml increments by touching the DIALYSATE FLOW RATE window to display the desired flow rate, then touching the FLOW VERIFY button. At startup the flow rate defaults to 500 ml/min.

Dialysate temperature

The dialysate temperature may be set between 35.5 and 39°C. When the machine is turned on, the default temperature setting is 37°C. To enter a different temperature; the operator touches the TEMPERATURE window, enters the desired value in the keypad then touches the keypad ENT button. To restore the existing set temperature, touch the keypad RST button then the ENT button.

Dialysate Preparation/Proportioning

The machine may be set by a qualified service technician to accept dialysate concentrates from one of several mixing ratios. The default proportion is either acetate concentrate requiring 34 parts water to 1 acetate concentrate proportioning, or bicarbonate and acid concentrates requiring 34 water to 1 acid concentrate to 1.8 bicarbonate concentrate containing 59 mEq/L sodium in the bicarbonate concentrate.

The 34:1 or 34:1:1.8 proportioning ratio used by the machine for a particular treatment is determined by the placement of the concentrate lines at the start of the self test routine. If only the acid/acetate concentrate port interlock is open, the machine will proportion for acetate dialysis. If both the acid/acetate and bicarbonate concentrate lines are open, the machine will proportion for bicarbonate dialysis. In order to change the proportioning ratio the machine *must* go into the Rinse Mode.

Other availabe proportioning ratios include 32.77 parts water to 1 part acid concentrate to 1.23 parts bicarbonate concentrate, and 42.6 parts water to 1 part acid concentrate to 1.4 parts bicarbonate concentrate.

Treatment Data

The System 1000 records treatment parameters and data. This data may be obtained by touching the MENUS then DATA REPORT buttons.

Data report information includes prescribed treatment time, elapsed treatment time, treatment time remaining, target UF, UF removed, UF remaining, total blood processed and total heparin infused.

The total heparin infused includes the heparin infused during the Prime and Dialyze Modes.

| | | |
|---|---|---|
| Prescribed Treatment Time | ▪ | h:m |
| Elapsed Treatment Time | ▪ | h:m |
| Treatment Time Remaining | ▪ | h:m |
| Target UF | ▪ | L |
| UF Removed | ▪ | L |
| UF Remaining | ▪ | L |
| Total Blood Processed | ▪ | L |
| Total Infused Heparin | ▪ | ml |
| Syringe type | Bolus size | |
| UF rate | | |
| Concentrate type | | |
| Date | Time of day | |
| Statement about calculated UF rate | | |

Sample Data Report

Keypad

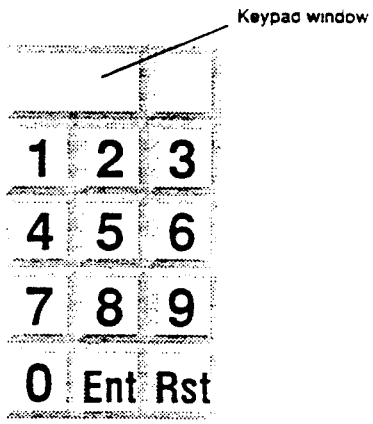

Keypad window

The operator uses a keypad to enter the heparin pump rate, the dialysate temperature, the prescribed treatment time, the target fluid loss, and the manual UF rate as required. The keypad appears when the appropriate monitor window is touched.

A value is entered by touching the appropriate number buttons. The value is displayed in the keypad window. To enter the displayed value, the ENT button is touched. If a mistake is made, touch the RST button to restore the previously set value.

If no change to the set value is required, the operator may touch the RST then ENT buttons or wait approximately 15 seconds for the keypad to disappear without changing the set value.

Operation

This section provides the qualified operator with the recommended operating procedure to be used in the preparation and use of the Drake Willock System 1000 Single Patient Delivery System. There are several possible variations of the pre-dialysis rinse procedure depending upon the disinfection method chosen by the attending physician/center; e.g., overnight disinfection with a chemical or pre-dialysis disinfection with sodium hypochlorite. Regardless of the type of disinfection used, all procedures *must* include the verification of an acceptable level of residual disinfectant by a test specific for the disinfectant used, the verification of the proper dialysate and the pre-dialysis system check.

WARNING: The attending physician is responsible for any changes to the procedures.

Supplies

- Syringe for withdrawing samples of solution from the dialysate line sample port
- Determination test specific for the chemical disinfectant used
- Dialysate meter (or other test recommended by the attending physician) for testing the dialysate
- 10 or 20 mL syringe for the heparin pump
- Container(s) with enough concentrate for the setup and dialysis time
- Hydrophobic transducer protector(s) ▪ to place on the pressure fitting(s)
- Dialyzer ▪
- Blood lines ▪
- Hemostats, 3
- Saline
- Heparin, if prescribed
- Gloves
- Personal safety supplies required by the facility

Pre-Setup

- The patient is disconnected from the blood lines and dialyzer.
- The machine is connected to the water supply and the water is off.
- The drain line is in the drain.
- The power cord is plugged in and the mains power switch is on.
- The front panel power switch is off.
- The acid/acetate concentrate line (pink connector) is connected to the acid/acetate rinse port (pink).
- The bicarbonate concentrate line (blue connector) is connected to the bicarbonate rinse port (blue).
- The disinfect line (yellow connector) is connected to the disinfect rinse port (yellow).
- The dialysate lines are connected to the rinse block.

a  Althin CD Medical recommends the use of Althin CD Medical dialyzers, blood lines and transducer protectors.

Rinse Machine (Before Dialysis)

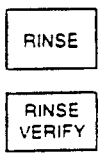

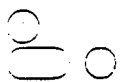

1. Turn on the water supply.

2. Turn on the machine.

To turn on the machine, press the power switch.

3. Initiate the Rinse Mode.

To initiate Rinse, touch the RINSE button, then touch the RINSE VERIFY button (within approximately 3 seconds).

4. Touch the RESET button as required to clear alarms.

5. If the machine had no disinfectant in the fluid path and is to be disinfected, go to step 6.

If the machine had formaldehyde or another disinfectant in the fluid path, go to step 7.

6. Disinfect the fluid path, as required.

Refer to Disinfect Machine Fluid Pathway in the Special Operations section of this manual for specific disinfection procedures.

7. Rinse the disinfectant from the fluid path, as required.

To rinse the fluid path, continue rinsing the fluid path with water for approximately 15 minutes.

Note: The rinse out time may be reduced by increasing the dialysate flow rate.

8. Test the rinse solution for residual disinfectant, as required.

To test for residual disinfectant:

a. Withdraw a sample of the rinse solution from the dialysate lines.

b. Perform a residual disinfectant determination test on the sample.

WARNING: To ensure that the disinfectant level in the dialyzer circuit is below a level acceptable for patient safety, sample the rinse solution in the dialysate lines.

Make sure that the determination test is specific for the disinfectant used.

Make sure that the determination test shows a sufficiently low level of disinfectant in the rinse solution before going on to the next step. Refer to the attending physician's directives for the acceptable limit and the AAMI standard for hemodialysis.

c. Remove the disinfectant warning sign from the machine, as required.

9. Connect the concentrate(s).

WARNING: Make sure there is an adequate supply of concentrate(s) in the containers(s) for the entire dialysis treatment including setup.

For acetate dialysis:

a. Connect the acid/acetate concentrate line (pink connector) to a full container of acetate concentrate.

For bicarbonate dialysis:

a. Connect the acid/acetate concentrate line (pink connector) to a full container of acid concentrate.

b. Connect the bicarbonate concentrate line (blue connector) to a full container of bicarbonate concentrate.

10. After the conductivity and temperature stabilize, initiate the Self Test Mode.

NOTE: If there are any extracorporeal alarms, touch the RESET button to clear the alarms and access the TEST button.

Do not manually turn on the blood pump during Self Test or a blood pump overspeed alarm will occur.

Make sure the machine is not in manual bypass or the self test will fail.

To initiate Self Test, touch the TEST button.

*The machine will prompt the operator for the following information:*

*At the beginning of Self Test,* a. BLD PRESS TEST: ARE PRESS LUERS PLUGGED?

If the blood lines have been set up, make sure the pressure monitor lines are clamped with hemostats, then touch the YES button.

If the blood lines have not been set up, make sure the pressure luers are plugged then touch the YES button.

b. VERIFY AUDIO ALARM/ALARM LAMP?

If there is an audible alarm and the main alarm lamp is flashing, touch the YES button.

*At the end of Self Test,* c. IS CONDUCTIVITY CORRECT?

Test the dialysate.

To test the dialysate:

1) Obtain a sample of dialysate from the dialysate line sample port.

2) Perform a dialysate determination test on the sample. Make sure that the instrument used to perform this test has been calibrated for accuracy.

3) Make sure that the conductivity value is appropriate for the concentrates being used.

4) If the displayed conductivity matches the independent test value, touch the YES button.

If the displayed conductivity does not match the independent test value, touch the NO button and refer to the Problem Solving section of this manual.

d. ARE PRESSURE LUERS VENTED?

Unplug/unclamp the pressure luers.

11. Set up the dialyzer and blood lines, as required.

12. Initiate the Prime Mode.

To initiate Prime, touch the PRIME button.

13. Prime the dialyzer and blood lines.

Refer to your center's procedures for detailed actions.

To prime the dialyzer and blood lines:

a. Touch the ARMED / DISARM button to disarm the extracorporeal alarms.

b. Touch the RESET button, as required.

c. Set the blood pump flow rate.

d. Turn on the blood pump, as required.

e. Set a manual UF rate, as required.

To connect the dialyzer connectors to the dialyzer:

a. Press the manual bypass button.

b. Connect the dialyzer connectors to the appropriate dialyzer ports.

c. Press the manual bypass button.

To load the heparin pump:

a. Fill the syringe with heparin.

b. Connect the heparin line to the syringe.

c. Clamp the heparin line but do not prime the line.

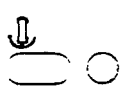

14. Set the treatment parameters; i.e., prescribed dialysis time and desired fluid loss.

To set the prescribed dialysis time:

a. Touch the PRESCRIBED TIME window.
    b. Use the keypad to input the prescribed dialysis time in hours and minutes.
    c. Touch the keypad ENT button to enter the prescribed dialysis time as displayed in the keypad window.

To set the desired fluid loss:

a. Touch the TARGET UF window.
    b. Use the keypad to input the desired fluid loss in liters.
    c. Touch the keypad ENT button to enter the fluid loss as displayed in the keypad window.

15. Turn off the blood pump, as required.

Start Dialysis

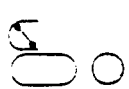

Note: If an extracorporeal alarm exists, clear and reset the alarm before touching the START button.

1. Touch the START button (button #5).

Use your center's procedures for detailed actions, beginning dialysis includes turning on the blood pump and setting the correct flow rate.

If a UF rate lower than the calculated rate is desired at treatment initiation, enter a low manual UF rate before turning on the blood pump. Otherwise the calculated UF rate will start as soon as the blood pump starts.

Note: When the blood pump is off and a manual rate is entered, the UF rate is displayed as OFF. When the blood pump starts, the UF rate automatically goes to the manual UF rate entered.

To initiate heparin infusion:

a. Unclamp the heparin line.
b. Set the heparin infusion rate.
   1) Touch the HEPARIN PUMP window.
   2) Enter the desired infusion rate in milliliters per hour using the keypad.
c. With the blood pump on, give a heparin bolus.
   1) Touch the HEPARIN PUMP window.
   2) Then touch the BOLUS button.

Discontinue Dialysis

1. Discontinue dialysis.

Return the extracorporeal blood to the patient, turn off the blood pump, clamp the blood lines and disconnect the blood lines from the patient.

If a minimum UF rate (other than zero) is desired for returning the patient's blood after the target UF is reached:

a. Enter a new target UF higher than the current UF removed.
   b. *Immediately* enter the specific manual UF rate desired.

Use your center's procedure for detailed actions.

WARNING: Make sure that the patient is disconnected from the dialyzer and blood lines before going on to the next step.

2. Record the treatment data from the data report before initiating rinse.

Note: Starting the Rinse Mode erases portions of the data report.

3. Disconnect the dialysate lines from the dialyzer and connect them to the machine rinse block.

a. Press the manual bypass button.
   b. Connect the dialyzer connectors to the rinse block.
   c. Press the manual bypass button.

4. Start the Rinse Mode.

Prepare Machine for Another Patient (if required)

1. Make sure there is an adequate supply of concentrate(s) in the containers(s) for the entire dialysis treatment including setup.
2. Continue the predialysis preparation by completing Rinse Machine (Before Dialysis) steps 10 through 15.

Rinse Machine (After Dialysis)

1. Connect the concentrate lines to the machine.

After acetate dialysis, connect the acid/acetate concentrate line (pink connector) to the acid/acetate rinse port (pink).

After bicarbonate dialysis, connect the bicarbonate concentrate line (blue connector) to the bicarbonate rinse port (blue), then connect the acid/acetate concentrate line (pink connector) to the acid/acetate rinse port (pink).

2. Rinse the machine with water for 10 minutes.

Note: Higher dialysate flow rates will shorten the rinse time.

CAUTION: Be sure to rinse the machine with water before introducing new chemicals into the fluidpath. Otherwise, precipitates or other deposits in the flowpath may result from reactions of various chemical mixtures.

3. If the machine is to be disinfected, refer to Disinfect Machine Fluid Pathway in the Special Operations section of this manual.

If the machine is to be turned off, go to step 4.

4. Turn off the machine.

To turn off the machine, press the front panel power switch. Turn off the mains power switch at night.

5. Turn off the water supply.

Special Operations

This section provides detailed instructions on the specialized functions of the System 1000 machine.

Control Ultrafiltration

The System 1000 automatically calculates and maintains the ultrafiltration removal rate from the prescribed treatment time and the total ultrafiltrate to be removed.

The operator enters the prescribed treatment time in the PRESCRIBED TIME window and the desired fluid to be removed in the TARGET UF window. The machine automatically calculates the UF rate. The desired volume of fluid is removed from the patient's blood. The total volume of fluid removed (in liters) is displayed continuously in the UF REMOVED window.

To set the prescribed dialysis time:

a. Touch the PRESCRIBED TIME window.
b. Use the keypad to input the prescribed dialysis time in hours and minutes.
c. Touch the keypad ENT button to enter the prescribed dialysis time as displayed in the keypad window.

To change the prescribed dialysis time after dialysis has started:

a. Touch the ELAPSED TIME window.
b. Use the keypad to input the prescribed dialysis time in hours and minutes.
c. Touch the keypad ENT button to enter the prescribed dialysis time as displayed in the keypad window.

If the previously set treatment time is to be restored, touch the RST then the ENT buttons.

To set the desired fluid loss:

a. Touch the TARGET UF window.

b. Use the keypad to input the desired fluid loss in liters.

c. Touch the keypad ENT button to enter the fluid loss as displayed in the keypad window.

To change the desired fluid loss after dialysis has started:

a. Touch the UF REMOVED window.

b. Use the keypad to input the new desired fluid loss in liters.

c. Touch the keypad ENT button to enter the fluid loss as displayed in the keypad window.

If the previously set desired fluid loss is to be restored, touch the RST then ENT buttons.

To set a manual UF rate (as in response to a hypotensive episode):

a. Touch the UF RATE window.

b. Use the keypad to input the desired UF rate in liters per hour.

c. Touch the keypad ENT button to enter the UF rate as displayed in the keypad window.

To return to the calculated UF rate from a manual UF rate after dialysis has started:

a. Touch the UF REMOVED window. The previously set desired fluid loss is displayed in the keypad window.

b. Touch the keypad ENT button to re-enter this desired fluid loss.

Automatically the UF rate will change to the calculated value.

To continue removing a minimal amount of fluid from a patient after the target UF has been reached (Operator can not get to the patient for a few minutes to discontinue dialysis.):

a. Touch the UF REMOVED window.

b. Determine the new desired target fluid loss.

New target UF = target UF that has already been removed + maximum amount of additional fluid to be removed from the patient c. Use the keypad to input the new target UF.

d. Touch the keypad ENT button to enter the fluid loss as displayed in the keypad window.

e. *Immediately*, set the manual minimum UF rate.

WARNING: If the manual UF rate is not set immediately, a very high calculated UF rate will be set since the prescribed treatment time has been met or only a small amount of time remains.

Heparin

To set or change the heparin pump infusion rate:

a. Touch the HEPARIN PUMP window.

b. Use the keypad to input the heparin pump infusion rate.

c. Touch the keypad ENT button to enter the heparin pump infusion rate.

If the previously set heparin pump rate is to be restored, touch the RST then ENT buttons.

To stop infusion / Turn off the heparin pump:

a. Touch the HEPARIN PUMP window.

b. Use the keypad to input a .0 heparin pump infusion rate.

c. Touch the keypad ENT button.

To infuse a heparin bolus:

> Note:
> The bolus size, either 0.5 or 1 ml, is set by the service technician a. Touch the HEPARIN PUMP display.

b. Touch the BOLUS button.

To determine the total heparin infused:

a. Touch the MENUS button.

b. Touch the DATA REPORT button.

c. Note the TOTAL INFUSED HEPARIN.

Blood Pump

To turn on the blood pump:

a. Press the blood pump power switch. The switch lamp will light.

To set a blood flow rate:

a. Touch the BLOOD PUMP display bar in the area of the desired flow rate. The blood pump speed may be set in 10 ml/min increments.

b. Move your finger sideways slightly until the desired flow rate is visible in the blood pump digital window.

c. Touch the $Q_b$ VERIFY button.

To change blood pump speed:

a. Touch the BLOOD PUMP display bar in the area of the desired flow rate.

b. Move your finger sideways slightly until the desired flow rate is visible in the blood pump digital window.

c. Touch the $Q_b$ VERIFY button.

To determine total blood processed:

a. Touch the MENUS button.

b. Touch the DATA REPORT button.

c. Note the TOTAL BLOOD PROCESSED.

To turn off the blood pump:

a. Press the blood pump power switch. The switch lamp will turn off.

Alarm Limits

To *manually* set the arterial, venous and TMP alarm limits (in dialyze).

a. Touch the SET LIMITS button. The arterial and venous alarm limits will automatically set to ±50 mmHg around the displayed pressures. The minimum low venous alarm limit is +10 mmHg. The TMP alarm limits automatically set to ±35 mmHg around the displayed TMP. The minimum low TMP alarm limit is −80 mmHg. The maximum high TMP alarm limit is +500 mmHg.

To open and re-center the arterial or venous pressure alarm limits:

a. Touch the arterial or venous analog display bar anywhere along the display.

The alarm limits will open and re-center around the displayed value. After approximately 10 seconds the alarm limits will reset to ±50 mmHg of the displayed value.

To determine the primary conductivity alarm limits:

a. Touch the CONDUCTIVITY window.

The primary conductivity alarm limits will be displayed in the window. The primary conductivity alarm limits are set to ±5% of the displayed conductivity value when the conductivity is verified by the operator during Self Test.

To determine the TMP alarm limits:

a. Touch the TMP window.

The TMP alarm limits will be displayed in the window. During dialyze, the TMP alarm limits are set to ±35 mmHg of the displayed TMP value approximately one minute after the blood pump is turned on, the blood pump rate changed, or the UF rate changed. The minimum low TMP alarm limit is -80 mmHg. The maximum high TMP alarm limit is +500 mmHg.

To open and re-center the arterial, venous and TMP alarm limits:

a. Touch the RESET button.

The alarm limits will open and re-center around the displayed value. After approximately 10 seconds the arterial and venous alarm limits will reset to ±50 mmHg of the displayed value. The TMP alarm limits will reset to ±35 mmHg of the displayed value.

Dialysate Flow Rate

The dialysate flow rate may be set from 500 to 1000 ml/min in 100 ml increments.

To set the dialysate flow rate:

a. Touch the DIALYSATE FLOW window.

b. Touch the window repeatedly until the desired flow rate is indicated in the window.

c. When the desired flow rate is displayed press the $Q_d$ VERIFY button.

Dialysate Temperature

The dialysate temperature may be set between 35.5 and 39°C. When the machine is turned on, the default temperature setting is 37°C.

To change the dialysate temperature:

a. Touch the TEMPERATURE display.

b. Use the keypad to input the desired dialysate temperature between 35.5 and 39°C.

c. Touch the keypad ENT button to enter the desired temperature as displayed in the keypad window.

If the previously set dialysate temperature is to be restored, touch the RST then ENT buttons.

Help Window

To view the help window:

a. Touch the HELP button.

To close the help window:

a. Touch the HELP or MAIN SCREEN button.

Data Report

To view the data report:

a. Touch the MENUS button.

b. Touch the DATA REPORT button.

To close the data report:

a. Touch the DATA REPORT or MAIN SCREEN button.

Disinfect Machine Fluid Pathway

Alternative disinfection methods are provided for disinfecting the fluid path. Althin CD Medical, Inc. recommends that regular cultures be taken of the dialysate to ensure that the bacterial level in the dialysate is acceptable.

With formaldehyde:

Supplies
- Gloves resistant to the disinfectant
- Formaldehyde (37% formaldehyde solution or "Formalin"), USP grade or better.

Preconditions
- The patient is disconnected from the dialyzer and blood lines.
- The machine is in rinse and has been rinsed for at least 10 minutes prior to infusing formaldehyde.

Procedure

WARNING: Be careful when handling formaldehyde. Read and follow the instructions for the safe handling of formaldehyde on the warning label on the formaldehyde bottle and follow your center's guidelines for use.

1. Connect the disinfect line (yellow connector) to a container of 37% formaldehyde.
2. Connect the acid/acetate concentrate line (pink connector) to the disinfect rinse port (yellow).
3. Infuse formaldehyde into the fluid path for approximately 15 minutes.
4. Obtain a sample of the disinfect solution from the drain line. Make sure that formaldehyde is present in the sample before going on to the next step.
5. Disconnect the machine from the formaldehyde supply.

To disconnect the machine:

a. Connect the acid/acetate concentrate line (pink connector) to the acid/acetate rinse port (pink).
   b. Wait approximately 15 seconds for the disinfect line to drain, then connect the disinfect line (yellow connector) to the disinfect rinse port (yellow).

6. Turn off the machine.

To turn off the machine, press the power switch. Turn off the mains switch at night.

7. Label the machine with a formaldehyde warning sign on which the date and time have been recorded.
8. Turn off the water.

WARNING: Formaldehyde must remain in the fluidpath for at least two hours for adequate disinfection.

With sodium hypochlorite (bleach):

Supplies
- Gloves resistant to the disinfectant
- 1.75% solution of sodium hypochlorite Dilute one part household bleach (4 to 6% sodium hypochlorite) with two parts filtered water. This solution should be capped and labeled. This bleach mixture should only be kept for two days and stored in a cool, dark place. Approximately 200 ml of diluted bleach are required each time this procedure is performed.

Preconditions
- The patient is disconnected from the dialyzer and blood lines.
- The machine is in rinse and has been rinsed for at least 10 minutes prior to infusing bleach.

Procedure

1. Connect the disinfect line (yellow connector) to a container of 200 ml of 1.75% bleach solution.
2. Connect the acid/acetate concentrate line (pink connector) to the disinfect rinse port (yellow).
3. Allow diluted bleach to infuse into the fluid path for 15 minutes.
4. After the 15 minutes, disconnect the machine from the bleach supply.

To disconnect the machine:

a. Connect the acid/acetate concentrate line (pink connector) to the acid/acetate rinse port (pink).

b. Wait approximately 15 seconds for the disinfect line to drain, then connect the disinfect line (yellow connector) to the disinfect rinse port (yellow).

6. Rinse the machine until it is free of bleach.

7. After 15 minutes, obtain a sample of the rinse solution and check for residual sodium hypochlorite.

a. Check for residual bleach content with a test specific for sodium hypochlorite.

b. If the residual bleach content is within acceptable limits, the machine can be prepared for dialysis. If the machine is not within acceptable limits continue to rinse the machine until the level is acceptable.

WARNING: Make sure that the determination test shows a sufficiently low level of disinfectant in the rinse solution before dialysis. Refer to the attending physician's directives for the acceptable limit and the AAMI standard for hemodialysis.

To ensure that the disinfectant level in the dialyzer circuit is below a level acceptable for patient safety, sample the rinse solution in the dialysate lines.

Make sure that the determination test is specific for the disinfectant used.

Note: If the machine is to remain idle for an extended period of time, keep the machine rinsing until beginning preparation for dialysis With Actril* solution:

Supplies
- Gloves resistant to the disinfectant
- Actril* solution, approximately 200 ml
  - *Trademark of Renal Systems
- Actril residual test strips
- Actril Relative indicator strips Preconditions
- The patient is disconnected from the dialyzer and blood lines
- The machine is in rinse and has been rinsed for at least 10 minutes prior to infusing a disinfectant.

Procedure

WARNING: Be careful when handling disinfectants. Read and follow the instructions for the safe handling of disinfectants on the warning label on the bottle.

1. Connect the disinfect line (yellow connector) to a container of Actril solution.

Refer to the disinfectant labeling for detailed instructions.

2. Connect the acid/acetate concentrate line (pink connector) to the disinfect rinse port (yellow).

3. Infuse disinfectant into the fluid path for approximately 15 minutes.

4. Test for the presence of Actril at the drain line.

a. Take a sample from the drain line.

b. Test the sample using the directions given on the Actril Relative Indicator Test Strips container.

c. Continue infusing Actril solution as required.

5. After the needed infusion, turn off the machine.

6. Disconnect the machine from the Actril supply.

To disconnect the machine:

a. Connect the acid/acetate concentrate line (pink connector) to the acid/acetate rinse port (pink).

b. Wait approximately 15 seconds for the disinfect line to drain, then connect the disinfect line (yellow connector) to the disinfect rinse port (yellow).

7. Label the machine with a disinfectant warning sign on which the date, time and type of disinfectant have been recorded.

8. Allow the Actril solution to remain in the fluid pathway for at least 30 minutes.

WARNING: Make sure that the disinfectant remains in the fluid pathway long enough for adequate disinfection. Refer to the chemical disinfectant manufacturer's labeling for detailed information.

9. Before the next use, rinse the fluid pathway for at least 10 minutes with water.

10. Test a dialyzer circuit sample of rinse solution for the presence of Actril.
    a. Withdraw a sample of the rinse solution from the dialyzer circuit.
    b. Test the sample for residual disinfectant using Actril Residual Test Strips. Refer to the Actril labeling for detailed actions.

WARNING: Make sure that the determination test shows a sufficiently low level of disinfectant in the rinse solution before dialysis. Refer to the attending physician's directives for the acceptable limit, the chemical disinfectant manufacturer's labeling and the AAMI standard for hemodialysis.

To ensure that the disinfectant level in the dialyzer circuit is below a level acceptable for patient safety, sample the rinse solution in the dialysate lines.

Make sure that the determination test is specific for the disinfectant used.

With Nephrex° solution:

Supplies
- Gloves resistant to the disinfectant
- Nephrex° HD disinfecting solution concentrate
  ° Trademark of Surgeon
- Nephres HD disinfecting solution effectiveness test kit
- Nephrex residual test kit Preconditions
- The patient is disconnected from the dialyzer and blood lines.
- The machine is in rinse and has been rinsed for at least 10 minutes prior to infusing a disinfectant.
- Fresh activated Nephrex concentrate has been prepared by adding 3 ml of activator to 150 ml of concentrate. Refer to the Nephrex labeling for detailed actions.

Procedure

WARNING: Be careful when handling disinfectants. Read and follow the instructions for the safe handling of disinfectants on the warning label on the bottle.

CAUTION: Use activated Nephrex concentrate within one hour of preparation.

1. Connect the disinfect line (yellow connector) to a container of activated Nephrex concentrate.

Refer to the disinfectant labeling for detailed instructions.

2. Connect the acid/acetate concentrate line (pink connector) to the disinfect rinse port (yellow).

3. Infuse disinfectant into the fluid path for approximately 15 minutes.

4. Test for the presence of Nephrex at the drain line.
   a. Take a sample from the drain line.
   b. Test the sample using the directions given on the Nephrex disinfecting solution effectiveness kit container.
   c. Continue infusing Nephrex solution as required.

5. Infuse unactivated Nephrex concentrate for approximately 3 minutes.
   a. Disconnect the disinfect line from the activated Nephrex supply.
   b. Connect it to a container of unactivated Nephrex concentrate (approximately 50 ml).

CAUTION: Undiluted (unproportioned) activated Nephrex may form a gel or gummy solid after prolonged storage.

6. After the needed infusion, turn off the machine.
7. Disconnect the machine from the unactivated Nephrex supply.

To disconnect the machine:
   a. Connect the acid/acetate concentrate line (pink connector) to the acid/acetate rinse port (pink).
   b. Wait approximately 15 seconds for the disinfect line to drain, then connect the disinfect line (yellow connector) to the disinfect rinse port (yellow).

8. Label the machine with a disinfectant warning sign on which the date, time and type of disinfectant have been recorded.
9. Allow the Nephrex solution to remain in the fluid pathway for at least 15 minutes.

WARNING: Make sure that the disinfectant remains in the fluid pathway long enough for adequate disinfection. Refer to the chemical disinfectant manufacturer's labeling for detailed information.

10. Before the next use, rinse the fluid pathway for at least 10 minutes with water.
11. Test a dialyzer circuit sample of rinse solution for the presence of Nephrex.
    a. Withdraw a sample of the rinse solution from the dialyzer circuit.
    b. Test the sample for residual disinfectant using Nephrex residual test kit. Refer to the Nephrex labeling for detailed actions.

WARNING: Make sure that the determination test shows a sufficiently low level of disinfectant in the rinse solution before dialysis. Refer to the attending physician's directives for the acceptable limit, the chemical disinfectant manufacturer's labeling and the AAMI standard for hemodialysis.

To ensure that the disinfectant level in the dialyzer circuit is below a level acceptable for patient safety, sample the rinse solution in the dialysate lines.

Make sure that the determination test is specific for the disinfectant used.

Clean and disinfect machine external surfaces

Supplies
- Mild detergent solution, such as a mild dishwashing liquid in water
- Diluted bleach solution [4 part household bleach (5.25% sodium hypochlorite) and 126 parts cold water], for example, 40 ml household bleach and 1260 ml cold water
- Gloves resistant to the disinfectant Procedure 1. Wipe off surface soil, as required, with a mild detergent solution.
2. Wipe all external surfaces with diluted bleach solution.
3. Wipe all external surfaces with plain water.

CAUTION: Do not use other disinfecting agents or allow diluted bleach to dry on the external surfaces or damage may result.

Keypad

To access the keypad

Touch the desired monitor window; i.e., TEMPERATURE, HEPARIN RATE, PRESCRIBED TIME, ELAPSED TIME, TARGET UF, UF REMOVED, UF RATE.

To enter a value

1. Touch the number button for the first digit in the number.

The number will be displayed in the keypad window.

2. Touch the number button for the second digit.

The second digit will be displayed to the right of the first digit.

3. Continue the above steps for the required number of digits.

4. When the correct value is displayed in the keypad window, touch the ENT button to enter the value.

If a mistake is made in entering a number, touch the RST button. The last set monitor value will be displayed in the keypad window. Now enter the new number as above.

Examples:

To enter a heparin rate of 2.5 ml/h:

1. Touch the HEPARIN PUMP window.

2. Touch the 2 button.

The keypad window displays:  | .2 |

3. Touch the 5 button.

The keypad window displays:  | 2.5 |

4. Touch the ENT button.

The HEPARIN PUMP window displays:  | 2.5 |

To enter a dialysate temperature of 38.5°C:

1. Touch the TEMPERATURE window.

2. Touch the 3 button.

The keypad window displays:  | .3 |

3. Touch the 8 button.

The keypad window displays:  | 3.8 |

4. Touch the 5 button.

The keypad window displays:  | 38.5 |

5. Touch the ENT button.

The TEMPERATURE window displays the actual dialysate temperature.

To enter a prescribed treatment time of 3 hours and 5 minutes:

1. Touch the PRESCRIBED TIME or ELAPSED TIME window.

2. Touch the 3 button.

The keypad window displays:  | :03 |

2. Touch the 0 button.

The keypad window displays:  | :30 |

3. Touch the 5 button.

The keypad window displays:  | 3:05 |

4. Touch the ENT button.

The PRESCRIBED TIME window displays:  | 3:05 |

If dialysis has started, the ELAPSED TIME window displays the actual elapsed time.

To enter a target fluid loss of 2.35 L:

1. Touch the TARGET UF or UF REMOVED window.

2. Touch the 2 button.

The keypad window displays:  | .02 |

3. Touch the 3 button.

The keypad window displays:  | .23 |

4. Touch the 5 button.

The keypad window displays: 

5. Touch the ENT button.

The TARGET UF window displays: 

If dialysis has started, the UF REMOVED window displays the actual fluid volume removed.

To enter a manual UF rate of 0.13 L/h:

1. Touch the UF RATE window.

2. Touch the 1 button.

The keypad window displays: .01

3. Touch the 3 button.

The keypad window displays: 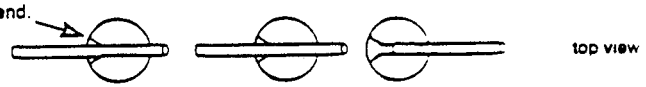

4. Touch the ENT button.

The UF RATE window displays: 

If the blood pump is stopped, the UF RATE window displays .0 L/h until the blood pump starts. When the blood pump starts the window displays MANUAL .13 L/h.

Blood Lines

To load the double blood line clip:

Wide opening end.

top view side view a.   b.   c.

a. With the line between the thumb and clip, press the line into the wide opening end of the slot.

b. With a rolling-sliding motions of the thumb, press the line into the slot.

c. Continue the rolling-sliding motion along the length of the slot.

To remove a line from the double blood line clip:

Wide opening end.

top view side view a.   b.   c.

a. Grasp the line on the wide opening end of the slot.

b. Pull the line out away from the machine and toward the slot.

c. Continue pulling in the direction of the slot until the line is free.

To load the single blood line clip:

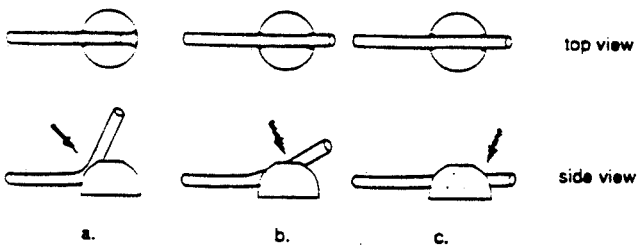

a. With the line between the thumb and clip, press the line into one end of the slot.

b. With a rolling-sliding motions of the thumb, press the line into the slot.

c. Continue the rolling-sliding motion along the length of the slot.

To remove a line from the single blood line clip:

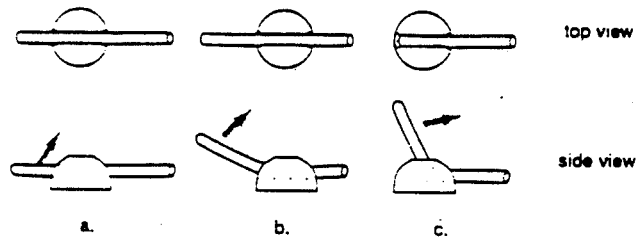

a. Grasp the line on one end of the slot.

b. Pull the line out away from the machine and toward the slot.

c. Continue pulling in the direction of the slot until the line is free.

To load the heparin pump:

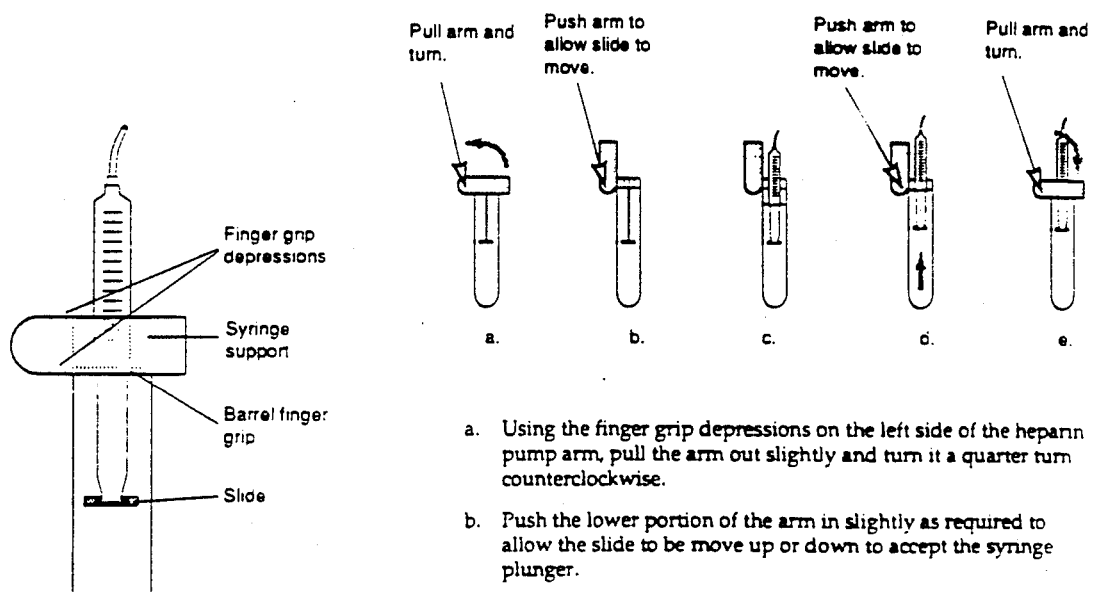

a. Using the finger grip depressions on the left side of the heparin pump arm, pull the arm out slightly and turn it a quarter turn counterclockwise.

b. Push the lower portion of the arm in slightly as required to allow the slide to be move up or down to accept the syringe plunger.

c. Position the syringe plunger in the slide slot.

d. Push the lower portion of the arm in slightly and move the slide with syringe up until the barrel finger grips contact the lower surface of the syringe support.

e. Using the finger grip depressions on the left side of the heparin pump arm, pull the arm out slightly and turn it a quarter turn clockwise. The arm should cover the barrel finger grips.

To load the air detector:

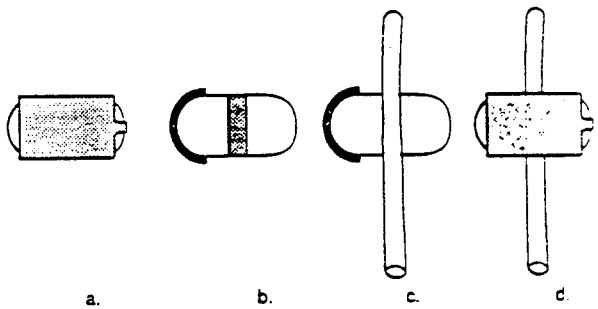

a. Pull the right side of the air detector cover out from the machine.

b. Open the cover.

c. Insert the line in the air detector slot.

d. Close the cover.

To load the line clamp:

WARNING   Be careful not to stick your fingers in the clamping area of the line clamp.

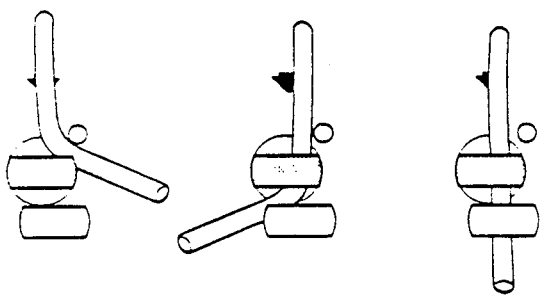

a. Route the blood line to the right between the upper guide and the clamp.

b. Route the blood line to the left between the clamp and the lower guide.

c. Straighten the blood line.

To remove a line from the line clamp:

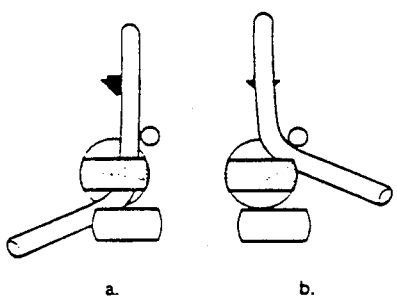

a. Pull the blood line to the left between the clamp and the lower guide.

b. Pull the blood line to the right to remove the line from the clamping area.

To load the blood pump:

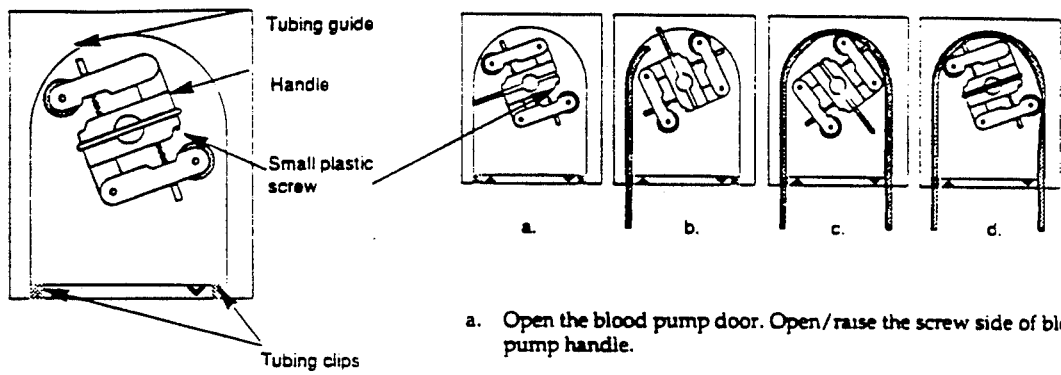

a. Open the blood pump door. Open/raise the screw side of blood pump handle.

b. Route the blood pump segment between blood pump head and the blood pump wall.

c. Rotate the pump head as required and continue loading the pump segment. Make sure the tubing is in the tubing clips and between the tubing guides.

d. Fold the handle and close the blood pump door.

Blood Line Layouts

With prepump arterial drip chamber:

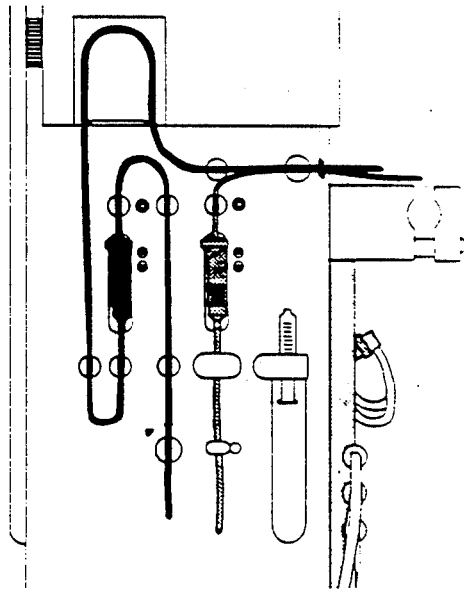

With post pump arterial drip chamber:

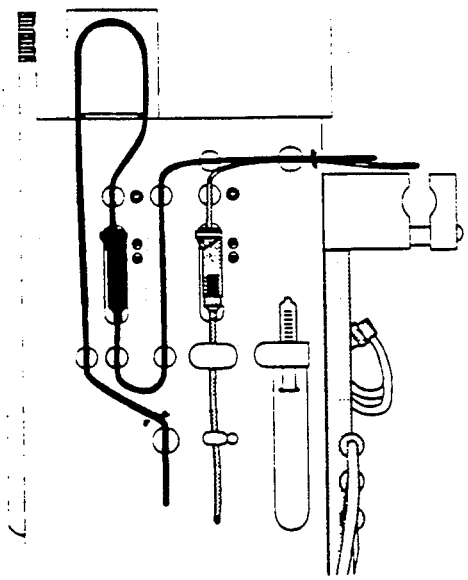

With no arterial drip chamber:

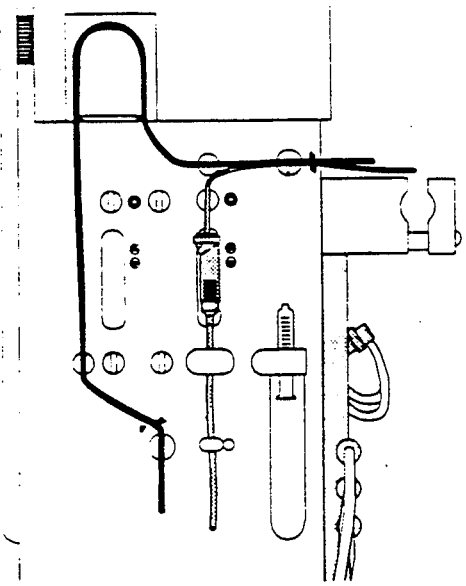

Problem Solving

The following is a list of some operator-correctable problems. If a machine problem occurs, first check this list. If the problem still cannot be corrected, contact a qualified service technician.

WARNING:
Problem solving and repair of this machine should be performed by trained and authorized personnel only. If your center does not have technical personnel trained in the repair of this machine, service may be obtained through Althin CD Medical, Inc. Contact your Field Service Representative.

Patient

Respond to a Hypotensive Episode

Note:
The following procedure should be followed when the operator wishes to quickly minimize the ultrafiltration rate during dialysis.

1. Press the UF RATE window.
2. Use the calculator keypad to input the desired UF rate in liters per hour.
3. Press the calculator ENT button to enter the UF rate as displayed in the calculator window.
4. Treat the patient for hypotension.
   Use a procedure recommended by the attending physician.
5. When indicated, resume dialysis or terminate treatment.
   Follow the attending physician's directives.
   To return to the calculated UF rate:
   a. Press the UF REMOVED window. The previously set desired fluid loss is displayed in the calculator window.
   b. Press the calculator ENT button to re-enter this desired fluid loss.
   To change the desired fluid loss:
   a. Press the UF REMOVED window.
   b. Use the calculator keypad to input the new desired fluid loss in liters.
   c. Press the calculator ENT button to enter the fluid loss as displayed in the calculator window.

Blood Pump

Blood pump will not turn

1. Blood pump door is not fully closed.
   Fully close the blood pump door.
2. Foreign object jammed in the blood pump.
   a. Turn off the blood pump.
   b. Remove the foreign object.
   c. Turn on the blood pump flow.
   d. If it still will not turn, discontinue dialysis according to your center's procedure.
3. OVERSPEED alarm
   a. Turn off the blood pump.
   b. Wait 5 seconds.
   c. Turn on the blood pump.
   d. If you get another overspeed alarm, discontinue dialysis according to your center's procedure.
4. OVERSPEED alarm during the Self Test Mode.
   a. Turn off the blood pump. Do not manually turn on the blood pump during the Self Test Mode.

Self Test

Self Test failed

Note: If the TMP did not pass Self Test, check for air in the fluid path. Remove the air as required. Then repeat Self Test.

1. Start Self Test again.
   a. Make sure the pressure luers are properly plugged and the conductivity is checked with an independent test against a known standard.
   b. Repeat self test.
   c. If the test fails again, have the machine service by a qualified service technician.

Pulse spot

The pulse spot is not flashing

1. Internal machine failure.
   a. Discontinue dialysis according to your center's procedure.
   b. Have the machine service by a qualified service technician.

Air Detector

Air detector alarm

1. Check for air in the blood line.

If there is no air, make sure the line is properly positioned in the air detector.

2. Worn air detector bumper.

Refer replacement of the bumper to a qualified service technician.

Blood Leak Detector

Blood leak alarm

1. Leak in the dialyzer membrane.
   a. Check for the presence of blood in the "from dialyzer" dialysate line.
   b. If no blood is visible, obtain a sample of used dialysate from the sample port.
   c. Verify the presence of blood in the used dialysate, using your center's procedure.
   d. Use your center's procedure for the correct action to take when a minor or major blood leak occurs.
3. The blood detector is dirty.

Have a qualified service technician clean the blood detector.

4. The blood detector LED is burned out.

Have the machine repaired by a qualified service technician.

Air in Dialysate Circuit

Excessive air in circuit

1. Loose or non-sealing dialysate line connector.

Securely attach the connector to the dialyzer. If air is still present, discontinue dialysis.

2. Dialyzer UF coefficient too low for the desired UF rate.
   a. Reduce the UF rate.
   b. Use a dialyzer with an appropriate (larger) UF index.
3. Have a qualified service technician check for a loose fitting.
   a. Inspect the hydraulic circuit for location where air is being drawn in.
   b. Tighten loose fitting.

Ultrafiltration

Weight removed from patient not as expected.

1. Erroneous accounting of patient predialysis weight, food and fluid intake and output during dialysis treatment.

Recalculate the weight to be removed. Closely monitor eating, drinking and elimination during treatment. Be sure to account for priming and rinseback if applicable. Refer to the "UF Control Worksheet" in the Appendix of this manual.

Rinse

Machine will not go into rinse.

WARNING
Make sure that the patient is disconnected from the dialyzer and blood lines before starting the rinse mode.

1. The dialysate lines are not on the rinse block.

Make sure the dialysate connectors are securely connected to the rinse block.

2. The RINSE VERIFY button was not pressed.

Make sure the RINSE VERIFY button is pressed within approximately 5 seconds after the RINSE button is pressed.

Conductivity

Conductivity alarm

1. Concentrate container is empty.

Refill the concentrate container.

2. Open end of concentrate line is not at the bottom of the container.

Place the end of the concentrate line at the bottom of the container.

3. Undissolved bicarbonate salts have settled to the bottom of the container.

Gently shake or rock the container to mix the solution.

4. Concentrate lines in the wrong machine fittings or containers.

Reconnect the concentrate lines to the correct machine fittings and/or containers.

Make sure the correct concentrate is in the container.

For acetate dialysis:

Make sure that acid/acetate concentrate line is connected to a container of acetate concentrate.

Make sure the bicarbonate concentrate line is connected to the bicarbonate rinse fitting.

For bicarbonate dialysis:

Make sure that acid/acetate concentrate line is connected to a container of acid concentrate.

Make sure the bicarbonate concentrate line is connected to a container of bicarbonate concentrate.

Dialysate conductivity not as expected.

1. Using the wrong concentrate(s).

Check the manufacturer's labels on the concentrate containers to make sure that the correct concentrate(s) is being used.

2. Impure water (conductivity higher than expected).

Confirm the purity of the water and proper functioning of the water pretreatment equipment.

3. Wrong concentrate formulation or combination being used.

Check the manufacturer's labels on the concentrate containers to make sure that the concentrate(s) being used will yield the correct dialysate ionic profile as prescribed.

4. Proportioning error.

Call service.

5. Bicarbonate precipitate

Rinse fluid path with vinegar

Power off alarm

1. Power cord is unplugged.

Plug in the power cord.

2. The wall outlet has stopped providing power.

Discontinue dialysis according to your center's "power-loss" procedure.

WARNING:
   Be sure to remove the venous blood line from the line clamp before discontinuing dialysis during a power fail alarm.

Reference

This section describes in detail the use and operation video screen touch panel controls.

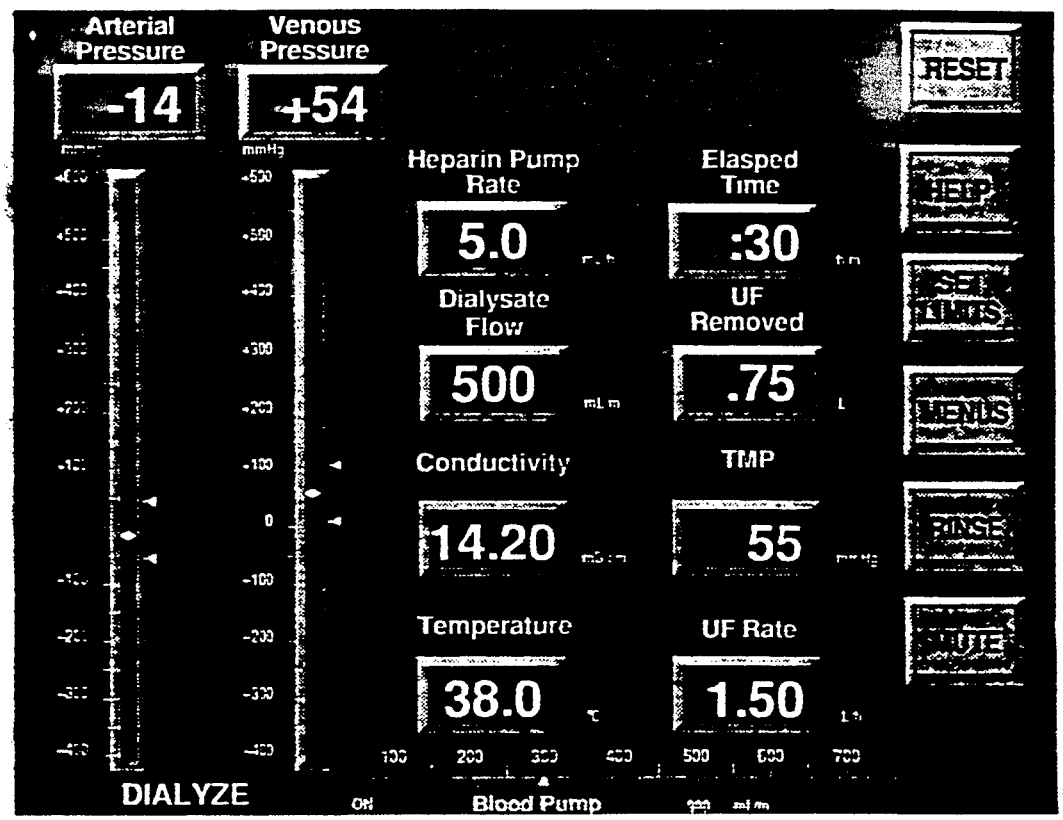

Monitor windows

VENOUS PRESSURE window

Displays the pressure in the venous drip chamber.

ARTERIAL PRESSURE window

Displays the pressure in the arterial drip chamber.

HEPARIN PUMP window

Displays the heparin pump infusion rate.

When the heparin pump is off, OFF is displayed above the window.

DIALYSATE FLOW window

Displays the dialysate flow rate. When the machine is in bypass, BYPASS is flashed above the window.

CONDUCTIVITY window

Displays the conductivity of the dialysate.

Displays the conductivity alarm limits when the CONDUCTIVITY window is pressed.

The window reverts to display the actual conductivity after approximately 10 seconds.

TEMPERATURE window

Displays the temperature of the dialysate.

Displays the minimum and maximum settable temperature when the TEMPERATURE window is pressed.

PRESCRIBED TIME window

> Displays the operator adjusted dialysis treatment time in hours and minutes.
>
> Changes to the ELAPSED TIME window when dialysis is started.

TARGET UF window

> Displays the operator adjusted desired fluid loss in liters.
>
> Changes to the UF REMOVED window when dialysis is started.

TMP window

> Displays the transmembrane pressure as calculated by the blood pressure out minus the dialysate pressure in.
>
> Displays the TMP alarm limits when the TMP window is touched. The TMP alarm limits are active while the machine is in the Dialyze Mode. Approximately one minute after the UF rate is set, the TMP alarm limits close to ±35 mmHg around the actual TMP at that time. If the UF rate is changed, the blood pump stops, starts or blood pump rate changes; the TMP alarm limits open for approximately one minute then close to ±35 mmHg around the actual TMP at that time. The alarm limits may be set manually by pressing the SET LIMITS button.

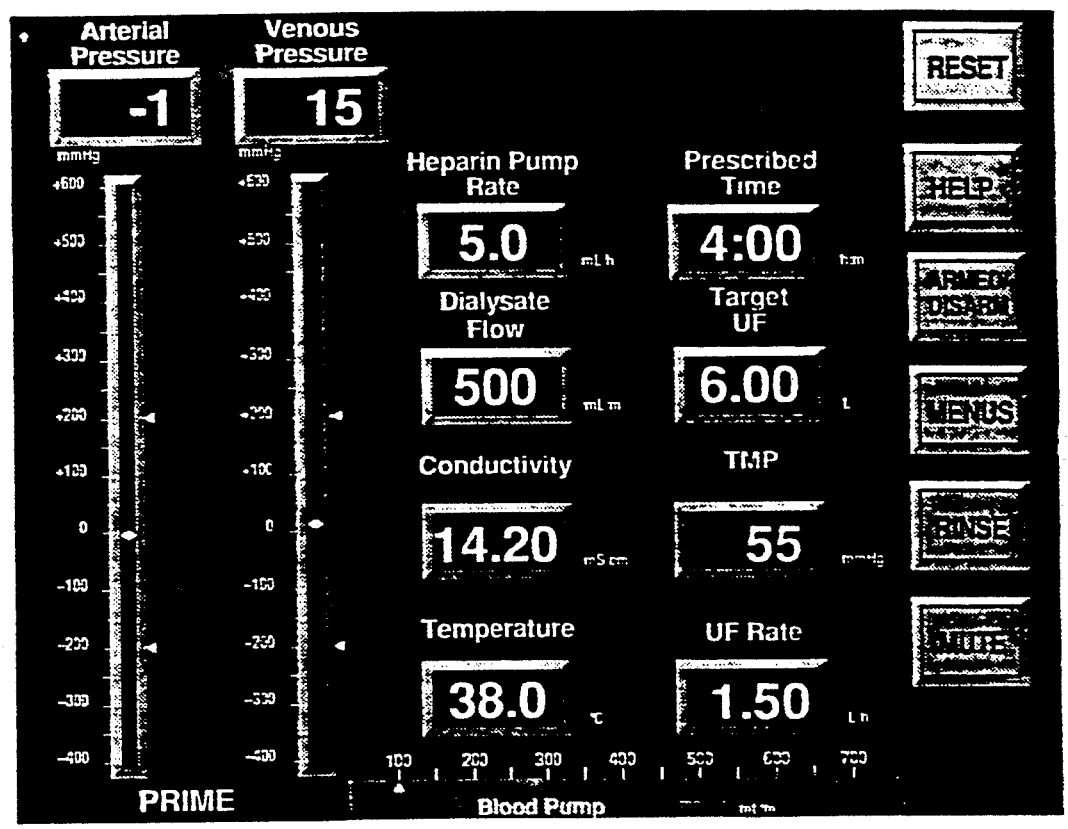

ELAPSED TIME window

> Displays the actual elapsed time after the START button has been touched while the blood pump turned (i.e., periods of time in which the blood pump does not turn are not counted in the displayed value).
>
> Displays the prescribed dialysis time when the window is touched after dialysis has started.

UF REMOVED window

> Displays the actual ultrafiltrate removed after the START button has been touched.

Displays the operator adjusted target fluid loss when the window is touched after dialysis has started.

UF RATE window

Displays the ultrafiltration rate.

The ultrafiltration rate may be set in one of two methods; i.e., manually by entering the operator calculated ultrafiltration rate or indirectly by entering the prescribed dialysis time and target fluid loss with the machine calculating the ultrafiltration rate. When the operator manually enters the ultrafiltration rate MANUAL is displayed above the UF RATE window. When the machine calculates the ultrafiltration rate from the operator inputted dialysis time and target fluid loss, then CALCULATED is displayed above the UF RATE window.

Buttons

The appearance function of the buttons change as required during operation.

RESET button (button #1)

Resets extracorporeal alarm conditions when the alarm situation is corrected.

TEST button (button #1)

Appears, in the rinse mode, when the conductivity and temperature reach the normal operating range. Initiates the Self Test Mode.

PRIME button (button #1)

Appears after the satisfactory completion of the Self Test Mode. Initiates the Prime Mode.

MAIN SCREEN button (button #1)

Appears when the MENUS, PROGRAM or RINSE button is touched (menus, program or rinse screen respectively). Returns the display to the main screen.

SET LIMITS button (button #3)

Sets the arterial pressure, venous pressure and TMP alarm limits in the dialyze mode. The limits will set immediately.

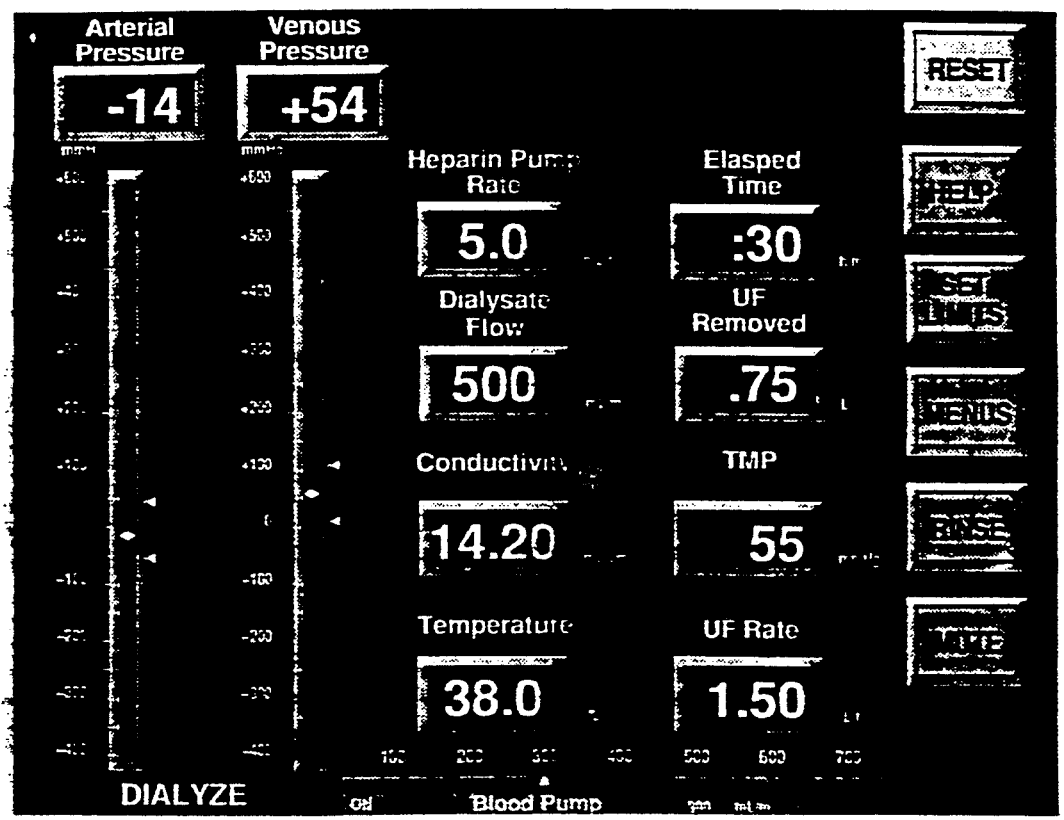

ARMED/DISARM button (button #3)

Disarms the air and blood leak detector alarms and sets the opens the arterial (−400 to +600 mmHg) and venous (±200 mmHg) alarm limits windows during the Prime Mode. The disarm period lasts approximately 5 minutes while the blood pump is on.

While the alarms are disarmed, the ARMED/ DISARM button displays ARMED/ DISARM in dark letters on a light field (reverse). The extracorporeal alarms may be manually rearmed by touching the button while it is displayed in reverse.

After the disarmed period the air and blood leak detector alarms become active and the arterial and venous pressure alarm limits close to ±50 mmHg around the respective indicated pressure.

PROGRAM button (button #3)

Appears when the MENUS button is touched (menus screen). This button will be used for future machine functions.

MENUS button (button #4)

Displays the menus screen with additional control options such as data report and future machine functions.

SND button (button #4)

Appears when the MENUS button is touched (menus screen). This button will be used for future machine functions.

RINSE button (button #5)

Initiates the Rinse Mode when the rinse interlocks are met.

START button (button #5)

Starts the Dialyze Mode.

DATA REPORT button (button #5)

Appears when the MENUS button is touched (menus screen). Displays the data report containing treatment information such as prescribed treatment time, elapsed treatment time, target UF, UF removed, UF remaining, total blood processed and total heparin infused.

MUTE button (button #6)

Silences most audio alarms for approximately 100 seconds.

$Q_b$ VERIFY button (button #7) (Button #7 appears when required.)

Appears when the blood pump display is touched. Sets the blood pump speed to the value indicated in the display. If the $Q_b$ VERIFY button is not touched within approximately − second after the blood pump display was changed, the button will disappear and the blood pump rate will continue at its previous setting.

Qb
VERIFY

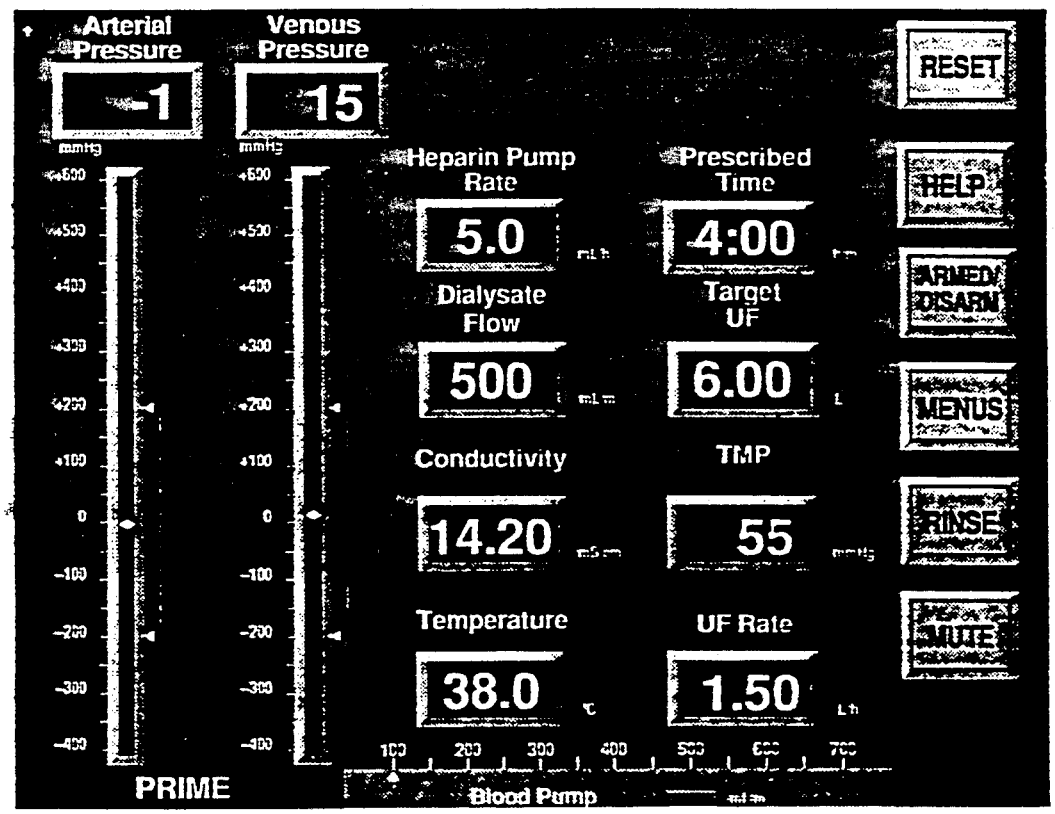

Q_d VERIFY button (button #7) (Button #7 appears when required.)

Appears when the DIALYSATE window is touched. Sets the dialysate flow rate to the value displayed in the window. If the Q_d VERIFY button is not touched within approximately 3 second after the window was pressed, the button will disappear and the dialysate flow rate will continue at its previous setting.

RINSE VERIFY button (button #7) (Button #7 appears when required.)

Appears when the RINSE button is touched and the dialysate lines are on the rinse block. Starts the rinse mode. If the RINSE VERIFY button is not touched within approximately 3 second after the RINSE button was pressed, the verify button will disappear and the machine will continue at its previous mode.

BOLUS button (button #7) (Button #7 appears when required.)

Appears when the HEPARIN PUMP window is touched. Delivers a bolus of heparin. If the BOLUS button is not touched within approximately 3 second after the window was pressed, the button will disappear. The bolus size is set by the service technician, either 0.5 or 1 ml.

Blood pump display

Displays the blood pump setting in milliliters per minute in 10 ml/min increments on an analog scale and in a digital display. The touch sensitive analog scale is used to input the desired blood pump setting.

When the blood pump is off, OFF is displayed in the blood pump display.

When the blood pump is on, ON is displayed in the blood pump display.

Arterial and venous pressure displays and alarm limit indicators

In order to prevent nuisance alarms, the arterial or venous pressure alarm limit must be violated for more than 5 seconds to cause an arterial or venous pressure alarm.

During the Dialyze Mode with the blood pump power switch turned on, the low venous pressure alarm limit will not go below +10 mmHg.

During the rinse mode, the arterial pressure alarm limits are wide open; i.e., −400 to +600 mmHg. The venous pressure alarm limits are set ±200 mmHg around the indicated venous pressure at the beginning of the Rinse Mode.

When the blood pump is started or turned off, or the rate changed, the arterial pressure alarm limits open to −400 to +600 mmHg, the venous alarm limits open to ±200 mmHg around the appropriate indicated pressure. After 10 seconds the alarm limits close to ±50 mmHg around the respective indicated pressure.

The arterial and venous alarm limits may be manually set to ±50 mmHg of the indicated pressures by touching the SET LIMITS button.

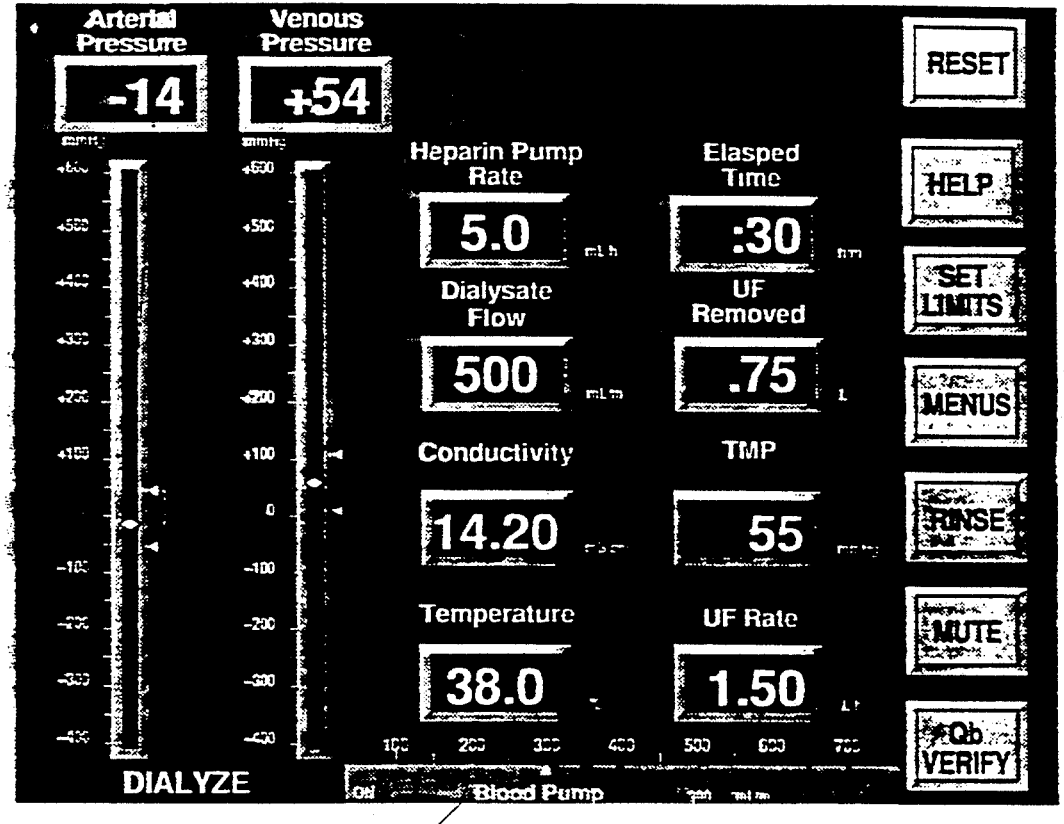

Glossary

Terms

These terms are defined as they apply to hemodialysis and the System 1000. The definitions are not intended to be comprehensive.

Air embolus

An air bubble (bolus or foam) carried by the bloodstream to a vessel small enough to be blocked by the bubble.

Arterial

The portion of the extracorporeal circuit which carries blood from the patient to the dialyzer.

Arterial pressure

Referring to the extracorporeal circuit, the pressure in the arterial drip chamber. The drip chamber may be between the access and the blood pump, thus measuring the pull or suction created by the blood pump, or between the blood pump and the dialyzer, measuring the pressure in the blood line as it enters the dialyzer.

Blood pump

A mechanical device for propelling blood through an extracorporeal circuit, usually by means of rollers compressing special tubing and pushing blood through tubing (peristaltic action).

Button

An area of the touch panel used by the operator to control machine operation.

Concentrate

The concentrated solution of salts which, when diluted with precise amounts of water, forms dialysate.

Conductivity

The ease with which an electric current is carried or conducted; used as a measure of dialysate salt composition.

Conductivity meter

An electronic measuring device which indicates the relative amount of conductive material in solution.

Delivery system

An electro-mechanical device which prepares dialyzing fluid (solution), monitors its preparation, and monitors various parameters of the dialysis treatment.

Dialysate

The dialyzing solution produced by the delivery system by combining precise amounts of water and chemicals. The solution typically includes physiological quantities of sodium chloride, potassium chloride, calcium chloride, magnesium chloride, sodium acetate and/or sodium bicarbonate.

Dialysate pressure

The positive or negative pressure exerted on the membrane in the dialysate compartment of the dialyzer.

Dialyzer

The "artificial kidney" through which blood and dialysate flow, separated by a semi-permeable membrane, allowing dialysis and ultrafiltration to take place.

Disinfectant

A chemical that destroys most micro-organisms.

Drip chamber

An enlarged portion of the blood tubing where air is trapped and pressure can be monitored.

Effluent

The outflow from something (usually liquid); in this application dialyzing fluid that has been "used." It contains solutes not originally present.

Extracorporeal

Outside the body; generally refers to blood being circulated outside the body.

Flowmeter

A device for indicating rate of flow of liquid past a given point.

Gram

The basic unit of weight in the metric system; the weight of one cubic centimeter of water at 4°C.

1000 g = 1 kg; 454 g = 1 lb; 28.4 g = 1 oz

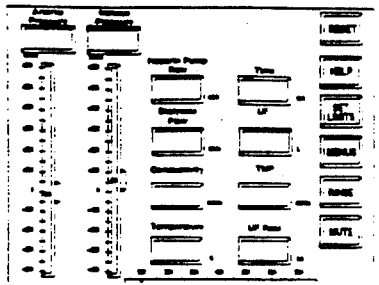

Main Screen

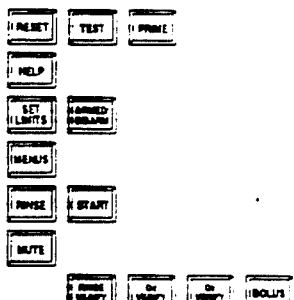

Main Screen Buttons

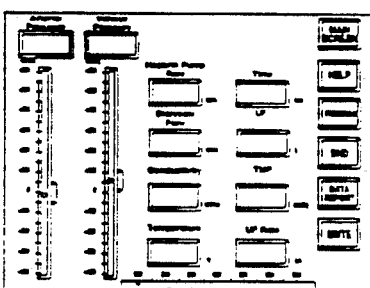

Menus Screen

Hemodialysis

The process of removing accumulated metabolic waste products from the blood and restoring water-electrolyte and acid/base balance by circulating blood through an artificial kidney.

Heparin

A chemical that slows the natural clotting of blood.

Heparin pump

An electro-mechanical device used to infuse heparin into the extracorporeal circuit.

High-flux dialyzer

A dialyzer having an in-vivo UF coefficient generally greater than 8 ml/h/mmHg.

Hydrophobic transducer protector

A transducer protector that does not allow liquid to pass through it.

Inch of mercury

A unit of pressure.

1 inHg = 3386.4 Pa = 25.4 mmHg = 13.6 in$H_2$O

Inch of water

A unit of pressure.

1 in$H_2$O = 249.09 Pa = 1.8 mmHg = 0.07 inHg

Kilogram

A metric unit of weight.

1 kg = 1000 g = 2.2 lb

LED

Light emitting diode; a solid-state, low-current lamp used as an indicator.

Liter

The basic unit of volume in the metric system.

1 L = 1000 ml = 1.057 qt (US)

Main screen

The video screen display that contains the standard operator controls including button #1 as RESET, PRIME or TEST. The main screen is the standard or default operator's screen.

Menus screen

The video screen display that contains the specialized operator controls including the PROGRAM, SND and DATA REPORT buttons. The menus screen is displayed after the MENUS button is touched.

Milliliter

A metric unit of volume.

1 ml = 0.001 L = 1 cc

Millimeters of mercury

A metric measure of pressure or vacuum.

1 mmHg = 133.32 Pa = 0.02 psi

Millisiemens per centimeter

A metric unit of conductivity measurement same as millimho per centimeter.

Negative pressure

Pressure which is below atmospheric or "minus" (suction)

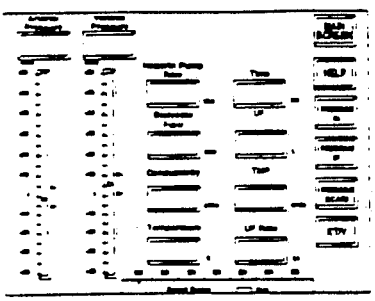

Program Screen

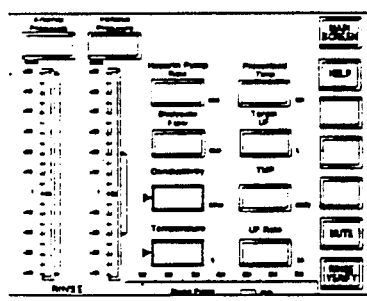

Rinse Screen

Normal operating range

A function is in the "normal operating range" when its value is between the low and high alarm limits.

Pascal

A unit of pressure.

1 Pa = 1 N/m² = 0.0075 mmHg

Pound per square inch

A unit of pressure.

1 psi = 0.07 bar = 51.7 mmHg

Program screen

The video screen display that contains the specialized operator controls used to select machine programable functions including programable sodium, programable UF control, and probramable bicarb. The program screen is displayed after the MENUS then PROGRAM buttons are touched.

Proportioning pump

A mechanical device which measures precise amounts of water and concentrate.

Renal

Pertaining to the kidneys; from the Latin "renis."

Rinse screen

The video screen display that contains the standard operator controls for the rinse mode options, including the HEAT CLEAN and CHEMICAL buttons. The rinse screen is displayed after the RINSE button is touched while the dialysate connectors are on the rinse block.

Saline

Containing salt - "saline" usually refers to an isotonic (0.9%) sodium chloride solution used to prime the dialyzer before dialysis; and to rinse blood back to the patient upon completion of dialysis; may be given during hemodialysis to prevent or correct hypotension.

Sodium hypochlorite

The active ingredient of common household bleach; used for cleaning dialysate fluid pathways of delivery systems of biological materials. It does not remove precipitates.

Standard bath

The dialysate obtained by proportioning 1 part acid concentrate to 34 parts water to 1.8 parts bicarbonate concentrate for bicarbonate dialysate or 1 part acetate concentrate to 34 parts water for acetate concentrate.

Standard dialysate

Standard bath

Sterile

Completely free of any living microorganisms.

Thermistor

A temperature sensing device used in electrical temperature control circuits. A small sensitive metal device that changes its electric characteristics with temperature change.

Transmembrane pressure

The hydrostatic pressure difference inside the dialyzer across the membrane from the blood side to the dialysate side.

$$TMP = \frac{B_i + B_o}{2} - \frac{D_i + D_o}{2}$$

where:

$B_i$ = blood pressure in $B_o$ = blood pressure out $D_i$ = dialysate pressure in $D_o$ = dialysate pressure out The usual approximation of $B_o - D_i$ is used to determine the TMP that is displayed on the System 1000 screen.

Ultrafiltration

The process by which water (with electrolytes) moves across the dialyzer membrane as a net result of transmembrane and osmotic pressure differences between the blood and the dialysate. For a given osmotic pressure, the greater the transmembrane pressure the more rapid the ultrafiltration.

Ultrafiltration coefficient (KUF)

The amount of liquid that passes through the dialyzer is given by ml/h/mmHg.

Ultrasonic

High frequency sound waves that are above the normal hearing range. Such sound waves are often used to detect air bubbles in the venous line.

Venous

The portion of the extracorporeal circuit which carries blood from the dialyzer to the patient.

Video screen

The CRT (screen) that displays machine functions and controls.

Window

An area of the video screen that displays the value of monitored functions.

Symbols and Abbreviations

| | |
|---|---|
| A | ampere |
| AAMI | Association for the Advancement of Medical Instrumentation |
| ac | alternating current |
| Btu | British thermal unit |
| cc | cubic centimeter |
| CC | direct current *(international symbol)* |
| cm | centimeter |
| dc | direct current |
| ft | foot |
| g | gram |
| gal/min | gallon per minute |
| h | hour |
| Hb/L | hemoglobin per liter |
| Hz | hertz |
| ID | inside diameter |
| in | inch |
| inHg | inch of mercury |
| $inH_2O$ | inch of water |
| kg | kilogram |
| kPa | kilopascal |
| KUF | coefficient of ultrafiltration |
| L | liter |
| L/h | liter per hour |
| lb | pound |

| | |
|---|---|
| m | meter |
| mA | milliampere |
| mEq/L | milliequivalent per liter |
| mg | milligram |
| min | minute |
| ml | milliliter |
| ml/h | milliliter per hour |
| ml/min | milliliter per minute |
| mm | millimeter |
| mmHg | millimeter of mercury |
| mS/cm | millisiemens per centimeter |
| oz | ounce |
| Pa | pascal |
| psig | pound per square inch, gauge |
| qt | quart |
| s | second |
| µA | microampere |
| µL | microliter |
| V | volt |
| W | watt |
| °C | degree Celsius |
| °F | degree Fahrenheit |
| < | less than |
| > | greater than |

Machine Mode Matrix

| Mode | Machine status area displays | Machine action |
|---|---|---|
| power on | POWER ON | • The machine is powering up. The electrical circuits are energizing. The electrical circuits are warming up. |
| standby | STANDBY | • The main alarm lamp flashes.<br>• The blood pump will not operate.<br>• The line clamp is clamped.<br>• The audio alarm sounds.<br>• The machine is in bypass.<br>• The heparin pump is stopped.<br>• The UF rate is automatically set at 0 L/h (off). |
| rinse | RINSE | • The dialyzer connectors *must* be on rinse block to start rinse.<br>• The blood pump will:<br>  – operate if the dialyzer connectors remain on the rinse block.<br>  – not operate if the dialyzer connectors are removed from the rinse block.<br>• The line clamp will:<br>  – remain open if the dialyzer connectors remain on the rinse block.<br>  – clamp if the dialyzer connectors are removed from the rinse block.<br>• The UF rate is automatically set at 3.60 L/h.<br>• Pressures between flow equalizer cavities are relieved so excessive vacuum does not develop in the flow path.<br>• The bypass valve cycles into bypass for 5 seconds every minute.<br>• Concentrate may be introduced into the fluid path. (Proportioning ratio is determined by acid/acetate and bicarbonate rinse port interlocks.)<br>• Air detector and blood leak detector machine responses (other than the visual alarm indicator) are disabled.<br>• The arterial pressure alarm limits are –400 and +600 mmHg.<br>• The venous pressure alarm limits are ±200 mmHg around the indicated venous pressure approximately 10 seconds after the blood pump turned on, off or rate changed.<br>• The TMP alarm limits are ±200 mmHg around the indicated TMP approximately 1 minute after the UF rate is changed or the blood pump is turned on, off or rate changed.<br>• The audio alarm inhibited except for a no supply alarm, an arterial pressure alarm, a venous pressure alarm, or power failure alarm.<br>• If manual bypass has been selected, the machine will remain in manual bypass for no more than 1 minute. |

| Mode | Machine status window displays | Machine action |
|---|---|---|
| rinse with conductivity and temperature in operating range | RINSE | • The audio alarm will beep 3 times.<br>• The main alarm lamp flashes.<br>• The dialyzer connectors *must* be on rinse block to start rinse.<br>• The blood pump will:<br>  – operate if the dialyzer connectors remain on the rinse block.<br>  – not operate if the dialyzer connectors are removed from the rinse block.<br>• The line clamp will:<br>  – remain open if the dialyzer connectors remain on the rinse block.<br>  – clamp if the dialyzer connectors are removed from the rinse block.<br>• The UF rate is automatically set at 3.60 L/h.<br>• Pressures between flow equalizer cavities are relieved so excessive vacuum does not develop in the flow path.<br>• The bypass valve cycles into bypass for 5 seconds every minute.<br>• Concentrate may be introduced into the fluid path.<br>• Air detector and blood leak detector machine responses (other than the visual alarm indicator) are disabled.<br>• The arterial pressure alarm limits are –400 and +600 mmHg.<br>• The venous pressure alarm limits are ±200 mmHg around the indicated venous pressure 10 seconds after the blood pump turned on, off or rate changed.<br>• The TMP alarm limits are ±200 mmHg around the indicated TMP approximately 1 minute after the UF rate is changed or the blood pump is turned on, off or rate changed.<br>• The audio alarm inhibited except for a no supply alarm, an arterial pressure alarm, a venous pressure alarm, or power failure alarm.<br>• If manual bypass has been selected, the machine will remain in manual bypass for no more than 1 minute. |
| self test | SELF TEST | • Proportioning ratio as determined by acid/acetate and bicarbonate rinse port interlocks is set.<br>• The data report is cleared.<br>• The blood pump will automatically turn on and off.<br>• The line clamp will automatically clamp and unclamp.<br>• The primary conductivity alarm limits are set to ±5% around the dialysate conductivity which has been verified against an external calibrated conductivity meter.<br>• The audio alarm beeps 2 times to prompt the operator to verify conductivity.<br>• The audio alarm beeps 3 times to prompt the operator if the test failed.<br><br>The following functions are tested during self test:<br>• Venous and arterial pressure test<br>  – Operator prompt appearing in the instruction window: BLOOD PRESSURE TEST: ARE PRESSURE LUERS PLUGGED? |
| Mode | Machine status window displays | Machine action |
|  |  |   – Venous high low pressure alarm<br>  – Operator prompt appearing in the instruction window: VERIFY AUDIO ALARM/ALARM LAMP?<br>  – Blood pump stops during an extracorporeal alarm<br>  – Arterial high pressure alarm<br>  – Arterial and venous pressure accuracy<br>  – Venous low pressure alarm<br>  – Arterial low pressure alarm<br>• Blood leak alarm<br>• UF system test<br>  – UF system checked for leaks<br>  – UF metering device functionality<br>• TMP test<br>  – TMP calculation<br>  – TMP stability<br>  – TMP high pressure alarm<br>  – TMP low pressure alarm<br>• Temperature test<br>  – Primary high temperature alarm<br>  – Primary low temperature alarm<br>  – Redundant high temperature high alarm<br>  – Temperature stability<br>• Conductivity test<br>  – Simulated high conductivity/high temperature alarm<br>  – Primary high conductivity high limit<br>  – Primary low conductivity alarm limit<br>  – Redundant high conductivity high limit<br>  – Redundant low conductivity alarm limit<br>  – Backup high conductivity high limit<br>  – Backup low conductivity alarm limit<br>  – Conductivity stability |

- Air detector test
  - Backup air detect alarm
  - Primary air detect alarm (Tested if a liquid filled line is in the air detector.)
  - Simulated bubble
- Conductivity verify test
  - Operator prompt appearing in the instruction window: IS CONDUCTIVITY CORRECT?
  - Sets primary conductivity alarm limits ±5% of displayed value

| Mode | Machine status window displays | Machine action |
|---|---|---|
| | | • Luer test<br>   – Operator prompt appearing in the instruction window: ARE PRESSURE LUERS VENTED? |
| prime | PRIME | • The main alarm lamp flashes at a slow rate.<br>• The blood pump will operate.<br>• The line clamp is open.<br>• The self test has been successfully completed.<br>• The extracorporeal alarms may be disarmed for 5 minutes.<br>• The UF rate may be manually set from 0 to 0.5 L/h.<br>When the extracorporeal alarms are armed:<br>  – The arterial pressure alarm limit set to ±50 mmHg around the indicated arterial pressure when the PRIME button was pressed or 10 seconds after the blood pump is turned on, off or rate changed.<br>  – The venous pressure alarm limit is ±50 mmHg around the indicated venous pressure when the PRIME button was pressed or 10 seconds after the blood pump is turned on, off or rate changed.<br>  – The TMP alarm limits set to ±35 mmHg (within the range –80 to +500 mmHg) around the indicated pressure, approximately 1 minute after the blood pump is turned on, the blood pump rate is changed or the UF rate is changed.<br>  – The minimum low venous pressure alarm limit is approximately +10 mmHg<br>  – The air and blood leak detector machine alarm responses are active.<br>When the extracorporeal alarms are disarmed:<br>  – The arterial pressure alarm limits are –400 and +600 mmHg.<br>  – The venous pressure alarm limits are ±200 mmHg around the indicated venous pressure when the ARMED / DISARM button is pressed or 10 seconds after the blood pump starts, blood pump power switch is turned off or the blood pump rate is changed.<br>  – The TMP alarm limits are ±200 mmHg (within the range –80 to +500 mmHg) around the indicated TMP approximately 1 minute after the UF rate is changed or the blood pump is turned on, off or rate changed.<br>  – The air and blood leak detector machine alarm responses are disabled (except for the visual indicator). |
| dialyze | DIALYZE | • All alarms are functional. No alarm condition exists.<br>• The blood pump will operate.<br>• The line clamp is open.<br>• The UF rate is at the calculated value (from the PRESCRIBED TIME and TARGET UF), unless manually overridden.<br>• The heparin pump will operate.<br>• The elapsed time is accumulated. |

| Mode | Machine status window displays | Machine action |
|---|---|---|
| | | • While the blood pump is stopped and/or the machine is in bypass the elapsed time is not accumulated.<br>• The main alarm lamp is off.<br>• The accumulated ultrafiltrate removed is displayed.<br>• The TMP alarm limits are spread to ±200 mmHg around the indicated TMP for approximately 1 minute when the blood pump or the UF rate is changed. The maximum high TMP alarm limit is +500 mmHg. The minimum low TMP is –80 mmHg (may be technician set closer to zero).<br>• The TMP alarm limits set to ±35 mmHg (within the range –80 to +500 mmHg) around the indicated pressure, approximately 1 minute after the blood pump is turned on, the blood pump rate is changed or the UF rate is changed.<br>• The SET LIMITS button may be used to manually set the TMP, arterial pressure, venous pressure alarm limit windows.<br>• The arterial pressure alarm limits spread to –400 and +600 mmHg, for approximately 10 seconds, when the blood pump is started or rate is changed.<br>• The venous pressure alarm limits spread to ±200 mmHg around the indicated venous pressure, for approximately 10 seconds, when the blood pump is started or rate is changed.<br>• The arterial and venous pressure alarm limits set to ±50 mmHg of the indicated value approximately 10 seconds after the blood pump is started or rate is changed.<br>• The minimum low venous pressure alarm limit is approximately +10 mmHg. |
| alarm | ALARM | • An alarm indicator flashes to indicate the monitor that is in alarm.<br>• The main alarm lamp flashes.<br>• Audio alarm sounds.<br>Refer to the Alarm section of this manual for additional information. |

Data Report Worksheet

Patient _____ Date _____

Prescribed Treatment Time = _____ h:m

Elapsed Treatment Time = _____ h:m

Treatment Time Remaining = _____ h:m

Target UF = _____ L

UF Removed = _____ L

UF Remaining = _____ L

Total Blood Processed = _____ L

Total Infused Heparin = _____ ml

Syringe _____ Bolus _____ ml

UF rate·

Concentrate ☐ Acetate ☐ Bicarbonate

Calculated UF rate has been overridden. ☐ yes ☐ no

Data Report Worksheet

Patient _____  Date _____

Prescribed Treatment Time  =  _____  h:m

Elapsed Treatment Time  =  _____  h:m

Treatment Time Remaining  =  _____  h:m

Target UF  =  _____  L

UF Removed  =  _____  L

UF Remaining  =  _____  L

Total Blood Processed  =  _____  L

Total Infused Heparin  =  _____  ml

Syringe _____  Bolus _____ ml

UF rate

Concentrate  ❑ Acetate    ❑ Bicarbonate

Calculated UF rate has been overridden.   ❑ yes   ❑ no

UF Control Worksheet

Patient: _____  Date: _____

Find weight to remove:

Pre dialysis weight      _____ lb  or  _____ kg

–  Desired weight      _____ lb  or  _____ kg

=  Desired weight to remove _____ lb ÷ 2.2 _____ kg

Find volume to remove:

Desired weight to remove _____ kg × 1000 = _____ ml

+  Priming saline intake      _____ ml

+  P.O. intake (add foods which have high water content only)      _____ ml

+  I.V. fluid intake      _____ ml

+  Rinseback saline intake      _____ ml

=  Total volume to remove      _____ ml ÷ 1000 = _____ L

Fluid Removal Analysis (Optional after dialysis.)

Find actual fluid removed:

Pre dialysis weight (from scale) _____ lb ÷ 2.2 = _____ kg x 1000 = _____ ml

+ Priming saline intake (actual) _____ ml

+ P.O. intake (actual) _____ ml

+ I.V. fluid intake (actual) _____ ml

+ Rinseback saline (actual) _____ ml

= Subtotal _____ ml

− Output during dialysis (urine, emesis, etc.) _____ ml

= Total actual pre dialysis weight (subtotal) _____ ml ÷ 1000 = _____ L

Post dialysis weight (from scale) _____ lb ÷ 2.2 = _____ kg = _____ L

− Solid food intake _____ kg = _____ L

= Total adjusted post dialysis weight (subtotal) _____ L

Total actual pre dialysis weight (from above) _____ L

− Total adjusted post dialysis weight (from above) _____ L

= Actual volume removed (total) _____ L

Conversion Chart – Pounds to Kilograms to Milliliters

| Pound | Kilogram | Milliliter | Pound | Kilogram | Milliliter |
|---|---|---|---|---|---|
| 1/4 | .11 | 110 | 10 | 4.55 | 4550 |
| 1/2 | .23 | 230 | 10 1/4 | 4.66 | 4660 |
| 3/4 | .34 | 340 | 10 1/2 | 4.77 | 4770 |
|  |  |  | 10 3/4 | 4.89 | 4890 |
| 1 | .45 | 450 |  |  |  |
| 1 1/4 | .57 | 570 | 11 | 5 | 5000 |
| 1 1/2 | .68 | 680 | 12 | 5.45 | 5450 |
| 1 3/4 | .80 | 800 | 13 | 5.91 | 5910 |
|  |  |  | 14 | 6.36 | 6360 |
| 2 | .91 | 910 | 15 | 6.82 | 6820 |
| 2 1/4 | 1.02 | 1020 | 16 | 7.27 | 7270 |
| 2 1/2 | 1.14 | 1140 | 17 | 7.73 | 7730 |
| 2 3/4 | 1.25 | 1250 | 18 | 8.18 | 8180 |
|  |  |  | 19 | 8.64 | 8640 |
| 3 | 1.36 | 1360 | 20 | 9.09 | 9090 |
| 3 1/4 | 1.48 | 1480 |  |  |  |
| 3 1/2 | 1.59 | 1590 | 21 | 9.45 | 9450 |
| 3 3/4 | 1.70 | 1700 | 22 | 10 | 10000 |
|  |  |  | 23 | 10.45 | 10450 |
| 4 | 1.82 | 1820 | 24 | 10.91 | 10910 |
| 4 1/4 | 1.93 | 1930 | 25 | 11.36 | 11360 |
| 4 1/2 | 2.05 | 2050 |  |  |  |
| 4 3/4 | 2.16 | 2160 | 26 | 11.80 | 11800 |
|  |  |  | 27 | 12.26 | 12260 |
| 5 | 2.27 | 2270 | 28 | 12.71 | 12710 |
| 5 1/4 | 2.39 | 2390 | 29 | 13.17 | 13170 |
| 5 1/2 | 2.5 | 2500 | 30 | 13.62 | 13620 |
| 5 3/4 | 2.61 | 2610 |  |  |  |
| 6 | 2.73 | 2730 | 31 | 14.07 | 14070 |
| 6 1/4 | 2.84 | 2840 | 32 | 14.53 | 14530 |
| 6 1/2 | 2.95 | 2950 | 33 | 14.98 | 14980 |
| 6 3/4 | 3.07 | 3070 | 34 | 15.44 | 15440 |
|  |  |  | 35 | 15.89 | 15890 |
| 7 | 3.18 | 3180 | 36 | 16.34 | 16340 |
| 7 1/4 | 3.30 | 3300 | 37 | 16.80 | 16800 |
| 7 1/2 | 3.41 | 3410 | 38 | 17.25 | 17250 |
| 7 3/4 | 3.52 | 3520 | 39 | 17.71 | 17710 |
|  |  |  | 40 | 18.16 | 18160 |
| 8 | 3.64 | 3640 |  |  |  |
| 8 1/4 | 3.75 | 3750 | 41 | 18.61 | 18610 |
| 8 1/2 | 3.86 | 3860 | 42 | 19.07 | 19070 |
| 8 3/4 | 3.98 | 3980 | 43 | 19.52 | 19520 |
|  |  |  | 44 | 19.98 | 19980 |
| 9 | 4.09 | 4090 | 45 | 20.43 | 20430 |
| 9 1/4 | 4.20 | 4200 |  |  |  |
| 9 1/2 | 4.32 | 4320 |  |  |  |
| 9 3/4 | 4.43 | 4430 |  |  |  |

The following checklist is a procedural reminder suggested by Althin CD Medical to be used for the preparation and use of the Drake Willock System 1000 Single Patient Delivery System. Do not attempt to use this checklist without thorough familiarization with the System 1000 Operator's Manual. Refer to the operator's manual for advisories, cautions and warnings.

Drake Willock System 1000 Single Patient Delivery System

Pre-Setup
- The patient is disconnected from the blood lines and dialyzer.
- The machine is connected to the water supply and the water is off.
- The drain line is in the drain.
- The power cord is plugged in and the mains power switch is on.
- The front panel power switch is off.
- The acid/acetate concentrate line (pink connector) is connected to the acid/acetate rinse port (pink).
- The bicarbonate concentrate line (blue connector) is connected to the bicarbonate rinse port (blue).
- The dialysate lines (yellow connector) are connected to the rinse port (yellow).

Rinse Machine (Before Dialysis)

1. Turn on the water supply.
2. Turn on the machine.
3. Initiate the Rinse Mode.

Touch RINSE button, then touch RINSE VERIFY button.

4. Touch RESET button as required.
5. If the machine had no disinfectant in the fluid path and is to be disinfected, go to step 6.

If the machine had formaldehyde or another disinfectant in the fluid path, go to step 7.

6. Disinfect the fluid path, as required.
7. Rinse the disinfectant from the fluid path, as required.
8. Test the rinse solution for residual disinfectant, as required.
9. Connect the concentrate(s).

For <u>acetate</u> dialysis:

a. Connect the acid/acetate concentrate line (pink connector) to a full container of acetate concentrate.

For <u>bicarbonate</u> dialysis:

a. Connect the acid/acetate concentrate line (pink connector) to a full container of acid concentrate.

b. Connect the bicarbonate concentrate line (blue connector) to a full container of bicarbonate concentrate.

10. After the conductivity and temperature stabilize, initiate the Self Test Mode.

Touch the TEST button.

Note: If there are any extracorporeal alarms, touch the RESET button to clear the alarms and access the TEST button.

Do not manually turn on the blood pump during Self Test or a blood pump overspeed alarm will occur.

Make sure the machine is not in manual bypass or the Self Test will fail.

Test the dialysate.

11. Set up the dialyzer and blood lines, as required.
12. Initiate Prime, touch the PRIME button.
13. Prime the dialyzer and blood lines.

a. Touch the ARMED / DISARM button to disarm the extracorporeal alarms.

b. Touch the RESET button, as required.

c. Set the blood pump flow rate.

d. Turn on the blood pump, as required.

To connect the dialyzer connectors to the dialyzer:

a. Press the manual bypass button.

b. Connect the dialyzer connectors to the appropriate dialyzer ports.

c. Press the manual bypass button.

To load the heparin pump:

a. Fill the syringe with heparin.

b. Connect the heparin line to the syringe.

c. Clamp the heparin line but do not prime the line.

14. Set the treatment parameters; i.e., prescribed dialysis time and desired fluid loss.
15. Turn off the blood pump, as required.

Start Dialysis

Note: If an extracorporeal alarm exists, clear and reset the alarm before touching the START button.

1. Touch the START button (button #5).

Note: If a UF rate lower than the calculated rate is desired at treatment initiation, enter a low manual UF rate before turning on the blood pump. Otherwise the calculated UF rate will start as soon as the blood pump starts.

To initiate heparin infusion:

a. With the blood pump on, give a heparin bolus.

b. Unclamp the heparin line.

c. Set the heparin infusion rate.

Discontinue Dialysis

1. Discontinue dialysis.

Note: If a minimum UF rate (other than zero) is desired for returning the patient's blood after the target UF is reached:

a. Enter a new Target UF higher than the current UF removed.

b. *Immediately* enter the specific manual UF rate desired.

2. Record the treatment data from the data report before initiating rinse.
3. Disconnect the dialysate lines from the dialyzer and connect them to the machine rinse block.

Prepare Machine for Another Patient (if required) (Patient disconnected)

1. Initiate the Rinse Mode.
2. Make sure there is an adequate supply of concentrate(s) in the containers(s) for the entire dialysis treatment including setup.
3. Continue the predialysis preparation by completing Rinse Machine (Before Dialysis) steps 10 through 15.

Rinse Machine (After Dialysis) (Patient disconnected)

1. Connect the concentrate lines to the machine.

After acetate dialysis:

a. Connect the acid/acetate concentrate line (pink connector) to the acid/acetate rinse port (pink)

After bicarbonate dialysis:

a. Connect the bicarbonate concentrate line (blue connector) to the bicarbonate rinse port (blue)

b. Connect the acid/acetate concentrate line (pink connector) to the acid/acetate rinse port (pink)

2. Initiate the Rinse Mode.
3. Rinse the machine with water for 10 minutes.
4. If the machine is to be disinfected, refer to Disinfect Machine Fluid Pathway in the Special Operations section of this manual.

If the machine is to be turned off, go to step 5.
5. Turn off the machine.
6. Turn off the water supply.

*Do not attempt to use this checklist without thorough familiarization with the System 1000 Operator's Manual. Refer to the operator's manual for advisories, cautions and warnings.*

Disinfect Machine Fluid Pathway

With formaldehyde:

1. Connect the disinfect line (yellow connector) to a container of 37% formaldehyde.
2. Connect the acid/acetate concentrate line (pink connector) to the disinfect rinse port (yellow).
3. Infuse formaldehyde into the fluid path for approximately 15 minutes.
4. Obtain a sample of the disinfect solution from the drain line. Make sure that formaldehyde is present in the sample before going on to the next step.
5. Disconnect the machine from the formaldehyde supply.

a. Connect the acid/acetate concentrate line (pink connector) to the acid/acetate rinse port (pink).

b. Allow the disinfect line to drain, then connect the disinfect line (yellow connector) to the disinfect rinse port (yellow).

6. Turn off the machine.
7. Label the machine with a formaldehyde warning sign on which the date and time have been recorded.
8. Turn off the water.

With sodium hypochlorite (bleach):

1. Connect the disinfect line (yellow connector) to a container of 200 mL of 1.75% bleach solution.
2. Connect the acid/acetate concentrate line (pink connector) to the disinfect rinse port (yellow).
3. Allow diluted bleach to infuse into the fluid path for 15 minutes.
4. After the 15 minutes, rinse the disinfect line for approximately 2 minutes.
5. After the two minutes, disconnect the machine from the bleach supply.

a. Connect the acid/acetate concentrate line (pink connector) to the acid/acetate rinse port (pink).

b. Allow the disinfect line to drain, then connect the disinfect line (yellow connector) to the disinfect rinse port (yellow).

6. Rinse the machine until it is free of bleach.
7. After 15 minutes, obtain a sample of the rinse solution and check for residual sodium hypochlorite.

Exhibit 3

Laboratory Report

System 1000 Development

Architecture

General Description

Main Controller Hardware (Host)

The System 1000 machine is controlled by an 80XX microprocessor (uP) and three 8040 microcontrollers (uC). The 80XX uP is located on an IBM PC/AT compatible motherboard, with its primary responsibilities being:

- User interface (CRT display and touch screen)
- State machine control (Rinse, Prime, Dialyze,...)
- Microcontroller communications
- Conducting self tests
- Calibrations The firmware for the 80XX uP is located on the Memory Board, which plugs into the motherboard. The Memory Board can hold up to 384K of ROM (read only memory). In addition it also contains 8K of nonvolatile static RAM (random access memory) (for calibrations and machine parameters), a memory card interface, an RS-232 interface, and a time of day clock. The 80XX uP has access to 256K of dynamic RAM located on the motherboard.

The 80XX uP controls the operation of the machine through its connection to the following additional boards which are plugged into the motherboard:

- EGA display board
- Touch screen interface board
- Blood Pump system controller board
- UF/Proportioning system controller board
- I/O system controller board
- RS-232 board (optional for patient blood pressure monitor)

Main Controller Software (Host)

The host control program is written in the 'C' programming language. The program source code is compiled, linked and loaded into programmable read only memory. This memory resides on the embedded hardware system memory board.

The purpose of the host control program is to:

- Gather data from the Input/Output, Blood Pump and Ultrafiltration controller sub-systems, and output control functions to the various controller sub-systems.
- Input data from user interface touch screen.
- Monitor the data for violation of alarm limits and unsafe operating conditions, and to set the appropriate program alarm condition indicators;
- Evaluate the data to determine the current operating state of the control program, i.e. Standby, Rinse, Self Test, Prime and Dialyze.
- Update the display data to the CRT portion of the user interface.

Blood Pump Control System

Five subsystems are controlled or monitored by the blood pump controller. They are:

- Blood pump

- Blood pressure measurement (arterial, venous and expansion chamber)
- Heparin delivery
- Level adjust
- Ambient temperature

Blood Pump Controller

The purpose of the blood pump controller is to supply power to the blood pump motor such that the pump head will turn and pump at a rate selected by the operator.

The blood pump controller system consists of the following major components:

| Description | Location |
| --- | --- |
| User parameter entry | Host controller |
| Software Speed Error Control | Bld Pmp Controller |
| Hardware Speed Error Control | BP Power Board |
| Optical speed sensor | On motor shaft |
| Motor Power Driver Circuitry | BP Power Board |

The operator enters the desired blood pump rate information on the video screen (CRT) touch panel. The host controller (80XX microprocessor) converts this information to the appropriate motor rate which it then sends to the Blood Pump controller (8040) on the Blood Pump Controller board. The 8040 controller converts the motor rate information to an analog level, which is fed to a motor speed control IC (LM2917-8) on the Blood Pump Power board.

An optical speed sensor is mounted on the rear shaft of the blood pump motor, with an LED being positioned on one side of the shaft, and a photo transistor on the opposite side. The shaft has two holes drilled through it, with each hole being perpendicular to the shaft and to each other. This results in four optical pulses received per shaft revolution.

This tachometer signal is monitored by both the LM2917-8 and the 8040 controller. The LM2917-8 provides quick responding speed control by comparing the motor speed with the desired speed information from the 8040. The result of this comparison is an error signal which provides an input to the motor power driver circuit.

The motor power driver provides a +24 V pulse width modulated drive to the motor at a frequency of approximately 30 KHz. This drive is current limit protected, to prevent damage in the event of a stalled motor.

The 8040 compares the tachometer motor speed information with the desired speed commanded by the 80XX and corrects the level provided to the LM2917-8 accordingly. In this way the 8040 guarantees the ultimate accuracy of the pump, with the LM2917-8 circuit not requiring any calibration. In addition, the 8040 can monitor for control problems, such as under speed or over speed, which may result from failures in the LM2917-8 or motor drive circuitry.

The 8040 also monitors the motor speed independent of the tachometer signal using the motor's back EMF. Periodically (every 0.5 second) the motor drive is turned off for approximately 6 millisecond and the voltage at the motor terminals is measured. Though this does not result in as precise an indication as the tachometer signal, gross failures can be determined, such as when the tachometer signal is lost.

Blood Pressure Measurement

The blood pressure measurements include the venous, arterial and expansion chamber (for Single Needle treatment) pressures. All three measurement systems include identical hardware. Each pressure is sensed by a SenSym SCX15 gauge sensing pressure transducer mounted to the Blood Pump Power board. Each transducer is connected to a differential amplifier designed to provide a measurement range from −400 to +600 mmHg. The output of each amplifier drives an A/D input channel of the Blood Pump Control system, at which point it is converted to a 10 bit digital value. The calibration of the each pressure input is handled entirely in software, requiring that the design of each amplifier guarantee that its output remain within the A/D input range of 0 to +5 V over the input pressure range and over all component tolerances.

Heparin Delivery

Heparin delivery is accomplished by stepping a stepper motor which rotates the pinion of a rack and pinion mechanism. The pinion moves the rack, and the mechanical fixture is such that the plunger of the heparin syringe moves the same distance. The stepper motor is controlled by the 8040 microcontroller located on the Blood Pump Controller board. When the operator enters a desired heparin rate in milliliters per hour (mL/h) via the front panel touch screen, the host 80XX microprocessor converts this information to the appropriate motor step rate and passes it to the Blood Pump microcontroller. The Blood Pump microcontroller outputs a motor step rate logic signal to the Blood Pump Power board where the heparin motor power drive circuitry energizes the appropriate stepper motor coil.

The motor step rate logic signal from the Blood Pump microcontroller is also input to the IO Controller board 8040 microcontroller. The IO microcontroller monitors this signal to determine if the heparin motor is going the appropriate speed. If it determines that an overspeed condition exists, it disables the heparin motor via a disable line that goes to the Blood Pump Power board.

There are two optical sensors to provide information about the state of the heparin pump. The disengage sensor detects when the front panel syringe holder arm is in the disengage position. The end-of-stroke sensor detects when the pinion is raised up on the rack, which occurs when the gear teeth are not meshed. This is an indication of an overpressure condition. The Blood Pump microcontroller monitors the state of these sensors and passes the information to the host 80XX microprocessor.

Level Adjust

The level adjust system allows the operator to change the blood level in the arterial and venous drip chambers. A level up and level down button exists for each drip chamber. The 8040 microcontroller on the Blood Pump Controller board monitors the button positions. When a button is pressed, a valve selects that drip chamber and power is supplied to the motor such that the pump head of a peristaltic pump rotates to apply a positive or negative pressure to the drip chamber. The software logic only accepts one button press at a time. If two buttons are pressed simultaneously, both are ignored.

The motor drive circuitry is located on the Blood Pump Power Board. The motor may be driven in the forward or reverse direction. A direction signal from the Blood Pump Controller Board, along with a pulse width modulated motor rate signal controls two bipolar half bridge motor drivers. Both half bridge motor drivers receive the same motor rate signal, while the motor direction signal is high at one and low at the other to determine the direction the motor runs. The half bridge drivers provide a 24 V pulse width modulated drive voltage of approximately 30 KHz to the motor.

Ambient Temperature Control

The purpose of the cabinet cooling system is to keep the internal temperature of the cabinet lower than the 50°C maximum temperature at which that the electronic components are guaranteed to operate. (Most electronic components are rated to operate at 60°C, the exception is the solid state relay used for heater control.) A fan is located at the base of the cabinet and exhausts the warm cabinet air. An intake vent for the ambient room temperature is located below the CRT on the back of the machine.

The cabinet cooling system consists of the following major components:

| Description | Location |
|---|---|
| Cabinet Fan | Base of cabinet |

| | |
|---|---|
| Blood Pump Temperature IC | Blood Pump Power Bd |
| Misc IO Temperature IC | Misc IO Electronics Power Bd |
| Software Fan Control | Host controller |
| Cabinet Fan Drive | Blood Pump Power Bd |

The two LM35DZ temperature ICs are located on the Blood Pump and Misc IO Electronics power boards. This IC outputs a voltage linear with temperature in °C (10.0 mV/°C). These temperature readings are input to the fan control software.

The fan control software always responds to the higher of the two temperatures. Typical values are as follows. At 46°C the fan turns on in the low speed mode and at 48°C it turns on in the high speed mode. There is a 2°C of hysteresis at these threshold temperatures, i.e. the fan returns to low speed at 46°C and turns off at 44°C. In addition, at 60°C a cabinet temperature alarm occurs that results in the machine shutdown state.

The fan power driver is located on the Blood Pump Power board. A motor rate signal from the Blood Pump Controller board determines the duty cycle of a 30 KHz pulse width modulated signal. This signal is input into a passive filter to provide a DC signal to the motor.

UF/Proportioning Control System

The UF/Proportioning Control system monitors and controls the System 1000 dialysate preparation. Six subsystems are controlled or monitored by the UF/Proportioning system. They are:

a. Temperature Control
b. Proportioning Control
c. Flow Control
d. UF Removal Control
e. Conductivity Monitoring
f. Temperature Monitoring

Temperature Control

The UF/PROP system controls the dialysate temperature by enabling a zero voltage crossing solid state relay, which provides the power to a 1500 W heater, with a 5 Hz pulse width modulated digital signal (heater enable signal). The duty cycle of the heater enable signal is updated every 0.5 seconds with the sum of the past duty cycle and a temperature error correction value. The correction value is proportional to the difference between the desired temperature (stored by the host) and the measured control temperature (measured immediately down stream of the heater housing).

The host determined desired temperature is calculated using the user entered desired temperature and the stable "B" conductivity probe temperature. If the stable "B" conductivity probe temperature is different from the user entered desired temperature by more than 0.05°C, then the control temperature threshold sent to the UF/PROP controller is updated so that the "B" conductivity probe temperature will equal the user entered desired temperature. In this way, the dialysate temperature at the "B" conductivity probe will be adjusted so that flow rate and ambient temperature effects on the "B" conductivity probe temperature (and the primary temperature, displayed on the video screen) will be compensated. This control temperature adjustment is performed a maximum of every 5 minutes.

Proportioning Control

The UF/PROP system controls the concentrate(s) to water proportioning ratios by controlling the dialysate flow rate, the "A" concentrate flow rate, and the "B" concentrate flow rate.

The "A" and "B" concentrate pumps are stepper motor driven (each by a cam/follower) diaphragm pumps which deliver a calibrated volume of concentrate per stepper motor revolution. Their flow rates are controlled by controlling the speed of the stepper motors. The concentrate pumps are unidirectional and utilize the proper actuation of a three-way valve for their intake and output pumping strokes. The intake stroke is synchronized by a signal that is generated by an optical interrupter sensor which senses a pin mounted on the cam of the pump assembly.

The UF/PROP controller utilizes the fact that the stepper motors require 200 motor steps per revolution (between each synchronization pulse) to check the concentrate pumps for stepping errors. If late or early synchronization pulses are received then the associated error conditions are reported on the screen during the Technician Mode of the machine.

During the Rinse Mode, the host determines the concentrate treatment mode based on the "A" and "B" rinse port interlock information. If the "B" concentrate line is not on the "B" rinse port, a bicarbonate treatment is initiated by setting the proportioning ratios and the conductivity alarm limits appropriately. Conversely, if the "B" concentrate line is in the "B" rinse port, an acetate treatment is initiated. Using the dialysate flow rate and the proportioning ratios, the host determines the associated concentrate flow rates and stores the two concentrate pump speeds in the UF/PROP controller. The porportioning mode (for acetate or bicarbonate dialysis) cannot be changed in the Prime or Dialyze Modes.

The control of the dialysate flow rate is described in the Flow Control section of the UF/PROP controller description.

Flow Control

The UF/PROP system controls the dialysate flow rate by controlling the time between the switching of the flow equalizer (volumetric pump) valves (provided that all the fluid within the flow equalizer chambers has been exchanged).

The average flow equalizer volume is calibrated (measured) during the Calibration Mode. The time between the switching of the flow equalizer valves is scaled by the host (according to the calibration constant) and stored in the UF/PROP controller so that the user entered desired dialysate flow rate is achieved.

To guarantee the complete fluid transfer to/from the flow equalizer chambers two flow sensors are located within the fluid path to detect the absence of dialysate flow. The time at which both sensors detect no flow has been defined as end-of-stroke. The end-of-stroke time has been defined as the time between moment end-of-stroke was sensed and the desired flow equalizer valve switch time. Since the supply pump speed controls the instantaneous dialysate flow rate, the UF/PROP controller servos the supply pump speed in order to maintain a consistent end-of-stroke time.

Since the flow equalizer volume is calibrated and the end-of-stroke time is controlled, the UF/PROP system can accurately control the dialysate flow rate to the user entered value.

UF Removal Control

The UF/PROP system controls the UF removal rate by controlling the time between the switching of the UF removal metering device valves. The UF/PROP system controls the accumulated UF volume by counting the number of UF removal meter strokes.

Since the UF removal metering device volume is calibrated (measured) in the Calibration Mode, the rate which the host (80XX microprocessor) passes to the UF/PROP controller (number of seconds between valve switches) is scaled so that the user entered UF removal rate is achieved.

In the same way, the user entered UF removal volume is scaled by the UF metering device's stroke volume to a number of UF meter strokes. The host passes the number of UF meter strokes to the UF/PROP controller. The UF/PROP controller will then switch the UF removal meter valves and decrement the stroke number, at the desired rate, as long as the stroke number is greater than zero. The host can then calculate the UF removal volume accumulated by subtracting the number of UF strokes remaining, scaled by the stroke volume, from the operator entered desired UF removal volume. The accumulated volume is displayed during the Dialyze Mode. This value remains during the Rinse Mode and is cleared upon the entry of the Self Test Mode.

In Rinse, the UF removal rate is 3.6 L/h and screen indicates no UF volume accumulated. During the Self Test Mode, no UF removal occurs except for during specific self tests performed by the machine (no UF volume is accumulated). In the Prime Mode, the UF removal rate is set by the operator and is no greater than 0.5 L/h (no UF volume is accumulated). During the Dialyze Mode, the UF removal rate is set by the operator and is limited to be between 0.1 and 4.00 L/h. For UF removal to occur in the Dialyze Mode the following conditions must be met:

1. A target UF volume and a UF rate have been entered (or treatment time and target UF volume have been entered and a machine calculated UF rate is used).
2. The blood pump is pumping.
3. The target UF volume has not been reached.

Conductivity Monitoring

Conductivity is used as a measurement of the electrolyte composition of the dialysate. Conductivity is usually defined as the ability of a solution to pass electrical current. The conductivity of dialysate will vary due to the temperature and the electrolyte composition of the dialysate.

The UF/PROP system measures conductivity at two locations in the flow path using alternating current resistance measurements between each of the conductivity probes' electrode pairs. The two flow path locations are at the "A" conductivity probe and the "B" conductivity probe, which are located immediately down stream of the "A" and "B" mixpoints/ mixchambers, respectively. One electrode of each of the probes is stimulated with a 1 kHz ac voltage while the other is held at virtual ground (current sense electrode). Two voltages are produced by the resistance measurement circuit. The ratio of the voltages is proportional to the resistance of the respective probe. The resistance of the probes has been modeled as a function of temperature and conductivity. Since each of the conductivity probes contains a thermistor, the temperature at each of the probes is known. Using the model that was derived for the probes, the temperature measured at the probes, and the resistance measured at the probes the conductivity is calculated.

Each conductivity probe is calibrated during the Calibration Mode, at which time the resistance of each probe is measured at a known conductivity and temperature (by the use of an external reference meter) for the scaling of the probe's base resistance in the relationship described previously.

The UF/PROP system generates alarms from the measured conductivities at the "A" and "B" probes. Since these conductivity alarms are used to verify the proportioning ratios, the alarms are generated by testing the "A" conductivity and the "B" portion of the total conductivity ("B" portion = "B" conductivity − "A" conductivity). The alarm limits are determined from the concentrate treatment mode and are stored in the UF/PROP controller by the host. Therefore only during a bicarb treatment would the host store a non-zero expected "B" conductivity portion.

The host determines the concentrate treatment mode during the Rinse Mode by reading the "A" and "B" rinse port interlock information. If the "B" concentrate line is not on the "B" rinse port, a bicarbonate treatment is initiated by setting the proportioning ratios and the conductivity alarm limits appropriately. Conversely, if the "B" concentrate line is in the "B" rinse port, an acetate treatment is initiated. Upon exiting the Rinse Mode the concentrate treatment mode is set for the remainder of the dialysis treatment (concentrate treatment mode is only adjusted in the Rinse Mode).

Temperature Monitoring

The UF/PROP system measures the dialysate temperature at three locations in the fluid path. The first location is directly after the heater and this thermistor, the heater thermistor, is used for the primary temperature control feedback. The next two thermistors are contained in the "A" and "B" conductivity probes. These temperatures are used to temperature compensate the "A" and "B" conductivity measurements. The "B" conductivity temperature is also used to generate a backup high temperature alarm.

The temperature measurement circuit used throughout the machine consists of a voltage divider with a Thevenin Equivalent circuit of 3062 Ω in series with a 7.55 V supply. The voltage divider circuit when connected to the thermistor used in the temperature measurement system referenced to ground produces the voltage to temperature relationship of T (°C) = (3.77V - Vtemp) * 12.73 (°C/V) + 37°C.

The tolerance on the component parameters used in the temperature measurement system can be as great as 10%, therefore the temperature to voltage relationship must be calibrated. Calibration of the temperature measurements is a two point calibration done at 30 and 40°C. The calibration procedure results in a calibration constant for both the slope and the offset for each temperature probe/circuit.

In the UF/PROP controller the voltage described above as Vtemp is measured for the three temperature probes in its system on a scheduled basis (every 0.2 seconds for the "A" and "B" temperatures and every 1 second for the heater temperature).

The temperature that is displayed on the video screen is measured at the primary ("dialysate") conductivity probe, located just before the bypass valve, by the IO controller.

Miscellaneous Input/Output Control Systems

Nine subsystems are controlled or monitored by the I/O control system. They are:

- Air detector
- Blood leak detector
- Dialysate pressure monitor
- Heparin pump overspeed monitor
- Bypass system and flow sensor
- Conductivity monitor
- Temperature monitor
- Line clamp
- Power fail alarm

Air Detector

The air detector assembly utilizes a set of 2 MHz piezo crystals. One crystal functions as an ultrasonic transmitter and the second crystal functions as a receiver. The emitter and detector are housed into identical assemblies. There is a distance of 0.20 inch between these assemblies into which the venous blood line is placed during dialysis. The emitter is driven by a 2 MHz squarewave that is derived from a crystal oscillator located on the I/O Electrical Power board. When there is fluid in the blood line between the crystal assemblies, the 2 MHz signal is coupled to the detector assembly. The return signal from the detector assembly is amplified and rectified by two independent circuits also located on the I/O Electrical Power board. These dc output levels are monitored using two different methods. The first method is the software generated alarm and the second is the hardware generated alarm.

Software Alarm Detection (Primary Alarm)

One output is fed from the I/O Electrical Power board to an A to D converter and read by the 8040 microcontroller on the I/O Controller board. This value is averaged over a 400 msec time period and reduced by multiplying it by 15/16 and subtracting 50 mV (for noise immunity). This new value is then converted back to an analog level to be used as an alarm limit. This software generated limit is compared to the rectified dc signal from the detector. The output state of this comparator is monitored by the on-board 8040. When the unaveraged signal falls below the software generated limit for longer than a calibratable time period, an alarm occurs. Sensitivity of the software alarm is 10 microlitres at 300 mL/min blood flow.

Hardware Alarm Detection (Secondary Alarm)

The hardware alarm is redundant to the software generated alarm. This alarm uses two comparators on the I/O Electrical Power board.

One comparator looks for a minimum dc level from the rectified detector signal which guarantees the presence of fluid in the venous tubing. The second comparator is ac coupled to react to a large air bubble in the tubing. Sensitivity of this detector is approximately 300 microlitres at 300 mL/min blood flow. Both comparator outputs are wire OR'd together so that either comparator will generate an alarm.

Blood Leak Detector

The detector assembly consists of a high efficiency green LED and a photocell. These components are installed into a housing through which spent dialysate passes. Both of these components connect to the I/O Hydraulic Power board. The LED is connected to a voltage to current converter on the I/O Hydraulic Power board. The input to this circuitry comes from the I/O Controller board. The photocell is tied to the +5 V reference supply through a 750k ohm resistor. This provides a voltage divider which is monitored on the I/O Controller board.

The current through the LED is adjustable and controlled via a D to A output from the I/O Controller board. The light intensity of the LED is adjusted to illuminate the photocell to a point where its resistance is below the alarm threshold. During a blood leak, the presence of blood in the housing attenuates the light striking the photocell which causes an increase in both the photocell resistance and voltage. The increase in voltage (monitored by the microcontroller on the I/O controller board) results in a blood leak alarm.

Dialysate Pressure Monitor

The dialysate pressure is sensed by a resistive bridge pressure transducer located just upstream of the dialyzer. The transducer is connected to a differential amplifier circuit on the IO Hydraulics Power board designed to provide a measurement from −400 to +500 mmHg. The differential amplifier circuit also has an offset input that comes from a software calibratable variable, DAC_OFFSET. The output of the amplifier drives an A/D input channel of the IO Controller system, at which point it is converted to a 10 bit digital value. The calibration of the pressure input is handled entirely in the software, requiring that the design of the amplifier guarantee that the output remains within the A/D input range of 0 to +5 V over the input pressure range and over all component tolerances.

Heparin Pump Overspeed Monitor

To insure that the heparin pump does not exceed its set speed, the IO controller board software monitors a clock signal from the Blood Pump Controller board that is equivalent to 1/4th the heparin pump step rate. In the event that a heparin pump overspeed occurs, the IO controller board disables the heparin pump via a hardware line that goes to the Blood Pump Power board and notifies the host of the alarm.

To determine if the heparin pump is running the correct speed, the time it takes for ten clock signals to occur is measured (and stored in variable HEPTIMER) and compared against a minimum time period that is set by the host (HP_P_MIN). If the measured period is less than the host set limit, a normal speed alarm occurs. The host is notified of the normal speed alarm and the heparin pump is disabled via the hardware line to the Blood Pump Power board.

When the heparin pump rate changes, the host resets the minimum time period, HP_P_MIN, and the IO controller waits for the first clock signal to restart the timer (this first clock is not counted as one of the ten). In this way, the alarm logic is resynchronized with the heparin pump stepper motor.

The IO controller board also monitors the total amount of heparin delivered in the high speed bolus mode. When it receives clock signals at a rate faster than a predetermined speed, it assumes the pump is operating in the high speed mode. It has a high speed counter, H_SPD_CNTR, that is set by the host. If more high speed counts occur than are in the counter, a high speed alarm occurs. The host is notified of the high speed alarm and the heparin pump is disabled via the hardware line to the Blood Pump Power board.

Bypass System and Flow Sensor

The bypass mode is initiated when a primary dialysate alarm is detected by the IO Controller board, when a redundant dialysate alarm is detected by the UF/PROP Controller board, when the host requests bypass, or when the manual bypass button is pushed.

The bypass valve is in the bypass position when deenergized. It is driven from the nominal +24 V supply with a straight on/off transistor control on the IO Hydraulics Power board.

To verify that there is not a failure in the bypass system, a flow sensor just downstream of the predialyzer bypass valve checks for flow. If flow exists during the bypass mode, a Bypass Fail Alarm is set and the machine is put in the safe, nonfunctional, Shutdown state. If there is no flow when not in the bypass mode, a No Flow alarm is generated.

This flow sensor consists of two thermistors. The first is a reference thermistor used to determine the fluid temperature. The second thermistor uses thermal dilution to sense the fluid flow. The voltage outputs from the thermistors on the IO Hydraulics Power board drive A/D input channels on the IO Controller board where they are converted to 10 bit digital values. A software algorithm in the IO Controller code uses these inputs to determine the flow condition. The design of the voltage divider guarantees that the output remains within the A/D input range of 0 to +5 V over the input temperature/flow range and over all component tolerances.

Conductivity Monitoring

The conductivity probe itself consists of two stainless steel probes inserted into the flowpath just prior to the dialyzer. The drive signal for the conductivity probes is a capacitive coupled squarewave generated on the I/O Hydraulic board. This signal is sent to the conductivity probe and a monitor circuit. Both the monitor circuit and the return signal are rectified and filtered. These dc values are routed to I/O Controller board along with the temperature signal.

On the I/O controller board, the temperature, conductivity, and conductivity reference signals are input to an A to D converter that is monitored by an on board 8040 microcontroller. The microcontroller calculates the temperature compensated conductivity. This value is then displayed on the CRT as the conductivity in milliSiemens.

Temperature Monitoring

The thermistor installed in the conductivity probe changes its' resistance in response to changes in temperature. This conductivity probe is located just prior to the bypass valve and is the final temperature and conductivity measurement point. The values for conductivity and temperature measured at this point are displayed on the CRT and are used to generate the primary alarms for patient safety. If either value is outside of set limits, a bypass condition and audio alarm occur.

The thermistor is wired to a resistor divider network on the I/O hydraulic board. The output of this divider network is sent to the Miscellaneous I/O controller board where it is monitored by the on board 8040 microcontroller via an A to D converter network. From this information, the controller calculates the temperature using offset and gain inrmation stored in the host from the calibration. Calibration of the temperature measurement is a two point calibration done at 30 and 40°C.

Line Clamp

The line clamp opens with a solenoid and clamps with a spring return. When the solenoid is not energized, the spring pushes the plunger away from the solenoid. This causes the plunger to clamp the blood tubing. When the solenoid is energized, it pulls the plunger in with enough force to overcome the spring force. This unclamps the blood tubing. In the event of a power failure, the solenoid is de-energized causing the blood line to be clamped.

The solenoid is controlled by the line clamp board. On the line clamp board is a pulse width modulated current controller. This circuit applies sufficient current to the line clamp solenoid to pull in the plunger. After pull in, the controller ramps the current down to a level capable of holding the line clamp open. This cut back in current reduces the temperature of the solenoid, resulting in a more reliable device. Also located on the line clamp board, is a quick release circuit which helps dissipate the power stored in the solenoid. The result of this circuitry is a quicker and more repeatable clamp time over the life of the machine.

Control for the line clamp comes from the Miscellaneous I/O controller board via the I/O power board. The control signal for clamp and unclamp is optically coupled on the line clamp board. This provides electrical isolation between the high voltage used to operate the line clamp and the low voltage used for the control signals from the microprocessor.

Power Fail Alarm

The power fail alarm circuitry is located on the Misc I/O Electrical Power board, and includes a CMOS power state flip flop powered by a 1 Farad (F) capacitor. The flip flop, which can be toggled by either the front panel power button or the 80XX system controller, provides the following functions:

- When power is not supplied to the machine (i.e. when the +5 V supply is off) and when the flip flop is in the on state, then power is supplied from the 1 F capacitor to the audio alarm device. When power is supplied to the machine, the flip flop's output state is read by the 80XX, which provides indication of the intended machine power state. Also, when the flip flop is in the on state, power is supplied to the front panel power switch LED.

- The first function listed above results in the power fail alarm. The alarm occurs either if the machine loses power while it is running, or if the front panel power button is pressed "on" when there is no power supplied to the machine. The alarm can be silenced by toggling the flip flop off through pressing "off" the front panel power button.

Power System

The System 1000 power system consists of the following primary components:

- Power line circuit breaker/power switch
- Power transformer input fuse
- Power transformer
- Unregulated +24 V power supply
- +5 V, +12 V and −12 V logic power supplies All current from the power plug passes through the power line circuit breaker, which doubles as a main power switch. Both sides of the power line are broken by the circuit breaker. Two loads are fed from the breaker, the dialysate heater and the power transformer. Because the transformer draws much less power than the heater, a fuse is in series with its primary, which protects the transformer from a shorted secondary winding.

The transformer has three secondaries: a 20 Vac winding which supplies the +24 V supply, a 120 Vac secondary which supplies the logic power supply, and a 20 Vac winding which supplies the isolated voltage to the RS-232 interface. The +24V supply provides power to the machine's motors and solenoids, as well as to a +12V switcher which powers the CRT display. The logic power supply provides power to all the digital and low power analog circuitry.

Memory Controller Board

The memory controller board is designed to plug into the (IBM XT compatible) motherboard, and provides the following functions:

1. Six 28-pin EPROM sites allowing 384 Kbytes of ROM (read only memory) for program storage.
2. 8K bytes of non-volatile memory (CMOS RAM with self contained battery).
3. Realtime clock module (self contained with battery).
4. Asynchronous serial communications port (requires external isolation buffers, provided on a separate board).
5. External memory card interface (requires separate personality board).

6. 4 position dip switch for machine configuration control.

This board is designed to operate in conjunction with a modified motherboard. The modification involves disabling the motherboard's data buffers above address 256K. The memory controller's ROM space is mapped into the address space from 256K to 640K, with the portion between 256K and 312K being mapped also to address range 832K to 888K. The code at this upper address range is configured as a BIOS extension, which results in the ROM being given control by the motherboard's BIOS software following power on initialization. Unlike the standard BIOS extensions, the System 1000 code does not return to the BIOS after being given control.

Additional features:

A jumper (JP5) provides the capability of selecting an alternate memory configuration (presently disables ROM chip select functions, allowing operation with a floppy disk and second 256K of RAM) for development purposes. During normal operation, the jumper is either removed or placed on pins 2 and 3.

Circuitry is provided to insert memory wait states for any read or write operation of either memory or I/O (except memory refresh operations on the motherboard RAM array). This compensates for the added buffer delays, as well as the slower (than RAM) ROM devices.

Circuitry is also provided to extend the trailing edge of the write strobes (for both memory and I/O) so that the data buffers remain enabled well beyond the end of the PC Bus write strobes.

Programmable array logic (PAL) devices are used for address decoding for both memory and I/O devices.

System Architecture Block Diagram
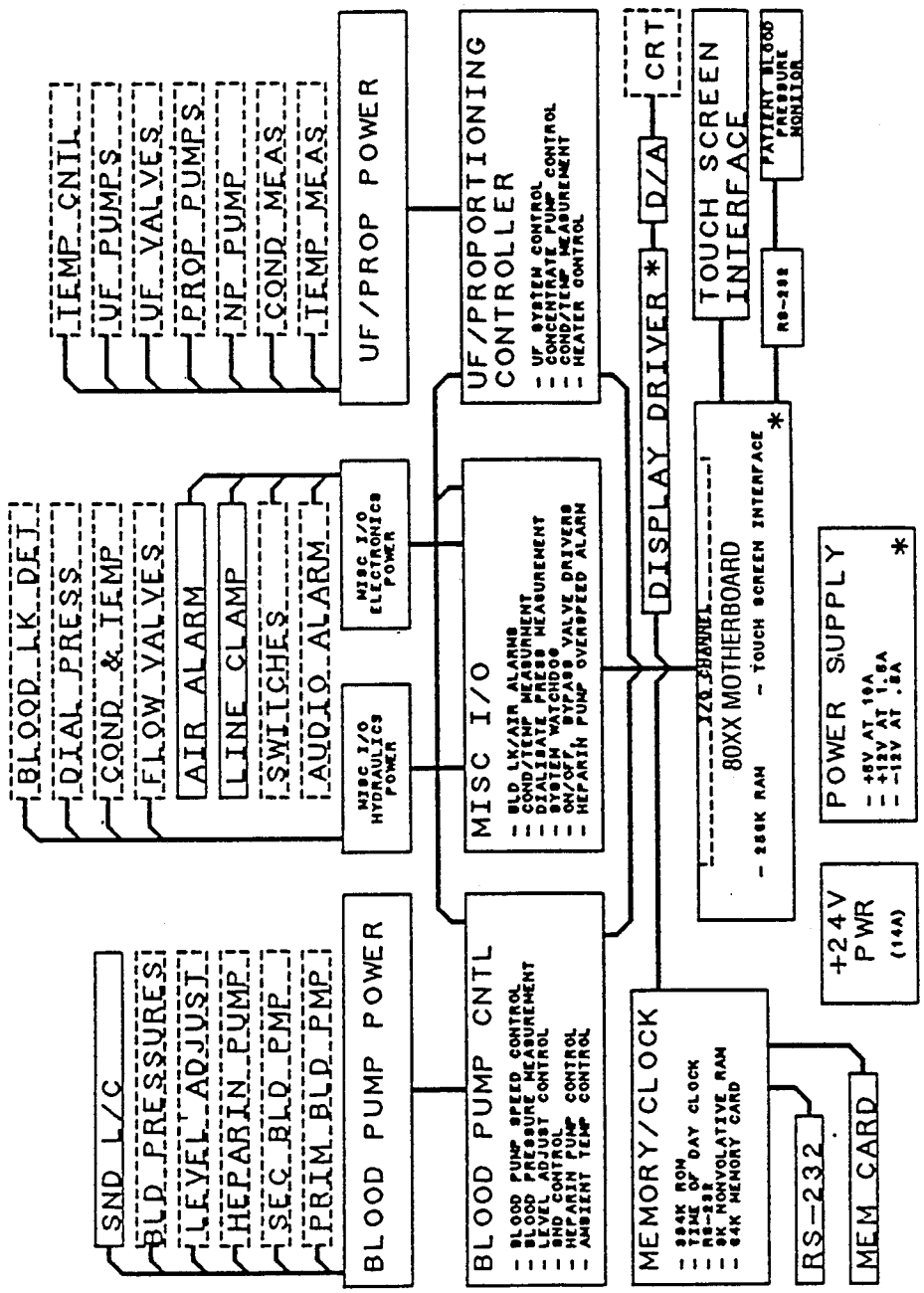

Software Flow Charts
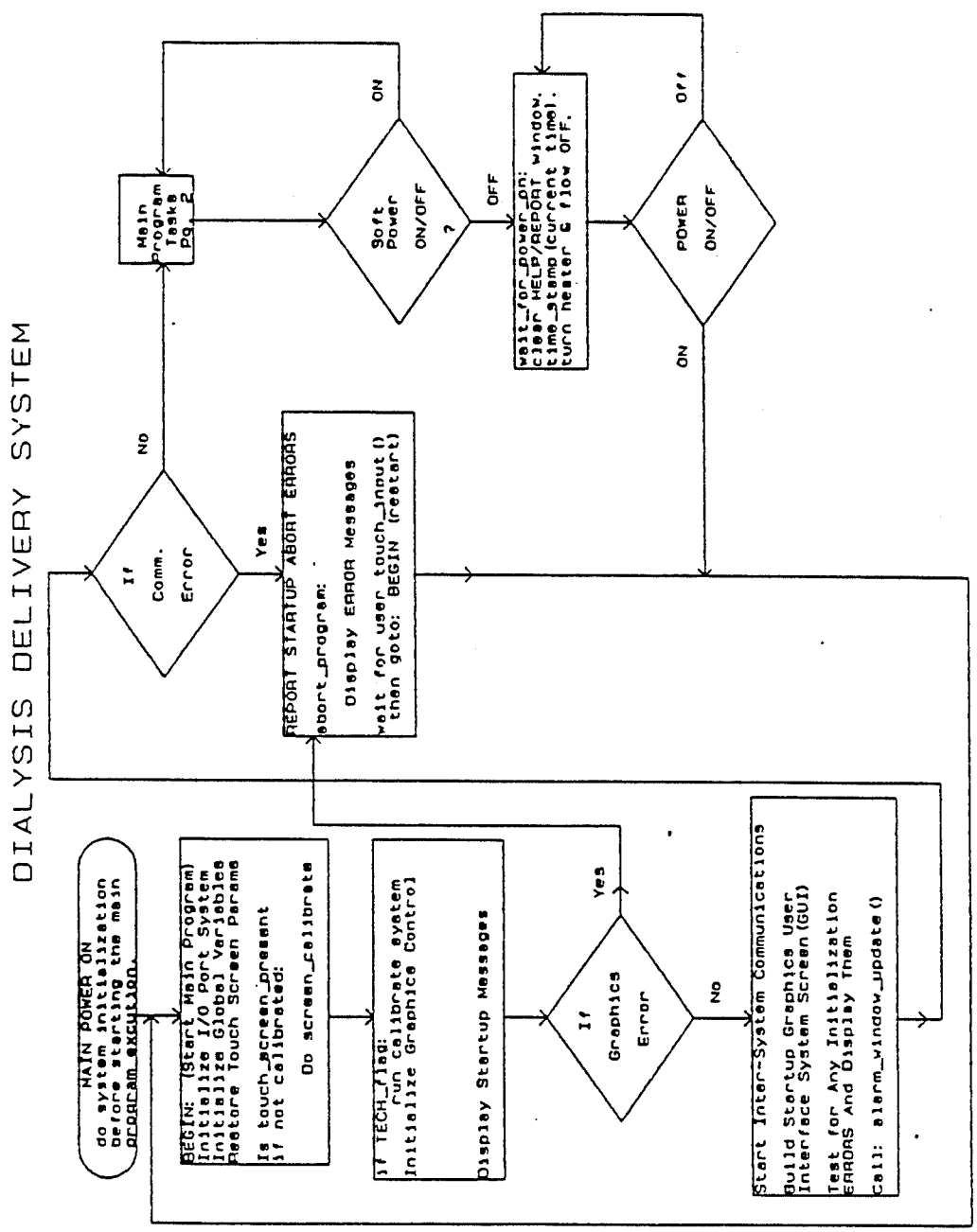
Dialysate Delivery System

MAIN PROGRAM TASKS

(from page 1) Main Program Tasks → system_activity().
/*
update w activity indicator,
update blink color palettes
*/

→ data_input().
/*
update local time clock,
input data from controllers,
scale the data.
*/

→ get_dip_switch_data().
bp_communications().
up_communications().
io_communications().
port_communications().

→ limit_pos_test().
/*
update Arterial and venous
bargraph limit indicators.
*/

↓ verify_test().
/*
test for HELP/REPORT
ALARM window time out.
display activity indicator
*/

→ data_output().
/*
output data IO System
BP System, UP System,
test and set output for
the NO FLOW and BYPASS
FAIL display logic
*/

→ gd_schedule().
/*
update GUI display windows
*/

→ self_test().
/*
do self test as the system
demands
*/

↓ error_test().
/*
display any pending-ERROR
messages
*/

→ test_state().
/*
update alarm logic, test the
state flow and update the
system state machine
*/

→ notdone + key_functions().
/*
input data from the debug
keyboard or get new position
data from the touch screen
*/

→ Return (to page 1)

Main Program Tasks

I/O Controller Software
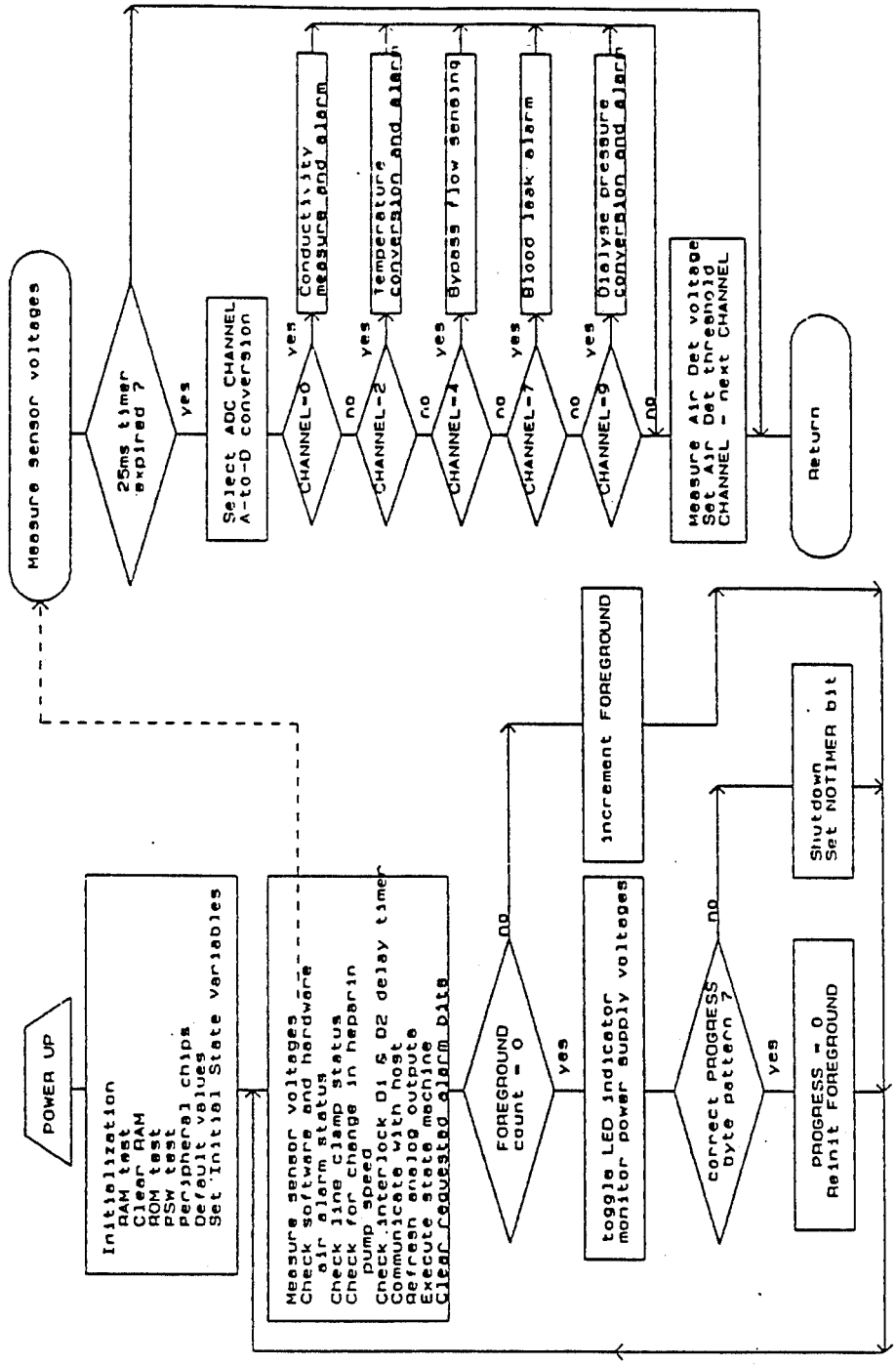
I/O Controller Software page 1

I/O Controller Software
*continued*

The circles represent I/O controller states that are characterized by the following parameters:

Shutdown: Machine in bypass, line clamp damped, bloopd pump disabled, heparin pump disabled Dialyze: If extracorporeal alarm, controller stops blood pump and clamps line clamp.
If dialysate alarm, controller puts machine in bypass.
If heparin overspeed alarm, controller stops heparin pump.

Prime: If extracorporeal alarm, controller stops blood pump and clamps line clamp.
If dialysate alarm, controller puts machine in bypass.
If heparin overspeed alarm, controller stops heparin pump.

Prime Disarm: If dialysate alarm, puts machine in bypass. If extracorporeal alarm (blood leak and air detector only), no controller response.

Rinse: Controller does *not* take alarm response actions joutlined in Dialyze state.

The lines denot state transitions with the required signal(s) to make the transition noted beside the lines. These control signals are detailed in the Legend.

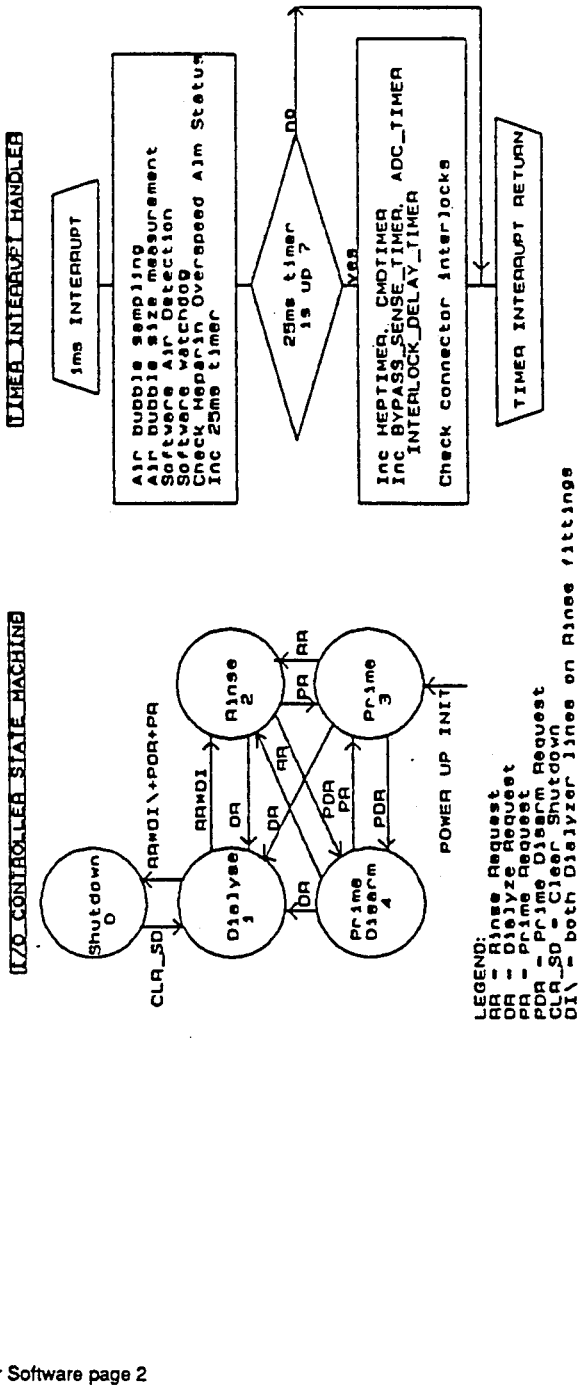

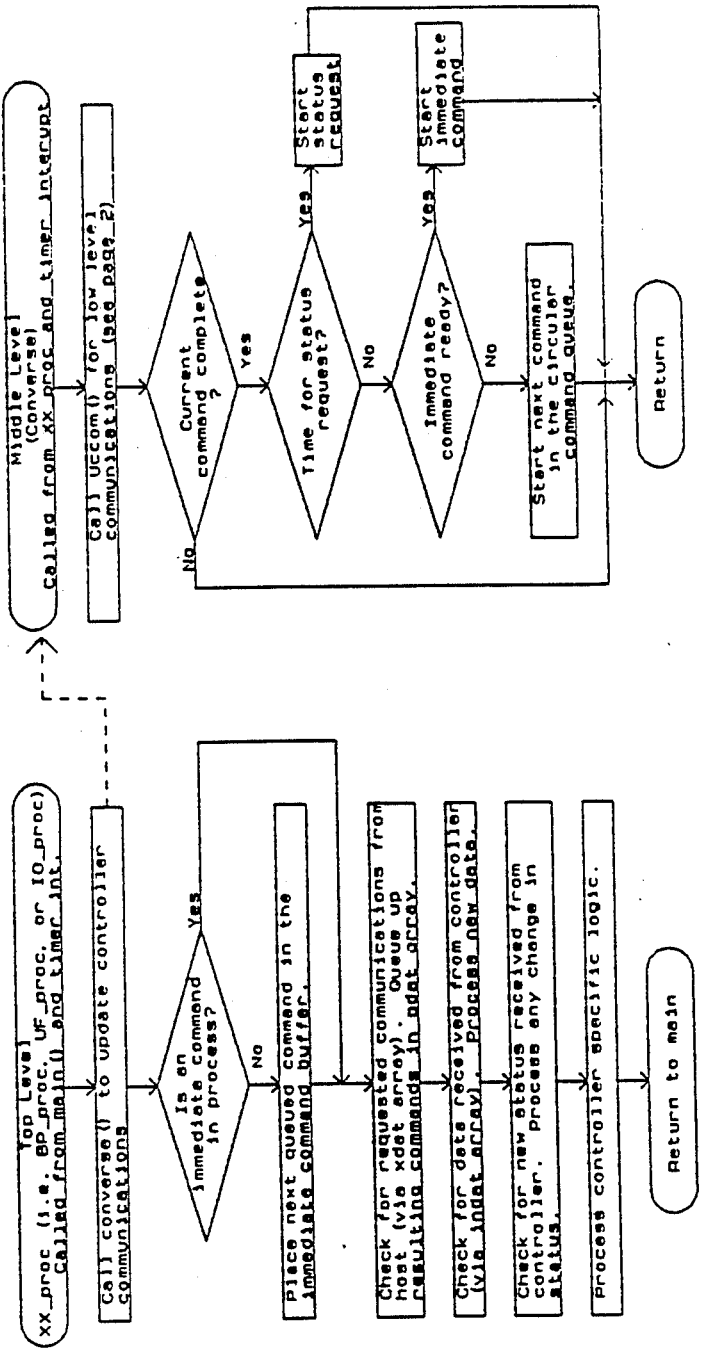
Host Software page 1

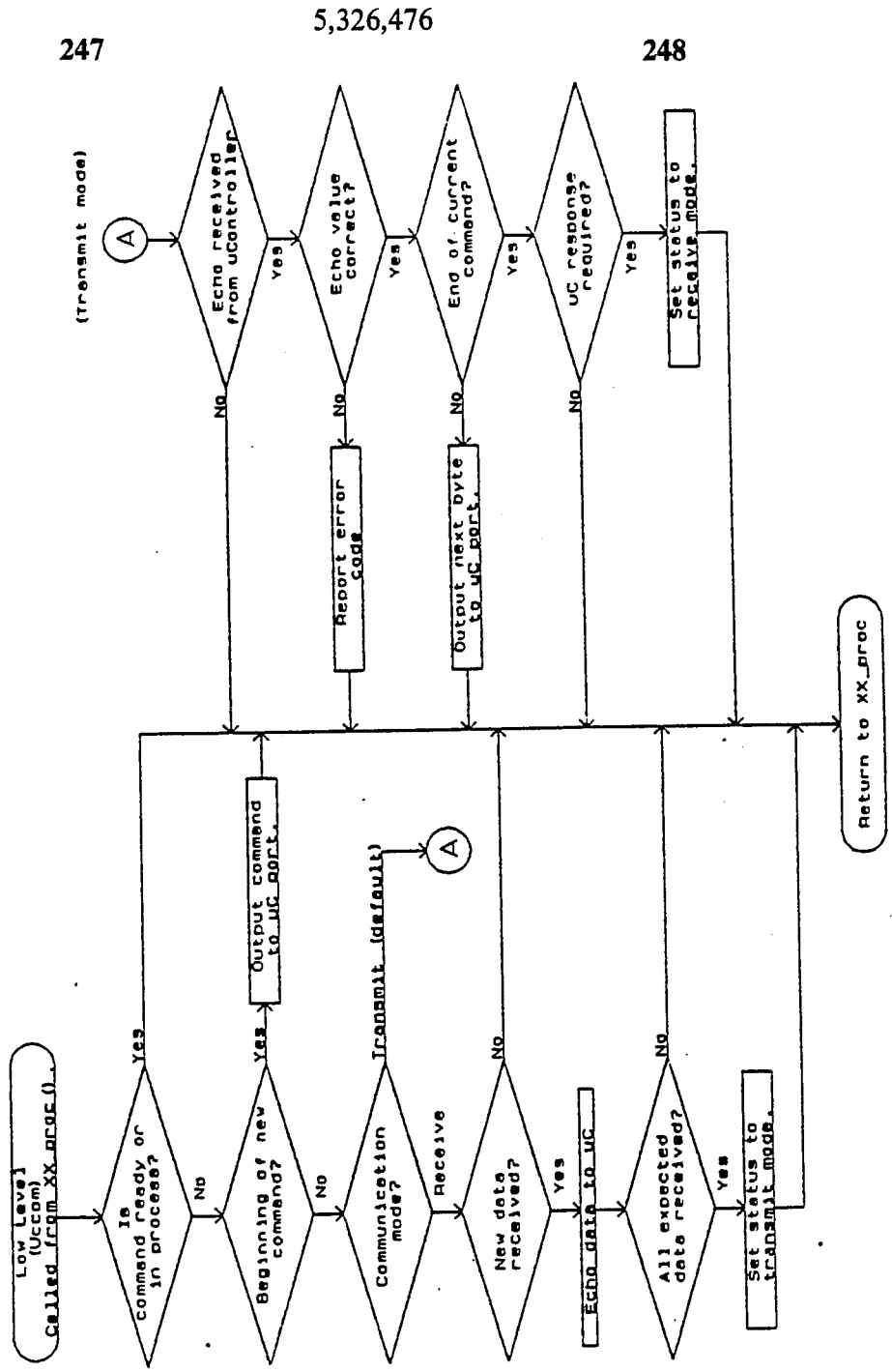
Host Communications
*continued*
Host Software page 2

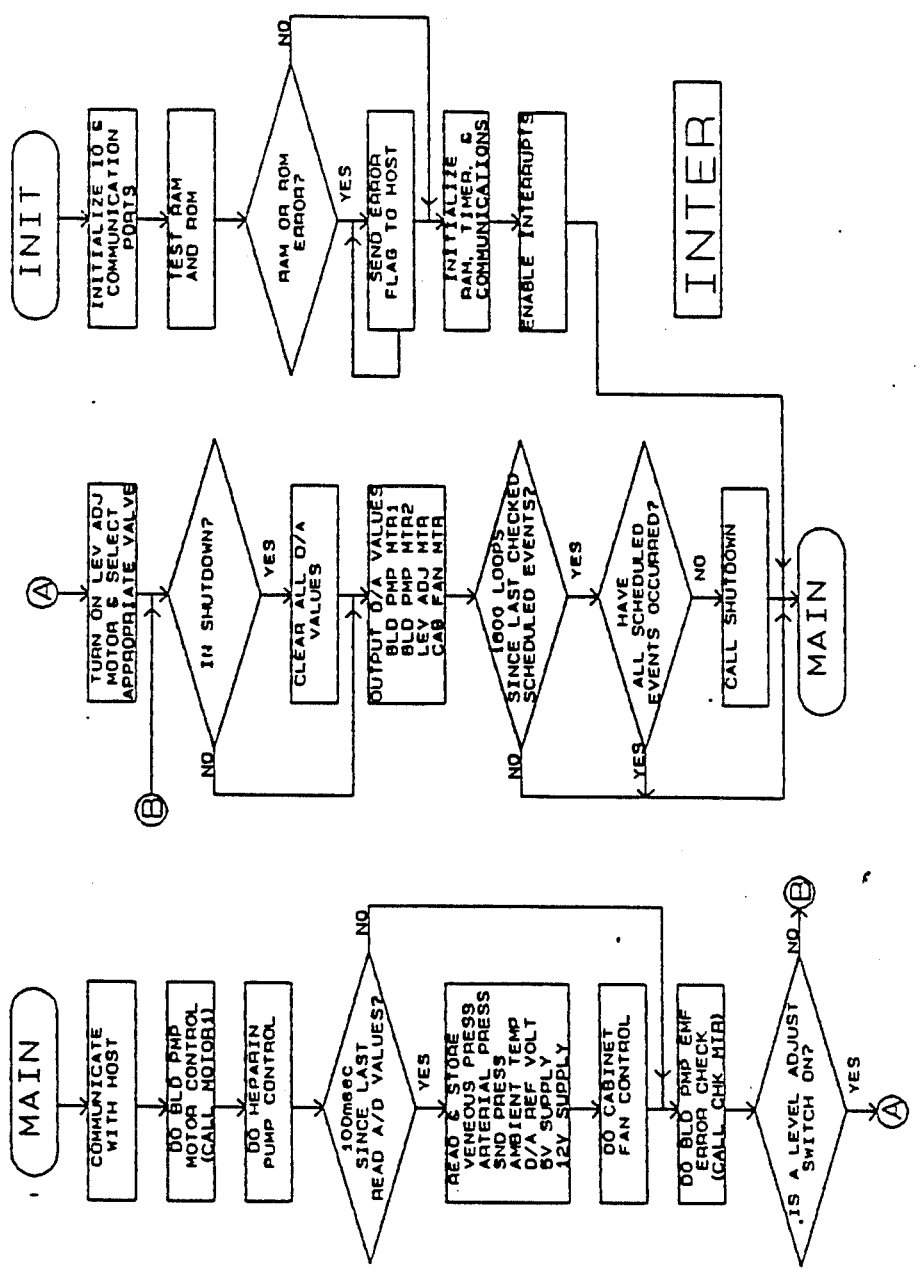

Blood Pump Controller Software
*continued*
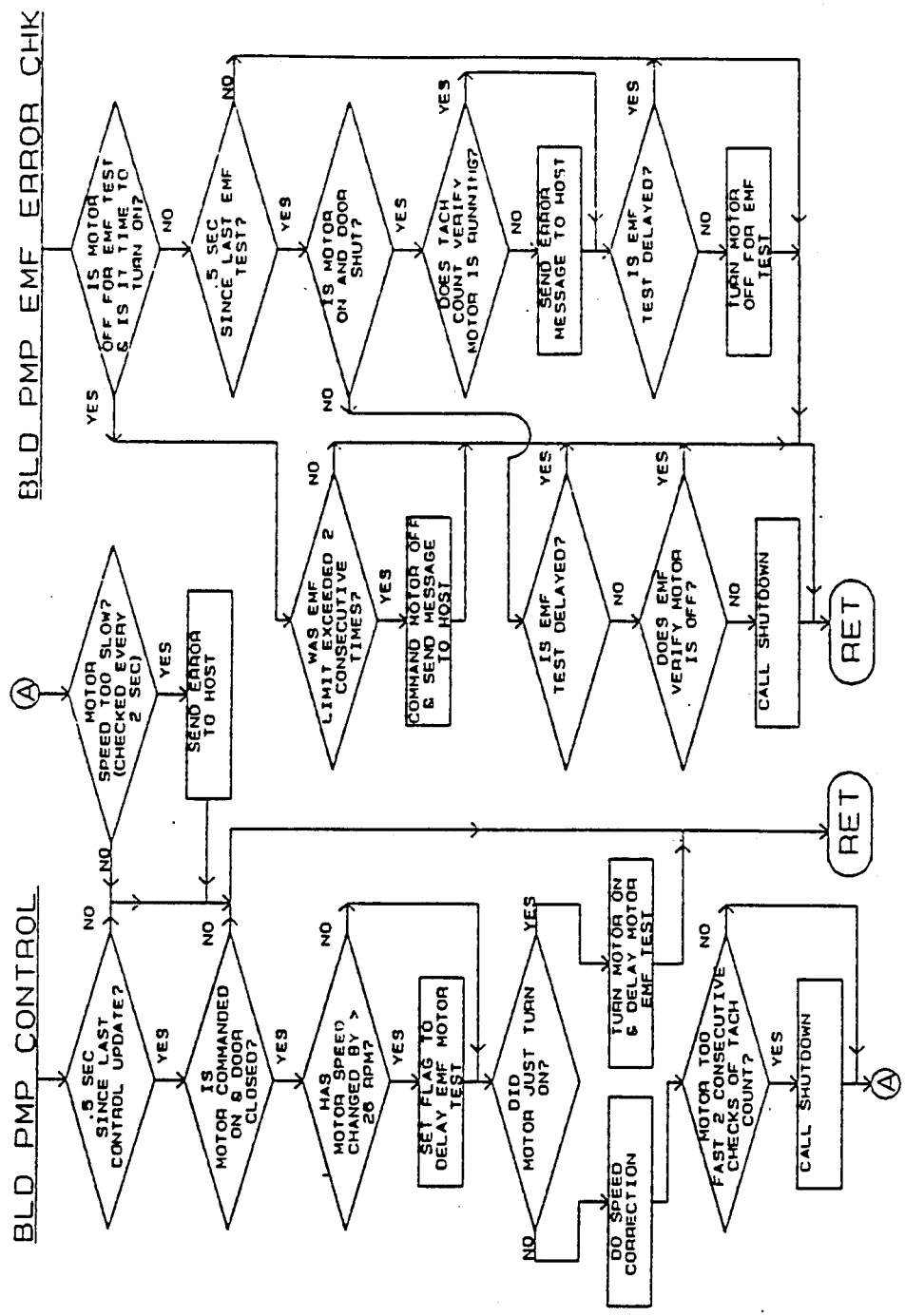
Blood Pump Controller Software page 2

Blood Pump Controller Software *continued*
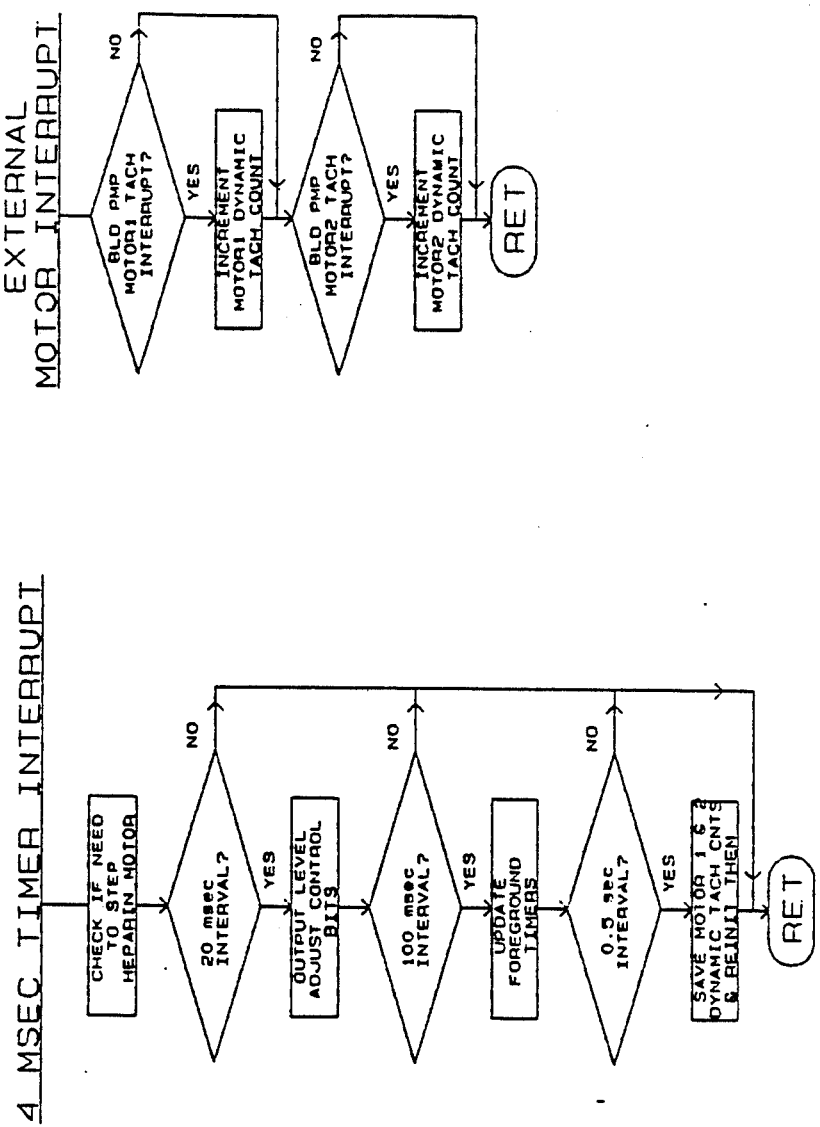
Blood Pump Controller Software page 3

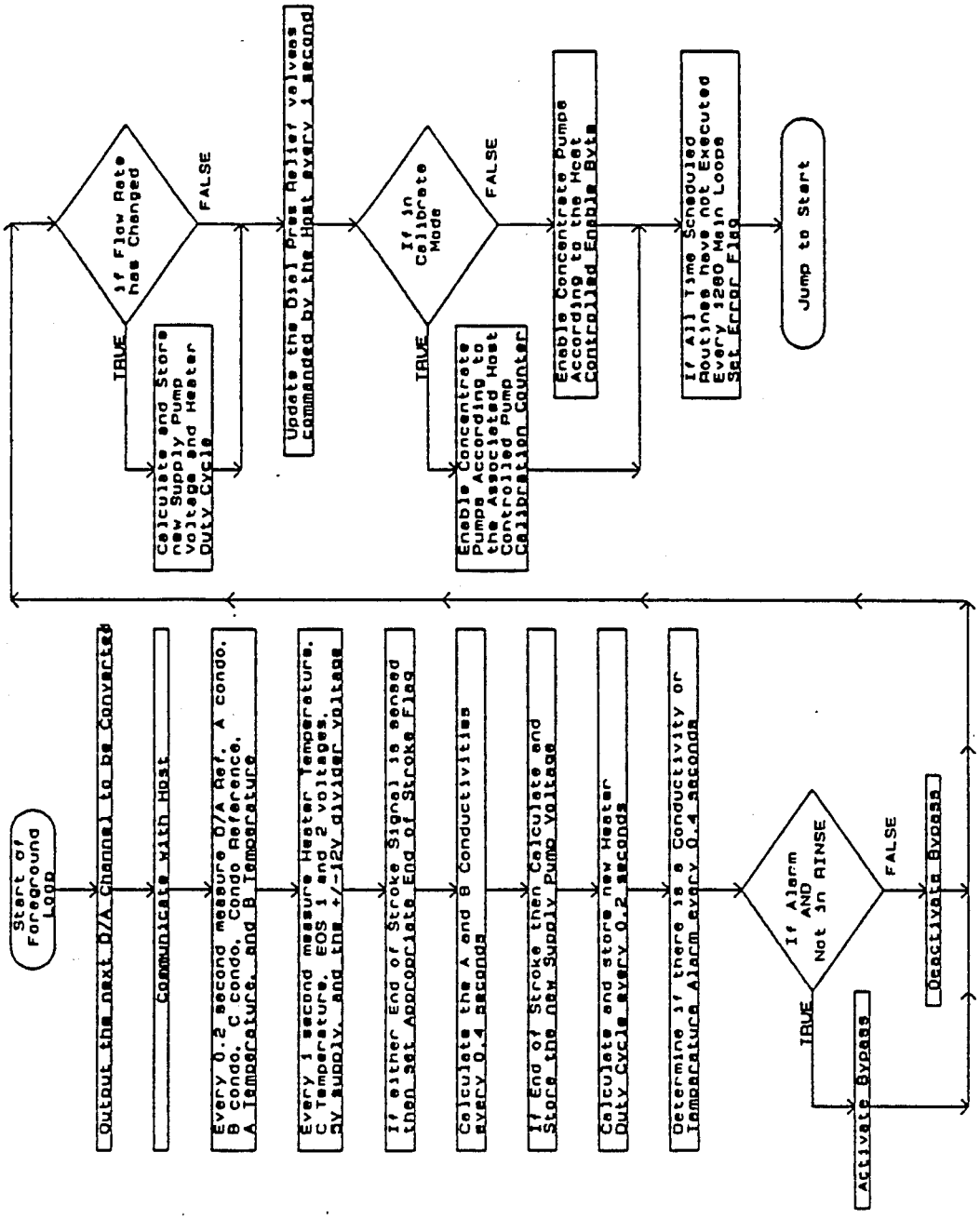
UF Controller Foreground (Main Loop)

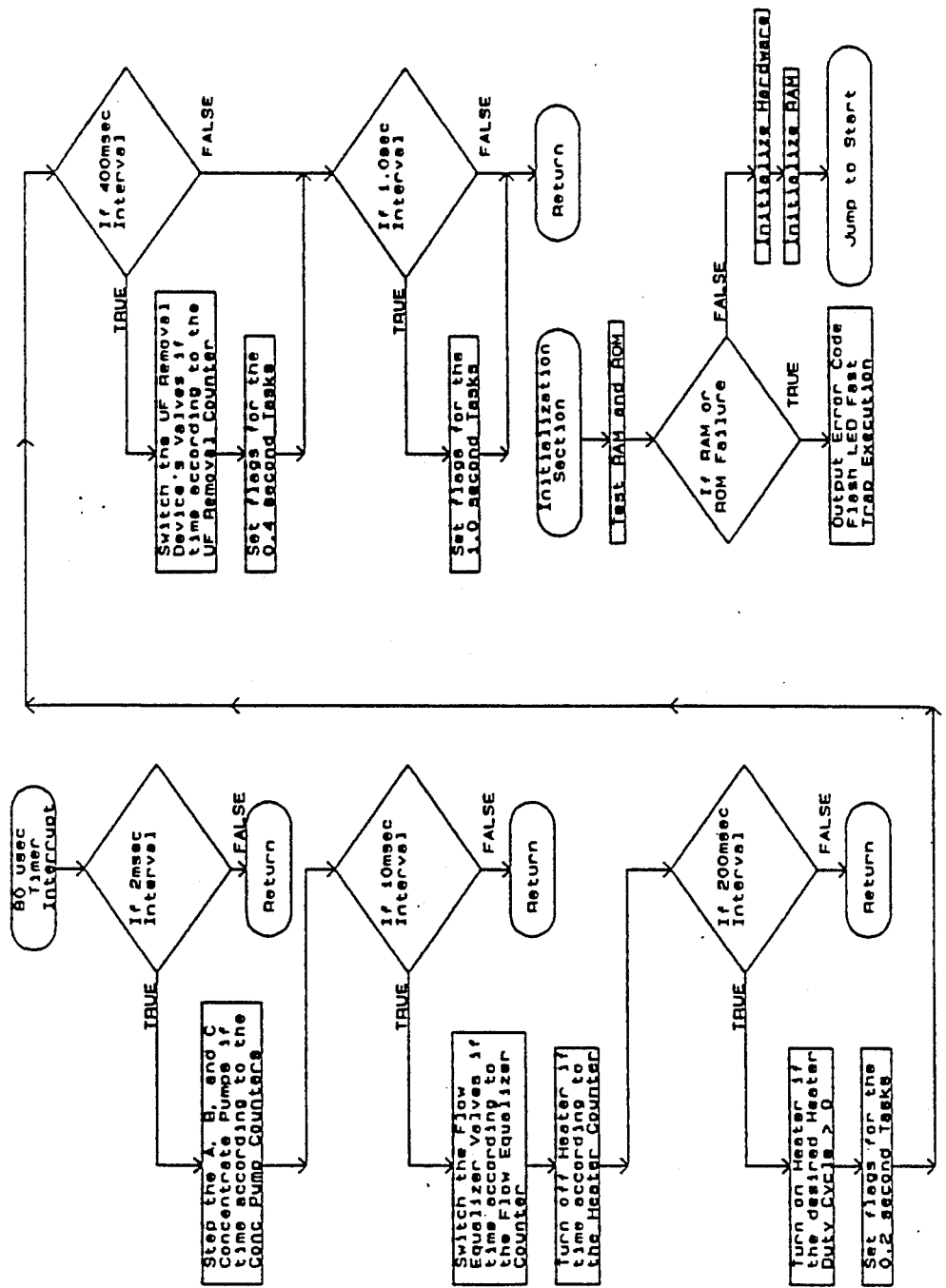
UF Contoller Background and Initialization

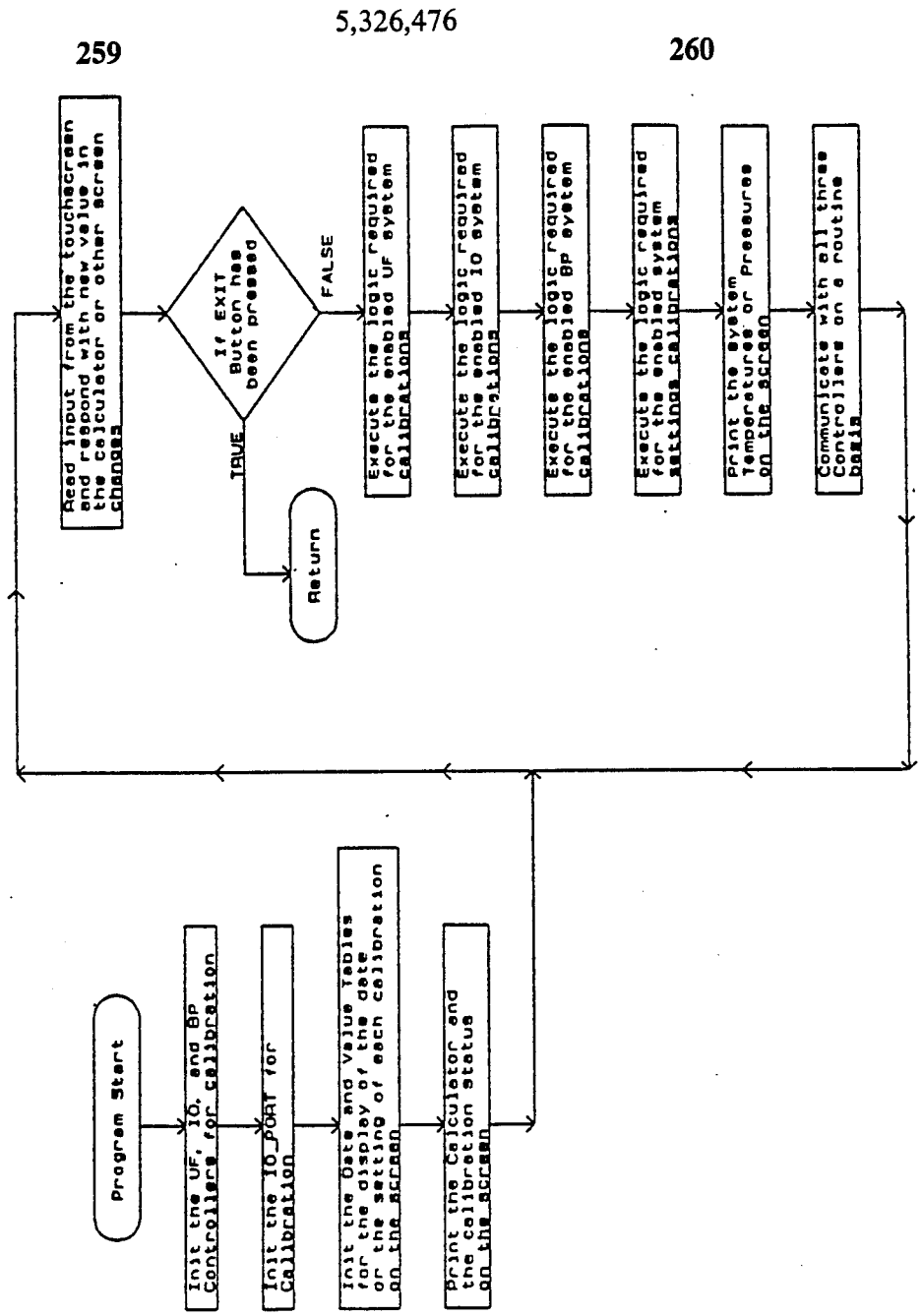
Calibration Mode Flow Chart

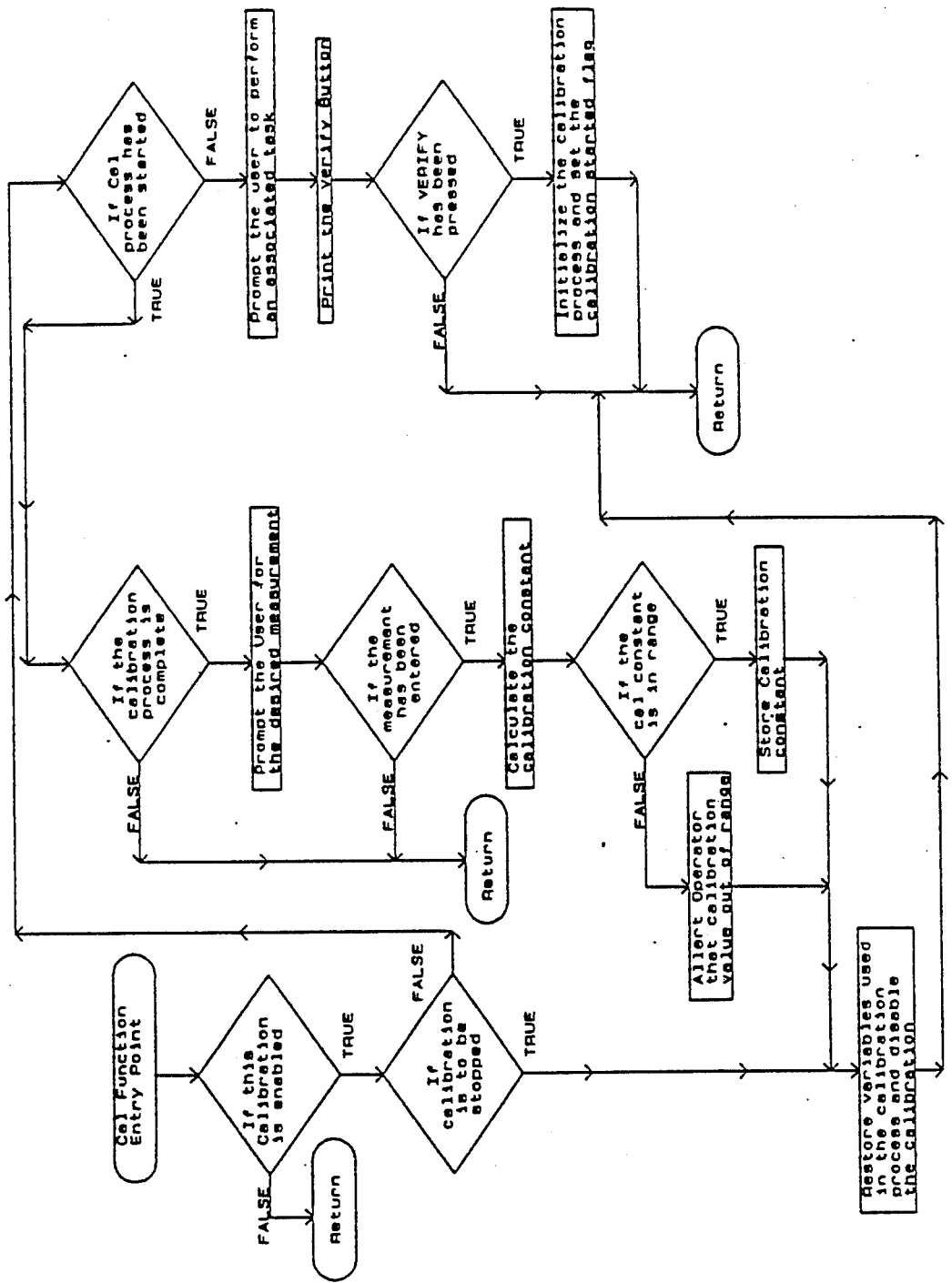
Sample Device Calibration Logic

Plan

Development Process

The development of the System 1000 hardware/software control system has directly involved a team including degreed electrical engineers with design experience in both hardware and software, and some with over eight years of experience in the dialysis industry. The design effort has consisted of the following four parallel efforts:

1. Main Controller/User Interface hardware/software design
2. Blood Pump System hardware/software design
3. UF/Proportioning System hardware/software design
4. Misc I/O System hardware/software design The main controller design is based on an IBM PC/AT compatible architecture using an 80XX microprocessor, allowing the use of proven and readily available development tools. The main control software was written in the C language, using the Borland Turbo C revision 2.0 compiler. The compiler's extensive code checking facilities were utilized during the development to reduce the occurrance of coding errors.

The other three systems are each centered around an 8040 (8048 family) microcontroller, with software written in 8040 assembly language. The 8040 microcontroller systems communicate with the 80XX via the PC bus and are capable of functioning and being tested by themselves, independent of the rest of the machine. This allowed them to be developed and tested with a standard personal computer (PC), with relatively simple PC test software.

The system design has been guided by a top level machine specification, which specifies machine features (e.g. programmable sodium, UF control, and cleanable surfaces) and operational requirements (e.g. dialysate flow rate range, input voltage range, and heparin pump syringe sizes). Interpretation of these requirements at the detailed level has evolved as the design progressed. Prior to any detailed design, an initial plan was made which specified the general control architecture, with machine functions being divided among the three 8040 controller systems.

On a biweekly interval, the design team has met to discuss progress and design issues. This format has not only served as a reporting function, but also as a peer review of design issues. In addition, prototype and final design reviews have been held for each circuit board. The 8040 microcontroller code has been reviewed by a team member unfamiliar with the associated design details, providing input on code structure and clarity.

As the user interface was being developed several experienced dialysis nurses provided input on the user interface, identifying potential operator problems and safety concerns.

Prior to the first clinical monitoring machine being installed, extensive validation testing was done to each subsystem, with formal test reports being written to document the results. In addition a validation test protocol was written, consisting of 994 test items, which verifies virtually every operational feature in every machine state. An experienced dialysis nurse spend several weeks with the machine, validating and manupulating the user interface and identifying potential operation problems and safety concerns. As a final verification, the machine was subjected to six simulated dialysis treatments, with the requirement that no operational problems occur. The treatment conditions were all preplanned, guaranteeing that a wide diversity of conditions were tested.

Monitoring machines are operating in three clinical sites and has sucessfully performed more than 410 treatments as of January 7, 1991. The studies will continue in these and additional clinical locations.

Software Specifications

Overview

The purpose of this specification is to describe the process requirements in the development of the System 1000 Software Control System. This document specifies the general software strategy, the operating system and the programming languages used.

Requirements

Safety

Tests will be done at system power up time and before each patient treatment on hardware devices and the system memory (programmed read-only-memory, ROM, and random-access-memory, RAM).

A software 'watchdog' timer will be utilized to ensure that the background tasks and all critical foreground tasks are active. If any of these monitored tasks become inactive, the machine should revert to a safe state and alert the operator.

User I/O Interface

The display portion of the human interface will be compatible with EGA/VGA graphic interface hardware. In addition, the display messages will be selectable for human language differences (i.e., English, French, German, Italian; and at a future time include Japanese, and possible other symbolic or iconic languages).

Interprocessor Communication

The communications used within the hardware system will be via the system bus. This hardware system typically would include various microcontroller driven peripheral interface devices for the control of: the blood pumps; a heparin pump; valve actuators; etc. Within the scope of this confidence level, the communications between both the main system and the microcontrollers must be verified using redundant acknowledgements. If a communication response is not received by either system within a predetermined time, a machine failure is assumed and a safety shutdown will be initiated.

Remote Computer Communication

A serial interface will be provided for remote query of the system by a PC-type computer using a customized interface program.

Module Header Information

The following information is to be included in an abstract portion of the header information of each software partition or software sub-system.

- Each software partition or sub-system must describe in general the module's purpose and highlight any specific input or output requirements.

- A complete revision history of each partition or sub- system must be included along with the date and a description of the changes. Also, all versions of host system software that the module is compatible with will be listed.

- A description of the programming language used for the partition or sub-system if it differs from the native language used for programming the system.

Control Architecture

In general, the basic context of the operating system is described as a polled system with interrupt driven background events occurring randomly.

The foreground activity is the polled portion of the operating system. During the foreground execution time, various sub-routines or functions are called to gather and input data into temporary storage memory; scale, compute and evaluate limit violations, and set appropriate alarm flags; evaluate state machine flow path data and update the execution of the state machine; output current data to the various hardware sub-systems; update the current data for the graphics display system; and test the system and reactivate the watchdog timer.

In the background portion of the operating system the microcontroller based peripheral interface hardware communications will take place, as well as all interrupt driven devices and activities. Also, the interrupt processing software must provide a means to test the reactivated watchdog timer.

Regardless of the foreground or background activity, the operating system generally must feature safety and reliability, and detected errors must be safely dealt with.

Programming Languages

The programming language of choice for the development of the various partitions and sub-systems of the System 1000 Software Control System are versions of the popular 'C' language. Specifically, Borland International Turbo C Version 2.0 (an ANSI version of 'C') and the Borland International Macro Assembler Version 1.0.

The 'C' language version chosen follows the traditional reference for 'C', the book 'The C Programming Language', by Brian W. Kernighan and Dennis M. Ritchie (which will be referred to as "K&R" from now on). A more complete reference to the 'C' language is the ANSI extensions, ANSI Subcommittee X3J11 (i.e., ANSI 3.7. & ANSI 3.8.) The following conventions will be adhered to:

- ANSI constructs will be used as the programming guideline.
- The interface methods that are used between languages must be indicated (i.e., stack passing, file control block (FCB) or parameter block, etc.).
- Any compatibility problems must be indicated and the solution used to resolve the incompatibility.
- If a special software is used, a description of the programming language used (with appropriate warnings) for the implementation of the partition or sub-system must be provided. Also, the version number of the special software must be listed in the modules written using it.
- If a purchased library is used in any program module, the version number of the purchased library must be listed. Also, a description of the functions used and any special considerations taken in implementation must be provided.

Programming Conventions

The following conventions for program entities, such as: local or global variables, local or global constants, and local or global storage arrays functions and etc., are to be used as the preferred guidelines for module interface within the System 1000 Software Control System or operating system.

Defines

All pre-defined constants, whether local or global, used within a module are to be upper case letters. The use of underscore and numerals is acceptable only if not used for the first character position of the defined name.

Variables

All local variables used within a module are to be lower case letters. The use of underscore and numerals is acceptable only if not used for the first character position of the local variable name.

Generally, all global variables used by any module are to have the first character of the name in an upper case letter, the use of underscore and numerals is acceptable only if not used for the first character position of the global variable name.

Macros

All macros are to be upper case letters, the use of underscore and numerals is acceptable only if not used for the first character position of the defined macro. To ensure the integrity of the macro with respect to the order of precedence of its operations, any parameters used in the macro should be enclosed in parenthesis.

The following is an example:

define MACRO_A(x) (((x) == ON) ? 1 : 0)

Structures

Structure tag names should be used whenever a structure is defined more than once, with the actual structure definition only existing in one place. The structure tag name should consist of lower case letters.

The structure name should follow the same convention previously described for variables.

Elements used within a structure are to be lower case letters, the use of underscore and numerals is acceptable only if not used for the first character position of the element.

Functions

All function names used in a module can be either upper or lower case letters, the use of underscore and numerals is acceptable only if not used for the first character position of the function name.

Security Features

- The machine calibrations cannot be modified without the use of a tool. A tool for this purpose can be a specially coded memory card that is plugged into the machine, or a literal tool required to open the cabinet to gain access to a calibration switch.
- The host software will verify, at power on time, that the expected three versions of controller software are present in the three slave controllers.

Miscellaneous Programming Requirements

File Access Functions

No file access library routines should be included in the software [e.g. fopen()]. If file access functions are included for test purposes, they should be conditionally compiled when the constant ROMMABLE has a value of 0.

Structure and Constant Initialization

Structures and constants used by multiple modules should not be defined more than once.

Memory Usage

Large allocations of DATA memory through the declarations of arrays is discouraged. This includes allocating the arrays that are either global or static. The preferred alternative is allocating them on the heap using malloc(). If global access is required to the array, then a global pointer can be declared which points to the memory. In the large memory model the DATA memory is limited to 64K, much of which is used for string declarations.

Prohibited Functions

The following functions cannot be used, because they don't function properly in ROM:

| | | |
|---|---|---|
| delay() | textbackground() | textmode() |
| clrscr() | textcolor() | sleep() |
| bioscom() | | |

Compiler Checking

All compiler warnings should be recognized and explained.

Prototypes for all functions must exist.

Compiler options settings

Large memory model

C calling convention

Floating point emulation

Default character type: signed

Byte alignment

Underbars generated

Duplicate strings merged

Standard stack frame

Stack overflow tested

Optimized for size
Register variables used
Register optimization used
Jump optimization used
Nested comments off
ANSI keywords only off Enabled Portability Warnings
- Non-portable pointer conversion
- Non-portable pointer assignment
- Non-portable pointer comparison
- Constant out of range in comparison
- Conversion may lose significant digits
- Mixing pointers to signed and unsigned char Enabled ANSI Violations Warnings
- 'ident' not part of structure
- Zero length structure
- Void functions may not return a value
- Both return and return of a value used
- Suspicious pointer conversion
- Undefined structure 'ident'
- Redefinition of 'ident' is not identical
- Hexadecimal or octal constant too large Enabled Common Warnings
- Unreachable code
- Code has no effect
- Possible use of 'ident' before definition
- 'ident' is assigned a value which is never used
- Parameter 'ident' is never used
- Possibly incorrect assignment Enabled Uncommon Warnings
- Superfluous & with function or array
- 'ident' declared but never used
- Ambiguous operators need parentheses
- Structure passed by value
- No declaration for function 'ident'
- Call to function with no prototype

Linker Options
Segments initialized

Stack warning

Case-sensitive link off (the linking process used to generate the EPROM code version does not function properly if case sensitive linking is used.)

Software Sub-system

Description

Each partition or sub-system must include the following as part of its header information:
- an identification banner must appear as part of the header
- the project name
- a module name or number
- a version number
- an origin date

- a revision date
- the author's name
- the company name and/or division
- the company address
- a copyright date or dates
- the usage violation and restriction information The following is an example of the header block that will appear at the top of each software partition or sub-system.

```
Project Name : System 1000
Module Name :
Version # :
Origin Date :
Revision Date:
Author Name:

Company    : Althin CD Medical, Inc.

Address    : 13520 S.E. Pheasant Ct.
             Milwaukie, OR 97222
Copyright (1988 - 1990) All Rights Reserved Any use of this program other than for the specific
purpose of controlling System 1000 dialysis equipment or
associated peripheral equipment is strictly prohibited.
```

/*
  Purpose :
*/

In addition, a revision history block containing the following information will appear directly after the header information in each software partition or sub- system.

```
            Revision History
```

/*
Date  Author       Description
*/

Criticality

General Description

Patient safety has been a primary consideration since the conception of the System 1000. The absence of patient hazards as a result of single component failures has been a design rule. In addition, the Self Test Mode has been implemented which ensures that redundant safety mechanisms are fully functional prior to each treatment. The self testing is also used to test non safety related functions to reduce the chances that a nuisance failure is uncovered during a dialysis treatment.

The following lists some of the major design contributions to the machine's safety.

1. Redundant conductivity alarms, with redundant conductivity probes
2. Redundant temperature alarms, with redundant probes
3. Redundant air detector systems
4. Self test verification of venous pressure measurement accuracy using the arterial pressure measurement as reference.
5. Self test verification of the volumetric UF system
6. Three independent A/D measuring systems whose accuracies are compared during selftest.
7. Continuous monitoring of the power supply voltages.
8. Continuous monitoring of the internal ambient temperature.

9. Use of a hardware shutdown line which forces the machine into a safe, nonfunctional condition. All four microprocessors and a hardware watchdog circuit can activate this line.
10. Interlock switches on the dialysate and concentrate line rinse fittings allow the machine logic to prevent inappropriate state changes.
11. Bypass fail detection.
Fault Tree Analysis
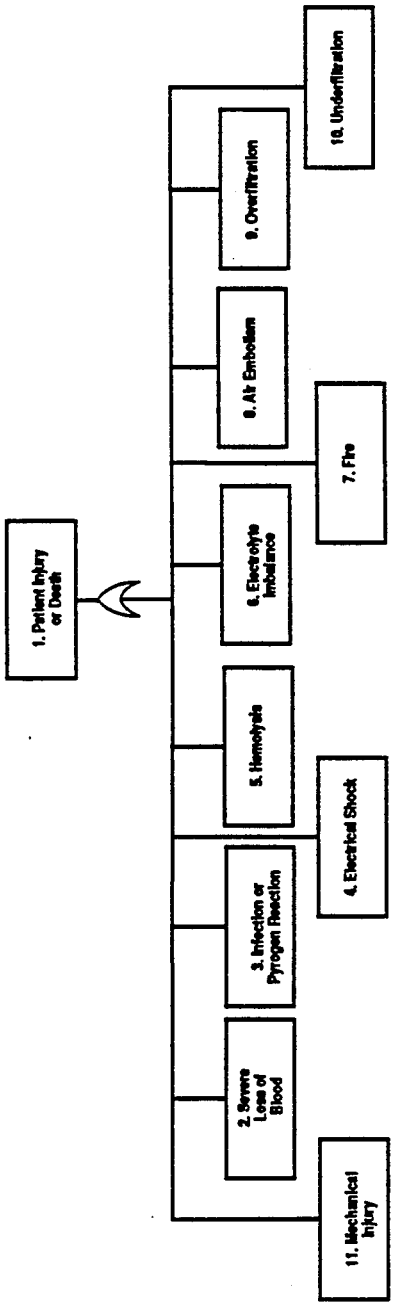

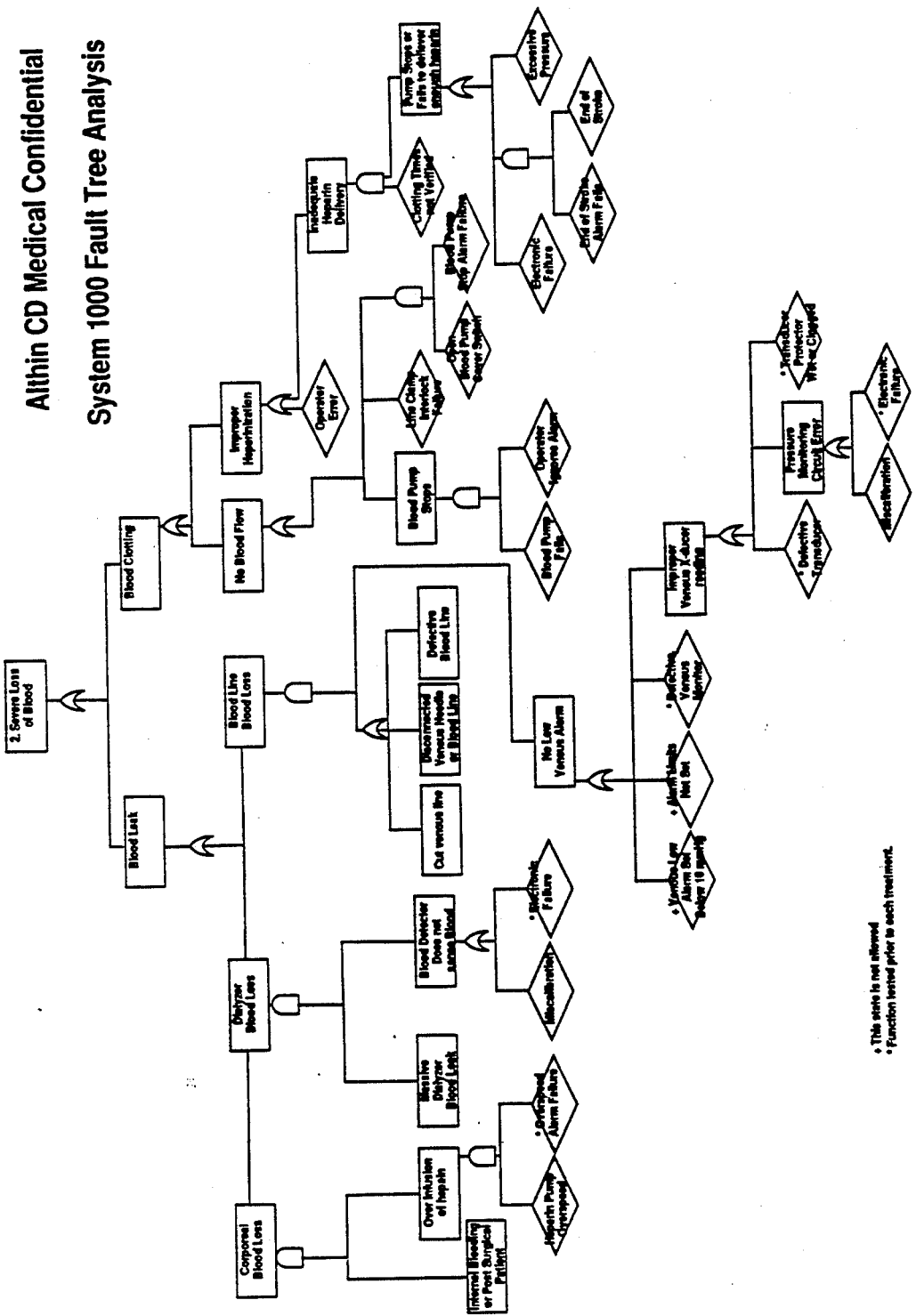

Althin CD Medical Confidential
System 1000 Fault Tree Analysis
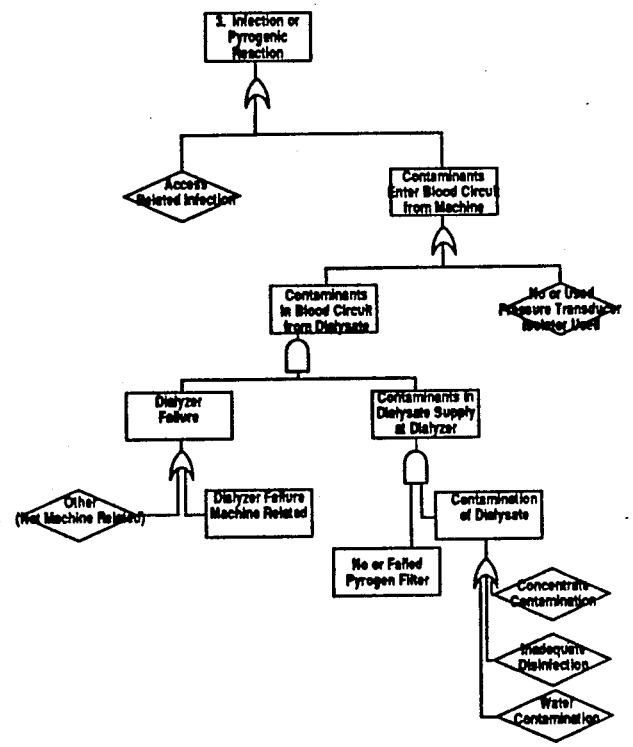
Althin CD Medical Confidential
System 1000 Fault Tree Analysis
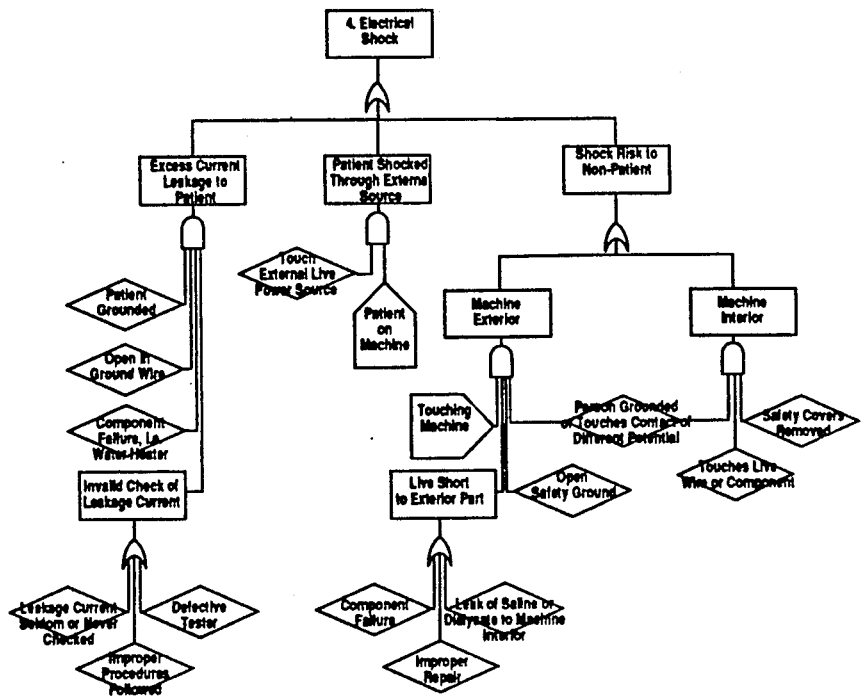

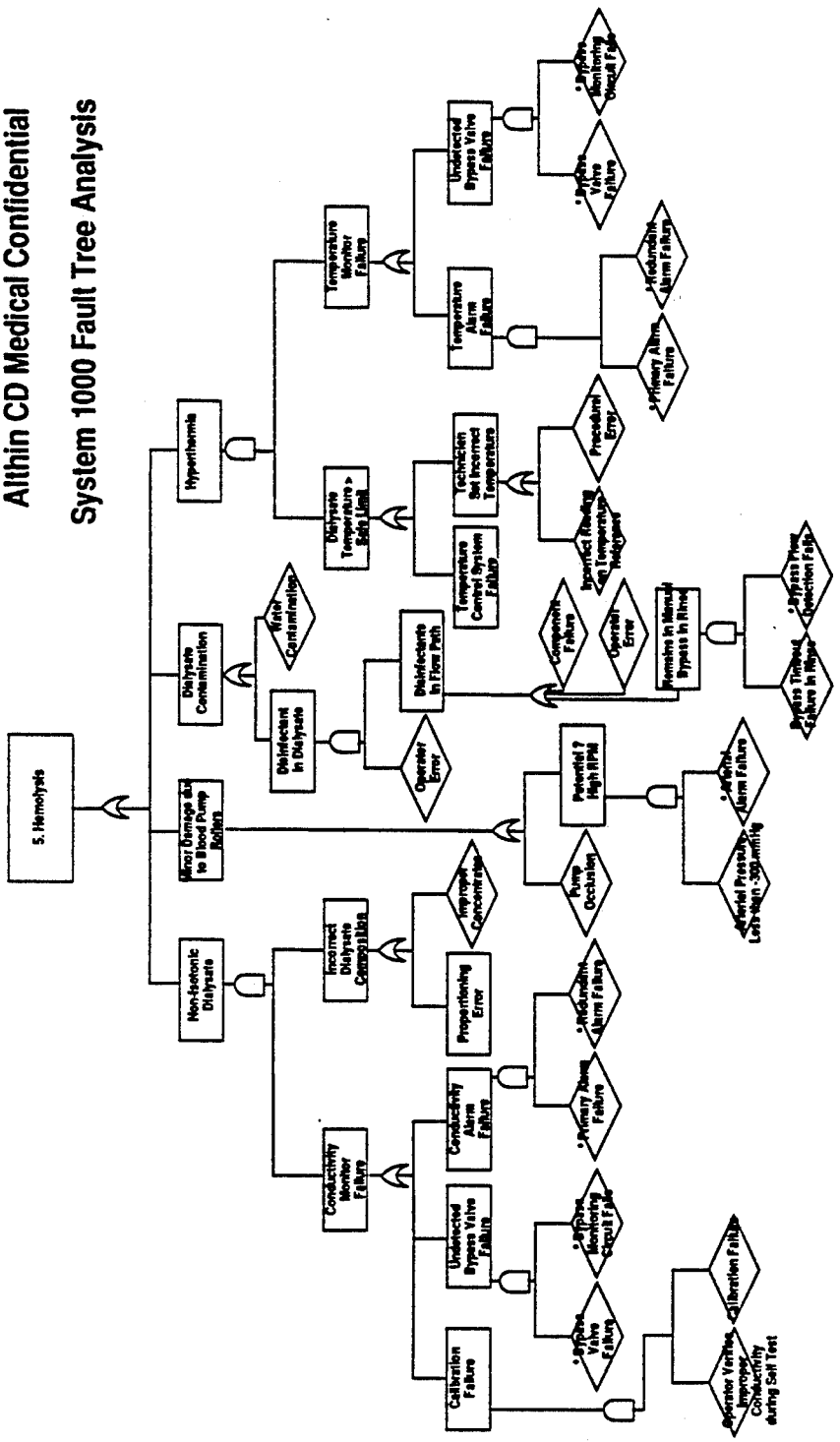

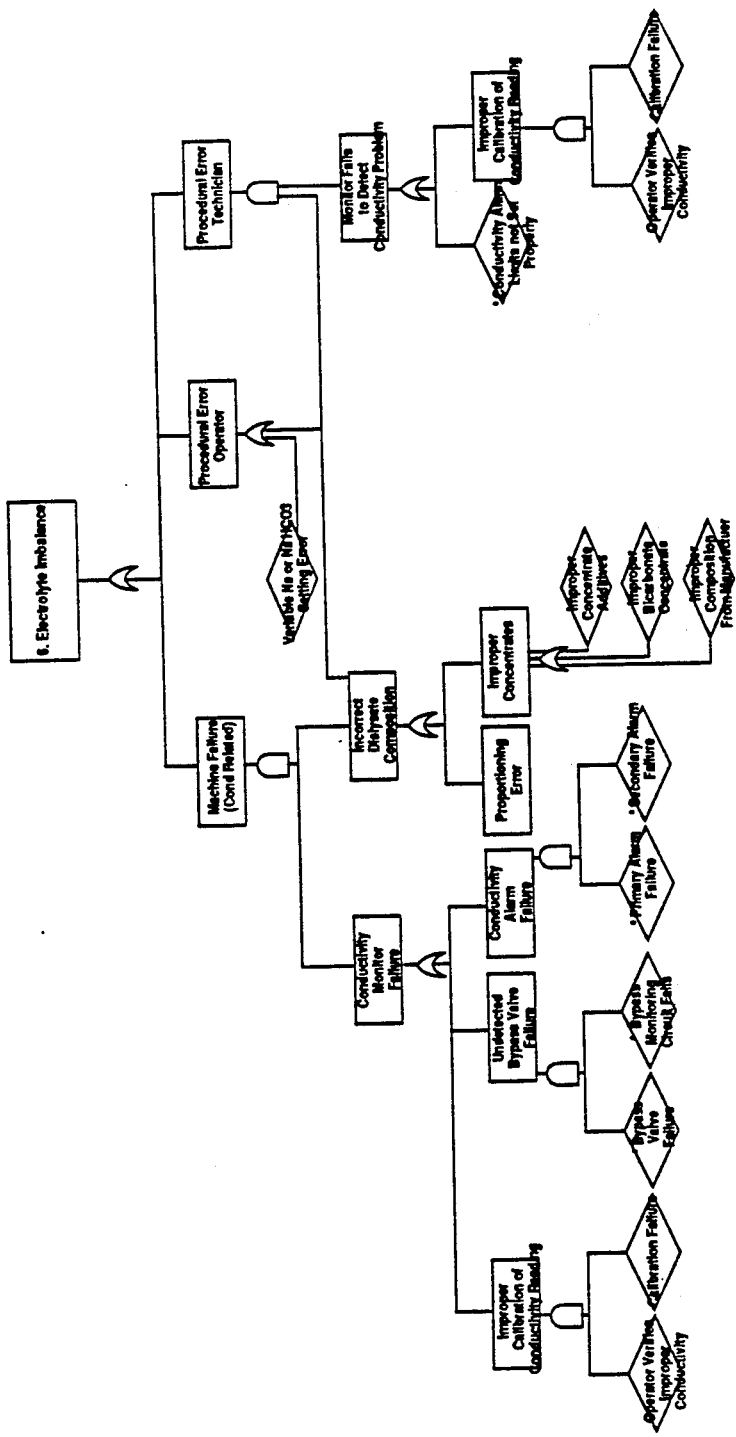

Althin CD Medical Confidential
System 1000 Fault Tree Analysis
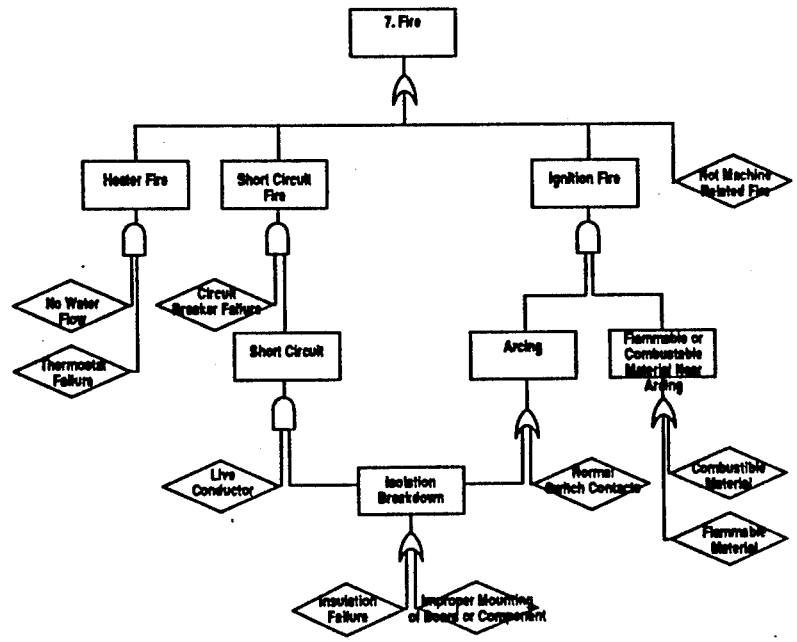
Althin CD Medical Confidential
System 1000 Fault Tree Analysis
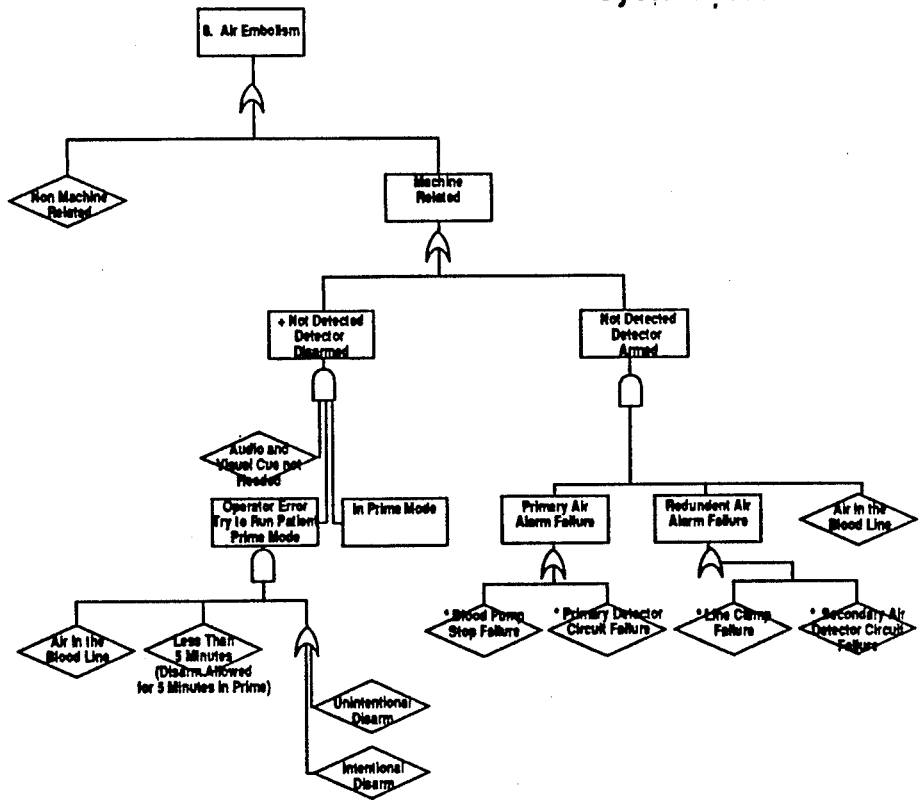
+ Air Detector cannot be disarmed in the Dialyze mode
* Function tested prior to each treatment.

Althin CD Medical Confidential
System 1000 Fault Tree Analysis
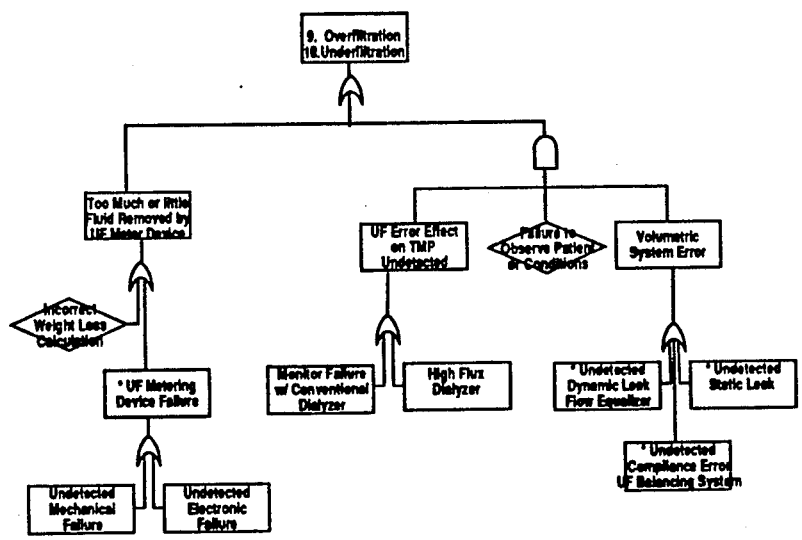
* Function tested prior to each treatment.
Althin CD Medical Confidential
System 1000 Fault Tree Analysis
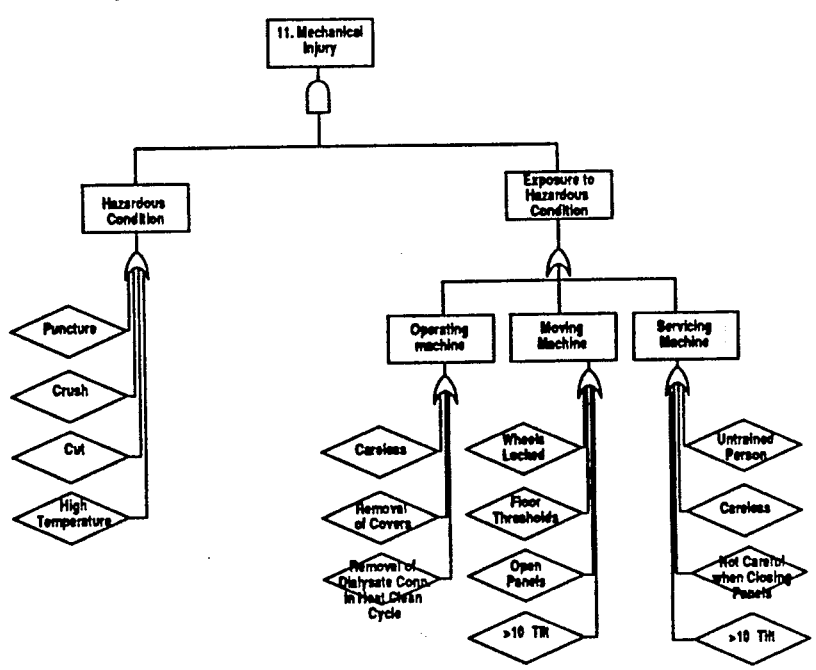

Safety System

The following report is a detailed description of the System 1000 safety systems. Included in the description for each system are its basic function, the components that make up the system, and a discussion of the safety aspects of the system.

A total of fourteen safety systems are defined as follows.

| | | | |
|---|---|---|---|
| 1. | Temperature | 8. | Touch Screen |
| 2. | Conductivity | 9. | Nonvolatile Memory |
| 3. | Venous Pressure | 10. | RS-232 Interface |
| 4. | Air Detector | 11. | UF Protective System |
| 5. | Blood Leak Detector | 12. | Programmable Sodium |
| 6. | Main Controller (80XX) | 13. | Programmable UF |
| 7. | Power Supply | 14. | External Memory Card |

Temperature

Function

Controls the dialysate temperature to a user set level (from 35 to 39°C), and provides an independent temperature monitoring system which alarms at technician set limits. The alarm response includes halting the flow of dialysate through the dialyzer.

Safety Requirements

A dialysate temperature protective system (which is independent of any control system) prevents dialysate with a temperature greater than 41°C from reaching the dialyzer and activates audible and visual alarms. This system is tested prior to each treatment during Self Test and if found to be non-functional, the machine will not allow the opertor to initiate the Prime or Dialyze Modes there by preventing the operator from dialyzing a patient.

System Components

- Temperature Controller
- Dialysate Heater
  - Temperature control thermistor located just downstream of the heater (T1)
  - Temperature monitor thermistor located in the second ("B") conductivity probe (T2)
  - The UF/Proportioning uC (microcontroller) controls the power (via duty cycle) to the heater based on T1 and T2 measurements. The T2 measurement is used for a fine adjustment, with a limited correction ability of ±2.8°C. The 80XX uP (microprocessor) provides temperature control information for the UF/Prop uC.
- Primary Temperature Monitor
  - Temperature monitor thermistor in the final ("dialysate") conductivity probe (T3).
  - The 80XX uP provides technician adjustable high and low alarm limits to the Misc I/O uC.
  - The Misc I/O uC monitors T3 for a temperature outside of technician adjustable limits (upper limit is 41°C maximum).
  - The Misc I/O uC directly deactivates the bypass valve (removing flow to the dialyzer) during a primary temperature alarm.
  - The Misc I/O uC indirectly (via the 80XX uP) triggers audible and visual alarms.
- Backup Temperature Monitor
  - Temperature monitor thermistor in the "B" conductivity probe (T2)
  - The UF/Prop uC monitors T2 for a temperature greater than 41°C.

- The UF/Prop uC directly deactivates the bypass valve (removing flow to the dialyzer) during a backup temperature alarm.
- The UF/Prop uC indirectly (via the 80XX uP) triggers audible and visual alarms.
- The 80XX uP provides T2 temperature calibration information to the UF/Prop uC.

- Bypass Valve Fail Detection
    - The Misc I/O uC monitors the flow state through the dialyzer using a thermistor based flow detector. This information is displayed on the video screen for operator verification.
    - The 80XX uP verifies the flow state information from the Misc I/O uC for consistency with the intended state of the bypass valve.
    - If flow exists during an intended bypass condition, then the system shutdown line is activated, which halts dialysate and blood flow.

Safety Discussion

Since the UF/Prop uC is responsible for controlling the temperature, the Misc I/O uC provides an independent safety system. The safety system contains three major components who's functions must be verified at the beginning of each treatment. These are:

1. The Misc I/O uC's ability to measure the dialysate temperature using the primary conductivity probe thermistor (T3)
2. The Misc uC's ability to alarm off of a temperature outside of the 80XX uP supplied alarm limits
3. The Misc uC's ability to deactivate the bypass valve The following tests are therefore performed during Self Test.

1. T3 measurement accuracy test - The 80XX uP compares the Misc I/O uC's T3 measurement with the UF/Prop uC's measurement of the T2 temperature and verifies that they are within 1°C of each other. In addition, the T3 temperature is continuously displayed on the front panel, allowing user verification of its accuracy.
2. Misc I/O alarm test - The 80XX uP consecutively generates both primary temperature alarms by first setting the upper alarm limit to a value below the current temperature, and then by setting the lower alarm limit to a value above the current temperature. An upper alarm is also generated through hardware by shunting the thermistor (T3) with a resistance. In each case, a reported alarm condition from the Misc I/O uC is verified by the 80XX uP.

The following additional test is also performed during the pretreatment testing to guarantee a fully functional system.

3. UF/Prop alarm test - Similar to the Misc I/O alarm test described in item #2 above, the backup high temperature alarm in the UF/Prop uC is tested by moving the alarm limit so that it forces an alarm conditions. The alarm response is then verified.

Conductivity

Function

Controls the concentrate proportioning ratio to a user set level, and provides an independent conductivity monitoring system which alarms at a maximum deviation of ±5% of the desired conductivity. The alarm response includes halting the flow of dialysate through the dialyzer.

Safety Requirements

A dialysate concentrate protective system (which is independent of any control system) prevents dialysate with a concentration deviation greater than ±5% of the desired concentration from reaching the dialyzer, and activates audible and visual alarms. This system is tested prior to each treatment during Self Test and if found to be non-functional, the machine will not allow the opertor to initiate the Prime or Dialyze Modes there by preventing the operator from dialyzing a patient.

System Components

- Concentration Control
  - Stepper motor driven volumetric concentrate pump(s)
  - The UF/Prop uC controls the speed of the concentrate pump (s).
  - The 80XX uP provides concentrate pump speed information to the UF/Prop uC based on the desired concentration information entered by the user, the dialysate flow rate, and on the concentrate pump calibration.
- Primary Conductivity Monitor
  - Final (patient) conductivity probe just upstream of the bypass valve (C3)
  - The Misc I/O uC calculates the primary conductivity limits at ±5% of the measured conductivity after user verification that the conductivity is acceptable.
  - The 80XX uP verifies that the ±5% conductivity limit calculation is correct.
  - The Misc I/O uC monitors C3 for a conductivity outside of the alarm limits.
  - The Misc I/O uC directly deactivates the bypass valve (removing flow through the dialyzer) during a primary conductivity alarm.
  - The Misc I/O uC indirectly (via the 80XX uP) triggers an audible and visual alarm.
- Backup Conductivity Alarm
  - The primary conductivity measurement, provided to the 80XX uP by the Misc I/O uC.
  - The 80XX uP monitors this measurement for a conductivity outside of technician settable limits.
  - The lower limit can be set within a range of 9 to 14 mS/cm.
  - The upper limit can be set within a range of 13 to 19 mS/cm.
  - The 80XX uP deactivates the bypass valve (via the Misc I/O uC) during a backup conductivity alarm condition.
  - The 80XX uP activates an audible and visual alarm.
- Redundant Conductivity Monitor
  - The conductivity probe just downstream of the "B" mix point (C2)
  - The conductivity probe just downstream of the "A" mix point (C1)
  - The 80XX uP provides conductivity limit information to the UF/Prop uC. The limits are based on the concentrate type (acetate or bicarb), the proportioning ratio, and the desired sodium concentration.
  - The UF/Prop uC monitors C1 for an acetate (or "A" part with bicarb treatment) conductivity, alarming if the conductivity is outside of the "A" part limits.
  - The UF/Prop uC monitors the difference between the C2 and C1 conductivity measurements for a "B" part (with bicarb) conductivity, alarming if the conductivity is outside of the "B" part limits.
  - The UF/Prop uC directly deactivates the bypass valve (removing flow through the dialyzer) during a backup conductivity alarm.
  - The UF/Prop uC indirectly (via the 80XX uP) triggers an audible and visual alarm.

- Bypass Valve Fail Detection (see same section under Temperature System Components)

Safety Discussion

Since the UF/Prop uC is responsible for controlling the concentration, the Misc I/O uC provides an independent safety system. The safety system contains four major components who's functions must be verified at the beginning of each treatment. These are:

1. The Misc I/O uC's ability to measure the dialysate conductivity using the primary ("dialysate") conductivity probe (C3)
2. The Misc I/O uC's ability to calculate conductivity alarm limits that are ±5% of the measured conductivity
3. The Misc I/O uC's ability to recognize a conductivity outside the desired alarm limits
4. The Misc I/O uC's ability to deactivate the bypass valve The following tests are therefore performed during the pretreatment testing.

1. C3 measurement accuracy test - The 80XX uP compares the Misc I/O uC's C3 measurement with the UF/Prop uC's measurement of the C2 conductivity probe and verifies that they are within 0.3 mS/cm of each other. The C3 conductivity measurement is continuously displayed on the front panel and must be verified in the Self Test Mode, allowing user verification of its accuracy.
2. Alarm limit calculation test - The user is requested to verify that the displayed conductivity is acceptable. After this verification is received, the 80XX uP commands the Misc I/O uC to calculate alarm limits at ±5% around the current conductivity. The 80XX uP then reads these limits and verifies that they are correct.
3. Misc I/O alarm test - The 80XX uP consecutively generates both primary conductivity alarms by first setting the upper alarm limit to a value below the current conductivity, and then by setting the lower alarm limit to a value above the current conductivity. An upper alarm is also generated through hardware by forcing the conductivity amplifier output to a high value. In each case, a reported alarm condition from the Misc I/O uC is verified by the 80XX uP.
4. Bypass verification - During the alarm conditions described in item 3 above, the 80XX uP verifies bypass by testing for a no flow condition through the dialyzer.

The following additional tests are also performed during the pretreatment testing to guarantee a fully functional system.

5. UF/Prop alarm test - Similar to the Misc I/O alarm test described in item #3 above, the "A" and "B" probe redundant alarms in the UF/Prop uC are tested by moving their alarm limits so that they force high and low redundant alarm conditions. The alarm responses for each case are verified.
6. 80XX uP alarm test - The 80XX uP tests the backup alarm limits by moving them so that they force high and low backup alarm conditions. An alarm response is verified for each.

Venous Pressure

Function

Monitors the pressure in the venous drip chamber, and latches an alarm condition when the pressure is outside of set limits. An alarm condition stops the blood pump and clamps the line clamp.

Safety Requirements

A protective system to protect the patient from extracorporeal blood loss to the environment which: stops the blood pump, clamps the line clamp, activates audible and visual alarms, sets the ultrafiltration rate to zero. This system is tested prior to each treatment during Self Test and if found to be non-functional, the machine will not allow the opertor to initiate the Prime or Dialyze Modes there by preventing the operator from dialyzing a patient. The minimum low pressure limit must not be less than +10 mmHg.

System Components

- Venous and arterial pressure transducers
- The Blood Pump uC measures the venous and arterial pressure transducer outputs and provides these measurements to the 80XX uP.
- The 80XX uP calibrates the venous pressure reading and compares it with alarm limits that form a ±50 mmHg window. On detection of a venous alarm condition, the 80XX uP creates an audio and visual alarm, commands the Blood Pump uC to stop the blood pump, and commands the Misc I/O uC to clamp the line clamp (which in turn redundantly stops the blood pump). An alarm condition is maintained until a reset is commanded by the user (via the 80XX uP).

Safety Discussion

The venous alarm window is increased to ±200 mmHg when the blood pump is off to prevent the occurance of an alarm as a result of the blood pump being turned off. The alarm window closes again to ±50 mmHg around the current venous pressure ten seconds after the blood pump starts, which allows the venous pressure time to stabilize.

In addition, during a Prime Disarm mode of operation, the venous window is always ±200 mmHg to allow convenience in setting up and priming the blood lines. This mode automatically times out after five minutes.

The safety system contains three major components who's functions must be verified at the beginning of each treatment. These are:

1. The 80XX uP's ability to obtain the venous pressure
2. The 80XX uP's ability to recognize a pressure outside of the alarm limits
3. The 80XX uP's ability to stop the blood pump The following tests are therefore performed during Self Test.

1. The 80XX uP vents the venous and arterial pressure transducers together (via the Blood Pump controller) and pumps them to a positive pressure between 100 mmHg and 500 mmHg. The accuracy of the two monitors is compared. If the pressures are not within 50 mmHg of each other the test fails.
2. The 80XX uP creates both high and low venous pressure alarms by pumping the venous pressure above and below the limit window using the level adjust pump. An alarm response is verified for each. For the first alarm response, the user is asked to verify the existence of audible and visual alarms.
3. For each alarm occurrence, the 80XX uP receives verification from the Blood Pump uC that the blood pump is stopped. This verification is based on the absence of the blood pump motor tachometer signal (which is independent of the pump's commanded state).

The following additional tests are also performed during the pretreatment testing to guarantee a fully functional system.

4. The 80XX uP creates both high and low arterial pressure alarms using the level adjust pump, with the alarm responses verified.
5. The 80XX uP verifies the performance of the level adjust pump by ensuring that when it pumps up both the arterial and venous pressure transducers for two seconds that the resulting pressure increase is between 100 and 500 mmHg.

Air Detector

Function

Monitors for the presence of air in the venous blood line upstream of the line clamp, and latches an alarm condition when an air bubble is detected. An alarm condition stops the blood pump and clamps the line clamp.

Safety Requirements

A protective system to protect the patient from air infusion which:

- Stops the blood pump
- Clamps the line clamp
- Activates audible and visual alarms
- Sets the ultrafiltration rate to zero during an alarm condition
- Does not have a single fault mode that disables the alarm that is not immediately detectible
- Does not have a double fault mode that disables the alarm, where either of the two faults cannot be detected prior to each treatment.
- This system is tested prior to each treatment during Self Test and if found to be non-functional, the machine will not allow the opertor to initiate the Prime or Dialyze Modes there by preventing the operator from dialyzing a patient.

System Components

- An ultrasonic transducer transmitter, which the 80XX uP can disable for testing.
- Ultrasonic air detection sensor, consisting of one ultrasonic transducer receiver, which drives the input of two independent and parallel amplifiers. The output of the two amplifiers are referred to as output #1 and output #2.
- Air alarm output #1 is monitored by the Misc I/O uC for air and bubble detection.
- The Misc I/O uC directly clamps the line clamp.
- The Misc I/O uC directly stops the blood pump.
- Air alarm output #2 latches a hardware latch, which directly clamps the line clamp.
- When the line clamp clamps, an optical sensor disables the blood pump.
- Both the Misc I/O uC and the 80XX uP must independently act to reset or disable the hardware latch.
- An air disarm mode (in Prime Mode only), initiated by the user, disables all air alarms for 5 minutes, as timed by the 80XX uP. Neither the 80XX uP nor the Misc I/O uC will enter the disarm mode from a non-Prime Mode.

Safety Discussion

A single ultrasonic transmitter transducer and a single ultrasonic receiver transducer are used because these devices do not have conceivable nondetectable failure modes.

The air alarm can be disabled for a limited time period in the Prime Mode for the purposes of setting up the blood lines and dialyzer. During this disarm period, the audio alarm beeps every thirty seconds. The operator is discouraged from dialyzing in the Prime Mode because of the following machine conditions:

- UF rate is limited to 0.5 liter per hour (L/h), with a default rate of 0. The calculated UF rate based on treatment time and desired UF volume is not activated until the Dialyze Mode begins.
- The UF rate will not automatically drop to zero when the desired UF volume is achieved.
- The accumulated treatment time, UF, blood, and heparin parameters are forced to zero until the Dialyze Mode begins.

The safety system contains a major component who's functions must be verified at the beginning of each treatment. This is:

- The ability of the hardware air detector (from the #2 output) to detect air and in response to clamp the line clamp and stop the blood pump.

The following test is therefore performed during the Self Test.

- With the ultrasonic transmitter disabled (with or without fluid filled tubing in the detector housing) and the software air detector (from output #1) disabled, the 80XX uP verifies that when the hardware air detector (from output #2) is enabled (not reset), that the line clamp is clamped and the blood pump is stopped. This is done twice, once with just the 80XX uP enabling it, and once with just the Misc I/O uC enabling it.
- This system is tested prior to each treatment during Self Test and if found to be non-functional, the machine will not allow the opertor to initiate the Prime or Dialyze Modes there by preventing the operator from dialyzing a patient.

Blood Leak Detector

Function

Monitors for the presence of blood in the dialysate down stream of the dialyzer. When blood is detected, an alarm condition is latched, which stops the blood pump.

Safety Requirements

A protective system to protect the patient from extracorporeal blood loss through the dialyzer which: can detect a leak rate of 0.5 mL/min when in alarm stops the blood pump, activates audible and visual alarms, sets the ultrafiltration rate to zero during an alarm condition. This system is tested prior to each treatment during Self Test and if found to be non-functional, the machine will not allow the opertor to initiate the Prime or Dialyze Modes there by preventing the operator from dialyzing a patient.

System Components

- Optical blood leak detector, utilizing a green LED light source and a cadmium sulfide light detector.
- The Misc I/O uC monitors an analog level representing the amount of light on the light detector, and creates an alarm condition when the light level drops below a calibrated threshold.
- The Misc I/O uC can adjust the intensity of the LED light source for purposes of testing and varying the blood leak threshold.
- The Misc I/O uC directly stops the blood pump and indirectly (via the 80XX uP) clamps the line clamp.

Safety Discussion

The safety system contains two major components who's functions must be verified at the beginning of each treatment. These are:

1. The Misc I/O uC's ability to detect a drop in light level at the light detector
2. The Misc I/O uC's ability to stop the blood pump The following tests are therefore performed during the pretreatment testing.

1. The 80XX uP reduces the light intensity of the LED light source (via the Misc I/O uC) to 80% of its normal operating level.
2. The 80XX uP verifies that the Misc I/O uC reports a blood leak alarm condition in response to item #1, and that the blood pump stops (via the Blood Pump uC).

Main Controllers (80XX uP, 8040 uCs)

Function

The 80XX supervises the operation of the machine, including maintaining the machine state (i.e.; Rinse, Disinfect, Dialyze, etc), performing self testing, handling calibrations, and providing the user interface.

The 8040 microcontrollers handle specific machine related functions for the Blood Pump, UF/ Proportioning, and Misc I/O Systems. In addition, each controller functions as a watchdog for the 80XX, forcing the system into a nonfunctional safe state if the 80XX discontinues its interprocessor communication.

Safety Requirements

As related to functions that are elements of safety systems, single failures should not result in an immediate hazard, and single failures that are hazardous when combined with a second failure should be detectible at the beginning of every treatment.

System Components

- 80XX microprocessor
- Program memory (ROM)
- Temporary memory (RAM)
- Interprocessor communication system
- Blood Pump Controller 8040 and program ROM
- UF/Prop Controller 8040 and program ROM
- Misc I/O Controller 8040 and program ROM
- Microcontroller A/D converters
- Hardware watchdog

Safety Discussion

The 80XX performs the following safety related functions:

- Saves and retrieves calibration constants in the nonvolatile memory (NVRAM), and uses these constants during machine operation. Monitors the arterial and venous pressures, and generates alarms when they violate their alarm limits. The alarm response includes clamping of the line clamp (via the Misc I/O uC) and stopping the blood pump (via the Blood Pump uC).
- Calculates the TMP (transmembrane pressure) by subtracting the dialysate pressure from the venous pressure. Compares the results with the TMP alarm limits, generating an alarm if a violation is detected.
- Maintains communication with the three microcontrollers, providing them calibration, machine state, and operational parameters. In addition, the communication system serves as a watchdog, ensuring that the 80XX and the 8040 controllers are functioning.
- Performs the pretreatment selftest.
- Controls the active machine state, which can be Calibrate, Rinse, Self Test, Prime, Prime Disarm, or Dialyze.
- Accepts operating information and parameters from the user via the CRT (video display) touch screen (e.g. blood flow rate, dialysate temperature, UF rate).
- Displays operating conditions and status on the video display.

Of these listed functions, the following are verified during selftests for other safety systems.

- The use of the nonvolatile memory for calibrations. The "Nonvolatile Memory" section discusses the nonvolatile memory integrity, and calibrations that have safety significance (e.g.; conductivity) are verified as part of the associated safety function's self test (conductivity calibration failure would cause the conductivity self test to fail due to insufficient accuracy).
- The arterial and venous pressure alarms.
- The TMP alarm.

Except for the watchdog functions, the 8040 microcontrollers handle safety related functions that are included in the other sections of this report.

To ensure general integrity of the control system, the following tests are performed during the pretreatment testing.

1. The watchdog function handled by each 8040 microcontroller is tested by individually halting communication to each 8040 and verifying a resulting system shutdown condition.
2. The system's A/D (analog to digital) converters are compared with each other to verify accuracy. Each of the three controller systems (BP, UF, and I/O) utilize D/A converters in a successive approximation algorithm to provide A/D functions. For Self Test purposes, the D/A output from the Misc I/O controller can be connected to the A/D inputs of the BP and UF controllers simultaneously. Self testing involves outputting a range of levels through the Misc I/O D/A converter and verifying that similar levels are read by the BP and UF A/D converters.
3. A self test verification test consists of verifying that each self test has successfully executed prior to exiting the Self Test state.

In addition to these pretreatment self tests, the following safety testing is also performed.

4. An inadvertent transition from the Dialyze state to Rinse is potentially safety critical, since the air detector would be disabled and the bypass valve would cycle independent of temperature or conductivity. However, dialysis during Rinse is prevented by disabling the blood pump when the dialysate lines are not both on their rinse fittings. In addition to this safeguard, before the air detector can be disarmed or the bypass valve can cycle, both the 80XX and the Misc I/O 8040 must be in the Rinse state. Before either enters the Rinse state from Dialyze, the operator must press the RINSE and RINSE VERIFY buttons and both dialyzer lines must be verified on their rinse fittings (using the optical interlock switches). The 80XX filters out the Rinse request from the Misc I/O Controller when the dialyzer line interlocks are not in the proper state. The only way the Misc I/O Controller can receive a Rinse request without the proper interlock condition being met is if a failure exists in the system logic. If this situation does occur, then the Misc I/O Controller activates the system shutdown line.

Power Supply

Function

Provide low voltage power to the entire machine.

Safety Requirements

The raising or lowering of any supply voltage shall not place the machine in an unsafe state.

System Components

- +5V regulated supply
- +12V regulated supply
- −12V regulated supply
- +24V unregulated supply

Safety Discussion

The +5V supply is used to power the digital logic, including the 80XX microprocessor and the 8040 microcontrollers. The ±12 V supplies power analog circuitry, and the +24 V provides power to power loads, such as valve solenoids and motors.

All three of the microcontrollers measure the +5 V supply level. They also measure a voltage that is derived from the combination of the +12 V and −12 V supplies, which provides indication if either one changes. The +24 V supply is measured by the Blood Pump Controller.

If the +5 V supply suddenly changes to a level that incapacitates the +5 V control logic, then the hardware watchdog (which the Misc I/O Controller services) times out and forces a system shutdown.

Touch Screen

Function

Provide for user control of the machine through sensing of touch contact on the CRT surface (video display).

Safety Requirements

Critical control and alarm parameters entered via the touch screen should be ensured to be without error.

System Components

- Touch screen pad mounted to CRT face 8039 touch screen controller (or vendor supplied controller)
- Serial keyboard interface to 80XX uP (or bus interface with vendor controller)

Safety Discussion

- Concentrate level
- Heparin pump rate
- UF rate
- Dialysate temperature

When these parameters are entered by the operator, through software checking it is redundantly verified that the parameter that is displayed on the screen is identical to the value that is ultimately stored and used by the machine. When the data is being input by the operator, it is placed into two redundant memory locations. One of these locations is used to derive the value being displayed on the screen. The other location is copied to the final destination of the parameter when the entry is complete. The value is then read back from its final destination, and verified to be equal to the value that was used for the display.

The control system is designed to protect against random touches, which may result from someone bumping up against the screen, or from a failing touch screen. No therapy changes can result from single touches, by requiring that all such changes be verified with an addition touch. An example is the blood pump rate selection. Through a single touch to a rate select area on the screen, a new blood pump rate can be selected. However, the new rate is not implemented until a Verify button is pressed. If the Verify button is not pressed, then after a timeout period the new rate selection is request is not acted upon. All changes in therapy are displayed on the CRT and are available to the operator for verification after they are entered.

Nonvolatile Memory

Function

Provides a modifiable yet nonvolatile memory for calibration and machine state information.

Safety Requirements

Critical data stored in the nonvolatile memory should be ensured to be without error.

System Components

- 80XX uP writes to and reads from memory
- 8K of static CMOS RAM
- Battery energy storage

Safety Discussion

All data stored in the nonvolatile memory will be stored twice, with one version complimented. Every time data in the memory is used, the two versions will be compared.

RS-232 Interface

Function

Provides a communication port through which data can be transferred to an external computer.

Safety Requirements

Because an external device of unknown characteristics can be attached to this interface, the interface must meet the 4 KV isolation requirement that is imposed on the primary line voltage components.

In addition, if the machine operation can be controlled through this interface, then the safety of the source of the control data and the data path must be ensured.

System Components

- Isolated RS-232 interface
- Isolated low voltage for powering the interface

Safety Discussion

Currently the RS-232 interface is configured for transmitting data from the machine for care provider reference purposes. Therefore there is no safety criticallity associated with this interface.

UF Protective System

Function

Ensures that the UF system is functioning properly.

Safety Requirements

A protective system independent of any control system which prevents the output of the equipment from varying from the desired value of the controlling parameter and causing a hazard to the patient. An acceptable method for complying is to measure and alarm off of the transmembrane pressure (TMP).

The TMP alarm system is tested prior to each treatment during Self Test and if found to be non-functional, the machine will not allow the opertor to initiate the Prime or Dialyze Modes there by preventing the operator from dialyzing a patient.

System Components

- Dialysate pressure transducer (pre dialyzer).
- Venous pressure transducer.
- The Blood Pump uC monitors the venous pressure.
- The Misc I/O uC monitors the dialysate pressure.
- The 80XX uP compares the dialysate pressure minus the venous pressure (TMP) with ±35mmHg alarm limits.
- The 80XX uP generates an audible and visual alarm during a TMP alarm condition.

Safety Discussion

The UF Control system is responsible for controlling the UF rate, as well as the dialysate flow control components which are responsible for guaranteeing a balanced volumetric system. The TMP alarm system is independent, consisting of the dialysate pressure measured by the Misc I/O Controller, and the venous pressure measured by the Blood Pump Controller.

The following pretreatment tests are performed, which not only verify the function of the TMP alarm, but also verify the function of the volumetric control system. During these tests, there is no dialyzer connected to the machine.

1. The 80XX calculation of TMP is redundantly calculated, and verified to be accurate.
2. The function of the UF metering device is tested by removing two metered strokes and verifying that the dialysate pressure is reduced by an expected amount.
3. The accuracy of the volumetric control system is verified by measuring the dialysate pressure drift rate over a period of time with a zero UF rate.
4. The high TMP alarm is tested by setting the high limit below the current TMP, and the low TMP alarm is tested by setting the low limit above the current TMP. The high limit is also tested by increasing the TMP through the removal of UF until the upper TMP limit is violated.

Programmable Sodium

Function

Allow the sodium level to change throughout the treatment based on information entered by the user at the beginning of the treatment. As the sodium level is changed, the conductivity alarm limits are also changed accordingly.

Safety Requirements

Single failures should not result in an immediate hazard, and single failures that are hazardous when combined with a second failure should be detectible at the beginning of every treatment.

System Components

- 80XX uP
- Nonvolatile memory

Safety Discussion

This system is tested prior to each treatment during Self Test and if found to be non-functional, the machine will not allow the opertor to initiate the Prime or Dialyze Modes there by preventing the operator from dialyzing a patient. The following safety critical tasks are involved with this function:

1. Accepting program data from the operator
2. Modifying the proportioning rate at times and by amounts dictated by the entered data.
3. Modifying the conductivity alarms to prevent alarm occurrences during the proportioning rate transitions.

Programmable UF

Function

Allow the UF rate to change throughout the treatment based on information entered by the user at the beginning of the treatment.

Safety Requirements

Single failures should not result in an immediate hazard, and single failures that are hazardous when combined with a second failure should be detectible at the beginning of every treatment.

System Components

- 80XX uP
- Nonvolatile memory

Safety Discussion

This system is tested prior to each treatment during Self Test and if found to be non-functional, the machine will not allow the opertor to initiate the Prime or Dialyze Modes there by preventing the operator from dialyzing a patient. The following safety critical tasks are involved with this function:

1. Accepting program data from the operator
2. Modifying the UF rate at times and by amounts dictated by the entered data.

External Memory Card

Function

Provides an external memory device which can be written to or read from by the machine. Treatment data can be written which can later be analyzed using a computer. Calibration data can be saved for later recall after hardware maintenance. A specially coded card can serve as a tool for technician access to special calibration and troubleshooting operating modes.

Safety Requirements

Since this device has no control function, it is not considered a safety critical device.

Self Test Summary

During Self Test, the machine automatically performs the machine related pre-dialysis "operator tests." The essential alarms, monitors and functions are checked. If any test fails, the machine will not allow the operator to initiate the Prime or Dialyze Modes there by preventing the operator from dialyzing a patient.

Below are the tests with their relevant parameters that are included in the Self Test routine.

Venous/Arterial Pressure Test

Background

This test is primarily intended to verify the functionality of the high and low venous and arterial pressure alarms. The testing results in verification of the following additional functions:

- User verification of the functionality of the main alarm lamp and audio alarm (during high venous alarm only). Functionality of the line clamp (tested during high venous alarm). Verification of the relative accuracy of the arterial and venous pressure measurement systems. Functionality of the level adjust system. Verification that the state machine is alerted of all pressure alarms. Verification that the blood pump stops during during all pressure alarms.
- The line clamp is disabled after the first high venous alarm condition to reduce the noise level during Self Test.

Test Sequence

Test Setup

The operator is asked to verify that the pressure luers are plugged. It is verified that no preexisting alarms exist, and the blood pump is turned on. The arterial and venous pressure alarm limits are closed to ±50 mmHg around the current pressures.

High Venous Test and Audio and Main Alarm Lamp Function

The level adjust pump is run for two seconds to increase the venous pressure and cause an alarm. After the alarm occurs, the operator is asked to verify the audio alarm and main alarm lamp response. The venous alarm window is then set to ±200 mmHg around the current pressure, and the alarm is reset.

High Arterial Test

The arterial and venous pressure transducers are vented together, increasing the arterial pressure and decreasing the venous pressure. After the arterial alarm occurs, both the venous and arterial pressure limits are set to ±50 mmHg around the current pressures. The alarm is then reset.

Level Adjust/Pressure Accuracy Test

It is then verified that the venous and arterial pressures are within 50 mmHg of each other, to verify their relative accuracies. To verify the level adjust system, it is also confirmed that the venous pressure is greater than 100 mmHg and less than 500 mmHg.

Low Venous Test

The pressure transducers are then isolated from each other, and the venous pressure is decreased by running the level adjust pump for two seconds. After the alarm, the venous pressure limits are set to ±200 mmHg around the current pressure, and the alarm is reset.

Low Arterial Test

The arterial and venous pressure transducers are vented together, decreasing the arterial pressure and increasing the venous pressure. After the arterial alarm occurs, the arterial pressure limit is set to ±200 mmHg around the current pressure. The alarm is then reset.

Blood Leak Detector Test

Background

This test verifies that the blood leak detector alarm is functional by simulating a blood leak. The blood leak detector consists of an LED (light source) and a photocell (light detector). During a blood leak, the light level at the photocell is dimmed, resulting in the detection of a blood leak. During this test, the LED light level is dimmed, and a blood leak response is verified.

The following blood leak alarm responses are verified by the blood leak self test:

- The acknowledgement of the blood leak alarm by the state machine.
- The commanding of the alarm lamp to flash.
- The stopping of the blood pump.

Test Sequence

Test Setup

It is verified that no preexisting blood leak alarms exist and that the blood pump is turned on.

Generation of Blood Leak Alarm

The LED light level is decreased to 80% of the non-blood alarm threshold level. The alarm responses should result within nine seconds.

Resetting of Alarm

The LED light level is restored to its original value, and after a two second delay, the alarm is reset. The alarm is required to reset within nine seconds.

UF Test

Background

The UF Self Test checks for leaks in the UF system and for functionality of the UF removal metering device. To accomplish this, the system is closed by isolated the dialysate pressure relief valve, and approximately 3 mL of fluid is removed via two strokes of the UF removal metering device. The dialysate pressure must decrease from its vented pressure by 95 to 330 mmHg. Stability is then tested by averaging the pressure over 20 seconds, waiting 20 seconds, and then taking a second average over 20 seconds. The two averaged pressure readings must be within 50 mmHg of each other. To begin this self test, the vented dialysate pressure must be between −100 and +100 mmHg and the dialysate lines must be on the rinse block.

This test also checks the TMP calculation by subtracting the dialysate pressure from the venous pressure and comparing this result to the TMP value the host calculates and displays. These two values must be within 10 mmHg.

Test Sequence

Test Vented Dialysate Pressure

The dialysate pressure relief valve is opened and the dialysate pressure must measure between −100 and +100 mmHg.

TMP Calculation Test

TMP is calculated from the dialysate and venous pressures. This value must be within 10 mmHg of the host calculated and displayed TMP. The high TMP alarm limit is set to +700 mmHg and the low limit to −700 mmHg.

UF Integrity Test

The dialysate pressure relief valve is closed and the approximately 3 mL of fluid is removed via the UF removal metering device. The average dialysate pressure is measured over 20 seconds. This average pressure must be 95 mmHg to 330 mmHg lower than the vented pressure. After 20 seconds the average pressure is measured again over a 20 second period. The two average pressure readings must be within 50 mmHg of each other to pass the stability test. The dialysate pressure relief valve is then opened.

TMP Limit Test

Background

This test checks the TMP alarm limits.

Test Sequence

Delay to Vent Dialysate Pressure

The dialysate pressure relief valve was opened at the end of the UF Test. There is a 20 second delay before this test begins to allow the pressure time to vent.

Test Vented Dialysate Pressure

The dialysate pressure relief valve is opened and the dialysate pressure must measure between ±100 mmHg. The high TMP limit is set to +700 mmHg and the low limit to −700 mmHg.

Measure Average TMP

The average TMP is measured over a 20 second period.

High TMP Alarm Test

The high alarm is verified by decreasing the high alarm limit 100 mmHg below the average TMP. The alarm is verified and the limit is reset. It is verified the alarm clears.

Low TMP Alarm Test

The low alarm is verified by increasing the low alarm limit 100 mmHg above the average TMP. The alarm is verified and the limit is reset. It is verified the alarm clears.

Second High TMP Alarm Test

The high alarm limit is set to 200 mmHg above the average TMP. The dialysate pressure relief valve is closed and fluid is removed via the UF removal metering device until the high TMP alarm limit is violated creating an alarm. The dialysate pressure relief valve is then opened. It is verified the alarm clears.

Reset Limits

The high limit is set to +500 mmHg and the low limit is set to −80 mmHg.

Temperature Test

Background

There are two separate temperataure alarms that are verified. These are:

- The Primary alarm is set by the Miscellaneous IO controller board which monitors the primary temperature probe. When this limit is violated the temperature window blinks and the word ALARM is displayed above the window.

- The Redundant high alarm is set by UF controller board which monitors the "A" and "B" temperature probes. If either of these probes is in alarm, the temperature window blinks and the word BACKUP is displayed above the window. There is no redundant low alarm.

Test Sequence

Note: All alarm verifications include checking the controller and host alarm, the main alarm lamp and bypass response.

Primary High Alarm

The primary high alarm is verified by decreasing the high alarm limit 0.5°C below the current temperature.

Primary Low Alarm

The primary low alarm is verified by increasing the low alarm limit 0.5°C above the current temperature.

Redundant High Alarm

The redundant high alarm is verified by decreasing the reduntant high alarm limit 1°C below the current temperature.

Temperature Stability

To insure that the temperature is stable, it is verified that the temperature at the primary probe and at the "B" probe are within 1°C of each other.

Conductivity Test

Background

There are three separate conductivity alarms that are verified. These are:

- The Primary alarm is set by the Miscellaneous IO controller board which monitors the primary conductivity probe. These are the tightest limits, set to ±5% during the last Self Test, Conductivity Verification. However, at the time conductivity selftest is performed, these limits are still at their wide default setting. When this limit is violated the conductivity window blinks and the word ALARM is displayed above the window.
- The Redundant alarm is set by UF controller board which monitors the "A" and "B" conductivity probes. If either of these probes are in alarm, the conductivity window blinks and the word BACKUP is displayed above the window.
- The host (80XX microprocessor) has technician settable alarm limits, with default values of 12 mS/cm and 16 mS/cm. If the conductivity reading from the primary conductivity probe exceeds these limits, the conductivity window blinks (no message is written above the window).

Note: The dialysate pressure relief valve is closed during this Self Test.

Test Sequence

Note: All alarm verifications include checking the controller and host alarm, the main alarm lamp and bypass response.

Simulated High Conductivity /High Temperature

A high conductivity and temperature is simulated with hardware forcing the conductivity up to ~20 mS/cm and the temperature to ~50°C. The primary and host conductivity alarms, and the primary temperature alarm are verified.

Primary High Alarm

The primary high alarm is verified by decreasing the high alarm limit 0.5 mS/cm below the current conductivity.

Primary Low Alarm

The primary low alarm is verified by increasing the low alarm limit 0.5 mS/cm above the current conductivity.

Redundant High Alarm

The redundant high alarms ("A" and "B") are verified by decreasing their high alarm limits 0.5 mS/cm below their respective current conductivity values.

Redundant Low Alarm

The redundant low alarms ("A" and "B") are verified by increasing their low alarm limits 0.5 mS/cm above their respective current conductivity values. Also at this time, the redundant bypass function is verified by checking that the flow sensor indicates no flow.

Host High Alarm

The host high alarm is verified by decreasing the high alarm limit 0.5 mS/cm below the current conductivity.

Host Low Alarm

The host low alarm is verified by increasing the low alarm limit 0.5 mS/cm above the current conductivity.

Conductivity Stability

To insure that the conductivity is stable, it is verified that the conductivity at the primary probe and at the "B" probe are within 3 mS/cm of each other.

Air Detector Test

Background

The air detector test verifies the functionality of the backup air detector, and also the primary air detector if fluid filled tubing is installed in the air detector.

The primary air detector is implemented in software, and as a result has a programmable sensitivity. Its nominal sensitivity is such that it would detect a 10 mL bubble. The primary air alarm cannot be disabled, however its alarm response (i.e.; line clamp clamped, stopped blood pump, audio alarm, etc.) can be disabled.

The backup air detector is completely implemented in hardware, with a nonadjustable sensitivity. Its nominal sensitivity allows it to detect a 300 mL bubble, which is adequate to prevent a major injury to the patient. The backup air detector's alarm response of clamping the line clamp and stopping the blood pump is completely implemented in hardware. The backup air detector can be disabled only when two microprocessors (the 80XX host and the 8040 Misc I/O Controller) both activate their respective disable lines simultaneously. The self test verifies individually that each microprocessor can enable the backup alarm. When the Misc I/O Controller is enabling the alarm, it is referred to as "alarm #1", and when the 80XX is enabling it, it is referred to as "alarm #2".

Both air detectors are based on passing an ultrasonic signal through the blood line and detecting a sudden drop in the resulting signal level. The backup air detector is tested by disabling the generation of the ultrasonic signal, enabling the backup alarm, and verifying that the line clamp clamps. The primary alarm is tested by disabling the ultrasonic signal for 20 msec verifying a primary air alarm is reported to the state machine.

Test Sequence

Test Setup

The backup air alarm is disabled, and the alarm responses to the primary alarm are disabled. It is verified that the line clamp is open.

Backup Alarm Test (#1)

The backup alarm is enabled via the Misc I/O microprocessor only, the air detector ultrasonic signal generator is disabled, and an alarm response is verified to occur. The verified alarm response consists of a clamped line clamp, and a reported primary and backup alarm to the state machine. The ultrasonic signal is then enabled, the backup alarm is disabled, and the alarm is reset.

Backup Alarm Test (#2)

The backup alarm is enabled via the host 80XX microprocessor only, the air detector ultrasonic signal generator is disabled, and an alarm response is again verified to occur within nine seconds. The ultrasonic signal is then enabled, the backup alarm is disabled, and the alarm is reset.

Bubble Test

After the previous air alarm was reset, the existance of a primary alarm is then tested. If a primary alarm exists, then it is assumed that the air detector is not loaded with fluid filled tubing, and therefore the bubble test is skipped. If a primary alarm does not exist, then the bubble test is initiated by disabling the ultrasonic signal for 20 msec. It is then verified that a primary air alarm is reported to the state machine. The alarm is then reset.

Conductivity Verify Test

Background

The conductivity verify test is executed only if all other Self Test routines have passed.

At this time the operator is asked to verify that the displayed conductivity is correct. Prior to this, the primary conductivity limits are at their default values of 12 mS/cm and 16 mS/cm. After the conductivity is verified, the primary conductivity alarm limits are set to ±5% around the current conductivity.

The "A" probe conductivity is verified by the UF Controller to be within 10% of a calculated nominal value based on concentrate type and proportioning ratio. Prior to this, the "A" probe conductivity limits are at their default values of ±14.3% around this calculated nominal conductivity. After this verification, the "A" probe limits are set to ±14.3% around the current conductivity.

The "B" probe conductivity is also verified by the UF Controller to be within 10% of a calculated nominal value. The conductivity limits of the "B" probe are handled differently depending on whether the proportioning mode is acetate or bicarb. In the acetate mode, the default "B" probe limits are ±14.3% around the calculated nominal value. After verification, the "B" probe conductivity limits are set to 14.3% around the current conductivity. In the bicarb mode, the alarm limits are set around the "B" part conductivity, which is the difference between the "B" and "A" probe conductivies. The default "B" part limits are set to ±2 mS/cm around the calculated nominal "B" part conductivity. After verification, the "B" part conductivity limits are set to ±2 mS/cm around the current "B" part conductivity.

Test Sequence

Verify Conductivity

Operator presses yes or no button to verify that the displayed conductivity is correct.

"A" and "B" Probe Conductivity Range

Verifies "A" and "B" probe conductivities to be within expected ranges.

Verify 5% Limits

The 5% limits are calculated and compared to the 5% limits calculated by the Miscellaneous IO controller. The two calculations must yield limits within 0.1 mS/cm of each other.

Luer Test

Background

Since the blood pressure test requires that the blood pressure luers be plugged, this test verifies that the luers are unplugged before Prime Mode is entered.

This test is not executed if blood pressure test fails.

Test Sequence

Display a message asking the operator if the luers are vented.

If the operator presses "YES", then the test passes.

If "NO" is pressed, then the test fails.

Test Results

Blood Pump

Power Supply Measurement

Introduction

To allow for checking of the power supply values on the Blood Pump Controller board by the host, they are read via the analog to digital converter and their values are stored in memory. The +5 and +24 volt power supply analog inputs are attenuated by resistor dividers to provide nominal values at 3.00 V and 3.42 V, respectively. The +12 volt supply and −12 volt supply are measured on one analog input by having the supplys at either end of a resistor divider with a nominal input voltage of 2.84 volts.

The accuracy of the measurement is dependent on the the resistor divider tolerance (using 1% resistors), the resolution and offset errors of the 8 bit analog to digital conversion. The resolution of the 8 bit A/D measurement is: $(1/255) * 5 V = 19.6$ mV/bit. As a 10 bit monotonic D/A is used, this contributes to a negative error only. The maximum offset error is ±31.5 mV.

The tolerances for the 5 V, 24 V and ±12 V resistor dividers are ±24 mV, ±59 mV, and ±113 mV respectively excluding supply voltage variations. Therefore, the total tolerances are:

5 V supply:     −75.1 to 55.5 mV

24 V supply:    −110.1 to 90.5 mV

±12 V supply:   −164.1 to 144.5 mV

Data

To determine the accuracy of the power supply readings the actual power supply and analog input voltages were measured and the readings stored in memory were recorded.

| +5 V ANALOG INPUT Expected (±.01V) | +5 V ANALOG INPUT | CALC VOLT **VALUE | % DIFF VOLT | ADC VAR EXP. MEAS | CALC SUPPLY *** | % DIFF |
|---|---|---|---|---|---|---|
| 2.856 | *2.87 | 2.87 | 0.0 | 147 | 4.79 | 3.9 |

* The supply voltage was 4.76 volts ±.02 V (measured on high side of R13 on the Blood Pump Controller board). The low analog input voltage is a result of the low power supply voltage. The expected analog voltage is calculated from the measured supply voltage.
** CALC VOLTAGE = (ADC value)/(ADC range) * (Full scale voltage) = (147/255) * 5 V(1020/1023) = 2.87 V
*** CALC SUPPLY VOLTAGE = CALC VOLTAGE * 5 V/3 V = 4.79 V

| +12/-12V ANALOG INPUT EXP (±.01 V) | +12/-12V ANALOG INPUT MEAS | ADC VARIABLE VALUE | CALC *VOLTAGE | % DIFF |
|---|---|---|---|---|
| 2.744 | *2.74 | 141 | 2.76 | 0.7 |

* The supply voltages were 12.00 volts (measured on high side of R15 on the Blood Pump Controller board) and 12.25 volts (measured on low side of R16 on BP Controller board). The difference between the nominal input voltage and the measured input voltage (2.84 V − 2.74 V = 0.10 V) can be attributed to the −12 V supply being at −12.25 V.

| +24 V ANALOG INPUT EXP. (±.01 V) | +24 V ANALOG INPUT MEAS | CALC VOLT **VALUE | % DIFF VOLT *** | ADC VAR | CALC SUPPLY | % DIFF |
|---|---|---|---|---|---|---|
| 3.249 | *3.26 | 3.25 - 0.0 | 166 - 22.8 - | 0.0 | 3.27 | 167 22.9 |

* This voltage was measured on RZ3 pin 10 on the Blood Pump Controller board. The +24 volt supply was measured at 22.82 ±0.01 volts at the high side of R26 on the Blood Pump Power board. The measured voltage at the analog input is 0.16 V below the nominal input voltage of 3.42 V. This can be attributed to the low supply voltage and resistor tolerance.

Summary

The calculated voltages for the +5, 12 and −12 volt supplies were within 10 mV and 20 mV of the measured input voltages to the A/D converter, respectively.

This difference may be attributed to the tolerance of the measurement (±10 mV) and/or the tolerance of the AD conversion (19.6 mV). The calculated voltage for the +24 V supply was the same as the measured input voltage.

This data shows that the accuracy of the power supply measurements are within the expected tolerance range.

Heparin Pump Controller Performance

Description

The purpose of the heparin pump system is to deliver an operator specified amount of heparin to the patient. The operator may select the heparin pump to operate in a normal mode and deliver 0.5 to 5.5 mL/h or a high speed mode to deliver a bolus amount of heparin quickly. (The size of the bolus is a software setting available to technicians.)

The heparin pump controller system is comprised of the following major components:

| Description | Location |
|---|---|
| User parameter entry | Host controller |
| Motor power driver circuitry | Bld Pmp Power board |
| Optical end of stroke sensor | On rack/pinion fixture |
| Optical rack engage sensor | On engage arm fixture |
| Software speed control | Bld Pmp Controller bd |
| Software overspeed check | IO Controller board |

Heparin delivery is accomplished by stepping a stepper motor which rotates the pinion of a rack and pinion mechanism. The pinion moves the rack, and the mechanical fixture is such that the plunger of the heparin syringe moves the same distance. Therefore, the amount of heparin delivered is a function of the diameter of the syringe and the distance traveled by the rack.

There are two optical sensor to provide information about the state of the heparin pump. The engage sensor detects when the front panel syringe holder arm is in the disengage position. If it is in the disengage position a DISENGAGE message is displayed on the front panel (CRT). The end-of-stroke sensor detects when the pinion is raised up on the rack, which results when the gear teeth are no longer meshed. This condition occurs if the syringe plunger is at the bottom of the syringe (syringe is empty) or if heparin is pumped into a high pressure. An over-pressure message is displayed on the front panel during this condition.

The operator enters the desired heparin delivery rate via the CRT touch screen. The host controller (80XX microprocessor) converts this information to a stepper motor step rate and sends it to the blood pump controller (8040 microprocessor) on the Blood Pump Controller board. At the same time the host sends a heparin pump overspeed alarm limit to the IO controller on the IO Controller board. The alarm limit is set to 5% over the desired rate. The IO controller monitors the heparin motor step signal period and compares this to the alarm limit. An overspeed condition exists when the period is less than the alarm limit, in which case the IO controller sends an alarm to the host and disables the heparin pump motor driver.

The operator may also request a bolus to be infused at a high speed rate via the CRT touch screen. When this occurs the host sends the total number of motor steps to be taken at the high rate to both the Blood Pump Controller and the IO controller. The controller sets the overspeed alarm if an excessive number of high speed steps occur.

The high step rate mode also results when the rack and pinion have not meshed correctly. This occurs if the heparin pump is on and an end of stroke is detected after the front panel syringe holder arm has just been engaged. During this condition the heparin motor runs at the high rate until the rack and pinion mesh. The maximum time it is allowed to run in this mode is 1.7 seconds. To prevent this mode from triggering an overspeed alarm, the high speed alarm limit in the IO controller is set to an appropriate value each time the syringe holder arm is disengaged.

Test Data

Flow Accuracy

Motor Speed Accuracy

The accuracy of the stepper motor controller was tested by measuring the distance the heparin pump rack moved with a dial indicator in a given amount of time. This test was done when the motor speed was in the normal speed range and when it was in the high speed bolus mode. The heparin pump variables were set using the UCCOM1A test program that reads and writes to controller variables.

In the bolus mode, the controller receives the total number of motor steps to be taken in the variable, BOLSTEP. The motor is stepped once every 4 milliseconds. BOLSTEP was set to the value calculated to move the rack one inch:

Motor Steps/Inch = steps/motor rev * gear ratio * shaft rev/in
= 48 * 300 * 0.5991716
= 8628.07
= ~8628

The bolus speed test was run with 10 pound and 20 pound loads on the rack, as well as with no load. The 10 pound load represents the maximum the heparin pump is required to drive as defined by design specification. At greater loads, the heparin pump mechanism is designed to disengage the rack and pinion. The 20 pound load test was done by defeating this design feature. Ten tests were run at each load. A summary of this data is given below.

Bolus Speed Test

| Distance Traveled @ | 0 lb | 10 lb | 20 lb |
|---|---|---|---|
| Average | 0.9993 | 0.9999 | 0.9958 |
| Std Dev | 0.0026 | 0.0020 | 0.0023 |
| % Avg.Error | 0.07 | 0.01 | 0.42 |

In addition to validating the accuracy of the stepper motor controller, the above data also shows the motor delivers the torque required to move the rack with a 20 pound load.

In the normal speed mode, the controller receives a number in the HDCOUNT variable which it interprets as the number of 4 millisecond counts between motor steps. This determines the motor speed. The relationship between heparin rate and HDCOUNT is:

HDCOUNT = (syringe area cm$^2$) * (294.39E-6 cm/step) * (counts/ (3600 sec/h) * (1/.004 count/sec) * step) (1/desired rate h/mL)

HDCOUNT correlates to speed as follows:
Speed(in/h) = (1/HDCOUNT step/count) * (1/.004 count/sec) * (1/8628 in/steps) * (3600 sec/h)

The above test was repeated at normal speeds representing 0.5 mL/h, 1.0 mL/h, and 5.5 mL/h flow rates assuming a 12 cc Monoject syringe (area = 1.936 cm2). This was done at no load only. The motor was allowed to run for over one hour.

Normal Rate Speed Test

| Rate (mL/h) | HDCOUNT | Calculated speed (in/h) | Measured Error | Percent |
|---|---|---|---|---|
| 0.5 | 1026 | 0.1017 | 0.1018 | .10 |
| 1.0 | 513 | 0.2034 | 0.2049 | .74 |
| 5.5 | 94 | 1.1185 | 1.1088 | -.86 |

Heparin Flow Vs Pump Speed

To validate the relationship between motor speed as determined by the HDCOUNT variable and heparin flow rate in mL/h, volumetric testing was done. This test was done on the System 1000 monitoring machine #1 using a 12 cc Monoject syringe. The heparin rate was set via the CRT touch panel and the fluid pumped into a pre-weighed covered flask. Two tests were done at 0.5 mL/h and one at 5.5 mL/h. Each test was one hour long. Prior to each test, a bolus was delivered to remove any slack in the mechanism. The results are below.

Volume Accuracy Test

| Rate (mL/h) | Volume (mL/h) | Percent Error |
|---|---|---|
| 0.5 | 0.489 | 2.2 |
| 0.5 | 0.496 | 0.8 |
| 5.5 | 5.45 | 0.9 |

Also, the amount of fluid delivered by a 1 cc bolus was measured. Thirty four bolus runs delivered an average bolus volume of 0.989 mL with the worst case volume of 0.973 mL. This is an average error of 1.1% and a worse case error of 2.7%.

Power Derating

The power derating of the heparin pump motor drive circuitry located on the Blood Pump Power board was determined with the motor operating at the maximum bolus speed with each drive transistor providing a 125 Hz output signal.

The following is the data for the zener diode, 1N4746.

1N4746
| | |
|---|---|
| Power | 0.216 W |
| Ambient Temp | 26.1°C |
| Lead Temperature | 52.2°C |
| Junction to Lead | 21.6°C |
| Junction to Ambient Rise | 47.7°C |
| Max Tj | 200°C |
| Max Ta | 60°C |
| Derating | 65.9% |

The drive for the heparin pump motor consists of four darlington transistors in two ULN2003A ICs. There are 7 transistors per IC. The maximum continuous power specified for one IC is 833mW at 60°C.

| Transistor U7 | U3 | Use | Power (mW) |
|---|---|---|---|
| A | D | Heparin motor drive, 50% duty cycle | 119 |
| B | E | Heparin motor drive, 50% duty cycle | 119 |
| C | F | Level adjust drive | 30 |
| D | | Level adjust drive | 30 |
| E | C | Heparin signal inverter, 50% duty cycle | 2 |
| F | B | Heparin disable buffer | 4 |

| | A | Shutdown buffer | 23 |
| | G | Heparin disable LED drive | 8 |
| G | | Not used | |

To determine the power derating of the ULN2003 all devices within the IC and their typical usage must be considered. Typically the level adjust motor is turned on for less than 30 seconds at a time. This is not long enough for its power dissipation to add to a stable thermal equilibrium. The heparin disable buffer, heparin disable LED drive, and the shutdown buffer are all off during normal machine operation. Therefore, only the the power dissipation of the heparin motor drive and heparin signal inverter transistors contribute to the continuous power disipation of the package.

*Typical Motor Driver (ULN2003) Power*

| Total Power | % Derated |
|---|---|
| 240 mW | 71 |

It is worth noting that the energy dissipated in the switching time of the heparin drive transistor is 0.8 mJ. This is 42% of the total energy dissipated when running at 125 Hz. However, a more typical sustained running frequency is 0.157 Hz which correlates to a 5.5 mL/h delivery rate with a 10 cc syringe. At this slow step rate the energy dissipated in the switching time drops to less than 1% of the total energy dissipated.

The current limit resistors, 68 ohm 5 W, dissipate 1.64 W. This gives a power derating of 67%.

Overspeed Alarm Function

During normal speed operation the IO controller monitors the heparin motor step rate. After 40 heparin motor steps, it checks the time elapsed and compares this to the alarm limit, HP_P_MIN. If the time elapsed is less than the alarm limit, the motor is stepping faster than desired and an overspeed alarm is signaled.

To verify the alarm functioned, the heparin pump was turned on via the front panel of the monitoring machine #1. The alarm limit was then altered to a number 6% greater than was set by the host. (This was done using a separate program, UCCOM1A, that reads and writes to controller variables.) It was verified that the heparin overspeed alarm was activated.

During high speed operation, the total number of motor steps is monitored by the IO controller. When a bolus is requested, the negative of the required number of steps (plus some tolerance) is put in the IO alarm limit variable, H_SPD_CNTR. If this number of high speed steps is exceeded, the overspeed alarm is set.

To verify this alarm functions, the total number of allowed high speed steps in the IO variable, H_SPD_CNTR, was set to –5 using the UCCOM1A program on the integration machine. Then a bolus was begun. It was verified that the overspeed alarm resulted.

Summary

The errors of the heparin motor controller in bolus and normal speed modes were a maximum of 0.42% and 0.86% respectively. These errors increased to a maximum of 2.7% and 2.2% respectively in the volumetric testing. This increase in error can be attributed to the error inherent in the mechanical fixture and variation in syringe size.

Data was presented showing that the heparin motor drive surpassed the design goal of 50% power derating. The zener diode is derated by 65.9%, the ULN2003 darlington transistor array ICs is 71% derated, and the current limit resistor is 67% derated.

The heparin pump overspeed alarm was tested and found functional in both the normal and bolus speed modes.

Ambient Temperature Control

Description

The purpose of the cabinet cooling system is to keep the internal temperature of the cabinet lower than the 50°C maximum temperature at which the electronic components are guaranteed to operate. A fan is located at the base of the cabinet and exhausts the warm cabinet air. An intake vent for the ambient room temperature is located below the CRT on the back of the machine.

The cabinet cooling system consists of the following major components:

Description
Location
Cabinet Fan*                             Base of cabinet
Blood Pump Temperature IC                Blood Pump Power Bd
Misc IO Temperature IC                   Misc IO Electronics Power Bd
Software Fan Control                     Host controller
Cabinet Fan Drive                        Blood Pump Power Bd The two LM35DZ temperature ICs are located on the Blood Pump and Misc IO Electronics power boards. This IC outputs a voltage linear with temperature in °C (10.0 mV/°C). These temperature readings are input to the fan control software.

The fan control software always responds to the higher of the two temperatures. The control temperatures at which the fan turns on or off are set in the host software. The control temperatures are set as follows: at 46°C it turns on the fan in the low speed mode and at 48°C it turns on the fan in the high speed mode. There is a 2°C of hysteresis at these threshold temperatures; i.e., the fan returns to low speed at 46°C and turns off at 44°C. In addition, at 60°C a cabinet temperature alarm occurs that results in the machine shutdown state.

The fan power driver located on the Blood Pump Power board provides an unfiltered pulse width modulated signal at a frequency of approximately 30 KHz to the fan motor. Testing was done using Rev Z10 of the Blood Pump Power board.

Data

Fan Cooling Capability

To determine the cooling capability of the fan, the machine was allowed to stabilize at its maximum internal temperature without the fan on. The cabinet was closed, the blood pump was on, and the dialysate flow rate was set to 1000 mL/min. After the cabinet temperature had stabilized the fan was turned on. The temperatures from the temperature ICs on the IO and Blood Pump power boards were sampled every minute and are shown on the graphs below.

The accuracy of this data is dependent on the accuracy of the LM35DC temperature IC and the resolution of the D/A conversion. The accuracy of the LM35DZ is ±2°C over the full temperature range of −55 to 150°C.

The resolution of the D/A converter is as follows:
Blood Pump IC:      5 V/255 = 19.6 mV
                    19.6 mV * (1°C/10 mV) = 1.96°C
Misc IO IC:         5 V/1023 = 4.9 mV
                    4.9 mV * (1°C/10mV) = 0.49°C This resolution adds a negative error only as a monotonic D/A converter is used. The temperature reading of the Blood Pump IC is within −4 to +2°C of actual and the reading of the Misc IO IC is within −2.5 to +2 °C.

The fan was run at four separate speeds (motor voltages) by setting the FAN_RATE variable to 180, 195, 210 and 255. These FAN_RATE variables correspond to 20 V, 22 V, 25 V, and 26 V applied to the fan. The graphs below show the results.

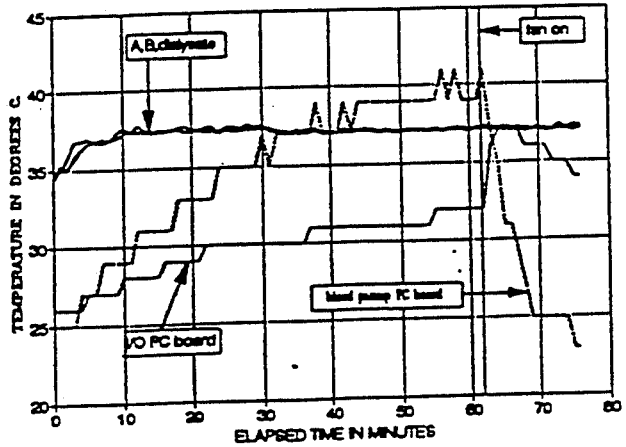

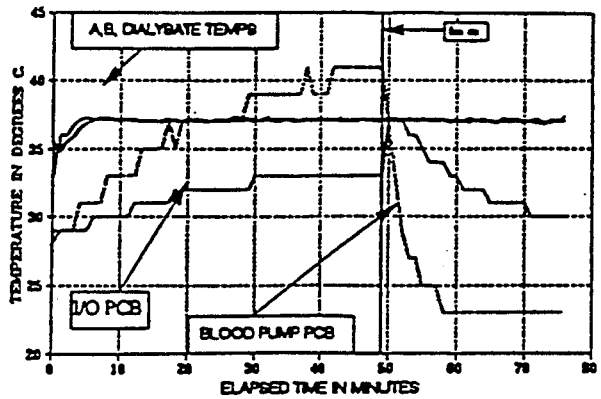

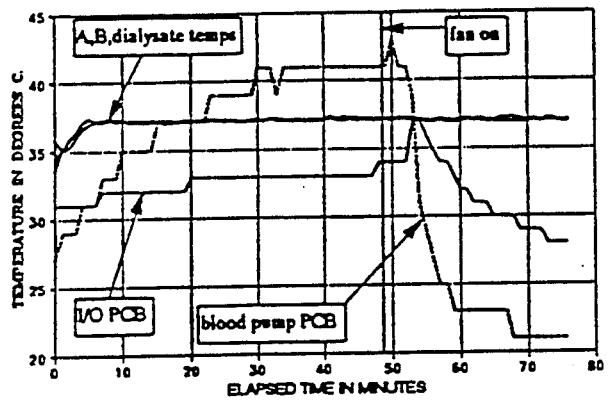

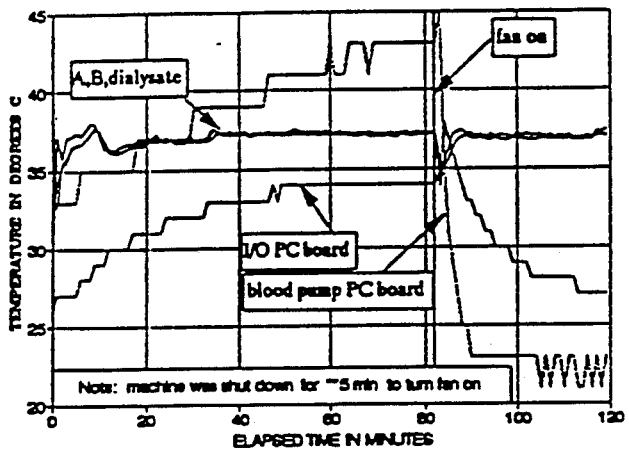

The temperature IC on the Blood Pump Power board reports the higher temperature prior to the fan being turned on. When the fan turns on, the temperature at the Blood Pump Power board decreases rapidly, the temperature at the Misc. IO Power board increases momentarily and then decreases gradually. This is understandable when the location of these boards is considered. The Blood Pump Power board is located just below the CRT, perpendicular to the front panel, close to the air intake vent. The Misc IO Electronics Power board is mounted to the bottom of the front panel. Prior to fan turn on, the temperature at the Blood Pump Power board is greater than at the Misc IO Power board because it is higher, and hot air rises. When the fan turns on, the temperature at the Blood Pump Power board decreases rapidly as it is close the intake vent. The temperature at the Misc IO Power board increases initially as the warm air from the top part of the cabinet is drawn past on its way to the exhaust at the base of the machine. The temperature at the Misc IO Power board decreases more gradually as there is less air flow around this board due to the location of other components.

The amount the cabinet temperature rises above ambient temperature without the fan on may be determined by the graphs. The assumption is made that the stabilized temperature at the blood pump power board with the fan on is the ambient temperature. This data indicates a maximum temperature rise of 24°C.

For each graph the Cool Down Rate is calculated. This is defined as:

$$\text{Cool Down Rate} = \frac{\text{Max Temp} - \text{Min Temp}}{\text{Time Min Temp Reached} - \text{Fan On Time}}$$

| Fan Rate | Blood Pump Power board | Misc IO Power board |
|---|---|---|
| 180 | (41 - 23)/(76 - 62) = 1.28°C / min | (37 - 34)/(75 - 62) = 0.23°C / min |
| 195 | (41 - 23)/(58 - 49) = 2.0°C / min | (37 - 30)/(71 - 49) = 0.32°C / min |
| 210 | (43 - 23)/(59 - 49) = 2.0°C / min | (37 - 28)/(73 - 49) = 0.37°C / min |
| 255 | (45 - 23)/(90 - 82) = 2.75°C / min | (38 - 27)/(112 - 82) = 0.37°C / min |

The cool down rate is not linear as it is a function of the air convection currents within the cabinet.

Another important factor in considering the speed at which to operate the fan besides the cooling effectiveness is the noise level. The following are the subjective impressions of the noise level at each fan rate made by the technician who ran the test. "At 255, the sound of the fan was the loudest sound produced by the machine. The sound produced by the fan was markedly less at 210, though still quite noticeable. At 195 the fan was all but silent, and at 180 it could not be heard above the other machine sounds."

The data from the graph with the fan rate set to 255 was compared to temperature data obtained from thermocouples placed throughout the cabinet taken simultaneously. The Blood Pump Power board maximum and minimum temperature is compared to the temperature recorded by a thermocouple located on the top right corner of the Mother board. The Misc IO Power board maximum and minimum temperature is compared to the temperature of the thermal couple located at the top of the switching power supply board. The results are below.

| | Thermo-couple | Board Temp IC | |
|---|---|---|---|
| Blood Pump | 38 | 45 | Prior to fan on |
| Temperature | 23 | 23 | Fan on |
| Misc IO | 46 | 38 | Prior to fan on |
| Temperature | 27 | 27 | Fan on |

The readings with the fan on are identical. However, the temperatures just prior to fan turn on vary considerably. This highlights the fact that convection air currents are a major factor and slight differences in location are significant.

In the base of the machine is located the heater solid state relay. To maintain its desired 50% power derating at 120 V nominal line voltage, the cabinet temperature must be 50°C or less. Therefore, the temperature at the base of the machine is of particular concern. A temperature sensor located above the solid state relay showed that the temperature initially increased approximately 8°C at fan turn on before decreasing slowly. This occured at all fan speeds.

Summary

Data was collected to show the fan's effectiveness at cooling the cabinet temperature running at four different speeds. The data showed that all speeds were effective at cooling the temperature at the Blood Pump Power board and the IO Electronics Power board.

This data also showed a maximum ambient to cabinet temperature difference of 24°C. This indicates that at ambient temperature of 22°C or greater the fan will turn on at the low speed rate.

The software fan control was tested and it was verified that the fan turned on and off at the preset rates and at the preset temperatures.

Level Adjust

Description

The level adjust system allows the operator to change the blood level in the arterial, veneous, and expansion drip chambers. Level up and level down buttons exist for each drip chamber. When a button is pressed, a valve selects that drip chamber and power is supplied to the motor such that the pump head of a peristaltic pump rotates to apply a positive or negetive pressure to the drip chamber. The control logic only accepts one button press at a time.

The level adjust motor may be driven in the forward or reverse direction. A direction signal along with a pulse width modulated motor rate signal controls two bipolar half bridge motor drivers. Both half bridge motor drivers receive the same motor rate signal, while the motor direction signal is high at one and low at the other to determine the direction the motor runs. The half bridge drivers provide a 24 V pulse width modulated drive voltage of approximately 30 KHz to the motor.

Test Data

Power Derating

The power derating of the level adjust motor drive circuitry located on the Blood Pump Power board (rev Z10) was determined under the worse case condition of the pump head being held in position so that it would not turn. Also, power derating was determined at a typical load of pumping against +400 mmHg pressure. The motor voltage was 12 V.

Data for both half bridge motor drivers (UDN2935Z) is shown below. The driver sinking current is defined as the one with the input at pin 2 high. The driver sourcing current has the input at pin 2 low. One half bridge driver was mounted on each side of the AAVID 530122 heatsink. The table below shows the data.

*Sinking Current Motor Driver*

|  | Pump Stopped | +400mmHg Pressure |
|---|---|---|
| Power | 1.37 W | 0.24 W |
| Ambient Temp | 26°C | 26°C |
| Case Temperature | 46°C | 39°C |
| Junction to Case Rise* | 5.5°C | 1°C |
| Junction to Ambient Rise | 25.5°C | 14°C |
| Max Tj | 150°C | 150°C |
| Max Ta | 60°C | 60°C |
| Derating | 72% | 84% |

*Sourcing Current Motor Driver*

|  | Pump Stopped |
|---|---|
| Power | 0.42 W |
| Ambient Temp | 22.6°C |
| Case Temperature | 44.2°C |
| Junction to Case Rise* | 1.7°C |
| Junction to Ambient Rise | 23.3°C |
| Max Tj | 150°C |
| Max Ta | 60°C |
| Derating | 74% |

* $\theta jc = 4°C / W$

Flow Rate Vs Pressure

The flow rate the level adjust system is able to deliver when pumping air against a +600 mmHg pressure and exhausting air from a −300 mmHg pressure was measured. These pressure values were selected as the maximum pressures expected to be used in a clinical situation. The time to empty/fill 25 mL of water with the level adjust motor at 12 V and 15 V was measured. (A D/A value of 146 was used to set the motor voltage at 12 V and 168 to set the motor voltage at 15 V.)

|  | 12 V | 15 V |
|---|---|---|
| +600mmHg | 1.24 mL/sec | 1.59 mL/sec |
| -300mmHg | 0.53 mL/sec | 0.74 mL/sec |

In addition, the motor pump head speed was measured at 57 rpm with 12 volts applied to the motor and at 75 rpm with 15 volts applied to the motor.

Summary

The power derating of the UDN2935Z half bridge motor drivers that power the level adjust motor was examined. Under the unlikely condition that the motor is stalled the sinking driver was 72% derated and the sourcing driver was 74% derated. This exceeds the design goal of 50% derating.

Data was presented that showed the slowest flow rate occurred when exhausting air (raising the fluid level) at a pressure of -300 mmHg. Typical drip chambers range in volume from 8 mL to 18 mL. At 0.53 mL/sec it would take 34 seconds to fill the 18 mL drip chamber.

Blood Pump Controller

Description

The purpose of the blood pump controller is to supply power to the blood pump motor such that the pump head will turn and pump at a rate selected by the operator.

The blood pump controller system consists of the following major components:

| Description | Location |
|---|---|
| User parameter entry | Host controller |
| Software Speed Error Control | Bld Pmp Controller |
| Hardware Speed Error Control | BP Power Board |
| Optical speed sensor | On motor shaft |
| Motor Power Driver Circuitry | BP Power Board |

The operator enters the desired blood pump rate information on the CRT touch panel. The host controller (80XX microprocessor) converts this information to the appropriate motor rate which it then sends to the Blood Pump controller (8040) on the Blood Pump Controller board. The 8040 controller converts the motor rate information to an analog level, which is fed to a motor speed control IC (LM2917-8) on the Blood Pump Power board.

An optical speed sensor is mounted on the rear saft of the blood pump motor, with an LED being positioned on one side of the shaft, and a photo transistor on the opposite side. The shaft has two holes drilled through it, with each hole being perpendicular to the shaft and to each other. This results in four optical pulses received per shaft revolution.

This tachometer signal is monitored by both the LM2917-8 and the 8040 controller. The LM2917-8 provides quick responding speed control by comparing the motor speed with the desired speed information from the 8040. The result of this comparison is an error signal which provides an input to the motor power driver circuit.

The motor power driver provides a +24V pulse width modulated drive to the motor at a frequency of approximately 30 KHz. This drive is current limit protected, to prevent damage in the event of a stalled motor.

The 8040 compares the tachometer motor speed information with the desired speed commanded by the 80XX and corrects the level provided to the LM2917-8 accordingly. In this way the 8040 guarantees the ultimate accuracy of the pump, with the LM2917-8 circuit not requiring any calibration. In addition, the 8040 can monitor for control problems, such as under speed or over speed, which may result from failures in the LM2917-8 or motor drive circuitry.

The 8040 also monitors the motor speed independent of the tachometer signal using the motor's back EMF. Periodically (every 0.5 second) the motor drive is turned off for approximately 6 msec and the voltage at the motor terminals is measured. Though this does not result in as precise an indication as the tachometer signal, gross failures can be determined, such as when the tachometer signal is lost.

Test Data

Flow Accuracy

*Motor Speed Accuracy*

The accuracy of the motor controller was tested both under a heavy tubing load (occluded water filled T8 tubing) and under no load. The speed of the pump head was independently measured using an event counter connected to a reed switch, with a magnet mounted to the pump head, such that the reed switch was activated once per pump head revolution. This measured speed was compared with the expected pump speed, which is based on the value of the blood pump controller's DES_CNT1 variable. DES_CNT1 is set by the 80XX host to control the pump rate. The blood pump controller interprets DES_CNT1 as the number of motor tachometer pulses that should occur in 0.5 second, times 16. The relationship between pump head RPM and DES_CNT1 is $RPM = (DES\_CNT1 * 2/16)$ pulses/sec 60 sec/min /

4 pulses/mtr shaft rev /

18.93 mtr shaft rev/pump shaft rev $RPM = DES\_CNT1 / 10.096$

The following are the test results:

| DES_CNT1 | Expected RPM | Actual No Load | Error No Load | Actual Loaded | Error Loaded |
|---|---|---|---|---|---|
| 50 | 4.9525 | 4.9565 | 0.08% | 4.9565 | 0.08% |
| 100 | 9.9049 | 9.9135 | 0.09% | 9.9094 | 0.05% |
| 530 | 52.4960 | 52.5363 | 0.08% | 52.5118 | 0.03% |
| 1100 | 108.9540 | 109.0118 | 0.05% | 109.0516 | 0.09% |
| 1400 | 138.6688 | 138.7748 | 0.08% | 138.7179 | 0.04% |

The 80XX host converts the blood flow rate entered by the operator (Q) to a DES_CNT1 value using the following nominal relationship:

DES_CNT1 = Q mL/min /

5.9 mL/pump rev 18.93 mtr shaft rev/pump shaft rev /

60 sec/min 4 tach pulses/mtr shaft rev 0.5 sec/sample period

16 Des_cnts/tach pulse

= 1.711 Q

This relationship assumes .25 inch ID blood tubing. The actual expression includes a calibration term which allows the calculated DES_CNT1 to be incremented or decremented in 1% steps.

This conversion performed by the host was verified by setting the blood flow rate from the front panel to various levels, after which the Blood Pump controller's 8040 was interrogated to determine the current value of DES_CNT1. The following results were obtained:

| Desired Blood Flow | Expected DES_CNT1 | Actual DES_CNT1 |
|---|---|---|
| 100 | 171 | 171 |
| 200 | 342 | 342 |
| 300 | 513 | 513 |
| 400 | 684 | 684 |
| 500 | 855 | 855 |
| 600 | 1026 | 1026 |
| 700 | 1197 | 1197 |

*Blood Flow Vs Pump Speed*

The relationship between the pump speed and the pumped fluid flow rate was determined by measuring the amount of water pumped over a measured period of time. The following shows the results with 0.25 inch ID tubing:

| Pump Speed RPM | Flow Rate mL/min | mL/rev |
|---|---|---|
| 10 | 60.0 | 6.0 |
| 20 | 115.0 | 5.8 |
| 30 | 169.0 | 5.6 |
| 40 | 225.0 | 5.6 |

| | | |
|---|---|---|
| 50 | 282.5 | 5.7 |
| 60 | 340.0 | 5.7 |
| 70 | 410.0 | 5.9 |
| 80 | 465.0 | 5.8 |
| 90 | 523.3 | 5.8 |
| 100 | 585.0 | 5.8 |
| 110 | 640.0 | 5.8 |
| 120 | 704.0 | 5.9 |
| 130 | 760.0 | 5.8 |

The average of the mL/rev column is 5.8.

Drive Torque

Torque Requirements

To gain an estimate of the worst case load requirements for the blood pump, the pump was loaded with T8 tubing, which was filled with water and occluded. The motor current was then measured while running at 124 RPM (equivalent to 720 mL/min with 0.25 inch tubing). The resulting current averaged 2.1 A.

Dynamometer tests showed that a motor current of 2.0 A while running at 110 RPM is approximately equal to a motor load of 120 oz-in.

Drive Capability

Data was taken to determine the drive capability of the blood pump by connecting the pump shaft to a dynamometer, and then at various

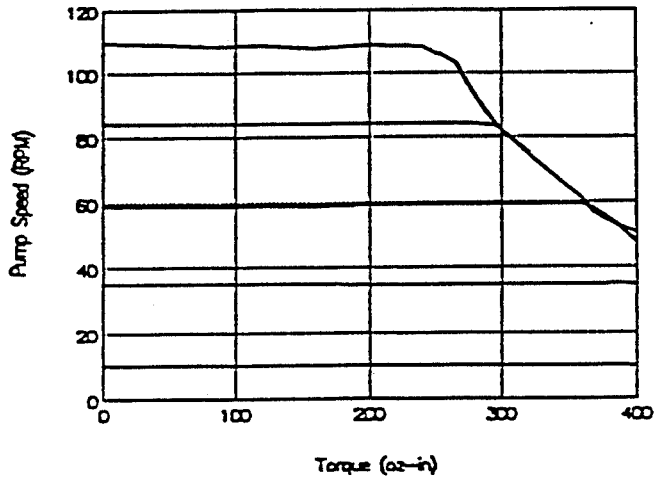

Blood Pump Torque Vs Speed no load pump speeds increasing the mechanical load to 400 ounce inches. The results show that the pump can maintain a speed of up to 50 RPM under a 400 oz-in load. For speeds greater than 50 RPM, the maximum torque decreases linearly down to 240 oz-in at 110 RPM. Though the motor wasn't tested above 110 RPM, extrapolation of the data indicates that it will drive 200 oz-in at a speed of 120 RPM. The torque-speed limit is a result of the motor driver's current limit function, which protects the circuitry from damage under excessive loads.

Power Derating

Drive Transistor and Catch Diode

The power derating of the blood pump driver circuitry located on the Blood Pump Power board (revision Z10) was determined under the worst case condition of the pump head being secured so that it would not turn. This resulted in the driver circuitry being in continuous current limit with a motor current of 6.2 A. The test was performed originally with the MTP3055E driver transistor (Q5) and MUR805 diode (D1) mounted to a common heat sink (CD Medical part number M-1991-00-00) with the following results.

|  | MTP3055E | MUR805 |
|---|---|---|
| Power | 4.7 W | 3.4 W |
| Case Rise | 45°C | 48°C |
| Junction Rise | 60°C | 58°C |
| Max Tj | 150°C | 175°C |
| Max Ta | 60°C | 60°C |
| Derating | 33% | 50% |

Motor Stalled/ Single Heat Sink

It is acknowledged that the lower case rise of the MTP3055E is inconsistent with its higher power dissipation. It is suspected that this is a result of the difficulty of measuring the transistor's on voltage accurately. It is further suspected that the actual MTP3055E's power dissipation is closer to the MUR805's dissipation of 3.4 W, since the case temperature rises are similar. This analysis will continue to utilize the 4.7 W dissipation however, since this is will result in a more conservative derating.

Because of the low derating of the MTP3055E, the heat sink configuration was changed so that the MTP3055E and and MUR805 were mounted to two separate Aavid E5304B heat sinks. Actually two MTP3055E transistors were mounted to one, and two MUR805 diodes were mounted to the other, but since the additional components are for the second blood pump, they would not be expected to contribute any power during the primary blood pump operation. The following summarizes the derating data using the two heat sinks.

|  | MTP3055E | MUR805 |
|---|---|---|
| Power | 4.7 W | 3.4 W |
| Case Rise | 35°C | 35°C |
| Junction Rise | 49°C | 45°C |
| Max Tj | 150°C | 175 °C |
| Max Ta | 60°C | 60°C |
| Derating | 45% | 61% |

Motor Stalled/ Double Heat Sink

The design goal was to maintain a 50% or greater derating for all power components. As can be seen, the MTP3055E is only derated 45%. However this is a very conservative figure, since the test was done during a motor stall condition, which is unrealistic during normal operation. Testing of the original single heat sink configuration, with the pump driving a constant 360 oz-in load, has shown that the MTP3055E case rise was 24°C compared to 43°C during a stall. This implies that the transistor was only dissipating 24/43 = 56% of the stall power. Applying this information to the double heat sink data results in the following:

|  | MTP3055E |
|---|---|
| Power | 2.6 W |
| Case Rise | 20°C |
| Junction Rise | 27°C |
| Max Tj | 150°C |
| Max Ta | 60°C |
| Derating | 70% |

360 oz-in Load/Double Heat Sink
(Calculated Data)

The 360 oz-in load is still a conservative estimate when considering that a very heavy tubing load is approximately equal to 120 oz-in (see Torque Requirements in this report).

*Shutdown Transistor*

The TIP105 shutdown transistor on the Blood Pump Power board (Q8) supplies +24 V current to the following loads:

- blood pump motor
- level adjust motor
- heparin pump motor

As a result, its power dissipation and temperature rise was accessed during the following worst case condition:

- blood pump motor on and stalled (current limit)
- level adjust motor on and stalled
- heparin pump motor on but not stepping From photos taken of TIP105's voltage and current under this condition, the power dissipation is estimated to be 0.8 V * 1 A = 0.8 W. Under this same condition the transistor case temperature rise was 50 – 24 = 26°C. The junction to case temperature rise is 1.56°C/W * 0.8W = 1.2°C, resulting in a total junction temperature rise of 27.2°C. The following is the derating information.

|  | TIP105 |
|---|---|
| Power | 0.8W |
| Case Rise | 26°C |
| Junction Rise | 27.2°C |
| Max Tj | 150°C |
| Max Ta | 60°C |
| Derating | 70% |

Worst Case Shutdown Transistor Derating

Summary

Data was presented showing that the blood pump controller maintains the pump speed within 0.1% of the expected rate. Actual fluid pumping accuracy tests were not performed because of the dependency on the tubing tolerances. Accuracy with any particular blood line set can be optimized through the blood pump calibration.

Blood pump drive requirements were conservatively determined to be 120 oz-in at a speed of 120 RPM (700 mL/min with 0.25-inch ID tubing). Test results indicate that the pump is capable of driving a 200 oz-in load at a speed of 120 RPM.

The power derating of the blood pump motor drive components were examined, which consist of drive transistor Q5 (MTP3055E) and the catch diode D1 (MUR805). Under the extreme condition of a stalled motor, the transistor was 45% derated and the diode was 61% derated. Even though the transistor derating did not meet the design goal of 50%, its derating was 70% under a still conservative load condition of 360 oz-in.

Power derating of the Q8 shutdown transistor was also determined. This transistor conducts the +24V current to the blood pump motor, level adjust motor, and heparin pump motor. Under the extreme condition of a stalled blood pump and level adjust motor, the derating was 70%.

Extracorporeal Blood Pressure Measurement

Description

The extracorporeal blood pressure measurements include the venous, arterial and expansion chamber (for Single Needle treatment) pressures. All three measurement systems include identical hardware. Each pressure is sensed by a SenSym SCX15 pressure transducer mounted to the Blood Pump Power board. Each transducer is connected to a differential amplifier designed to provide a measurement range from –400 to +600 mmHg. The output of each amplifier drives an A/D input channel of the Blood Pump Control system, at which point it is converted to a 10 bit digital value. The calibration of the each pressure input is handled entirely in software, requiring that the design of each amplifier guarantee that its output remain within the A/D input range of 0 to +5 V over the input pressure range and over all component tolerances.

Since all three pressure systems are identical, qualification testing was only performed on the venous system.

Test Data

The venous pressure system was tested by applying a pressure to the venous pressure transducer, and measuring the pressure independently using a mercury manometer. The input pressure was stepped from +650 to –450 mmHg in 50 mmHg steps. For each pressure the differential amplifier output voltage was recorded, along with the converted digital value which was communicated from the Blood Pump controller board's 8040 microcontroller.

Over the applied pressure range the amplifier output ranged from 0.603 to 4.09 volts, well within the required 0 to 5 V range. A linear regression of the output voltage provides the following relationship between pressure and voltage:

$V = .003167 * P + 2.0301$ with an r.SUPER2.SUPER value of 0.999988. This expression was used in reverse to calculate P from the measured V values, and the difference between these calculated pressures and the measured pressures were plotted as shown.

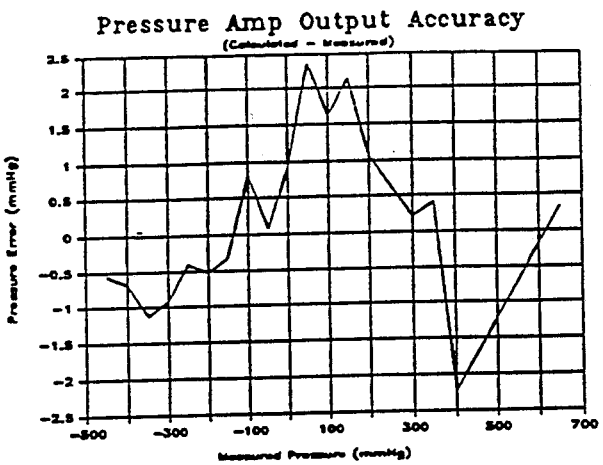

The A/D values can be compared with the measured voltages using the following expression:

A/D value = V/5 * 1023

By using this expression in reverse to calculate A/D input voltages, and then subtracting the measured voltages, the plot resulted.

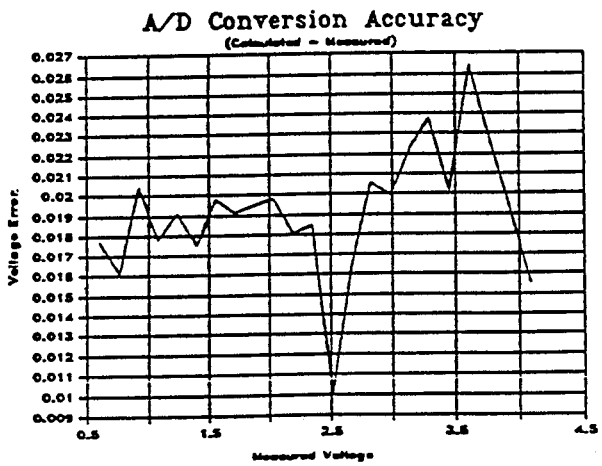

The average of these errors is 19.1 mV, suggesting that an input offset to the A/D converter existed. This offset would be compensated with the software calibration of the pressure input.

In the System 1000, the pressure is calibrated at two points, typically 0 and 300 mmHg. Calibrating the A/D values around these two pressures and then plotting the error between these calibrated pressures and the measured pressures results in the following graph:

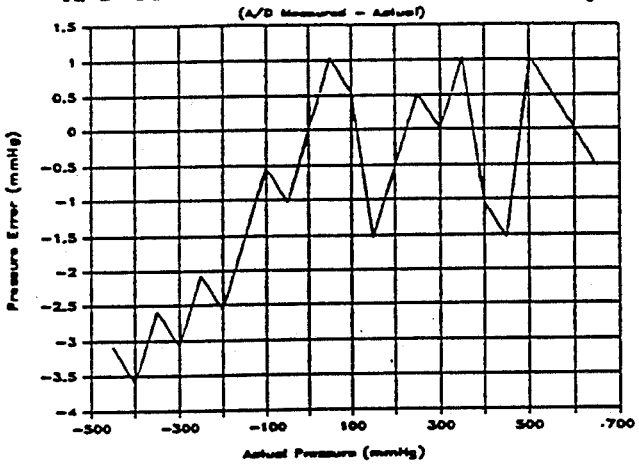

A/D Pressure Measurement Accuracy

Summary

The extracorporeal blood pressure measurement system was analyzed using the venous pressure input, which is identical to the arterial and expansion chamber pressure inputs. The testing consisted of applying a pressure to the pressure transducer input, and then measuring the output of the pressure amplifier output and the output of the A/D converter. The applied pressure range was from −450 to +650 mmHg. The displayed pressure range of the venous and arterial pressures in the machine is −400 to +600 mmHg.

An analysis of the pressure amplifier output shows a pressure tranducer linearity of within ±2.5mmHg over the applied pressure range. The same data reveals a peak error near zero pressure, indicating a slight gain difference between positive and negative pressures.

A comparison of the applied pressure with a calibrated A/D pressure output indicates a pressure accuracy of +1.0 to 1.5 mmHg over the calibrated range of 0 to +300 mmHg, and an accuracy of +1.0 to −3.5 mmHg over the entire applied pressure range. Accuracy of the negative pressure range could potentially be improved by implementing a separate calibration gain for this range. However, even with the single calibration range, the accuracy is within the desired resolution of ±5 mmHg.

Blood Pump Control System Power Requirements

Description

The Blood Pump Control system consists of the Blood Pump Controller board and the Blood Pump Power board. The Blood Pump Controller board utilizes +5V and ±12V, which it receives through the Mother board connector. The Blood Pump Power board also utilizes these same voltages, which it receives through harnessing from the Blood Pump Controller board. In addition the Power board utilizes +24V, which it receives through harnessing directly from the +24V power supply.

Test Data

The +5 V, +12 V, and −12 V current loads for the Blood Pump system were measured by plugging the Blood Pump Controller board into a Mother board extender card, and inserting a current meter in series with the power connection being measured. Since the +5 V supply uses two connector pins, one was left disconnected during its measurement. The state of the Blood Pump System during the measurements was with the blood pump off, the level adjust pump off, and the heparin pump motor energized but not stepping. This was not felt to have significant impact on the measurements since these functions draw power primarily from the +24 V supply. The following are the results:

| Power Supply | W/ Power Brd (mA) | W/O Power Brd (mA) | Calc Pwr Brd (mA) |
|---|---|---|---|
| +5V | 316.0 | 251.0 | 65.0 |
| +12V | 120.5 | 24.2 | 96.3 |
| -12V | 16.5 | 16.3 | 0.2 |
| +5V | | | |
| ±12V | | | |

The W/ Power Brd column was measured with the Power board plugged into the Controller board, while the W/O Power Brd column was measured with the Power board unplugged. The Calc Pwr Brd column is the difference between the previous two columns.

The +24 V supply current was measured at the point where it connects to the Blood Pump Power board. During all measurements the heparin pump was energized but not stepping. Measurements were taken with the following Blood Pump conditions:

- Blood pump off
- Blood pump running with new 0.25-inch ID tubing at 250 mL/min (Low load).
- Blood pump running new water filled occluded T8 tubing at 500 mL/min (Heavy load).

For each of the above conditions, two measurements were taken, one with the level adjust pump off and one with it on. The measurements were not stable, therefore each data point is shown as a range, with the average of the high and low values in parenthesis. The results are shown in the following table, with all values in mA:

| Blood Pump Load | Level Adjust Off | Level Adjust On |
|---|---|---|
| Off | 387 - 429 (408) | 542 - 629 (586) |
| Low Load | 806 - 1043 (925) | 944 - 1212 (1078) |
| Heavy Load | 2120 - 2140 (2130) | 2270 - 2290 (2280) |
| | | +24V |

By taking an average of the differences between the Level Adjust pump being on and off gives an approximate level adjust current draw of 160 mA. By averaging the differences between the Blood Pump being on and off gives approximate blood pump current draws of 504 mA for the low load and 1.71 A for the heavy load.

Summary

The power supply requirements for the Blood Pump Control system were measured, which included current measurements for the +5 V, +12 V, -12 V, and +24 V supplies. The following table summarizes the results. The low value for the +24 V current is with the Level Adjust and Blood Pump motors off. The high value is with the Level Adjust on and the Blood Pump running at 500 mL/min while loaded with water filled occluded T8 tubing.

| Power Supply | Load Current (mA) |
|---|---|
| +5V | 316.0 |
| +12V | 120.5 |
| -12V | 16.5 |
| +24V | 408 - 2280 |

UF/Proportioning System

Proportioning Control

Description

The purpose of the concentrate pump controller is to provide the proper drive signals for each concentrate pump assembly so that user specified proportioning ratios can be accurately controlled. Each concentrate pump consists of a stepper motor driven (by a cam/follower) diaphragm pump assembly that utilizes the proper actuation of a three way solenoid valve for its intake and output pumping strokes. The valve actuation (intake stroke) is synchronized by a signal that is generated by an optical interrupter sensor which senses a pin mounted on the cam of the pump assembly. When the controller receives a synchronization pulse it actuates the associated pump's valve for a given number of stepper motor steps ("A" pump 28 steps and "B" pump 100 steps). The "A" concentrate pump has a 14% intake stroke duty cycle and the "B" concentrate pump has a 50% intake stroke duty cycle, due to cam configuration. The "A" concentrate pump cam has an 86% output stroke duty cycle to minimize the "A" concentrate output flow rate dead time. Since the maximum "B" concentrate pump's flow rate is nearly twice the "A" its flow duty cycle can not be altered to give it a longer duration output stroke (the "B" concentrate is also easily desired at low pressure).

The UF/PROP controller utilizes the fact that the number of motor steps between each synchronization pulse is 200 to check the concentrate pumps for stepping errors. If the synch pulse is received late then the motor is assumed to be skipping steps and the error is reported. If received early, the synch pulse is reported as a noise error (these error conditions are displayed in technician mode).

The four phase, 200 step/rev stepper motors used in the concentrate pumps are driven in the full step mode, which utilizes the relationship that two coil states are always in the inverse state (ON/OFF) of the other two. Therefore only two logic lines are used to step the four phases of each motor. For each motor these two logic lines are inverted and the resulting four signals are buffered by NPN transistors contained in ULN2065 ICs. These four open collector outputs are connected to the ends of the two motor coils and the coils' center taps are connected to the +24V supply. The inductive currents produced by the stepper motors' coils are conducted through the flyback diodes in the ULN2065 through a Zener diode connected to the +24V supply. The resulting collector voltage, limited by the Zener diode, is used to help quicken the deenergization of each coil. This increases the maximum speed attainable by the motors and more importantly increases their output torque capability at all speeds (coil denergizes through only 22 V, since the center taps are connected to the +24 V supply).

When the operator enters the desired dialysate flow rate the host (80XX microcontroller) converts this flow rate, the technician set proportioning ratio (unless acetate proportioning is determined from the concentrate interlock sensors), and the concentrate pump calibration constant to the concentrate pump speed. The concentrate pump speed is in the form of a time between stepper motor steps and has units of the 7.8125 μsec per step (2/256 msec per step). The speed (period) calculated is then written to the UF/PROP controller (8040).

Test Data

Proportioning Accuracy

The proportioning accuracy testing was done in four pieces (not including the total system verification). The first test was to determine if the UF/PROP controller (8040) controls the speed of the concentrate pumps to the desired speeds it is passed. This test measured a speed error of less than 0.06% (less than the measurement error).

The second test, which was done to illustrate the correct concentrate pump valve timing, showed that within 0.5% the "A" concentrate pump has an intake stroke duty cycle of 14% and the "B" concentrate pump has an intake stroke duty cycle of 50%. The error is most likely experimental error since it is less than the error associated with a one step (which is 0.5%). In any case the error is of an acceptable level.

The third test was to verify that the controller is passed the correct concentrate pump speeds from the host. The speed the controller is passed is dependent on the dialysate flow rate, the proportioning ratio, and the concentrate pump's calibration constant. The test data collected demonstrates that the desired pump speeds sent to the controller are the correct speeds as represented by their integer values. The quantization error introduced by the integer pump speeds (and dialysate flow rates) was analyzed to show that the maximum proportioning ratio error introduced was less than 0.12%.

Extensive testing was done to show that the proportioning pumps' stroke volumes are constant over flow rate and pumping head height. The testing produced volume errors of less than 0.6% over the full range of tested parameters.

In conclusion, since the concentrate pump stroke volumes are constant over flow and head height, the actuation of the concentrate pump valves is correct, and the speed that the pumps are controlled to is correct then the concentrate pump flow rates must be accurate and stable.

The forth test used to verify the proportioning accuracy was to measure the dialysate flow rate accuracy. This test measured dialysate flow rate errors less than 0.4%.

| Set Flow (mL/min) | Measured Flow (mL/min) | Error |
|---|---|---|
| 500 | 501.6 | 0.32% |
| 700 | 701.6 | 0.23% |
| 900 | 900.83 | 0.09% |
| 500 | 498.7 | 0.26% |
| 700 | 700.97 | 0.13% |
| 1000 | 1000.1 | 0.01% |

The final proportioning accuracy test was to measure the System 1000 conductivity over many minutes and analyze the conductivity stability with a desired dialysate flow rate change. A graph of one sample run is presented below. The test conditions include acetate proportioning, dialysate flow rate of 500 mL/min from start to a time of 76 minutes, and dialysate flow rate of 800 mL/min from time of 76 minutes to test end.

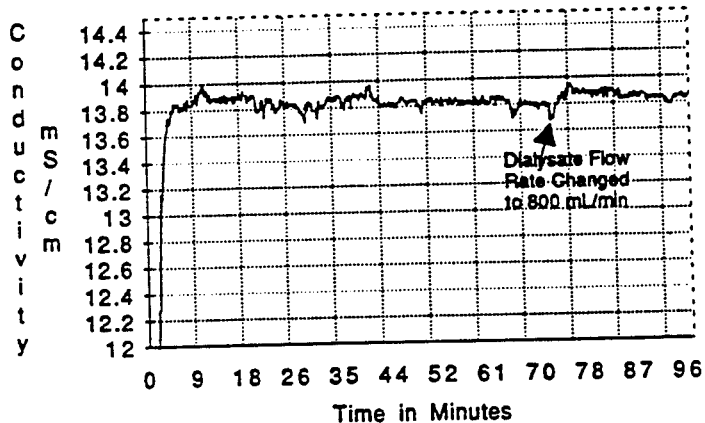

Similar testing to that above was done with a bicarb proportioning. Test results indicate that the short term final conductivity stability at 500 mL/min dialysate flow rate is ±0.1 mS/cm and at 1000 mL/min is ±0.05 mS/cm. The "A" and "B" probe conductivities indicate worst case short term conductivity stabilities of ±0.3 and 0.5 mS/cm at dialysate flow rates of 500 mL/min.

Proportioning Stability

The short term stability of the concentrate pumps' speeds can vary from step to step by as much as 50%, yet on a revolution to revolution basis the speed stability variability is limited to only 0.2% (2 msec per revolution at maximum speed of 60 RPM, minimum controller value of 641). These values represent the nature of the drive and are not thought of as deficiencies in the drive scheme.

The proportioning stability was measured a variety of ways. The first was to measure the period of each step of a repeating step waveform. This test showed that the expected step waveform was output, and was repeated over time.

The second test was to measure the number of steps over a multiple minute period knowing the desired step rate. This test is the same test as was used to verify the speed accuracy of the concentrate pumps. It shows the pump speeds to be stable and accurate to within 0.05% of the desired speed.

One of the final tests used to measure proportioning stability was to log the System 1000 machine conductivity over a many minute period. The test which generated the graph below was performed on the monitoring machine #1 with acetate proportioning at a dialysate flow rate of 500 mL/min. This graph shows that no measurable conductivity drift was noticed in a two hour period. The test also indicates that the short term conductivity stability at the final probe is on the order of ±0.05 mS/cm. The test also measured the "A" and "B" conductivity probe stabilities to be ±0.4 and 0.1 mS/cm, respectively.

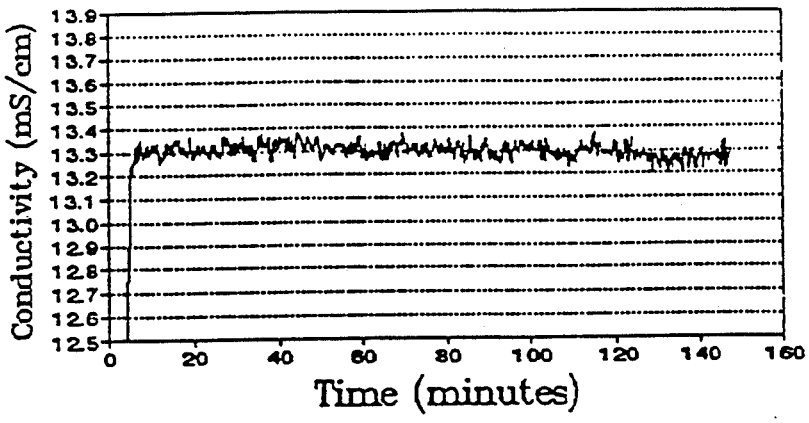

Subsequent testing of the machine was done which simulated a patient treatment using bicarb proportioning at a dialysate flow rate of 600 mL/min. Machine parameters were recorded throughout the treatment and the conductivity of the machine was found to be stable to within 0.1 mS (displayed conductivity was 13.3 mS ± 0.1 mS) over a 4 hour period.

The conductivity stability data over any other data illustrates the proportioning stability of the System 1000 machine.

Power Derating of Components

The power derating of the concentrate pump driver circuitry located on the UF/PROP POWER board (revision Z7) was measured/ calculated under the worst case conditions for the associated parts (maximum speed for the Zener diode and flyback resistor, and 0 RPM for the transistor driver package).

Many different drive schemes were tested to determine which could provide enough torque without producing an excessive amount of audible noise. The full step drive mode with the elevated voltage flyback current path was found to offer the best compromise of the two requirements. Dynometer testing was done to determine how much torque the motors are capable of delivering throughout the required speed range. The torque speed curve of the data collected is shown below.

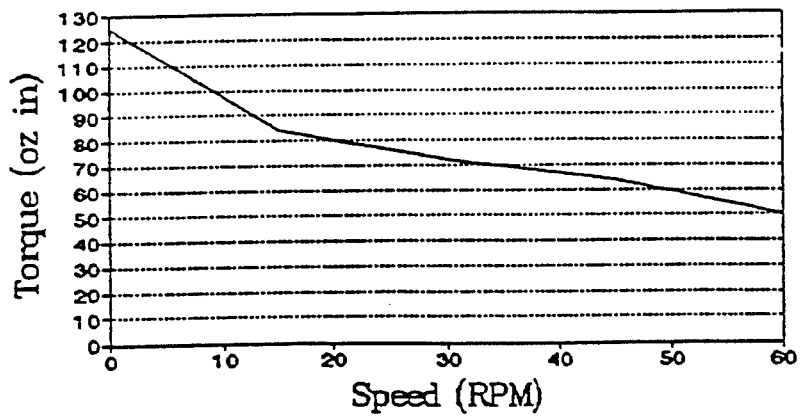

Transistor Driver Package ULN2065

The maximum temperature rise measured for this part under all the different test conditions was less than 26°C. The maximum power measured was less than 0.4 W. Since the thermal impedance of the part (junction to case) is 10 to 13°C/W (supplied by the manufacturer) the maximum junction to ambient rise can be determined to be less than 32°C. Typically these parts have a maximum junction temperature of 150°C (maximum junction temperature not specified by the manufacturer), therefore at the System 1000 design maximum internal ambient temperature of 60°C the maximum allowed temperature rise from junction to ambient is 90°C. Since the maximum measured rise was less than 32°C the part derating can be calculated to be greater than 64%.

A second way of verifying the part derating is to compare the maximum measured power of 0.4 W with the manufacturer's maximum power rating at the System 1000 maximum internal ambient specification of 60°C. The manufacturer specified that at 60°C the maximum package power dissipation should not exceed 2 W. This method indicates that the derating of the driver is 80%.

Zener Diode 1N4748

The Zener diode derating was calculated as 1 minus the measured power divided by the maximum allowed power at the maximum lead temperature (measured lead temperature rise plus the maximum ambient temperature). The maximum measured temperature rise was less than 20°C and the maximum power measured was 0.19 W. The manufacturer specifies the maximum power dissipation at a lead temperature of 85°C of 0.75 W. Therefore, the worst case derating of the Zener diodes is $1 - 0.19/0.75 = 74\%$.

Flyback Resistor 1k 2W

The maximum power in the resistor is only a function of the voltage that is placed across it. Since the voltage across this resistor is the Zener voltage (and not 100% duty cycle) the maximum power in the resistor is 24*24/1000 or 0.576 W. Therefore the derating is $1 - 0.576/2$ or 71%. This component never is operated at 100% duty cycle, so the actual derating is greater than 71%.

Summary

The System 1000 machine specification for proportioning accuracy is ±2%. The proportioning accuracy demonstrated by the System 1000 machine was shown to be better than 1%. The 1% value was the result of both the accuracy and stability measured during testing.

Dialysate Flow Control

Description

The purpose of the dialysate flow control system is to accurately control the dialysate flow rate in the System 1000 machine and minimize the flow dead time between flow equalizer valve switches. The System 1000 machine utilizes a double acting diaphragm metering device (referred to as the flow equalizer) to match the volume of dialysate delivered to the dialyzer with the volume of dialysate pumped back from the dialyzer.

The System 1000 flow path contains three pumps, two of which are powered by the same motor that runs at a constant speed (deair and dialysate pressure pumps). The deair pump is situated in a flow loop with the deair sprayer (directly after the "A" mixpoint) to produce a low pressure that removes the dissolved air in the water being prepared as dialysate. The dialysate pressure pump is in the post dialyzer flow circuit and provides the pressure which draws the fluid from the dialyzer and delivers it to the flow equalizer. This pump runs at a constant speed and has a recirculation flow path around it so that the flow through the pump remains constant even though the flow equalizer flow is pulsitile. The supply pump supplies the fresh dialysate flow to the flow equalizer. This pump's speed is controlled to accommodate different dialysate flow rates.

Since the flow equalizer has a fixed volume, the time between valve switches determines the dialysate flow rate, provided that the total volume of both sides of the flow equalizer have filled and/or emptied. To ensure a complete volume transfer in the flow equalizer, flow sensors (End of Stroke Sensors) have been strategically placed in the flow path to sense when the flow stops (End of Stroke). The valves will not switch before the end of stroke condition is sensed (unless a secondary timeout condition is encountered). Since the speed of the supply pump determines the instantaneous dialysate flow rate, it is controlled so that both end of stroke signals are received in a predefined amount of time before the desired valve switch time (this time is adjustable and is set to 1 second upon initialization). In this way, complete flow transfer of the flow equalizer is guaranteed every flow equalizer cycle and the dead time is controlled.

Test Data

The flow control system testing was split by function into five different parts.

Dialysate Flow Rate Accuracy

The dialysate flow rate accuracy was tested by first calibrating the flow rate using the calibration routine, then gravimetrically measuring the dialysate flow rate (drain flow rate) at different set flow rates. The testing illustrated a maximum dialysate flow rate error of less than 0.5%.

End of Stroke Reliability

The end of stroke reliability was tested by recording the number and frequency of the end of stroke errors that occur upon flow rate changes and dialysate pressure changes. Other testing counted the number of errors that occur over a multiple hour treatment when the machine is operated with typical treatment conditions. There are four different end of stroke errors:

*No flow alarm*

This error is reported when no end of stroke signal is sensed before the secondary flow cycle timeout occurs for four consecutive flow cycles.

*Early end of stroke on sensor 1*

This error is reported when sensor 1 senses an end of stroke condition before half of the flow cycle time has elapsed.

*Early end of stroke on sensor 2*

Same as above, except for end of stroke sensor 2.

*Too much time between end of stroke signals*

This error is reported when there is more than 2.55 seconds between the end of stroke signals.

Dialysate flow rate changes produced one set of early end of stroke errors (sensors 1 and 2) only when stepped from low to high flow. This condition is explainable by the fact that when the flow rate is stepped up the supply pump drive voltage is instantly increased to accommodate the higher flow rate yet the flow equalizer valve period left over from the lower flow rate is still counting down thereby creating the early end of stroke condition.

In summary, the end of stroke errors occur very seldom and are not considered likely enough or important enough for machine response. For troubleshooting purposes the machine will display the errors in technician mode only.

End of Stroke Dead Time Control (distribution around desired)

End of stroke dead time control testing was done in two tests. In the first test, the end of stroke time for each sensor was logged for a period of 45 minutes as two flow rate steps at 15 minute intervals were imposed on the machine. The second test was the same as the first except two dialysate pressure steps were introduced at 15 minute intervals. The end of stroke tests showed that the worst case step response to any of the above conditions was after the high to low flow rate step which took a total of 7 flow equalizer cycles to fully return back to the previous steady state conditions (at 500 mL/min flow rate 7 flow equalizer cycles takes a total of 95 seconds).

No Flow Alarm

The no flow alarm testing involved disabling the supply pump in the System 1000 machine after the flow rate has stabilized and measuring the number of flow equalizer cycles that occur before a no flow alarm error is displayed. With the supply pump disabled the machine will not have any dialysate flow and will not sense end of stroke. If end of stroke is not sensed the machine waits only 5 seconds after the time it expects the end of stroke signal and then switches the flow equalizer valves (secondary flow equalizer timeout). The above test repeatably indicated that after four secondary flow equalizer timeouts the no flow alarm error is reported.

Power Derating of Components

The deratings of the components involved with the flow control system were calculated under worst case conditions for each component at an internal ambient temperature of 60°C. The components involved include: the shutdown transistor, the supply pump drive circuitry, the deair/dialysate pressure pump circuitry, the flow equalizer valve drive circuitry, the rinse valve drive circuitry, and the end of stroke sensors/drivers.

Shutdown Transistor

The shutdown transistor is used as a redundant switch to the critical power loads (switched +24V supply) driven by the UF/PROP power board. The loads include: the supply pump, the deair pump, the two concentrate pumps, and the UF removal meter valves. Under worst case conditions (supply and deair motors stalled) the maximum current load on the transistor averages about 2.1 A. With an average current level of 2.1 A the power dissipated in shutdown transistor, Q11, was calculated to be 2.1 W. This power level corresponds to a derating of slightly greater than 50%. The derating is marginal yet the stalled motors condition in the System 1000 machine is a state which can last only a couple of minutes before the operator will have to turn the machine off to be repaired.

Supply pump drive circuitry

The supply pump drive circuitry utilizes a Pulse Width Modulated drive from the switched +24 V supply with a frequency of about 22 kHz and a peak current limit of about 2.5 A. When the supply pump drive circuit was tested the supply pump motor being used in the System 1000 machine was the type F motor. This is the reason why the current limit circuitry was set to operate at the extreme current of 2.5 A. When tested with the type F motor the drive transistor, Q10 was found to be derated by greater than 70% and the flyback diode, D22, 75%. Since the type F motor has been replaced with an type A ironless rotor motor (like the one used for the deair/dialysate pressure pumps) the circuit has been changed to be the same as was tested for the deair/dialysate pressure pump motor. This drive transistor, Q13, was determined to be derated by 68% and its flyback diode, D23, was found to be derated by 88%. Q10 and D22 will then be derated the same as the Q13 and D23 since the derating is independent of operating load (derating determined at stall).

Deair/dialysate pressure pumps drive circuitry

The deair/dialysate pressure pumps drive circuitry utilizes a Pulse Width Modulated drive from the switched +24V supply with a frequency of about 22 kHz and a peak current limit of about 1.6 A. When the current limit testing was done on the deair/dialysate pressure drive circuitry the motor used was type A. The derating of the deair/dialysate pressure pump drive transistor, Q13, was calculated under stall condition to be 68%. The derating of the deair/dialysate pressure pump flyback diode, D23, was calculated to be 88% during the same test.

Flow equalizer drive circuitry

The flow equalizer valve drivers, Q4 and Q5 (MTP3055E), conduct the current which power the flow equalizer valves. The current typically averages about 1.5 A at 50% duty cycle with a period range of 6.7 to 13.5 seconds. The power dissipated in the devices was calculated to be 0.11 W (at 100% duty cycle) and their derating was found to be greater than 86%.

There exists flyback diodes, D16 and D17 (MR501), on the UF/PROP power board which conduct current each time the associated flow equalizer valve set is deenergized. When tested no appreciable temperature rise was measured for the devices and the "on" duty cycle was measured to be less than 0.6%. Therefore derating of these devices is reasoned to be proper.

Rinse valve drive circuitry

The rinse valve driver, Q8 (MTP3055E), conducts the current which powers the rinse valve (SIRAI D301 with EF4 Soleniod). The current is less than 0.2 A. The derating for this device was not directly calculated since the current level is so low and no measurable temperature rise was found. The derating can be reasoned to be greater than 90% since the same device (MTP3055E) is used to switch currents levels that are 8 times greater than the rinse valve current and that device (flow equalizer valve driver) was found to be derated by over 86%.

End of stroke sensors and drive circuitry

The end of stroke sensors drivers are DC current sources, U9 and U10 (LM317), which energize the end of stroke sensors with 18.3 mA of current derived from the +24 V supply. When energized and placed in heated water the typical end of stroke sensor voltage drop is about 13 V. In air the sensor voltage is about 6 V. Since a current source is used to self heat the thermistors as the sensor temperature increases, the sensor resistance decreases, the power into the device drops. In this way the power delivered to the sensor is limited to insure proper sensor derating. When the sensor is in air, worst case, the power dissipated by the current source was measured to be 0.43 W with a temperature rise of 41.5°C. The part power derating was then calculated to be 52%. The derating was also calculated under worst case wet conditions and was found to be 69%. Since the dry sensor conditions won't typically exist in the System 1000 machine the 52% derating is presented for reference only.

Under worst case conditions, in air, the voltage across the end of stroke thermistors can be as low as 5.9 V (sensor resistance of 322 ohms) which from the resistance to temperature relationship of the Victory T35A11 thermistor suggests a thermistor temperature of about 110°C. The thermistors have a maximum continuous operation temperature of 325°C.

Using a dialysate temperature of 37°C and figuring the derating of the thermistors on temperature rise percentage basis, the derating of the thermistors is greater than 70%.

Summary

The dialysate flow rate accuracy demonstrated by the System 1000 machine of better than 0.5% easily meets the System 1000 machine specification of ±3%.

Testing illustrated the reliability of the end of stroke sensors and verified the proper indication of the associated end of stroke errors. The end of stroke dead time control testing proved that compensation to the most severe flow rate disturbances occurs in less than 8 flow equalizer cycles.

Finally, all the power components used in the flow equalizer control circuitry were found to be adequately derated.

UF Removal

Description

The purpose of the UF removal system is to accurately meter the volume of fluid removed from the dialysate and control the rate at which it is removed. The operator enters the volume of ultrafiltrate to remove and the UF removal rate. The host then converts these values using the appropriate calibration constant (the volume of the UF removal metering device) to the number of UF metering device strokes and the period between strokes. The UF/PROP controller is sent these values and, when the machine state is favorable, is commanded (through the use of an enable register) to commence UF removal.

The volume of the UF metering device is calibrated by having the operator measure the output weight of a multiple number of device strokes. Upon the entry of the total weight by the operator, the calibration routine calculates the average stroke weight (volume) and saves the calibration constant in the form of a percentage variance from the nominal. The UF removal metering device calibration constant has a range of ±12% and a resolution of 0.1 percent (calculated using a nominal volume of 1.5 mL).

Test Data

UF/PROP Controller Verification

The first test consisted of passing the UF/PROP controller a UF rate and then measuring the actual rate and analyzing the output waveform. The UF rate was measured by accumulating the output volume of the UF removal metering device and counting the number of strokes stroked by the device in a 30 minute period. The volume measurement produced less than 0.5% error and the stroke count measurement produced less than 0.05% error. This test could have introduced the volumetric error by incorrectly determining the UF removal meter's volume per stroke. This test was using the hydraulic test fixture for the purpose of verifying the correct timing of the UF removal meter valves. It can be concluded that the timing error associated with the UF removal meter is negligible and the stroke volume calibration is the critical link in the UF removal system.

The UF removal meter drive waveform was also analyzed to verify that the expected waveform was output for a given rate. Since the output waveform period is a multiple of 0.4 second periods (as designed) to achieve rates which are not even multiples of the 0.4 second period, the stroke period must alternate between the two 0.4 second multiple periods in which the desired period falls between. In this test, a desired stroke period of 1.4 seconds (3.5 * 0.4 seconds) was entered and the output waveform was recorded. The output period alternated between 1.2 and 1.6 second stroke periods as expected.

Calibration Verification

The second test of the UF removal system was to verify that the calibration of the UF removal meter volume correctly corrected the UF removal rate passed to the UF/PROP controller. This test verified that the correct rate is passed to the controller as determined by the UF removal meter's calibration constant. The associated error produced by the quantitization of the UF removal rate was also shown to be less than 0.05%.

Total System Accuracy

The final test of the UF removal system was done on a calibrated System 1000 machine. This test was done by entering a desired UF volume to be removed and a rate at which it was to be removed (in the dialyze mode). A volume of 1.00 L and a rate of 4.00 L/h were used for the test and the variables measured were the time for the volume to be removed, the volume output of the UF removal device and the actual volume removed across a dialyzer from a simulated patient.

The test results showed that the UF removal rate and accumulated volume accuracy, measured at the output of the UF removal device, to be better than 30 mL/h. The accuracy measured across the dialyzer was within 50 mL/h (the weight difference is believed to be caused by changes in the venous and arterial drip chamber levels).

Power Derating of Components

The power in the UF removal meter's valve drivers (MTP3055E) was measured to be 0.011 W. Since the allowable power dissipation in an MTP3055E is over 1 W the UF removal meter valve driver's deratings are greater than 90%.

Summary

The System 1000 machine specification states that the UF removal system will remove volume from the dialysate with an associated error of less than 2%. The machine UF removal error was demonstrated to be less than 1%.

A design goal for all System 1000 electrical components was, under worst case conditions, to achieve a derating of greater than 50% with an internal ambient temperature of 60°C. The UF removal system power components meet this design goal with greater than 90% deratings.

The data presented verifies that the UF removal system performs within the specifications of the System 1000 machine.

Conductivity Measurement

Description

The purpose of the conductivity measurement system is to accurately measure and report the temperature compensated dialysate conductivity from multiple locations within the fluid path. There are three conductivity probes in the System 1000 flow path. The first probe is situated directly after the air trap which is down stream of the "A" mixpoint and is referred to a the "A" conductivity probe. The second probe is right after the "B" mixchamber and is referred to as the "B" conductivity probe. The third, referred to as the primary probe, is immediately before the bypass valve. The "A" and "B" conductivity probes are used for backup alarms and for proportioning verification. The primary probe's conductivity is used for primary alarms and is the displayed conductivity. The "A" and "B" conductivities are measured and calculated by the UF/PROP microcontroller (8040) and are passed to the host on a routine basis. The primary conductivity is measured and calculated by the MISC/IO microcontroller and is passed to the host on a regular basis for the conductivity display. The conductivity probes are calibrated in the System 1000 machine's calibration mode by having the "A" concentrate pump run at a proportioning ratio of 40:1. When the primary conductivity is determined to be stable the three conductivities are set equal to an independent reference conductivity through the use of the three programmable gain constants contained within the two controllers.

The conductivity probes are essentially tubes of fluid, 0.375 inches in diameter and 1.2 inches in length, which separate two electrodes. One of the electrodes within each probe contains a thermistor so that the temperature within each probe can be measured.

The conductivity is measured by the controllers using circuitry which does an AC resistance measurement between each of the conductivity probe's electrodes. An AC resistance measurement is used since a DC resistance measurement would polarize the electrodes and produce incorrect measurements. One electrode of each conductivity probe is stimulated with a 1 kHz AC voltage while the other is held at virtual ground (current sense electrode). Two DC voltages are produced by the circuit, one of which is proportional to the negative peak of the AC stimulation voltage (VREF) and the other which is proportional to the negative peak of the AC probe current (VCONDO) as described below.

VREF(V) = Vprobe(V) / 3

VCONDO(V) = Iprobe(A) * 249Ω

Therefore the resistance of the probe can be calculated/measured by using the relationship below.

PROBE RESISTANCE(j) = 747Ω * VREF(V) / VCONDO(V)

The System 1000 conductivity probe resistance was modeled as a function of temperature and conductivity. The resulting relationship is entered below (C is conductivity in mS/cm at 25°C and T is temperature in °C).

PROBE RESISTANCE = 600Ω * 14 mS/cm / C * (38°C + 23°C) / (T + 23°C)

Therefore by substitution and algebra it can be shown that:

C = 600Ω * 14 mS/cm * 61°C / 747Ω * VCONDO / VREF / (T + 23°C)

The UF/PROP and MISC/IO controllers use the above equation to calculate conductivity. The conductivity is calibrated by the microcontrollers by scaling the constant in the above equation. In this way, the calibration can compensate for circuit and conductivity probe tolerances.

Test Data

The conductivity testing was done in many pieces at many different stages in the conductivity circuitry development. The key factors involved in verifying the conductivity measurement system include the modeling of the conductivity probes, the accuracy testing of the resistance measurement circuitry, the determination of the temperature compensation efficacy, and the accuracy testing of the conductivity measurement system.

The conductivity probe model defined the relationship between the probe resistance and conductivity and temperature. The probe resistance equation was previously presented.

A test was done to determine the accuracy of the resistance measurement used in the conductivity circuit. This test showed that, inside the resistance range of 400 to 4000 ohms, the circuit measured resistance with an associated error of less than ±0.25% (less than the tolerance on the test resistors of 1%). This resistance range corresponds to a conductivity range of 2.1 to 21 mS/cm (System 1000 conductivity range is 7 to 17 mS/cm) and an error in terms of conductivity of less than ±0.05 mS/cm (maximum at 20 mS/cm).

The temperature compensation of conductivity is an integral part of any conductivity measurement. The measurement is typically compensated to indicate conductivity at 25°C. This is the standard by which most (if not all) conductivity meters are based on, including the System 1000 conductivity measurement system.

Data was taken to verify the temperature compensation of the System 1000 conductivity measurement system. The test logged the system conductivities and temperatures to a data file (every 10 seconds) while the machine was proportioning at a constant ratio and the set temperature was being stepped between three temperatures at fifteen minute intervals. The testing indicated that the maximum deviation in conductivity due to a temperature step from 35 to 39°C was 0.13 mS/cm. This temperature range is the entire System 1000 operational temperature range. This is inside the System 1000 conductivity accuracy specification of ±0.2 mS/cm.

The final test done to verify the conductivity measurement was to vary the proportioning ratio, then at each ratio measure the conductivity with an external calibrated conductivity meter and compare it with the three System 1000 machine conductivities. The test showed that the four measured conductivities agreed to within 0.06 throughout the conductivity range of 11.11 to 15.81 mS/cm.

Summary

The testing done on the conductivity measurement system verifies that the machine accurately reports the dialysate conductivity with an error of less than ±0.10 mS/cm. This error is less than the System 1000 machine specification of ±0.20 mS/cm.

Temperature Measurement

Description

The purpose of the temperature measurement system is to accurately measure and report the dialysate fluid temperature from multiple locations in the System 1000 fluid path. The primary conductivity probe temperature is used for the temperature display, the primary temperature alarm source, and temperature compensation for the primary conductivity measurement. The "A" and "B" conductivity probe temperatures are used for conductivity temperature compensation and backup alarm generation.

The temperature measurement circuit used throughout the System 1000 machine consists of a voltage divider with a Thevenin Equivalent circuit of 3062 Ω in series with a 7.55 V supply. The voltage divider circuit when connected to a Dale thermistor referenced to ground with a resistance to temperature relationship of $$R(T) = 5000\Omega * 2.831 * \exp(-0.04162 * T) \, \Omega$$

produces a voltage to temperature relationship of $$T = (3.77 \text{ V} - V_{temp}) * 12.73 \, (°C/V) + 37°C.$$

The above relationship is the result of linearizing nonlinear functions at a 37°C midpoint. The temperature linearization above approximates the temperature to within ±0.1°C inside the temperature range of 30 to 44°C.

The tolerances on the above component parameters can be as much as 10%, therefore the temperature versus voltage relationship for each probe must be calibrated. Calibration of the temperature measurements is a two point calibration done at 30 and 40°C which results in a slope and an offset for each temperature probe. The temperature calibration is done at a high dialysate flow rate to minimize the temperature differential between the temperature probes. After the calibration data is collected, "A", "B", primary ("dialysate"), and the reference temperatures, at the desired set temperatures of 30 and 40°C. The calibration routine scales the System 1000 measured temperatures to be equal to the temperatures measured by an external temperature reference meter (placed in the dialysate line). The gains and offsets are stored in the nonvolatile RAM for later retrieval and use during the System 1000 machine initialization. The calibration gain has a ±12% adjustment range around the nominal and the calibration offset has a ±5°C adjustment range.

Test Data

The temperature accuracy tests were done by comparing the measured temperature at the primary conductivity probe with an external reference at several different desired temperatures and flow rates. Since the three temperature probes (contained in the "A", "B", and primary ("dialysate") conductivity probes) use the same thermistors and support circuitry, only one probe was formally tested as described above. Other data, presented in the System 1000 Temperature Control Test Report, indicates that the three measured temperatures are in agreement with each other except for offset differences due to location differences in the fluid path. The data presented below indicates a maximum temperature measurement error of 0.06°C.

| Set Temp | Flow | Ref Temp | Final Temp | Error |
|---|---|---|---|---|
| 38 | 500 | 37.68 | 37.70 | 0.02 |
| 42 | 800 | 41.24 | 41.21 | −0.03 |
| 42 | 500 | 41.39 | 41.36 | −0.03 |
| 34 | 800 | 33.90 | 33.96 | 0.06 |
| 34 | 500 | 33.96 | 34.02 | 0.06 |
| 38 | 800 | 37.37 | 37.38 | 0.01 |

Summary

The System 1000 machine specification states that the System 1000 temperature measurement system should measure temperature to within 0.3°C. The test data presented demonstrates that the System 1000 temperature measurement system is accurate to within 0.1°C.

Temperature Control

Description

The purpose of the temperature control system is to control the dialysate temperature to the temperature selected by the operator. The operator enters the desired dialysate temperature through the touch screen interface, the host converts this value using the appropriate calibration constant to a calibrated ADC value. The value is then written to the UF/PROP controller for uses as the initial temperature control threshold.

In the System 1000 machine there exists four separate temperature measurement probes. Three of the probes are contained in the three conductivity probes (A, B, and dialysate) and the forth is located immediately after the heater. The A and B conductivity probes are located just down stream of the A and B mixpoints, respectively. The A mixpoint is upstream of the B mixpoint and both mixpoints are downstream of the heater. The dialysate conductivity probe is located just before the bypass valve and serves as an independent monitor of the temperature and conductivity. The displayed temperature and conductivity are measured at the dialysate conductivity probe.

To improve the temperature step response to a dialysate flow rate change, when the UF/PROP controller is told to change the flow rate it steps the heater duty cycle by the ratio of the old and new flow rates. In this way, the heater duty cycle is immediately corrected.

Since the temperature control thermistor is located at the output of the heater housing, the temperature it uses for control purposes has a large amount of steady state instability (due to the flow rate fluctuations by the heater). Therefore the temperature control algorithm has a large time constant associated with its heater duty cycle correction. This is not a problem for flow step response times since a correction for flow rate changes is made immediately as was previously described.

Since the dialysate temperature at the dialyzer is dependent not only on the temperature controlled at the output of the heater housing but also the flow rate, the concentrate treatment type, the ambient temperature, and the concentrate temperature there exists a temperature compensation routine in the host. This routine determines that the temperature is stable when three successive readings, taken one minute apart, of the "B" probe temperature are within 0.05°C of each other. After the stability criteria is met, it corrects the temperature used for the control threshold by the difference in the temperature measured at the "B" probe and the user entered desired temperature. This temperature compensation is limited to a maximum of 2.8°C and can occur a maximum of every 20 minutes.

Test Data

Temperature control data was taken both on monitoring machine #1 and the stand alone flow path test station (an XT computer running a BASIC host/slave interface program linked to a UF/PROP controller, running its System 1000 control program, and a UF/PROP power board). Most of the step response tests were done on the stand alone flow path test station. These tests did not include the temperature correction logic contained within the System 1000 temperature control system. The temperature correction software was not thought to be needed for the temperature step response tests since the testing was mainly aimed at the UF/PROP control software.

The temperature control performance testing was divided into the following parts:

- Dialysate Temperature Control Accuracy
- Dialysate Temperature Control Stability
- Dialysate Temperature Step Response to:
  - Flow Changes
  - Desired Temperature Changes
  - Incoming Water Temperature Changes

Dialysate Temperature Control Accuracy

Temperature control accuracy was indirectly tested throughout the tests presented below. The test which best illustrates the temperature control accuracy is the temperature response to desired temperature changes test. This test demonstrated that the temperature control system is capable of controlling the dialysate temperature throughout the temperature range of 35 to 39°C to within 0.1°C.

Independent testing of the monitoring machine #1 was done which simulated a patient treatment using bicarb proportioning at a dialysate flow rate of 600 mL/min. The machine parameters were periodically recorded throughout the treatment. The data gathered indicates that the displayed temperature was within 0.2°C (after warm up) of the set temperature throughout the 4 hour treatment. The 0.2°C temperature difference was constant throughout the treatment and indicates a calibration offset.

Dialysate Temperature Control Stability

Temperature stability testing consisted of many different tests. The first testing was done on the flow path test station. It collected data over an eight hour period and measured an average final temperature probe temperature of 37.45 and the maximum variation from the average of 0.16°C. This variation seems high yet the standard deviation of the data was only 0.04°C. Using the standard deviation to describe the data, 95% of the time the final temperature probe temperature can be described as 37.45 ±0.08°C.

Further testing of the dialysate temperature stability consisted of multiple data log runs on the monitoring machine #1 during a variety of treatment conditions. These data files each typically contain about 2 to 3 hours worth of data. Graphs of the data have been prepared for the documentation of the testing and a typical graph has been entered below.

The first graph shows the dialysate temperature rise of the monitoring machine #1 at 500 mL/min dialysate flow rate from a cold start. Near 15 minutes into the test, the "B" conductivity probe temperature stabilizes at about 35.5°C. At this point the "B" temperature stability test passes (since its temperature is stable to within 0.05°C for three minutes) and the set temperature is corrected in order to bring the final and the "B" conductivity probe temperatures closer to the desired temperature of 37.2°C. It can be seen that the final and "B" conductivity probe temperatures are still increasing before and after the temperature correction is made (the temperature increase is very gradual and is within the stability test criterion). This is due to the fact that the internal ambient temperature is increasing (tubing and flow path component temperatures are increasing) and the final conductivity probe temperature is dependent on the flow path compartment internal ambient. After the correction the final temperature initially stabilizes to 37.2°C, at time t=27 minutes, and slowly increases to 37.5°C in next 14 minutes. At time t=41 minutes, the temperature correction software again corrects the set temperature (since the stability test passed and the 20 minute time between corrections elapsed). After the second correction the final and B conductivity probe temperatures stabilizes to 37.2°C (the set temperature).

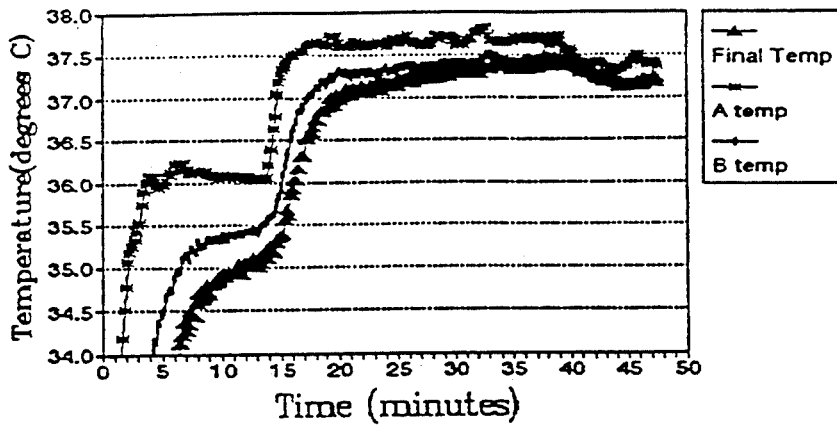

In conclusion, the time it takes for the machine dialysate temperature to completely stabilize is highly dependent on the flow path ambient temperature (machine ambient). The test presented below was performed with an ambient temperature of 18°C to show the effects of ambient temperature on dialysate warm up time.

Dialysate Temperature Step Response to Flow Changes

The temperature response to flow step testing was done on the stand alone flow path test fixture. The graph below shows the temperature response at the final conductivity probe to the largest flow steps possible in the System 1000 machine (1000 mL/min and 500 mL/min). When the flow rate is increased from 500 mL/min to 1000 mL/min there is an initial temperature decrease of 0.2°C that lasts less than 2 minutes. Then the temperature increases 1.1°C (or 0.8°C from the starting temperature). After 8 minutes the temperature decreases 0.5°C and stabilizes at a temperature 0.3°C above the starting temperature.

When the flow rate is decreased from 1000 mL/min to 500 mL/min the temperature increases 0.7°C. After 7 minutes the temperature decreased 1.0°C (or 0.3°C below the temperature at the 1000 mL/min flow rate) and decreases another 0.2°C in the last 20 minutes of the test due to flow path cooling at the lower flow rate.

The temperature difference due to flow rate differences is explainable by the fact that the fluid exposure time to the flow path (heat sink) is proportionly lower at the high flow as compared to the low. This DC offset is compensated in the System 1000 machine by the temperature correction logic using the "B" temperature. The data indicates no overshoot and no instability in the heater duty cycle in response to flow rate changes.

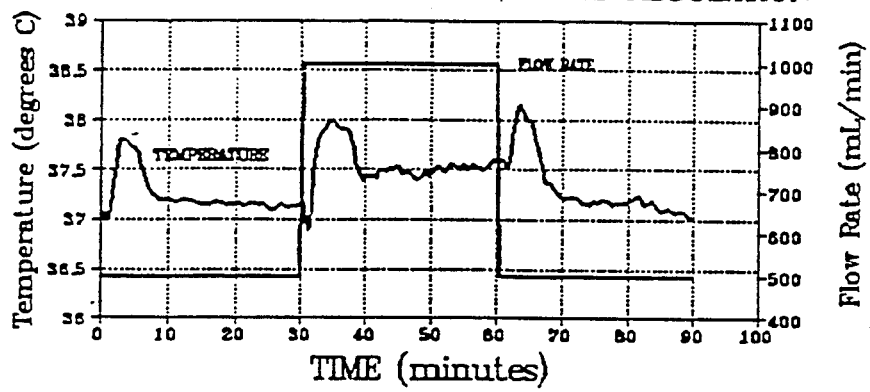

Dialysate Temperature Step Response to Desired Temperature Changes

The first temperature response to desired temperature steps testing was done on the stand alone flow path test fixture. The graph below shows the temperature response at the final conductivity probe to desired temperature steps of about 6°C (greater than the entire temperature adjustment range in the System 1000 machine). The temperature transitions occur without any overshoot and the temperatures are stable in less than 9 minutes.

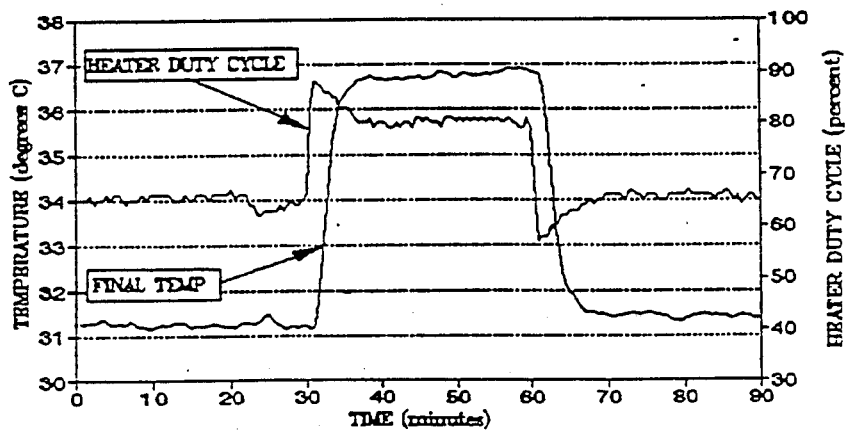

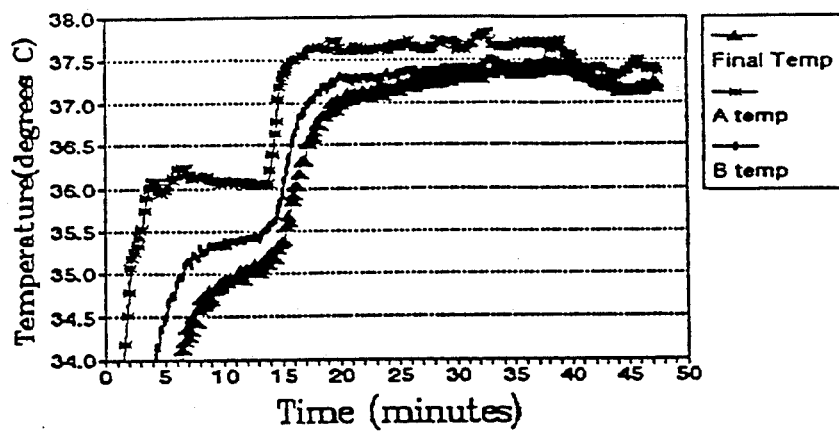

SATRN Temperatures versus Time From Cold Start

In conclusion, the time it takes for the machine dialysate temperature to completely stabilize is highly dependent on the flow path ambient temperature (machine ambient). The test presented below was performed with an ambient temperature of 18°C to show the effects of ambient temperature on dialysate warm up time.

Dialysate Temperature Step Response to Flow Changes

The temperature response to flow step testing was done on the stand alone flow path test fixture. The graph below shows the temperature response at the final conductivity probe to the largest flow steps possible in the System 1000 machine (1000 mL/min and 500 mL/min). When the flow rate is increased from 500 mL/min to 1000 mL/min there is an initial temperature decrease of 0.2°C that lasts less than 2 minutes. Then the temperature increases 1.1°C (or 0.8°C from the starting temperature). After 8 minutes the temperature decreases 0.5°C and stabilizes at a temperature 0.3°C above the starting temperature.

When the flow rate is decreased from 1000 mL/min to 500 mL/min the temperature increases 0.7°C. After 7 minutes the temperature decreased 1.0°C (or 0.3°C below the temperature at the 1000 mL/min flow rate) and decreases another 0.2°C in the last 20 minutes of the test due to flow path cooling at the lower flow rate.

The temperature difference due to flow rate differences is explainable by the fact that the fluid exposure time to the flow path (heat sink) is proportionly lower at the high flow as compared to the low. This DC offset is compensated in the System 1000 machine by the temperature correction logic using the "B" temperature. The data indicates no overshoot and no instability in the heater duty cycle in response to flow rate changes.

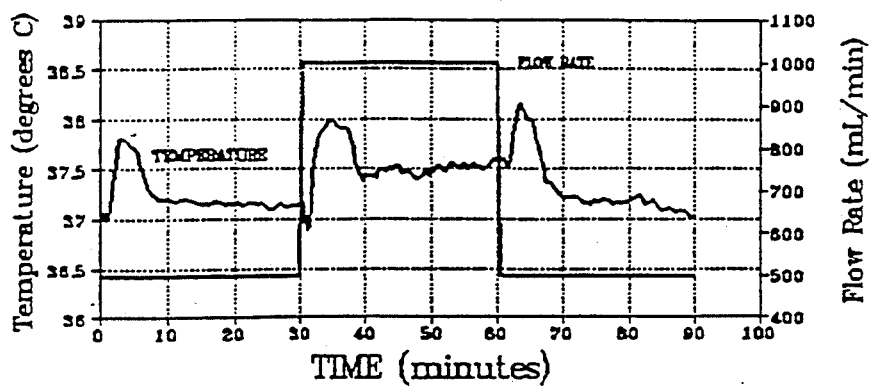

SATRN UF SUBSYSTEM TEMP CONTROL TESTS, LOAD REGULATION

Dialysate Temperature Step Response to Desired Temperature Changes

The first temperature response to desired temperature steps testing was done on the stand alone flow path test fixture. The graph below shows the temperature response at the final conductivity probe to desired temperature steps of about 6°C (greater than the entire temperature adjustment range in the System 1000 machine). The temperature transitions occur without any overshoot and the temperatures are stable in less than 9 minutes.

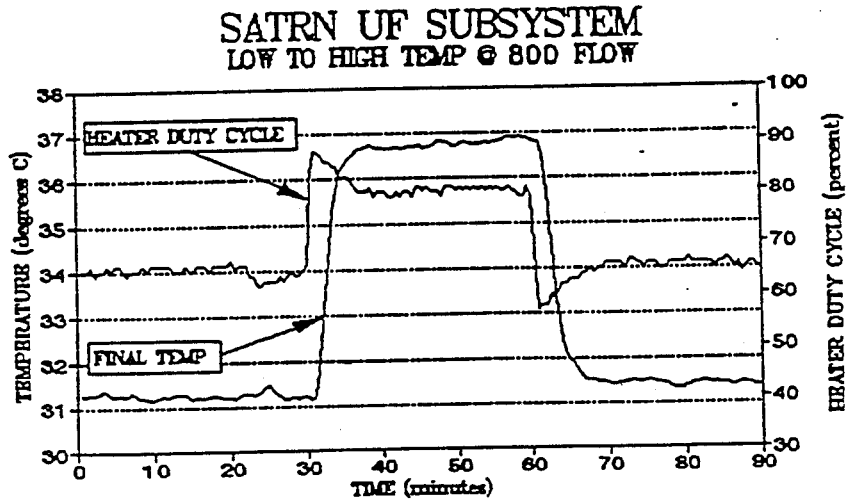

Other temperature testing of desired temperature step responses were done on the monitoring machine #1. The testing illustrates the efficacy of the temperature correction logic. The graph below shows the "B" conductivity probe temperature with an initial desired temperature setting of 37°C. After some time the temperature setting was changed to 35°C, and later yet the temperature was changed to 39°C. Upon close inspection, the B temperature can be seen to first stabilize at about 36.2°C at time equal to about 10 min. The temperature is then corrected and allowed to stabilize once again at nearly 37°C. After the temperature is stepped down, at time 37 minutes, the temperature falls down to about 35.3°C and then is corrected, after which it falls to 35°C. The same two steps can be seen when the temperature is stepped to 39°C. Without these fine adjustments, the final temperature probe may read temperatures of greater than 2°C different than the entered desired temperature.

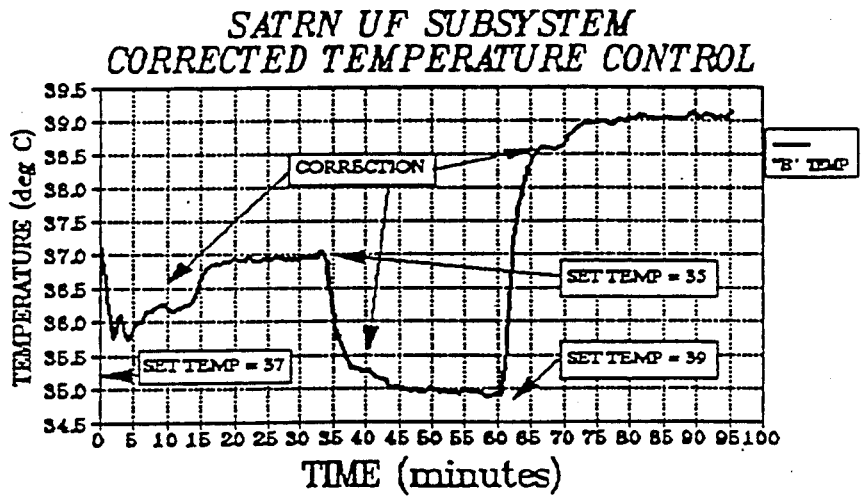

Dialysate Temperature Step Response to Incoming Water Temperature Changes

Temperature testing was done to measure the machine response to incoming water temperature steps. The final conductivity probe temperature, heater duty cycle, and the incoming water temperature were logged to a data file while the incoming water temperature was stepped from typical temperatures to temperatures less than the machine specification. The test was done at 500 and 1000 mL/min flow rates and the incoming water temperature steps were from 10°C to typically less than 5°C.

The testing revealed that the temperature instabilities at the final conductivity probe were much greater at the higher flow rates as compared to those at the lower flow rates. At 1000 mL/min dialysate flow rate the temperature spikes at the final conductivity probe in response to incoming water temperature steps of 5°C were about 1°C and required 5 minutes to be fully compensated. With the same test at 500 mL/min dialysate flow rate the temperature spikes were less than 0.2°C. Both tests verified that the heater duty cycle response to the incoming temperature steps was well behaved. The heater duty cycle responded with little to no overshoot, exhibited a stable steady state (heater duty cycle fluctuations of less than ±2%), and responded quickly from step to steady state (less than 2 minutes).

Power Derating of Components

The only power device associated with the temperature control system is the solid state relay. The solid state (SS) relay derating was calculated by using the component ratings for the heat sink, the isolation pad and the solid state relay. The ratings are a SS relay junction to case thermal impedance of 0.63°C/W, a SS relay maximum junction temperature of 100°C, a SS relay power approximation of 0.9 W/A, an isolation pad thermal impedance of 0.3°C/W, and a heatsink thermal impedance of 1.4°C/W. Since the System 1000 design maximum internal ambient temperature is 60°C the SS relay maximum junction to ambient temperature rise for a 50% derating is (100 - 60)/2 = 20°C. Then the maximum power dissipation for the relay is P = 20°C / (0.63+0.3 +1.4) = 8.58 W and the maximum current capacity for a 50% derating is I = 8.58W /(0.9W/A) = 9.5 A. Since the System 1000 heater is rated at 1500 W, when powered with 120 Vac its current draw is 12.5 A. Therefore to maintain 50% derating for the SS relay the fan must run.

At the System 1000 specification for the maximum internal ambient temperature of 50°C (60 is used as design spec) the maximum SS relay current is 11.9 A. The 50°C temperature brings the maximum SS relay current closer that drawn by the heater, yet to maintain the 50% derating the fan is still required.

Summary

The testing demonstrated that the temperature stabilizes in less than 20 minutes and that this time varies with the ambient temperature and the incoming water temperture. When the desired temperature was changed, the resulting temperature transitions occured without overshooting and the temperatures stabilized in less than 9 minutes. When the dialysate flow rate was changed, the temperature stabilized within 9 minutes.

Power Supply Measurement

Description

The purpose of the power supply measurement system is to allow continuous monitoring of the +5 volt, the +12 volt, and the -12 volt power supplies.

This is accomplished by use of two resistor dividers connected to analog inputs on the UF controller board. The first divider consists of a 10.0K 1% resistor (R13) connected to +5 volts and a 15.0K 1% resistor (R14) connected to analog ground. This provides a nominal voltage of 3.00 Vdc (if +5V = 5.00 Vdc) with a 0.8% tolerance. The second divider consists of a 15.0K 1% resistor (R15) connected to +12 volts and a 24.3K 1% resistor (R16) connected to -12 volts. This provides a nominal voltage of 2.840 Vdc (if +12V = 12.00 Vdc and −12V = 12.00 Vdc) with a 4% tolerance.

The voltages from these dividers are fed into two analog inputs on the UF controller board, where they are converted to digital values by a 10 bit A/D converter. The 10 bit value from the conversion is left justified to provide a 16 bit signed value with a resolution of 4.88 mVdc. This value is averaged in the UF controller software before being passed to the host system. (NOTE: The most significant bit is always set to 0.) These values may be multiplied by [5 volts/(215-25)]) to obtain voltage values.

Test Data

To support the power supply measurement process, the analog to digital conversion process was tested and shown to be accurate to within 1.1 bit (1024), or 5.3 mV over a range of 0 to 4.95 volts. An accuracy better that 2 mV (0.4 bit) was seen from 2 to 4.95 volts. This gives a 0.1% accuracy at voltages greater than 2 volts. A graph is included showing this accuracy.

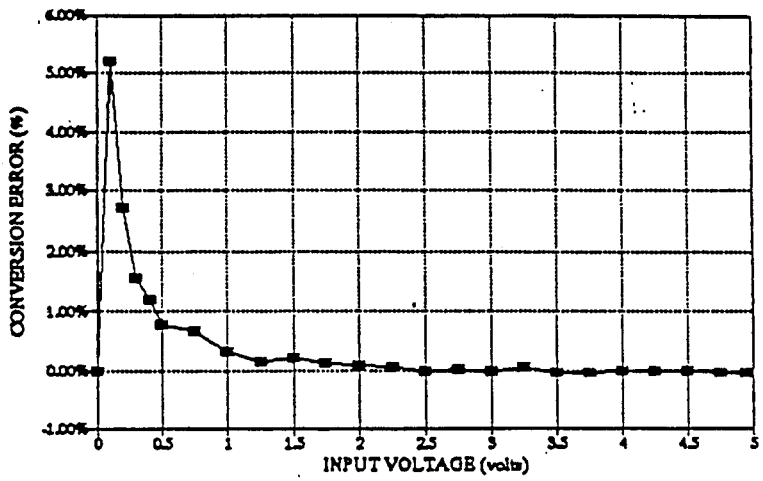

The divider voltages were measured with a digital voltmeter and compared to the digital values converted by the UF/PROP micro controller system (displayed as a tech message on the screen).

The first test measured the voltage at the junction of R13 and R14 (voltage divided from the +5 V supply) and the digital value converted by the UF/PROP micro controller (ADC channel 15, RAM location 100). The value stored in RAM was read several times, and the range of the values recorded.

DMM = 2.95  ADC = 19364 to 19370

The actual value of the +5 V supply (at junction of R13 and the +5 V supply) was measured as 4.92 V. The desired value at the junction of R14 & R13 would be 4.92/(15K+10K)*15K = 2.952

The ADC value was converted to a voltage by multiplying by the conversion factor (5 volts/(215-25) = 0.000152757), giving 2.9576 to 2.9585 volts which is nearly equal to the value measured by the DMM. The actual error was calculated and shown below.

(2.9576+2.9585)/2=2.95805, and [(2.95805/2.952)−1]*100=0.20%

The second test measured the voltage at the junction of R15 and R16 (the combination of the +12 V and the −12 V supplies) and the digital value converted by the UF/PROP micro controller (ADC channel 14, RAM location 98). Again, the value stored in RAM was read several times, and the range of the values recorded.

DMM = 2.97  ADC = 19476 to 19491

The actual values of the +12V (at R15) and the −12V (at R16) supplies were measured and recorded as follows:

+12V = 12.20 V −12V = −11.96V

The desired value at the junction of R15 and R16 would be

[12.2 − (−11.96)]/(15K+24.3K)*24.3K + (−11.96) = 2.9786

The ADC value was converted to a voltage by multiplying by the conversion factor [5 volts/(215-25) = 0.000152757], giving 2.9747 to 2.9770 volts which is nearly equal to the value measured by the DMM. The actual error was calculated and shown below.

(2.9747+2.9770)/2=2.9759, and [(2.9759/2.9786)−1]*100=0.09%

This gives an actual measurement error of 0.097%, well within the expected error range.

Summary

Measurement of the actual value of the +5 volt power supply voltage on the UF controller board can be accomplished with an accuracy of 1% (0.8% for the divider and 0.2% for the A/D conversion).

Measurement of the voltage resulting from the division of the +12V and −12V supplies on the UF controller board can be accomplished with an accuracy of 4.1% (4% for the divider and 0.1% for the A/D conversion).

This function will support verification of the digital and analog operational voltages in the electronic subsystems in the System 1000.

Miscellaneous Input/Output System

Blood Leak Detector

Circuit

The blood leak detection system consists of a green LED driven by a voltage-controlled current source, which in turn receives its input voltage from a digital-to-analog converter on the MISC I/O controller. The LED illuminates a photo detector on the other side of the blood leak detector housing. The photo detector is pulled up by a 750 K$\Omega$ resistor to +5 V. The voltage across the photo detector is fed to a A-to-D channel on the controller. Blood leaking from the blood tubing into the dialysate tubing results in higher photo detector resistance or higher voltage across it. Knowing the voltage theshold for a specific blood concentration allows for accurate detection of the blood leakage.

Test Set-Up

Using the harness for the monitoring machine #2, a blood leak detector circuit consisting of a green LED HLMP-3950 and a photocell CLAIREX CL-909L mounted in Polysulfone lenses were used to duplicate the actual blood leak detector components.

Different hemoglobin concentrations were used: 0, 35, 60, and 84 mg/liter. The sample solution was bathed in a temperature controlled water container at 38°C. A 7401 blood pump set at 200 mL/min circulated the liquid into the detection cell and back to the temperature-controlled bath.

An operational amplifier LM358 is used to force a programmable current in the green LED. The photocell is pulled up with a 750 K$\Omega$ resistor to a regulated supply voltage set at 9.8 volts. The cell voltage is then buffered by an LM358 before being measured by a data acquisition system using a COMPAQ computer.

Preliminary measurement showed that a black plastic bag around the test set-up was sufficient to eliminate the effect of ambient light and to simulate the internal cabinet.

Test Data

The test data show the photocell voltage as a function of the current in the green LED and the concentration of hemoglobin in the tap water. From the photocell voltage we can deduct its resistance by the formula:

V=9.8*R/(R+750) or R=750*V/(9.8 − V)

The law of transmission (Lambert law) states:

log(Iref/I) = aLc or log(Iref) − log(I) = aLc where a is the absorbancy index of hemoglobin, L the length of the medium in the direction of transmission, and c the concentration of hemoglobin, Iref is the illumination at zero concentration, and I the illumination at the concentration c, both measured at the end of the medium.

One of the purposes of the test is to establish a method to determine the concentration of leaked blood in the dialysate by optical means. The curve of photocell resistance versus illumination of the CL-909L cell provides a good approximation of that relation:

log(I) = −1.011*log(R) + 2.334543
(I being illumation in foot candles)

Cell Resistance Curves

Variation with Illumination CL-900 Series

Details of the regression:

| Illum | Resistance (Kohm) | log(I) | log(R) |
|---|---|---|---|
| 0.1 | 2000 | −1 | 3.30103 |
| 1 | 200 | 0 | 2.30103 |
| 7 | 30 | 0.8451 | 1.477121 |

Regression Output:
| | |
|---|---|
| Constant | 2.334543 |
| Std Err of Y Est | 0.009471 |
| R Squared | 0.999947 |
| No. of Observations | 3 |
| Degrees of Freedom | 1 |
| X Coefficient(s) | −1.011 |
| Std Err of Coef. | 0.0073 |

By subtracting log(I) from log(Iref), we thus obtain the term aLc for each concentration of hemoglobin. By dividing aLc by the concentration c we obtain the constant aL which is determined by the set-up and the characteristics of hemoglobin. We can see in the column A/concen that this factor is really constant for each test (within experimentation errors) and reasonably constant between tests given the fact we are dealing with a difference of two sets of numbers of similar magnitude because of the logarithmic operations.

DATA of log(Iref) = f(LED current) with tap water at 38°C.
04-25-1990 15:20:00  Hemoglobin concentration: 0 mg/L

| LED Current | Cell Voltage | Cell Resist (K ohms) | log(I)ref |
|---|---|---|---|
| 2.00 | 5.307 | 885.75 | -0.646 |
| 2.50 | 4.595 | 662.03 | -0.518 |
| 3.00 | 4.028 | 523.46 | -0.415 |
| 3.50 | 3.588 | 433.17 | -0.332 |
| *4.00* | *3.221* | *367.14* | *-0.259* |
| 4.50 | 2.927 | 319.36 | -0.198 |
| 5.00 | 2.680 | 282.33 | -0.144 |
| 5.50 | 2.471 | 252.82 | -0.095 |
| 6.00 | 2.294 | 229.21 | -0.052 |
| 6.50 | 2.137 | 209.18 | -0.012 |
| 7.00 | 2.004 | 192.78 | 0.024 |
| 7.50 | 1.889 | 179.05 | 0.056 |
| 8.00 | 1.783 | 166.77 | 0.088 |
| 8.50 | 1.692 | 156.50 | 0.115 |
| 9.00 | 1.606 | 146.99 | 0.143 |
| 9.50 | 1.534 | 139.15 | 0.167 |
| 10.00 | 1.468 | 132.12 | 0.190 |
| 10.50 | 1.406 | 125.60 | 0.212 |
| 11.00 | 1.348 | 119.58 | 0.234 |
| 11.50 | 1.296 | 114.34 | 0.253 |
| 12.00 | 1.251 | 109.75 | 0.271 |
| 12.50 | 1.206 | 105.20 | 0.290 |
| 13.00 | 1.164 | 101.05 | 0.308 |
| 13.50 | 1.127 | 97.45 | 0.323 |
| 14.00 | 1.090 | 93.89 | 0.340 |
| 14.50 | 1.059 | 90.87 | 0.354 |
| 15.00 | 1.027 | 87.83 | 0.369 |
| 15.50 | 0.998 | 85.00 | 0.384 |
| 16.00 | 0.972 | 82.55 | 0.396 |
| 16.50 | 0.946 | 80.16 | 0.409 |
| 17.00 | 0.923 | 77.97 | 0.421 |
| 17.50 | 0.900 | 75.83 | 0.434 |
| 18.00 | 0.879 | 73.89 | 0.445 |
| 18.50 | 0.861 | 72.22 | 0.455 |
| 19.00 | 0.838 | 70.16 | 0.468 |
| 19.50 | 0.819 | 68.38 | 0.479 |
| 20.00 | 0.802 | 66.83 | 0.489 |
| 20.00 | 0.804 | 67.05 | 0.488 |
| 19.50 | 0.821 | 68.56 | 0.478 |
| 19.00 | 0.841 | 70.43 | 0.466 |

DATA with 35mg/L hemoglobin at 38°C.
04-26-1990 09:42:41

| LED Current | Cell Voltage | Cell Resist (K ohms) | log(I) | log(Iref)-log(I) (or "A") | "A"/concen (c in g/L) |
|---|---|---|---|---|---|
| 2.00 | 6.035 | 1202.02 | -0.780 | 0.134 | 3.83 |
| 2.50 | 5.355 | 903.72 | -0.655 | 0.137 | 3.90 |
| 3.00 | 4.789 | 716.65 | -0.553 | 0.138 | 3.94 |
| 3.50 | 4.321 | 591.44 | -0.468 | 0.137 | 3.91 |
| *4.00* | *3.924* | *500.81* | *-0.395* | *0.136* | *3.90* |
| 4.50 | 3.604 | 436.16 | -0.335 | 0.137 | 3.91 |
| 5.00 | 3.328 | 385.68 | -0.281 | 0.137 | 3.91 |
| 5.50 | 3.089 | 345.20 | -0.232 | 0.137 | 3.91 |
| 6.00 | 2.882 | 312.50 | -0.188 | 0.136 | 3.89 |
| 6.50 | 2.705 | 285.95 | -0.149 | 0.137 | 3.92 |
| 7.00 | 2.543 | 262.81 | -0.112 | 0.136 | 3.89 |
| 7.50 | 2.405 | 243.89 | -0.079 | 0.136 | 3.88 |
| 8.00 | 2.283 | 227.75 | -0.049 | 0.137 | 3.91 |
| 8.50 | 2.175 | 213.91 | -0.022 | 0.137 | 3.92 |
| 9.00 | 2.072 | 201.12 | 0.005 | 0.138 | 3.93 |
| 9.50 | 1.977 | 189.48 | 0.031 | 0.136 | 3.87 |
| 10.00 | 1.897 | 180.02 | 0.054 | 0.136 | 3.88 |
| 10.50 | 1.823 | 171.37 | 0.076 | 0.136 | 3.90 |
| 11.00 | 1.752 | 163.32 | 0.097 | 0.137 | 3.91 |
| 11.50 | 1.687 | 155.90 | 0.117 | 0.136 | 3.89 |
| 12.00 | 1.628 | 149.46 | 0.136 | 0.136 | 3.88 |
| 12.50 | 1.575 | 143.64 | 0.153 | 0.137 | 3.91 |
| 13.00 | 1.523 | 138.00 | 0.171 | 0.137 | 3.91 |
| 13.50 | 1.478 | 133.15 | 0.186 | 0.137 | 3.92 |
| 14.00 | 1.431 | 128.26 | 0.203 | 0.137 | 3.91 |

| | | | | | |
|---|---|---|---|---|---|
| 14.50 | 1.392 | 124.18 | 0.217 | 0.137 | 3.92 |
| 15.00 | 1.353 | 120.08 | 0.232 | 0.137 | 3.92 |
| 15.50 | 1.316 | 116.33 | 0.246 | 0.138 | 3.94 |
| 16.00 | 1.284 | 113.05 | 0.258 | 0.138 | 3.95 |
| 16.50 | 1.251 | 109.75 | 0.271 | 0.138 | 3.94 |
| 17.00 | 1.219 | 106.52 | 0.284 | 0.137 | 3.91 |
| 17.50 | 1.189 | 103.56 | 0.297 | 0.137 | 3.91 |
| 18.00 | 1.159 | 100.57 | 0.310 | 0.135 | 3.87 |
| 18.50 | 1.135 | 98.26 | 0.320 | 0.135 | 3.86 |
| 19.00 | 1.110 | 95.83 | 0.331 | 0.137 | 3.91 |
| 19.50 | 1.087 | 93.61 | 0.341 | 0.138 | 3.94 |
| 20.00 | 1.066 | 91.58 | 0.351 | 0.138 | 3.95 |
| 20.00 | 1.067 | 91.63 | 0.351 | 0.137 | 3.92 |
| 19.50 | 1.091 | 93.98 | 0.339 | 0.139 | 3.96 |
| 19.00 | 1.116 | 96.36 | 0.328 | 0.138 | 3.93 |

DATA with 60 mg/L hemoglobin at 38 C.
04-26-1990 09:53:09

| LED Current | Cell Voltage | Cell Resist (K ohms) | log(I) | log(Iref)-log(I) (or "A") | "A"/concen (c in g/L) |
|---|---|---|---|---|---|
| 2.00 | 6.854 | 1744.50 | -0.943 | 0.298 | 4.96 |
| 2.50 | 6.220 | 1303.20 | -0.815 | 0.297 | 4.96 |
| 3.00 | 5.661 | 1025.64 | -0.710 | 0.295 | 4.92 |
| 3.50 | 5.193 | 845.52 | -0.625 | 0.294 | 4.90 |
| *4.00* | *4.787* | *716.22* | *-0.553* | *0.293* | *4.89* |
| 4.50 | 4.438 | 620.63 | -0.490 | 0.292 | 4.86 |
| 5.00 | 4.143 | 549.18 | -0.436 | 0.292 | 4.87 |
| 5.50 | 3.873 | 490.00 | -0.386 | 0.291 | 4.84 |
| 6.00 | 3.639 | 443.02 | -0.342 | 0.289 | 4.82 |
| 6.50 | 3.432 | 404.23 | -0.301 | 0.289 | 4.82 |
| 7.00 | 3.251 | 372.30 | -0.265 | 0.289 | 4.82 |
| 7.50 | 3.087 | 344.88 | -0.232 | 0.288 | 4.80 |
| 8.00 | 2.941 | 321.65 | -0.201 | 0.288 | 4.81 |
| 8.50 | 2.810 | 301.51 | -0.173 | 0.288 | 4.80 |
| 9.00 | 2.683 | 282.75 | -0.144 | 0.287 | 4.79 |
| 9.50 | 2.578 | 267.74 | -0.120 | 0.287 | 4.79 |
| 10.00 | 2.476 | 253.49 | -0.096 | 0.286 | 4.77 |
| 10.50 | 2.384 | 241.07 | -0.074 | 0.286 | 4.77 |
| 11.00 | 2.296 | 229.53 | -0.053 | 0.286 | 4.77 |
| 11.50 | 2.217 | 219.25 | -0.033 | 0.286 | 4.77 |
| 12.00 | 2.139 | 209.36 | -0.012 | 0.284 | 4.73 |
| 12.50 | 2.078 | 201.78 | 0.004 | 0.286 | 4.77 |
| 13.00 | 2.013 | 193.90 | 0.021 | 0.286 | 4.77 |
| 13.50 | 1.952 | 186.50 | 0.038 | 0.285 | 4.75 |
| 14.00 | 1.898 | 180.14 | 0.054 | 0.286 | 4.77 |
| 14.50 | 1.844 | 173.80 | 0.069 | 0.285 | 4.75 |
| 15.00 | 1.792 | 167.78 | 0.085 | 0.284 | 4.74 |
| 15.50 | 1.747 | 162.66 | 0.098 | 0.285 | 4.75 |
| 16.00 | 1.704 | 157.87 | 0.112 | 0.285 | 4.75 |
| 16.50 | 1.664 | 153.40 | 0.124 | 0.285 | 4.75 |
| 17.00 | 1.625 | 149.03 | 0.137 | 0.285 | 4.74 |
| 17.50 | 1.591 | 145.39 | 0.148 | 0.286 | 4.76 |
| 18.00 | 1.553 | 141.20 | 0.161 | 0.284 | 4.74 |
| 18.50 | 1.518 | 137.47 | 0.172 | 0.283 | 4.71 |
| 19.00 | 1.489 | 134.40 | 0.182 | 0.285 | 4.76 |
| 19.50 | 1.457 | 130.98 | 0.194 | 0.285 | 4.76 |
| 20.00 | 1.428 | 127.90 | 0.204 | 0.285 | 4.75 |
| 20.00 | 1.427 | 127.85 | 0.204 | 0.283 | 4.72 |
| 19.50 | 1.460 | 131.29 | 0.193 | 0.285 | 4.76 |
| 19.00 | 1.493 | 134.76 | 0.181 | 0.285 | 4.75 |

DATA with 84 mg/L hemoglobin at 38°C:
04-26-1990 10:31:18

| LED Current | Cell Voltage | Cell Resist (K ohms) | log(I) | log(Iref)-log(I) (or "A") | "A"/concen (c in g/L) |
|---|---|---|---|---|---|
| 2.00 | 7.52 | 2474.40 | -1.097 | 0.451 | 5.37 |
| 2.50 | 6.96 | 1841.56 | -0.967 | 0.449 | 5.35 |
| 3.00 | 6.45 | 1447.04 | -0.861 | 0.447 | 5.32 |
| 3.50 | 6.01 | 1189.44 | -0.775 | 0.444 | 5.28 |
| *4.00* | *5.61* | *1002.89* | *-0.700* | *0.441* | *5.25* |
| 4.50 | 5.26 | 869.56 | -0.638 | 0.440 | 5.24 |
| 5.00 | 4.96 | 767.66 | -0.583 | 0.439 | 5.23 |
| 5.50 | 4.68 | 686.69 | -0.534 | 0.439 | 5.22 |
| 6.00 | 4.43 | 618.88 | -0.488 | 0.436 | 5.19 |
| 6.50 | 4.21 | 564.15 | -0.448 | 0.436 | 5.19 |

| 401 | | | | | 402 |
|---|---|---|---|---|---|
| 7.00 | 4.01 | 520.24 | -0.412 | 0.436 | 5.19 |
| 7.50 | 3.84 | 482.28 | -0.379 | 0.435 | 5.18 |
| 8.00 | 3.67 | 448.53 | -0.347 | 0.434 | 5.17 |
| 8.50 | 3.51 | 418.84 | -0.317 | 0.432 | 5.15 |
| 9.00 | 3.38 | 393.97 | -0.290 | 0.433 | 5.15 |
| 9.50 | 3.25 | 372.14 | -0.265 | 0.432 | 5.14 |
| 10.00 | 3.13 | 352.66 | -0.241 | 0.431 | 5.13 |
| 10.50 | 3.02 | 334.86 | -0.219 | 0.431 | 5.13 |
| 11.00 | 2.92 | 318.53 | -0.197 | 0.430 | 5.12 |
| 11.50 | 2.83 | 304.24 | -0.177 | 0.430 | 5.12 |
| 12.00 | 2.75 | 291.98 | -0.158 | 0.430 | 5.12 |
| 12.50 | 2.66 | 279.43 | -0.139 | 0.429 | 5.11 |
| 13.00 | 2.58 | 268.22 | -0.121 | 0.429 | 5.10 |
| 13.50 | 2.51 | 257.66 | -0.104 | 0.427 | 5.08 |
| 14.00 | 2.44 | 249.23 | -0.089 | 0.429 | 5.10 |
| 14.50 | 2.38 | 239.96 | -0.072 | 0.426 | 5.08 |
| 15.00 | 2.32 | 232.92 | -0.059 | 0.428 | 5.10 |
| 15.50 | 2.26 | 225.15 | -0.044 | 0.428 | 5.09 |
| 16.00 | 2.21 | 218.37 | -0.031 | 0.427 | 5.09 |
| 16.50 | 2.16 | 212.00 | -0.018 | 0.427 | 5.08 |
| 17.00 | 2.11 | 205.83 | -0.005 | 0.426 | 5.08 |
| 17.50 | 2.06 | 199.92 | 0.008 | 0.426 | 5.07 |
| 18.00 | 2.02 | 194.61 | 0.020 | 0.425 | 5.06 |
| 18.50 | 1.98 | 190.07 | 0.030 | 0.425 | 5.06 |
| 19.00 | 1.94 | 184.64 | 0.043 | 0.425 | 5.06 |
| 19.50 | 1.90 | 180.54 | 0.053 | 0.426 | 5.08 |
| 20.00 | 1.87 | 176.65 | 0.062 | 0.427 | 5.08 |
| 20.00 | 1.87 | 177.10 | 0.061 | 0.427 | 5.08 |
| 19.50 | 1.90 | 180.48 | 0.053 | 0.425 | 5.06 |
| 19.00 | 1.94 | 185.40 | 0.041 | 0.425 | 5.06 |
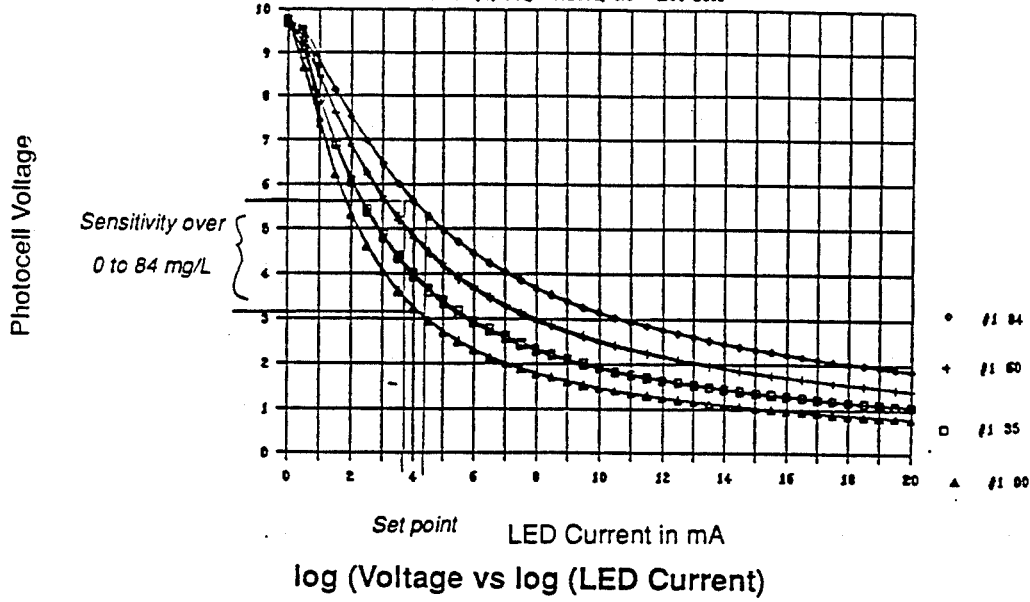
Blood Leak detector tests
log (Voltage vs log (LED Current)
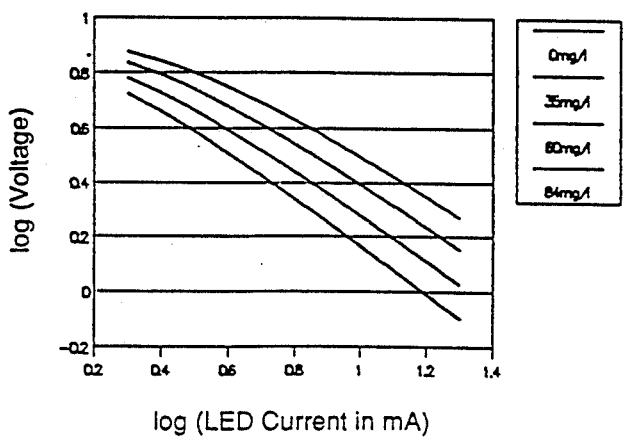

Application in Blood Leak Detection

The graph of the photocell voltage versus the LED current for different concentrations of hemoglobin is a good indication of the photocell/LED system overall sensitivity for detection of blood. By keeping the LED current at a constant value such as 4 mA the sensitivity is more than adequate for detecting 35 milligrams of hemoglobin per liter. This is represented by a 703 mV change is photocell voltage. A system can be constructed where the LED current and/or the photocell alarm threshold voltage may be varied to compensate for changes in the photocell versus LED current family of curves. The curves will change based on manufacturing variances in the photocells, LEDs and blood leak detector assembly.

Flow Sensing

General

Flow detection is accomplished by comparing the voltage across a self heating thermistor submerged in the flow path with its voltage at no flow, which is lower as a result of its higher body temperature due to reduced cooling by the surrounding liquid. Since, the no-flow thermistor voltage is also a function of the fluid temperature, we therefore need to know the fluid temperature through the use of a non-self-heating reference thermistor submerged in the same fluid. Unfortunately, thermistor unit-to-unit variation and its own geometry and mounting make it virtually impossible to sense the dialysate flow without calibration, which is done by adjusting the IO Controller variables BPS_A and BPS_B in the formula for VFLWSENSE,no-flow:

VFLWSENSE, no-flow = BPS_A * VFLWREF/64 + BPS_B if VFLWSENSE > VFLWSENSE, no-flow then FLOW = 1 else FLOW = 0

VFLWSENSE and VFLWREF are the values provided by the A-to-D converter, and the scaling factor 64 is used by the I/O controller to obtain the best computational accuracy with its 3-byte accumulator used in all math routines.

As one can foresee, the flow detection relies on a threshold that is a function of fluid temperature and thermistor resistance. The initial specification calls out a threshold of 5 mL/min. Such a flow rate will then result in flow indication statistically 50% of the time.

A suggested procedure to calibrate the flow detector is as follows:

- Set the dialysate temperature to a low temperature, e.g. 20°C, wait for stabilization, then note VFLWSENSE20,no-flow , VFLWREF20, VFLWSENSE20, 5 mL. The latter corresponds to 5 mL/min flow.

- Set the dialysate temperature to a high temperature, e.g. 40°C, wait for stabilization, then note VFLWSENSE40, no-flow , VFLWREF40, VFLWSENSE40, 5 mL.

- Derive BPS_A and BPS_B from the system of linear equations:
  VFLWSENSE20, 5 mL = BPS_A * VFLWREF20 / 64 + BPS_B
  VFLWSENSE40, 5 mL = BPS_A * VFLWREF40 / 64 + BPS_B The above approach can provide BPS_B to accurately detect a flow rate of 5 mL/min, but it is very difficult to establish or simulated. Thus alternatively VFLWSENSE,no-flow can be used in the equations to get another value of BPS_A and BPS_B. By adding an offset to BPS_B, a small flow can be detected.

Test Data

The following measurements were taken from the lab test system, with the data read directly by the data acquisition routine of a custom UCCOM program which allows a PC to communicate with a MISC I/O controller (no manual transcription involved except the external data which in this test is the flow rate), the data file is then imported to a spreadsheet for processing. In the following spreadsheet, the first three columns are data read directly from the controller, representing the temperature in hundredths of °C, and the numbers representing the sensing and the reference thermistor voltages, the "Flow" column is the flow rate as measured by a calibrated flow meter, manually entered at the time of data acquisition, the "Vflw0" column is the calculated values of flow threshold detection after BPS_A (=46.72) and BPS_B (=15032) are calculated with the 5 mL/min flow data at 21.95 and 40°C. The "FLOW" column results from the comparison between "Vflws" and "VFlw0", which is also done by the spreadsheet.

Averages:

| Temp | Vflws | Vflwref | Flow | Vflw0 | | Temperature = 21.95 | | |
|---|---|---|---|---|---|---|---|---|
| 2195 | 28841 | 17373 | 15 | 27716 | FLOW | | | |
| 2195 | 28960 | 17373 | 15 | 27716 | FLOW | Flow | Vref | Vflws |
| 2195 | 29066 | 17379 | 15 | 27720 | FLOW | 15 | 17375 | 28924 |
| 2195 | 28829 | 17376 | 15 | 27718 | FLOW | 10 | 17097 | 28470 |
| 2195 | 28439 | 17232 | 10 | 27613 | FLOW | 5 | 16694 | 27220 |
| 2195 | 28368 | 17112 | 10 | 27525 | FLOW | 0 | 16518 | 26408 |
| 2195 | 28465 | 17045 | 10 | 27476 | FLOW | | | |
| 2195 | 28607 | 16999 | 10 | 27443 | FLOW | | | |
| 2195 | 27187 | 16754 | 5 | 27264 | NO FLOW | | | |
| 2195 | 27308 | 16699 | 5 | 27224 | FLOW | | | |
| 2195 | 27129 | 16673 | 5 | 27205 | NO FLOW | | | |
| 2195 | 27256 | 16650 | 5 | 27188 | FLOW | | | |
| 2195 | 26542 | 16568 | 0 | 27128 | NO FLOW | | | |
| 2195 | 26380 | 16515 | 0 | 27089 | NO FLOW | | | |
| 2195 | 26372 | 16504 | 0 | 27081 | NO FLOW | | | |
| 2195 | 26338 | 16485 | 0 | 27067 | NO FLOW | | | |
| Temp | Vflws | Vflwref | Flow | Vflw0 | | Temperature = 27.85 | | |
| 2785 | 27429 | 14560 | 15 | 25662 | FLOW | | | |
| 2785 | 27491 | 14563 | 15 | 25664 | FLOW | Flow | Vref | Vsens |
| 2785 | 27137 | 14563 | 15 | 25664 | FLOW | 15 | 14561.5 | 27364.75 |
| 2785 | 27402 | 14560 | 15 | 25662 | FLOW | 10 | 14387.25 | 26877.5 |
| 2785 | 27005 | 14470 | 10 | 25596 | FLOW | 5 | 14127 | 25609.5 |
| 2785 | 26680 | 14378 | 10 | 25529 | FLOW | 0 | | |
| 2785 | 26948 | 14365 | 10 | 25520 | FLOW | | | |
| 2785 | 26877 | 14336 | 10 | 25498 | FLOW | | | |
| 2785 | 25633 | 14180 | 5 | 25385 | FLOW | | | |
| 2785 | 25741 | 14136 | 5 | 25352 | FLOW | | | |
| 2785 | 25529 | 14112 | 5 | 25335 | FLOW | | | |
| 2785 | 25535 | 14080 | 5 | 25312 | FLOW | | | |
| Temp | Vflws | Vflwref | Flow | Vflw0 | | Temperature = 31.675 | | |
| 3163 | 26089 | 13019 | 15 | 24537 | FLOW | | | |
| 3163 | 26165 | 13017 | 15 | 24535 | FLOW | Flow | Vref | Vsens |
| 3163 | 26098 | 13021 | 15 | 24538 | FLOW | 15 | 13017.25 | 26175.25 |
| 3163 | 26349 | 13012 | 15 | 24532 | FLOW | 10 | 12863 | 25696.5 |
| 3169 | 25747 | 12932 | 10 | 24473 | FLOW | 5 | 12805 | 24690 |
| 3169 | 25688 | 12838 | 10 | 24405 | FLOW | 0 | 12781 | 24193.25 |
| 3169 | 25647 | 12832 | 10 | 24400 | FLOW | | | |
| 3169 | 25704 | 12850 | 10 | 24413 | FLOW | | | |
| 3169 | 24621 | 12832 | 5 | 24400 | FLOW | | | |
| 3169 | 24945 | 12818 | 5 | 24390 | FLOW | | | |
| 3169 | 24594 | 12800 | 5 | 24377 | FLOW | | | |
| 3169 | 24600 | 12770 | 5 | 24355 | FLOW | | | |
| 3169 | 24134 | 12768 | 0 | 24354 | NO FLOW | | | |
| 3169 | 24058 | 12797 | 0 | 24375 | NO FLOW | | | |
| 3169 | 23981 | 12789 | 0 | 24369 | NO FLOW | | | |
| 3169 | 24050 | 12742 | 0 | 24335 | NO FLOW | | | |
| Temp | Vflws | Vflwref | Flow | Vflw0 | | Temperature = 34.175 | | |
| 3419 | 25415 | 12055 | 15 | 23833 | FLOW | | | |
| 3419 | 25547 | 12046 | 15 | 23826 | FLOW | Flow | Vref | Vsens |
| 3419 | 25596 | 12041 | 15 | 23823 | FLOW | 15 | 12043.5 | 25508.25 |
| 3419 | 25475 | 12032 | 15 | 23816 | FLOW | 10 | 11928.75 | 25111.5 |
| 3413 | 25096 | 11941 | 10 | 23750 | FLOW | 5 | 11832.75 | 24118.25 |
| 3413 | 25143 | 11936 | 10 | 23746 | FLOW | 0 | 12005.25 | 23541 |
| 3413 | 25158 | 11926 | 10 | 23739 | FLOW | | | |
| 3413 | 25049 | 11912 | 10 | 23729 | FLOW | | | |
| 3419 | 24181 | 11872 | 5 | 23699 | FLOW | | | |
| 3419 | 24235 | 11840 | 5 | 23676 | FLOW | | | |
| 3419 | 24020 | 11811 | 5 | 23655 | FLOW | | | |
| 3419 | 24037 | 11808 | 5 | 23653 | FLOW | | | |
| 3419 | 23606 | 12021 | 0 | 23808 | NO FLOW | | | |
| 3419 | 23523 | 12000 | 0 | 23793 | NO FLOW | | | |
| 3419 | 23520 | 12000 | 0 | 23793 | NO FLOW | | | |
| 3419 | 23515 | 12000 | 0 | 23793 | NO FLOW | | | |
| Temp | Vflws | Vflwref | Flow | Vflw0 | | Temperature = 37.62 | | |
| 3759 | 24595 | 10816 | 15 | 22928 | FLOW | | | |
| 3759 | 24624 | 10841 | 15 | 22947 | FLOW | Flow | Vref | Vsens |
| 3759 | 24574 | 10816 | 15 | 22928 | FLOW | 15 | 10825 | 24572 |
| 3759 | 24495 | 10827 | 15 | 22936 | FLOW | 10 | 10774.75 | 24212 |
| 3759 | 24242 | 10784 | 10 | 22905 | FLOW | 5 | 10752 | 23277 |

| Temp | Vflws | Vflwref | Flow | Vflw0 | | | | |
|---|---|---|---|---|---|---|---|---|
| 3759 | 24255 | 10779 | 10 | 22901 | FLOW | 0 | 10786.5 | 22633.75 |
| 3759 | 24188 | 10763 | 10 | 22890 | FLOW | | | |
| 3759 | 24163 | 10773 | 10 | 22897 | FLOW | | | |
| 3765 | 23124 | 10752 | 5 | 22882 | FLOW | | | |
| 3765 | 23403 | 10752 | 5 | 22882 | FLOW | | | |
| 3765 | 23263 | 10752 | 5 | 22882 | FLOW | | | |
| 3765 | 23318 | 10752 | 5 | 22882 | FLOW | | | |
| 3765 | 22691 | 10816 | 0 | 22928 | NO FLOW | | | |
| 3765 | 22650 | 10816 | 0 | 22928 | NO FLOW | | | |
| 3765 | 22618 | 10808 | 0 | 22923 | NO FLOW | | | |
| 3765 | 22576 | 10706 | 0 | 22848 | NO FLOW | | | |
| Temp | Vflws | Vflwref | Flow | Vflw0 | Temperature = 40.0275 | | | |
| 3996 | 23989 | 10077 | 15 | 22389 | FLOW | | | |
| 3996 | 24039 | 10057 | 15 | 22374 | FLOW | Flow | Vref | Vsens |
| 3996 | 23998 | 10060 | 15 | 22376 | FLOW | 15 | 10066 | 23979.75 |
| 3996 | 23893 | 10070 | 15 | 22384 | FLOW | 10 | 10019 | 23830.5 |
| 3996 | 23846 | 10016 | 10 | 22344 | FLOW | 5 | 10021 | 22348.5 |
| 3996 | 23827 | 10034 | 10 | 22357 | FLOW | 0 | 10077.5 | 22101.5 |
| 4002 | 23843 | 10013 | 10 | 22342 | FLOW | | | |
| 4002 | 23806 | 10013 | 10 | 22342 | FLOW | | | |
| 4008 | 22423 | 10048 | 5 | 22368 | FLOW | | | |
| 4008 | 22197 | 10016 | 5 | 22344 | NO FLOW | | | |
| 4008 | 22425 | 10016 | 5 | 22344 | FLOW | | | |
| 4008 | 22349 | 10004 | 5 | 22336 | FLOW | | | |
| 4008 | 22191 | 10071 | 0 | 22385 | NO FLOW | | | |
| 4008 | 22059 | 10077 | 0 | 22389 | NO FLOW | | | |
| 4008 | 22058 | 10077 | 0 | 22389 | NO FLOW | | | |
| 4008 | 22098 | 10085 | 0 | 22395 | NO FLOW | | | |

The attached set of line-and-markers plots of the data illustrates the proper behavior of the flow detectors.

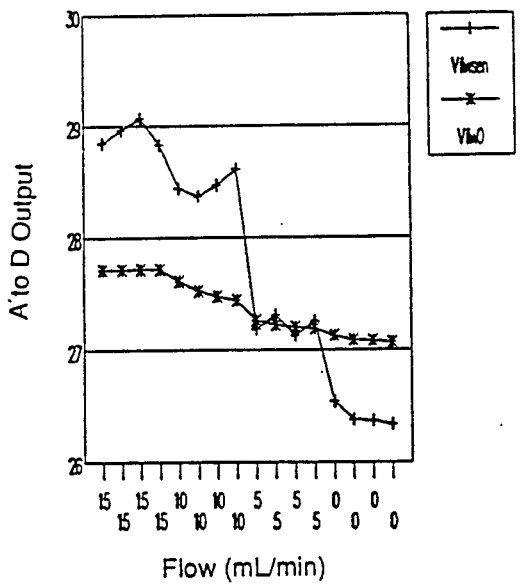

Vflwsen and Vflow0 vs Flow
Tested at 21.95°C

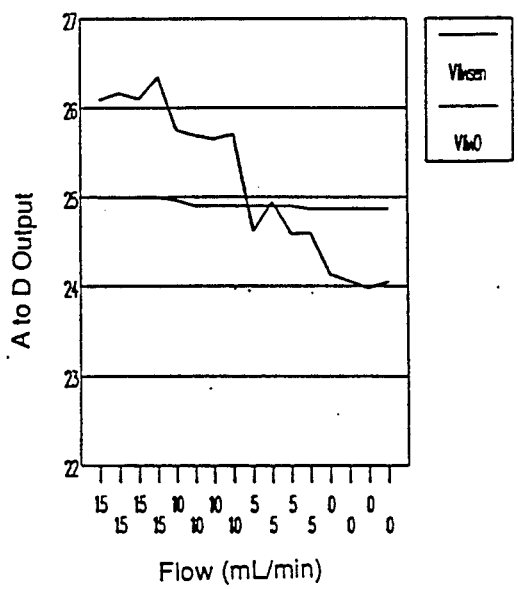

Vflwsen and Vflow0 vs Flow
Tested at 26.7°C

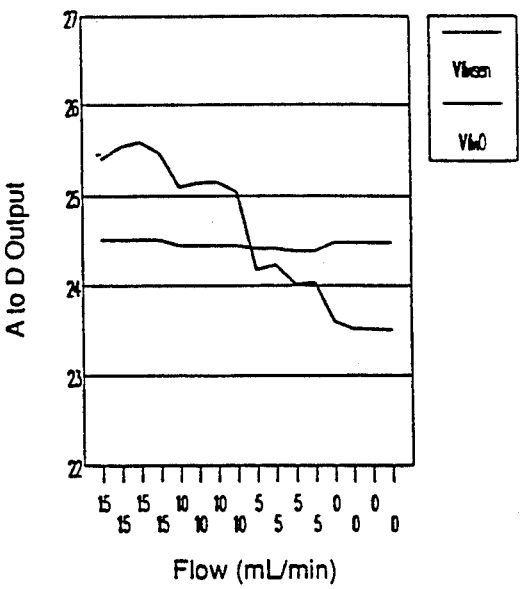

Vflwsen and Vflow0 vs Flow
Tested at 34.1°C

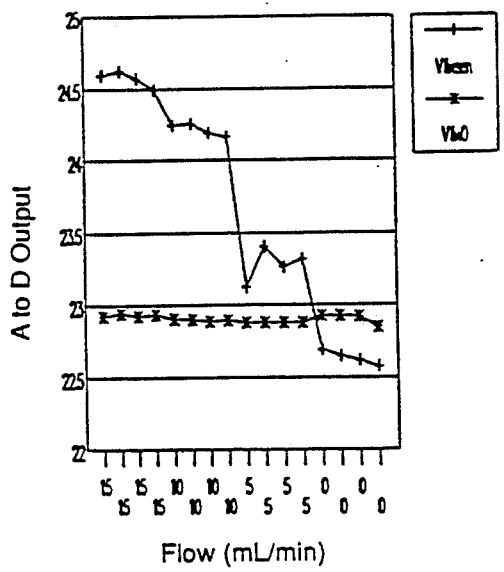

Vflwsen and Vflow0 vs Flow
Tested at 37.62°C

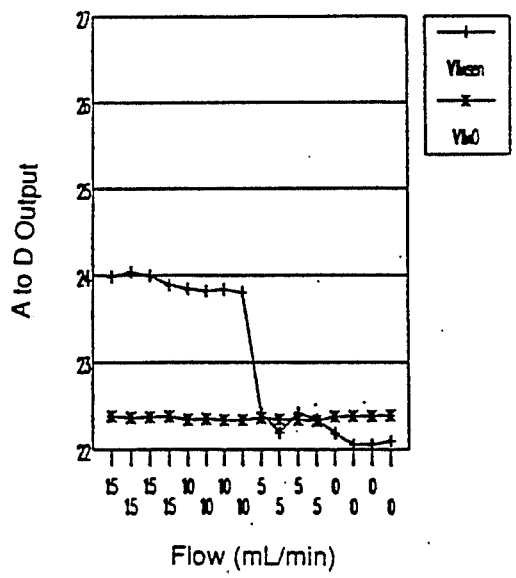

Vflwsen and Vflow0 vs Flow
Tested at 40°C

Conclusion

From the test data, one can see that after the necessary calibration for the flow sensing thermistor, the flow sensing detection system gives correct indication of flow as low as 5 mL/min.

Air Detector

System Description

The purpose of the air detection system is to detect a 10 microliter air bubble in the venous blood line at different flow rates. When a bubble is detected during a dialysis treatment, the stoppage of the blood pump and the clamping of the line clamp protect the patient.

The air detection system consists of a 2-MHz crystal-controlled oscillator driving a 2-MHz piezoelectric ultrasound transmitter. The ultrasound is transmitted through the blood tubing by means of an acrylic bumper, and again received by an identical piezoelectric ceramic transducer through an identical bumper. The received signal is amplified by two identical amplifiers to a detectable level of 1.5 to 5.5 V peak-to-peak, depending on the snugness of the mechanical contacts. The 2-MHz signal is then fed to a peak-to-peak detector circuit in each channel to become a DC signal of 0.5 to 4.5 V. The peak-to-peak detector is inherently AC-coupled, resulting in a zero volt output in case of amplifier failure. A test input is provided to simulate an oscillator failure condition during Self Test. One of the two similar outputs of the detectors is fed into an A-to-D converter. A software routine periodically reads the level of the DC signal to compute a long term average level against which the instantaneous amplitude of the ultrasound level is compared to detect the presence of air bubbles. The time constant of the digital filter used in the computation of the detection level is 400 msec. Fifteen sixteenths of the average level minus 50 mV (for noise immunity) is used as detection threshold. Thus the software forms an automatic gain control to accommodate variations in the mechanical coupling of the 2-MHz ultrasound. The output of the comparator is read every 0.96 msec to detect the presence of an air bubble by effectively measuring the time the air bubble passes under the detection window. This time is compared to a host-programmable time which is a complex function of the flow rate, the diameter of the blood tube, and the size of the bubble to be detected. When the bubble time exceeds the programmed value, a software air alarm flag is set. In order to take into account many small bubbles equivalent to a large bubble, the software actually counts up by 16, until the programmed count limit is reached, when air is present under the detection window, and counts down by 1, with 0 being the lower limit, when no air is detected. Given the fact that air bubbles are only occasionally present, the count stays most of the time at zero.

The other detector output is fed to a bandpass filter to detect large air bubbles (300 microliters) as a backup. The output of this hardware air detector is latched so that it can clamp the blood line until reset by the host. A hardware air alarm bit is also set to inform the host of the alarm condition. Another comparator also sets the alarm bit and clamps the line clamp when a level of less than 0.5 V is put out by the peak-to-peak detector to indicate either a possible circuit failure or a large air gap, such as when the blood tubing is removed from the detector.

Test Set-Up

In order to check the correct operation of the air detection system, a water circuit with a Cole-Palmer N044-40C flow meter, a DW thermometer #A-0097-0C-00, a calibrated syringe assembly to inject 10 µL bubbles one at a time, the air detector assembly connected to the I/O controller with its hardware and software, a fluid reservoir with wrap-around heater, temperature sensor and control to keep the water temperature at 38°C, and finally a media pump capable of up to 1000 mL/min. The venous tubing going through the detector was of type B-D Drake-Willock #8881.

Test Procedure and Test Data

The fluid was circulated at 100 to 750 mL/min in 50 mL/min increments. A 10 uL air bubble generated by one turn on the syringe assembly knob was then injected into the flow path. The software parameter BBTIME was then varied to determine the detection threshold. At each flow rate, a photograph of the output of the comparator that the software strobes every 0.96 msec was taken so that the passage time of the bubble could be compared with the actual BBTIME by the formula INT(TIME/0.96)*16. This is because 0.96 msec is the sampling period of the software air detector and the software counts up by 16 every time air is present under the detection window as previously explained. Also because of the sampling mechanism, there may be a difference of 16 between BBTIME and the calculated value of BBCOUNT=INT(TIME/0.96)*16.

| Alarm Flow mL/min | Calc Time ms | Test data BBCOUNT | BBTIME |
|---|---|---|---|
| 100 | 88.5 | 1472 | 1300 |
| 150 | 36.2 | 592 | 620 * |
| 200 | 21.1 | 336 | 330 |
| 250 | 16.1 | 256 | 250 |
| 300 | 10.2 | 160 | 150 |
| 350 | 9.35 | 144 | 125 |
| 400 | 7.75 | 128 | 120 |
| 450 | 6.95 | 112 | 112 |
| 500 | 6.35 | 96 | 98 * |
| 550 | 5.8 | 96 | 96 |
| 600 | 6.2 | 96 | 96 |
| 650 | 5.8 | 96 | 96 |
| 700 | 5.65 | 80 | 96 *1 |
| 750 | 6.15 | 96 | 95 |

Notes: * denotes line in which the calculated BBCOUNT is less than BBTIME

*1 the value without integer truncating is 94.16667

It is observed that at low flow rate, the movement of the air bubble in the tubing is irregular, so that there are a lot of variations between test data for different trials. On the other hand, at high flow rate, the unexpected fluid dynamics make the detection time (the time the air bubble is seen under the detection window) virtually unchanged between 500 to 750 mL/min flow rates. The true relationship between the fluid flow rate and the speed of the air bubble in the vertically downward direction is obviously a function of fluid viscosity, the diameter of the tubing, the size of the air bubble, and the flow rate itself.

As to the three instances where BBCOUNT is less than BBTIME, a plausible explanation is in the limitations of the experiment where not all the possible pictures were taken and correlated with the BBTIME data.

Another air detector assembly was built and tested. Measurements were made in the same test set-up as the previous test. A Tek type 464 oscilloscope was used instead of TEK-2221. Following are the test results:

| Flow Reading | Flow mtr #1 | #2 | #3 | Avg | Detection times BBTIME | |
|---|---|---|---|---|---|---|
| 100 | 10 | 12 | 140 | 120 | 126.7 | 2096 |
| 150 | 14 | 45 | 44 | 44 | 44.3 | 736 |
| 200 | 18 | 24 | 24 | 25 | 24.3 | 400 |
| 250 | 22 | 16 | 17 | 16.5 | 16.5 | 272 |
| 300 | 26 | 12 | 12.5 | 13 | 12.5 | 208 |
| 350 | 30 | 10.5 | 10 | 10.5 | 10.3 | 160 |
| 400 | 34 | 9 | 9.5 | 9 | 9.2 | 144 |
| 450 | 38 | 8 | 8 | 8.5 | 8.2 | 128 |
| 500 | 42 | 8.5 | 7.5 | 7 | 7.7 | 112 |
| 550 | 46 | 7 | 7.5 | 7.5 | 7.3 | 112 |
| 600 | 50 | 7 | 7 | 7 | 7.0 | 112 |
| 650 | 54 | 6.5 | 6.5 | 7 | 6.7 | 96 |
| 700 | 58 | 6 | 6.5 | 6 | 6.2 | 96 |
| 750 | 62 | 5.5 | 6 | 5.5 | 5.7 | 80 |

Flow in mL/min

Detection times in milliseconds

Flow meter readings were used to derive the flow rate.

A graphic comparison of the two test data is below.

Detection Time vs Flow

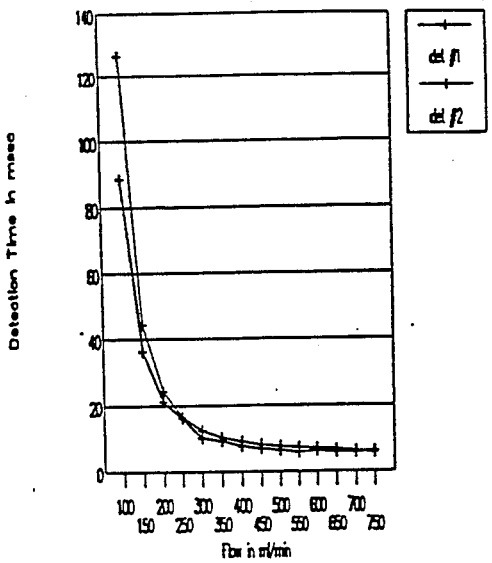

As one can see, the detection times are virtually the same in high flow rate but diverge at low flow rate. As explained earlier, this is due to irregularity in the movement of bubble in the tubing because of two opposing forces: the floating force tries to push the bubble up but the dragging force tries to pull the bubble along with the flow in the downward direction.

From the tests one can conclude that, in order to detect 10 uL air bubble in a tubing of 0.184 inch I.D., the parameter BBTIME should be set according to the last column (BBTIME) of the test data for the first detector assembly to be on the safe side.

Hardware Air Detector Sensitivity

In order to determine the threshold of detection of the hardware air detector with a blood flow rate of 500 mL/min, further tests with an improved test set-up were done. In this set-up, the blood line was bifurcated into two branches, one free-flowing, and one clamped so that an air bubble of any volume can be created by injecting air into the tubing with the aid of a syringe. Once the right amount of air is in the clamped tube and the measurement equipment ready, the clamp is released to let the bubble out. A venous tubing section (Drake Willock #8881) fitted with an air detector assembly from the monitoring machine #2 with downward flow was used to determine the detection sensitivity. Temperature- controlled water at 38°C was used in this test. The flow meter used was a Cole-Palmer NO44-40C with its accompanying calibration chart.

Experimental Results

Bubbles of 300 µL down to 150 µL consistently result in alarms. On the other hand bubbles of 50 µL result in no alarm. At 100 µL, they result in alarm almost half the time. Scope photos confirm that it takes a large enough bubble to result in a sufficient signal swing at the input of the comparator to reach the detection threshold. This is a direct result of the capacitive coupling of the signal and the RC filter network, which together form a bandpass filter. Thus the hardware air bubble detector is presently too sensitive (on the safe side). Further adjustments of the filter network will be done to set the detection threshold to 300 µL at 500 mL/min flow as per the specification.

Line Clamp

General

The LINE CLAMP DRIVER is a PWB assembly that, when its input is HIGH, will energize the solenoid to unclamp the blood tubing. Vice versa, when the input level is LOW or the inputs are not connected, the driver is not energized resulting in the solenoid in quiescent state and the blood tubing clamped.

The LINE CLAMP driver requires 120 ±2 Vac input and can be controlled by a TTL compatible signal at its logic input.

The driver when energized and in steady state is a constant current source, independent of the AC voltage variation within the specified range. In reality, the solenoid current is maintained constant as long as there is sufficient voltage to operate the pulse-width modulator driving a FET as a switch.

When the UNCLAMP signal is first applied to the logic input, the FET switch is turned fully on for about 100 msec, resulting in a solenoid current of 1.5 to 2.5 A depending on the solenoid series resistance and the actual AC voltage. Then the current will decay down to a steady state current as the current feedback loop comes into action. The latter controls the duty cycle of the pulse-width modulator driving the FET on and off, resulting in an average steady state current of about 200 mA.

In order to minimize the clamp response time, a quick release circuit is added to the basic circuit to quickly dissipate the solenoid stored energy when the clamp signal is received. This added circuit does not by any means interfere with the pull-in or the normal operation of the line clamp.

The solenoid is equiped with a silicon rubber pad to attenuate the plunger-to-frame contact noise during pull-in. The thickness of this rubber pad as well as the hold current affect the clamp response time of the line clamp.

Test Data

Following are the test data related to the release time of the solenoid as a function of hold current and rubber pad thickness.

| Hold current (mA) | Pad thickness (inches) | Time w/o quick release circuit (ms) | Time w/ quick release circuit (ms) |
|---|---|---|---|
| 50 | 1/16 | 381 | 188 |
| 100 | 1/16 | 407 | 188 |
| 250 | 3/32 | 109 | 50 |
| 100 | 3/32 | 134 * | 56 * |

* data after 70,000 cycles to simulate pad compression.

The unclamp time is measured to be about 30 msec. At 200 mA hold current, thermal measurement shows that the solenoid case temperature rise is 20 to 22°C above ambient. At 300 mA hold current, the case temperature rise is about 30°C.

Life Test

Two line clamps and two pre-production line clamp drivers were put into life test to determine product life in an accelerated manner. The mechanical aspect of the test is subject of a separate report by the mechanical engineering group. In summary, the system under test went through a total of 500,000 cycles without any failure or malfunction.

Stress Analysis

Switching transistor

In the unclamp state, the current in the solenoid averages 200 mA and the duty cycle of the MOSFET (Q5) switch is about 10%. The transistor used (IRF733) has an ON resistance of 2.5 ohms. Thus the resistive loss in the transistor is 2.5*0.2*0.2*0.1= 0.01 W which is negligible. Assuming a typical DC voltage of 170 V, rise and fall times of 100 nses, the switching loss is calculated to be about 22 mW.

In the clamped state, the switching transistor is totally turned off and there is no heat dissipation.

During the pull-in period, the drain current is about 2 A for some 300 msec. Thus the energy loss in the transistor is about $2.5*2*2*.3 = 3$ joules. As the unclamp action is very infrequent, there is virtually no thermal stress on the switching transistor Q5.

Power resistors R15/R17

The peak DC voltage is $132*1.41 = 187V$. Thus the power in the two power resistors is $(187-15)^2/5000 = 5.92$ W. Two 7-W power resistors are used, thus their derating is $5.92/14 = 0.42$.

Quick-release zener D6.

The zener D6 absorbs the magnetic energy of the solenoid during its release. That energy amounts to $(5mH)*(0.2A)^2/2 = .0001$ joules at each clamp action. This energy is too low to stress the zener diode D6.

Solenoid winding

The power dissipated in the solenoid in the unclamp state is $85*0.2*0.2=3.4W$ where 85 $\Omega$ is the resistance of the solenoid at ambient temperature. This is relatively a low power dissipation for a 2-inch diameter solenoid.

Audio Alarm Loudness

Purpose

The purpose of this test is to determine if the alarm transducer meets IEC 601-2-16 loudness specification of 65 dB at 1 meter.

Procedure

With the machine in an alarm condition and the speaker holes taped closed inside and out, monitor the audio output from a distance of 1 meter using a sound meter set for "FAST" response and "A" weighted. Measure from all four faces.

Equipment

Tripod and Tripod Adapter

Sound Meter: B&K Impulse Precision Sound Meter, Type 2209, D-9056-00-01

Conditions

Speaker and alarm transducer were mounted back to back and in the same plane as the blood pump power board. The speaker was facing down and the transducer up. The cabinet was closed and the 1 F cap used as the alarm power source was charged. The test area was free of hard walls and consisted of 5-ft office partitions configured as a narrow rectangle open at each end.

Additional Information

Cabinet material is 3/16 ABS.

Test Data

Front 65 to 66 dB - measured from the front center both with and without the speaker holes covered.

Right 74 dB - measured from the outside end of the dialyzer holder with a Freseneous F80 dialyzer in place.

Back 78 to 79 dB - measured from the hydraulics cover.

Left 70 to 74 dB - measured from the IV pole knob.

Six Minute Test

The machine was put in an alarm condition with the machine turned off (power fail). The audio intensity at the start of the test measured 66 dB. The audio intensity at the end of the six minutes was 65 dB. The observer's position relative to the sound intensity meter is critical and affects the test results. The sound intensity from the back of the machine measured 74 dB at the end of the six minutes.

Conclusion

The audio alarm loudness was measured to be higher or equal to the IEC specification in the four directions.

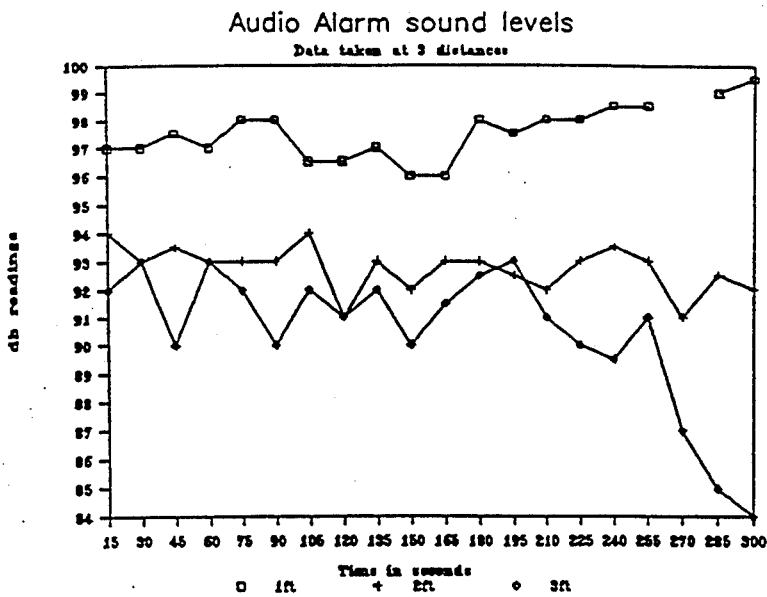

Power Fail Alarm Duration

Another test was set up to determine whether the duration of the alarm in a power fail situation is at least five minutes. In the three following tests, the microphone was placed at 1, 2, and 3 feet respectively from the transducer to determine whether any appreciable weakening of the sound level occurred as the energy storage capacitor was discharged.

The data show some variations in the sound level. This is due to the variations of the standing waves with the operator himself. On the average there is no appreciable sound level reduction after five minutes of testing in each case. However, the capacitor voltage did decrease from 5 V to about 4.33 V after five minutes of testing. If 2 V is the minimum operating voltage of the transducer, then by extrapolation of the discharge curve, one can say that the sound could last as long as 20 minutes. In reality, the transducer is capable of working down to 0.6 V, but with resulting reduced sound level.

Attached are the graphs showing the sound level and the capacitor voltage as functions of time for the three measurements.

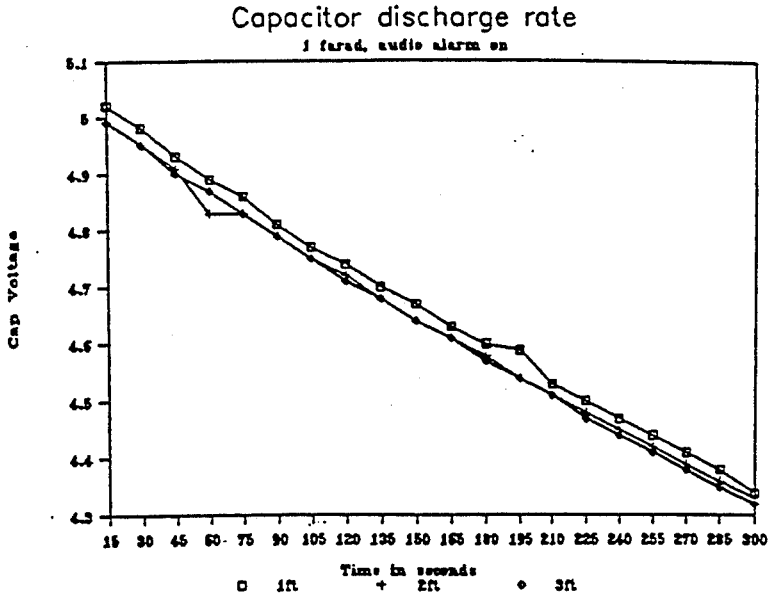

Power Supply Measurement Accuracy

General

The monitoring of the +5 V power supply uses a 10,000 and 15,000 ohm 1% precision voltage divider. The +12 V and –12 V power supplies are jointly monitored with a 15,000 and 24,300 ohm voltage divider.

Test Data

| | | | |
|---|---|---|---|
| Actual | +12 V | 12.06 | |
| Actual | –12 V | –12.20 | |
| Actual | +5 V | 4.93 | |

| Signal | Reading | Cal | Meas'd | Ideal | Max | Min |
|---|---|---|---|---|---|---|
| VPS1(±12 V) | 18048 | 2.7566 | 2.74 | 2.80 | 2.9147 | 2.6857 |
|  | 17824 | 2.7224 | | | | |
| VPS2 (5 V) | 19392 | 2.9619 | 2.96 | 2.96 | 2.9817 | 2.9343 |

The readings were taken from the display provided by a program on the PC which can read any memory location of the micro-controller. The calculated values are derived using the formula 5*Reading/32736. The 32736 value is the A-to-D number corresponding to 5 V, which results from the 10 bit A/D measurement being shifted left five binary positions. The measured values were obtained using a DVM. The ideal values correspond to the voltage divider output voltages actual power supply voltages. The maximum and minimum values correspond to worst case values of the resistors. One should note that while the VPS2 value is very constant, VPS1 fluctuates between the two recorded values.

Detection Threshold

Following are the calculations for different scenarios of the two +12 V and –12 V power supplies. One can see that only in the cases of a single power supply going too low that one can realistically detect the problem. If their magnitudes vary in the same percentage, the monitor voltage does not go out of the normal variation range to allow for accurate fault location.

| | Nominal | Max | Min | 12V–5% | –12V+5% | both–5% |
|---|---|---|---|---|---|---|
| V top | 12.06 | 12.06 | 12.06 | 11.4 | 12 | 11.4 |
| R top | 15000 | 14850 | 15150 | 15000 | 15000 | 15000 |
| R bottom | 24300 | 24543 | 24057 | 24300 | 24300 | 24300 |
| V bottom | –12.2 | –12.2 | –12.2 | –12 | –11.4 | –11.4 |
| Vmonitor | 2.800 | 2.915 | 2.686 | 2.469 | 3.069 | 2.698 |

Conclusions

The test data show that the A-to-D conversion is highly accurate. An out-of-spec condition of the +5 V power supply can be easily detected. The detection of an out-of-spec condition of the +12 V or –12 V power supply can also be easily detected assuming that only one of the two supplies is out of specification.

Memory Board Circuit
General Description

The Memory board is an IBM PC/AT compatible board that provides the following:

- 6 ea. 28-pin EPROM sites ( 27512 (64Kx8) * 6 = 384 Kbytes )
- 1 ea. 28-pin CMOS RAM site ( Dallas DS1225Y (8Kx8) )
- 1 ea. Dallas DS1287 AT compatible RealTime Clock module /w battery
- 1 ea. NS16450 (NS8250 compatible) Asynchronous Serial Port
- 1 ea. External Memory Card interface (uses external personality board)
- 1 ea. Intel 8255 Programable Peripheral Inteface supports DS1287 RTC 4 position DIP switch input Serial port & Ext. Memory Card configuration inputs

- 1 ea. Scope trigger output for debugging support

Board Subsections

The board is divided into several major sections:

1. Root Level - Overall subsystem interconnection and PC Bus Buffers
2. PC Bus Connector
3. Board Control - General board control logic (also I/O Decoder)
4. Memory Array - EPROM & CMOS memory and support circuitry
5. External Memory Card Interface
6. External Memory Card Interface connector
7. Serial Port - Standard PC (NS8250 compatible) Serial Port
8. RealTime Clock - RTC & configuration inputs

Root Level

This is the root level sheet. It contains the PC Bus interface buffers and hierarchial interface to the lower level schematic sheets.

PC Bus control signal buffer IC

PC Bus Address buffers (also AEN control signal) ICs

PC Bus data buffer IC

Local data buffer for I/O mapped devices IC

Jumper for selecting Serial port interrupt

Jumper 1-2 for no interrupts

Jumper 1-3 for IRQ3 ( COM2: use port address 02F8h )

Jumper 2-4 for IRQ4 ( COM1: use port address 03F8h )

PC BUS Connector

This contains the actual PC Bus connector ( P1 ) and the decoupling capacitors.

Board Control

This is the main control logic. It generates the signals that control the data buffers' direction and enabling. It also generates the PC Bus Wait States and decoding of I/O addresses.

Wait State Generator

This circuit is activated by any read or write operation of either memory or I/O as long as B_DACK0\ (buffered PC Bus DACK0\) is false (high). If B_DACK0\ is true (low) then the operation is a memory refresh operation which does not need (and should avoid) a wait state insertion.

Write DEN Stretchers

These circuits extend the trailing edge of the write strobes (for both memory and I/O) so that the data buffers remain enabled well beyond the end of the write PC Bus write strobes MEMW\ & IOW\. This is to meet the requirement to hold the data valid after the removal of the write strobe (most designs use the command strobes to enable the data buffers).

When a strobe goes true (low) it sets a flip-flop which generates a xxx_DATA_ENABLE signal. When the strobe is negated (goes high) the flip-flop remains set until the next rising edge of the PC Bus signal CLOCK.

A pair of NAND gates function as negative input OR gates to generate xxx_DATA_ENABLE signals for the memory & I/O address spaces. These are not gated by address decoding, requiring later logic to generate the final enable signals to the data buffers.

Buffer Direction Control

This is an R-S flip-flop that generates the data direction control signal (DT/R\) that is provided directly to the data direction control signal of all data buffers.

The flip-flop is always to the "write from CPU" direction prior to the leading edge of any strobe by the assertion of the PC Bus signal ALE. This ensures the earliest possible availability of data during a write operation.

DT/R\ = high => "WRITE from CPU to memory or I/O"

DT/R\ = low => "READ from CPU to memory or I/O"

I/O Command Delays

This circuit delays the leading edge of the I/O command strobes until the first rising edge of the PC Bus signal CLOCK after the command strobe has been asserted. The trailing edge of the command strobes are unchanged (other than propogation delays).

This provides additional address set-up prior to command assertion required by some I/O devices.

Note: This circuit is similar but complementary to the "Write DEN Stretchers".

Memory Buffer Control

This circuit generates address gated data enable signals to the memory devices' data buffers.

Board Data Buffer Control

This circuit is simply an AND gate used as a negative true input NOR gate. If any local data buffer is enabled the board's main data buffer is enabled.

I/O Decoder & Buffer Control

U14 is a PAL16L8 that combines the I/O address decoding functions and I/O buffer control functions. It also generates a fully decoded and gated signal DEBUG_TRIG\ to be used as a debugging aid.

The PAL design specification is in the file S2_IO_02.PDS. The signal B_AEN (buffered PC Bus AEN) must be false (low) to identify a bus cycle as a valid I/O operation rather than a DMA cycle. The signal B_IOW\ (buffered PC Bus IOW\) must be true (low) to activate the DEBUG_TRIG\ signal, it has no other use in this PAL.

The signal I/O_DATA_ENABLE (high true) is used to gate with valid I/O address to enable the IO_BUF_EN\ signal which enables the local I/O data buffer (U6, sheet 1). The signals CLOCK_CS\ & SERIAL_CS\ (both low true) are the fully decoded chip select signals to U38-6 & U33-14, respectively.

Memory Array

The Memory array is isolated from the main address bus by 74LS244 octal buffers and from the main data bus by a 74LS245 bi-directional octal buffer.

CONTROL LOGIC : The chip decoding is implemented with a PAL16L8.

A jumper (JP5) provides the capability of selecting an alternate memory map for development purposes. During normal operation, the jumper is either removed or placed on pins 2-3. This allows production units to be built without JP5 installed. The pull-up resistor (R13) is always required.

The outputs of the PAL are six chip selects for the EPROM's, a chip select for the Non-volatile CMOS RAM, and a chip select for the External Memory Card. A 74LS30 eight input NAND gate is used as a low true input OR gate to generate the signal MEM_SEL that is used by the Memory Buffer Control logic to enable the memory aray & main board data buffers.

External Memory Card Interface

This consists primarily of address & data buffers for the External Memory Card interface.

This circuit is connected to an external Parsonality board with the actual memory card connector and additional buffering. The CARD_xxxx signals (from sheet 6) are dependent on the particular personality board installed. They can be read by the CPU to determine the type and status of the External Memory Card.

The enabling of the address & control signal buffers (U28, U29, U30) is normally controlled by the personality board for the External Memory Card. A jumper (JP6) is provided for manually forcing the enabling of the buffers. The jumper (JP6) is not necessary for production units. The pull-up resistor (R14) is always required.

External Memory Card Interface Connector

This is the physical connection for the External Memory Card (P 2) and the Serial Port (P 4).

Serial Port

The Serial Port is a fully PC compatible serial port using a National NS16450 chip which is a superset of the National NS8250.

The signals are buffered with standard TTL buffers. The actual drivers/ receivers (RS-232 or RS-485) are on a small external board that also includes the appropriate connector and optical isolation.

Real Time Clock

The Dallas Semiconductor DS1287Y Real Time Clock module (U39) has an on-board crystal and lithium battery. It also includes an Intel 8255 Programable Peripheral Interface to support the DS1287Y and to read the status/configuration information from the DIP switches (SW1), the External Memory Card, and the Serial Port buffer/ isolation board.

The 8255 is used to implement a "virtual bus" to interface to the DS1287Y because the DS1287Y is unable to operate at the full PC Bus speed. Port A of the 8255 is used as a bi-directional data bus and the upper half of port C is used to generate the control signals (the DS1287Y is configured, by the grounding of pin 1, to operate with Intel style control signals).

Unfortunately, the 8255 has the characteristic that any time the mode of any port is changed (in this case to change the data direction of port A) all outputs of all ports are set to low. Additionally, at reset or power-up, all ports are set to inputs and allowed to float high. This requires that all circuitry attached to the 8255 must be able to accept outputs that may be both all low or all high. This required the addition of a package of NAND gates (74LS00) between port C of the 8255 and the control inputs of the DS1287Y to allow proper opeeration of the DS1287Y.

Modification

The modification inverts the 8255 outputs PC.5 & PC.4 before they are applied to the RD\ & WR\ (respectively) inputs of the DS1287. These signals are also gated with the inverse of PC.6 (which, uninverted, provides the CS\ signal to the DS1287). This combination prevents the assertion (low) of the DS1287 RD\ & WR\ signals at the same time (which is an illegal operation) for both the power-up/reset condition of all 8255 outputs high and the condition of all 8255 outputs low when the direction of 8255 port A is reversed. The last gate of the 74LS00 package is used to invert the high true B_RESET signal and apply it to the DS1287.

Timing Analysis

Access/Setup times are determined by the PC Bus clock speed, PC Motherboard propogation delays, PC interface board propogation delays, and the number of inserted wait states.

CPU Access/Setup Times

There are two data access times that must be considered :

1. Address to data
2. Command Strobe to data

The worst case must always be used.

All times assume zero inserted wait states. If N wait states are inserted the Access/Setup times will be increased by N CPU clock cycles Tcy.

CPU Timings

All times are the same for both Memory and I/O transfers. All times are worst case.

| 80XX | Symbol Parameter | 5 MHz | 8 MHz | 10 MHz |
|---|---|---|---|---|
| Tcy | CLK Cycle Period | 200 nS | 125 nS | 100 nS |
| Tclav | Address Valid Delay | 110 nS | 60 nS | 50 nS |
| Tdvcl | Data in Setup Time | 30 nS | 20 nS | 5 nS |
| Tcldx | Data in Hold Time | 10 nS | 10 nS | 10 nS |
| Tcldv | Data out Valid Delay | 110 nS | 60 nS | 50 nS |
| Tchdx | Data out Hold Time | 10 nS | 10 nS | 10 nS |

| 8288 | Symbol Parameter | not specified by CPU clock speed |
|---|---|---|
| Tclml | Command Active Delay | 35 nS |
| Tclmh | Command Inactive Delay | 45 nS |

References: 5 MHz & 8 MHz - Intel 1988
10 MHz - Siemens SAB8086

Read Data Access

The data is sampled by the CPU at the begining (CLK falling, high to low) of the CPU T4 clock cycle. There is a required setup time of Tdvcl and a required hold time of Tcldx.

Write Data Setup

The data is available from the CPU at the begining (CLK falling, high to low) of the CPU T2 clock cycle, after the Tcldv dealy. The data remains valid until the middle (CLK rising, low to high) of the CPU T4 clock cycle.

Address to Data

The address is made available at the begining (CLK falling, high to low) of the CPU T1 clock cycle after the delay Tclav.

Addr. Read Access = ( 3 * Tcy ) - Tclav - Tdvcl
Addr. Write Setup = Tcy - Tclav + Tcldv

|  | 5 MHz | 8 MHz | 10 MHz |
|---|---|---|---|
| ( 3 * Tcy ) | 600 nS | 375 nS | 300 nS |
| Tclav | 110 nS | 60 nS | 50 nS |
| Tdvcl | 30 nS | 20 nS | 5 nS |
| Addr. Read Access = | 460 nS | 295 nS | 245 nS |

|  | 5 MHz | 8 MHz | 10 MHz |
|---|---|---|---|
| Tcy | 200 nS | 125 nS | 100 nS |
| Tclav | 110 nS | 60 nS | 50 nS |
| + Tcldv | 110 nS | 60 nS | 50 nS |
| Addr. Write Setup = | 200 nS | 125 nS | 100 nS |

Command Strobe to Data

Command Strobes are generated by the 8288 Bus Controller.

The Command Strobes are asserted at the begining ( CLK falling, high to low ) of the CPU T2 clock cycle after the delay Tclml.

Cmd. Read Access = ( 2 * Tcy ) - Tclml - Tdvcl
Cmd. Write Setup = - Tclml + Tcldv

|  | 5 MHz | 8 MHz | 10 MHz |
|---|---|---|---|
| ( 2 * Tcy ) | 400 nS | 250 nS | 100 nS |
| Tclml | 35 nS | 35 nS | 35 nS |
| Tdvcl | 30 nS | 20 nS | 5 nS |
| Cmd. Read Access = |  |  |  |

|  | 5 MHz | 8 MHz | 10 MHz |
|---|---|---|---|
| Tclml | 35 nS | 35 nS | 35 nS |
| + Tcldv | 110 nS | 60 nS | 50 nS |
| Cmd. Write Setup = | 75 nS | 25 nS | 15 nS |

PC Bus Access/Setup Times

PC Bus (Read) Access Time is the time from the assertion of the command strobe (MEMR\, MEMW\, IOR\, IOW\) on the PC Bus until the data from the PC interface board is stable on the data lines of the PC Bus.

PC Bus (Write) Setup Time is the time from the assertion of the command strobe on the PC Bus until the data from the PC interface board is stable on the data lines of the PC Bus.

NOTE: The following description of the PC Motherboard implementation refers only to the DTK Model PIM-TB10-Z.

Command Strobes & Clock

The PC Bus command strobes (MEMR\, MEMW\, IOR\, IOW\) are directly driven on the PC Bus by an 8288 Bus Controller. The data bus of the 80XX CPU is isolated from the PC Bus data lines by a 74LS245 (U23) octal transceiver. Therfore, the PC Bus Access & Setup time are calculated from the data sheets for the 80XX CPU & 8288 Bus Controller, subtracting the propogation delay of the 74LS245 buffer (12 nS typical, 18 nS maximum re: TI TTL Data vol 2, 1985).

The skew & propogation delays between the 80XX CPU, 8284 Bus Controller, and the PC Bus must also be considered. The 80XX & 8288 are physically connected directly to the CLK output of the 8284 Clock Generator (U91-8). This clock signal is buffered from the PC Bus by a 74LS244 (U17-17->3) (12 nS typical, 18 nS maximum re: TI TTL Data vol 2, 1985). This shortens the apparent delay from the PC Bus CLK (B20) transitions to the change of the PC Bus command strobes' state.

The CRITICAL FACTOR for read access times is the state of the data at the 80XX CPU's data pins with respect to the clock signal at the 80XX CPU's CLK (19) pin.

Another factor (that actually improves the situation) is that if the interface is designed correctly (the Chip Select signals are derived exclusively from the contents of the PC Bus address lines, and NOT gated by a command strobe) the access time from address to data is not affected by the command strobes. The command strobes affect the access time from command assertion to data output enable (which is generally shorter that address to data).

The PC Bus command strobes from the 8288 are identical with respect to the CPU clock and CPU bus cycle states. All further references to "command strobes" apply to all of the PC Bus command strobes.

The command strobes are change state when the CLK signal falls from high to low. The I/O_CH_READY PC Bus (A10) is sampled on the first falling edge of CLK after the command strobe has been asserted.

NOTE: The DTK model PIM-TB10-Z PC clone has some strange Ready logic.

Data Path

The 80XX CPU data bus is buffered from the PC Bus data lines by a 74LS245 (U23). The propogation delay of the 74LS245 (8 nsec typical, 12 nsec maximum, re: TI TTL Data vol2, 1985) must be included in the calulations.

Read Data Sampling

The read data is sampled by the 80XX CPU on the same falling (high to low) edge of the CLK signal that causes the command signal to go false.

|  |  | 5 MHz | 8 MHz | 10MHz |
|---|---|---|---|---|
| Tdvcl | Data In Setup |  | 30 | 20 |
| Tcldx | Data In Hold |  | 10 | 10 |

Write Data Availablilty

The write data is available from the 80XX CPU after the same falling (high to low) edge of the CLK signal that causes the command strobe to go true. The write data is held valid by the 80XX CPU until after the rising (low to high) edge of the CLK after the command strobe goes false.

|  |  | 5 MHz | 8 MHz | 10 MHz |
|---|---|---|---|---|
| Tcldv | Data Valid Delay |  | 110 | 60 |
| Tchdx | Data Hold |  | 10 | 10 |

| PC Bus | 8288 |
|---|---|
| MEMW\ (B11) | AMWC\ (8) |
| MEMR\ (B12) | MRDC\ (7) |
| IOW\ (B13) | AIOWC\ (12) |
| IOR\ (B14) | IORC\ (13) |

CLOCK ( B20 )   CLK ( 2 ) buffered by 74LS244
ALE ( B28 )     ALE ( 5 )

5 MHz = 80C88AL
8 MHz = 80C88AL-2

NOTE : The 8288 Bus Controller generates two additional command strobes, MWTC\ (8288-9) & IOWC\ (8288-11). These are identical to AMWC\ & AIOWC\, respectively, except that they are asserted exactly one full CPU clock cycle later. These signals are not used in the PC Bus environment.

General Access Times

There are two possible limiting factors for Access/Setup times :

1. Address to data
2. Command to data

Each must be calculated and the Access/Setup time is the worst of the two.

EPROM Memory Array Access/Setup Times

Address to Data
Early Address Availability - ? nS
Board Address Buffers    74LS244    18 nS
Array Address Buffers    74LS244    18 nS
EPROM Addresss to Data   27512-25   250 nS
Array Address Buffer     74LS245    12 nS
Board Address Buffer     74LS245    12 nS
Note: ALE gating of Chip Select causes unneeded delay
Command to Data
Board Command Buffer              74LS244    18 nS
EPROM Output Enable to Data       27512-25   100 nS
Array Address Buffer              74LS245    12 nS
Board Address Buffer              74LS245    12 nS

Miscellaneous Design Issues

Bus Capacitive Loadings

Address

Main Internal Address Bus - A_D[0..7] :
5 pf     74LS244    U4 (U3, U2)    Board buffer ( BUS DRIVERS )
4 pf     PAL16L8    U14            I/O Decoder
5 pf     74LS244    U16 (U15)      Memory Array buffer
4 pf     PAL16L8    U18            Memory Decoder
5 pf     74LS244    U30 (U29, U28) External Memory Card buffer
10 pf    NS16450    U33            Asynchronous Serial Port
10 pf    8255       U38            Programable Peripheral Interface Memory Address Bus - A[0..7] :
5 pf     74LS244    U16 (U15)    Memory Array buffer
36 pf    27512      U20-U25      EPROM ( 6 * 6 pf )
10 pf    DS1225     U27          NonVolatile RAM module

Data

Main Internal Data Bus - B_D[0..7] :
6.5 pf   74LS245    U5     Board Buffer
6.5 pf   74LS245    U6     I/O Data Bus Buffer
6.5 pf   74LS245    U17    Memory Buffer
6.5 pf   74LS245    U31    External Memory Buffer I/O Data Bus - IOD[0..7] :
6.5 pf   74LS245    U6     I/O Data Bus Buffer
20 pf    NS16450    U33    Asynchronous Serial Port
20 pf    8255       U38    Programable Peripheral Interface Memory Data Bus - D[0..7] :
6.5 pf   74LS245    U17        Memory Buffer
72 pf    27512      U20-U25    EPROM ( 6 * 12 pf )
10 pf    DS1225     U27        NonVolatile RAM module

Safety Verify Functions

Description

The System 1000 Safety Verify Functions include functions which alert the operator of a safety system failure and take necessary the action to prevent immediate patient injury.

Safety systems are those which protect the patient from unsafe conditions that may occur during a normal dialysis treatment. The Safety Verify Functions include:

1. System hardware watchdog
2. Interprocessor communication verification
3. Bypass failure alarm
4. System selftests
5. Blood pump failure alarms

Test Data

System Hardware Watchdog

The hardware watchdog is located on the Misc I/O Controller board, and must have its input toggled by the Misc I/O Controller periodically to prevent it from activating the system Shutdown line. An activated Shutdown line forces the machine into an inoperable yet safe condition.

Tests were performed to determine the watchdog's timeout time, and to ensure that a shutdown condition resulted when its input was no longer toggled. The test was conducted by setting the CTRL_WATCHDOG bit of the Misc I/O Controller's CONTROL variable, which disables the toggling of the watchdog input.

Test results showed the normal watchdog toggle rate to be approximately 1 KHz, and the watchdog timeout period was about 1.5 seconds. The activation of the shutdown line was verified.

Interprocessor Communication Integrity

To ensure that the machine is placed in a safe operating condition in the event that the main 80XX controller fails, the three microcontrollers that it communicates with require constant servicing. If the 80XX fails to communicate with one of the microcontrollers within a specified time period, the microcontroller will activate the system shutdown line. This function is disabled on each microcontroller board if the board's JP4 test jumper is installed.

This function was tested on each of the three microcontroller boards, both with and without the JP4 jumper installed. On 5/7/90 in the integration prototype machine the Blood Pump Controller (software version 21.4) and the UF Controller (software version 1.7) were tested. Neither activated the shutdown line with their respective jumpers installed. With the jumpers removed, each activated shutdown after 10 seconds from the time that communication with the host 80XX was terminated. The Misc I/O Controller was tested on 5/14 (software version 8.0). No shutdown occured with the jumper installed, while after 6 seconds of no host communication the shutdown line was activated.

If one of the microcontrollers fail to respond to the host during communication, the host initiates a system shutdown. This was tested by forcing the reset pin of the UF Controller to ground for a sustained period of time. Within a couple of seconds, the host displayed both "Controller error at UF com port" followed by "No UF response... port terminated", with a shutdown condition resulting.

Bypass Fail Alarm

The bypass fail alarm is based on the intended state of the bypass valve, and whether dialysate flow is detected by a thermal flow detector located between the bypass valve and the dialyzer. If the bypass valve is commanded to bypass the dialyzer flow circuit, and the flow sensor detects flow, then a bypass fail alarm results. This alarm results in a machine shutdown condition.

This alarm was tested by shorting the bypass valve driver (Q8) on the Misc I/O Hydraulics Power board, which forced the bypass valve into the non bypass state. When the machine was powered up and left in Standby mode, the bypass fail alarm occured within 30 seconds.

In addition, with this simulated failure, a bypass fail alarm resulted during the conductivity alarm self test two out of three times (one time a self test failure resulted first).

Self Test

The following self tests are performed by the first clinical monitoring version of the System 1000 machine:

Arterial/Venous Pressure Test

Verifies operation of the high and low arterial and venous pressure alarms, the level adjust system, and the relative accuracy of the arterial and venous pressure measurements. Verifies operation of the audible alarm and main alarm lamp.

Blood Leak Detector Test

Verifies the operation of the blood leak detector.

UF Test

Verifies operation of the UF removal metering device, tests for leaks in the UF system, and verifies the operation of the high and low TMP alarms.

Temperature Alarm Test

Verifies the operation of the dialysate temperature alarms, which include the primary high and low alarms and the redundant high alarm.

Conductivity Alarm Test

Verifies the operation of the dialysate conductivity alarms, which include the ±5% primary high and low alarms, the A and B part redundant high and low alarms, and the fixed backup high and low alarms.

Air Detector Test

Verifies the operation of the primary (software) air detector alarm and the backup (hardware alarm).

Conductivity Verify Test

Asks the operator to verify the primary conductivity measurement, and then calculates the primary limits around this value. Also verifies that the A and B part conductivity measurements are reasonable, and then sets the redundant limits around these values.

Test Data

Each of these self tests was verified by simulating a failure condition of the function being tested and confirming that a self test failure resulted. A self test failure ensures patient safety by preventing the machine's Prime or Dialyze mode from being entered. The following details the simulated failure used for each test, along with the resulting failure message that was displayed.

Arterial/Venous Pressure Test

The venous pressure luer was not plugged as is required for the test. This prevented the venous pressure from being pumped above its upper limit, and resulted in the following error message: "Bld Press Test: No high ven." This simulated either a level adjust failure or a venous pressure measurement failure.

This test was repeated with the arterial pressure luer not plugged, with the following error message resulting: "Bld Press Test: No high art".

The calibration of the arterial pressure was then offset so that the measured pressure was 60 mmHg at atmospheric pressure. The self test then reported: "Bld Press Test: No press match." This simulated a pressure measurement accuracy failure.

Blood Leak Detector Test

For this test a simulated blood leak detector was used, consisting of the LED and photocell assemblies used in the actual detector, coupled together inside an opaque tube. The LED and photocell were first pulled apart to the extremes of the tube (approximately three inches) and the blood leak system was calibrated. It was verified that the blood leak detector self test successfully passed. The LED and photocell were then repositioned closer together (about one inch apart). This time the self test reported: "Blood Leak Fail: No alarm." This test simulated a failure caused by either an increase in the LED intensity or a decrease in the photocell resistance.

UF Test

The test was verified on a machine with flow path problems that prevented it from building any dialysate pressure when the UF removal metering device was run. The following error message resulted: "UF Tst: TMP Not In Range".

Temperature Alarm Test

This test was not verified because of the difficulty involved in simulating a failure. The self test verifies these alarms by momentarily changing the alarm limits to force an alarm based on the currently measured temperature value. The high temperature alarm test included in the Conductivity Alarm Test was tested however (refer to the next section).

Conductivity Alarm Test

The hardware test line which forces the primary conductivity amplifier to output a high value was defeated with a clip lead (pin 20 of U26 on the Misc I/O Controller board was shorted to ground). The following error message resulted: "Cond Test: High Alarm Failed." This simulated a primary conductivity circuit failure.

The hardware test line referred to in the previous paragraph also forces a primary high temperature alarm, however since the conductivity alarm is tested first, if it fails the temperature alarm is never tested. Therefore just the high temperature alarm test was defeated by disconnecting the output of the comparator which shunts the temperature measuring thermistor during the self- test (pin 1 of U14 on the Misc I/O Hydraulics Power board). This resulted in the following message: "Cond Test: Hi Temp Alarm Failed." This simulated a primary temperature circuit failure.

Since the redundant conductivity self test verifies that there is no dialysate flow during the alarm, a bypass valve failure was simulated by shorting the bypass valve driver on the Misc I/O Hydraulics Power board (Q8). The conductivity self test was run three times with this failure mode, one time resulting in the following error message: "Cond Tst: Redundnt Hi Alm Failed." The other two times resulted in a Bypass Fail alarm, with a machine shutdown resulting.

Air Detector Test

The primary (software) air alarm was disabled by shorting the output capacitor of the primary ultrasonic receiver amplifier (C6 on the Misc I/O Electrical Power board). This resulted in the following message: "Air Fail: No soft alarm".
The backup (hardware) air alarm was then disabled by shorting the output capacitor of the backup ultrasonic receiver amplifier (C8 on the Misc I/O Electrical Power board). This resulted in the following message: "Air Fail: No line clamp".

Conductivity Verify Test

The machine was run in bicarb mode (bicarb concentrate line not on rinse fitting), with resistors used for the conductivity probes to simulate normal bicarb conductivities (8 mS/cm for the A probe, 13 mS/cm for the B probe). With this arrangement, the conductivity verify test successfully passed. Then the resistors for the A and B probes were reversed (A now measuring 13 mS/cm and B measuring 8 mS/cm). The following error message resulted: "Cond Verify Error".

Blood Pump Failure Alarms

The blood pump failure alarms consist of the Blood Pump Stop alarm and the Blood Pump Overspeed alarm. The Stop alarm occurs after 30 seconds from the time when the pump stops turning if the host has not commanded the pump to stop. This situation can exist if the blood pump drive circuit fails, the blood pump door is opened, or the blood pump is turned off by the Blood Pump controller because of an overspeed condition. The Overspeed alarm occurs if the controller detects the pump running at a faster rate than is expected. The controller uses two independent methods for determining pump speed: an optical tach signal, and the motor's back EMF voltage. An overspeed condition can result if the tach signal is lost (using the EMF voltage as an indication), or if the motor drive circuit fails.

The Blood Pump Stop alarm was tested by running the blood pump in Dialyze mode, and unplugging the tach signal/door switch connector (JP2) on the Blood Pump Power board. This effectively opened the door switch, which caused the controller to stop the pump. After approximately 30 seconds an alarm resulted, with the message "Blood Pump Stop Alarm" being displayed in the error window, and the audio alarm and the main alarm lamp being activated.

The Blood Pump Overspeed alarm was tested with three different failure modes: a complete loss of the tach signal, a partial loss of the tach signal (with one of the motor shaft holes plugged), and a drive circuit failure resulting in full power being applied to the motor.

The loss of the tach signal failure was created by removing the tach sensor assembly from the rear of the motor. This failure was tested both while the motor was running at 200 RPM and from initial pump turn on. When the failure occured while the pump was running, the pump began running at high speed for approximately two seconds before turning off with the message "Blood Pump Over Speed Alarm" being displayed in the error window. When the failure occured while the pump was turned off, then after the pump was turned on it ran at high speed for approximately four seconds until turning off with the same message. In both cases, after about 30 seconds from the time that the motor was turned off, a Blood Pump Stop Alarm occured.

The partial loss of tach signal failure was created by taping over one of the two holes on the motor shaft used for tach sensing. This effectively caused the motor to run at twice the desired speed, and relied upon the back EMF sensing to trigger the alarm. From motor turn on, within four seconds the motor turned off with "Blood Pump Over Speed Alarm" being displayed. Thirty seconds after the pump stopped a Blood Pump Stop alarm resulted.

The drive circuit failure was created by shorting the output of the pulse width modulator (Pin 1 of U2 on the Blood Pump Power board) to ground. This failure was created both while the motor was running at approximately 200 mL/min and while the motor was off. In both cases, the failure caused the motor to immediately run at high speed, and after approximately four seconds the motor stopped due to a machine shutdown condition. The messages "Bld Pmp Overspeed Alarm" and "BP Control Shutdown" were displayed in the error window.

Summary

The Safety Verify Functions monitor critical system functions and provide indication of and machine response to hardware failures that could cause patient injury. These failures include those that could disable the primary safety alarms (e.g. dialysate and extracorporeal alarms), as well as others that could result in immediate patient risk (e.g. bypass fail alarm).

The Safety Verify Functions were tested by simulating hardware or calibration failures, and verifying the expected results. All functions tested were verified to be effective at identifying the simulated failures.

Power Supply System

Introduction

The System 1000 is meant to be operated off line power at 100, 120, 200, 220 or 240 volts AC determined by a voltage selector switch, at 50 or 60 Hertz. Input protection is provided by a 20 amp circuit breaker when operated from 120 volts. Power is supplied to the system in two forms; transformer isolated with multiple voltage taps and non-isolated line voltage.

The non-isolated power is provided for the dialysate heater circuit and is switched by means of a solid state relay.

Isolated power is provided for all other requirements including the system +24 volt, +5 volts, +12 volts and −12 volt DC supplies.

Isolation Transformer

Power isolation is provided by a purchased transformer specified with 4000 volts RMS input to output isolation. Isolated power is provided as 21 volts AC for the system unregulated 24 volt DC supply, as 120 AC to the system switching power supply and as 20 volts AC which is specified to be isolated (4000 volts RMS) from the other secondaries and may be used with auxiliary circuits to be connect to other equipment. In addition to providing high voltage isolation the transformer design is important in meeting equipment leakage current specifications (typically 100 micro-amp chassis).

Testing Data

Transformer leakage current (120 VAC applied):

3.5 uA forward;

3.0 uA reverse.

Transformer isolation (hi-pot.):

Tested 3 KV between primaries and secondaries, tested 3 KV between auxiliary power secondary and other secondaries, 600 V between all secondaries. Isolation was maintained during all tests (no voltage breakdown).

Transformer outputs:

24 volt supply load regulation (1 amp to 10 amp loading at power supply board): 9%, with measured output voltages of 28.3 VDC and 25.7 VDC (V primary = 118).

20 VAC Auxiliary power maintains 20.9 VAC with a 0.19 A load (V primary = 117).

120 VAC supply (switching power supply loaded 100 watts):

maintains 123 VAC output (Vprimary = 117).

Temperature rise:

19°C without load;

32°C full load (24V @10A, 20VAC @0.25A, 120VAC @1A).

Switching Power Supply

A commercial power supply is used to provide +5, +12 and −12 volt regulated power to the system.

Test Data

| OUTPUTS | MAX. LOADS as tested | LOAD REG. |
|---|---|---|
| +5 V | 10 amps | 0.00% |
| +12 V | 1.5 amps | 0.08% |
| 12 V | 1.0 amps | 0.08% |

Line regulation was less than 0.1% tested at 85 and 132 VAC.

Power Loads Test Data

Non-Isolated Line Voltage

The only non-isolated power load is the dialysate heater. The heater element is available as 100, 120, 200, 220 and 240 volt options. The power specification for the elements is 1500 watts ±5%. The thermostat and all associated wiring is adequately rated for this load.

| 24 VOLT LOADS | |
|---|---|
| Blood Pump Sub System | Current In Amperes |
| Blood Pump motor (with tubing,500 mL/min flow) | 1.40 |
| Heparin Pump (Type C) | 0.360 |
| Level Adjust motor (Type A) | 0.330 |
| Level Adjust valves (Type CM) | 0.040 |
| Fan (Innovative) | 0.21 |
| Blood Pump Power total | 2.34 |

| UF Power Sub System | Current In Amperes |
|---|---|
| Flow Equal. valves (Type M 4 on) | 1.56 |
| UF Removal Valves (Type M 1 on) | 0.390 |
| Rinse Valve (Type MS) | 0.10 |
| Proportioning pumps (Type V PH268-23 2 on) | 1.16 |
| Proportioning valves (Type M 2 on) | 0.780 |
| UF Power total | 3.99 |

| I/O Sub System | Current in Amperes |
|---|---|
| CRT (Type C B/W) | 1.18 |
| ON/OFF valve (Type S) | 0.30 |
| Bypass valve (Type S) | 0.30 |
| Supply Pump (Type M @ 500mL/mi.) | 0.390 |
| De-air/air Pump (Type M @ 500mL/min) | 0.840 |
| I/O total | 3.01 |

| | Current in Amperes |
|---|---|
| 24 VOLT SYSTEM TOTAL | 9.34 |

All above measured at nominal line voltage.

PCB LOADS +5VDC, +12VDC AND -12VDC Measured

| | +5 | +12 | -12 |
|---|---|---|---|
| BLD PUMP CONT. | 0.251 | 0.0242 | 0.0163 |
| BLD PUMP POWER | 0.065 | 0.0963 | 0.0002 |
| UF CONTROLLER | 0.220 | 0.0244 | 0.0164 |
| UF POWER | 0.068 | 0.0483 | 0.0162 |
| MISC I/O CONT. | 0.356 | 0.0253 | 0.0160 |
| I/O ELEC. POWER | 0.121 | 0.0166 | N/A |
| I/O HYDR. POWER | 0.005 | 0.0371 | 0.0024 |
| ALARM LAMP (50%) | 0.169 | N/A | N/A |
| MEMORY BOARD | 0.699 | N/A | N/A |
| MOTHER BOARD | 1.72 | 0.030 | 0.002 |
| VIDEO DRIVER | 1.28 | N/A | N/A |
| TOTAL SYSTEM CURRENT | +5 | +12 | -12 |
| | 4.95 | 0.302 | .008 |

Mechanical Assemblies

Air Detector

The function of the air detector is to detect 10 microliter and greater volumes of air in the venous blood line. This specification is to be valid at blood flow rates up to 700 mL/min. The method of detection used is very similar to that used in the current 480 line of equipment. A two megaHertz continuous wave ultrasonic energy beam is passed through the blood tubing wall, through the blood, and then back through the tubing again. The signal is then picked up with an ultrasonic receiver, and passed along to the rest of the electronics. When an air bubble passes through the ultrasonic beam it reflects the waves impinging on it, therefore creating a 'shadow' that the receiver sees as a decrease in received energy.

The System 1000 air detector uses a rigid acrylic bumper. This eliminates the wear related problems experienced with elastomeric bumpers. The bumpers are also set a fixed distance apart. The idea behind the fixed bumpers was that if the moving parts of a spring loaded system could be removed, and still maintain good detector operation, a simpler and more reliable system would be made. The only problem found in using the fixed bumpers was an increase in the sensitivity of the detector to blood tubing movements. This problem was greatly reduced by making a hinged cover that securely holds the blood tubing in between the two bumpers.

Line Clamp

Design

The function of the line clamp is to stop fluid flow in the blood tubing. The clamping is done via a spring loaded plunger that pinches the blood tubing closed. To open the line clamp the plunger is pushed open and held open with an electric solenoid. With this design, even in the event of an electrical power outage, the spring will clamp the blood tubing and stop fluid flow.

The spring for this line clamp was designed with fatigue as it's prominent mode of operation. The final design produces only 35350 psi of shear stress at it's minimum operating height. This stress level is only 13.7% of the ultimate tensile strength of the wire, therefore ensuring a cyclic lifetime of over 1 million cycles. With a conservative estimate of 40 cycles per dialysis treatment, or 262000 cycles for a 7 year life, the spring far exceeds the required life, by design.

The high temperature problems of some solenoid actuated line clamps were fixed by the electrical design team. The problem of conducting heat to external parts was reduced in this design by limiting the heat conduction paths to user accessible parts. The combination of these two solutions has resulted in line clamp that has a very minimal temperature rise when in operation.

Life Test Results

Two line clamp assemblies were set up in an automated test fixture that ran 24 hours a day. The purpose behind this test was to subject the line clamps to an extreme number of cycles and see how the design held up. The results after 470000 cycles were as follows:

- One of the occlusion springs force dropped 0.6 lbf over the life of the test, while the other springs force stayed constant. The data on the spring that changed does show a changing force over the whole test, with the values going up and down. The other assembly was very consistent in its force during the test.
- One solenoid showed 0.001 inch wear on its internal bushing, with no wear exhibited on the shaft that runs through it.
- One occlusion plate bearing showed 0.002 inch of wear.
- The polyurethane bumper/plug only exhibited a maximum of 0.003 inch of compression and wear.
- The occlusion gap of the devices decreased by 0.011 inch on one unit, and 0.003 inch on the other.
- A pressurized blood tubing was placed in the line clamp to test the life of the tubing itself. With 16 psig pressure in the line, a total of 3121 cycles were recorded before a leak was detected.

All of the above results show that this device is an extremely stable and reliable line clamp. The 470000 cycles calculated out to 25 years of life at 40 cycles per dialysis treatment. The 3000 plus cycles that the piece of blood tubing lasted before leaking is approximately 75 times the required life.

Qualification Test Results

The line clamp was tested to determine its ability to occlude against pressure, and its ability to maintain a clamped state. The blood tubing was pressurized to 30 psig and the clamp was able to shut off the flow. The pressure was then increased to 35 psig with the clamp still closed, and no leaks were noted. The method used to determine whether the tubing was occluded or not, was based on using the conductivity of the salt water in the tubing. The conductivity went to zero for a fully occluded tubing, but one case was noted where this didn't occur. This case occurred when the blood tubing was located near the gap that is between the clamp block and the occlusion plate. The leak that occurred was on an ionic scale though, as compared to a fluid leak.

The line clamp occlusion time was checked to ensure that an air bubble will be stopped before reaching the line clamp. The maximum time to occlude the blood tubing was 32.6 milliseconds. This time is in agreement with previous measurements taken on the life test line clamps.

The ability to occlude against 30 psig (1551 mmHg.) is over double the allowable venous pressure of 600 mmHg.

The calculated occlusion time necessary to stop a bubble at a blood flow rate of 700 mL/min is 70 milliseconds. The measured time is less than half of this value, therefore the bubbles will be stopped before they reach the line clamp.

Level Adjusters

The function of the level adjuster assembly is to provide positive and negative pressure to the arterial and venous drip chambers in order to adjust the levels of blood in the extracorporeal blood path. It is composed of a peristaltic pump driven by a reversible gearmotor. The output of the pump is connected to a valve manifold which directs the pumping action to either of two paths. The assembly is made up mainly of off-the-shelf components, and development consisted largely of selecting components which had the desired characteristics.

Principal areas of development were as follows:

Pump Cartridges

The pumps used feature replaceable tubing cartridges. Tubing of different materials and sizes were compared. Considerations included adequate pumping rate at the desired maximum positive and negative pressures (+600 and −300 mmHg, respectively) and durability. We found that a 5 mm ID silicone tubing cartridge best fulfilled our needs. This cartridge provided a worst-case pumping rate (at −300 mmHg) of about 20 to 30 mL/min. Life testing showed that the tubing's expected life was well in excess of a recommended yearly replacement interval.

Gearmotor

The requirements here were adequate torque, reasonable power consumption, and sufficient durability. We tested three motors. A 12 Vdc worm-gear drive motor functioned well enough but had excessive current requirements. A 24-volt version of the same motor solved this problem but suffered from random stalling. The version that we settled on was a much smaller inline gearmotor. This motor fit into the machine better, and its noisier operation was not considered to be a handicap. Although nominally rated at 12 Vdc, the motor in the System 1000 is run on pulse-width modulated dc. The free-running voltage is about 20 volts, dropping to about 14 to 15 with the tubing cartridge loaded.

Valve Manifold

This consists of an aluminum block on which are mounted two or three miniature 2-way solenoid valves. The pump is connected to one port, and, depending on which valve is energized, the pumping action is routed to one of two or three outlet ports. Two very similar types of valves were tested. One of them (type A) proved to be prone to corrosion and jamming of the solenoid plunger. The other valve (type C) has so far been satisfactory.

Life Test Data

Most life testing was done using a relatively sophisticated fixture, controlled by a programmable controller, which caused each of two pumps under test to alternately pump to the required positive and negative pressures. The solenoid valves were alternately actuated as well. Periodically the pumping rate was measured by pumping against a constant positive or negative pressure and measuring the rate at which water was displaced in a graduated burette.

Heparin Pump

The function of the heparin pump is to precisely dispense heparin from a syringe to the extracorporeal blood lines. The linear motion used to move the syringe is produced by a simple rack and pinion drive mechanism. The pinion is driven by a geared stepper motor which provides a positioning resolution of 0.000116 inch, before mechanical compliance.

The difficulties in loading the syringe were reduced in the new design. The syringe plunger is first attached to the rack gear, which is then slid upwards until the ears of the syringe stop against the cabinet. A spring loaded arm is then used to hold the syringe in place. This process allows the heparin pump mechanism to be positioned with the syringe in place.

A very simplified approach of clutching the motor to the rack gear was used. The gearbox output shaft is used to carry the main drive pinion gear. To disengage the pinion from the rack the motor carrier/mount is pivoted away from the rack gear, therefore disengaging the pinion from the rack. This approach has only one power transmission point external to the gearbox. This minimizes backlash in the drive system, and maximizes the power transmission efficiency of the drive. This same mechanism is also used to detect the end of the syringe stroke, or an overpressure state in the syringe. The natural force that tends to separate any two gears that are transmitting a force tries to pivot the motor carrier away from the rack. To keep the motor carrier in place during injection, a spring is used to hold it down. When the linear force on the rack gear exceeds approximately 10 lbf, the motor carrier pivots away from the rack and triggers an optical switch. This switch is then use to signal an overpressure/end-of-stroke condition.

A larger speed range was achieved by going to a numerically lower gear ratio in the gearbox. This change required the use of a larger motor, but the now expanded infusion rates allow for a bolus feature. The bolus feature not only allows a bolus to be given, but is an excellent method for removing any backlash in the drive system.

Life Test Results

One heparin pump assembly was set up in an automated test fixture. The main purpose behind this life test, besides trying to find any unexpected problems, was to verify the operation of the overpressure/ end-of-stroke mode.

One problem that showed up early in the testing was the method of connecting the gearbox output shaft to the pinion drive shaft. A simple cross pin in the gearbox shaft mated into a cross slot in the pinion shaft, but the pin failed. This problem was easily solved by going to a long output shaft on the gearbox and installing the pinion gear onto it. This solution added very little cost to the gearbox, and in the process removed two parts from the assembly.

A problem did show up in the testing and operation of the overpressure/ end-of-stroke mode. The problem amounted to the high coefficient of friction at the pinion gear to rack gear interface. The friction force would build up to a point that the pinion tooth couldn't slide up the mating rack tooth. When this occurred the stepper motor would either break the gearbox, or reverse its direction of rotation. Many different combinations of rack and pinion materials were tried until an acceptable solution was found. The results of the testing are as follows, with the "number of cycles" equaling the number of cycles the mechanism work flawlessly.

| Pinion Material | Rack Material | Number of Cycles |
| --- | --- | --- |
| Stainless | Stainless | 1000 to 1500 |
| Aluminum | Stainless | 32 |
| Teflon/Aluminum | Stainless | 778 |
| Brass | Stainless | 5875 |
| Teflon/Stainless | Teflon/Stainless | 12803* |
| Teflon/Stainless | Stainless | 11843* |

* Denotes that the test was stopped without a failure.

The Teflon/Aluminum is a hard anodize with Teflon impregnated into it, while the Teflon/Stainless is an electroless nickel plating and Teflon on the Stainless part.

The Teflon/Stainless pinion running on the Stainless rack was the combination of choice. With this combination the pump worked extremely well and with 11843 cycles, that works out to be approximately 19 years of life at four end-of-stroke cycles a day.

Qualification Test Results

The overpressure/end-of-stroke test was conducted using a 20 cc Monojet syringe at the 'bolus' rate, and at 5.5 mL/h.

| Infusion Rate | Average Pressure | Standard Deviation |
| --- | --- | --- |
| Bolus | 28.3 psig | 0.646 psig |
| 5.5 mL/h | 23.6 psig | 0.418 psig |

The calculated minimum shut off pressure for this syringe was 20.3 psig. The results of the 5.5 mL/h rate are an acceptable 16.3% above the minimum. The higher pressures seen at the 'bolus' rate are due the greater speed at which the infusion takes place.

Blood Pump

The blood pump is a peristaltic pump. It consist of a rotor, a U shaped race which is built into the front of the machine and a tube segment which is part of the disposable blood tubing that is changed each treatment.

The rotor has two rollers mounted on pivoting arms. Each arm has a spring which forces the roller out toward the race, compressing the tubing. The outward movement is limited by a stop screw. This adjustment prevents large movements of the arm as it moves on and off the tubing.

The race is built into the machine. It is backed up by gussets to improve rigidity. The blood pump segment is made from clear PVC. Blood pump segments of 6, 7, and 8-mm ID and 1/4-inch ID can be accomodated.

Test Results

A test was done to determine the occlusion force of the roller on the tubing. The force required on the roller to just lift the pivot arm off the screw stop was 9.8 to 10 lbs.

A series of tests were done to characterize the performance of the blood pump over the specified range of inlet and outlet pressures and nominal pump rates. These tests were run with both the 0.25-inch ID and 8-mm ID pump segments.

The results showed that the pumping accuracies over the entire range of inlet and outlet pressures compared favorably with previous blood pump designs.

Flow Equalizer

The flow equalizer has two primary functions, which are closely related. It controls an equal flow to and from the dialyzer as part of the ultrafiltration control system. It also controls overall flow through the machine as part of the proportioning system.

The flow equalizer works in conjunction with the UF removal flow meter to control ultrafiltration. If flows to and from the dialyzer are equal, any additional fluid that is withdrawn between the two flow control points must come from the blood through the dialyzer membrane. The UF removal flowmeter provides this function by accurate metering fluid out downstream of the dialyzer before it re-enters the flow equalizer. Depending on the UF removal rate the dialysate pressure automatically goes to a pressure sufficiently lower than the blood pressure in the dialyzer such that the prescribed UF removal flow is drawn through the dialyzer membrane.

The desired accuracy of this device is much better than any flow control device on the market. According to our design specification it should maintain flow to the dialyzer to within ±0.5 mL/min of flow returning from the dialyzer. With dialysate flows up to 1000 mL/min that is an accuracy of ±0.05%.

This accuracy is attainable by the nature of the device. It is a cavity separated into two chambers by a diaphragm and valved such that fluid entering one side displaces the same volume which exits the other side. There are two of these devices so that, in one, incoming fresh dialysate displaces an equal amount of fluid to the drain while, in the other cavity, fluid returning from the dialyzer displaces an equal volume of fluid going to the dialyzer. By switching these functions between the two cavities, a relatively constant flow can be maintained.

There are three categories of flow equalizer inaccuracies; air leak in or fluid leak out in the controlled volume between the flow equalizers, leakage through the valves, and compliance in the flow equalizer. The first problem is fairly easily detected visually and is primarily a maintenance issue. Leakage through the valve is an important design issue since it is difficult to detect and correct.

Compliance is also a design issue. It is an error that is caused by volume difference associated with pressure. At the beginning of a flow cycle of the block that is connected the dialyzer, the full side is pressurized to about 15 psig. This occurred on the previous cycle at end of stroke and was controlled by the supply regulator. The empty side is at approximately drain pressure. After flow has cycled through the dialyzer the returning fluid side goes up to about 15 psig as controlled by the input pressure equalizer. The output side after emptying goes to dialysate pressure approximately. Therefore inaccuracies occur due to differences in the supply pressure and the input pressure equalizer pressure or due to differences in pressure going out to the drain and out to the dialyzer.

The input pressure equalizer very accurately controls pressure of fluid returning from the dialyzer to the supply pressure. This is accomplished by a device that has a chamber separated by a diaphragm which has a valve mounted on one side. Flow from the supply regulator flows through one side. Fluid returning from the dialyzer flows through the other side. Recirculation flow around the dialysate pump is controlled by the valve. At end of stroke the full pump flow is recirculated and therefore pressure can very accurately be controlled.

Both pressures of fluids exiting the flow equalizer are controlled by the output pressure equalizer. It has a chamber separated by a diaphragm with valves attached on both sides. The two fluids enter on each side of the diaphragm and exit through the ports controlled by the two valves. Therefore the flow stream going to the higher pressure forces the diaphragm to the other side, restricting flow and creating a pressure drop that boost the pressure to equal the pressure on the higher side.

The flow equalizer controls overall flow through the machine. This flow could vary as much as 10% with no problems if it were not for the fact that it is part of the proportioning system. It meters dialysate flow while two concentrate pumps meter concentrate into the flow path. They work together to accurately control proportioning ratios. According to the design specification the proportioning ratio should be accurate within ±2%. This ratio accuracy is dependent on flow equalizer accuracy (F) and concentrate pump accuracy (C). For acetate proportioning there are 35 parts of dialysate per part of acetate concentrate so the ratio accuracy is $$\frac{35(1+F) - 35}{(1-C)\,35} = 0.02$$

$$F = .02 - 1.02C$$

If concentrate pump accuracy is assumed to be ±1.4%, which is very generous, flow equalizer accuracy has to be ±0.57% which is also easily accomplished In addition to accurately proportioning the fluids, they must also be well mixed to maintain a relatively constant conductivity. This objective is achieved partially by having mix chambers, but also by maintaining a fairly constant flow through the machine. It is desirable, then, to have the diaphragms reach end of stroke at very near the time for the valves to switch. This controlled no flow time must occur when flow is varied from 500 to 1000 mL/min and dialysate pressure changes from −400 to +600 mmHg. It is accomplished by a system that incorporates pressure equalizers, end of stroke sensors and speed control on the supply pump.

The pressure equalizers control both input pressures to be equal and both output pressures equal. Since both blocks are identical there is an equal pressure drop across a equal restriction and therefore equal flow.

The end of stroke sensor, which are thermistors mounted at the outlets to the flow equalizer sense the abrupt change in flow at end of stroke. Based on a comparison of time until end of stroke with required time until valves switch the speed is controlled to the supply pump. The system attempts to control no flow time to 1 second. If time for valve switch comes before the end of stroke has been sensed, the proportioners are stopped until an end of stroke occurs and then the valves are switched. This procedure preserves the proportioning ratio while allowing the flow to drop.

Test Data

Valve Leakage

Valve leakage was tested at both the inlet and outlet. Out of 8 valves, the minimum pressure that caused leakage was 50 psig. Outlet pressures exceeded 100 psig with no leakage.

The data demonstrates that the valves far exceed their requirements. They will be exposed to a maximum of 20 psig in the machine.

Due to their construction the type M valves function much better than diaphragm valves that have been used in this application. The diaphragm valves are very sensitive to outlet pressure which is exposed to the whole diaphragm area and provides a substantial force. Due to the bellows design outlet pressure provides no vertical force on the valve stem. The advantage of this feature was demonstrated by no leakage with outlet pressures exceeding 100 psig.

Flow Equalization Accuracy

Accuracy test were performed throughout the project. Accuracy ranged from −12 to +6.6 mL/h at 750 mL/min flow to −14.4 to +33.6 mL/h at 750 mL/min flow. On the first clinical machine the error increased to +60 mL/h.

A fairly extensive investigation revealed that this accuracy reduction has two causes. There was a compliance error due to flexing of the wall on the flow equalizer block. These blocks were somewhat thinner due to two dimensions which were slightly out of specification but had been accepted.

Also this flexing problem may have existed before but was masked due to better pressure matching by the output pressure equalizer. The output pressure equalizer was capable of maintaining equal pressures during no flow at end of stroke previously because the valve was better able to prevent pressure leaks. The valve size had to be increased, though, due to a reliability problem. This change decreased its sealing ability.

The accuracy problem was partially corrected by sandwiching the block between two 3/16 inch stainless steel plates. To prevent the block from being sucked in under a vacuum, a 1.5 inch diameter disk 0.005 inch thick of double sticky tape was applied at the center between the outer blocks and the steel plates and between the two center blocks.

Additional accuracy improvement was achieved by changing the seat on the output pressure equalizer to reduce its surface area in contact with the valve. The changes brought the acurracy back within the design specification of ±30 mL/h.

Flow Control

Two complete flow paths have been operating 24 hours per day. One has operated for about 15 months and the other for 12 months. One flow path ran on concentrates for 1 month. It was bleached regularly on a daily basis for six months. The valves have operated flawlessly.

UF Removal Flowmeter

The UF removal flowmeter consists of two identical cavities separated by a thin elastomer diaphragm. Each of the cavities is connected to the common port of a 3-way solenoid valve. When one of the valves is actuated and a fluid under pressure is applied to the normally closed port, the associated cavity fills, forcing the diaphragm against the wall of the opposite cavity and forcing any fluid in that cavity out through the normally open port of the associated valve. When the first valve is released and the other valve is actuated the diaphragm moves back, forcing fluid out of the unpressurized side of the flowmeter. Since the amount of fluid released with each movement of the diaphragm is always the same, this device can be used to very accurately meter the flow from inlet to outlet.

Areas of Development

*Design of Cavities*

It was necessary to determine the optimal cavity volume, which had to be small enough to provide good resolution of flow measurement and large enough to reduce the importance of valving errors. A cavity volume of 1 to 1.5 mL was found to be suitable.

Cavities with smooth surfaces were found to lead to unpredictable diaphragm movement, so various patterns of grooves were tested. A single pair of diametrical grooves proved satisfactory.

Initial testing with three connector passages joining each cavity to the valve port showed poor purging of fluid from the flowmeter, and a single passage near the top of the cavity gave best results.

A related problem was providing a sealing surface between the cavities. Since the diaphragm is a soft elastomer, it was important to avoid concentrated squeeze on it. It was found that good results could be obtained by using essentially flat sealing surfaces, with a very small (<0.01 inch) sealing ring. If assembly torque was controlled to 7 to 9 in-lb, repeatable performance was possible.

*Diaphragm*

The main considerations for diaphragm selection include resistance to swelling or degradation by heat-clean temperature fluids and by disinfectants. Although the chemical environment is less severe than that found in the proportioners (the disinfectants are diluted 34:1) the thinness of the diaphragm material exacerbates the effect of fluid contact. In the course of development we tested various materials including EPR, EPDM, and silicone. Most materials tested swelled so much after prolonged fluid contact that the diaphragm tended to get creases and folds, resulting in erratic stroke volumes. Eventually we found a particular formulation of silicone rubber which showed no water absorption or swelling after several weeks of immersion in the whole range of fluid environments.

Other important considerations are physical properties including stiffness and tear resistance. An excessively high durometer material will not readily conform to the cavity shape, while an excessively soft material becomes severely deformed by the pressure of the sealing surfaces, becoming extruded into the cavity and resulting in wrinkles. The Silicone material in a 0.020-inch thick sheet has proved to be the best so far.

Valves

A prime requirement for the UFR flowmeter control valve is minimum actuation time. This is because of the large pressure differential across the valve. All the valves tested are make-before-break, and there is an interval when the inlet and outlet ports are connected directly. Testing showed that there was a small net stroke volume error directly related to the pressure across the valve. In some early tests we used four 2-way valves with a small delay between the closing of one pair and the opening of the other pair. The amount of improvement did not justify the added complexity. Instead, the flow path design was changed to reduce the required pressure drop across the valves to less than 5 psi. At this value the flow through error becomes exceedingly small.

Another consideration for the valve is durability. A typical valve must be able to withstand continuous immersion in water, dialysate, or disinfectant solution, as well as periodic exposure to temperatures in the range of 90 to 95°C.

Initially a type MS valve was used, but the valve was unable to withstand the operating conditions for suitable lengths of time. Eventually the same type M 3-way valve, used in the proportioners was substituted. These valves have superior flow and flow through characteristics, and are rated for 50 million cycles. They have performed faultlessly in the life testing.

Gear Pumps

Description

There are three magnetic drive gear pumps in the System 1000 hydraulic system, the deair, supply, and dialysate pumps. They have a cylindrical 316 stainless steel housing with two 1/8 inch NPT ports positioned radially at 180° to each other. The 1/2-inch long gears are molded from carbon filled polyphenylene sulfide. The central gear is connected through a shaft to a teflon coated cylindrical magnet which is surrounded by a stainless steel cup. A ring shaped magnet which is attached to the motor shaft surrounds the cup and provides a magnetic coupling. This coupling allows a completely enclosed pump with no seals.

Deair Pump/Dialysate Pump Assembly

The deair and dialysate pumps are mounted on the same 24 V dc motor, at opposite ends.

The deair pump draws the water/"A" concentrate mixture from the air gap chamber at atmospheric pressure through the sprayer where it drops to −500 mmHg at the pump inlet. The voltage to the motor is calibrated to provide this pressure while the machine is operating at 1000 mL/min flow.

The deair pump exhausts to the air trap where air bubbles out. That amount of fluid which is in excess of the required flow, recirculates from the air trap into the air gap chamber. Both of these chamber provide mixing for "A" concentrate and water.

If RPM's to the deair pump remain constant, its flow would never change since it draws from a fixed pressure through a fixed restriction and delivers to a fixed pressure. Its flow will change somewhat, however, due to changes in load on the dialysate pump. The desired flow of the deair pump is about 1.5 L/min. This flow provides recirculation flow of 500 L/min at the maximum flow of 1000 mL/min and therefore provides good concentrate mixing.

The dialysate pump draws from the dialyzer which can have pressure from −400 to +600 mL/min. At its outlet is a restriction which provides a pressure of 11.5 to 28 psig to the UF removal regulator depending on dialysate flow and pressure.

Flow through the dialysate pressure pump should be well in excess of 1000 mL/min to assure good pressure regulation by the input pressure regulator. If the flow exceeds 1.4 L/min, there should be good pressure regulation with a wide safety margin.

The supply pump is controlled to provide end of stroke at very near end of time as described in the flow equalizer report. It draws from the air trap and therefore always has an inlet pressure of slightly under atmospheric pressure. Its outlet pressure is a maximum of about 14 psig during flow and 16 psig at end of stroke. Since it has the same motor as the double ended motor it has a capacity well in excess of its required flow.

Test Results

Testing was conducted on the bench to determine the capacity of the two pumps under a range of conditions. Initially we looked at flows after calibrating the motor voltage to provide −500 mmHg deair pressure which set the deair pump flow. Dialysate pump input pressure was controlled at −400 mmHg while varying output pressure.

As dialysate pump output pressure was increased from 6 to 25 psig and voltage was increased to maintain deair pressure, dialysate pump capacity dropped from 1500 to 1269 mL/min. The required motor voltage went from 18.10 to 20.58 V.

The flows are acceptable at high pressure. Pressure studies showed that output pressures during flow range from 20 to 25 psig as dialysate pressure was changed from 50 to 500 mmHg. With the pressure equalizer in place output pressure of the dialysate pump at −400 mmHg dialysate pressure should be very near those at 500 mmHg since the output of the flow equalizer is being boosted to drain pressure. The flow under these conditions dropped to 1332 mL/min which would provide 332 mmHg of recirculation. That rate should be sufficient for good pressure regulation.

A test was done to determine how deair pressure and deaeration might be affected by hydraulic changes that the dialysate pump is exposed to and due to voltage tolerance. The deair pressure was calibrated at 700 mL/min flow and 0 mmHg dialysate pressure. The deair pressure ranged from −452 to −520 mmHg due to the changing load on the dialysate pump from the extremes; −400 mmHg dialysate pressure and 1000 mL/min flow to +400 mmHg and 500 mL/min flow. The $pO_2$ ranged from 111 to 128 which is within the desired range. When ±10% voltage tolerance is combined with the range of hydraulic conditions, the deair pressure goes from −385 to −615 mmHg and $pO_2$ from 88 to 143. Other dialysis machines sold in the US have been tested and $pO_2$ values of 150 and above were found.

The sprayer restriction has a major impact on deair and dialysate pump flow since the motor voltage is calibrated to provide a deair pressure of −500 mmHg. Therefore the pressure drop through the sprayer is 500 mmHg and the flow required to provide that pressure drop will vary with tolerances of the sprayer. That required flow along with the tolerances of the pump will determine the required RPM's of the motor. That RPM, along with the tolerances of the dialysate pump will determine the dialysate pump flow under the hydraulic conditions of for the calibration. Due to dialysate flow and pressure changes the output of the dialysate pump goes from 11.5 to 25 psig and the input goes from −400 to +600 mmHg. On top of all these conditions, we have a voltage tolerance ±10%.

We performed test to determine what flow variation we would see in a sample of 12 sprayers. With a 500 mmHg pressure differential the flow varied from 1788 to 1509. We determined that part of this fluctuation is due to the spray cone blocking part of the orifice when it is screwed into the block. These same sprayers were retested with a 0.020-inch thick washer, spacer installed to prevent the obstruction. The flow varied from 1654 to 1923. The flow was increased but was no more consistent.

This flow range is somewhat high and may be difficult to achieve with the motor that we are using. We decided to go to the next smaller size nozzle. The first nozzle was rated at 0.50 gal/min at 10 psig. The next smaller one is rated at 0.41 gal/min at 10 psig. Based on our current average flow of 1740 mL/min multiplied by the ratio of the rated flows we should expect an average flow of 1426 mL/min.

Pressure Regulators

There are five pressure regulators in the flow path; water pressure, supply, and UF removal regulators, and the input and output pressure equalizers.

Many of the parts are common to the various regulators. The supply regulator and input and output pressure equalizers use the following common parts; body, diaphragm, valve stem, diaphragm backing plates, and hardware. The supply regulator uses the same spring adjustment part as the type A regulator.

The water pressure regulator is brought off the shelf. The supply pressure can be set at 7 psig. The pressure requirement is merely enough to overcome the restrictions of the inlet water valve, heat exchanger, heater, and supply valve before dropping into the air gap at atmospheric pressure.

The supply regulator is a spring adjusted pressure relief valve. When the force of fluid pressure on the diaphragm area exceeds the spring force the supply regulator valve opens and allows recirculation back to the input of the supply pump. During a stroke of the flow equalizer, the supply regulator valve is closed and the pressure is controlled by voltage (RPM) to the supply pump. At the end of stroke, pressure in the supply regulator climbs to its adjusted set point and the valve opens to recirculate the full flow of the supply pump.

The input and output pressure equalizers work similarly and their function is described in the flow equalizer report.

The UF removal regulator provides a relatively constant pressure of 5 psig to the UF removal flow meter. There is a flow restriction down stream of the dialysate pump which must provide a pressure at the inlet to the UF removal regulator that is above its control pressure. It receives a pusitile flow controlled by the 1.5 mL strokes of the UF removal flow meter. Its input pressure varies with dialysate flow and pressure.

The regulator is borrowed from the 480 where it serves a similar function. The spring was changed to allow a slightly higher control pressure. This was necessary to assure that the higher 4 L/h UF removal rate could be achieved.

Results

The water pressure regulator is the same as the one in the 480 and is used in the same application so no specific testing was done on it. It is set at 8 psig in the clinical machine.

The supply regulator is set to 16 psig. This pressure is sufficient to provide full flow at 1000 mL/min and 400 mmHg dialysate pressure.

The latest valve stem in the supply regulator has been in the B prototype hydraulics for 4 months. It is in this regulator that the stem is forced against the seat the hardest since it must resist the full spring force when there is no pressure under the diaphragm. This force is about 25 lb. Inspection of the valve reveals a ring where it contacts the orifice but no major deformation.

An extensive test was done to observe on a chart reorder the four pressures of the two pressure equalizers under the full range of hydraulic conditions in a simulated treatment. Pressures were monitored at flows of 500, 800 and 1000 mL/min and dialysate pressures of −400 to +600 mmHg. Dialysate pressures were achieved by adjusting blood flows and UF removal rates.

The two input pressures tracked beautifully at all dialysate pressures and flows of 500 and 800 mL/min. The dialysate pump side dropped lower than the supply pump side at 1000 mL/min flow. They tracked well at +600 mmHg dialysate pressure but the differential increased from 1 to 7 psi as the dialysate pressure went from 300 to −400 mmHg. This phenomenon is due to insufficient capacity of the dialysate pump. It can be corrected by increasing the voltage to the double pump motor.

Pressures up and downstream of the UF removal regulator were tested under the same conditions as the pressure equalizer test. The minimum input pressure of 11.5 psig occurred at 500 mL/min flow and a negative dialysate pressure. The maximum pressure of 28 psig occurred at end of stroke when flow was set at 1000 mL/min and dialysate pressure was 500 mmHg (the maximum tested). The output pressure remained within 205 to 280 mmHg. This minimum pressure is sufficient to provide a 4 L/min UF removal rate and the pressure differential is low enough to have a minimal impact on accuracy.

Proportioning Pumps

The design of the System 1000 proportioners combines a reciprocating plunger with a molded-on elastomeric diaphragm. The motion of the plunger is controlled by motor-driven cam and a return spring. Fluid motion is controlled by a three-way solenoid valve whose action is keyed to the plunger position. The use of a stepper motor to drive the cam allows precise control of both the speed of the pump and the operation of the valve. The cam shape is optimized relative to the mixing flowpath to provide a constant rate of infusion of concentrate.

Areas Of Development

Cam Profile

In the "A" concentrate pump the cam provides a uniform 0.1 inch lift over about 310 degrees of rotation. The plunger forces approximately 1 mL of concentrate out of the diaphragm cavity. At this point the 3-way valve is actuated and the cam radius decreases over about 50 degrees. A concentric coil spring returns the plunger to its original position at uniform acceleration. Fresh concentrate is drawn into the diaphragm cavity.

The "B" concentrate pump normally operates at a higher speed, and in order to ensure complete filling during the intake stroke, it was necessary to increase the intake duration to 180 degrees. These optimum cam profiles were arrived at after exhaustive testing of various configurations.

Extended performance testing of the cams involved measuring stroke volume accuracy over the specified range of flows and inlet and outlet pressures. Overall stroke volume accuracy (using 3.75-foot inlet line) was about ±0.6%.

Material Selection

For low-stress components such as the pump body and the plunger cartridge, primary importance was given to good chemical and temperature characteristics and resistance to cracking. For these components CPVC, Delrin, and Ultem were found to be satisfactory. The cam and cam follower materials are relatively heavily loaded, and materials such as brass, Noryl, glass-filled plastics, and Nytuff-coated aluminum were evaluated in the accelerated test fixture. Delrin AF was found to have superior durability. The metal parts of the pumps - plunger stems, cam-follower carriers, and fasteners - are made of 316 stainless. Both the accelerated cam/cam follower life test and the proportioner life test show that the selected materials will have adequate durability for the specified life of the machine.

Plunger Material

Owing to the extreme chemical and temperature environments within the pumping chamber, a great deal of work was required to find a suitable elastomer for the plunger. Eventually a precisely-defined EPDM compound was specified.

This compound has been life tested for the equivalent of 9 months of worst-case clinical use without impairment of function.

Control Valves

Important considerations in selecting the valve included:

- rapid actuation and release to minimize backflow through the valve cavity
- adequate orifice size to handle the high instantaneous fluid velocities during the inlet stroke
- resistance to chemical attack and to high temperature
- durability - life expectancy in excess of 50 million cycles Initially a type MS 3-way valve was used, but after problems with durability, it was replaced with a type M 3-way valve. Testing has shown the type M valve to have superior flow characteristics and low backflow. This valve shows chemical and temperature resistance far superior to the type MS valve.

Spring

A variety of springs were compared to arrive at the optimum combination of minumum spring force consistent with proportioning accuracy and long life. Based upon the results of these test a new spring was designed and produced. So far this spring has been tested in excess of 50 million cycles (5+ years worst-case clinical use equivalent) with no failure.

Other Considerations

- Effect of high and low inlet and outlet pressures: Both A and B proportioners are normally required to draw concentrate from a container only 2 to 3 feet below the pump, it was deemed prudent to determine the effect of a raised concentrate container on the pumping accuracy. Tests showed that raising the inlet pressure had a small but predictable effect on the stroke volume. Tests indicate that most of this error is due to backflow through the valve during actuation or release when there is a momentary uninterrupted path for fluid through the valve. A much lesser effect is in distortion of the diaphragm which tends to reduce stroke volume. Tests confirm that the stroke volume error is closely related to the actuation time of the valve being used. The currently used valve showed a maximum flowthrough per stroke of less than 0.01 mL at a pressure differential across the valve of 3 psi.

- Effect of inlet line length and diameter: There appears to be a complex interrelationship between the characteristics of the inlet line the action of the valve, and resultant stroke volume. At minimum pump rates the inlet line has no effect on stroke volume. As the rate increases, a 'supercharging' effect produces an increase in stroke volume. It appears that the rapidly moving fluid in the inlet line tends to slow the closing of the valve and to pressurize the diaphragm cavity. (In fact, the pressure pulse tends to distort the diaphragm and increase the pump capacity momentarily. This effect is documented by a set of comparisons of inlet lengths coupled with comparison of diaphragms of different durometers.) Eventually, at still higher speed, stroke volume falls off rapidly due to incomplete filling of the pump cavity. The supercharging effect is affected by inlet tube length and valve actuation time. The maximum pump rate before stroke volume falloff is directly related to inlet tube diameter. Numerous tests were carried out to quantify the errors and to arrive at the optimal inlet tube. Eventually a silicone rubber inlet line 45 inches long by 0.125 ID was decided on. This resulted in acceptable stroke volume accuracy over the desired flow range (<0.5% at 36 rpm). The above studies were done using water as the pumped fluid. It was later discovered that the use of the denser concentrate (specific gravity = 1.16) exagerated the problems, particularly the high flow dropoff. Use of a 0.187 ID inlet tube rectified the problem. Fortunately this phenomenon appeared to be limited to pumps using the type S valves. When the type M valve was substituted the net error (supercharging vs. dropoff) at 900 mL/min flowrate was about 1% with either size tubing.

- Effect of inlet concentrate filter: A filter on the concentrate inlet line is to prevent particulate matter from damaging the valve seal or entering the flowpath. The two effects that such a filter can have are increased negative pressure on the valve inlet (both initially and after extended use) and effects associated with the trapping of a volume of air inside the filter. A number of filter types were tested and found not to affect proportioner performance significantly.

Test Fixtures

A number of test fixtures were developed in order to evaluate the performance and durability of various designs, components, and materials. These included the following:

1. PC-based controller circuits which allowed controlling the motor speed and valve action of the proportioners. These were used in conjunction with various mass-measurement fixtures to track pump stroke volumes and pump rates. In some tests there were additional provisions for producing variable inlet and outlet pressures.

2. A motor driven test fixture on which up to eight cams could be mounted and rotated at accurately controlled speeds. The fixture included provision for testing the springs and the cam follower assemblies. With this fixture it was possible to run accelerated tests on the above components and to arrive at opitimal configurations and materials in a relatively short period of time.

3. A life test fixture using valves, heaters, and a programmable controller. With this fixture it was possible to simulate all of the chemical and temperature environments to which the proportioners would be subjected to in clinical use. Over the past seven months this fixture has been used to determine the durability of the proportioners (particularly the plunger diaphragms and the valves) as well as to evaluate such ancillary components as concentrate filters. While such a fixture necessarily must operate under real-time conditions, some of the components have been under test for the equivalent of 9 months clinical usage.

In addition to the above described fixtures, proportioners were mounted in a series of hydraulic prototype modules as well as in the first of the clinical prototypes. Over a period of months, upward of 6000 hours have been accumulated on the various proportioners.

Dialysate Flow Control System Performance

Description

The purpose of the dialysate flow control system is to accurately control the dialysate flow rate in the System 1000 machine and minimize the flow dead time between flow equalizer valve switches. The System 1000 machine utilizes a double acting diaphragm metering device (referred to as the flow equalizer) to match the volume of dialysate delivered to the dialyzer with the volume of dialysate pumped back from the dialyzer.

The System 1000 flow path contains three pumps, two of which are powered by the same motor which runs at a constant speed (deair and negative pressure pumps). The deair pump is situated in a flow loop with the deair sprayer (directly after the A mixpoint) to produce a low pressure that removes the dissolved air in the water being prepared as dialysate. The negative pressure pump is in the post dialyzer flow circuit and provides the pressure which draws the fluid from the dialyzer and delivers it to the flow equalizer. This pump runs at a constant speed and has a recirculation flow path around it so that the flow through the pump remains constant even though the flow equalizer flow is pulsitile. The supply pump the pump which supplies the fresh dialysate flow to the flow equalizer. This pump's speed is controlled to accomodate different dialysate flow rates.

Since the flow equalizer has a fixed volume, the time between valve switches determines the dialysate flow rate provided that the total volume of one side of the flow equalizer has been filled and the other side emptied. To ensure a complete volume transfer in the flow equalizer, flow sensors (End of Stroke Sensors) have been strategically placed in the flow path to sense when the flow stops (End of Stroke). The valves will not switch before the end of stroke condition is sensed (unless a secondary timeout condition is encountered). The speed of the supply pump determines the instantaneous flow rate of the dialysate and is controlled so as to minimize the end of stroke time (the time remaining in the flow cycle until valve switch). In this way, complete flow transfer of the flow equalizer is guaranteed every flow equalizer cycle and the dead time is minimized.

Test Data

The flow control system testing was split by function into six different parts.

Dialysate Flow Rate Accuracy

The dialysate flow rate accuracy was tested by first calibrating the flow rate using the calibration routine, then gravimetrically measuring the dialysate flow rate (drain flow rate) at different set flow rates. The testing illustrated a maximum dialysate flow rate error of less than 0.5%.

End of Stroke Reliability

The end of stroke reliability was tested by recording the number and frequency of the end of stroke errors that occur upon flow rate changes and dialysate pressure changes. The end of stroke errors consist of four different errors:

*No flow alarm*

This error is reported when no end of stroke signal is sensed before the secondary flow cycle timeout occurs for four consecutive flow cycles.

*Early end of stroke on sensor 1*

This error is reported when sensor 1 senses an end of stroke condition before half of the flow cycle time has elapsed.

*Early end of stroke on sensor 2*

Same as above, except for end of stroke sensor 2.

*Too much time between end of stroke signals*

This error is reported when there is more than 2.55 seconds between the end of stroke signals.

Dialysate flow rate changes produced one set of early end of stroke errors (sensors 1 and 2) only when stepped from low to high flow. This condition is explainable by the fact that when the flow rate is stepped up the supply pump drive voltage is instantly increased to accommodate the higher flow rate yet the flow equalizer valve period left over from the lower flow rate is still counting down thereby creating the early end of stroke condition. In summary, the end of stroke errors occur very seldom and are not considered likely enough or important enough for machine response. For trouble-shooting purposes the machine will display the errors in technician mode only.

End of Stroke Dead Time Control (distribution around desired)

End of stroke dead time control testing was done in two tests. In the first test, the end of stroke time for each sensor was logged for a period of 45 minutes as two flow rate steps at 15 minute intervals were imposed on the machine. The second test was the same as the first except two dialysate pressure steps were introduced at 15 minute intervals. The end of stroke tests showed that the worst case step response to any of the above conditions was after the high to low flow rate step which took a total of 7 flow equalizer cycles to fully return back to the previous steady state conditions (at 500 mL/min flow rate 7 flow equalizer cycles takes a total of 95 seconds).

No Flow Alarm

The no flow alarm testing involved disabling the supply pump in the System 1000 machine after the flow rate stabilized and measuring the number of flow equalizer cycles that occur before a no flow alarm error is displayed. With the supply pump disabled the machine will not have any dialysate flow and will not sense end of stroke. If end of stroke is not sensed the machine waits only 5 seconds after the time it expects the end of stroke signal and then switches the flow equalizer valves (secondary flow equalizer timeout). The above test repeatably indicated that after four secondary flow equalizer timeouts the no flow alarm error is reported.

Closed System Integrity

Power Derating of Components

The deratings of the components involved with the flow control system were calculated under worst case conditions for each component. The components involved include:

Supply pump drive circuitry

Deair/negative pressure pumps drive circuitry

Flow equalizer drive circuitry

Rinse valve drive circuitry

End of stroke sensors and drive circuitry

Toxicity Testing

The toxicity testing consisted of three parts: a biological reactivity test, hemolysis test, and heavy metals test. These tests were performed on a sample of a 24 hour 3 liter recirculation water extract of the entire dialysate flow path. The biological testing was comparable to the Elution Method of USP XXII "Biological Reactivity Test" #87; the mammalian cell line was MRC-5, human embryonic lung tissue. Hemolysis testing was performed using rabbit blood and the amount of hemolytic activity of the extract was measured. The test for heavy metals was based upon USP XXII "Heavy Metals Test" #231. The flow path extract (undiluted) passed all three tests. It was found to be non-toxic to the cells and induced less than 5% hemolysis; the total concentration of heavy metals was less than 10 ppm.

Exhibit 4
Preliminary Draft System 1000 Maintenance Manual
Drake Willock System 1000
Single Patient Delivery System
Maintenance Manual
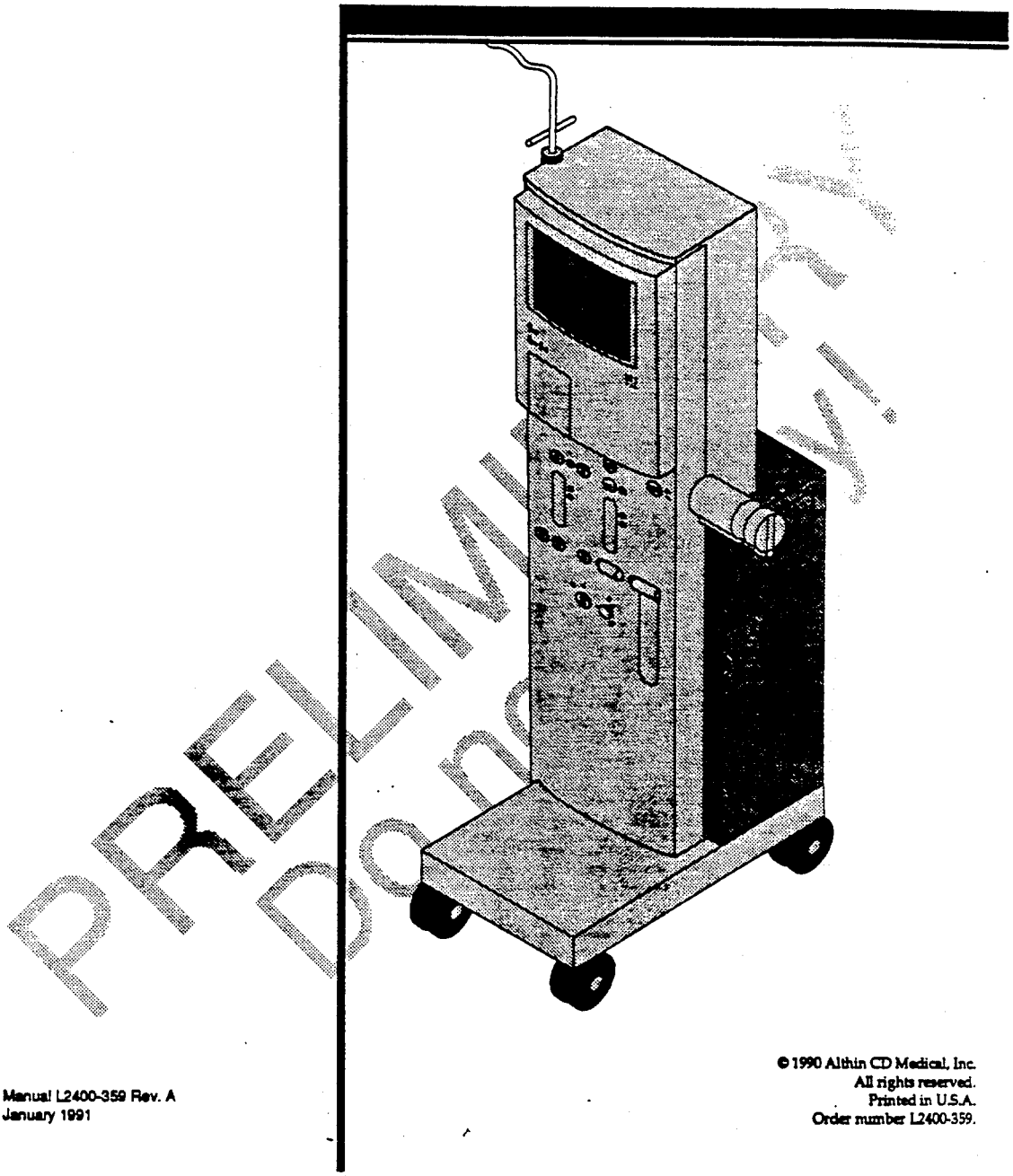
Manual L2400-359 Rev. A
January 1991
© 1990 Althin CD Medical, Inc.
All rights reserved.
Printed in U.S.A.
Order number L2400-359.

WARNING

This device is manufactured and intended for use only as prescribed by a physician. Modification, alteration, or lack of maintenance procedures as described in the labeling, may adversely affect the safety and efficacy of this device. The manufacturer is not responsible for malfunctions that compromise patient safety as a result of alteration, neglect, or misuse.

Replacement parts may vary from those shown in this manual. Should you have questions on those parts please contact Althin CD Medical, Inc.

The actual appearance of the machine may vary from the illustrations in this manual.

This publication may not be reproduced, stored in a retrieval system, or transmitted in whole or in part, in any form or by any means, electronic, mechanical, photocopying, recording, or otherwise, without the prior written permission of Althin CD Medical, Inc.

™ Trademark of Althin CD Medical, Inc.
Drake Willock is a trademark of Althin CD Medical, Inc.

— The Althin Group —

Althin CD Medical, Inc.
Drake Willock Division
13520 S.E. Pheasant Court
Portland, Oregon 97222

Phone
503-659-3355
800-547-5534

Telefax
503-652-0225

Table of Contents

Introduction

Product Description ............................................................................................................1
Prerequisites ..........................................................................................................................1
Indications .............................................................................................................................1
Contraindications .................................................................................................................1
Product Improvement Policy .............................................................................................2
Technical Support ................................................................................................................2
Maintenance Manual ...........................................................................................................2

Safety Summary

Cautions ..................................................................................................................................1
Warnings ................................................................................................................................1

Introduction

Product Description

The Drake Willock ™ System 1000 is a single-patient hemodialysis delivery system, which will provide dialysate at the prescribed temperature and ionic concentration to be used for hemodialysis treatment. It will have the ability to monitor machine, dialysate and blood circuit functions during dialysis. The machine is based on volumetric proportioning, volumetric ultrafiltration and digital electronics. The machine and treatment parameters are displayed on a CRT (video monitor). The operator control is done through a interactive touch screen which also makes the machine very easy to clean and use.

The machine has an automated self test prior to the start of each dialysis, this ensures that all of the essential monitoring and alarm functions of the machine are tested before each patient treatment. The automatic self test eliminates the risk that a busy clinician will forget to perform the required machine checks prior to each treatment.

To enhance treatment quality assurance, the machine records essential treatment data such as actual treatment time. This actual treatment time clock stops when alarms interrupt dialysis by stopping the blood pump or bypassing the dialysate around the dialyzer. One of the major problems with the dialysis treatments given today is the non-delivery of the prescription (e.g.; the patient is taken off treatment 5 minutes early, repeated alarms stop the blood pump or divert the dialysate to drain stopping the treatment). The data report allows the operator of the machine to know the precise time spent on dialysis enabling the clinician to determine if the dialysis prescription was delivered.

Prerequisites

The service technician must:

- have a basic knowledge of electronics and hydraulics.
- have a basic knowledge of troubleshooting and preventive maintenance techniques.
- be thoroughly familiar with the contents of the operator's and maintenance manuals for this machine and all accessory devices that will be used with this machine.
- be sufficiently trained in the operation and maintenance of this machine and able to distinguish normal from aberrant machine behavior.

The System 1000 Single Patient Delivery System must:

- be in good working order and certified as such by the attending physician.
- be operated only in accordance with the machine specifications listed by Althin CD-Medical and with the operating instructions contained within the System 1000 System Operator's Manual and machine labeling. The attending physician is responsible for any changes to the procedures.

Indications

The System 1000 Single Patient Delivery System is indicated for use when a parallel flow dialyzer is chosen for use in chronic or acute hemodialysis treatments.

Contraindications

The System 1000 Single Patient Delivery System is not designed, sold or intended for any use except as indicated above. Furthermore, it is not intended to be used outside of the device specifications or limitations.

The System 1000 Single Patient Delivery System is not intended to be a substitute for the monitoring of the patient or of the patient's extracorporeal blood circuit by qualified personnel.

Product Improvement Policy

Drake Willock dialysis equipment was designed and built to the performance requirements stated in the product specifications.

It is the corporate policy to perform continuous product improvement research that often results in modifications to enhance patient safety or treatment effectiveness without incurring any obligation to make the same or similar changes to all equipment previously built and/or sold. When such improvements occur we will, from time to time, inform the owners of Drake Willock dialysis equipment and offer any available upgrades at reasonable prices. These upgrades, however, should not be construed as corrections of deficiencies, as the equipment met all the original product specifications when delivered.

Any product which, in the opinion of Althin CD Medical proves not to have met product specifications will be remedied by us.

Should pre-owned Drake Willock equipment be purchased and reconditioned, the equipment should not be used until testing and analysis demonstrate that the equipment meets the original or upgraded specifications.

Technical Support

Althin CD Medical offers technical support, technical training, consultation and machine service upon request. Contact your local Althin CD Medical service representative for additional information.

Maintenance Manual

This manual provides the qualified service technician with readily-available information regarding the Drake Willock System 1000 Single Patient Delivery System, its care, theory of operation and preventive maintenance. This manual includes information and instructions for all of the options of the System 1000 Single Patient Delivery System. Please disregard those sections of the manual that refer to features not in your machine.

This manual may be propped up for easy reference by opening the front cover then folding back the lower portion of the cover to form an easel.

A glossary of terms and abbreviations used in this manual is included in the Appendix.

Replacement Parts and Electrical Schematics manual packets are available upon request.

Safety Summary

This summary does not contain all the safety statements in this manual. Other warnings and cautions are included within the manual text.

Cautions

A CAUTION is a statement identifying conditions or practices that could result in equipment or other property damage.

Warnings

A WARNING is a statement identifying conditions or practices that could result in personal injury or loss of life.

WARNING  Maintenance should be performed by qualified service personnel only.

WARNING  Federal law restricts this device to sale by or on order of a physician.

WARNING  Do:
- read the operator's and maintenance manuals prior to servicing this machine.
- keep this and other associated manuals readily available for use by new operators or qualified service personnel.
- use the proper power cord.
- refer power cord changes to qualified service personnel.
- ensure that a qualified electrician or technician inspects the machine for proper electrical grounding at installation before dialysis is initiated.

- disconnect power before removing protective panels, performing soldering, replacing components, or removing or replacing printed circuit boards.
- use fresh cleaning and disinfection chemicals.
- make sure that all modules are bolted together before moving the machine.
- unlock the wheels before attempting to move the machine.

WARNING Do not:
- under any circumstances perform any testing or maintenance of this machine while dialysis is in progress.
- cut or remove the round grounding prong from the plug.
- use any adapter device on the power cord for the purpose of plugging into a non-grounded power source.
- use an extension cord.

WARNING Do not:
- remove covers or panels when the machine is connected to a power source.
- operate the machine without covers and panels properly installed.
- remove any caution, warning or other descriptive labels from the machine.
- operate this machine in an explosive environment or near flammable anesthetics.
- perform internal service or adjustment of this machine unless another person capable of rendering first aid and resuscitation is present.
- touch exposed connections and components while power is supplied.
- use the I.V. pole as a handle for moving the machine.

CAUTION
1. Static discharge may damage electronic components.
   - Both MOS and Bipolar integrated circuits maybe damaged by discharge of static electricity.
   - Both digital and linear integrated circuits may also be damaged.
   - Static damage may occur not only to integrated circuits mounted on the circuit board, but also to detached integrated circuits.
   - Static damage may not be immediately evident.
   - Static damage is cumulative.
2. Do not remove or plug in any electronic component or assembly while power is applied to the machine.
3. Use only silicone base O-ring lubricant; other lubricants may damage the O-rings.
4. It is necessary to perform some of the adjustments with the covers removed. Use extra care to prevent fluids from entering or contacting the electronics of the machine.

Machine Disinfection

Althin CD Medical, Inc. recommends the use only of disinfectants and cleaning agents that are specifically mentioned in the pertinent sections of this manual.

Other products on the market, besides the disinfectants we recommend, are being used with apparent success by some customers. Since these products may contain chemicals that might degrade or destroy components of the machines, or cause other problems, Althin CD Medical, Inc. assumes no responsibility for equipment damage resulting from the use of such products. The merits of each product should be evaluated by the user before purchase.

Althin CD Medical, Inc. will provide information upon written request regarding known machine incompatibilities with specific products.

WARNING   If alternate disinfectants are used, be sure to test the dialysate for residual disinfectant before each connection of a patient. Use a test method specific for the disinfectant and that is sensitive enough to produce accurate determinations of "safe" residual levels of disinfectant.

Hydraulic Theory

Overview

The hydraulic system of the System 1000 hemodialysis machine is designed to heat incoming water to approximately human body temperature, mix it with dialysate concentrate in physiologically correct proportions and infuse it through an artifical kidney to effect hemodialysis therapy. In doing this, it also accurately measures the amount of fluid entering and exiting the artifical kidney and can adjust these volumes to control the fluid removal from the patient. Operation of the hydraulic components is controlled by a microprocessor.

Dialysate Circuit

Incoming Water Pressure Regulator

After entering the bottom of the hydraulic module the water pressure is reduced and stabilized by the water pressure regulator to the factory recommended level of 20 psi.

Water On/Off Valve

When power is on, the on/off valve opens to allow water to flow into the hydraulic circuit. When the power is off, the valve is closed preventing water from entering the machine.

Heat Exchanger

Heat is transferred from the effluent dialysate to the incoming water as the two liquids pass in counter current direction in adjacent heat exchanger compartments. This heat transfer preheats the incoming water, thus reducing the time the heater is on.

Heater, Thermistor, Safety Thermostat

The water is heated to the desired temperature by a 1500 watt heater. On the output of the heater is a thermistor. The thermistor acts like a variable resistor with changes in resistance being inversely proportional to changes in temperature. The thermistor sends a signal to the microprocessors, which then turns the heater on or off to maintain or increase the temperature.

Next to the heater is a thermostat which prevents the heater from exceeding a temperature of 130°C (266°F). The thermostat turns off power to the heater to prevent damage in case of a runaway temperature circuit failure.

"A" Concentrate Pump

The acid/acetate concentrate is pumped from its container into the air gap chamber through a fixed volume cam driven pump called the "A" concentrate pump. The pump uses a stepper motor that can be calibrated to a precise number of rotations per minute. A cam on the pump shaft moves a flexible diaphragm that delivers a fixed volume of concentrate each rotation. An optical sensor on the cam verifies the cam position for the microcontroller.

Using the dialysate flowrate and the concentrate information entered into the system by the operator, the microprocessor calculates the amount of concentrate necessary to achieve correct ratios of water and concentrate(s) for hemodialysis therapy. By adjusting the speed of the cam, the pump can be controlled to deliver a prescribed volume of concentrate. The pump will automatically compensate for changes in the dialysate flow rate in the event that the flow rate is changed during the procedure.

During Rinse, the "A" concentrate line is attached to the "A" rinse fitting and receives rinse water from this port.

In the disinfect mode, the "A" concentrate line is attached to the disinfectant rinse fitting and the "A" concentrate pump delivers disinfectant to the fluid path.

Supply Manifold

The supply manifold controls the incoming water flow, mixes the "A" dialysate concentrate component, removes most of the dissolved air from the water and monitors the "A" concentrate conductivity. The supply manifold is composed of four components: the supply valve/air gap chamber, the deaeration system, the air trap and the "A" conductivity probe. This manifold also contains the inlet for the "A" concentrate pump. The "A" concentrate pump is described in another section of the Hydraulic Theory.

The "A" and "B" rinse fittings connect through a common line to the supply manifold and draw rinse water from this source.

Supply Valve/Air Gap Chamber

Heated water enters this chamber through a lever activated supply valve at the top of the cylinder. The lever mechanism is operated by a float in the adjacent air trap chamber. The float in the air trap chamber controls the flow of water into the hydraulic system by causing the air gap valve to open when the fluid level supporting the float drops and by closing the valve when the fluid level rises.

The volume of incoming water is determined by the quantity of water entering the flow equalizer. In normal operation, as the supply pump draws solution from the air trap chamber to fill the flow equalizer, the air trap float is pulled downward. Lowering the float causes the supply valve to open letting water flow into the air gap chamber during the fill cycle of the flow equalizer. When the flow equalizer is full and the supply pump no longer draws solution from the air trap, the fluid level in the air trap rises, causing the float to shut off the supply valve. This cycle is repeated during every fill phase of the flow equalizer.

The air gap at the top of this chamber is at atmospheric pressure and acts as a barrier to prevent the back flow of incoming water into the input line in the event of a drop in the incoming water pressure.

"A" Rinse Fitting

The "A" rinse fitting is located on the right side panel of the machine. This fitting is connected to the common channel of the supply manifold and uses this channel as the source of water for rinsing the "A" concentrate line. When the "A" concentrate line is attached and the power is on, this fitting supplies water to rinse the "A" concentrate line and "A" concentrate pump. During the rinse mode and when the machine is turned off, the "A" concentrate line is inserted into this fitting.

A proximity sensor built into the "A" rinse fitting senses when the "A" concentrate line is attached to this rinse fitting. Some machine functions such as the rinse cycle and the disinfect mode require specific input from this fitting before they may be activated. This input helps prevent misapplication of the equipment.

"B" Rinse Fitting

The rinse fitting for the bicarbonate line is located on the right side panel of the machine cabinet. This fitting is connected to the common channel of the supply manifold and uses this channel as the source of water for rinsing the "B" concentrate line. When the "B" concentrate line is not in use during acetate dialysis or during rinse, it is connected to its rinse fitting and recirculates the solution being proportioned.

A proximity sensor built into the "B" rinse fitting signals the microprocessor when the "B" concentrate line is in this fitting. Some machine functions such as the rinse cycle and the disinfect mode require specific input from this fitting before they may be activated. This input helps prevent misapplication of the equipment.

Deaeration System

The deaeration system is composed of the deaeration sprayer, the air removal pump and a loop that transfers the deaerated fluid from the deaeration sprayer chamber to the air trap chamber. The deaeration system is connected to the other supply manifold components by a common channel in the supply manifold. Its purpose is to remove the dissolved gases that are trapped in the water used to make up dialysate. If non deaerated water was allowed to circulate through the machine, these dissolved gasses would affect the accuracy of the fluid removal system.

The air removal sprayer facilitates the removal of air from the dialysate solution. The air removal pump moves fluid at approximately 1500 mL/min through the loop connecting it to the supply manifold and pulls the solution through the air removal sprayer nozzle at this rate. The sprayer nozzle restricts the flow so that a partial vacuum of approximately 500 mmHg is created in the air removal sprayer chamber. The water that passes through the air removal sprayer is deflected into a cone shaped spray pattern. This exposes a large surface area of water to a 500 mmHg vacuum. The vacuum decreases the concentration of air that the water can hold in solution and the large surface area increases the rate at which the air comes out of the water thus enhancing the air removal function.

Vented Air Trap

The purpose of the vented air trap is to allow air liberated by the deaeration sprayer to leave the system through a common channel at the top of the air gap and air trap chambers that is open to the atmosphere. This air trap also contains a float that helps control the flow of water into the system by means of the float/lever mechanism previously mentioned in the Supply Valve/Air Gap Chamber section.

The air removal pump loop delivers the de-aerated dialysate to the air trap chamber via a port slightly elevated from the bottom of the air trap chamber. This elevated port allows air bubbles may rise to the surface independent of the common fluid path.

"A" Conductivity Probe

Conductivity is usually defined as the ability of a solution to pass an electrical current. Measurement of the conductivity of the dialysate is used to determine that the solutions are being correctly proportioned based on the electrolyte composition of the product. The conductivity of dialysate will vary due to the temperature and the electrolyte composition of the dialysate concentrate used.

Two stainless steel electrodes positioned in the supply manifold flow path monitor the conductivity of the solution. A thermistor in one of the probes supplies the conductivity circuitry with information that is used to compensate for the effect temperature has on the conductivity reading.

The first conductivity probe ("A") in the flow path is located in the supply manifold before the "B" mix point. Tis probe measures the conductivity of the water and "A" concentrate only.

"B" Concentrate Pump

When using bicarbonate dialysis therapy, the bicarbonate concentrate is pumped from its container into the supply manifold through a fixed volume cam driven pump similar to the "A" concentrate pump. The pump uses a stepper motor that can be calibrated to a precise number of rotations per minute and a cam on the pump shaft to move a flexible diaphragm that delivers a fixed volume of concentrate per each rotation. An optical sensor on the cam verifies the cam position for the microprocessor.

Using dialysate flowrate and concentrate information entered into the system microprocessor by the operator, the microprocessor calculates the amount of concentrate necessary to achieve correct ratios for hemodialysis therapy. By adjusting the speed of the cam, the rate of flow through the pump cavity can be controlled to deliver a prescribed volume of concentrate in the ratio requested by the operator. Once it is set, the pump will automatically compensate for changes in the dialysate flow rate in the event that the dialysate flow rate is changed during the procedure.

During rinse, the concentrate motor operates at a nominal ratio of 1.8:34 and pumps 1 mL of rinse fluid to 34 mL of water to flush concentrate or disinfectant from the concentrate pump chamber. In the rinse mode, the "B" concentrate line is attached to the "B" rinse fitting and receives rinse water from this port.

Supply Pump Recirculation Loop

The supply pump recirculation loop mixes the "B" concentrate component, monitors the total conductivity, regulates the pressure and pumps the solution to the flow equalizer. This loop contains the inlet for the "B" concentrate pump, bicarbonate mix chamber, the "B" conductivity probe, the supply pump, the supply regulator and a dialysate filter (optional.) The loop configuration helps to mix the bicarbonate concentrate by recirculating the solution through the "B" mix chamber. The loop also acts as a conduit for flow that is diverted by the pressure supply regulator at the end of each flow equalizer fill cycle.

"B" Mix Chamber

During hemodialysis therapy, the solution that enters the "B" mix chamber from the supply manifold contains water and acetate concentrate or water and the acid and bicarbonate components of bicarbonate dialysate. This chamber mixes the solution before it is monitored by the "B" conductivity probe.

"B" Conductivity Probe

The second conductivity probe in the flow path is located at the outlet of the "B" mix chamber in the dialysate supply recirculation loop. Two stainless steel probes in the flow path, one containing a thermistor to compensate for temperature differences, measure the the electrolytic content of the solution that leaves the "B" mix chamber.

The "B" probe monitors the total conductivity of the dialysate solution at this point in the flowpath. The conductivity circuitry subtracts the "A" conductivity probe reading from the "B" conductivity probe reading and compares the difference to the expected result based upon the concentrate formulation data entered by the operator. In the acetate therapy mode, the difference of this calculation should be zero and is used to recheck the "A" conductivity probe reading. When bicarbonate dialysis therapy is used, the microprocessor calculates the "B" portion of the solution and compares the result to the expected value for that concentrate formulation.

Conductivity measurements are affected by temperature and the thermistor gives the circuitry input for this variable. The thermistor in the "B" conductivity probe also supplies the input for the redundant high temperature alarm circuit.

Supply Pump

The supply pump has two functions. The first is to supply the flow and pressure to fill the flow equalizer with fluid. The supply pump operates at a flowrate approximately 50 mL/min higher than the dialysate flowrate set by the operator. This extra margin insures an adequate supply of solution to fill the flow equalizer. It produces a pressure that is regulated to a maximum of 12.5 psi to propel the fresh dialysate into the flow equalizer.

The second function is to create a flow through the supply pump recirculation loop. When the flow equalizer reaches the filled state, the the pressure in the pressure regulator increases to a preset limit, causing it to divert solution into the recirculation loop. This creates a flow through the recirculation loop that helps mix the contents of the "B" mix chamber.

Dialysate Filter (optional)

The dialysate filter is used to stop any foreign material from reaching the flow equalizer.

Pressure Regulator

This back pressure regulator is set to approximately 16 psi. The solution flow is directed to the flow equalizer for filling the compartments. When the flow equalizer compartments reach the end of the fill cycle, pressure builds up in the supply loop. At approximately 16 psi the regulator opens up to allow solution to flow through the supply pump recirculation loop momentarily until the flow equalizer begins another fill cycle. Constant repetition of this pressure buildup and pressure valve operation creates a flow into the supply pump recirculation loop.

Input Pressure Equalizer

At the inlet of the flow equalizer is a pressure equalizer. This device along with the output pressure equalizer matches the relative pressure differences between the inflow and outflow of the flow equalizer so that the compartments fill and empty at an even rate.

The pressure equalizer is a chamber divided by a flexible diaphragm into two compartments. At the center of the diaphragm is a valve that is designed to fit into an outlet port on one side of the compartment. Solution from the supply pump recirculation loop flows unimpeded through the compartment without the valve and into the flow equalizer. The other compartment in the pressure equalizer contains solution flowing from the dialyzer to the effluent compartments of the flow equalizer and is also part of the dialysate pressure pump recirculation loop. This returning fluid is pressurized by the dialysate pressure pump.

The input pressure equalizer matches the pressure of the solution returning from the dialyzer/rinse block with the supply pump pressure filling the flow equalizer. Whenever this supply pump pressure is greater than the pressure generated in the other compartment by the dialysate pressure pump, the diaphragm forces the valve to restrict the flow of fluid in the pump recirculation loop. This causes an increase in the dialysate pressure that shortly matches the supply pump pressure. By forcing the pressure of the fluid in the dialysate pump recirculation loop to equal the supply pump pressure, the relative difference between these two pressures as measured in the flow equalizer is nearly equal and the flow equalizer fills at an even rate.

Flow Equalizer

The flow equalizer is made of two nearly identical chambers. Each chamber is comprised of two compartments (one pre-dialyzer and one post-dialyzer), separated by a diaphragm and four solenoid actuated valves that control the filling and emptying of the compartments. The supply pump pressurizes the input to the pre-pump forcing it to fill. In phase 1 of the UF control cycle, while C-1 the pre-dialyzer compartment is filling with fresh dialysate the diaphragm separating it from the C-2 compartment transverses the cavity forcing an equal amount of effluent dialysate from the C-2 compartment to the drain. In this cycle, the amount of fresh dialysate entering the C-1 compartment is equal to the effluent dialysate in C-2 being displaced.

At the same time, effluent dialysate enters C-4 post-dialyzer compartment forcing the diaphragm to transverse the cavity, thereby pushing an equal amount of fresh dialysate out of the C-3 compartment to the dialyzer.

In phase 2, the solenoid valves which route the flow into and out of the flow equalizer package all turn off for a short period of time (125 msec). This valve shut-off time helps eliminate any significant effect on ultrafiltration accuracy that would result from two solenoid valves being open at the same time.

In phase 3, a different group of flow equalizer solenoid valves is then energized. This causes compartment C-2 to fill with effluent dialysate forcing the fresh dialysate in C-1 to flow toward the dialyzer. The C-3 compartment fills with fresh dialysate pushing the effluent dialysate in C-4 to flow to the drain. By balancing the flow of dialysate to and from the dialyzer, with two flow equalizer compartments, the dialysate flow to the dialyzer can be accurately measured over a wide range of flowrates. After phase 3 is complete the solenoid valves on the UF diaphragm pump shut off again in phase 4 and then the whole cycle starts over again in phase 1.

Output Pressure Equalizer

At the exit of the diaphragm flow equalizer is another pressure equalizer. This device equalizes the pressure differences between the outflow of the pre and post equalizers, so that the diaphram cavities fill and empty at an even rate. Flowing on one side of the output pressure equalizer is the fresh solution going to the dialyzer. In the compartment on the other side is the fluid leaving the dialyzer and on its way to the drain.

The pressure equalizer is a chamber divided by a flexible diaphragm. At the center of the diaphragm, facing in opposite directions, are two valves. The valves are held by the diaphragm so that they are suspended above openings on either side of the chamber. Fluid enters each compartment formed by the diaphragm at the end of the chamber parallel to the diaphragm and exits through the openings on the side. When the pressure is equal on either side of the diaphragm, flow through each compartment is unimpeded. When the pressure on one side of the diaphragm is greater in relation to the other side, it causes the valve to restrict or occlude the opening on the side at the lower pressure. With its outlet blocked, incoming fluid increases the pressure until it equals the higher pressure on the other side of the diaphragm. This forces the valve to open and normal flow to resume.

If pressure differences were allowed to persist, the compartments would empty at a rate determined by the pressure differences on either side of the dialyzer. These relative pressure differences could cause uneven emptying. By restricting the flow of the lower pressure fluid and forcing it to equalibrate with the higher pressure, the pressure equalizer ensures that the flow into and out of the pre and post flow equalizers will be at nearly equal rates

End Of Stroke Sensors

End of stroke sensors are located in the flow path at the inlet of the output pressure equalizer. These sensors verify when the flow equalizer compartments have reached the end of the fill cycle. When these compartments are full, the sensor sends a signal to the microprocessor, verifying that the compartments are full and the valve sequence must be changed. The open/close sequence of valves determines which compartments of the flow equalizer are filling and emptying.

Dialysate Monitoring Manifold

During hemodialysis therapy, the dialysate monitoring manifold checks the dialysate before it flows to the dialyzer and diverts unacceptable solution from the dialyzer. This manifold has two separate channels and contains: the final conductivity probe, a flow sensor and the dialysate pressure transducer. A loop containing the bypass valve connects the two channels such that solution leaving the channel with the conductivity probe must flow through the bypass valve before it reenters the second channel containing the flow sensor and pressure transducer.

Dialysate Conductivity Probe

The third conductivity probe is located in the manifold at the outlet of the output pressure equalizer. Composed of two stainless steel electrodes that protrude into the first channel in the manifold, this conductivity probe measures the total conductivity of the dialysate before it enters the artifical kidney. It compares the probes reading with the expected conductivity range based upon the concentrate formulation information previously entered by the operator. If the probe measures a value outside this range, its signal to the microprocessor activates the conductivity alarm and the bypass valve so that the solution is diverted to the drain and the operator is alerted.

Formulation information for the dialysate concentrate being used is entered into the machine's microprocessor by the operator. The conductivity circuitry processes this operator input and compares the monitored value with the expected range to determine if the system is functioning properly. If the conductivity is not within the preset range, this information will cause the bypass valve to shunt the solution away from the artifical kidney and alert the operator.

A thermistor is built into one of the electrodes. The thermistor allows the conductivity reading to be electronically corrected by the microprocessor for temperature differences. This thermistor supplies information for the temperature display and the primary high and low temperature alarm limits.

This probe provides the conductivity information that is displayred to the operator on the CRT.

Flow Sensor

A flow sensor is located in the the second manifold channel and is used to monitor the fluid flow through that point. Similar to the end of stroke sensor, the flow sensor contains a self heating variable resistor/thermistor. As current flows through the flow sensor it heats up. Being in the flow path, this element is cooled by the flow of fluid. When the flow flow stops, the sensor heats up, causing a change in the resisitance measured by the microprocessor. This change in the current through the thermistor due to the change in temperature tells the microprocessor that the flow has stopped. When the machine is in bypass, the lack of flow as measured by this sensor verifies the correct functioning of the bypass valve.

Dialysate Pressure Transducer

This pressure transducer senses the dialysate pressure and changes the pressure reading into an analog electrical signal proportional to pressure. This signal is used for the dialysate pressure display, alarms and control.

Bypass Valve

The bypass valve is located in a short loop that connects the conductivity probe channel of the dialysate monitoring manifold to the channel containing the flow sensor and the dialysate pressure transducer.

The bypass valve protects the patient in the event of a temperature or conductivity alarm by diverting unacceptable dialysate from the dialyzer. It is a 24 V dc three-way solenoid valve. During a dialysate temperature or conductivity alarm, an electronic signal causes the bypass valve to close the fluid path leading to the dialyzer. Instead the solution is shunted to a fluid path opening downstream from the dialyzer.

There is also a manual bypass mode that permits the operator to put the machine in bypass when a dialyzer is hooked up or sequential ultrafiltration therapy is performed.

Dialysate Sample Port

The sample port is provided as a opening for the operator to get a sample of the dialysate to test for conductivity or residual disinfectant. If dialysis in progress the dialyzer would be the next component in the flow path and this port allows for sampling the dialysate without interrupting the treatment. In the rinse mode, this port is used to test for disinfectant.

Dialyzer/Rinse Block

At this point in the fluid path the dialyzer is attached to the dialysate lines and is used to remove fluid and electrolytes from the patient. When the machine is not being used for a patient treatment and a dialyzer is not in use, the dialysate lines are attached to a rinse block. The rinse block allows the dialysate, rinse water or disinfectant to flow through the pre and post dialyzer lines.

Flow Sensor

Another flow sensor is located in the line leading the from dialyzer toward the dialysate pressure pump and is used to monitor the fluid flow through that point. The flow sensor contains a self heating variable resistor/thermistor. As current flows through the flow sensor it heats up. Being in the flow path, this element is cooled by the flow of fluid. When the flow stops, the sensor heats up, causing a change in the reisitance measured by the microprocessor. This change in the current through the thermistor due to the change in temperature tells the microprocessor that the flow has stopped. This flow sensor is used to check the UF system accuracy by monitoring the from dialyzer line during bypass to ensure that the flow equalizers are balanced and the flow has stopped.

Ultrafiltration System

The ultrafiltration system of the System 1000 machine allows the operator to remove a precise amount of fluid from a patient in a controlled manner. By controlling exactly how much dialysate is going to and returning from the dialyzer, accurate fluid removal is achieved. The main components of the UF system are the flow equalizer, the pressure equalizers, the dialysate pressure pump, the UF flow regulator, the UF flow meter, and the dialyzer.

Dialysate Pressure Pump Recirculation Loop

The dialysate pressure pump recirculation loop is located downstream from the dialyzer. It carries effluent dialysate from the dialyzer to the the flow equalizer. It also helps equalize the pressure differences in the compartments of the flow equalizer. A third function is to generate the pressure necessary to fill the UF flow meter. It contains; the dialysate pressure pump, the UF removal regulator, the UF flow meter, a sample port and the input pressure equalizer.

Dialysate Pressure Pump

The dialysate pressure pump is located in the dialysate flowpath. It operates in a loop that allows it to circulate fluid at a constant flow rate of 1500 mL/min without affecting the rate of fluid flow through the machine. By controlling the amount of fluid entering and leaving this loop, the dialysate pressure pump is used to change the pressure differences across the dialyzer membrane. The pressure and flow generated by this pump is also used to fill the UF flow meter and to fill and equalize the pressures in the flow equalizer. The dialysate pressure pump circulates fluid through the dialysate pressure pump recirculation loop at a rate higher than the rate of flow through the machine. As long as this pump receives adequate volume, it will not affect the flow dynamics of the main flowpath. When fluid is removed from this loop, the pump will attempt to replace it by demanding more volume from the main flowpath. Since the flow equalizer keeps the volume of dialysate going to and from the dialyzer constant, the only fluid available must come from the dialyzer. By precisely controlling the amount of fluid removed from the loop, the operator can control the amount of fluid removed from the patient via the dialyser.

The fluid pumped by the dialysate pressure pump is restricted by a flow restriction. This restriction provides sufficient pressure to the input of the removal regulator for normal operation.

The flow and pressure generated by the dialysate pressure pump is also used to fill the post dialyzer chambers in the flow equalizer. Through the dialysate pressure pump recirculation loop outlet in the input pressure equalizer this pump causes the flow equalizer compartments to fill when the valves open to let in fluid.

UF Removal Regulator

The dialysate pressure pump forces solution through the UF removal regulator. This regulator regulates the pressure at the input to the UF Flow Meter. This pressure is used to fill the UF Flow Meter.

UF Flow Meter

The UF flow meter is a measuring device composed of a precisely measured chamber with a small diaphragm separating it into two compartments. Each compartment has a three-way valve connecting it to the flowpath and to the drain. The UF flow meter is connected into the flowpath in the dialysate pressure pump recirculation loop between the dialysate pressure pump and the flow restriction and via the UF removal regulator. The dialysate pressure pump is restricted by the flow regulation and creates a positive pressure at this point which is regulated by the UF removal regulator that is used to fill the UF flow meter. A compartment fills when the microprocessor opens its valve to this positive pressure environment. When one compartment is filling, its companion compartment is emptying to the drain. Based upon knowing what volume is removed every time a compartment is opened, the microprocessor can measure precise amounts of fluid by sending a calculated number of open/close signals per minute to the valves. The rate of fluid removal is determined by the ultrafiltration information entered into the microprocessor by the operator. The microprocessor calculates the number of times per minute each valve must open to equal this UF volume.

When fluid leaves the system through the UF flow meter, less fluid is recirculated through the dialysate pressure recirculation loop. The volume of flow that leaves through the UF flow meter starves the input of the dialysate pressure pump by an equal amount. The starved negative pressure pump creates the necessary pressure to remove an amount of fluid from the dialyzer equal to the fluid removed from the system through the UF flow meter.

The flowpath from the fresh dialysate compartments of the flow equalizer to the dialyzer and back to the effluent compartments of the flow equalizer is a closed system except for two openings. One opening is the dialyzer. The other is the UF flow meter. When the volume in the dialysate pressure recirculation loop is reduced by solution being removed through the UF flow meter, a negative pressure is exerted on the dialyzer. As long as the ultrafiltration rate of the dialyzer is sufficient to remove the volume being demanded, an equal amount of fluid will be removed from the patient. Thus the operator can enter a predetermined fluid removal rate into the machine and the machine will automatically remove it from the patient.

Blood Leak Detector

Effluent dialysate expelled from the flow equalizer passes through and is monitored for the presence of blood in the blood leak detector. There is a light source and a photocell monitoring the light transmitted through the solution present in the cavity. If blood leaks through the dialyzer membrane, the blood passing through the blood leak detector will absorb a portion of the light, preventing it from reaching the photocell. The dimmed light then sets off a blood leak alarm protecting the patient by stopping the blood pump, clamping the venous line and warning the operator.

Heat Exchanger

The effluent solution is circulated through the heat exchanger on its way to the drain so that the incoming water may benefit from a transfer of heat and be warmed by this fluid.

Rinse Valve

The rinse valve connects to the fluid path immediately after the flow sensor on the downstream side of the dialyzer. When the System 1000 machine is in rinse, the microprocessor forces the UF flow meter to remove rinse fluid from the dialysate pressure recirculation loop at approximately 4 L/h to insure adequate flushing of this component. Since the flow equalizer maintains the closed loop configuration during the rinse and disinfect cycle, fluid must be added to the system at this point to replace the volume lost through the UF flow meter. The rinse valve allows fluid to flow into the pressure pump recirculation loop from the drain line. When this valve is activated, the drain line fluid replaces the volume removed by the UF flow meter.

Extracorporeal Circuit

The components described in this section are presented in the approximate order in which they appear in the extracorporeal circuit.

Blood Pump

The blood pump is a peristaltic pump that moves extracorporeal blood at the prescribed flow rate during dialysis. During extracorporeal alarms, the blood pump stops, occluding the pump segment of the arterial blood tubing. Blood pump tubing with blood pump segment inter-diameters of 1/4-inch, 6-mm, 7-mm and 8-mm may be used with the blood pump.

A blood pump cover interlock switch prevents the blood pump from operating unless the cover is fully closed. The blood pump alarm will activate if the pump stops or overspeeds.

Venous and Arterial Pressure Monitors

The monitors indicate pressures in the extracorporeal drip chambers.

Connected to the venous and arterial monitors is a small motor operated peristaltic pump, this pump is used to raise or lower the level of blood in the extracorporeal blood line drip chambers

Heparin Pump

The heparin pump is a syringe pump that infuses heparin into the blood flow circuit at an operator-adjustable rate. The heparin pump alarms when the motor is infusing heparin faster than the setting on the device. It also alarms when the heparin syringe is empty or the motor is stalled.

Air Detector

The air detector continuously monitors the blood flow for the presence of air bubbles in the venous blood line.

The air detector is comprised of two ultrasonic transducers, one for transmitting, the other for receiving. Whenever a single air bubble or tight cluster of air bubbles of sufficient size passes between the transducers, some of the focused ultrasonic energy that would otherwise be received by the other transducer is scattered or obstructed. The resulting drop in signal at the receiving transducer triggers an air detector alarm.

During an air detector alarm the audio alarm sounds, the blood pump stops and the line clamp occludes the venous blood line. The UF rate slowly goes to zero. The blood and dialysate pressures will slowly equalize across the dialyzer membrane.

Line Clamp

The line clamp occludes the venous blood line during an extracorporeal alarm.

Heat Cleaning

The following three conditions *must* be met in order to start the Heat Clean Mode:
- The machine is in the Rinse Mode.
- There is a low conductivity alarm.
- The HEAT CLEAN button is pressed.

When the Heat Clean Mode is initiated, the following occur:
- The heat clean valve is opened.
- The flow rate is lowered to 370 ml/min.
- The air removal pump speed is lowered by 2/3.
- The desired "dialysate" temperature is set to 85°C (97°C at the heater output).
- HEAT CLEAN is displayed in the machine status area.
- The HEAT CLEAN ABORT button appears.
- The blood pump, UF removal system and concentrate pumps operate as in the Rinse Mode.

Since the flow signal used for the supply pump flow rate servoing (end-of-stroke signal) is lost at higher temperatures, the supply pump is locked after approximately 3 minutes of elapsed heat clean time.

When the temperature at the dialyzer connectors is greater than 70°C, the bypass valve is controlled using the state of the rinse interlock information. If the interlocks are not met, the bypass valve will be in the bypass state to prevent the possible exposure of the operator to hot water.

The time required for the fluid path temperature to reach values required for disinfection (80 to 85°C) is largely dependent on the operating conditions of the machine when the Heat Clean Mode is initiated. If the "dialysate" temperature is above the low

* Reference Modern
Microbiology by Wayne
Umbert, 1962.

temperature alarm limit at the start of Heat Clean, the time required to reach 85°C at the dialyzer connectors is less than 30 minutes.

The heat clean state is put into the cool down mode after an 85°C primary conductivity probe temperature has been held for at least 15 minutes*. The cool down mode will operate at the machine calibrated maximum flow rate until the primary high temperature alarm has ceased. When the primary temperature is out of alarm, the machine will revert back to the Rinse Mode. This cool down mode requires only 10 minutes at a flow rate of 800 ml/min.

The HEAT CLEAN ABORT button permits the operator to manually start the cool down mode.

Preventive Maintenance

This section describes routine maintenance, calibration and adjustment procedures required for proper care of the System 1000 machine. Local environmental conditions such as inadequate water quality or the need for additional procedures such as routine acid flushes may require shorter periods between maintenance. As each maintenance procedure is completed, record the date and the type of maintenance in a log.

The System 1000 machine has been thoroughly factory-tested; fine adjustments however may be necessary prior to clinical use. If further adjustments are necessary they should be referred to a qualified service person.

Before any adjustments or calibrations are made, the system should be allowed to warm up for at least 10 minutes.

When maintenance is completed, perform a full functional check of the system. Ensure that the machine has been disinfected before returning it to clinical use.

Recommended Maintenance Schedule

With every maintenance of the machine:

Check and repair, replace, adjust or tighten as required:
  Hydraulic leaks
  Worn parts
  Loose parts and connections
  Discolored wires, terminals, relay contacts, and tubing
  Improperly seated circuit boards and modules
  Electrical connections
  Corroded valves As required:

Clean:
  External surfaces
  Concentrate and disinfect line rinse ports and rinse block Every month:

Rinse:
  Fluid path with vinegar

Every 3 months:

Clean:
  Fluid path with bleach
  Blood leak detector

Calibrate:
  Blood leak detector

As required or at least once a year:

Check/adjust:
  Blood pump occlusion

Every 6 months:

Perform all functional checks (per this manual):
  Calibrate if necessary

Every 12 months:

Check:
  Line cord ground continuity

As required:

Replace:
- O-rings
- Dialysate filter
- Concentrate filters
- Tubing
- Lamps
- Worn/defective parts
- Level adjust tubing Before prolonged storage:

Disinfect and drain:
- Fluid path

Supplies

Cleaning Supplies:
- Clean, dry cloths
- Basin
- Household bleach (5.25% sodium hypochlorite)
- Mild detergent solution (such as mild dishwashing detergent in water)
- Diluted bleach solution (4 parts fresh household bleach and 126 parts cold water); for example, 40 mL fresh household bleach and 1260 mL cold water
- Vinegar (5% acetic acid solution), (i.e., clean fresh white vinegar)
- pH color indicator strips, range pH 6 to 8

Test/Calibration Tools:
- Pressure test gauge, 0 to 30 psi
- Pressure test gauge, 750 to –750 mmHg
- Timer or stop watch
- Blood line set of the type to be used in therapy
- Syringe, 10 to 20 mL capacity (The type used for heparin infusion.)
- Syringe, approximately 50 mL capacity
- Three way stopcock
- Dialysate concentrate solution
- Electronic scale, minimum 3 kg capacity with 0.1 gram readability
- One liter capacity beaker
- Bucket with minimum 4 L capacity
- Temperature probe assembly with in-line monitoring capability, scale accurate within ±0.2°C in a 30 to 50°C range
- In-line conductivity meter
- Tube occluding forceps

CAUTION 1. Static discharge may damage electronic components.

- Both MOS and Bipolar integrated circuits maybe damaged by discharge of static electricity.

- Both digital and linear integrated circuits may also be damaged.

- Static damage may occur not only to integrated circuits mounted on the circuit board, but also to detached integrated circuits.

- Static damage may not be immediately evident.

- Static damage is cumulative.

2. Do not remove or plug in any electronic component or assembly while power is applied to the machine.

3. Use only silicone base O-ring lubricant; other lubricants may damage the O-rings.

4. It is necessary to perform some of the adjustments with the covers removed. Use extra care to prevent fluids from entering or contacting the electronics of the machine.

WARNING 1. Do not under any circumstances perform calibrations or testing of this machine while dialysis is in progress.

2. Disconnect power before removing protective panels, soldering, replacing components, or replacing printed circuit boards.

3. Use care when servicing the machine with power on or the machine plugged in.

4. Dangerous voltages exist at several points in the machine. To avoid personal injury, do not touch exposed connections and components while power is applied.

5. Servicing the CRT requires thorough knowledge of the shock hazard and handling precautions associated with this type of component.

6. Do not perform internal service or adjustment of this machine unless another person capable of rendering first aid and resuscitation is present.

7. If maintenance is to be performed after the machine has been used for dialysis, ensure that the fluid pathway has been cleaned.

8. Before performing any maintenance on the hydraulic system, turn off the power and the water.

9. After maintenance is completed, perform a complete functional test of the machine before returning it to clinical use.

10. After maintenance is completed, disinfect the machine with formaldehyde before returning it to clinical use. Allow formaldehyde to remain in the system for at least two hours.

11. Do not exceed the maintenance intervals given in the schedule or neglect to perform the maintenance as recommended.

Note   Refer to the "Safety Summary" section of this manual for other applicable information.

Unless otherwise noted, perform all dialysate circuit calibrations and adjustments with the machine operating under normal dialysis conditions (i.e., solution temperature at 38°C and within normal conductivity range).

Before opening the dialysate fluid pathway for maintenance, make sure the water supply is off.

Cleaning Procedures

Clean Fluid Path With Bleach

WARNING   If maintenance is to be performed after the machine has been used for dialysis, ensure that the fluid pathway has been cleaned.

Supplies
- 200 mL household bleach (5.25% sodium hypochlorite)
- Small beaker, approximately 500 mL capacity.

Precondition
- Patient disconnected.
- Machine has been rinsed for at least 10 minutes with water.
- Machine is in rinse mode.

Procedure

1. Connect the disinfect line (yellow connector) to a container of 200 ml of household bleach.

2. Connect the acid/acetate concentrate line (pink connector) to the disinfect rinse port (yellow).

3. Allow diluted bleach to infuse into the fluid path for 15 minutes.

4. After the 15 minutes, disconnect the machine from the bleach supply.

To disconnect the machine:

a. Connect the acid/acetate concentrate line (pink connector) to the acid/acetate rinse port (pink).

b. Wait approximately 15 seconds for the disinfect line to drain, then connect the disinfect line (yellow connector) to the disinfect rinse port (yellow).

CAUTION   Do not allow bleach to remain in the fluid path longer than the recommended time or damage may result.

5. Rinse the machine for approximately 30 minutes. Continue rinsing until a test specific for the presence of sodium hypochlorite is negative.
6. Turn off the power switch and water supply.

Rinse Fluid Path with Vinegar

Overview

To remove bicarbonate precipitate (insoluble calcium carbonate deposits) from the machine fluid path. Bicarbonate precipitate is a white to cream-colored deposit formed downstream of the bicarbonate mixpoint. Other precipitates and/or discolorations will not be removed by following this procedure.

It is important to follow this vinegar rinse procedure. If allowed to accumulate excessively, bicarbonate precipitate can cause problems with operation of the equipment.

This procedure will not prevent bicarbonate precipitate formation; it is only useful in controlling accumulation of the deposit. Perform this procedure as often as conditions indicate.

Supplies
- Vinegar (5% acetic acid solution)
- pH color indicator strips, range pH 6 to 8

Precondition
- Patient disconnected.
- Machine in rinse mode, rinsing with water.
- Dialysate flow rate is 1000 ml/min.

Procedure

1. Check the pH of the rinse water using a pH indicator strip. This will establish a baseline pH value to which the system should be rinsed after exposure to the vinegar.
2. Connect the disinfect line to the container of vinegar.
3. Connect the acid/acetate concentrate line to the disinfect rinse port.
4. Infuse approximately 800 ml of vinegar into the fluid path. This will take approximately 30 minutes.
5. Before the vinegar supply is completely exhausted, turn off the machine.
6. Allow the vinegar to remain in the fluid path for approximately 30 minutes. For high precipitate build-up allow 60 minutes.
7. Meanwhile, remove the acid/acetate concentrate line from the disinfect port
8. Remove the disinfect line from the vinegar supply and connect the line to the disinfect rinse fitting.
9. After the 30 minute dwell time, turn on the machine and start rinse.
10. Set the dialysate flow rate to 1000 ml/min.
11. Rinse the fluid path for at least 15 minutes.
12. Inspect the dialysate lines. If precipitate is still present, an infusion of another fresh supply of vinegar is required; repeat steps 2 through 10. If the lines are clean, go to the next step.
13. Using pH indicator strips, check the pH of the rinse water.
14. Continue rinsing as required until the pH of the rinse water has returned to the value noted in step 1, above.

Clean Blood Leak Detector

Supplies
- Clean, dry cloths
- Basin
- Mild detergent solution (such as mild dishwashing detergent in water)
- Diluted bleach solution (4 parts fresh household bleach and 126 parts cold water); for example, 40 mL fresh household bleach and 1260 mL cold water
- Cotton swabs
- O-ring lubricant

Preconditions

- Fluid path cleaned.
- Machine off.
- Water supply off.

CAUTION  Handle the sensors with care. Do not drop or allow them to get wet.

Procedure

1. Locate the blood leak detector on the back of the machine.
2. Remove the detector cover by rotating and pulling it toward you.
3. Clean the inside of the detector tube and the inner side of the detector cover.
4. Apply a thin film of O-ring lubricant on the end cap O-ring. Do not allow O-ring lubricant to get on the lenses.
5. Reinsert the cover by aligning it with the grooves and pushing as you turn to engage it.
6. Recalibrate the blood leak detector before returning the machine to clinical use.

Blood leak detector

Calibration/Adjustment Procedures

Overview

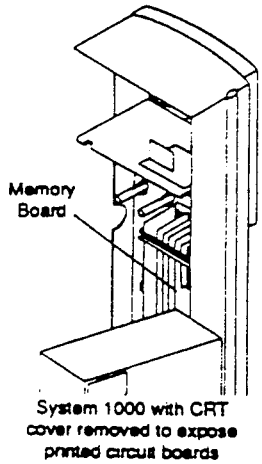

System 1000 with CRT cover removed to expose printed circuit boards

The System 1000 has a menu driven calibration mode. When the calibration mode is activated, on-screen prompts help inform the technician of the proper actions necessary to complete each calibration test/check. The manual contains the step by step procedure for calibrating the machine.

Technician actions involve collecting and measuring dialysate flow, ultrafiltrate and concentrate fluids; sampling temperature and conductivity; adjusting pump pressures; and inputting the results of these actions as instructed by the on-screen messages.

During normal operations, the operator does not have access to the calibration mode. An internal switch must be activated and the machine restarted to obtain the calibration mode. The calibration mode contains buttons that select individual tests and display instructions for completing the tests. If technician inputs are not within the expected range, a screen message alerts the technician.

When the calibrations are completed, the machine must be returned to the operational mode by turning off the calibration switch and restarting the machine using the mains power switch.

To Activate the Calibration Mode

Preconditions
- Power cord is plugged into the wall socket.
- Power switch is off.
- Hydraulic Module is open.

Procedure

1. Turn off the mains power switch.
2. Remove the splash shield covering the mother board and its associated boards.
3. Locate the memory board attached to the third slot from the right on the mother board bus. The memory board is identifiable by the large ribbon cable connected to the top of the board.
4. Locate the board component near the lower end of the memory board containing four small switches.
5. Push calibration switch #1 (closest to the rear of the machine) into the on position.
6. Reinstall the splash shield.
7. Turn on the mains power switch to reactivate the touch screen. It is not necessary to turn on the power switch.
8. When the screen is activated, touch the small dots that appear in sequence in the corners of the screen as instructed by the on screen message.

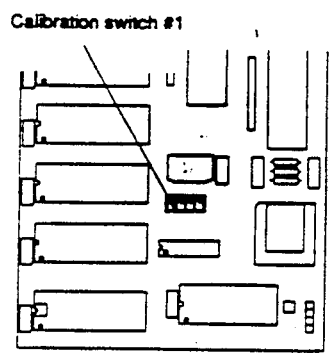

Memory board

9. When calibration screen #1 appears, touch the NEXT SCREEN button to activate calibration screen #2 if the following calibration procedures will be performed in order. Otherwise access the appropriate calibration screen for the calibration to be performed.

To Deactivate the Calibration Mode

1. Repeat above procedure through step 4.
2. Push the memory board calibration switch to the off position.
3. Replace the splash shield and close the Hydraulic Module.
4. Make sure the Operator screen appears upon the next machine start up.

Note: Upon turning on the mains power switch, the machine will become fully activated without the need of turning on the power switch.

Calibration Screen Guide
- To select a calibration line on the screen touch the NEXT UP or NEXT DOWN button until the desired is highlighted.
- To start a calibration procedure, select the desired test and touch the START CAL button.
- To stop a calibration procedure, touch the STOP CAL button.
- The STOP CAL button replaces the START CAL button whenever a calibration procedure is in progress.
- To access the other calibration screen, touch the NEXT SCREEN button.
- To enter a number, touch the appropriate numbers on the keypad and then touch the ENTER button twice.
- To correct an erroneous keypad entry, touch the CLEAR button.
- To put the machine into the operator mode, touch the EXIT button.
- A VERIFY button will appear when needed in a procedure.

Calibration screen #1

Calibration screen #2

8 Preventive Maintenance

Calibrate Input Water, Deair Pump and End-of-Stroke Pressures

Supplies
- Pressure test gauge (0 to 30 psi)
- Pressure test gauge (750 to -760 mmHg)

Preconditions
- Water supply is on.
- Power switch is on.
- Hydraulic Module is open.
- Calibration screen #2 is displayed.
- Machine is in the rinse mode and has rinsed for at least ten minutes.

Procedure

Note: Pressure calibrations *must* be performed with the machine at a 1000 mL/min dialysate flow rate and the pressure relief (rinse?) valve open. Selecting the DEAIR/NEG PRESS PUMP calibration line will put the machine in this operating condition.

Note: When inputting numerical information onto the touch screen calibration display, enter the number using the keypad then touch the ENTER button twice to enter data.

1. Select the DEAIR/NEG PRESS PUMP calibration line and press the START CAL button.

2. Calibrate the input water pressure as follows:
   a. Connect a pressure gauge (0 to 30 psi) to the input water test port on the input water pressure regulator.
   b. The input water pressure should be 8 ±1 psig.
   c. Adjust the input water pressure regulator as required until the pressure gauge indicates 8 ±1 psig.
   d. Disconnect the pressure test gauge.

3. Calibrate the deair pressure pump as follows:
   a. Connect a pressure test gauge (750 to -760 mmHg) to the test port in the line from the deair sprayer to the deair pump.

Note: At the bottom of the screen, the machine will prompt the user to enter the next deair pump voltage to be tested. At the top of the screen, the machine will prompt the user to verify the voltage entered when the deair pressure is correct.

b. Using the calibration keypad, enter a deair pump voltage that produces a deair pressure of 500 ±15 mmHg and touch the ENTER button twice.
   c. Disconnect the pressure test gauge.

Note: After the deair pump voltage is entered, the VERIFY button will be visible on the screen.

d. If additional pressures are to be calibrated, do not press the VERIFY button at this time.

If calibrating only the input water and deair pressures, press the VERIFY button and deactivate the calibration mode.

WARNING: Before resuming patient dialysis therapy, be sure the calibration switch is in the off position.

4. Calibrate the End-of-Stroke Pressure:
   a. Connect a pressure gauge (0 to 30 psi) to the input pressure regulator on the side that is connected to the supply regulator.
   b. The end-of-stroke pressure should be 16 ±1 psig.
   c. Adjust the supply regulator as required until the pressure gauge indicates 16 ±1 psig.
   d. Disconnect the pressure test gauge.
   e. Complete the deair pressure calibration by pressing the VERIFY button.
   f. Make sure the voltage printed on the deair pressure calibration line is the same value that was entered above.

Note    The next calibration procedure will be performed while the machine is operating in the Rinse Mode. All operation and calibration modes are accessible when the memory board calibration switch is on and there is no need to deactivate the calibration mode at this time if more calibrations are planned. Before resuming patient dialysis therapy, be sure the calibration switch is in the off position.

5. Calibrate the UF Removal Pressure:

a. Press the EXIT button initiate the Operator Mode.

b. Initiate the Rinse Mode.

1) Press the RINSE then RINSE VERIFY buttons.
      2) Make sure that RINSE is displayed in the machine status window.

c. Connect a pressure gauge (750 to -760 mmHg) in the line between the UF removal regulator and the UF removal metering device.

d. The UF removal pressure should be 200 to 300 mmHg.

e. Adjust the UF removal regulator as required until the pressure gauge indicates 200 to 300 mmHg.

f. Remove the pressure test gauge.

Calibrate Concentrate Pumps and UF Removal Metering Device

Note    The concentrate pump and UF removal metering device calibrations may be performed concurrently if the necessary scales and beakers are available.

Supplies:
- 1 to 3 electronic scale(s) (Minimum of 3 liter capacity with a 0.1 gram readability)
- 1 to 3 one liter beaker(s)
- Ultrafiltrate line port plug

Preconditions
- Mains switch is
- Power switch is off.
- Hydraulic module open.
- Calibration switch is on.
- Calibration screen #2 is displayed.

Procedure

1. Calibrate the acid/acetate concentrate pump:
   a. Select the A CONCENTRATE LINE calibration line.

Note    Removal of the concentrate line fitting prevents inaccuracies caused by water being unevenly retained by this fitting.

b. Remove the fitting from the end of the acid/acetate concentrate line.

c. Fill a 1 L beaker about half full of water.

d. Place the acid/acetate concentrate line in the breaker of water, press the START CAL button and press the VERIFY button.

e. Allow the concentrate pump to pump water from the one liter beaker until all visible signs of air have been removed from the concentrate line f. After the air has been cleared press the STOP CAL button.

Note    Be sure to remove the concentrate line from the beaker when instructed to. Removing this line at the appropriate time increases the accuracy of the measurement.

g. Wait until the concentrate pump has stopped, then remove the acid/acetate concentrate line from the breaker of water. Place the beaker of water on the scale and tare the scale.

Note

Tare the scale:
Zero the scale with the beaker of water at the beginning of a calibration so that the weight indicated on the scale is only the weight of the water that was added to or removed from the beaker.
Refer to your scales instructions for detailed actions.

h. Place the acid/acetate concentrate line in the beaker of water, press the START CAL button and press the VERIFY button.

Note An on-screen message will appear to count down the pump strokes.

i. Wait until 100 pump strokes have been completed as indicated by a pump stroke message printed on the screen.

j. The calibration system will then prompt the technician for the weight removed from the beaker.

1) Remove the concentrate line from the beaker.

2) Place the beaker of water on the scale and note the weight.

3) Enter the weight from the scale onto the calibration keypad and press the ENTER button twice.

k. Repeat the above procedure (clear air from concentrate line only if needed).

l. If both weights are within 1% of each other, enter the weight from the scale onto the calibration keypad and press the ENTER button twice.

If both weights are not within 1%, repeat the calibration.

If the third calibration weight is within 1% of either of the first two calibration weights, enter the weight from the scale onto the calibration keypad and press the ENTER button twice.

If the third calibration weight is not within 1% of either of the first two calibration weights, remove the machine from clinical service and consult the "Troubleshooting" section of this manual for further help.

m. Replace the fitting on the end of the acid/acetate concentrate line.

n. Connect the acid/acetate concentrate line to the acid/acetate rinse port.

3. Calibrate the bicarbonate concentrate pump:

a. Select the B CONCENTRATE LINE calibration line.

Note Removal of the concentrate line fitting prevents inaccuracies caused by water being unevenly retained by this fitting.

b. Remove the fitting from the end of the bicarbonate concentrate line.

c. Fill a 1 L beaker about half full of water.

d. Place the bicarbonate concentrate line in the breaker of water, press the START CAL button and press the VERIFY button.

e. Allow the concentrate pump to pump water from the one liter beaker until all visible signs of air have been removed from the concentrate line.

f. After the air has been cleared press the STOP CAL button.

Note Be sure to remove the concentrate line from the beaker when instructed to. Removing this line at the appropriate time increases the accuracy of the measurement.

g. Wait until the concentrate pump has stopped and then remove the bicarbonate concentrate line from the breaker of water. Place the beaker of water on the scale and tare the scale.

h. Place the bicarbonate concentrate line in the beaker of water, press the START CAL button and press the VERIFY button.

Note An on-screen message will appear to count down the pump strokes.

i. Wait until all 100 pump strokes have finished as indicated by the pump count message printed on the screen.

j. The calibration system will then prompt the user for the weight removed from the beaker.

1) Remove the concentrate line from the beaker.

2) Place the beaker of water on the scale and note the weight.

3) Enter the weight from the scale onto the calibration keypad and press the ENTER button twice.

k. Repeat the above procedure (clear air from concentrate line only if needed).

l. If both weights are within 0.1% of each other, enter the weight from the scale onto the calibration keypad and press the ENTER button twice.

If both weights are not within 0.1%, repeat the calibration.

If the third calibration weight is within 0.1% of either of the first two calibration weights, enter the weight from the scale onto the calibration keypad and press the ENTER button twice.

If the third calibration weight is not within 0.1% of either of the first two calibration weights, remove the machine from clinical service and consult the "Troubleshooting" section of this manual for further help.

m. Replace the fitting on the end of the bicarbonate concentrate line.

n. Connect the bicarbonate concentrate line to the bicarbonate rinse port.

4. Calibrate the UF Removal Metering Device:

a. Select UF REMOVAL PUMP calibration line.

b. Place the ultrafiltrate line in an empty 1 L beaker and make sure that a plug is placed on the ultrafiltrate line port to prevent air leaks through this port.

c. Press the START CAL button, then the VERIFY button.

d. When all the air has been cleared from the line press the STOP CAL button.

Note  Be sure to remove the ultrafiltrate line from the beaker when instructed to. Removing this line at the appropriate time increases the accuracy of the measurement.

e. Remove the ultrafiltrate line from the beaker and tare the scale with the beaker on the scale.

f. Place the ultrafiltrate line in the beaker, press the START CAL button and press the VERIFY button.

Note  An on-screen message will appear to count down the UF removal device strokes.

g. Wait until the UF removal device has completed 100 strokes (stroke count is printed on the screen).

Note  Be sure to remove the ultrafiltrate line from the beaker when instructed to. Removing this line at the appropriate time increases the accuracy of the measurement.

h. The calibration system will then prompt the user for the weight pumped into the beaker.

1) Remove the ultrafiltrate line from the beaker.

2) Place the beaker of water on the scale and note the weight.

3) Enter the weight from the scale onto the calibration keypad and press the ENTER button twice.

i. Repeat the above procedure (clear air from removal line only if needed).

j. If both weights are within 0.1% of each other, enter the weight from the scale onto the calibration keypad and press the ENTER button twice.

If both weights are not within 0.1%, repeat the calibration.

If the third calibration weight is within 0.1% of either of the first two calibration weights, enter the weight from the scale onto the calibration keypad and press the ENTER button twice.

If the third calibration weight is not within 0.1% of either of the first two calibration weights, remove the machine from clinical service and consult the "Troubleshooting" section of this manual for further help.

Calibrate Flow Equalizer

Supplies
- Electronic scale (Minimum of 3 liter capacity with a 0.1 gram readability)
- 4 L capacity bucket

Preconditions
- Water supply is on.
- Power switch is on.
- Calibration screen #2 is displayed.
- Machine is in the rinse mode and has rinsed for at least ten minutes.

Procedure

1. Select the DIALYSATE FLOW calibration line.
2. Place an empty 4 L bucket on a scale and tare the scale.
3. Press the START CAL, then VERIFY buttons.
4. Move quickly with the tared bucket to the drain line and upon the next End of Stroke place the drain line in the pre-tared bucket.
5. The calibration system will then count 20 dialysate flow cycles. At the end of the 19th cycle, the machine will prompt the technician with an audible beep and a screen message to remove the drain line from the bucket at the next End of Stroke.

Press the VERIFY button and wait at the drain to remove the line from the bucket upon the next End of Stroke.
6. After the next end of stroke (20th dialysate flow cycle), remove the drain line from the bucket.
7. The calibration system will then prompt the user for the weight increase of the bucket.
   a. Place the bucket on the original scale.
   b. Enter the weight from the scale onto the calibration keypad and press the ENTER button twice.
8. Repeat the above procedure.
9. If both weights are within 0.1% of each other, enter the weight from the scale onto the calibration keypad and press the ENTER button twice.

If both weights are not within 0.1%, repeat the calibration.

If the third calibration weight is within 0.1% of either of the first two calibration weights, enter the weight from the scale onto the calibration keypad and press the ENTER button twice.

If the third calibration weight is not within 0.1% of either of the first two calibration weights, remove the machine from clinical service and consult the "Troubleshooting" section of this manual for further help.

Calibrate Dialysate Temperature

Supplies
- Temperature probe assembly with in-line monitoring capability (scale accurate within ±0.2°C in a 30 to 50°C range)

Preconditions
- Power switch is on.
- Machine is operating in the calibrate mode.
- Calibration screen #2 is displayed.
- All panels are in place on the machine.
- Hydraulic module is closed.

Note: Temperature calibration *must* be performed with all panels in place and the hydraulic module closed to stabilize the internal temperature.

Note: Always check the calibration date on the temperature probe to ensure that the calibration is current.

Procedure

1. Select the TEMPERATURE calibration line.
2. Press the START CAL button. The calibration system will then prompt the user to place a temperature probe in the dialysate line.
3. Place the temperature probe in the dialysate line at the Hansen connectors and press the VERIFY button.
4. The calibration system will then adjust the temperature to approximately 30°C and when stable prompt the user to enter the measured temperature. This process takes approximately 15 minutes.

Enter the measured temperature into the calibration keypad and press the ENTER button twice.
5. The calibration system will then adjust the temperature to approximately 40°C and when stable it will prompt the user to enter the measured temperature. This process takes approximately another 15 minutes.

Enter the measured temperature into the calibration keypad and press the ENTER button twice.
6. The temperature calibration is complete after the heigher temperature (~40°C) is entered into the calibration keypad. The flow rate will then change back from 1000 to 500 ml/min and the desired temperature will then revert back to 37°C. (Approximately 10 minutes is needed for the temperature to equilibrate.)

Calibrate Dialysate Conductivity

Supplies
- Dialysate concentrate solution normally used
- In-line dialysate conductivity meter Note    Always check the calibration date on the conductivity probe to ensure that the calibration is current.

Preconditions
- Water supply is on.
- Power switch is on.
- Machine is displaying calibration screen #2.
- Temperature calibration was performed within the last two weeks.

Note    The calibration routine requires that the temperature calibration was performed within the last two weeks or the conductivity calibration will not be allowed.

1. Select the CONDUCTIVITY calibration line.
2. Press the START CAL button. The calibration system will then prompt the user to place a conductivity probe in the dialysate line. Use a conductivity probe that has been recently calibrated.
3. Place the conductivity probe in the dialysate line and press the VERIFY button.
4. Place the acid/acetate concentrate line in a container of acetate dialysate concentrate. The calibration system will then proportion the concentrate and when the conductivity is determined to be stable the calibration system will prompt the user for the measured conductivity.
5. Enter the measured conductivity onto the calibration keypad and press the ENTER key twice.
6. The acid/acetate concentrate pump will continue to proportion concentrate and the three displayed conductivities will now be calibrated from the previous procedure.

Set Supply Pump Voltage *Rating*

Preconditions
- Water supply is on.
- Power switch is on.
- Machine is in the calibration mode.

Procedure

1. Select the SUPPLY PUMP calibration line.
2. Press the START CAL button. The calibration system will then prompt the user to enter the supply pump voltage rating.
3. Use the keypad to enter an "18 V" voltage rating and press the ENTER button twice.
4. Make sure the voltage rating entered appears on the calibration line.

Calibrate Dialysate Pressure

Supplies
- A syringe (approximately 50 cc capacity)
- A stopcock (3-way)
- Pressure test gauge (750 to -760 mmHg)

Preconditions
- Water supply is on.
- Power switch is on.
- Machine is displaying calibration screen # 1.

Procedure

1. Select the DIALYSATE PRESSURE calibration line.
2. Press the START CAL button. The calibration system will then prompt the user to open the dialysate sample port to atmosphere. Open the sample port (double check that the sample port is open to atmosphere) then wait a few seconds before pressing the VERIFY button.
3. After the VERIFY button has been pressed and the coarse dialysate pressure offset has been determined by the calibration system, it will prompt the user to pressurize the dialysate line to a negative pressure and then measure the pressure.
4. Use a stopcock, a syringe, and a pressure meter to pressurize the dialysate line to a stable and known pressure. Press the VERIFY button upon the proper pressure stabilization and measurement.
5. The calibration system will prompt the user for the negative dialysate pressure (a negative sign will appear in the calculator window). Enter the pressure on the calibration keypad and press the ENTER button twice.
6. The calibration system will then prompt the user to pressurize the dialysate line positive and take a measurement. Repeat the procedure explained in step 4 for a positive pressure and press the VERIFY button
7. The calibration system will then prompt the user for the positive dialysate pressure. Enter the pressure on the calibration keypad and press the ENTER button twice.
9. The calibration is complete at this point and the dialysate pressure should be verified.

Calibrate Venous and Arterial Pressures

Supplies
- A stopcock (3-way)
- Tubing with two female luer connectors attached
- Pressure test gauge (750 to -760 mmHg)

Preconditions
- Blood tubing set of the type used for hemodialysis is installed on the machine.
- Power switch is on.
- Calibration switch is on and the calibration screen #1 is displayed.

Procedure

1. Use the UP or the DOWN button to select the VENOUS AND ART PRESS calibration line.
2. Press the START CAL button. The calibration system will then prompt the user to open the blood circuit to atmosphere.

Remove the transducer protectors and tubing from the venous and arterial pressure luers on the front of the machine and press the VERIFY button.

3. After the VERIFY button has been pressed, the calibration system will prompt the user to pressurize the blood circuit to a positive pressure and then measure the pressure. Use a piece of tubing with a female luer fitting on one end (to be connected to the arterial pressure fitting on the front of the machine) and a fitting on the other end which will provide two female fittings when assembled (one of the fittings is to be connected to the machine and the other is to have a pressure test gauge connected to it).

4. After the two pressure fittings on the front of the machine are connected together and to a pressure gauge the level adjust buttons can be used to pressurize the blood circuit under test.

5. When a pressure of greater than 300 mmHg is achieved and is determined to be stable (if not stable and leaks are present fix the leaks before the calibration is completed, the STOP CAL button can always be pressed to abort any active calibration). Enter the measured arterial and venous pressures on the calibration keypad and press the ENTER button twice.

6. The calibration is complete at this point and the venous and arterial pressures should now be verified using the same procedure.

Calibrate Blood Pump EMF

Preconditions
- Blood tubing set of the type used for hemodialysis is installed on the machine.
- Power switch is on.
- Calibration switch is on and the calibration screen #1 is displayed.

Procedure

1. Select the BLOOD PUMP MOTOR EMF calibration line.

2. Press the START CAL button. The calibration system will then rotate the blood pump at a speed of about 60 RPM for about 10 seconds. After which point the calibration will be complete.

3. Note that the date printed on the BLOOD PUMP MOTOR EMF calibration line is the current date.

Calibrate Blood Leak Detector

Preconditions
- Blood tubing set of the type used for hemodialysis is installed on the machine.
- Power switch is on.
- Calibration switch is on and the calibration screen #1 is displayed.

Procedure

1. Select the BLOOD LEAK DETECTOR calibration line.
2. Press the START CAL button. The calibration system will then calibrate the blood leak detector in less than 3 seconds.
3. Note that the date printed on the BLOOD LEAK DETECTOR calibration line is the current date.

Operator Specified Calibrations

Preconditions
- Water supply is on.
- Power switch is on.
- Machine is displaying calibration screen #1.

Note: The calibration settings listed in this section are operator specified and are dependent on clinical practices and procedures specified by the attending physician such as heparin syringe size, heparin bolus amount, blood tubing size, high and low temperature alarms and high and low conductivity alarms. The settings must be within the ranges specified or included in the listing of options below or else the screen will not accept them.

1. Calibrate the remaining System 1000 machine settings as follows:
   a. Select the associated calibration line.
   b. Press the START CAL button.
   c. Enter the appropriate value.
   d. Press the ENTER button twice.

2. Upon completion of this procedure, deactivate the calibration mode.

WARNING Before resuming patient dialysis therapy, be sure the calibration switch is in the off position.

The calibration setting ranges and options to be entered for the clinical System 1000 machines are listed below:

| | |
|---|---|
| AIR DETECTOR | 5 to 25 µL |
| LEVEL ADJ MTR RATING | 12 V (fixed) |
| BLOOD PUMP FLOW RATE | 6, 7 and 8 mm; 1/4 inch; and custom sizes |
| HEPARIN SYRINGE SIZE | Monoject 12 and 20cc, Becton Dickinson 10 and 20cc |
| HEPARIN BOLUS AMOUNT | 0.5 and 1.0cc. |
| HIGH TEMP LIMIT | 37 to 42°C |
| LOW TEMP LIMIT | 29 to 37°C |
| HIGH CONDO ALARM | 13 to 19 mS/cm |
| LOW CONDO LIMIT | 9 to 14 mS/cm |
| BICARB PROP RATIO | DRAKE |

APPENDIX B

APPLICATION OF GROGAN ET AL.

Company Confidential

SATRN User Interface (Preliminary)

Definitions

1. Dialyze Mode - Run the patient
   a. All alarms functional.
   b. Machine has successfully completed self test.
   c. Air Detector armed.

2. Alarm Mode - a subset of the dialyze mode that occurs when any parameter goes outside of the preset alarm limits.
   a. "Alarm" will appear in the bottom left hand corner of the screen.
   b. The main alarm lamp will light.
   c. Audio alarm will sound.

3. Rinse Mode - Rinse the machine with water, chemical or heat disinfect, introduce conductivity to the machine.
   a. Dialyzer connectors on Rinse block.
   b. Air detector disarmed.
   c. Machine set at preset UF rate. Pressures between flow equalizer cavities is relieved so excessive vacuum does not develop in the flow path.
   d. Bypass valve cycles into bypass for 5 seconds every minute.
   e. The Blood pump will run.
   f. Conductivity or Temperature alarm
   g. The audio alarm will beep 3 times when the conductivity comes into limits and the machine enters the standby mode.

h. The machine will come out of the rinse mode if any of the interlock conditions are not met.

4. Standby Mode - Equivalent to the warm rinse mode found in the 480 with the rinse features of the SATRN.
    a. If conductivity and temperature are within alarm limits the warm rinse mode may be entered by pressing the rinse switch.
    b. All rinse interlocks are met.
    c. Machine can pass to dialyze mode by successfully completing a self test and by the reset switch being pressed.
    d. Machine set at preset UF rate. Pressures between flow equalizer cavities is relieved so excessive vacuum does not develop in the flow path.

5. Ready Mode - Equivalent to the dialyze mode except the "Start" button has not been activated to start the UF, Variable Na, Variable HCO3 or KT/V programs.

6. Main Screen Switch - always takes operator back to the Main Screen.

7. Help Switch - will open a window above the temperature and UF rate displays which provides help information to the operator.

8. ETD Display - this will display the estimated time of dialysis.

9. RTD Display - After the "Start" switch has been pressed and dialysis has started the ETD display will change to the remaining time of dialysis display.

10. Set Limits - The set limits switch will allow the operator to set the alarm window around the arterial, venous, and conductivity values.
    a. Conductivity limits will be fixed at a physiological safe range, the set limit switch will only bring the conductivity limit closer to the displayed conductivity value if it is within this safe range.
    b. Venous low alarm limit will be at 0 mmHg and the alarm limit window will not go below this pressure.
    c. Both arterial and venous alarm limits will be set at the same time. A window will be set ± 40 mmHg from the displayed pressure, except in the case of point b.

11. Menus Switch - This switch will allow the operator to go to the Menus screen which can enable the operator to go on to the program or SND screens.

12. Rinse Switch - enables the operator to go into rinse provided that the safety interlock conditions are met. If rinse is possible the operator will go to the rinse screen where the heat clean and chemical disinfect options are available.

13. Dedicated switches which are not on the CRT include:
    a. On/Off switch - this switch allows the machine to be turned on for operation. It does not cut off the mains power to the machine.
    b. Blood Pump on/off switch - will turn on power to the blood pump.

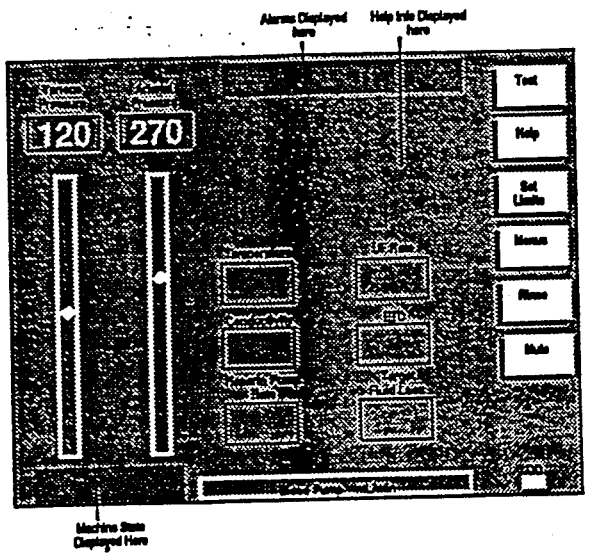

c. Manual Bypass switch - will divert the dialysate from the dialyzer to hook up the artificial kidney.
d. Reset switch - allows the operator to reset extracorporeal alarms when the condition is corrected.

Operation

Start Up

1. Press the on/off switch.

2. If a power failure had just occurred press reset once to go back into dialyze at the previous program.

3. To go into rinse, press the rinse switch once. If the rinse interlocks are met, the machine will go to the rinse screen, be in rinse mode and rinse will be displayed in the machine state window below the arterial and venous pressures.

Note    To go back to the main screen at any time press the "Main Screen" switch in the top right hand corner of all screens except the main screen.

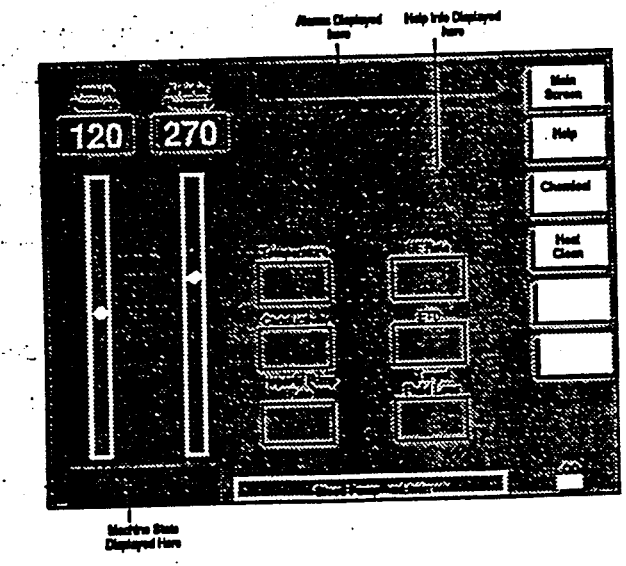

4. If the rinse interlocks are not met, the alarm window will display a message telling the operator that the rinse interlocks are not met.

5. Adjust the dialysate flow:
   Press the Qd window. Each time it is pressed it will cycle through the available dialysate flow rates. If the value displayed in the window is allowed to remain more than 5 seconds the dialysate flow will be controlled to that value.

6. Adjust the dialysate temperature:
   The temperature will come up at the previous dialysis set point. If another dialysate temperature is required: Press the temperature window. The calculator will appear at the side of the screen. Use the calculator keypad to input the desired dialysate temperature between 35.5 and 39. Temperatures outside of this temperature range will not change the set point. After the desired temperature appears in the calculator window, press the enter switch.

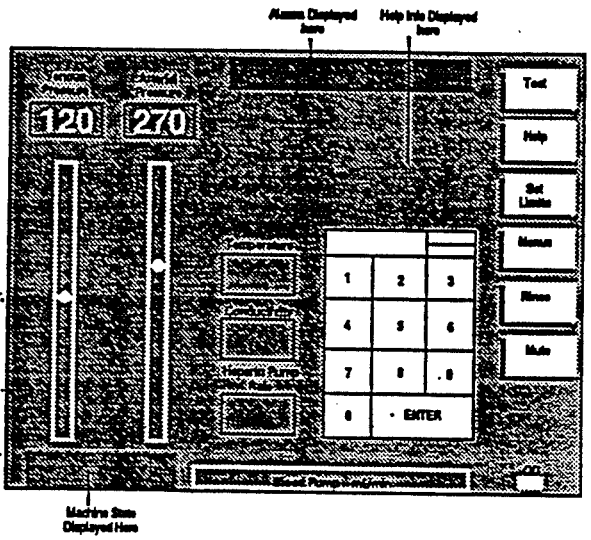

7. The operator should allow the machine to rinse for the appropriate amount of time and then check for residual disinfectant if the machine was recently disinfected.

8. After the residual disinfectant is rinsed from the machine, concentrate can be hooked up to the concentrate lines.

Note: If programmed QD, Na, HCO3 or KT/V is desired, these values can be programmed during the rinse mode.

9. When the conductivity is within the alarm limits the machine will automatically enter the standby mode.

10. A sample of the dialysate should be drawn from the machine and the conductivity of the sample checked. If the conductivity of the sample is correct then the test switch may be pressed and the machine will go into the self test mode. If the test mode is successful the Test Switch will change into the "Start Switch (The machine will shift to the ready mode if the UF has been programmed and the Dialyzer connectors are on the dialyzer).

Basic System Operation

The following procedure details the operator actions to enable the machine to be used for a linear UF removal and standard (non-varied) proportioning. If the Na and the bicarbonate are not going to be varied during the treatment then it is only necessary to set the Ultrafiltration parameters.

To set UF:
1. Press the ETD display. A calculator keypad will appear. Use the keypad to set the expected time of dialysis in hours and minutes.

Note — If the incorrect value has been input into the calculator, press the clear key and then enter the correct value.

Note — Setting the ETD will set it in any screen in which it shows. This value does not have to be set again once it is set 2. After the correct time in hours and minutes has been pressed in the calculator. Press the enter key.

3. Press the Target fluid loss display. (If the help switch is pressed within 2 seconds of pressing Target Fluid Loss

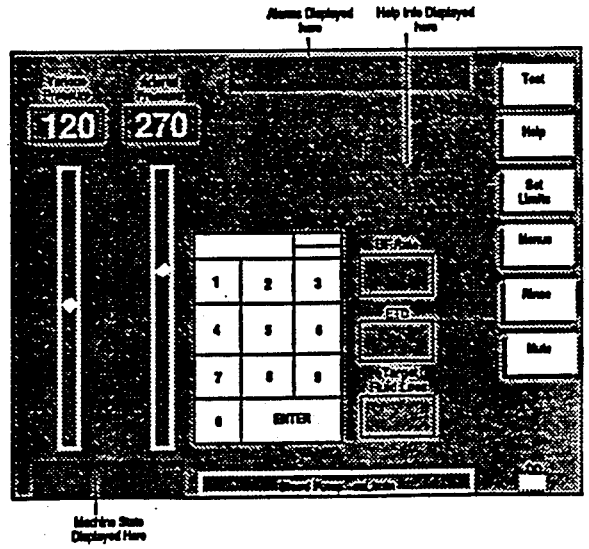

Company Confidential switch, the UF worksheet will appear in the help area).
  a. If the help switch is not pressed a calculator will appear. Use the keypad to set the desired ultrafiltrate to be removed for the treatment in liters per hour.
  b. If the UF worksheet is used enter each value with the calculator. When the worksheet is completely filled in the final value will be the target fluid loss.

4. After the target fluid loss has been entered, press the enter key.

Note — After the treatment has started if the patient has become hypotensive or it is necessary to go to a low ultrafiltration rate: Press the UF rate display once and the UF rate will go to the preset value of 100 mL/hr and the TMP alarm will delay for a minute and a new limit window will automatically go around the pressures caused by the 100 mL/h UF rate. To leave this minimum UF mode, press the UF rate display again and the machine will return to the previous UF rate and the TMP alarm will delay for a minute and will be set again around the TMP that results from resuming the UF rate.

Set the Heparin Pump Rate
1. Press the heparin pump rate display. The calculator will appear and a heparin time display will appear in the help window.

2. Enter the desired heparin pump infusion rate.

3. Press enter.

4. If preprogrammed heparin pump shut off is desired, press the heparin time display enter the heparin time (for instance 3.5 h for a 4 h dialysis).

5. Press enter.

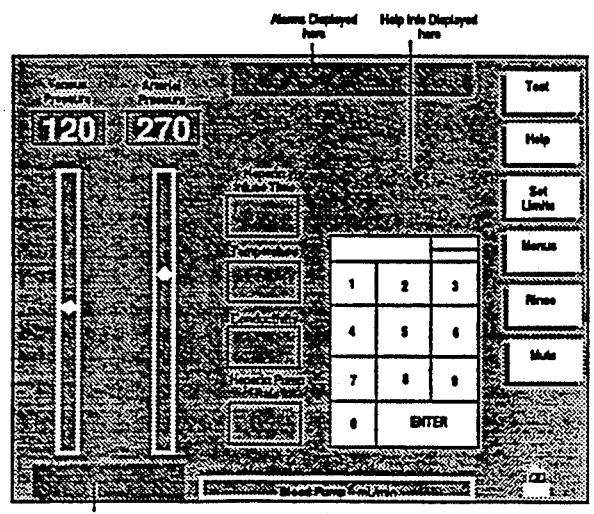

Company Confidential

Dialyzing the Patient
1. After the conductivity has been verified. Return to the main screen if necessary (by pressing Main Screen Switch). Then press the Test Switch. The machine will automatically self test the alarms and functions. If the machine has a problem it will not allow the operator to go further and will report a machine error. If the test is complete and there is no problem the machine state will change to the ready mode and the Test Switch will change to the Start Switch.

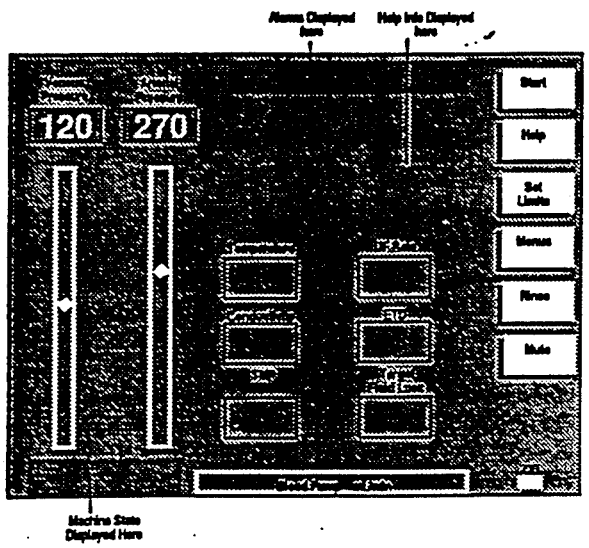

2. During the ready mode the dialyzer may be primed and the UF rate is ≈ 100 mL/h.

3. When the dialyzer is primed, set or make sure the UF and the heparin infusion rate have been set (if Na, KT/V Bicarbonate or UF programming is desired this should be done prior to putting the patient on the machine).

4. Hook the patient to the machine. To start the blood pump, press the blood pump switch and then press the desired blood pump flow rate on the touch screen.

5. After the patient is hooked to the machine and blood is flowing through the extracorporeal circuit press the Start Switch. This will start the UF mode and any other programmed variables. After ≈ 1 minute the machine will set the limits of the Venous, Arterial and the TMP. It will also close the alarm window around the conductivity

Company Confidential value. The Heparin rate display will change to the TMP display.

If it is necessary to change the heparin infusion rate: touch the TMP display and it will change to the Heparin Rate display. If the Heparin rate display is pressed the calculator will appear, input the new heparin infusion value and press the enter key and the new heparin infusion rate will be set. The heparin display will automatically change back to the TMP display in 2 minutes.

Extracorporeal Alarms
1. During an extracorporeal alarm. The UF rate will go to zero, the blood pump will stop and the line clamp will clamp. The machine will not count this time as dialysis time.

2. To get out of an extracorporeal alarm the operator must press the Reset Switch. The pressure alarms will be overridden for ≈ 5 seconds after reset has been pressed to allow the blood flow rate to return to its previous setting.

Change Pressure Limits
If it is necessary to change the alarm limits of the Venous, Arterial and the TMP. Press the set limits switch. The limits will automatically form a window around the pressure setting.

Programming
If it necessary to program NA, HCO3, KT/V or UF during treatment
a. Press "Menus".
b. When the switches change on the right hand side of the monitor press "Program".
c. When the switches change on the right hand side of the monitor, press either "Program UF", Program Na, KT/V or Program Bicarb depending on what variable is desired to be programmed.

To set the programmable Sodium:
1. Press "Program Na" switch. The program Na graph and switches should appear on part of the display.

2. Press the Standard Bath Na switch. The calculator appears. Enter the sodium value displayed on the concentrate container. Press enter. calculator disappears. The sodium value will be displayed in the Standard Bath Na window.

Company Confidential

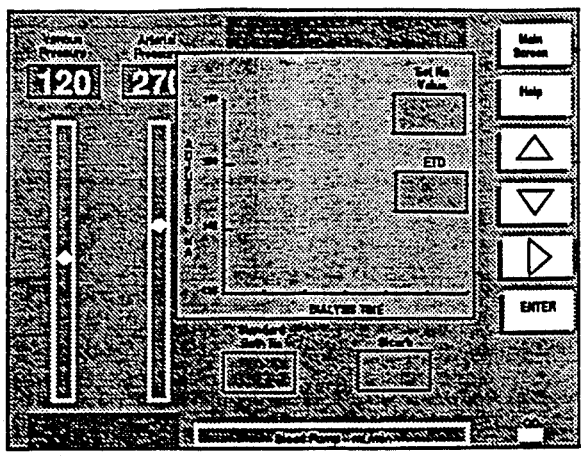

3. If the ETD was not entered previously press the ETD switch. The calculator appears. Enter the dialysis time in hours and minutes. Press enter. calculator disappears. The dialysis time will be displayed in the ETD window.

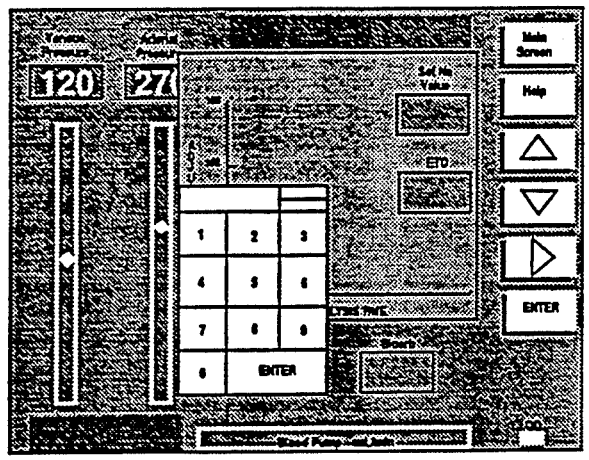

4. The Bicarb window will default to a "Ace" (acetate) position, touch the "Bicarb?" switch to change this to a "Bic" if a bicarbonate dialysis is to be run.

5. To set the variable sodium:
   a. The operator presses the approximate place on the graph of the desired starting sodium value. The actual value entered will be displayed in the Set Na Value window. This value can be fine tuned with the ▲ and ▼ arrow keys.

Company Confidential

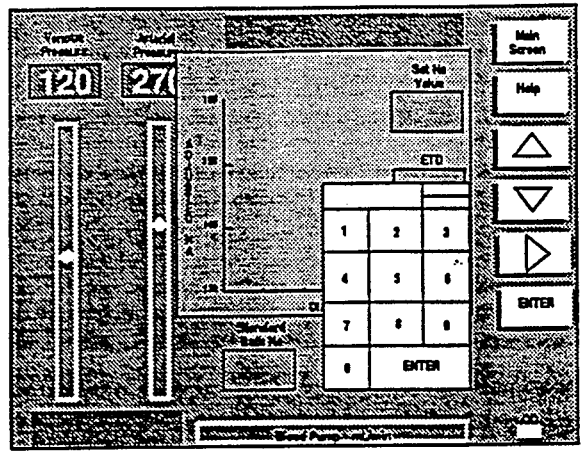

b. Then the operator will press the intersection point (NA/time) on the graph for the next sodium value desired. If the operator would like the sodium to vary in steps, the same sodium value as entered in step 5a should be entered Then the new sodium value should be entered at the same time coordinate on the graph. To view sodium values that have been previously entered use the ↓ arrow key to cycle through each sodium setting.

6. Sodium values should be entered for as many steps (20 minute steps) as desired. It is not required to enter a step for each 20 minute sequence. If 160 were the first point selected and 140 was selected 2 hours later. The machine would vary the sodium of the dialysate slowly lowering it to 140 over the two hours. If 160 was the first value selected and 160 was pressed in the two hour time coordinate, then 140 pressed in the two hour time coordinate. The dialysate sodium value for the first two

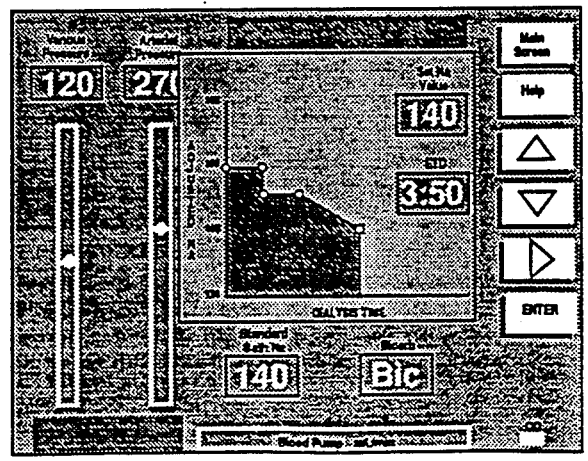

Company Confidential hours would be 160 and would change at the end two hour time frame to 140 where it would remain for the rest of the treatment unless another sodium value was selected. Step 5 should be repeated for all steps that the sodium should be changed to.

7. After all sodium values are entered on the machine, the enter key should be pressed and the program is set in the machine.

8. If another program or a program change is desired it can be reinput entirely or any of the values can be adjusted with the arrow keys and reentered.

Note   The ♦ switch will highlight the area selected. It will move one setting each time the ♦ switch is pressed. When the ♦ is pressed after the last value it will roll around back to the first value entered.

To Set the Programmable Ultrafiltration:
1. Press "Program UF" switch. The program UF graph and switches should appear on part of the display 2. If the ETD was not entered previously press the ETD switch. The calculator appears. Enter the dialysis time in hours and minutes. Press enter. calculator disappears. The dialysis time will be displayed in the ETD window.

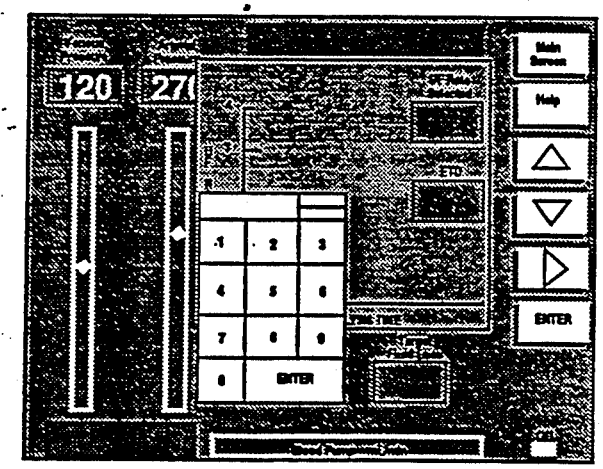

3. If the Target Fluid Loss was previously set the UF goal will appear in the display. If not touch the Target Fluid Loss display. The calculator appears. Enter the Target Fluid Loss in liters per hour. Press enter. The calculator disappears. The Target Fluid Loss will be displayed in the window.

Company Confidential

5. To program the UF removal:
   a. The operator presses the approximate place on the graph at the desired starting UF rate. The actual value entered will be displayed in the UF Rate Selected window. This value can be fine tuned with the ▲ and ▼ arrow keys.

b. Then the operator will press the intersection point (UF/time) on the graph for the next Ultrafiltration value desired. If the operator would like the UF to vary in steps, the same UF value as entered in step 5a should be entered Then the new UF value should be entered on the same time coordinate on the graph. To view UF values that have been previously input, use the ♦ arrow key to cycle through each UF rate setting.

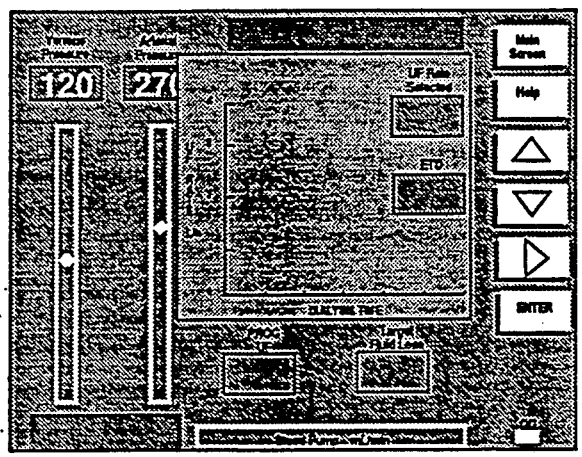

Note  As the operator sets the UF values in the graph the "Prog UF" display will show add each value until the display is equal to the Target Fluid Loss.

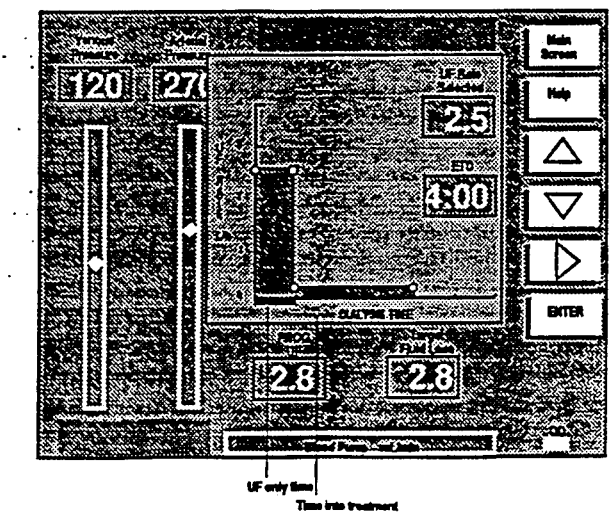

Company Confidential

6. Ultrafiltration values should be entered for as many steps (20 minute steps) as desired. It is not required to enter a step for each 20 minute sequence. If 1L/h were the first point selected and 0.5L/h was selected 2 hours later. The machine would control the ultrafiltration rate slowly lowering it to 0.5L/h over the two hours. If 1L/h was the first value selected and 1L/h was pressed in the two hour time coordinate, then 0.5L/h pressed in the two hour time coordinate. The ultrafiltration control rate for the first two hours would be 1L/h and would change at the end two hour time frame to 0.5 where it would remain for the rest of the treatment unless 0.5 L/h would exceed the Target UF value. Step 5 should be repeated for all the programmed UF rate changes desired.

7. After all UF rate variations are entered on the machine, the enter key should be pressed and the program is set in the machine.

8. If another program or a program change is desired it can be reinput entirely or any of the values can be adjusted with the arrow keys and reentered.

9. If sequential ultrafiltration is desired:
   a. Press the Manual switch once (while the UF program screen is on).
   b. Press the time coordinate on the graph when you would like the machine to go into sequential ultrafiltration.
   c. Press the manual switch once for each 20 minute interval that sequential UF is desired. A bar showing each 20 minute period should appear on the bottom of the UF graph. If the wrong time interval is selected press the manual bypass switch until it reaches the end of the ETD and the entered time value will be cleared and a new one entered.
   d. Press enter when the setting is correct.

To Set the Programmable Bicarbonate:

1. Press "Program Bicarb" switch. The program Bicarb graph and switches should appear on part of the display.

2. Press the Standard Bath Bicarbonate switch. The calculator appears. Enter the bicarbonate value displayed on the concentrate container. Press enter. The calculator disappears. The bicarbonate value will be displayed in the Standard Bath bicarbonate window.

3. If the ETD was not entered previously press the ETD switch. The calculator appears. Enter the dialysis time in hours and minutes. Press enter. calculator disappears. The dialysis time will be displayed in the ETD window.

4. To set the variable bicarbonate:

Company Confidential a. The operator presses the approximate place on the graph of the desired starting bicarbonate value. The actual value entered will be displayed in the Set Bicarbonate Value window. This value can be fine tuned with the ▲ and ▼ arrow keys.

b. Then the operator will press the intersection point (bicarbonate/time) on the graph for the next bicarbonate value desired. If the operator would like the bicarbonate to vary in steps, the same bicarbonate value as entered in step 4a should be entered. Then the new bicarbonate value should be entered at the same time coordinate on the graph.

To view bicarbonate values that have been previously entered use the ▶ arrow key to cycle through each bicarbonate setting.

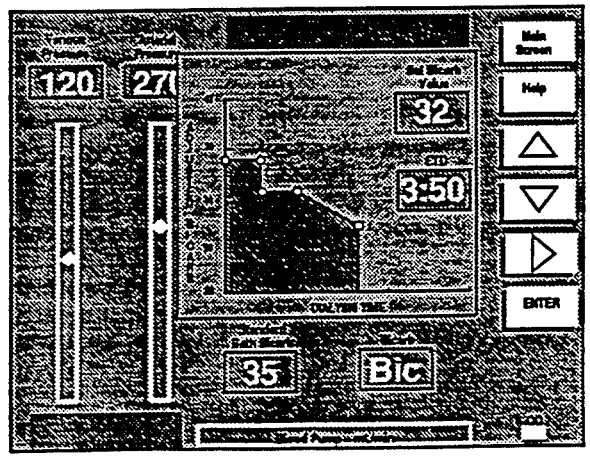

5. Bicarbonate values should be entered for as many steps (20 minute steps) as desired. It is not required to enter a step for each 20 minute sequence. If 35 meq/L were the first point selected and 32 was selected 2 hours later. The machine would vary the bicarbonate of the dialysate slowly lowering it to 32 over the two hours. If 35 was the first value selected and 35 was pressed in the two hour time coordinate, then 32 pressed in the two hour time coordinate. The dialysate bicarbonate value for the first two hours would be 35 and would change at the end two hour time frame to 32 where it would remain for the rest of the treatment unless another bicarbonate value was selected. Step 4 should be repeated for all steps that the bicarbonate should be changed to.

6. After all bicarbonate values are entered on the machine, the enter key should be pressed and the program is set in the machine.

Company Confidential

7. If another program or a program change is desired it can be reinput entirely or any of the values can be adjusted with the arrow keys and reentered.

Kinetic Modeling Program
During this mode the machine will automatically calculate the ETD and will update it as blood flow is changed or extracorporeal alarms interfere with treatment. In addition to calculating the optimum time of dialysis, the kinetic modeling program also displays the variables such as total blood treated.

1. Press "KT/V" switch.

2. Press the KOA display. Enter the KOA value of the dialyzer. Press the enter switch.

3. Press the V switch. Enter the physician calculated body urea distribution. Press the enter key.

4. Press the dialysis efficiency switch. Enter the value from 0.9 to 1.5 (adequacy of dialysis required). Press the enter switch.

5. The machine will automatically calculate the ETD and put this variable into all the other ETD windows on other screens.

Discontinue Dialysis
1. If the UF goal is reached the machine will go to 100mL/h UF rate, the RTD display will go to zero and the audio alarm will beep three times.

2. Lower the Blood flow rate. The arterial and venous alarms have a two second delay. It will be necessary to the Set Limits Switch a couple of times as these pressures are changed by lowering the blood pump speed.

3. Take the patient off the machine.
(Return extracorporeal blood to the patient, turn off the blood pump, clamp the blood lines and disconnect from the patient.)

Rinse Machine After Dialysis
1. Press the manual bypass switch.

2. Remove the dialyzer and the blood lines from the machine. Hook the dialyzer connectors to the rinse block.

3. Press the Rinse Switch.

Company Confidential

4. After acetate dialysis, connect the acid/acetate concentrate line to the acid/acetate rinse fitting.

Remove the acid/acetate concentrate line from the acetate concentrate container and connect it to the acid/acetate rinse fitting.

After bicarbonate dialysis, connect the bicarbonate concentrate line to the bicarbonate rinse fitting.

5. After acetate dialysis, rinse the machine with water for 15 minutes.

After bicarbonate dialysis;

a. Rinse the machine with acid concentrate and water for 5 minutes.
   b. Connect the acid/acetate concentrate line to the acid/acetate rinse fitting.
   c. Rinse the machine with water for at least 10 minutes.

Disinfect the Machine after Dialysis
1. Machine is in the rinse mode and has been rinsing with water at least 15 minutes. If the main screen is showing, press the rinse switch to go to the rinse screen.

Chemical Disinfection
   a. For Chemical disinfect move the chemical disinfect line into a container of 4 to 6% household bleach. Press the Chemical Disinfect Switch.
      The machine will infuse the bleach for 14 minutes, at the end of 14 minutes the audio alarm will beep 3 times.

b. The machine will continue rinsing. When the operator places the disinfect line into the disinfect fitting the machine will begin a programmed 10 water rinse.

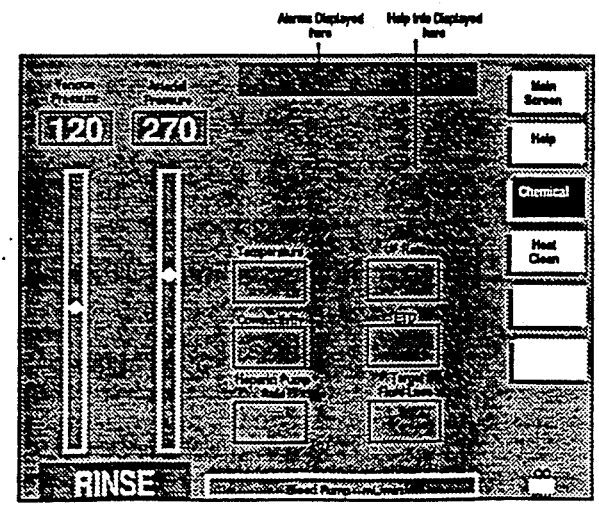

Company Confidential c. After 10 minutes the machine should be checked for residual bleach. If the machine is free of bleach, it can be prepared for the next patient or turned off.

Heat Clean
a. To heat clean the machine all concentrate lines should be in their appropriate fittings. Press the Heat Clean Switch.
The machine will go through the predetermined heat clean cycle (~30 to 45 minutes of heat and then cool down.

b. At the end of the Heat Clean cycle the machine will return to the rinse mode.

APPENDIX C

APPLICATION OF GROGAN ET AL.

System 1000 Development
Architecture
General Description
Main Controller Hardware (Host)

The System 1000 machine is controlled by an 80XX microprocessor (uP) and three 8040 microcontrollers (uC). The 80XX uP is located on an IBM PC/AT compatible motherboard, with its primary responsibilities being:
- User interface (CRT display and touch screen)
- State machine control (Rinse, Prime, Dialyze,...)
- Microcontroller communications
- Conducting self tests
- Calibrations The firmware for the 80XX uP is located on the Memory Board, which plugs into the motherboard. The Memory Board can hold up to 384K of ROM (read only memory). In addition it also contains 8K of nonvolatile static RAM (random access memory) (for calibrations and machine parameters), a memory card interface, an RS-232 interface, and a time of day clock. The 80XX uP has access to 256K of dynamic RAM located on the motherboard.

The 80XX uP controls the operation of the machine through its connection to the following additional boards which are plugged into the motherboard:

- EGA display board
- Touch screen interface board
- Blood Pump system controller board
- UF/Proportioning system controller board
- I/O system controller board
- RS-232 board (optional for patient blood pressure monitor)

Main Controller Software (Host)

The host control program is written in the 'C' programming language. The program source code is compiled, linked and loaded into programmable read only memory. This memory resides on the embedded hardware system memory board.

The purpose of the host control program is to:

- Gather data from the Input/Output, Blood Pump and Ultrafiltration controller sub-systems, and output control functions to the various controller sub-systems.
- Input data from user interface touch screen.
- Monitor the data for violation of alarm limits and unsafe operating conditions, and to set the appropriate program alarm condition indicators;
- Evaluate the data to determine the current operating state of the control program, i.e. Standby, Rinse, Self Test, Prime and Dialyze.
- Update the display data to the CRT portion of the user interface.

Blood Pump Control System

Five subsystems are controlled or monitored by the blood pump controller. They are:

- Blood pump
- Blood pressure measurement (arterial, venous and expansion chamber)
- Heparin delivery
- Level adjust
- Ambient temperature

Blood Pump Controller

The purpose of the blood pump controller is to supply power to the blood pump motor such that the pump head will turn and pump at a rate selected by the operator.

The blood pump controller system consists of the following major components:

| Description | Location |
|---|---|
| User parameter entry | Host controller |
| Software Speed Error Control | Bld Pmp Controller |
| Hardware Speed Error Control | BP Power Board |
| Optical speed sensor | On motor shaft |
| Motor Power Driver Circuitry | BP Power Board |

The operator enters the desired blood pump rate information on the video screen (CRT) touch panel. The host controller (80XX microprocessor) converts this information to the appropriate motor rate which it then sends to the Blood Pump controller (8040) on the Blood Pump Controller board. The 8040 controller converts the motor rate information to an analog level, which is fed to a motor speed control IC (LM2917-8) on the Blood Pump Power board.

An optical speed sensor is mounted on the rear shaft of the blood pump motor, with an LED being positioned on one side of the shaft, and a photo transistor on the opposite side. The shaft has two holes drilled through it, with each hole being perpendicular to the shaft and to each other. This results in four optical pulses received per shaft revolution.

This tachometer signal is monitored by both the LM2917-8 and the 8040 controller. The LM2917-8 provides quick responding speed control by comparing the motor speed with the desired speed information from the 8040. The result of this comparison is an error signal which provides an input to the motor power driver circuit.

The motor power driver provides a +24 V pulse width modulated drive to the motor at a frequency of approximately 30 KHz. This drive is current limit protected, to prevent damage in the event of a stalled motor.

The 8040 compares the tachometer motor speed information with the desired speed commanded by the 80XX and corrects the level provided to the LM2917-8 accordingly. In this way the 8040 guarantees the ultimate accuracy of the pump, with the LM2917-8 circuit not requiring any calibration. In addition, the 8040 can monitor for control problems, such as under speed or over speed, which may result from failures in the LM2917-8 or motor drive circuitry.

The 8040 also monitors the motor speed independent of the tachometer signal using the motor's back EMF. Periodically (every 0.5 second) the motor drive is turned off for approximately 6 millisecond and the voltage at the motor terminals is measured. Though this does not result in as precise an indication as the tachometer signal, gross failures can be determined, such as when the tachometer signal is lost.

Blood Pressure Measurement

The blood pressure measurements include the venous, arterial and expansion chamber (for Single Needle treatment) pressures. All three measurement systems include identical hardware. Each pressure is sensed by a SenSym SCX15 gauge sensing pressure transducer mounted to the Blood Pump Power board. Each transducer is connected to a differential amplifier designed to provide a measurement range from −400 to +600 mmHg. The output of each amplifier drives an A/D input channel of the Blood Pump Control system, at which point it is converted to a 10 bit digital value. The calibration of the each pressure input is handled entirely in software, requiring that the design of each amplifier guarantee that its output remain within the A/D input range of 0 to +5 V over the input pressure range and over all component tolerances.

Heparin Delivery

Heparin delivery is accomplished by stepping a stepper motor which rotates the pinion of a rack and pinion mechanism. The pinion moves the rack, and the mechanical fixture is such that the plunger of the heparin syringe moves the same distance. The stepper motor is controlled by the 8040 microcontroller located on the Blood Pump Controller board. When the operator enters a desired heparin rate in milliliters per hour (mL/h) via the front panel touch screen, the host 80XX microprocessor converts this information to the appropriate motor step rate and passes it to the Blood Pump microcontroller. The Blood Pump microcontroller outputs a motor step rate logic signal to the Blood Pump Power board where the heparin motor power drive circuitry energizes the appropriate stepper motor coil.

The motor step rate logic signal from the Blood Pump microcontroller is also input to the IO Controller board 8040 microcontroller. The IO microcontroller monitors this signal to determine if the heparin motor is going the appropriate speed. If it determines that an overspeed condition exists, it disables the heparin motor via a disable line that goes to the Blood Pump Power board.

There are two optical sensors to provide information about the state of the heparin pump. The disengage sensor detects when the front panel syringe holder arm is in the disengage position. The end-of-stroke sensor detects when the pinion is raised up on the rack, which occurs when the gear teeth are not meshed. This is an indication of an overpressure condition. The Blood Pump microcontroller monitors the state of these sensors and passes the information to the host 80XX microprocessor.

Level Adjust

The level adjust system allows the operator to change the blood level in the arterial and venous drip chambers. A level up and level down button exists for each drip chamber. The 8040 microcontroller on the Blood Pump Controller board monitors the button positions. When a button is pressed, a valve selects that drip chamber and power is supplied to the motor such that the pump head of a peristaltic pump rotates to apply a positive or negative pressure to the drip chamber. The software logic only accepts one button press at a time. If two buttons are pressed simultaneously, both are ignored.

The motor drive circuitry is located on the Blood Pump Power Board. The motor may be driven in the forward or reverse direction. A direction signal from the Blood Pump Controller Board, along with a pulse width modulated motor rate signal controls two bipolar half bridge motor drivers. Both half bridge motor drivers receive the same motor rate signal, while the motor direction signal is high at one and low at the other to determine the direction the motor runs. The half bridge drivers provide a 24 V pulse width modulated drive voltage of approximately 30 KHz to the motor.

Ambient Tempertature Control

The purpose of the cabinet cooling system is to keep the internal temperature of the cabinet lower than the 50°C maximum temperature at which that the electronic components are guaranteed to operate. (Most electronic components are rated to operate at 60°C, the exception is the solid state relay used for heater control.) A fan is located at the base of the cabinet and exhausts the warm cabinet air. An intake vent for the ambient room temperature is located below the CRT on the back of the machine.

The cabinet cooling system consists of the following major components:

| Description | Location |
| --- | --- |
| Cabinet Fan | Base of cabinet |
| Blood Pump Temperature IC | Blood Pump Power Bd |
| Misc IO Temperature IC | Misc IO Electronics Power Bd |
| Software Fan Control | Host controller |
| Cabinet Fan Drive | Blood Pump Power Bd |

The two LM35DZ temperature ICs are located on the Blood Pump and Misc IO Electronics power boards. This IC outputs a voltage linear with temperature in °C (10.0 mV/°C). These temperature readings are input to the fan control software.

The fan control software always responds to the higher of the two temperatures. Typical values are as follows. At 46°C the fan turns on in the low speed mode and at 48°C it turns on in the high speed mode. There is a 2°C of hysteresis at these threshold temperatures, i.e. the fan returns to low speed at 46°C and turns off at 44°C. In addition, at 60°C a cabinet temperature alarm occurs that results in the machine shutdown state.

The fan power driver is located on the Blood Pump Power board. A motor rate signal from the Blood Pump Controller board determines the duty cycle of a 30 KHz pulse width modulated signal. This signal is input into a passive filter to provide a DC signal to the motor.

UF/Proportioning Control System

The UF/Proportioning Control system monitors and controls the System 1000 dialysate preparation. Six subsystems are controlled or monitored by the UF/Proportioning system. They are:

a. Temperature Control
b. Proportioning Control
c. Flow Control
d. UF Removal Control
e. Conductivity Monitoring
f. Temperature Monitoring

Temperature Control

The UF/PROP system controls the dialysate temperature by enabling a zero voltage crossing solid state relay, which provides the power to a 1500 W heater, with a 5 Hz pulse width modulated digital signal (heater enable signal). The duty cycle of the heater enable signal is updated every 0.5 seconds with the sum of the past duty cycle and a temperature error correction value. The correction value is proportional to the difference between the desired temperature (stored by the host) and the measured control temperature (measured immediately down stream of the heater housing).

The host determined desired temperature is calculated using the user entered desired temperature and the stable "B" conductivity probe temperature. If the stable "B" conductivity probe temperature is different from the user entered desired temperature by more than 0.05°C, then the control temperature threshold sent to the UF/PROP controller is updated so that the "B" conductivity probe temperature will equal the user entered desired temperature. In this way, the dialysate temperature at the "B" conductivity probe will be adjusted so that flow rate and ambient temperature effects on the "B" conductivity probe temperature (and the primary temperature, displayed on the video screen) will be compensated. This control temperature adjustment is performed a maximum of every 5 minutes.

Proportioning Control

The UF/PROP system controls the concentrate(s) to water proportioning ratios by controlling the dialysate flow rate, the "A" concentrate flow rate, and the "B" concentrate flow rate.

The "A" and "B" concentrate pumps are stepper motor driven (each by a cam/follower) diaphragm pumps which deliver a calibrated volume of concentrate per stepper motor revolution. Their flow rates are controlled by controlling the speed of the stepper motors. The concentrate pumps are unidirectional and utilize the proper actuation of a three-way valve for their intake and output pumping strokes. The intake stroke is synchronized by a signal that is generated by an optical interrupter sensor which senses a pin mounted on the cam of the pump assembly.

The UF/PROP controller utilizes the fact that the stepper motors require 200 motor steps per revolution (between each synchronization pulse) to check the concentrate pumps for stepping errors. If late or early synchronization pulses are received then the associated error conditions are reported on the screen during the Technician Mode of the machine.

During the Rinse Mode, the host determines the concentrate treatment mode based on the "A" and "B" rinse port interlock information. If the "B" concentrate line is not on the "B" rinse port, a bicarbonate treatment is initiated by setting the proportioning ratios and the conductivity alarm limits appropriately. Conversely, if the "B" concentrate line is in the "B" rinse port, an acetate treatment is initiated. Using the dialysate flow rate and the proportioning ratios, the host determines the associated concentrate flow rates and stores the two concentrate pump speeds in the UF/PROP controller. The porportioning mode (for acetate or bicarbonate dialysis) cannot be changed in the Prime or Dialyze Modes.

The control of the dialysate flow rate is described in the Flow Control section of the UF/PROP controller description.

Flow Control

The UF/PROP system controls the dialysate flow rate by controlling the time between the switching of the flow equalizer (volumetric pump) valves (provided that all the fluid within the flow equalizer chambers has been exchanged).

The average flow equalizer volume is calibrated (measured) during the Calibration Mode. The time between the switching of the flow equalizer valves is scaled by the host (according to the calibration constant) and stored in the UF/PROP controller so that the user entered desired dialysate flow rate is achieved.

To guarantee the complete fluid transfer to/from the flow equalizer chambers two flow sensors are located within the fluid path to detect the absence of dialysate flow. The time at which both sensors detect no flow has been defined as end-of-stroke. The end-of-stroke time has been defined as the time between moment end-of-stroke was sensed and the desired flow equalizer valve switch time. Since the supply pump speed controls the instantaneous dialysate flow rate, the UF/PROP controller servos the supply pump speed in order to maintain a consistent end-of-stroke time.

Since the flow equalizer volume is calibrated and the end-of-stroke time is controlled, the UF/PROP system can accurately control the dialysate flow rate to the user entered value.

UF Removal Control

The UF/PROP system controls the UF removal rate by controlling the time between the switching of the UF removal metering device valves. The UF/PROP system controls the accumulated UF volume by counting the number of UF removal meter strokes.

Since the UF removal metering device volume is calibrated (measured) in the Calibration Mode, the rate which the host (80XX microprocessor) passes to the UF/PROP controller (number of seconds between valve switches) is scaled so that the user entered UF removal rate is achieved.

In the same way, the user entered UF removal volume is scaled by the UF metering device's stroke volume to a number of UF meter strokes. The host passes the number of UF meter strokes to the UF/PROP controller. The UF/PROP controller will then switch the UF removal meter valves and decrement the stroke number, at the desired rate, as long as the stroke number is greater than zero. The host can then calculate the UF removal volume accumulated by subtracting the number of UF strokes remaining, scaled by the stroke volume, from the operator entered desired UF removal volume. The accumulated volume is displayed during the Dialyze Mode. This value remains during the Rinse Mode and is cleared upon the entry of the Self Test Mode.

In Rinse, the UF removal rate is 3.6 L/h and screen indicates no UF volume accumulated. During the Self Test Mode, no UF removal occurs except for during specific self tests performed by the machine (no UF volume is accumulated). In the Prime Mode, the UF removal rate is set by the operator and is no greater than 0.5 L/h (no UF volume is accumulated). During the Dialyze Mode, the UF removal rate is set by the operator and is limited to be between 0.1 and 4.00 L/h. For UF removal to occur in the Dialyze Mode the following conditions must be met:

1. A target UF volume and a UF rate have been entered (or treatment time and target UF volume have been entered and a machine calculated UF rate is used).
2. The blood pump is pumping.
3. The target UF volume has not been reached.

Conductivity Monitoring

Conductivity is used as a measurement of the electrolyte composition of the dialysate. Conductivity is usually defined as the ability of a solution to pass electrical current. The conductivity of dialysate will vary due to the temperature and the electrolyte composition of the dialysate.

The UF/PROP system measures conductivity at two locations in the flow path using alternating current resistance measurements between each of the conductivity probes' electrode pairs. The two flow path locations are at the "A" conductivity probe and the "B" conductivity probe, which are located immediately down stream of the "A" and "B" mixpoints/ mixchambers, respectively.

One electrode of each of the probes is stimulated with a 1 kHz ac voltage while the other is held at virtual ground (current sense electrode). Two voltages are produced by the resistance measurement circuit. The ratio of the voltages is proportional to the resistance of the respective probe. The resistance of the probes has been modeled as a function of temperature and conductivity. Since each of the conductivity probes contains a thermistor, the temperature at each of the probes is known. Using the model that was derived for the probes, the temperature measured at the probes, and the resistance measured at the probes the conductivity is calculated.

Each conductivity probe is calibrated during the Calibration Mode, at which time the resistance of each probe is measured at a known conductivity and temperature (by the use of an external reference meter) for the scaling of the probe's base resistance in the relationship described previously.

The UF/PROP system generates alarms from the measured conductivities at the "A" and "B" probes. Since these conductivity alarms are used to verify the proportioning ratios, the alarms are generated by testing the "A" conductivity and the "B" portion of the total conductivity ("B" portion = "B" conductivity – "A" conductivity). The alarm limits are determined from the concentrate treatment mode and are stored in the UF/PROP controller by the host. Therefore only during a bicarb treatment would the host store a non-zero expected "B" conductivity portion.

The host determines the concentrate treatment mode during the Rinse Mode by reading the "A" and "B" rinse port interlock information. If the "B" concentrate line is not on the "B" rinse port, a bicarbonate treatment is initiated by setting the proportioning ratios and the conductivity alarm limits appropriately. Conversely, if the "B" concentrate line is in the "B" rinse port, an acetate treatment is initiated. Upon exiting the Rinse Mode the concentrate treatment mode is set for the remainder of the dialysis treatment (concentrate treatment mode is only adjusted in the Rinse Mode).

Temperature Monitoring

The UF/PROP system measures the dialysate temperature at three locations in the fluid path. The first location is directly after the heater and this thermistor, the heater thermistor, is used for the primary temperature control feedback. The next two thermistors are contained in the "A" and "B" conductivity probes. These temperatures are used to temperature compensate the "A" and "B" conductivity measurements. The "B" conductivity temperature is also used to generate a backup high temperature alarm.

The temperature measurement circuit used throughout the machine consists of a voltage divider with a Thevenin Equivalent circuit of $3062 \, \Omega$ in series with a 7.55 V supply. The voltage divider circuit when connected to the thermistor used in the temperature measurement system referenced to ground produces the voltage to temperature relationship of $$T \, (°C) = (3.77V - Vtemp) * 12.73 \, (°C/V) + 37°C.$$

The tolerance on the component parameters used in the temperature measurement system can be as great as 10%, therefore the temperature to voltage relationship must be calibrated. Calibration of the temperature measurements is a two point calibration done at 30 and 40°C. The calibration procedure results in a calibration constant for both the slope and the offset for each temperature probe/circuit.

In the UF/PROP controller the voltage described above as Vtemp is measured for the three temperature probes in its system on a scheduled basis (every 0.2 seconds for the "A" and "B" temperatures and every 1 second for the heater temperature).

The temperature that is displayed on the video screen is measured at the primary ("dialysate") conductivity probe, located just before the bypass valve, by the IO controller.

Miscellaneous Input/Output Control Systems

Nine subsystems are controlled or monitored by the I/O control system. They are:

- Air detector
- Blood leak detector
- Dialysate pressure monitor
- Heparin pump overspeed monitor
- Bypass system and flow sensor
- Conductivity monitor
- Temperature monitor
- Line clamp
- Power fail alarm

Air Detector

The air detector assembly utilizes a set of 2 MHz piezo crystals. One crystal functions as an ultrasonic transmitter and the second crystal functions as a receiver. The emitter and detector are housed into identical assemblies. There is a distance of 0.20 inch between these assemblies into which the venous blood line is placed during dialysis. The emitter is driven by a 2 MHz squarewave that is derived from a crystal oscillator located on the I/O Electrical Power board. When there is fluid in the blood line between the crystal assemblies, the 2 MHz signal is coupled to the detector assembly. The return signal from the detector assembly is amplified and rectified by two independent circuits also located on the I/O Electrical Power board. These dc output levels are monitored using two different methods. The first method is the software generated alarm and the second is the hardware generated alarm.

Software Alarm Detection (Primary Alarm)

One output is fed from the I/O Electrical Power board to an A to D converter and read by the 8040 microcontroller on the I/O Controller board. This value is averaged over a 400 msec time period and reduced by multiplying it by 15/16 and subtracting 50 mV (for noise immunity). This new value is then converted back to an analog level to be used as an alarm limit. This software generated limit is compared to the rectified dc signal from the detector. The output state of this comparator is monitored by the on-board 8040. When the unaveraged signal falls below the software generated limit for longer than a calibratable time period, an alarm occurs. Sensitivity of the software alarm is 10 microlitres at 300 mL/min blood flow.

Hardware Alarm Detection (Secondary Alarm)

The hardware alarm is redundant to the software generated alarm. This alarm uses two comparators on the I/O Electrical Power board. One comparator looks for a minimum dc level from the rectified detector signal which guarantees the presence of fluid in the venous tubing. The second comparator is ac coupled to react to a large air bubble in the tubing. Sensitivity of this detector is approximately 300 microlitres at 300 mL/min blood flow. Both comparator outputs are wire OR'd together so that either comparator will generate an alarm.

Blood Leak Detector

The detector assembly consists of a high efficiency green LED and a photocell. These components are installed into a housing through which spent dialysate passes. Both of these components connect to the I/O Hydraulic Power board. The LED is connected to a voltage to current converter on the I/O Hydraulic Power board. The input to this circuitry comes from the I/O Controller board. The photocell is tied to the +5 V reference supply through a 750k ohm resistor. This provides a voltage divider which is monitored on the I/O Controller board.

The current through the LED is adjustable and controlled via a D to A output from the I/O Controller board. The light intensity of the LED is adjusted to illuminate the photocell to a point where its resistance is below the alarm threshold. During a blood leak, the presence of blood in the housing attenuates the light striking the photocell which causes an increase in both the photocell resistance and voltage. The increase in voltage (monitored by the microcontroller on the I/O controller board) results in a blood leak alarm.

Dialysate Pressure Monitor

The dialysate pressure is sensed by a resistive bridge pressure transducer located just upstream of the dialyzer. The transducer is connected to a differential amplifier circuit on the IO Hydraulics Power board designed to provide a measurement from −400 to +500 mmHg. The differential amplifier circuit also has an offset input that comes from a software calibratable variable, DAC_OFFSET. The output of the amplifier drives an A/D input channel of the IO Controller system, at which point it is converted to a 10 bit digital value. The calibration of the pressure input is handled entirely in the software, requiring that the design of the amplifier guarantee that the output remains within the A/D input range of 0 to +5 V over the input pressure range and over all component tolerances.

Heparin Pump Overspeed Monitor

To insure that the heparin pump does not exceed its set speed, the IO controller board software monitors a clock signal from the Blood Pump Controller board that is equivalent to 1/4th the heparin pump step rate. In the event that a heparin pump overspeed occurs, the IO controller board disables the heparin pump via a hardware line that goes to the Blood Pump Power board and notifies the host of the alarm.

To determine if the heparin pump is running the correct speed, the time it takes for ten clock signals to occur is measured (and stored in variable HEPTIMER) and compared against a minimum time period that is set by the host (HP_P_MIN). If the measured period is less than the host set limit, a normal speed alarm occurs. The host is notified of the normal speed alarm and the heparin pump is disabled via the hardware line to the Blood Pump Power board.

When the heparin pump rate changes, the host resets the minimum time period, HP_P_MIN, and the IO controller waits for the first clock signal to restart the timer (this first clock is not counted as one of the ten). In this way, the alarm logic is resynchronized with the heparin pump stepper motor.

The IO controller board also monitors the total amount of heparin delivered in the high speed bolus mode. When it receives clock signals at a rate faster than a predetermined speed, it assumes the pump is operating in the high speed mode. It has a high speed counter, H_SPD_CNTR, that is set by the host. If more high speed counts occur than are in the counter, a high speed alarm occurs. The host is notified of the high speed alarm and the heparin pump is disabled via the hardware line to the Blood Pump Power board.

Bypass System and Flow Sensor

The bypass mode is initiated when a primary dialysate alarm is detected by the IO Controller board, when a redundant dialysate alarm is detected by the UF/PROP Controller board, when the host requests bypass, or when the manual bypass button is pushed.

The bypass valve is in the bypass position when deenergized. It is driven from the nominal +24 V supply with a straight on/off transistor control on the IO Hydraulics Power board.

To verify that there is not a failure in the bypass system, a flow sensor just downstream of the predialyzer bypass valve checks for flow. If flow exists during the bypass mode, a Bypass Fail Alarm is set and the machine is put in the safe, nonfunctional, Shutdown state. If there is no flow when not in the bypass mode, a No Flow alarm is generated.

This flow sensor consists of two thermistors. The first is a reference thermistor used to determine the fluid temperature. The second thermistor uses thermal dilution to sense the fluid flow. The voltage outputs from the thermistors on the IO Hydraulics Power board drive A/D input channels on the IO Controller board where they are converted to 10 bit digital values. A software algorithm in the IO Controller code uses these inputs to determine the flow condition. The design of the voltage divider guarantees that the output remains within the A/D input range of 0 to +5 V over the input temperature/flow range and over all component tolerances.

Conductivity Monitoring

The conductivity probe itself consists of two stainless steel probes inserted into the flowpath just prior to the dialyzer. The drive signal for the conductivity probes is a capacitive coupled squarewave generated on the I/O Hydraulic board. This signal is sent to the conductivity probe and a monitor circuit. Both the monitor circuit and the return signal are rectified and filtered. These dc values are routed to I/O Controller board along with the temperature signal.

On the I/O controller board, the temperature, conductivity, and conductivity reference signals are input to an A to D converter that is monitored by an on board 8040 microcontroller. The microcontroller calculates the temperature compensated conductivity. This value is then displayed on the CRT as the conductivity in milliSiemens.

Temperature Monitoring

The thermistor installed in the conductivity probe changes its' resistance in response to changes in temperature. This conductivity probe is located just prior to the bypass valve and is the final temperature and conductivity measurement point. The values for conductivity and temperature measured at this point are displayed on the CRT and are used to generate the primary alarms for patient safety. If either value is outside of set limits, a bypass condition and audio alarm occur.

The thermistor is wired to a resistor divider network on the I/O hydraulic board. The output of this divider network is sent to the Miscellaneous I/O controller board where it is monitored by the on board 8040 microcontroller via an A to D converter network. From this information, the controller calculates the temperature using offset and gain inrmation stored in the host from the calibration. Calibration of the temperature measurement is a two point calibration done at 30 and 40°C.

Line Clamp

The line clamp opens with a solenoid and clamps with a spring return. When the solenoid is not energized, the spring pushes the plunger away from the solenoid. This causes the plunger to clamp the blood tubing. When the solenoid is energized, it pulls the plunger in with enough force to overcome the spring force. This unclamps the blood tubing. In the event of a power failure, the solenoid is de-energized causing the blood line to be clamped.

The solenoid is controlled by the line clamp board. On the line clamp board is a pulse width modulated current controller. This circuit applies sufficient current to the line clamp solenoid to pull in the plunger. After pull in, the controller ramps the current down to a level capable of holding the line clamp open. This cut back in current reduces the temperature of the solenoid, resulting in a more reliable device. Also located on the line clamp board, is a quick release circuit which helps dissipate the (power) stored in the solenoid. The result of this circuitry is a quicker and more repeatable clamp time over the life of the machine.

[ENERGY] 

Control for the line clamp comes from the Miscellaneous I/O controller board via the I/O power board. The control signal for clamp and unclamp is optically coupled on the line clamp board. This provides electrical isolation between the high voltage used to operate the line clamp and the low voltage used for the control signals from the microprocessor.

Power Fail Alarm

The power fail alarm circuitry is located on the Misc I/O Electrical Power board, and includes a CMOS power state flip flop powered by a 1 Farad (F) capacitor. The flip flop, which can be toggled by either the front panel power button or the 80XX system controller, provides the following functions:

- When power is not supplied to the machine (i.e. when the +5 V supply is off) and when the flip flop is in the on state, then power is supplied from the 1 F capacitor to the audio alarm device. When power is supplied to the machine, the flip flop's output state is read by the 80XX, which provides indication of the intended machine power state. Also, when the flip flop is in the on state, power is supplied to the front panel power switch LED.

- The first function listed above results in the power fail alarm. The alarm occurs either if the machine loses power while it is running, or if the front panel power button is pressed "on" when there is no power supplied to the machine. The alarm can be silenced by toggling the flip flop off through pressing "off" the front panel power button.

Power System

The System 1000 power system consists of the following primary components:

- Power line circuit breaker/power switch
- Power transformer input fuse
- Power transformer
- Unregulated +24 V power supply
- +5 V, +12 V and -12 V logic power supplies All current from the power plug passes through the power line circuit breaker, which doubles as a main power switch. Both sides of the power line are broken by the circuit breaker. Two loads are fed from the breaker, the dialysate heater and the power transformer. Because the transformer draws much less power than the heater, a fuse is in series with its primary, which protects the transformer from a shorted secondary winding.

The transformer has three secondaries: a 20 Vac winding which supplies the +24 V supply, a 120 Vac secondary which supplies the logic power supply, and a 20 Vac winding which supplies the isolated voltage to the RS-232 interface. The +24V supply provides power to the machine's motors and solenoids, as well as to a +12V switcher which powers the CRT display. The logic power supply provides power to all the digital and low power analog circuitry.

Memory Controller Board

The memory controller board is designed to plug into the (IBM XT compatible) motherboard, and provides the following functions:

1. Six 28-pin EPROM sites allowing 384 Kbytes of ROM (read only memory) for program storage.
2. 8K bytes of non-volatile memory (CMOS RAM with self contained battery).
3. Realtime clock module (self contained with battery).

4. Asynchronous serial communications port (requires external isolation buffers, provided on a separate board).

5. External memory card interface (requires separate personality board).

6. 4 position dip switch for machine configuration control.

This board is designed to operate in conjunction with a modified motherboard. The modification involves disabling the motherboard's data buffers above address 256K. The memory controller's ROM space is mapped into the address space from 256K to 640K, with the portion between 256K and 312K being mapped also to address range 832K to 888K. The code at this upper address range is configured as a BIOS extension, which results in the ROM being given control by the motherboard's BIOS software following power on initialization. Unlike the standard BIOS extensions, the System 1000 code does not return to the BIOS after being given control.

Additional features:

A jumper (JP5) provides the capability of selecting an alternate memory configuration (presently disables ROM chip select functions, allowing operation with a floppy disk and second 256K of RAM) for development purposes. During normal operation, the jumper is either removed or placed on pins 2 and 3.

Circuitry is provided to insert memory wait states for any read or write operation of either memory or I/O (except memory refresh operations on the motherboard RAM array). This compensates for the added buffer delays, as well as the slower (than RAM) ROM devices.

Circuitry is also provided to extend the trailing edge of the write strobes (for both memory and I/O) so that the data buffers remain enabled well beyond the end of the PC Bus write strobes.

Programmable array logic (PAL) devices are used for address decoding for both memory and I/O devices.

System Architecture Block Diagram
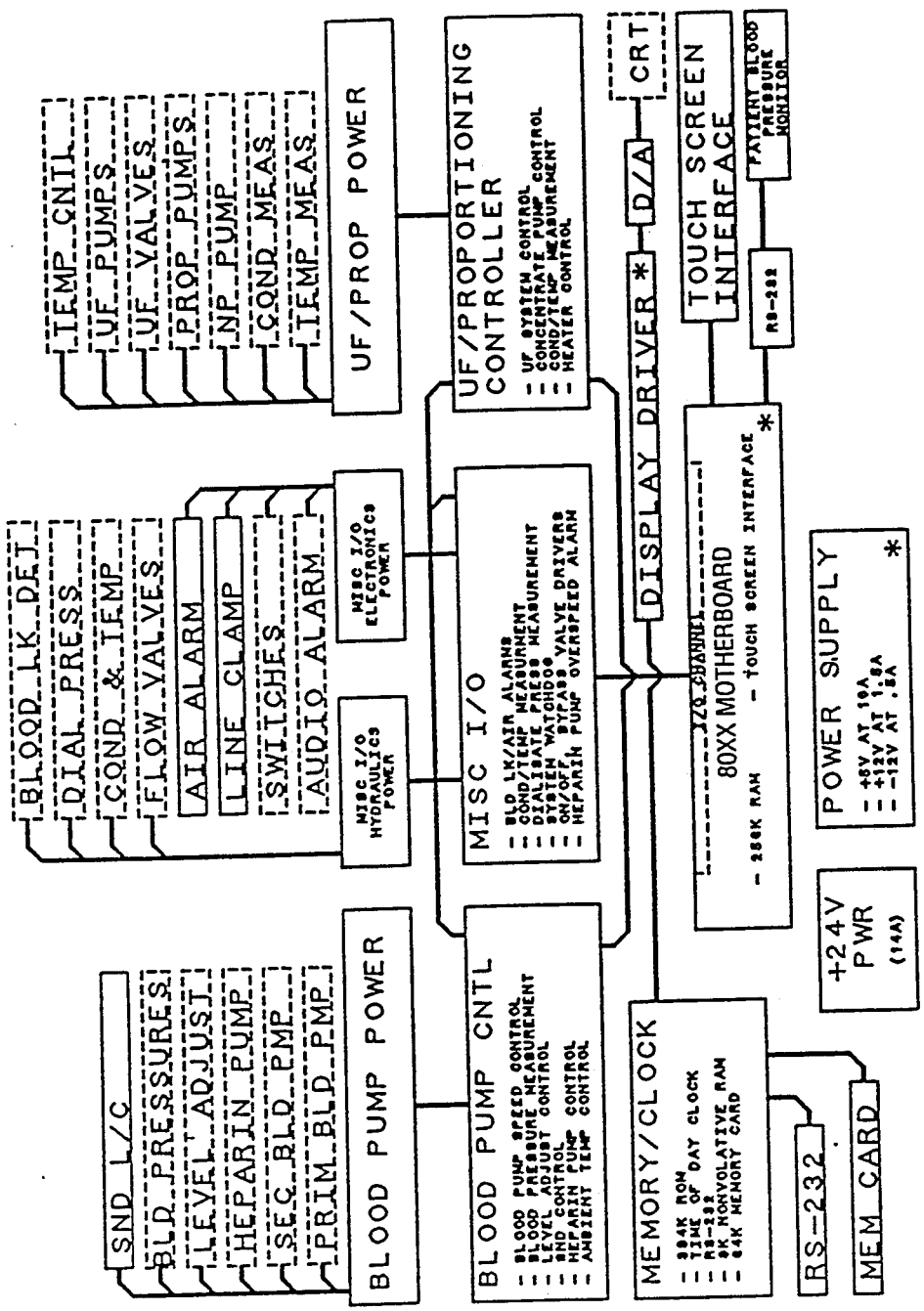

Software Flow Charts
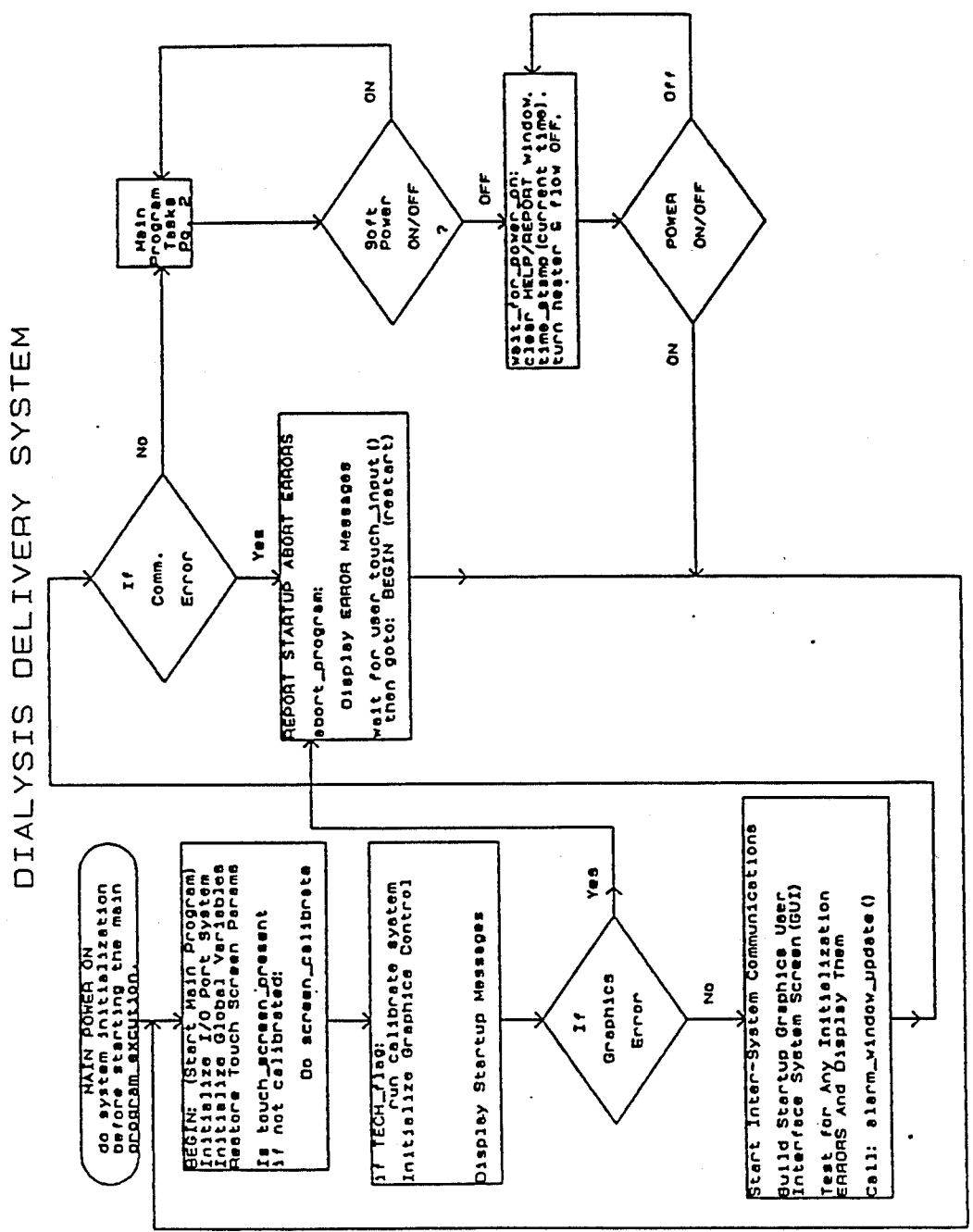
Dialysate Delivery System

MAIN PROGRAM TASKS error_test().
/*
display any pending ERROR messages
*/ test_state().
/*
update alarm logic, test the state flow and update the system state machine
*/ key_functions().
/*
notdone = key_functions().
input data from the debug keyboard or get new position data from the touch screen
*/

→ Return (to page 1)

verify_test().
/*
test for HELP/REPORT
ALARM window time out.
display activity indicator
*/ data_output().
/*
output data to IO System, BP System, UP System, test and set output for the NO FLOW and BYPASS FAIL display logic
*/ gui_schedule().
/*
update GUI display windows
*/ self_test().
/*
do self test as the system demands
*/

(from page 1)
Main Program Tasks system_activity().
/*
update M activity indicator, update blink color palettes
*/ data_input().
/*
update local time clock, input data from controllers, scale the data.
*/ get_dip_switch_data().
bp_communications().
up_communications().
io_communications().
port_communications().

limit_pos_test().
/*
update Arterial and venous bargraph limit indicators.
*/

Main Program Tasks

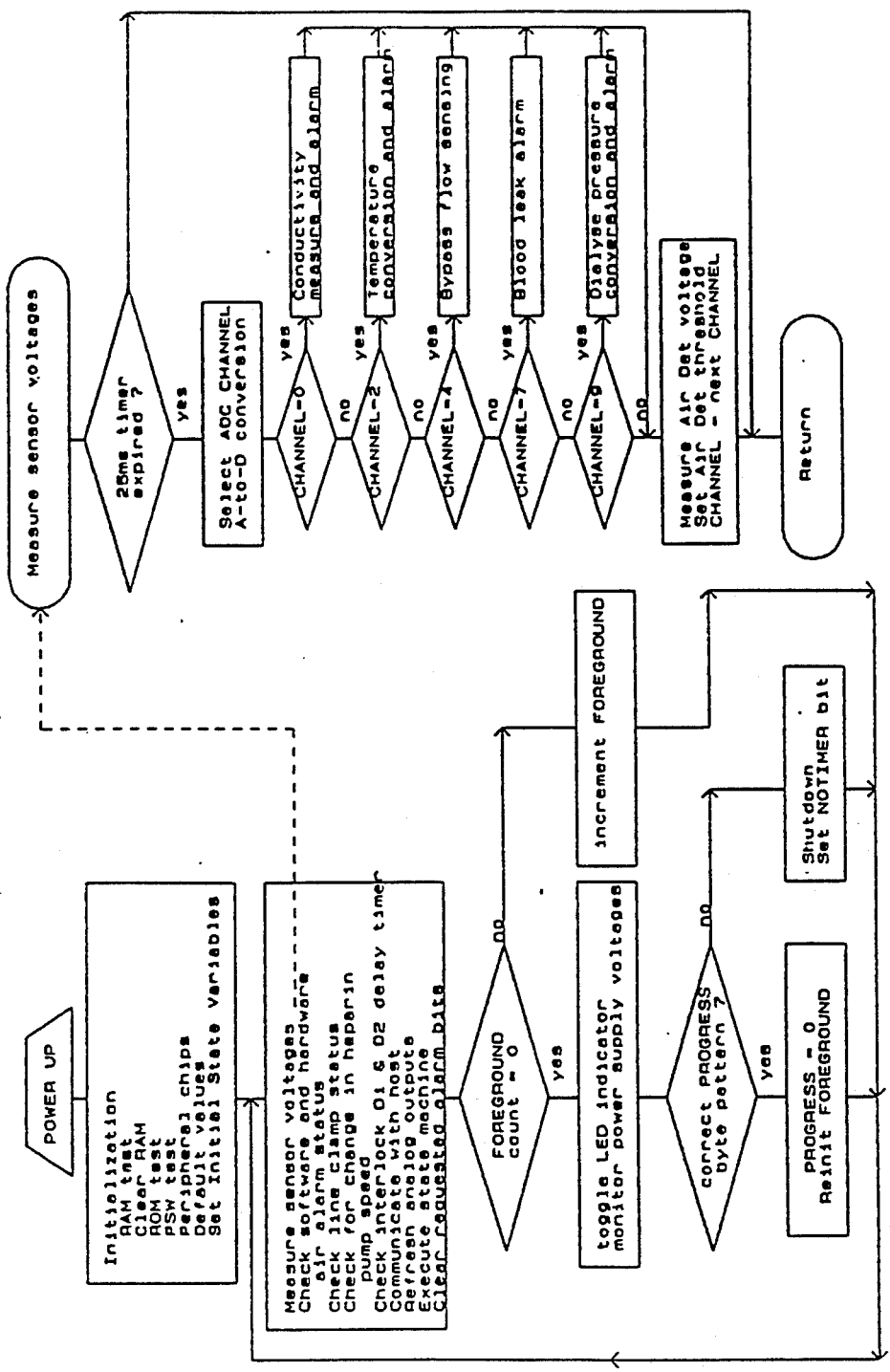
I/O Controller Software page 1

I/O Controller Software
*continued*

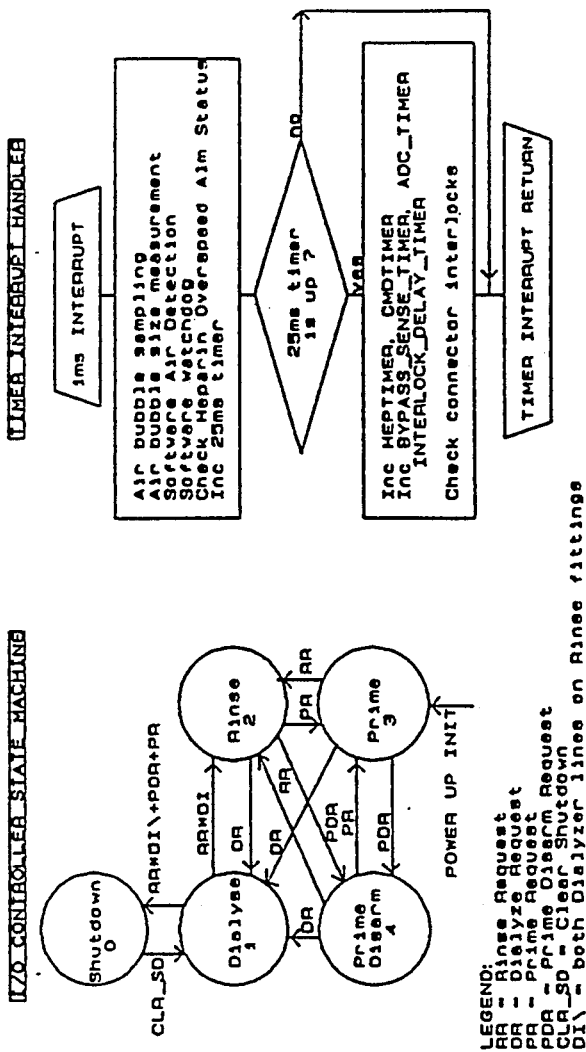

The circles represent I/O controller states that are charaterized by the following parameters:
Shutdown: Machine in bypass, line clamp clamped, bloopd pump disabled, heparin pump disabled
Dialyze: If extracorporeal alarm, controller stops blood pump and clamps line clamp.
  If dialysate alarm, controller puts machine in bypass.
  If heparin overspeed alarm, controller stops heparin pump.
Prime: If extracorporeal alarm, controller stops blood pump and clamps line clamp.
  If dialysate alarm, controller puts machine in bypass.
  If heparin overspeed alarm, controller stops heparin pump.
Prime Disarm: If dialysate alarm, puts machine in bypass. If extracorporeal alarm (blood leak and air detector only), no controller response.
Rinse: Controller does *not* take alarm response actions (outlined in Dialyze state.
The lines denot state transitions with the required signal(s) to make the transition noted beside the lines. These control signals are detailed in the Legend.

I/O Controller Software page 2

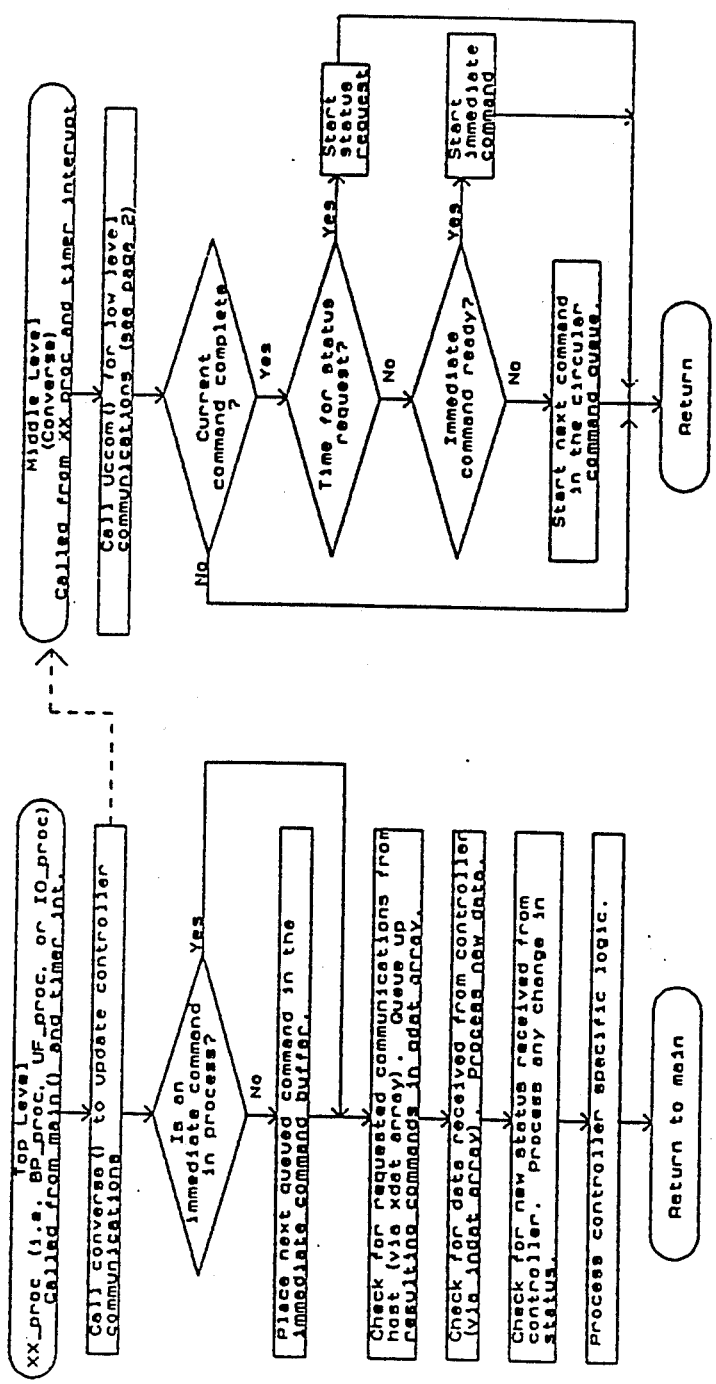
Host Software page 1

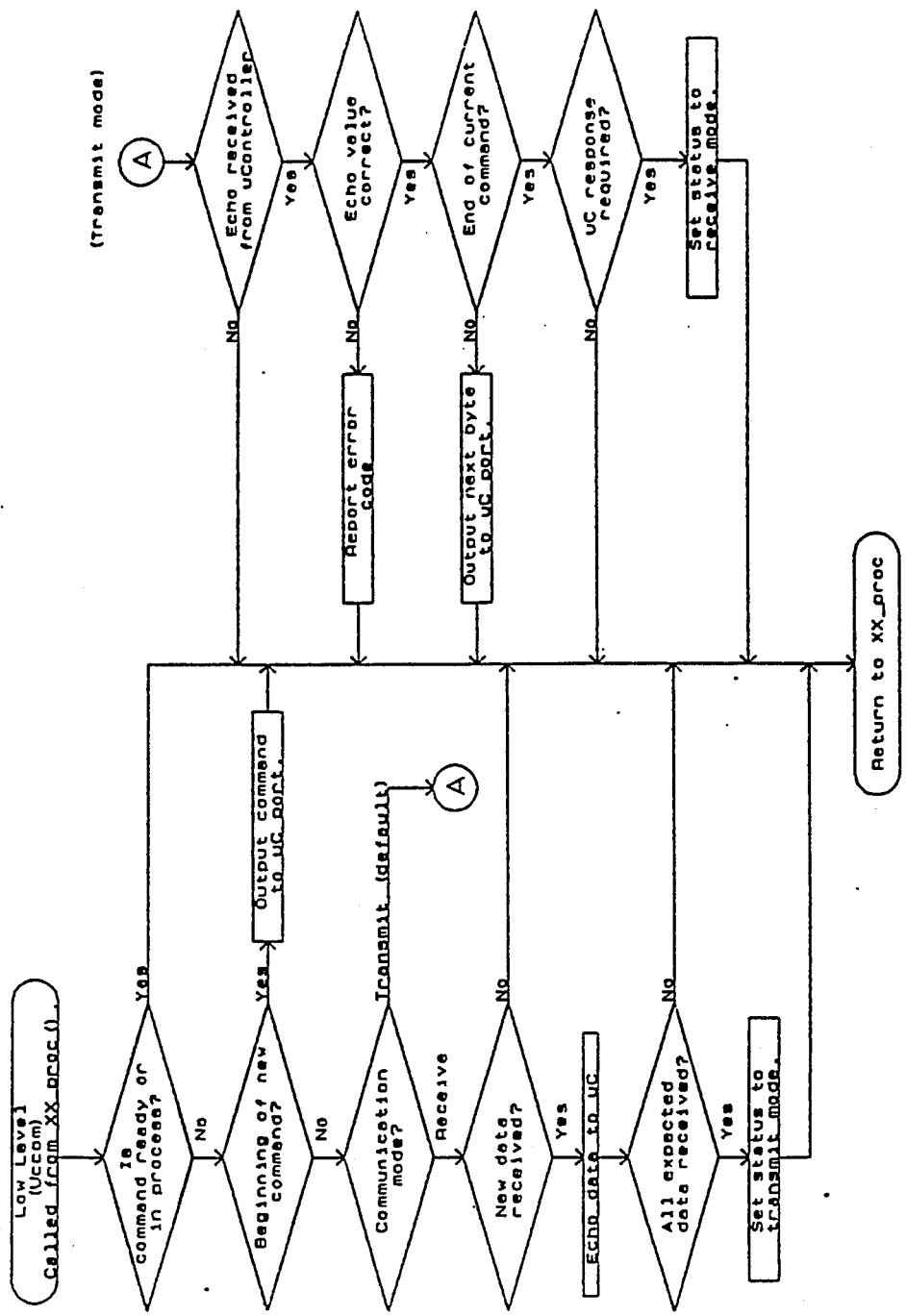
Host Software page 2

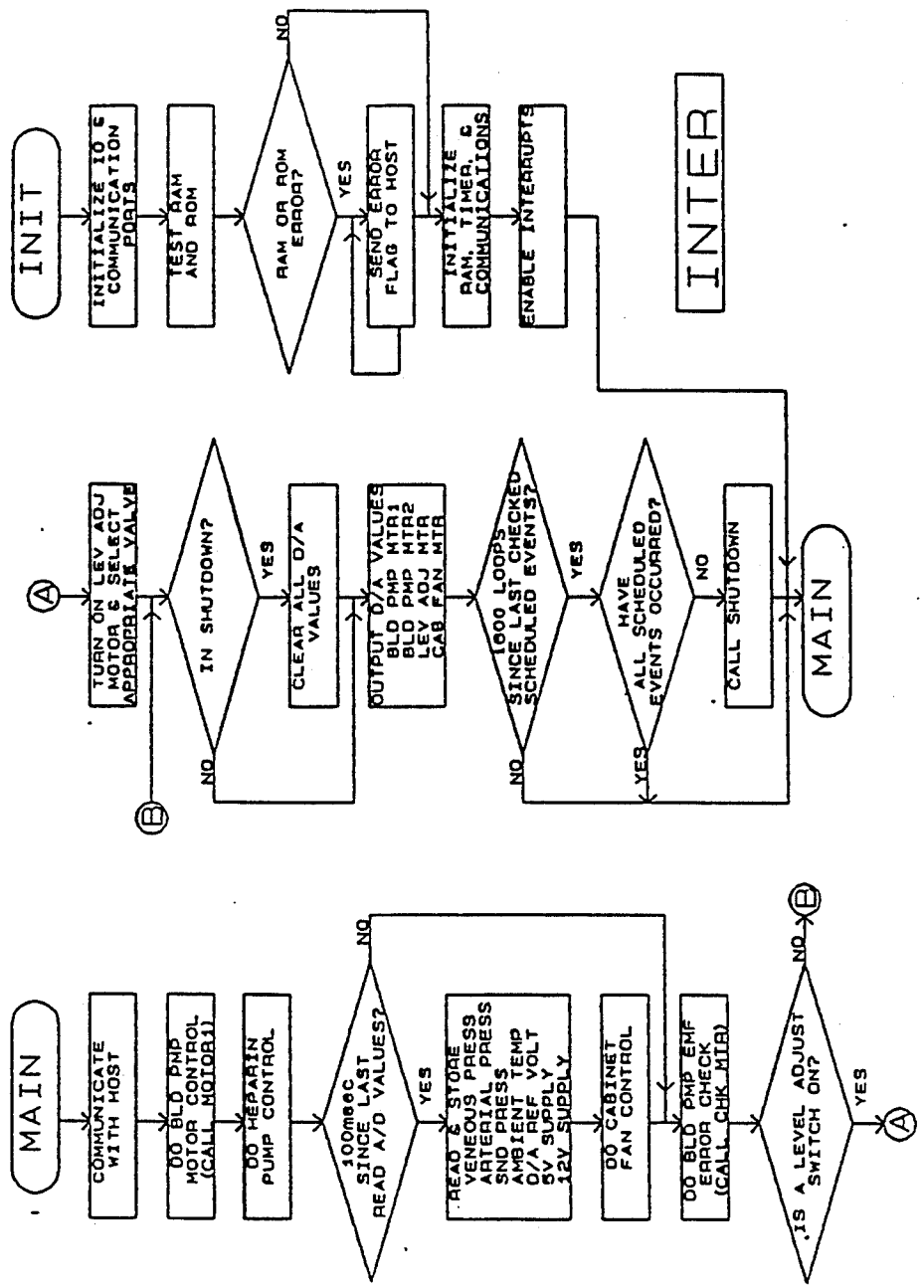
Blood Pump Controller Software page 1

Blood Pump Controller Software
*continued*
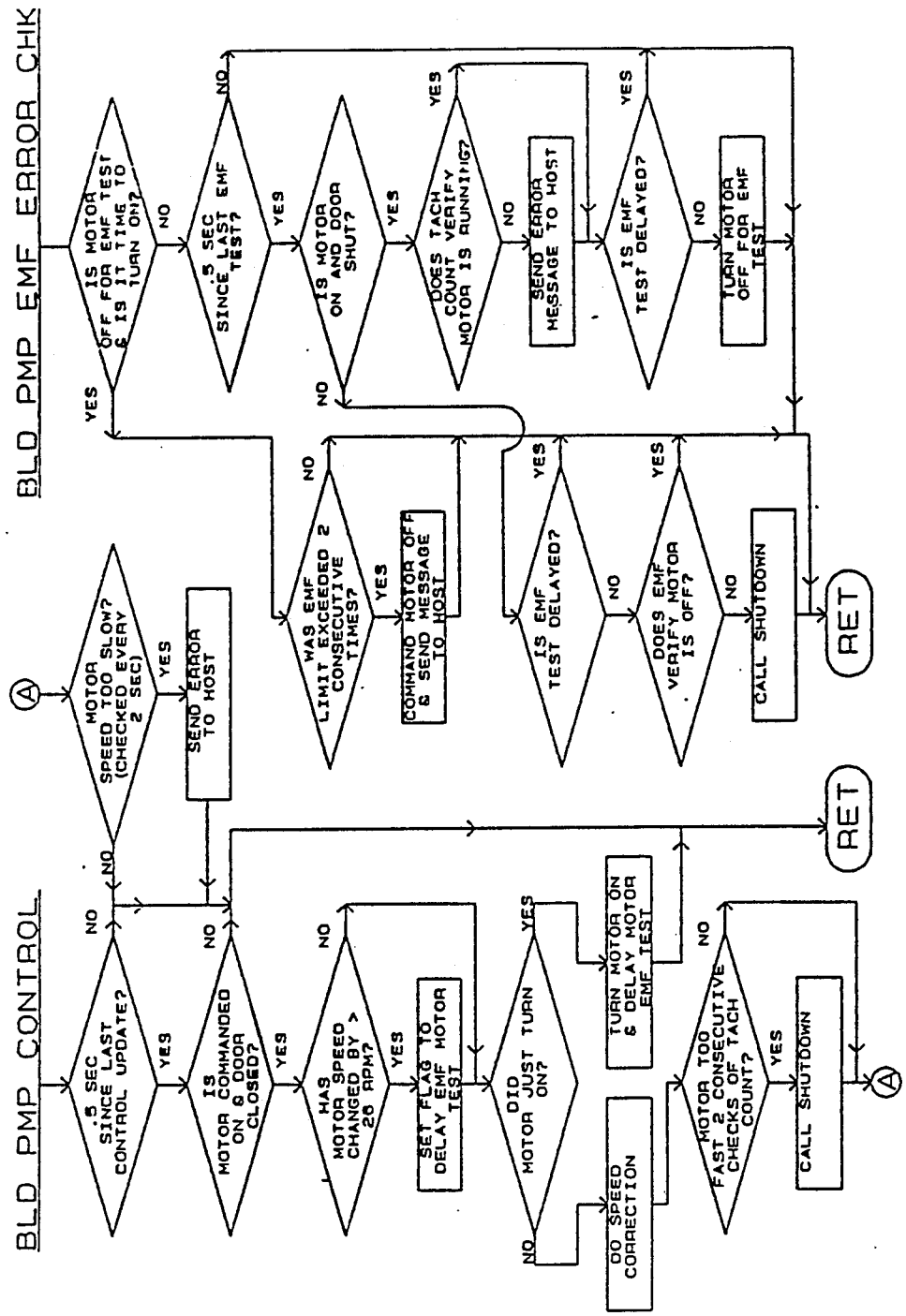
Blood Pump Controller Software page 2

Blood Pump Controller Software
*continued*
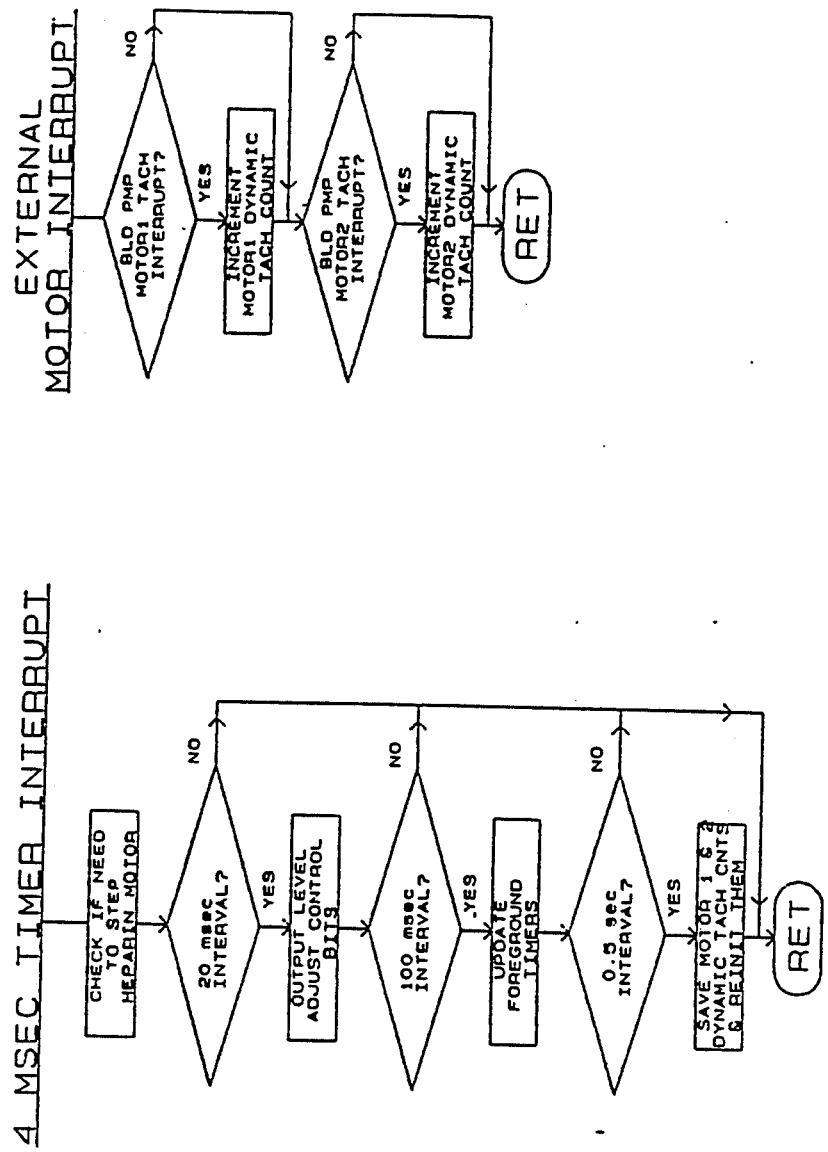
Blood Pump Controller Software page 3

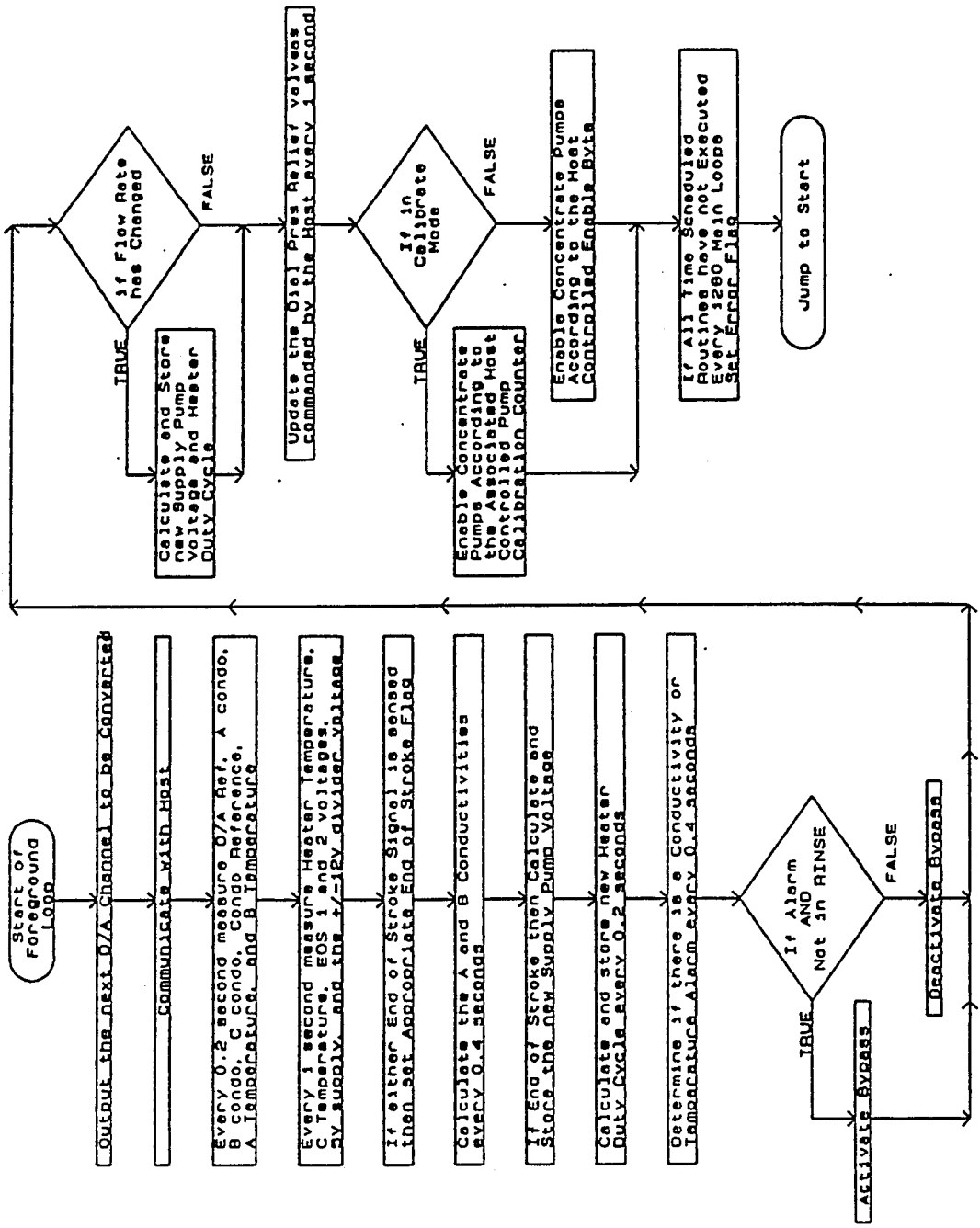
UF Controller Foreground (Main Loop)

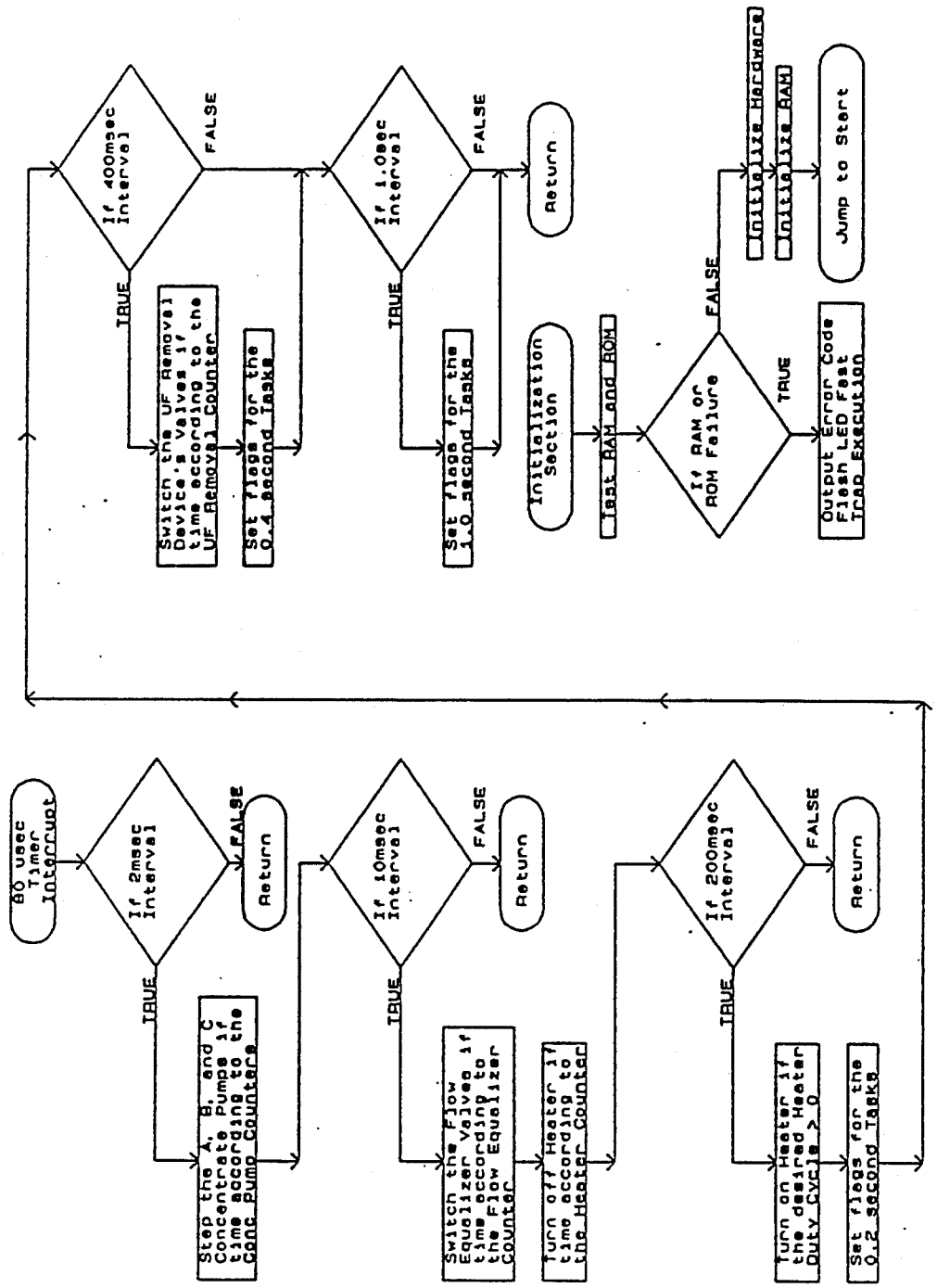
UF Controller Background and Initialization

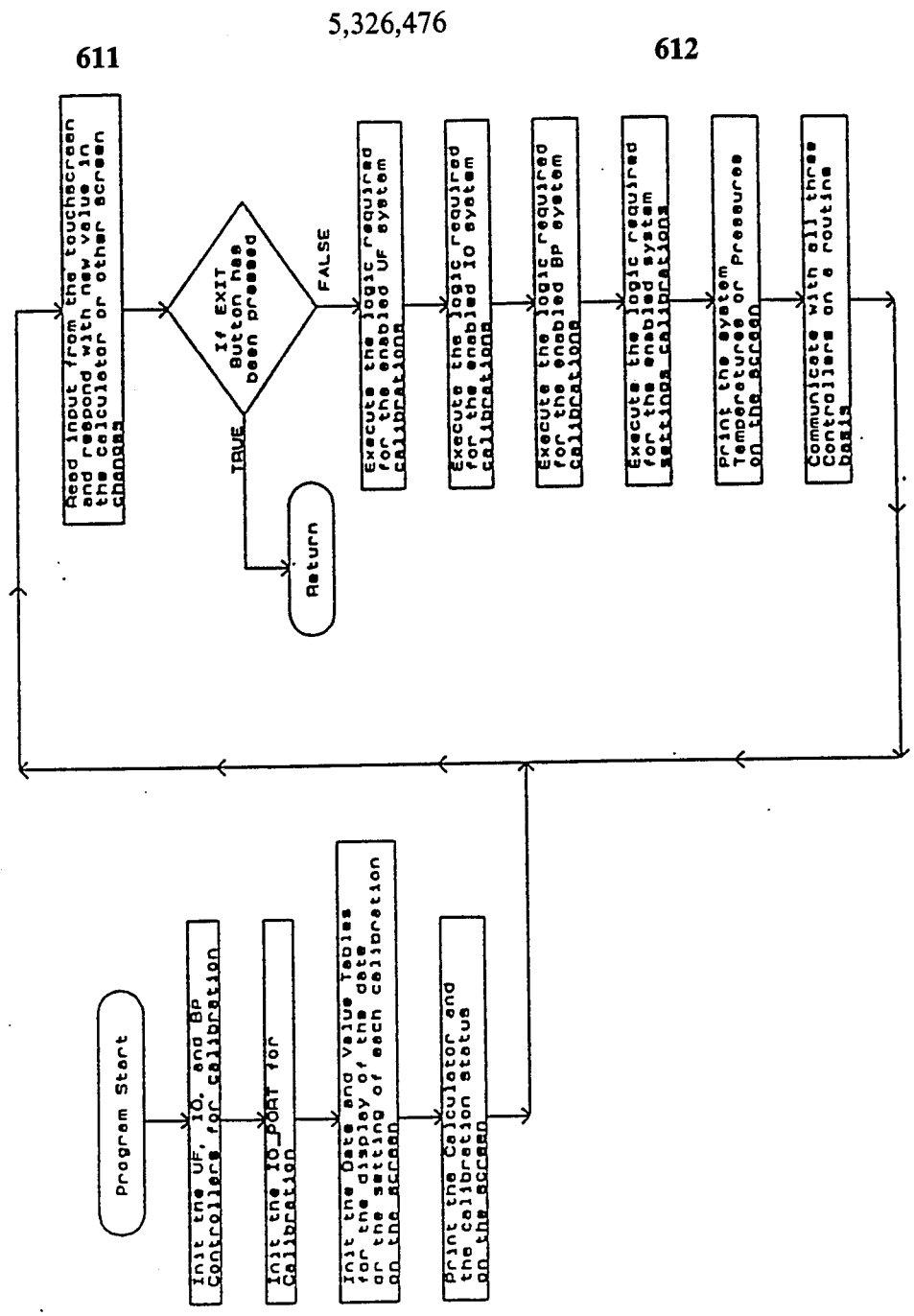
Calibration Mode Flow Chart

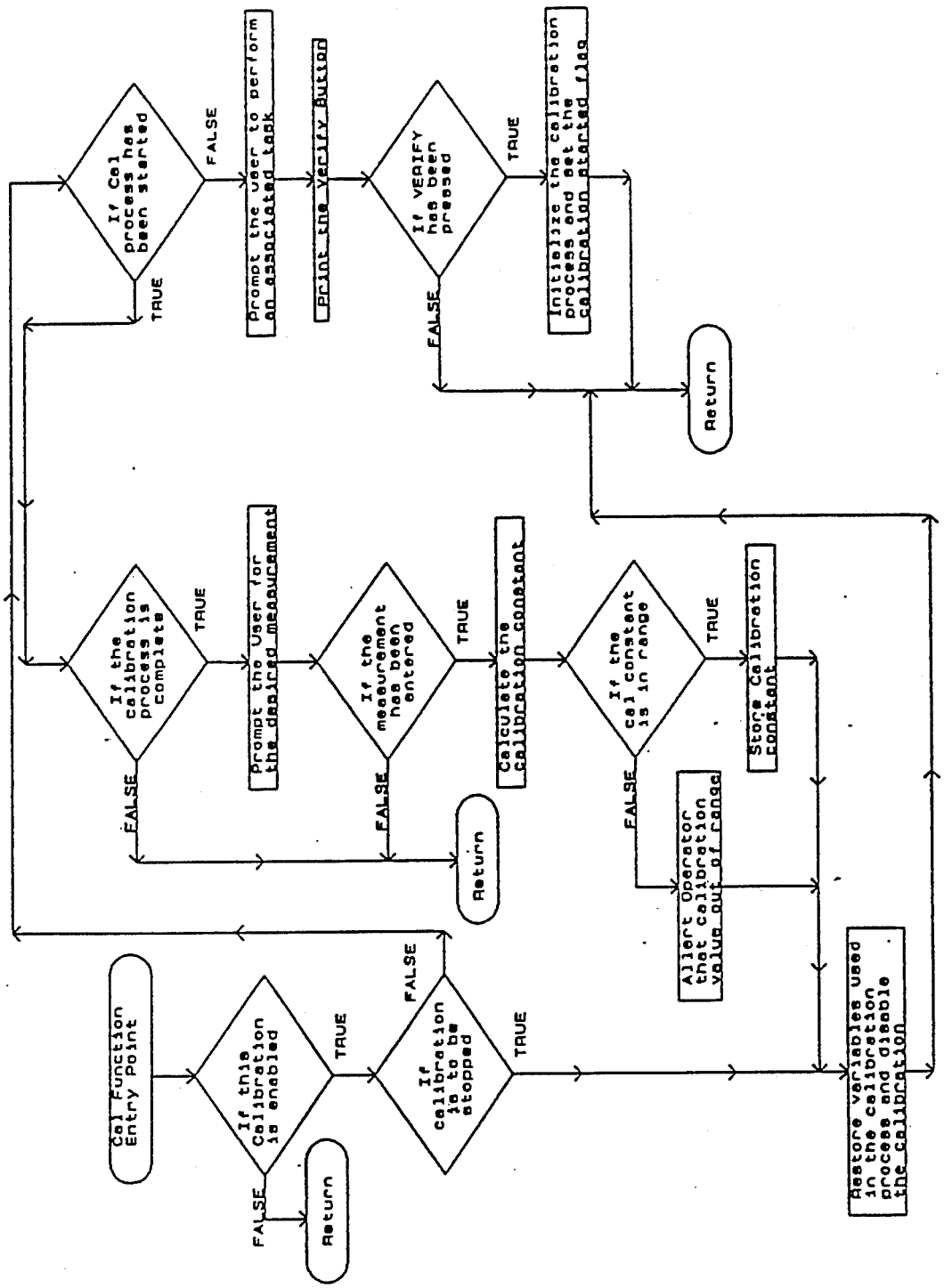
Sample Device Calibration Logic

APPENDIX D

APPLICATION OF GROGAN ET AL.

Programming

If it necessary to program NA, HCO3, KT/V or UF during treatment
   a. Press "Menus".
   b. When the switches change on the right hand side of the monitor press "Program".
   c. When the switches change on the right hand side of the monitor, press either "Program UF", Program Na, KT/V or Program Bicarb depending on what variable is desired to be programmed.
   d. After a program for NA, HCO3, KT/V or UF has been finished and the enter key pressed the screen returns to the program screen.

To set the programmable Sodium:
1. Press "Program Na" switch. The program Na graph and switches should appear on part of the display.

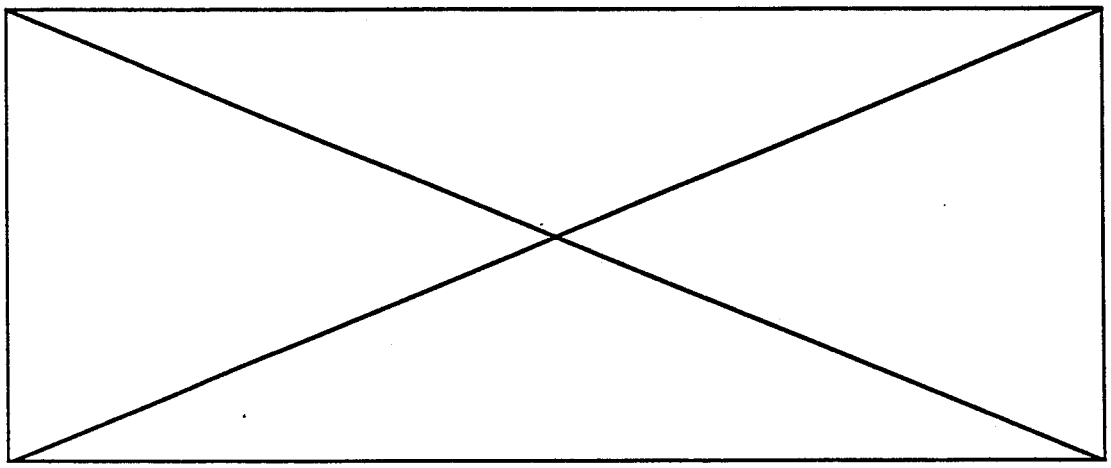

2. Press the Standard Bath Na switch. The calculator appears. Enter the sodium value displayed on the concentrate container. Press enter. calculator disappears. The sodium value will be displayed in the Standard Bath Na window.

3. If the Prescribed Time was not entered previously press the Prescribed Time switch. The calculator appears. Enter the dialysis time in hours and minutes. Press enter. calculator disappears. The dialysis time will be displayed in the Prescribed Time window.

4. The concentrate type window display the concentrate that is used, this information is based on the position of the concentrate connectors.

5. To set the variable sodium:
   a. The operator presses the approximate place on the graph of the desired starting sodium value. The actual value entered will be displayed in the Set Na Value window.
   b. Then the operator will press the intersection point (NA/time) on the graph for the next sodium value desired. If the operator would like the sodium to vary in steps, the same sodium value as entered in step 5a should be entered Then the new sodium value should be entered at the same time coordinate on the graph. To view sodium values that have been previously entered roll.

6. Sodium values should be entered for as many steps as desired. It is not required to enter a step for each 20 minute sequence. If 160 were the first point selected and 140 was selected 2 hours later. The machine would vary the sodium of the dialysate slowly lowering it to 140 over the two hours. If 160 was the first value selected and 160 was pressed in the two hour time coordinate, then 140 pressed in the two hour time coordinate. The dialysate sodium value for the first two hours would be 160 and would change at the end two hour time frame to 140 where it would remain for the rest of the treatment unless another sodium value was selected. Step 5 should be repeated for all steps that the sodium should be changed to.

7. After all sodium values are entered on the machine, the enter key should be pressed and the program is set in the machine.

8. If another program or a program change is desired it can be reinput entirely or any of the values can be adjusted with the arrow keys and reentered.

Note  The ♦ switch will highlight the area selected. It will move one setting each time the ♦ switch is pressed. When the ♦ is pressed after the last value it will roll around back to the first value entered. *If the screen resolution permits the operator to easily adjust the set value the ♦ switch, ▲ and▼ arrow keys will not be necessary and will not be present on the display.*

To Set the Programmable Ultrafiltration:
1. Press "Program UF" switch. The program UF graph and switches should appear on part of the display 2. If the Prescribed Time was not entered previously press the Prescribed Time switch. The calculator appears. Enter the dialysis time in hours and minutes. Press enter. calculator disappears. The dialysis time will be displayed in the Prescribed Time window.

3. If the Target Fluid Loss was previously set the UF goal will appear in the display. If not touch the Target Fluid Loss display. The calculator appears. Enter the Target Fluid Loss in liters per hour. Press enter. The calculator disappears. The Target Fluid Loss will be displayed in the window.

5. To program the UF removal:
   a. The operator presses the approximate place on the graph at the desired starting UF rate. The actual value entered will be displayed in the UF Rate Selected window. This value can be fine tuned with the s and t arrow keys.

b. Then the operator will press the intersection point (UF/time) on the graph for the next Ultrafiltration value desired. If the operator would like the UF to vary in steps, the same UF value as entered in step 5a should be entered Then the new UF value should be entered on the same time coordinate on the graph. To view UF values that have been previously input, use the ♦ arrow key to cycle through each UF rate setting.

Note  As the operator sets the UF values in the graph the "Prog UF" display will show add each value until the display is equal to the Target Fluid Loss.

6. Ultrafiltration values should be entered for as many steps (20 minute steps) as desired. It is not required to enter a step for each 20 minute sequence. If 1L/h were the first point selected and 0.5L/h was selected 2 hours later. The machine would control the ultrafiltration rate slowly lowering it to 0.5L/h over the two hours. If 1L/h was the first value selected and 1L/h was pressed in the two hour time coordinate, then 0.5L/h pressed in the two hour time coordinate. The ultrafiltration control rate for the first two hours would be 1L/h and would change at the end two hour time frame to 0.5 where it would remain for the rest of the treatment unless 0.5 L/h would exceed the Target UF value. Step 5 should be repeated for all the programmed UF rate changes desired.

7. After all UF rate variations are entered on the machine, the enter key should be pressed and the program is set in the machine.

8. If another program or a program change is desired it can be reinput entirely or any of the values can be adjusted with the arrow keys and reentered.

Note  The ♦ switch will highlight the area selected. It will move one setting each time the ♦ switch is pressed. When the ♦ is pressed after the last value it will roll around back to the first value entered. *If the screen resolution permits*

*the operator to easily adjust the set value the ♦ switch, ▲ and ▼ will not be necessary and will not be present on the display.*

9. If sequential ultrafiltration is desired:
    a. Press the Manual switch once (while the UF program screen is on).
    b. Press the time coordinate on the graph when you would like the machine to go into sequential ultrafiltration.
    c. Press the manual switch once for each 20 minute interval that sequential UF is desired. A bar showing each 20 minute period should appear on the bottom of the UF graph. If the wrong time interval is selected press the manual bypass switch until it reaches the end of the Prescribed Time and the entered time value will be cleared and a new one entered.
    d. Press enter when the setting is correct.

10. If the operator desires the Ultrafiltration to track along with the Na program. The operator should first program the Na. Then enter the UF program and press the UF Track Na switch and press enter. The machine will automatically remove at a higher UF rate when the sodium is high also.

To Set the Programmable Bicarbonate:

1. Press "Program Bicarb" switch. The program Bicarb graph and switches should appear on part of the display.

2. Press the Standard Bath Bicarbonate switch. The calculator appears. Enter the bicarbonate value displayed on the concentrate container. Press enter. The calculator disappears. The bicarbonate value will be displayed in the Standard Bath bicarbonate window.

3. If the Prescribed Time was not entered previously press the Prescribed Time switch. The calculator appears. Enter the dialysis time in hours and minutes. Press enter. calculator disappears. The dialysis time will be displayed in the Prescribed Time window.

4. To set the variable bicarbonate:
    a. The operator presses the approximate place on the graph of the desired starting bicarbonate value. The actual value entered will be displayed in the Set Bicarbonate Value window. This value can be fine tuned with the s and t arrow keys.

b. Then the operator will press the intersection point (bicarbonate/time) on the graph for the next bicarbonate value desired. If the operator would like the bicarbonate to vary in steps, the same bicarbonate value as entered in step 4a should be entered. Then the new bicarbonate value should be entered at the same time coordinate on the graph.

To view bicarbonate values that have been previously entered use the ♦ arrow key to cycle through each bicarbonate setting.

Note    The ♦ switch will highlight the area selected. It will move one setting each time the ♦ switch is pressed. When the Á is pressed after the last value it will roll around back to the first value entered. *If the screen resolution permits the operator to easily adjust the set value the ♦ switch, ▲ and ▼ will not be necessary and will not be present on the display.*

5. Bicarbonate values should be entered for as many steps (20 minute steps) as desired. It is not required to enter a step for each 20 minute sequence. If 35 meq/L were the first point selected and 32 was selected 2 hours later. The machine would vary the bicarbonate of the dialysate slowly lowering it to 32 over the two hours. If 35 was the first value selected and 35 was pressed in the two hour time coordinate, then 32 pressed in the two hour time coordinate. The dialysate bicarbonate value for the first two hours would be 35 and would change at the end two hour time frame to 32 where it would remain for the rest of the treatment unless another bicarbonate value was selected. Step 4 should be repeated for all steps that the bicarbonate should be changed to.

6. After all bicarbonate values are entered on the machine, the enter key should be pressed and the program is set in the machine.

7. If another program or a program change is desired it can be reinput entirely or any of the values can be adjusted with the arrow keys and reentered.

APPENDIX E

APPLICATION OF GROGAN ET AL.

1. Description of storing and retrieving patient data to and from a RAM card.

Transportation of data to and from the System 1000 machine will be possible through the use of a memory card (in addition to serial port communication).

The information stored and retrieved from the card include:
   1. Logging of treatment data to be later recalled for therapy analysis:
      - A, B, and Primary Temperatures
      - A, B, and Primary Conductivities
      - Veneous, Arterial, Dialysate, Systolic, and Diastolic Pressures
      - Blood flow rate, total blood processed
      - UF rate, total UF removed, UF goal
      - Machine state 2. Treatment prescription to be read by the machine for possible programmable Na, UF, Bicarb profile uploading.
      - UF rate profile over time
      - Na concentration profile over time
      - Bicarb concentration profile over time
      - Blood Pump flow rate
      - Treatment time
      - Goal UF removal volume
      - Dialysate flowrate
      - Dialysate temperature
      - Blood pressure measurement schedule and alarms
      - Heparin prescription 3. Unique codes stored on the card when read by the System 1000 machine will initiate special modes (calibration mode, technician mode, enable the blood pressure monitor function, modification of the parameters transmitted over the serial port for diagnostics,...)

1. Logging of treatment data to be later recalled for therapy analysis

Using a program written to interface with a memory card reader/writer that is run on an external personal computer, a person is able to program/format System 1000 memory cards. These formatted cards when connected to the system 1000 will identify what treatment parameters are to be stored in the card and how often. During a treatment the desired data will be stored on the card periodically as defined by the sample period formatted on the card. In this way, either the amount of data per treatment or the number of treatments per card can be maximized. This type of data logging enables physicians to characterize a patient's response to treatment variations. After identifying the interrelated treatment factors, the physician on subsequent treatments can limit the data stored to the card and possibly increase the sample rate. In this way, the maximum sample of the most important treatment parameters are saved.

If treatment characterization is not the goal an operator has the option of retrieving just the final treatment parameters for a treatment overview type of record.

To retrieve the data from the card the physician will use a memory card reader connected to a personal computer. A program will read the card and store its data in a file that can be read by most spreadsheets. The program will allow the physician to choose which treatment record is to be read from the card (by name and/or date indication).

Althin Drake Willock will also provide a kenetic modeling program which will analyze the data stored to the card. The modeling program will be used to generate the goal parameters for the next dialysis treatment (and is explained below).

2. Treatment prescription to be read by the machine for possible programmable Na, UF, Bicarb profile downloading.

Using a program written to interface with a memory card reader/writer that is run on an external personal computer, a person is able to program/format System 1000 memory cards. When these programmed cards are read by the System 1000, upon user command, various settings will be stored in the machine. The System 1000 machine will then require the operator to verify that each of the stored parameters is to be used by the machine. If no verification is made, machine operation is unchanged.

By programming a card for specific treatment parameters (blood and dialysate flow rates, dialysate temperature, UF removal goal, treatment time, and ...) and then instructing a nurse to use the machine settings on the card, a physician can gain more control of the dialysis session.

Programmable treatments can be set up on a personal computer using the kinetic modeling program written by Althin Drake Willock. This program will use past treatment data and daily conditions to generate and store Na concentration, UF rate and bicarb concentration profiles in the card (blood flow rate and other parameters are also calculated).

The physician will always be able to modify any of the program generated information (treatment profiles and settings) to better suit his knowledge and experimentation in the field.

3. Unique codes stored on the card when read by the System 1000 machine will initiate special modes (calibration mode, technician mode, enable the blood pressure monitor function, modification of the parameters transmitted over the serial port for diagnostics,...)

Certain modes of the System 1000 machine require special switch settings inside the machine for initiation. This is a good way of avoiding accidental mode initiation, yet the use of the memory card for this purpose is more convenient and just as secure. The memory card allows the user to change to technician mode without turning the machine off or opening the machine up. The calibration mode will still require the machine to be turned off before it can be entered, yet the opening of the machine can be avoided.

When used with a serial port monitor the memory card can request various types and amounts of information to be transferred over the serial port for remote machine diagnosis. If no serial monitor is available the information can be stored in the memory card so that the technician can be evaluate the information later, with the use of a card reading program.

The programming of the cards to perform the above described functions will be done by running an Althin Drake Willock program on a computer with a memory card reader/writer.

2. List of all System 1000 tech messages.

All of the quoted strings below are technician level warning messages.

The system name above message groups is for reference only.

References to items with parenthesis, like bp_input(), indicate software functions. Failures of functions, like an illegal index, should never occur yet when the code was written these messages aided the debugging process.

* The extremely useful technician messages are denoted with a "*" (these messages typically aid in the troubleshooting of mechanical malfunctions).

BLOOD PUMP SYSTEM
"illegal qlen in BP_XMIT"
"Blood Pump Low Speed"              *
"BP Control Shutdown"               *
"BP Command Error"                  *
"Blood Pump Overspeed Alarm"        *
"Bld Pmp Overspeed Alarm"           *·
"Illegal index in bp_xmit()"
"Illegal index in bp_input()"
"long timer error"

UF/PROP SYSTEM
"Too much time between EOS signals" *
"Early EOS detection"               *
"UF SHUTDOWN"                       *
"UF Command Error"                  *
"UF Time scheduled Event Error"     *
"Unidentified Error in MISC_ERRFLG"
"A Pump Noise"                      *
"A Pump Missed Steps"               *
"B Pump Noise"                      *
"B Pump Missed Steps"               *
"C Pump Noise"                      * (for three pump system)
"C Pump Missed Steps"               *
"A temperature probe error"         *
"B temperature probe error"         *

IO SYSTEM
"illegal qlen in IO_XMIT"
"IO_XMIT: bad stat chnge %d,%d"
"Illegal io_xmit() index"
"Illegal index in io_input()"
"Illegal index in ioport_xmit()"

IOPORT SYSTEM
"No 8255... port terminated"                *
"Set_pwr_state: hw_ver=1"
"Set_pwr_state: hw_ver=2"
"Set_power_state: Can't power on"           *
"Set_power_state: Can't power off"          *
"Converse: illegal return from uccom()"
"Switch failure in reset_port() function"
"Command buffer full in add_cmd()"
"Unrecognizable command in make_cmd()"
"Illegal number of data bytes in make_cmd()"
"Illegal number of data bytes in make_cmd()"

3. List of all routinely saved and retrieved machine states and settings.

All parameters below are saved every 30 seconds or upon any major machine state change. When the System 1000 machine is turned on, if the current time is less than 20 minutes later than the time stamp data (last time data was saved) all the below parameters are restored.

temperature correction accumulated uf volume removed
desired UF removal volume
UF removal rate
UF Override flag current machine state
previous machine state
selftest pass/fail flag time stamp
prescribed dialysis time
elapsed treatment time prescribed or elapsed treatment time display flag
manual or calculated uf rate display flag heparin pump rate accumulated blood
accumulated heparin window limits for
 conductivity, temperature, prescribed time, heparin ...

4. Cobe, Fresenius, and Drake Bicarb Proportioning Ratios

Bicarbonate Proportioning Ratios (Dialysate:Bicarb:Acid)
1. Cobe Concentrates       45    :1.43  :1
2. Fresenius Concentrates  35    :1.225 :1
3. Drake Concentrates      36.83 :1.83  :1

Acetate Proportioning Ratio  35   :0    :1

5. Schematics of the following circuitry:
   a. blood leak detector
       IO Hydraulic Power Board Page 8 of 8  REVZ6 b. interlock detectors
       IO Hydraulic Power Board Page 7 of 9  REVZ6 c. air detector
       IO Electric Power Board Page 3 of 3  REVZ9 d. conductivity and temperature monitors
       IO Hydraulic Power Board Page 5 of 8  REVZ6 e. flow sensors
       Bypass 1 and 2 Flow Sensors
        - IO Hydraulic Power Board Page 5 of 8  REVZ6
       End of Stroke Sensors
        - UF Power Board Page 8 of 9  REVZ9

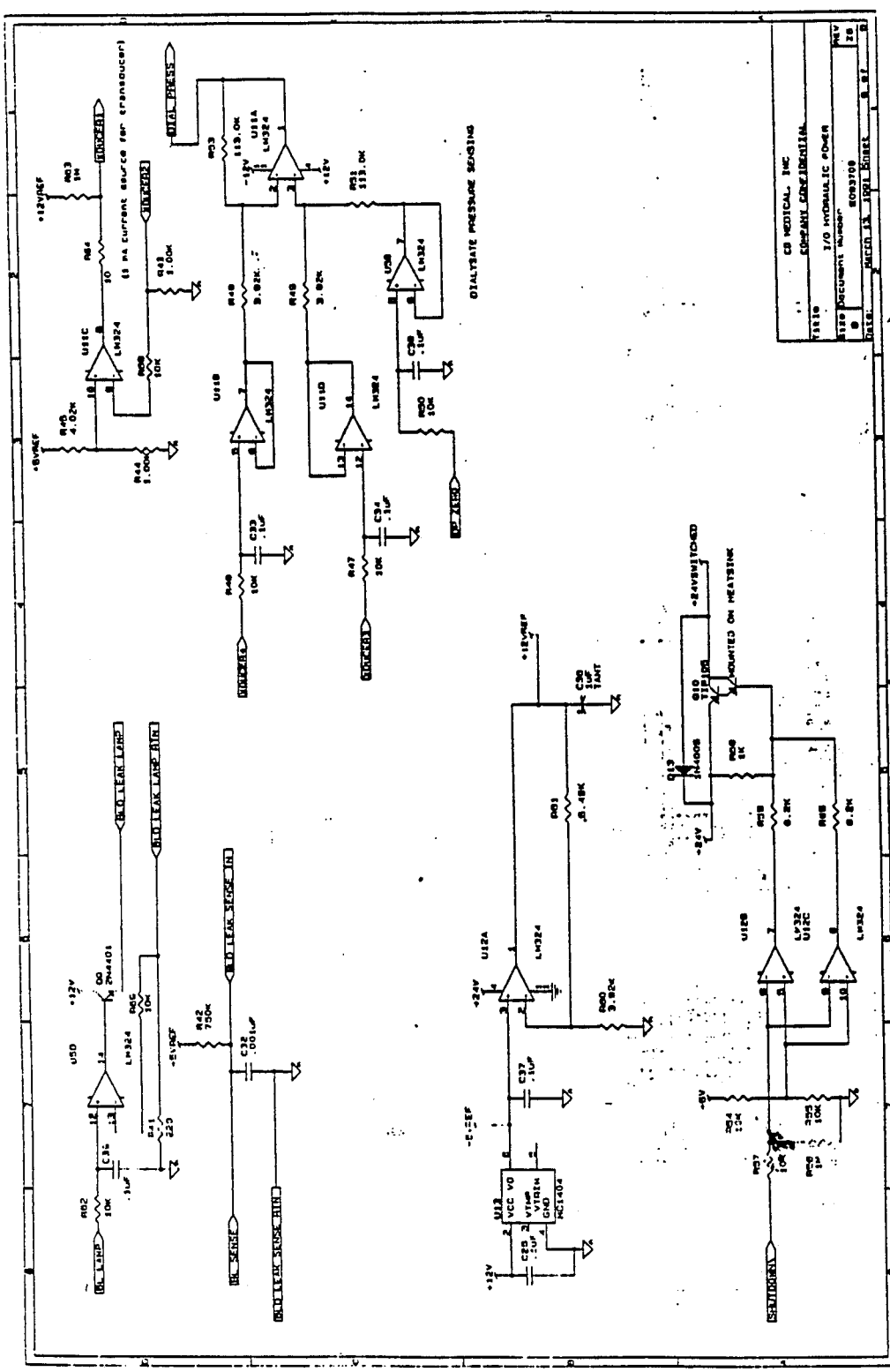

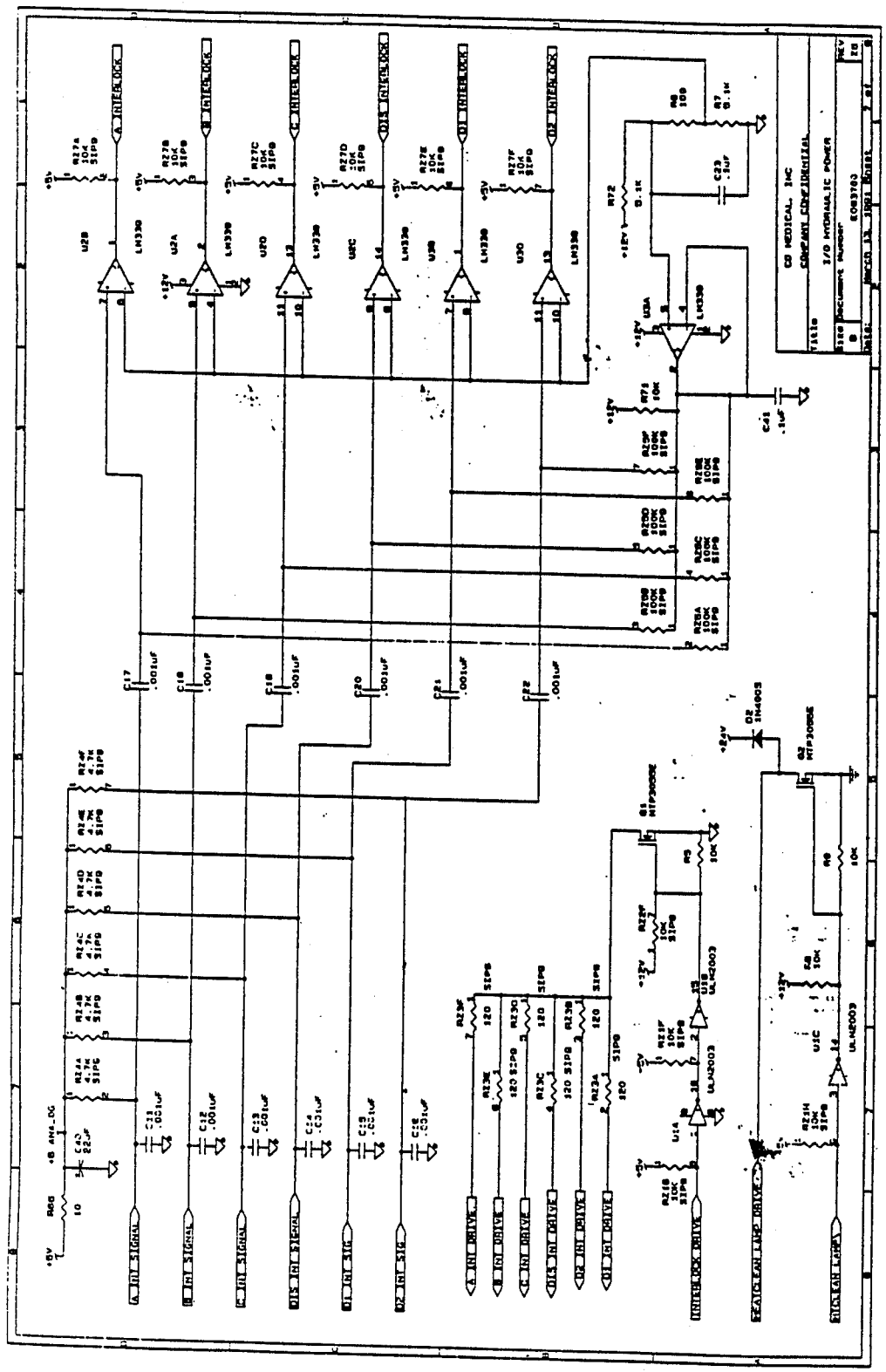
b. Interlock Circuits

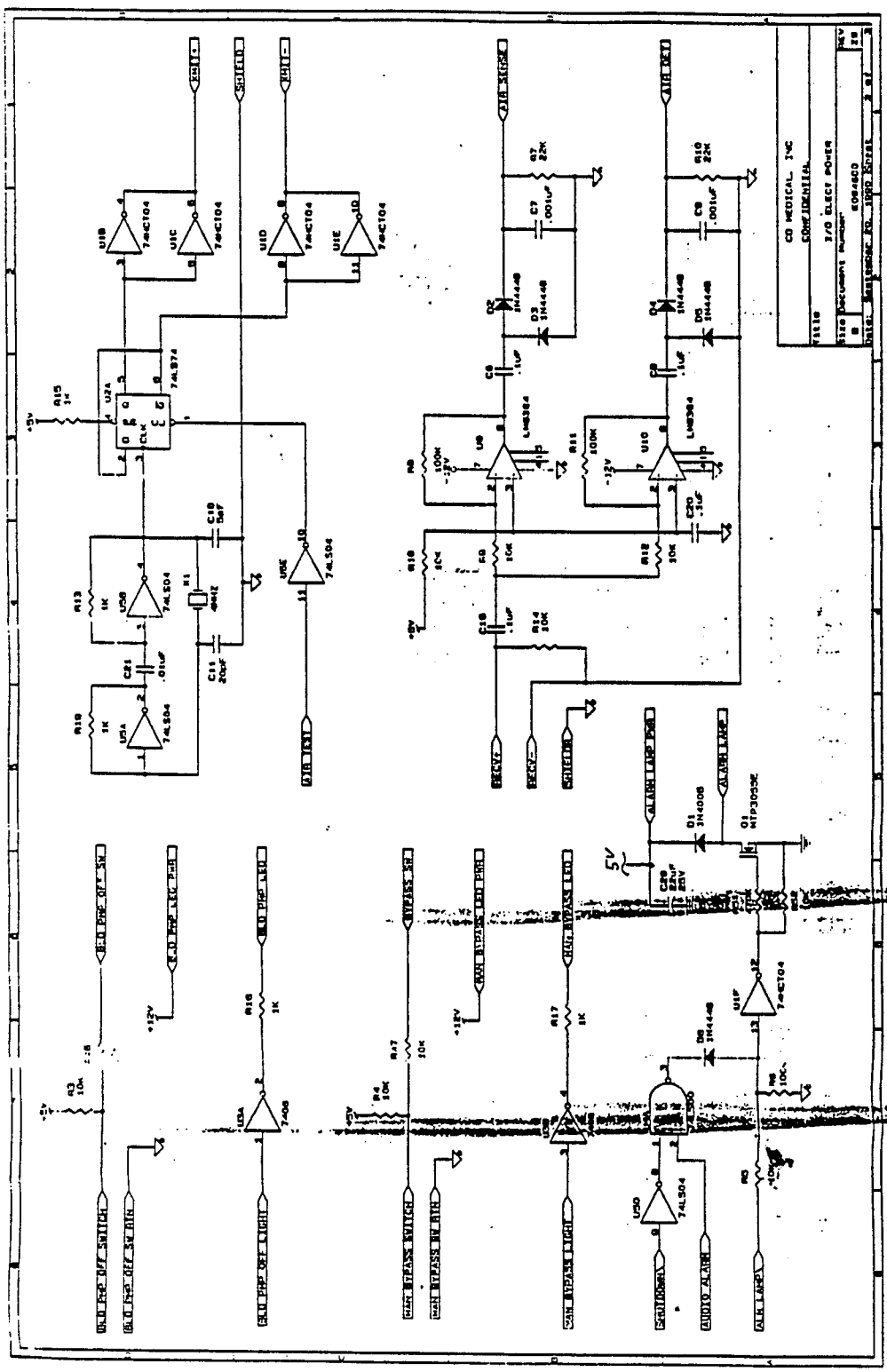

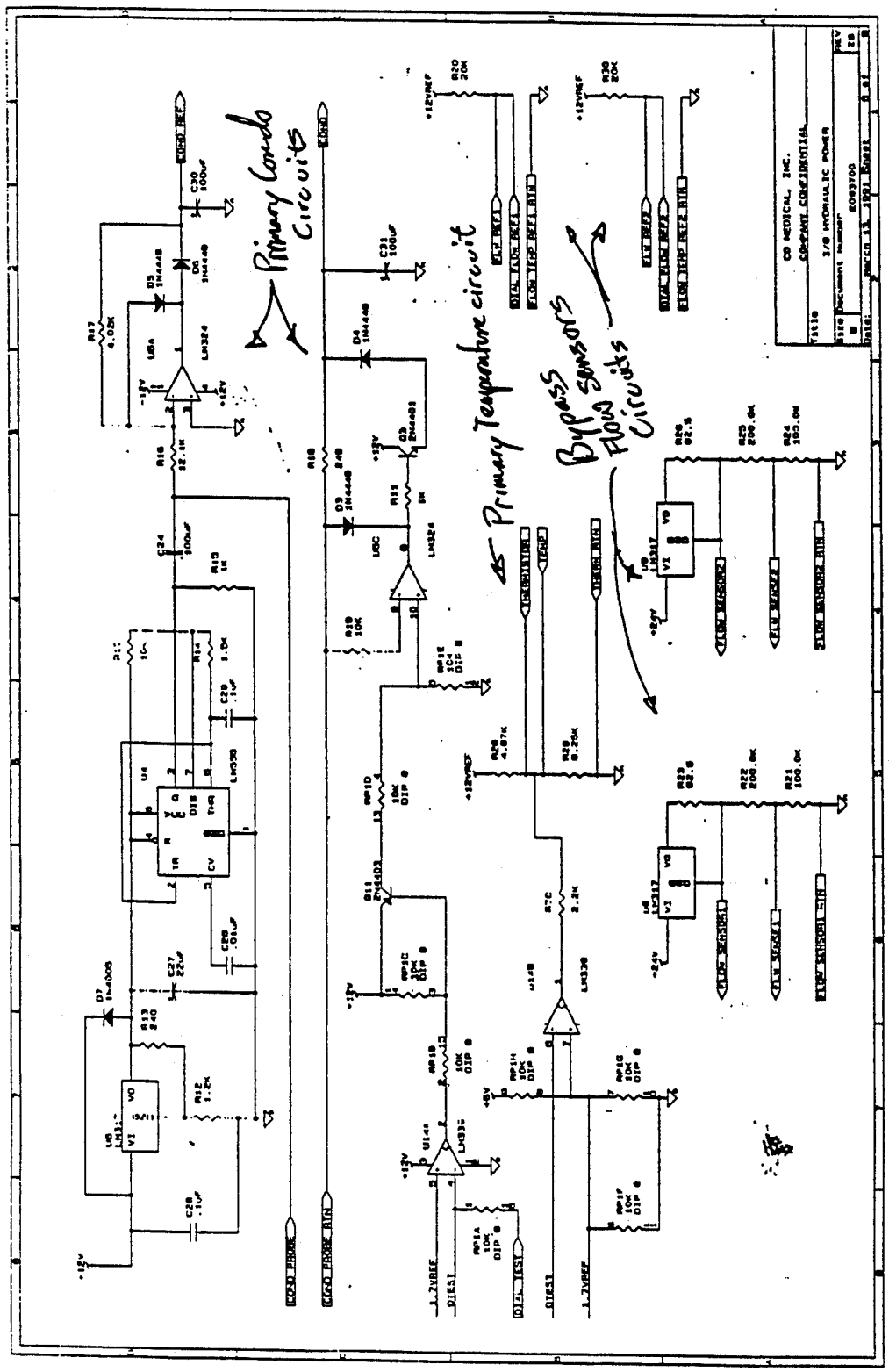

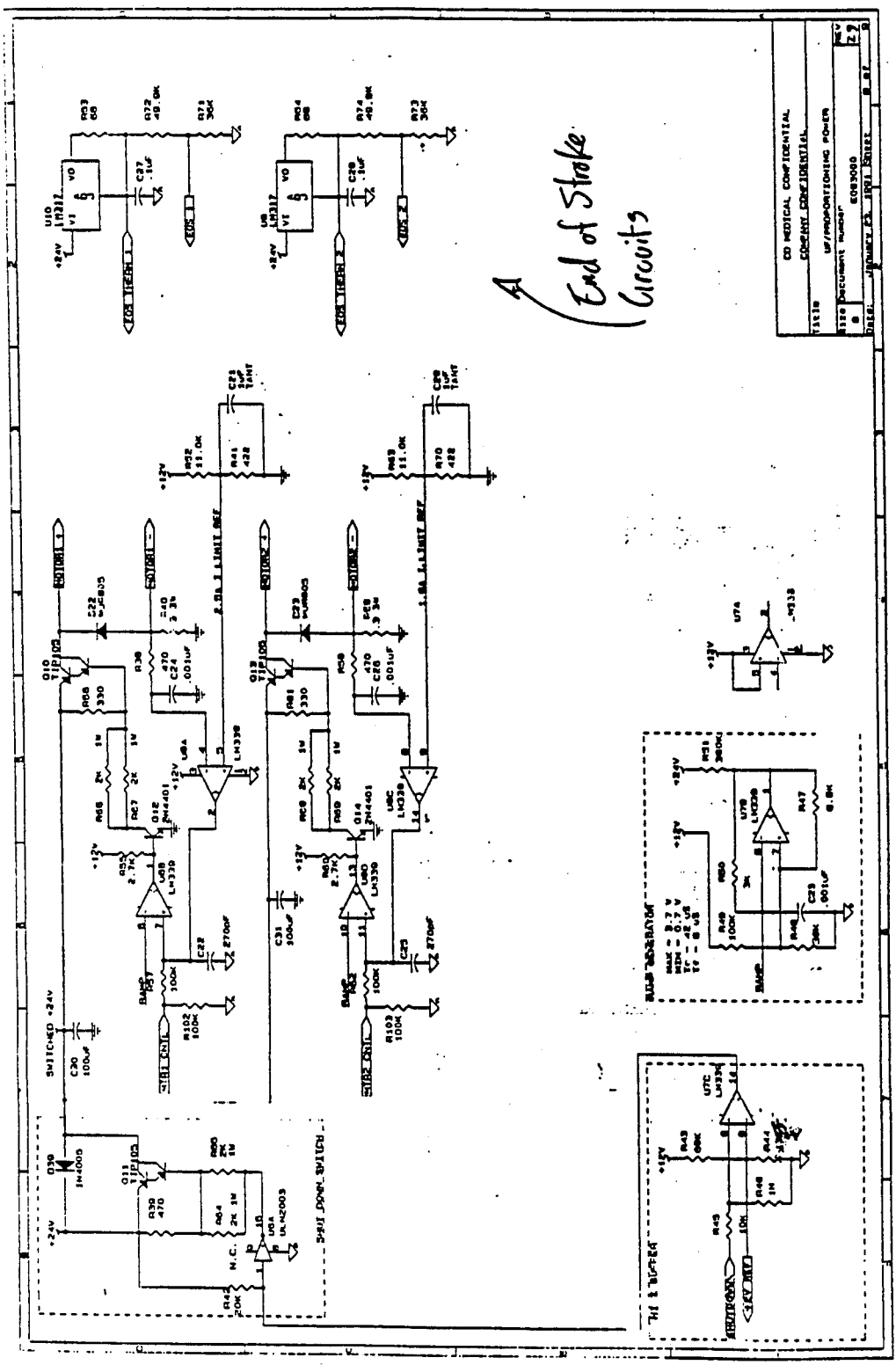

UF PROFILING SPECIFICATION

APPENDIX F

APPLICATION OF GROGAN ET AL.

Screen Operation:

When the Target UF meter is touched from the Prime or Dialyze screens, a new set of buttons will appear on the right side of the display, referred to as the UF screen. The buttons will be labeled MAIN SCREEN, TARGET UF, BLANK, UF DATA REPORT, PROFILE UF, BLANK (RESTART PROFILE), and BLANK (Verify). The functions for each button will be as follows;

UF Screen

| | |
|---|---|
| MAIN SCREEN | - Returns to main Dialyze or Prime screen. |
| TARGET UF | - Brings up the calculator for Target UF entry. |
| DATA REPORT | - Brings up a data report with UF parameters. |
| PROFILE UF | - Brings up the profiling graph and buttons. |
| RESTART PROFILE | - Brings up the profiling graph and buttons with the previous profile after a treatment change. |

Note: The Target UF window is accessible only in Prime or Dialyze modes.

When the PROFILE UF button is touched, a new set of buttons will appear on the screen, referred to as the UF Profile Screen, and the profiling graph will overlay the main screen. The buttons will be labeled LAST SCREEN, GRAPH UNLOCK/VERIFY (dual function), UF ONLY/VERIFY, SET CALC PROFILE, SET AVERAGE PROFILE, TEMPLATE PROFILES, and BLANK (Verify).

The RESTART PROFILE button will appear only in Dialyze mode after the user entered profile has been aborted by one of the following events; Target UF changed, Treatment time changed, UF rate changed manually, or UF rate set to minimum due to an alarm. When touched, the UF Profile screen will appear, as when the PROFILE UF button is touched. In addition, the graph will be initialized to the previous verified profile.

The functions of the UF Profiling Screen buttons will be as follows;

UF Profiling Screen:

| | |
|---|---|
| LAST SCREEN | - Returns to UF screen. |
| GRAPH UNLOCK | - Unlocks profiling graph. |
| GRAPH VERIFY | - Lock graph if profile meets target UF, otherwise brings up Profile Adjust screen. |
| SET CALC PROFILE | - Sets a constant UF profile at a rate which will reach target UF (must be unlocked). |
| UF ONLY | - Enables the graph for UF Only profiling (must be unlocked). |
| UF ONLY VERIFY | - Locks the profiled UF Only segments. |
| SET AVERAGE PROFILE | - Averages entire treatment profile with a straight line between the first uncompleted time segment and the last time segment of the treatment (must be unlocked). |
| TEMPLATE PROFILES | - Brings up the template profile screen. |

Initialization:

The minimum initial entry prior to UF profiling will be the treatment time and target UF. These will be entered via the calculator.

If the prescribed treatment time is not set prior to graph operation, the message TIME NOT SET will be displayed in the lower left hand corner of the graph. If the time is set and the target UF volume is not set, the message TARGET UF NOT SET will be displayed.

Graph Operation:

The graph will have a vertical axis scaled for 0 to 4.0 Liters/hour with 0.1 L/h resolution, indicating UF removal rate. The horizontal axis indicates treatment time and will be scaled for 0 to 6.0 hours, in 15 minute intervals.

A hilighted bar on the Y-axis will indicate the UF rate limits. A similar hilighted bar on the X-axis will indicate the precscribed treatment time.

A graph mode indicator will display the alternate function of the GRAPH LOCK/VERIFY button. It will be located in the lower right of the graph, displaying GRAPH MODE: X, where X is LOCK or UN-LOCK.

Arrows at the top and bottom of the graph will indicate the current active touch zones within the graph. Above the top arrow will be a number indicating the current UF rate for that time segment.

Each time segment will have a marker which graphically indicates the removal rate for that segment. While the graph is unlocked, touching a location on the graph between the maximum and minimum UF rates will cause the marker for that segment to move to the location of the touch. While the graph is in the locked state, a continuous line will join the segment markers and the markers will not move.

The profiling segment size is selected in calibration to 15, 30 or 60 minute intervals. For segment sizes other than 15 minutes, the individual markers and touchzones for each 15 minute time interval will operate collectively.

The selectable segment size will be added to the Sodium and Bicarbonate profiling options for overall machine consistency.

Three UF volume indicators will be displayed at the top of the graph:

- TARGET: This will indicate the entered target value.

- PROFILED: This will indicate the calculated volume represented by the profile at any time, updated each time a segment is altered. It will be used for comparison to the target volume while entering the profile, and when the GRAPH VERIFY button is touched.

- REMOVED: This will show the actual calculated UF volume removed during the treatment, up to the current time.

When the prescribed time and target UF have been set, the profiling graph will initially be set to a constant rate which will meet target UF over the prescribed time. This will appear as a straight horizontal line. It is intended to be a guideline, to assist the operator in selecting a profile that will meet the target UF volume.

At this time the operator has three options to select a UF profile. The first two options involve manually adjusting a profile. The third option is to recall a predetermined profile template, which is described in the next section.

To manually select a profile the operator can touch GRAPH UNLOCK, which will remove the line from the graph and enable user profiling. The operator has two options at this point, to profile UF rate for each time segment manually, or to set the starting and/or ending points of an average rate.

Average Method: The user can choose an averaged straight line profile by touching a graph location within the first and/or last time segments. Then by touching the SET AVERAGE PROFILE button, the remaining segment markers will be positioned in approximately in a straight line between the starting and ending markers.

Manual Method: By touching the graph at various points within the UF rate and treatment time limits, the user can "draw" a profile for the entire treatment. As the profile is drawn, the PROFILE value at the top of the graph will update continuously. This will assist the operator in selecting a profile that will come close to reaching the target UF.

Once a profile has been selected through one of these methods, the operator will touch GRAPH VERIFY. At this time the total profiled volume, or PROFILE value, will be compared to the target UF volume. If a difference exists, a new set of buttons will appear on the screen. Their labels will read LAST SCREEN, BLANK, ADJUST PROFILE, ADJUST TARGET, BLANK, BLANK, BLANK (VERIFY). This will be referred to as the UF profile verify screen.

Adjust UF Profile Screen

ADJUST TARGET — Brings up the verify button. If touched, the target UF value is changed to the PROFILE value, and the display goes back to UF profiling screen with graph locked.

ADJUST PROFILE — Automatically shifts graph up or down to meet target UF, using the following rules, and brings up the verify button. If the verify button is touched, the display will go to UF profiling screen with graph locked.

1. All segments of the profile will be adjusted equally, with the following exception: Any segment set to minimum UF or maximum UF rate will be "anchored." Those segments will not be changed to meet the target UF volume.

2. If the adjustment causes any segment(s) to violate the minimum or maximum rates, those segments will be set to the minimum or maximum, and the remaining segments will be equally adjusted by the excess volume using Rule 1 meet target UF.

3. Values will be rounded to one decimal places for graphical representation. However the actual UF rate is executed and displayed in 0.01 L/hr resolution.

4. If the target UF cannot be met following these rules, an error condition will be indicated, and the button will "honk" and not change back to GRAPH UNLOCK.

The profiling graph can be altered at any time during the treatment. Completed time segments will be represented as shaded bars, which of course cannot be altered. The operator can unlock the graph as before and select an average or manual profile to be performed over the remainder of the treatment. The current rate can be changed, and UF only can be started or stopped at any time during the treatment.

By touching the SET CALC PROFILE button while the graph is unlocked, all uncompleted profile segments will be set to a constant rate which will reach target UF removal. This can be used at any time the graph is unlocked, and will function as "clear" button during profiling, as it represents the initial profile prior to operator intervention.

If the graph has been entered and verified and is altered because of a change in target UF volume, total treatment time, or an alarm causes minimum UF, touching the RESET LAST PROFILE button on the UF Screen will cause the previous profile to appear on the graph. Completed time segments will indicate the last rate performed during that segment. If the Profile does not meet Target, the operator can then touch GRAPH UNLOCK and GRAPH VERIFY, which will take the normal action described above.

Profile Template Operations:

When button # 6 on the UF Profile screen is touched (TEMPLATE PROFILES), the following buttons appear on the right side of the screen; LAST SCREEN, MIRROR SODIUM, RECALL PROFILE #n, SAVE PROFILE #n, BLANK, BLANK, BLANK (Verify). The functions of the Template Profile screen will be as follows;

Template Profile Screen

LAST SCREEN    - Goes back to the UF Profile screen
MIRROR SODIUM - Sets a UF profile that resembles the Na profile
RECALL PROFILE #n - Recalls a profile from SRAM
SAVE PROFILE #n    - Saves the current profile to SRAM When the MIRROR SODIUM button is touched, the UF graph will be set to approximately the same XY coordinates as the Na profile, with no shifting to accommodate target UF goal. The operator will be required to verify and adjust the profile as needed.

The profile templates are intended to function as the name implies, as templates or basic shapes only. The operator will be required to verify and adjust the profile as needed.

When the RECALL PROFILE button is touched, the graph will be set to the stored profile, and the VERIFY button will appear. If no profiles have been stored, the button will honk and a message will appear in the instruction window indicating no profiles available.

If at least one profile is available, it will be displayed in the unlocked state, and the profile number on the button will increment if another profile is available. Each subsequent button touch will recall the next available profile and increment the button, until the 6th or last available profile is displayed. The button will then wrap around to the first profile. When the desired profile is displayed, the operator can touch VERIFY and LAST SCREEN to activate the profile.

The SAVE PROFILE #n button will initially be set to SAVE PROFILE prior to any button touches. On the first button touch it will hilight, change to SAVE PROFIE #1, and the verify button will appear. Each subsequent button touch will increment the profile position on the button, until the 6th position is reached, which will then wrap around to the first.

When the Verify button is touched, the current profile will overwrite any previous profile stored in the memory position displayed on the button.

Button position #5 should be saved for future expansion. Standard ROM'd profiles could be recalled with this button, as with the RECALL PROFILE #n button feature, when and if those are developed.

UF Only:

When the UF ONLY button is touched from the UF profile screen the graph will be enabled for UF Only profiled entry. The UF ONLY button will change to UF ONLY VERIFY.

When a segment is touched in this mode it will highlight a "B" in the Dialysis time bar, indicating UF only during that time segment. Conversely, when a highlighted segment is touched, it will remove the "B" from the time bar and turn off UF only during that segment.

If the UF ONLY VERIFY button is touched, the button will change back to UF ONLY and the selected segments will become active.

The highlighted "B's" will remain on the prescribed time axis indicating the selected UF Only segments. Completed, current, and future bypass time segments will be displayed this way.

When the machine is in UF Only the dialysate flow rate will be automatically lowered to 300 ml/min. It will be reset to the previously set flow rate automatically upon completion of the bypass sequence.

UF Only will override manual bypass. If manual bypass is active and the operator selects UF Only for the current time segment, the manual bypass will be canceled. The manual bypass button will be disabled during UF only, and will flash as in manual bypass.

The machine state indicator in the lower left corner of the main screen will indicate UF ONLY when UF Only is active. UF Only will be a sub-state of Dialyze.

Clocks and Treatment Parameters:

The prescribed treatment time will be entered via the calculator as before. This time will represent total treatment time, which will include UF Only time as well as dialysis time (blood and dialysate circulating through the dialyzer).

Separate clocks will be maintained for UF Only time and dialysis time. The elapsed treatment time in the treatment time window will display elapsed total treatment time during dialyze. Both UF only time and dialysis time will be displayed on the UF data report.

Dialysis time will not increase during UF Only, or during extracorporeal or dialysate alarms.

UF Only time will accumulate only during profiled UF Only time periods. It will not accumulate during extracorporeal alarms and when UF rate is set to zero.

UF removal will continue during manual and dialysate alarm bypass. Therefore, UF target may be reached prior to total treatment time. If so, UF rate will go to minimum until end of treatment time.

Total blood processed will accumulate only during dialysis time. Total infused heparin will accumulate any time heparin is infused, including while in UF only.

Alarms and messages:

If the profiled UF volume does not meet the target volume, because a parameter has been changed or if the user entered profile will not adjust to meet target volume when ADJUST PROFILE is touched, a message will appear in the warning window prompting the operator to readjust the profiling graph. In addition, the audio alarm will sound intermittently, approximately every 90 seconds.

If the UF rate was changed manually, the graph will be set to the new rate for the remaining treatment. If the target volume or treatment times are changed, the graph will be set to a constant rate which meets target volume. When this occurs, the RESTART PROFILE button will appear on the UF screen and operate as described above.

When the UF, UF profile, UF profile verify, or UF profile template screens are active and an extracorporeal or dialysate alarm occurs, the machine will go back to the main screen (PRIME or DIALYZE). If the profiling graph is unlocked, the most recent locked profile will be saved and will be displayed in the locked mode the next time the UF profiling screen is entered. If the UF Only mode is active, the last verified UF Only profiled segments will be active.

If the graph is unlocked when the UF Profile Screen is exited, because of an alarm or a LAST SCREEN button touch, an error beep will occur and a message will appear in the instruction window indicating "UF profile not verified."

UF Data Report:

This data report will overlay the Instruction Window and Alarm windows. The data included will be as follows:

Times:

Treatment Time
Elapsed Dialysis Time
Remaining Dialysis Time
Elapsed UF Only Time
Remaining UF Only Time Volumes:

UF Target
UF Removed
UF Remaining
UF Only Taget '
UF Only Removed
UF Only Remaining

APPENDIX G
APPLICATION OF GROGAN ET AL.
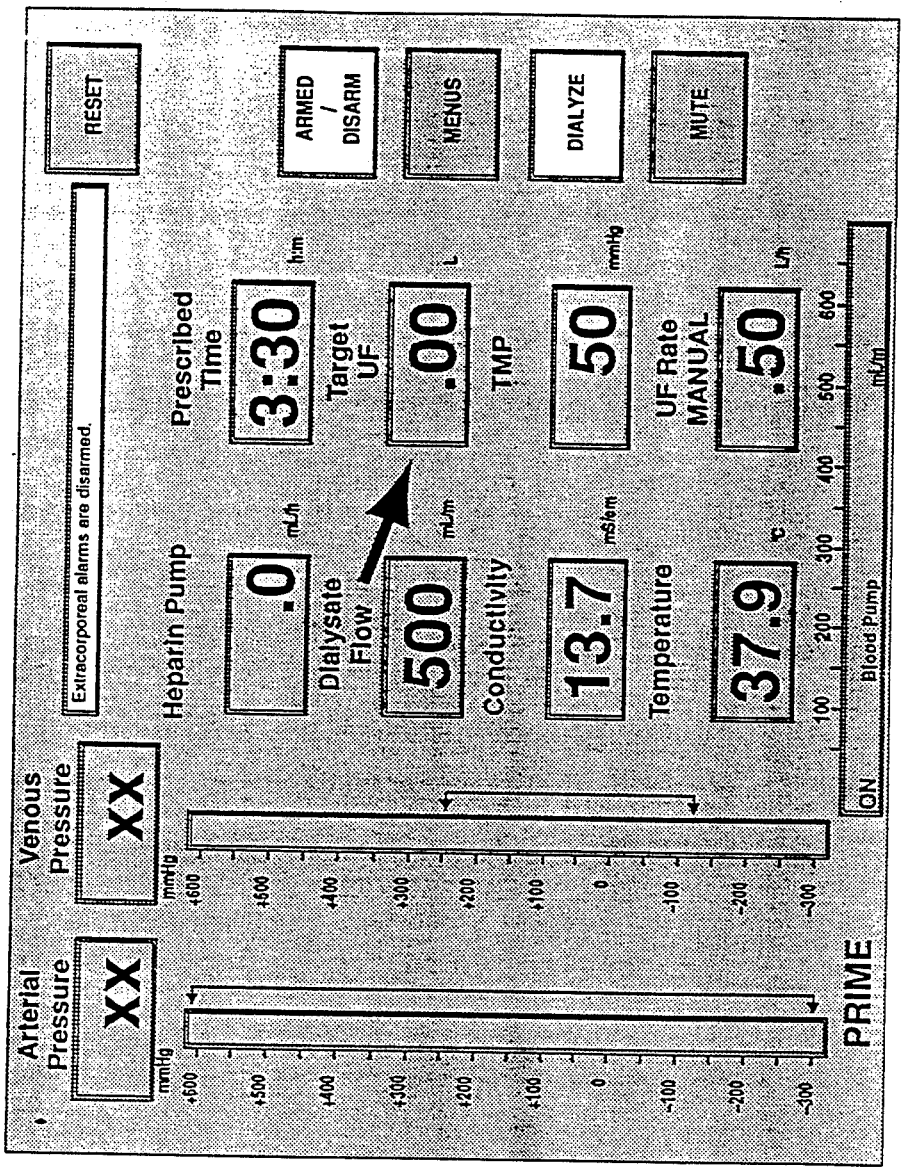
Touch the TARGET UF window.
    The UF control buttons appear.
    The maximum and minimum target UF values are displayed in the TARGET UF window.
The main screen in the Prime Mode, with all windows in the default state.

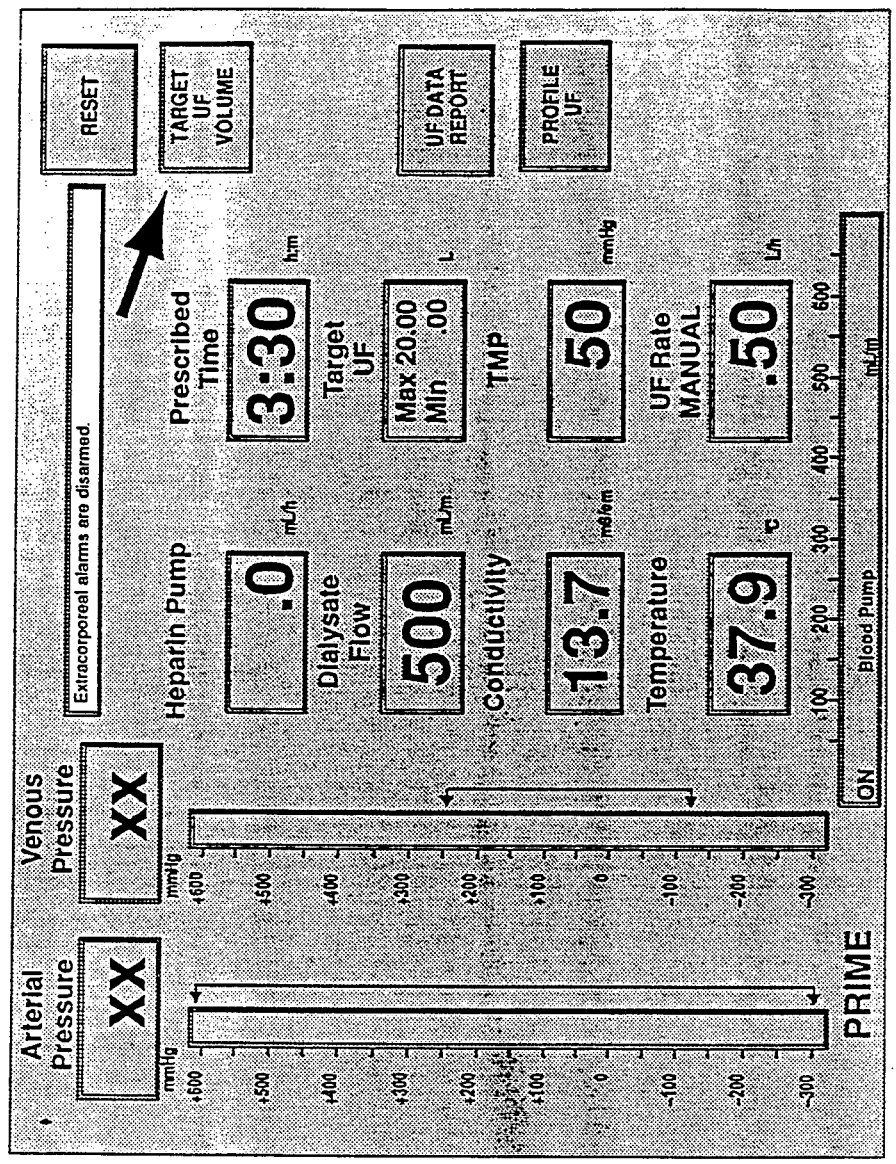
Touch the TARGET UF VOLUME button.
The key pad appears.

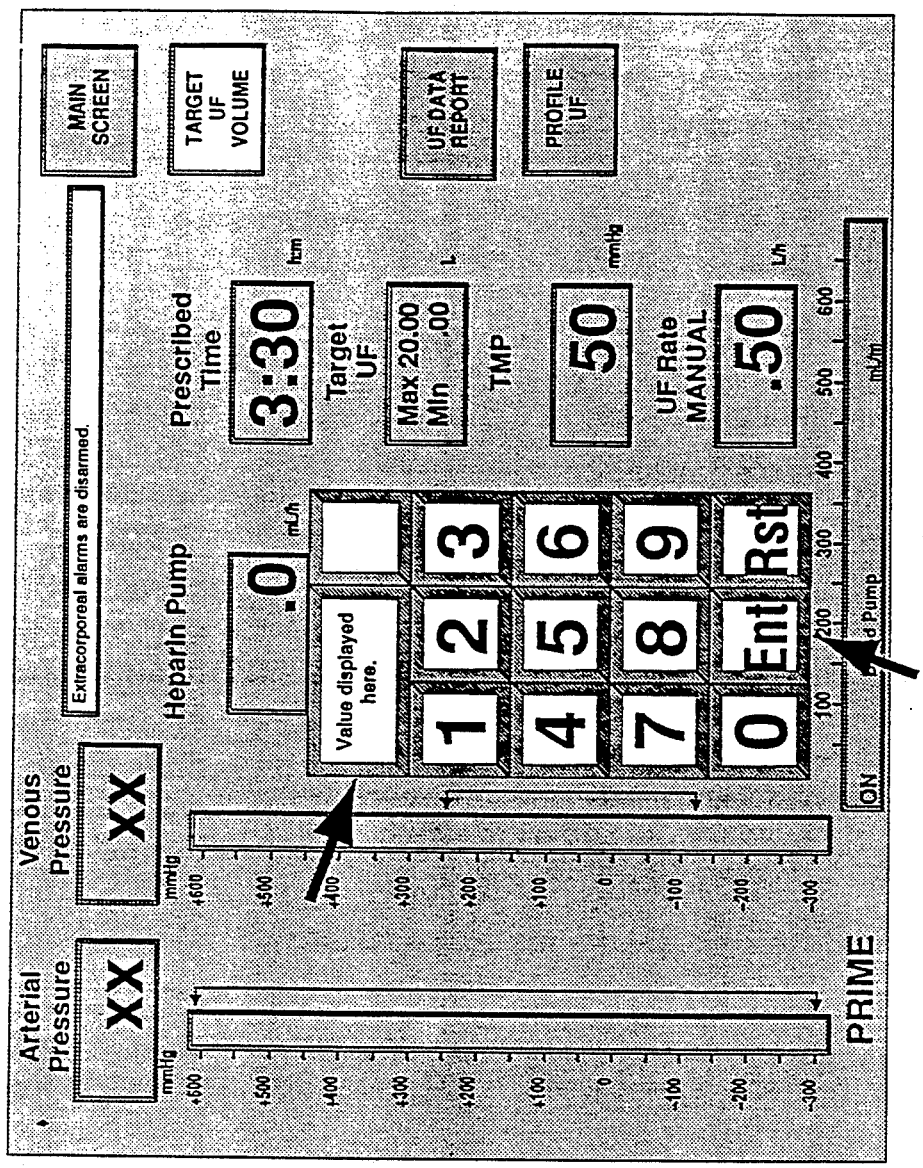
Enter the volume to be removed in liters.
The System 1000™ will calculate the required UF rate.

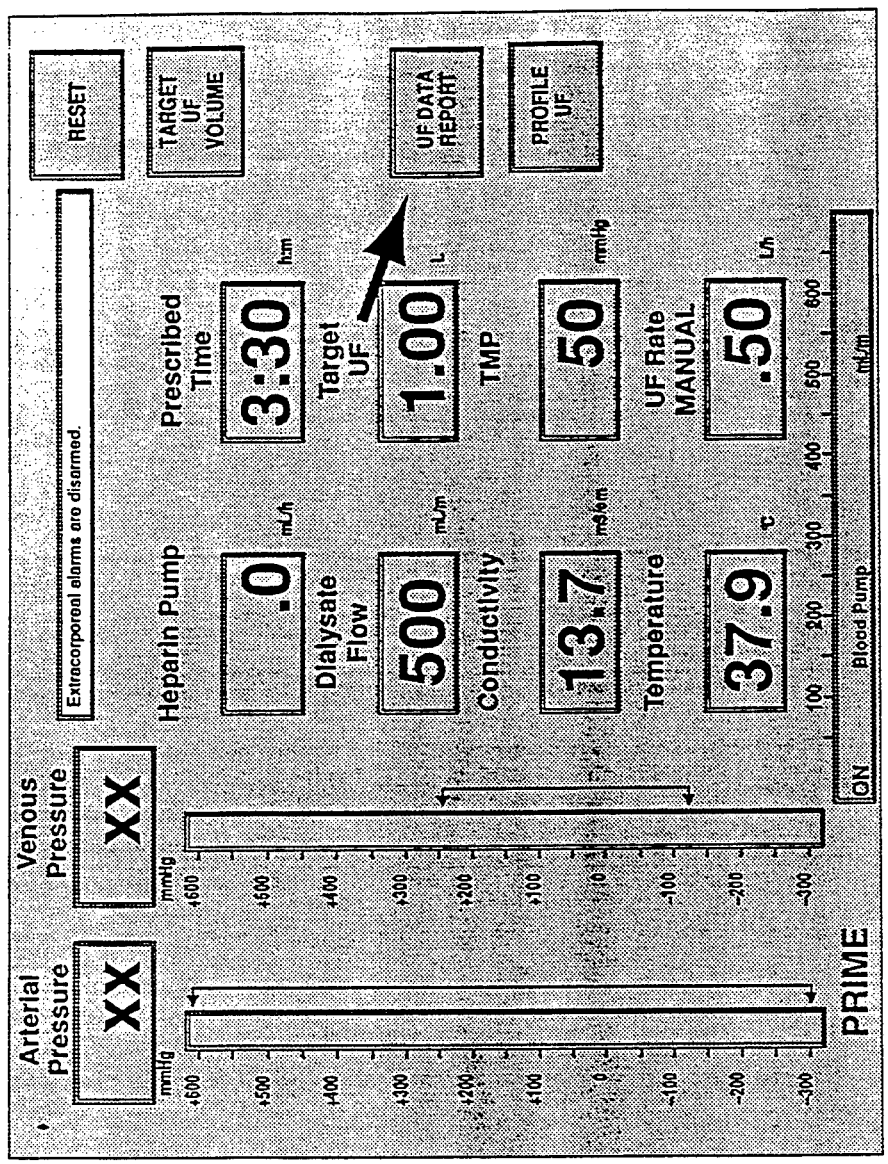
To view the UF Data Report, touch the UF DATA REPORT button.
The UF Data Report appears.

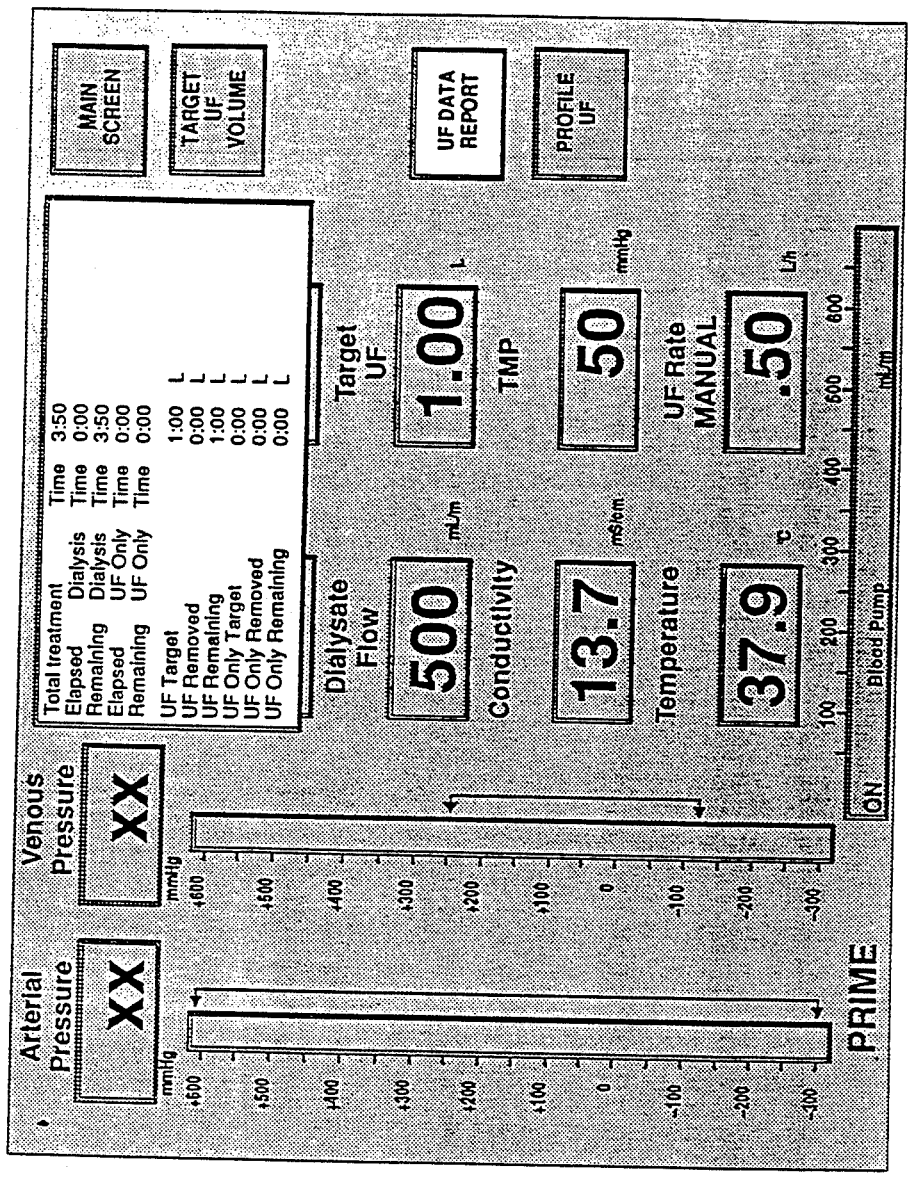

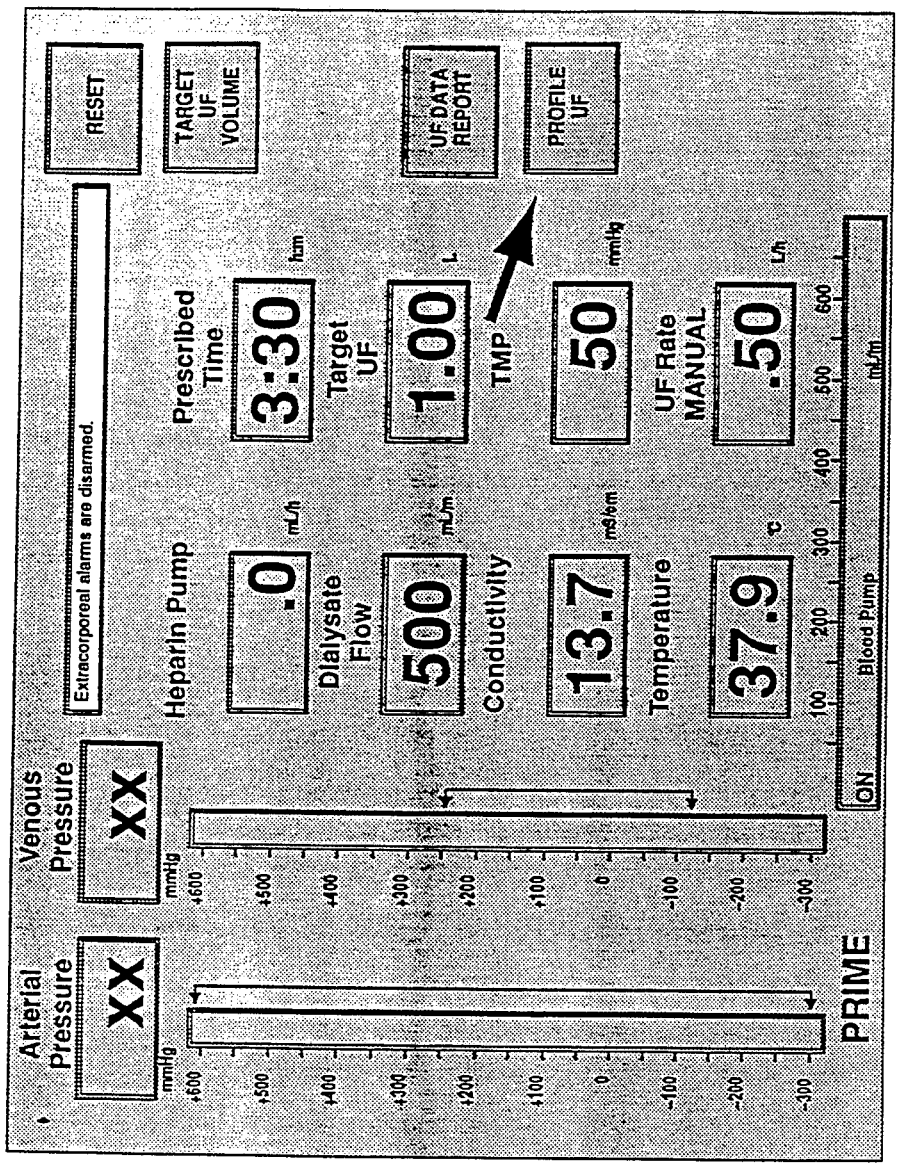
To profile UF,
touch the PROFILE UF button.
The UF profile controls appears.

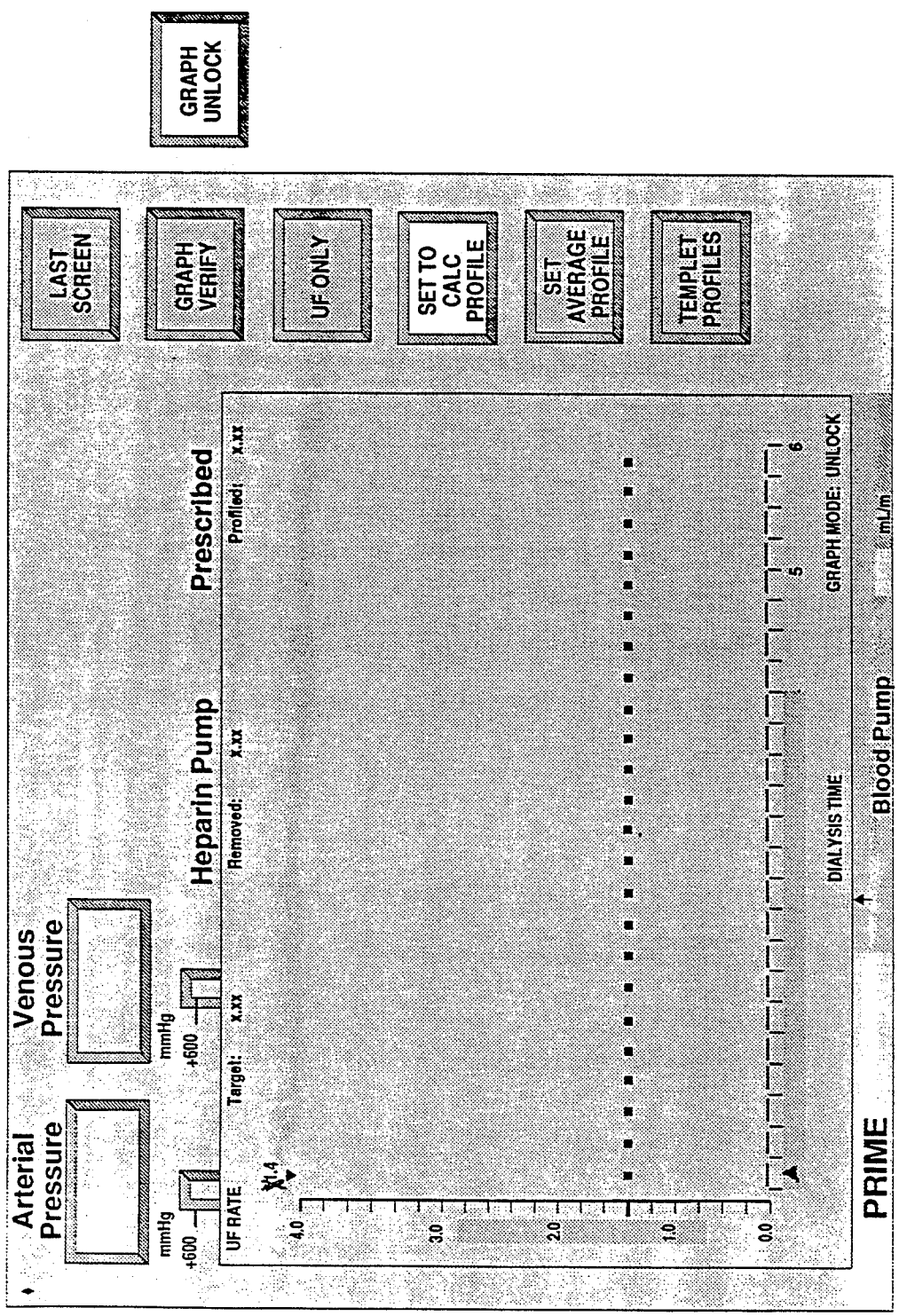

This is an illustration of the main profiling screen, or UF Profile screen. When the prescribed treatment time and target UF volume to be removed are entered, the UF profile is set to a calculated value which will meet target volume over the treatment time.

In this example, the prescribed treatment time is 5.0 hours (represented by a hilighted bar on the X axis), and the target volume is 9.50 liters. The rate has been calculated to 9.5L/5hr = 1.9 L/hr.

If prescribed time and/or target volume are not set an error message will appear in the lower left hand corner of the graph.

The minimum and maximum UF rates are represented by a hilighted bar on the Y axis (0.50 and 3.50 L/hr, respectively). They are set in the calibration mode.

The buttons GRAPH UNLOCK/GRAPH VERIFY and UF ONLY/UF ONLY VERIFY buttons are dual function, which will be explained later. The VERIFY button (position 7) is drawn at appropriate times, when a operator confirmation is required.

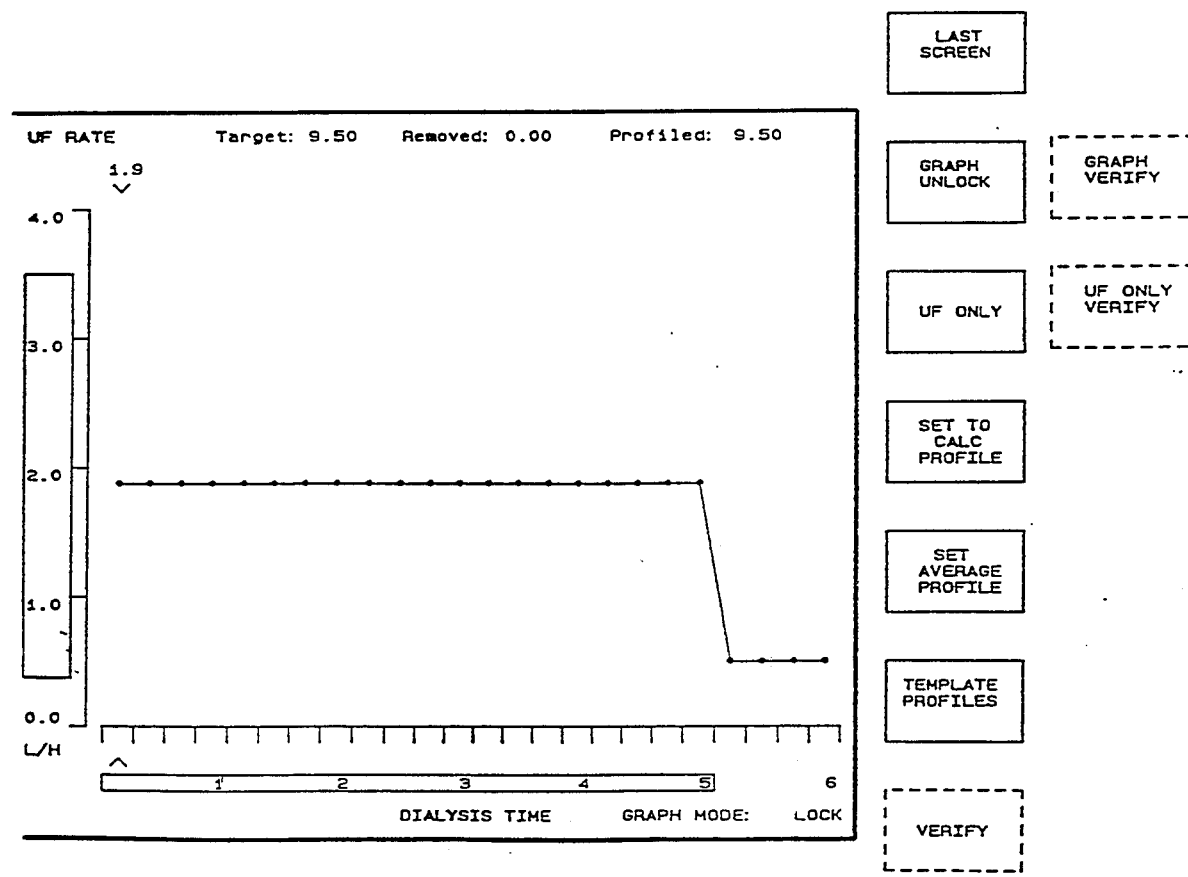

In this picture GRAPH UNLOCK has been touched, which removes the connecting line from the indicator "blips" and enables the graph for profiling.

The GRAPH UNLOCK button has changed to GRAPH VERIFY, and the mode indicator in the lower right hand corner of the graph indicates UNLOCK'ed status.

Notice that all blips beyond the 5 hour treatment time are set to the minimum UF rate. These cannot be altered unless the treatment time is extended.
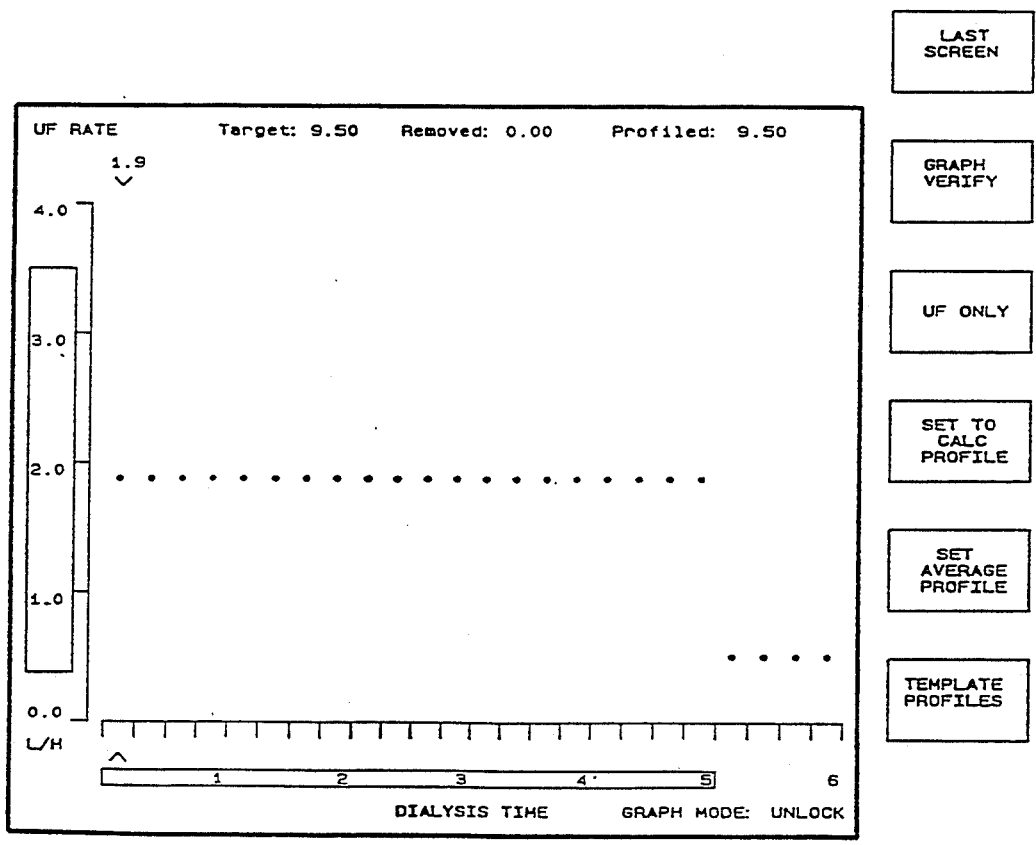

In this picture, the operator has touched the profiling graph at approximately of 2.7 L/hr (Y axis) in the first 15 minute time segment (X axis). The blip for that time segment immediately moves to the location of the touch.

In the unlocked mode the operator can "draw" a profile by touching any area on the graph. The corresponding blip for each time segment immediately moves to the location of the touch in that time segment.

If the touch occurs above the maximum UF rate (above the imaginary horizontal line at 3.5 L/hr), but within the graph area (below the imaginary horizontal line at 4.0 L/hr), the blip will be moved to the maximum rate. The opposite is true for touches below the minimum UF rate, and above the graph limit of 0 L/hr.

The "Profiled" value at the top of the graph has been changed to 9.54 L, reflecting the slight increase in the profile volume due to the change in the first time segment. This value represents the integral of the profile curve, or amount of fluid that would be removed by this profile.

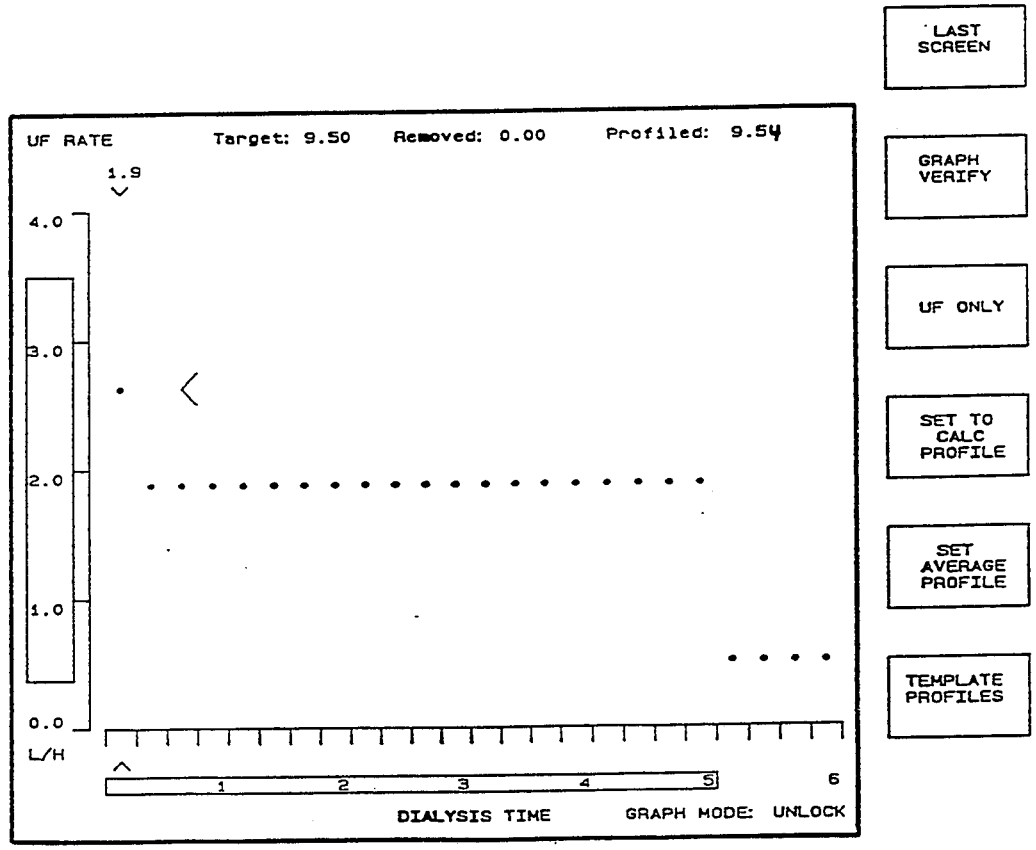

In this picture the operator has touched SET AVERAGE PROFILE, which causes the profile to be set to an approximate straight line between the first and last time segments. This feature can be used at any time that the profile is unlocked, and either the first or last time segment can be adjuted.

In the DIALYZE mode, the first uncompleted time segment would be the starting point for the average profile. Completed time segments are not altered at any time.

The Profiled value has been changed to 11.50, representing the large increase in the profile integral.

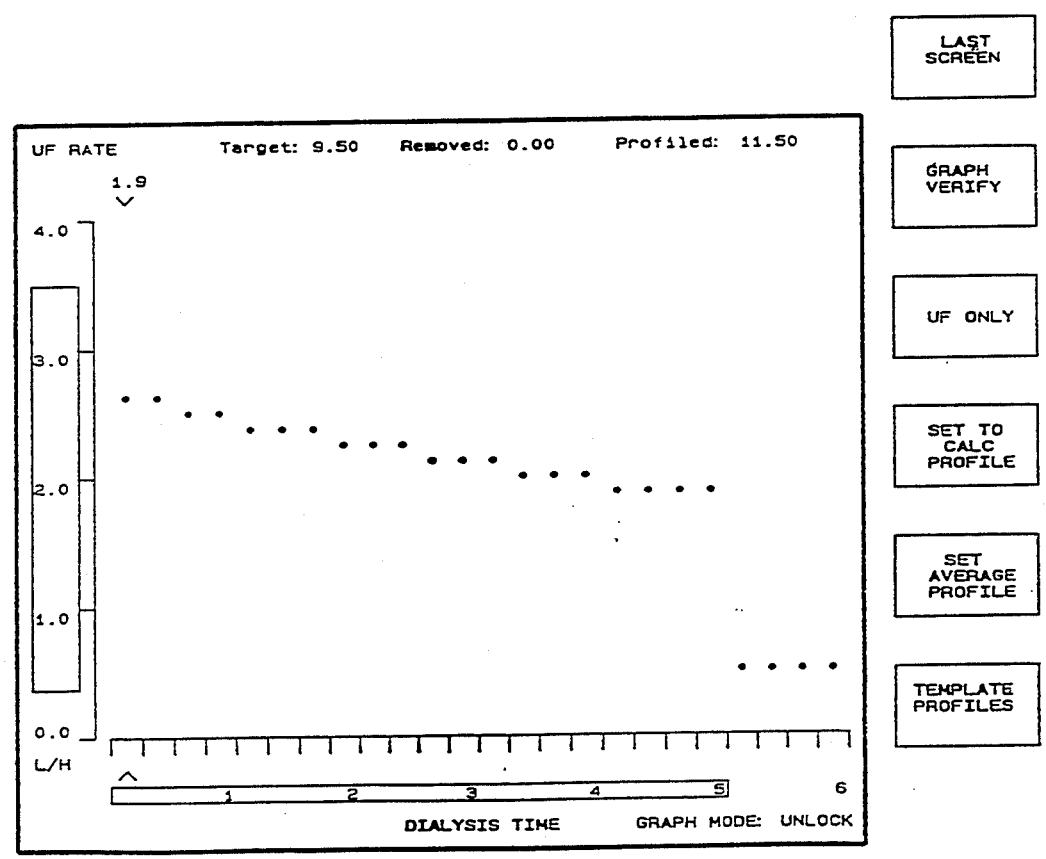

In this picture the operator has touched the GRAPH VERIFY button. If the Profiled value and Target value are equal, the graph will lock, the GRAPH VERIFY button will changed back to GRAPH UNLOCK, and a line is draw through each of the blips.

In this case the Profile and Target values are unequal. Therefore when the GRAPH VERIFY button is touched the UF Profile Adjust screen appears (next page).

Once a profile has been selected, either manually or with the AVERAGE or CALCULATED buttons, it must be verified to insure proper UF removal.

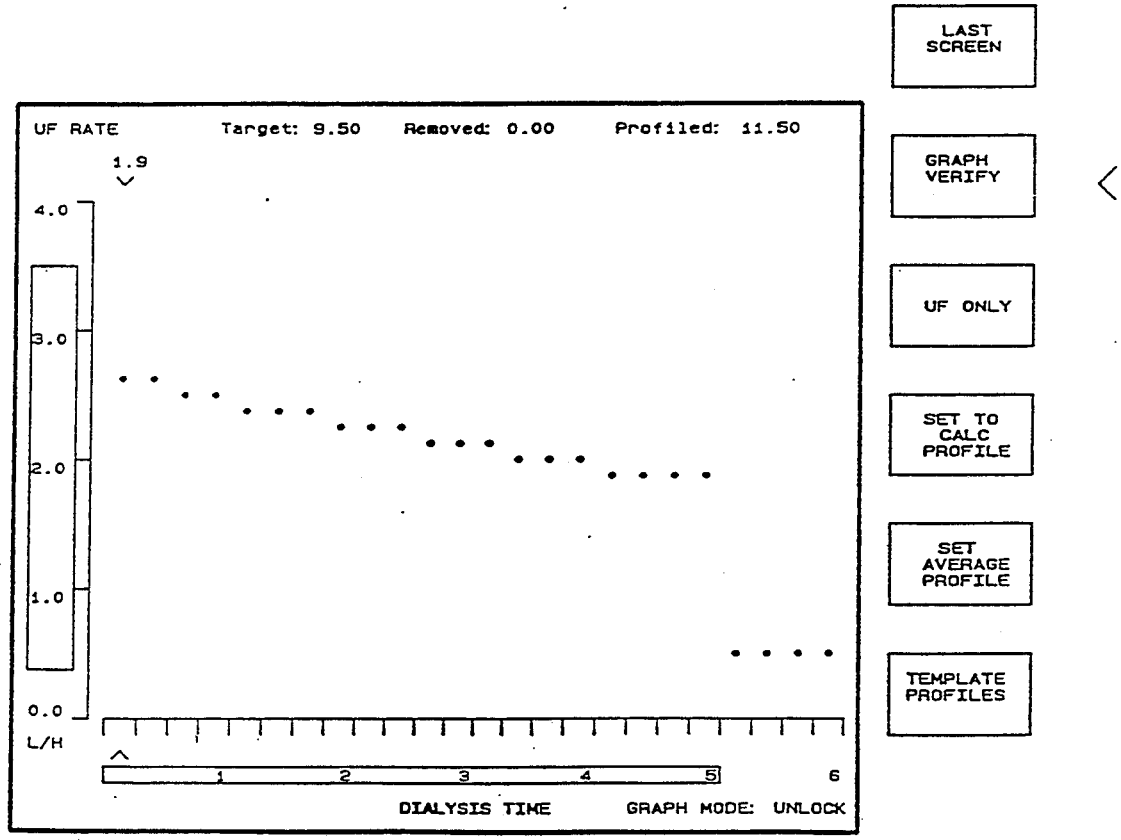

Here the operator has two options; Change the Target value to
the Profiled value, or make the profile adjust to the Target
value.

In this example the operator has touched ADJUST PROFILE, which
causes the profile to shift downward to match Target, and the
Profiled value indicates the shift.

The VERIFY button appears once the profile has shifted and meets
the Target. If allowed to time out (approximately 5 seconds) the
profile will shift upward to its original state. In this example
the VERIFY button is touched, causing the display to go back to
the UF Profile screen with the graph locked (next page).

The profile is adjusted by shifting each blip up or down in equal
amounts, so that the original shape of the profile is maintained.
If for some reason the profile will not adjust, an error honk
sounds and an error message appears in the Instruction Window.

From this screen, The LAST SCREEN button can be touched to go
back to the UF Profile screen with no adjustments to the profile
or Target value.

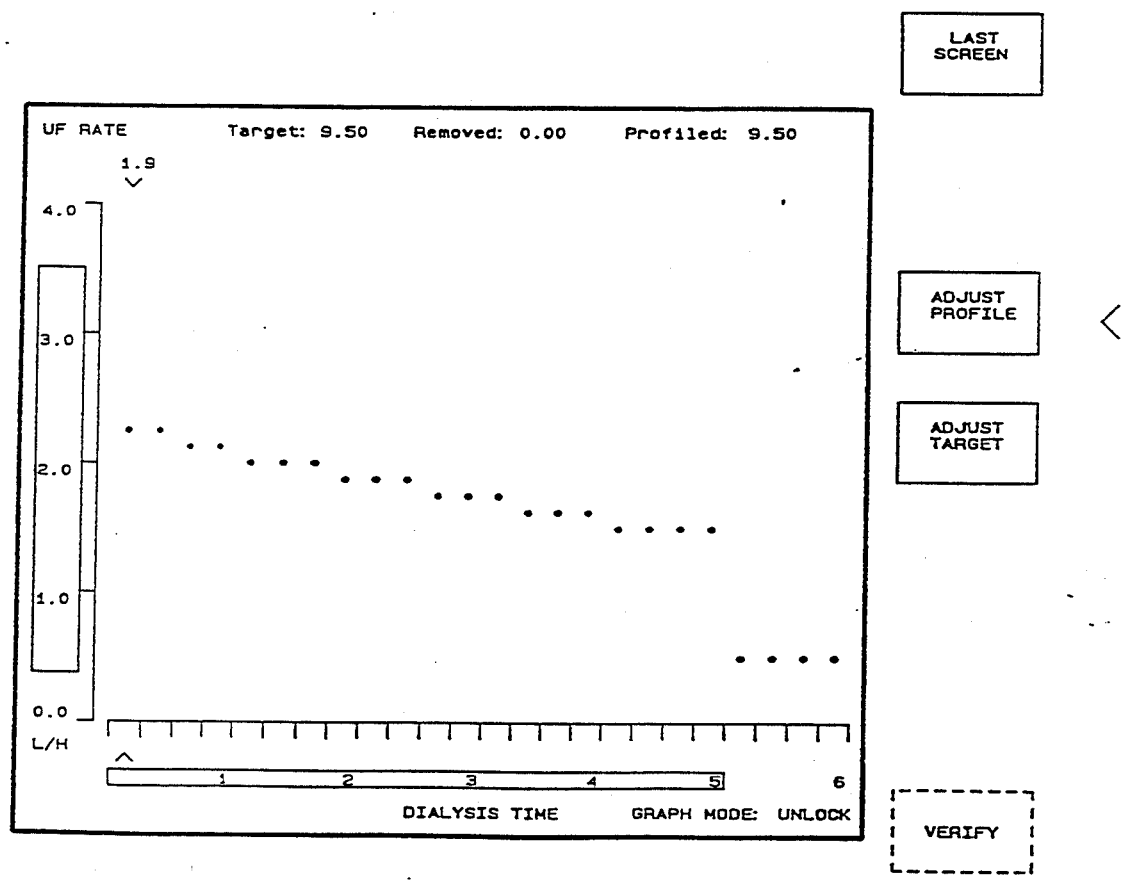

In this picture the shifted profile has been verified and the UF profile screen is present in the locked mode.

If the operator had touched the ADJUST TARGET button on the previous screen, the Target value would change to 11.50 and the VERIFY button would appear. Touching the VERIFY button would cause the display to go to the UF Profile screen, with the Target volume set to 11.50 L, and with the graph locked in its previous condition.

If the VERIFY button times out without being touched (approximately 5 seconds) the Target value will go back to 9.50 and the UF Profile Adjust screen would be active.

In this picture, the GRAPH UNLOCK button is touched, leading to the unlocked profile on the next page.

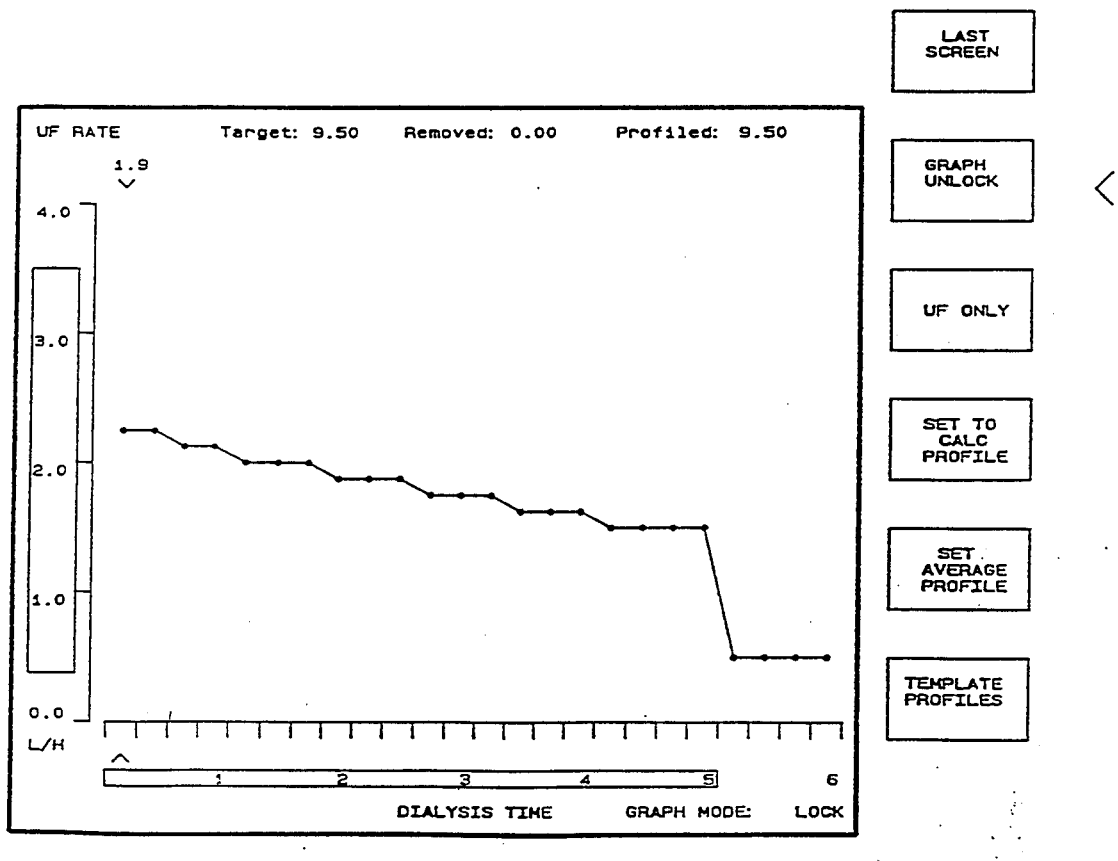

In this picture the SET TO CALC PROFILE button is touched. This button functions as a "clear" button after the original profile has been altered, resetting the profile to the origianl shape (next page).
From here the operator can draw a profile using the calculated profile as a reference, as it represents the target volume to be removed.
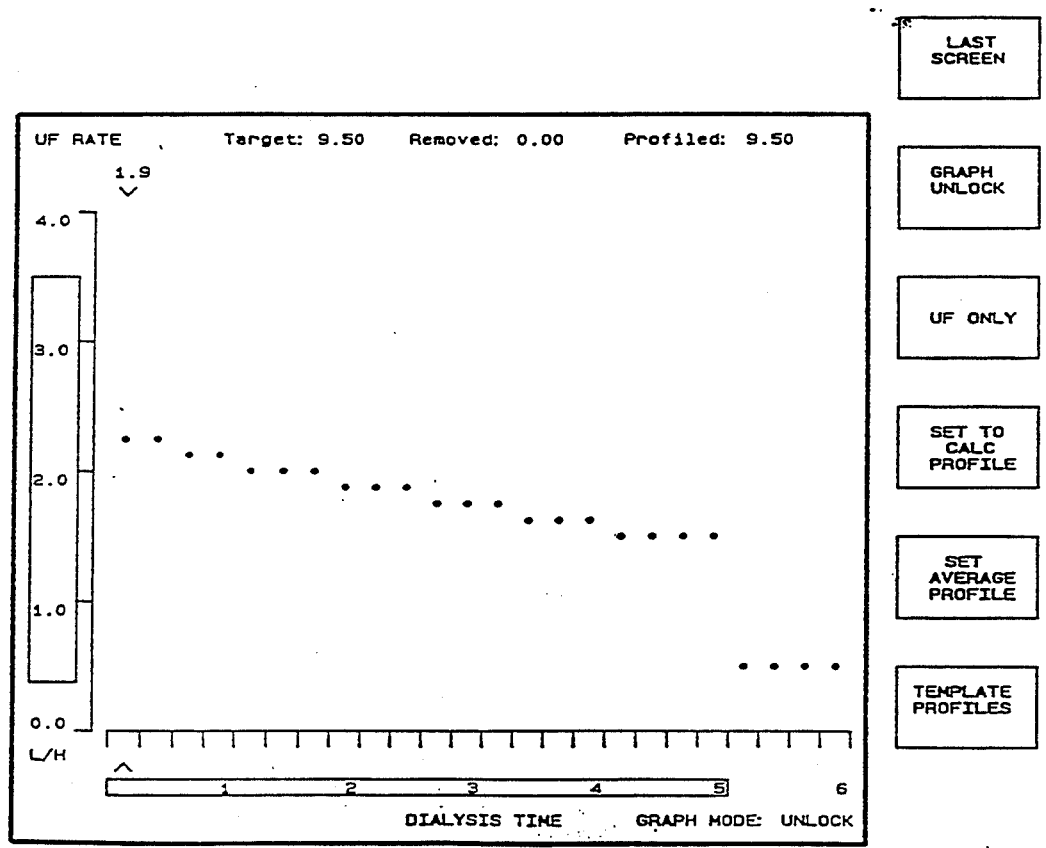

In this picture the profile has been "cleared" by the SET TO CALC button.

In some cases the calculated profile will differ slightly from the Target value, which will be indicated by a difference in the Profiled and Target values. In this case, if GRAPH VERIFY and ADJUST PROFILE are touched, the profile may not shift to a perfectly straight horizontal line. This is due to the algorithm used to match the profile to the Target value. It is "front weighted", which means that if the volume to shift is not evenly divisible by the number of remaining time segments, the earliest (front) time segments will be shifted by the minimum resolution until the profile meets the target.

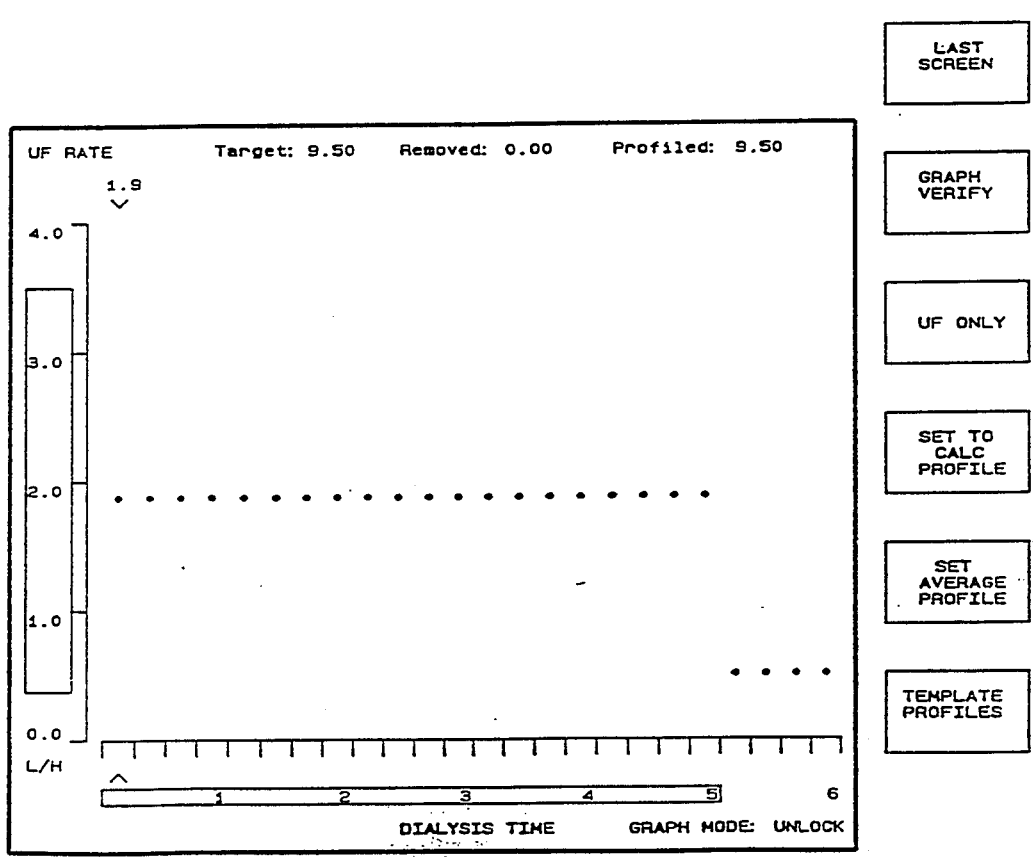

In this picture the operator has "drawn" a profile by touching the graph in the arrangement indicated by the blips. The blips pointed out by arrows have been set to the maximum and minimum UF rates, because the touches were at or outside those limits.

In this picture, the operator has profiling, and has touched GRAPH VERIFY to lock the profile. Notice that the Profiled and Target values are not equal. Now as the GRAPH VERIFY button is touched, the Adjust screen will appear (next page).

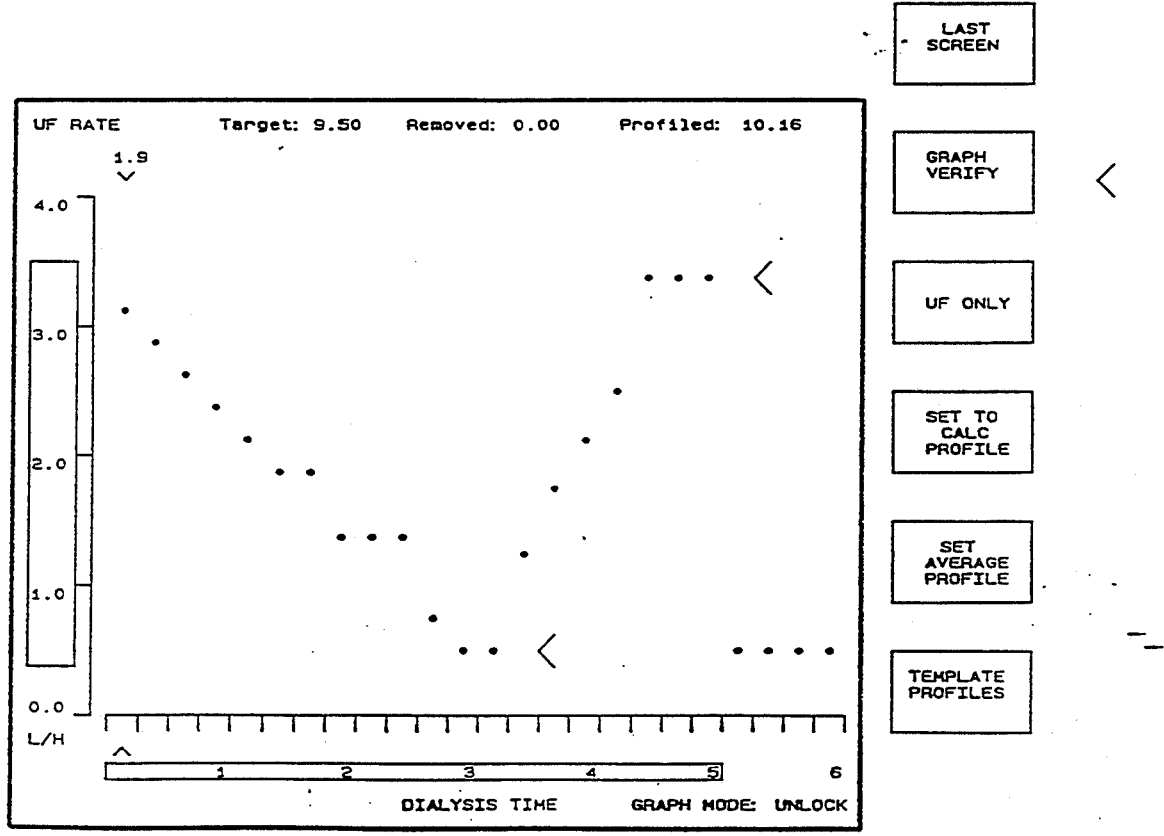

In this picture the UF Profile Adjust screen has been displayed, and the ADJUST PROFILE button has been touched.

Notice the segments that were previously set to maximum and minimum values. Those segments remained at those values. The shifting logic will not move a blip that has been set to a limit, and will not move a blip past a limit. If in the process of shifting a profile any blip meets or exceeds the rate limits, those blips are set to the limit, and the excess volume is evenly distributed (shifted) over the rest of the profile.

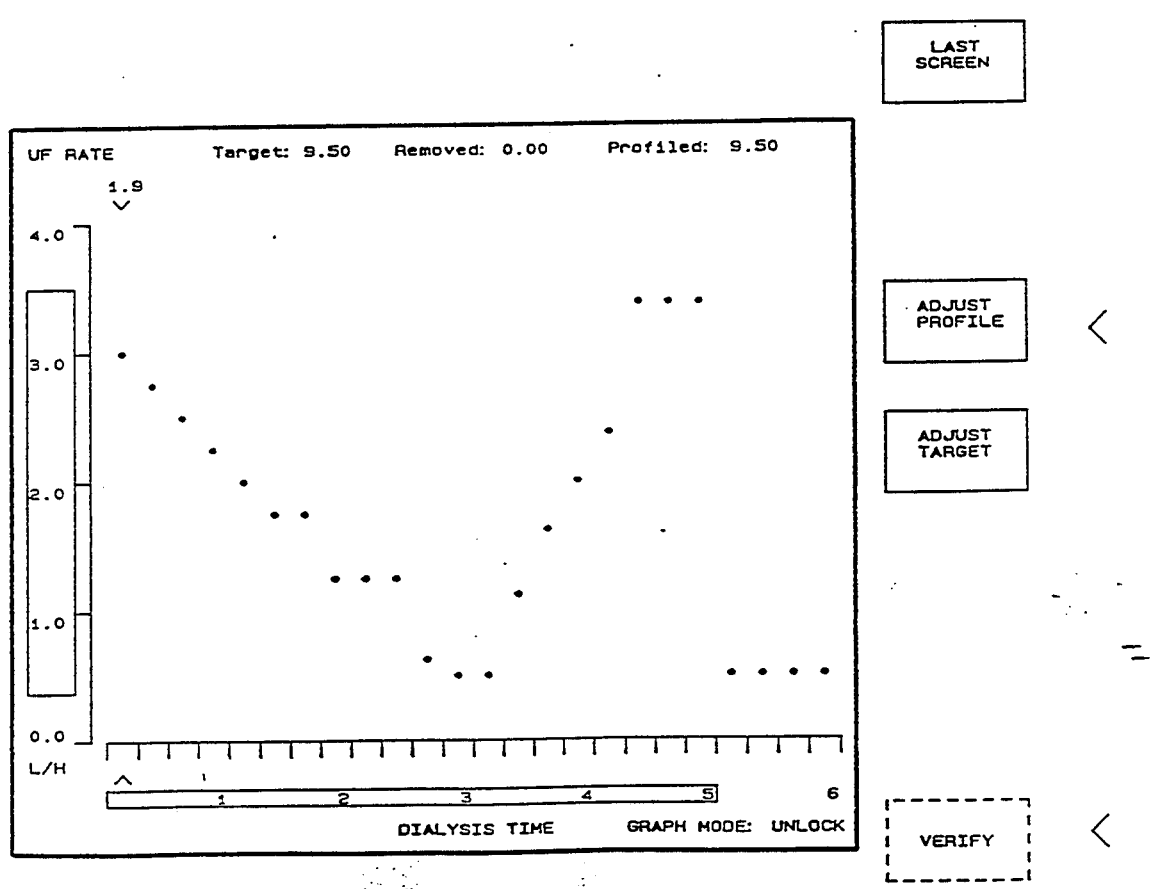

In this picture the shifted profile has been verified and the graph is in the locked mode.

The UF Only button is used to program UF Only time segments. UF Only is a machine state in which the UF system continues to remove fluid from the patient while the dialysate system is in bypass, meaning the dialysate in the dialyzer is stationary.

The UF ONLY button works similar to the GRAPH UNLOCK/GRAPH VERIFY button. It enables the graph for UF Only profiling. The UF ONLY button is disabled when the graph is in the locked state.

To begin UF Only profiling, the GRAPH UNLOCK and UF ONLY buttons are touched in sequence.

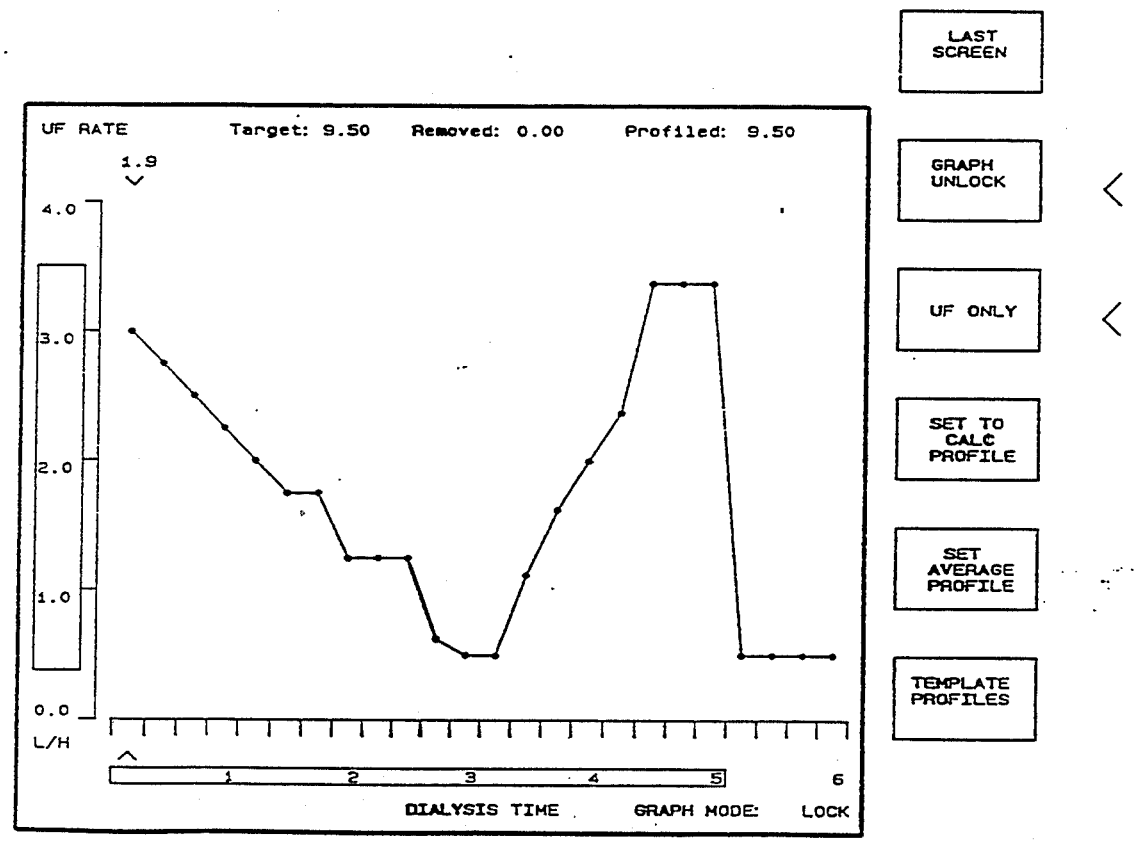

In this picture the graph is in the unlocked, UF Only entry mode. The UF ONLY button has changed to UF ONLY VERIFY, which works much like the GRAPH VERIFY button in that it locks the profiled values when touched in this state. Unlike the GRAPH VERIFY button, no shifting or adjustments take place with the UF Only feature.

In the UF Only profile mode, the blips will not respond to graph touches.

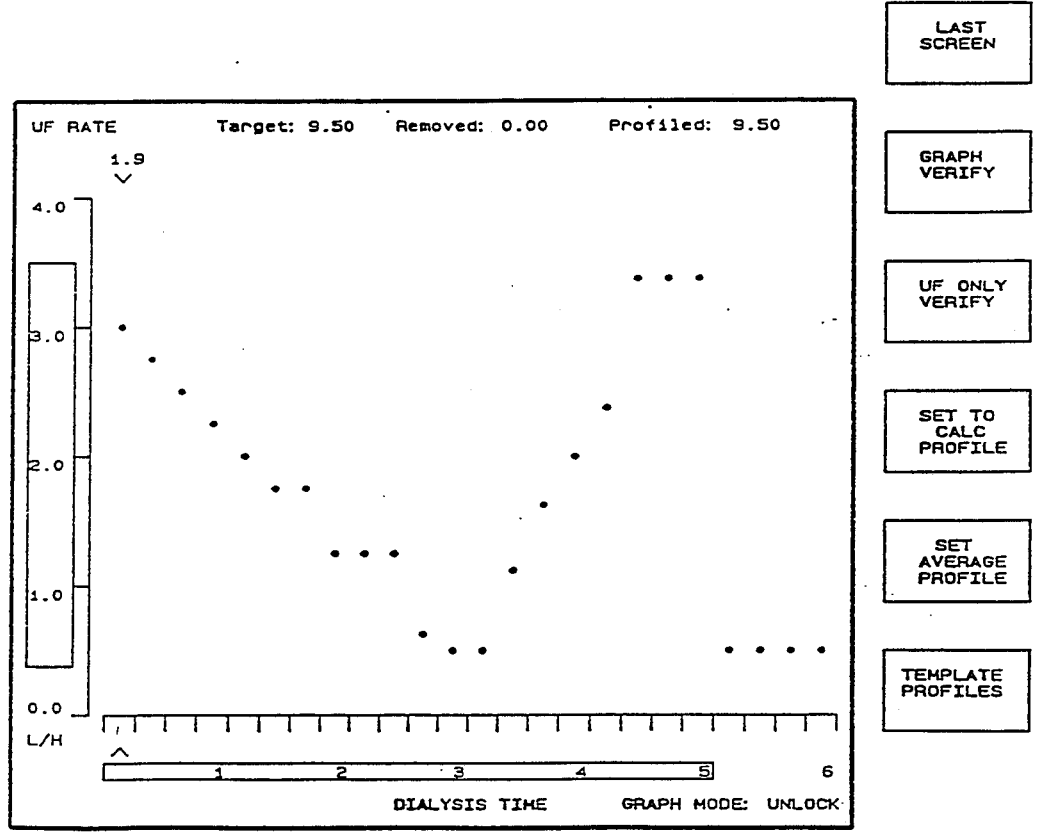

In this picture the graph has been touched in the third and fifteenth time segments. Any touch on the graph will toggle UF Only during that segment, regardless of the UF rate limits (indicated by the dashed boxes). If a segment is previously set to UF Only when touched, it will change back to non-UF Only, and vice-versa. The segment status is indicated by a "B" (Bypass) in the prescribed time bar.

Time segments beyond the prescribed treatment time cannot be set to UF Only.

Once UF Only segments have been selected, the UF ONLY VERIFY button is then touched, locking the indicated segments to perform UF Only, and the UF Profile screen is displayed (next page).

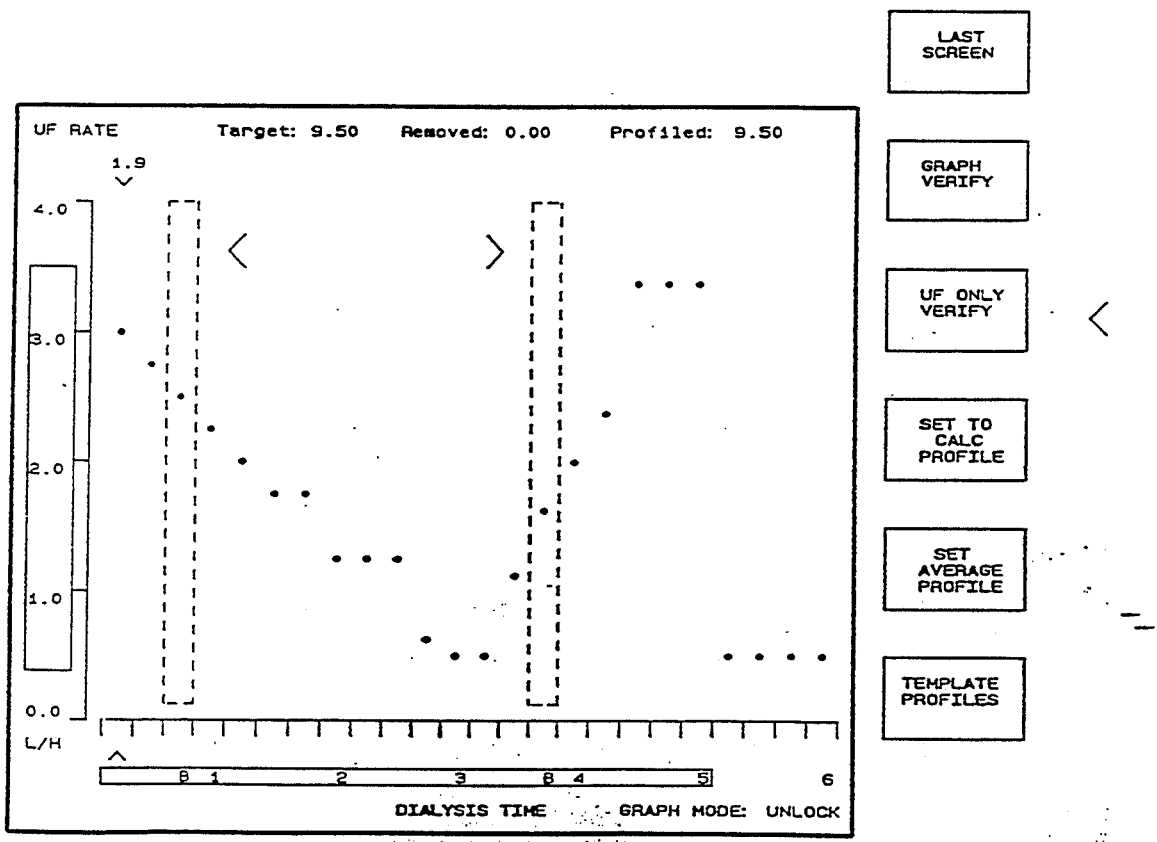

In this picture the UF Only time segments have been verified. The machine will enter the UF Only state at the :45 and 3:45 times in the treatment.
These UF Only time segments can be changed at any time, as long as that time segment has not been completed.
In this picture the TEMPLATE PROFILES button has been touched, leading to the UF Profile Templates screen (next page).
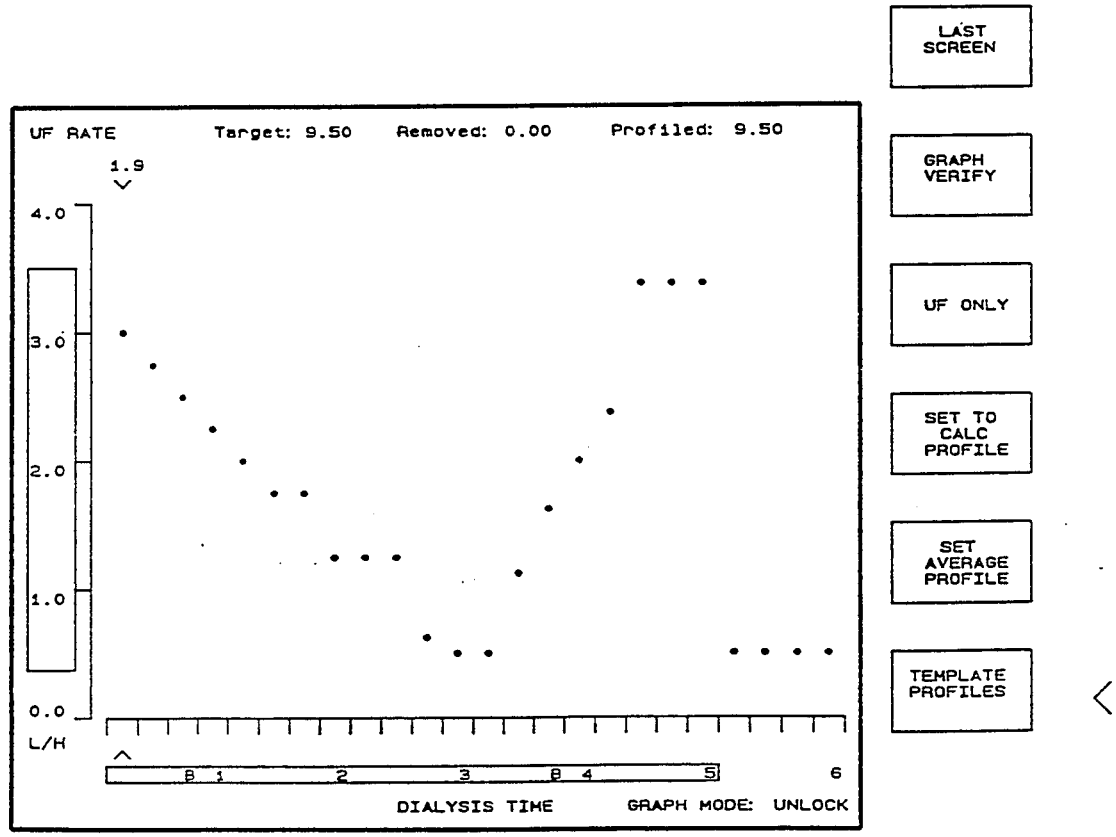

The SAVE PROFILE button touch has caused the VERIFY button to appear and "#1" to be appended to the SAVE PROFILE button.

If the SAVE PROFILE #1 button is touched again before the VERIFY button times out (approximately 5 seconds), it will change to SAVE PROFILE #2, and the VERIFY button timeout will be reset to 5 seconds. Subsequent touches (prior to VERIFY button timeout) will cause the "#n" to increment up to 6, and then loop back to 1, and so on.

If the VERIFY button is touched, the current profile will be stored in the memory location indicated on the SAVE PROFILE #n button, and will overwrite the profile previously stored there. If the VERIFY button times out, the profile is not saved and the SAVE PROFILE #n changes back to SAVE PROFILE.

In this picture the VERIFY button is touched, and the profile is stored in location #1.

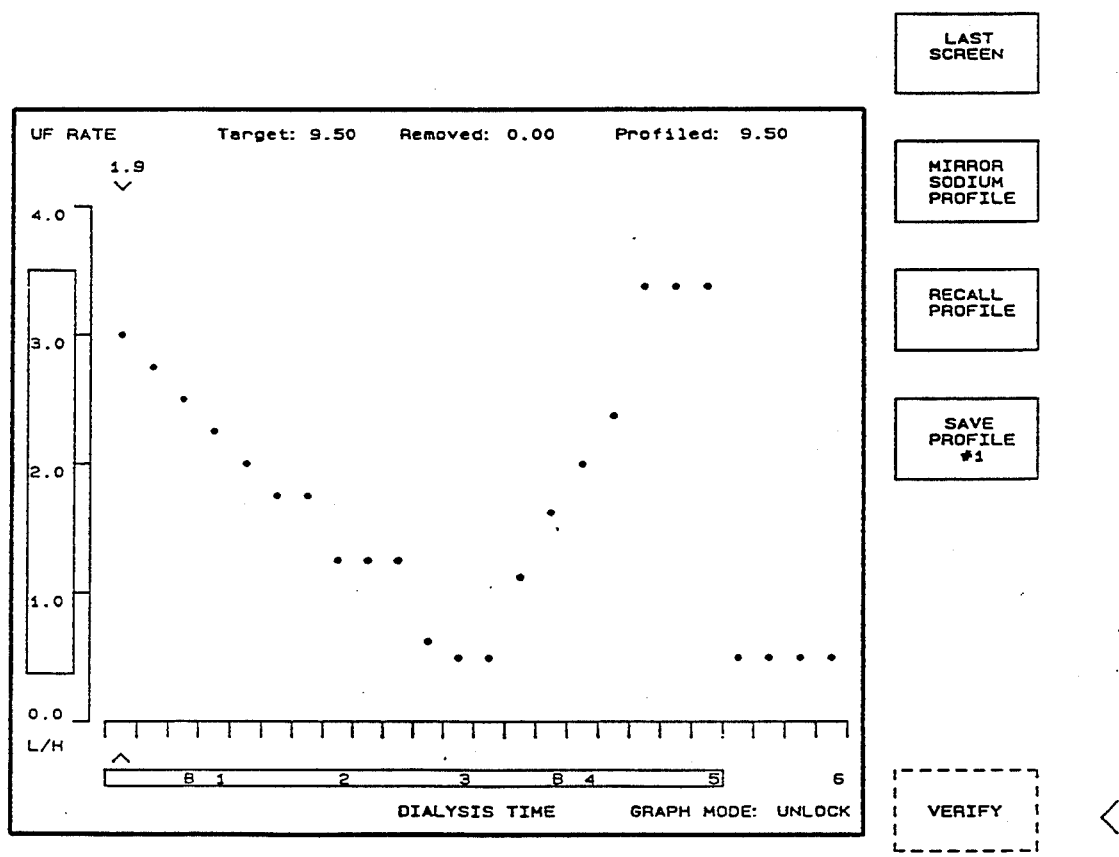

The Profile templates feature allows the operator to store and retrieve profile templates from treatment to treatment. The templates are stored in static RAM, and will remain after power loss. The SYSTEM 1000 will store and retrieve up to 6 templates.

In this picture the SAVE PROFILE has been touched, as the operator intends to store this profile.

From this screen, The LAST PAGE button can be touched to return to the UF Profile screen.

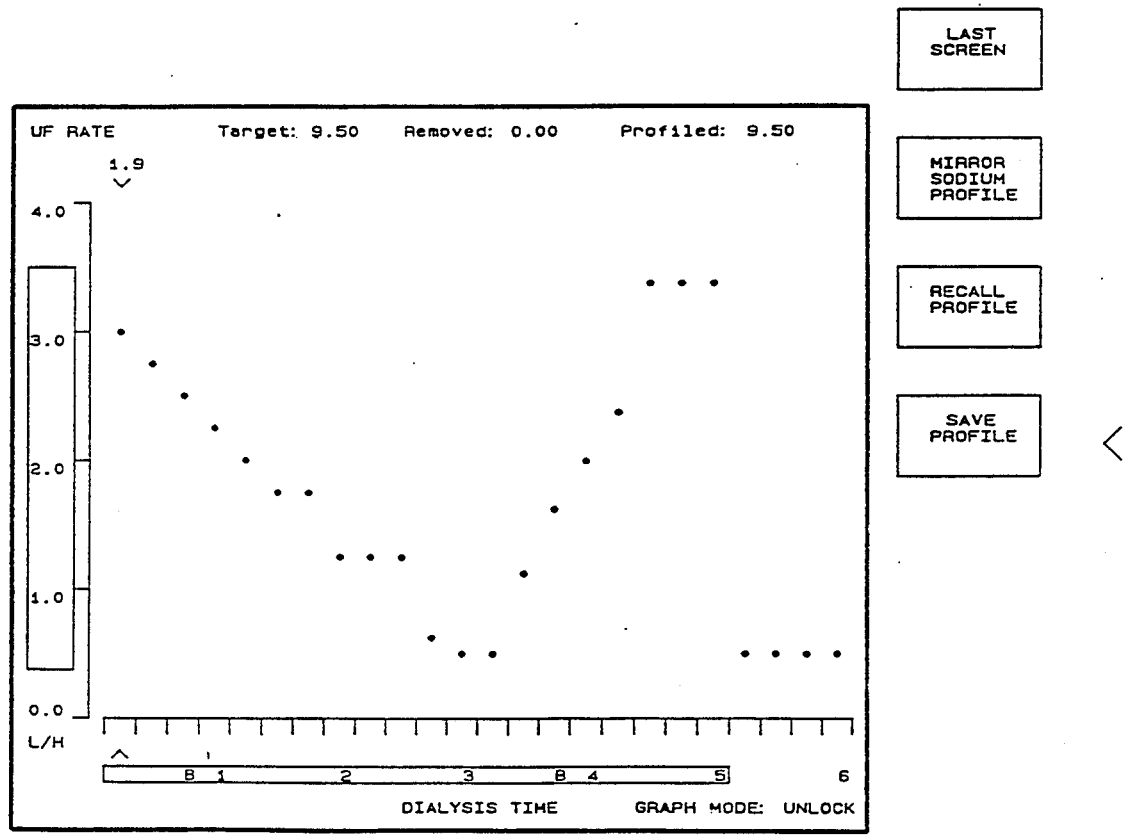

In this picture the operator has entered a new profile manually.
This is possible any time the graph is unlocked.
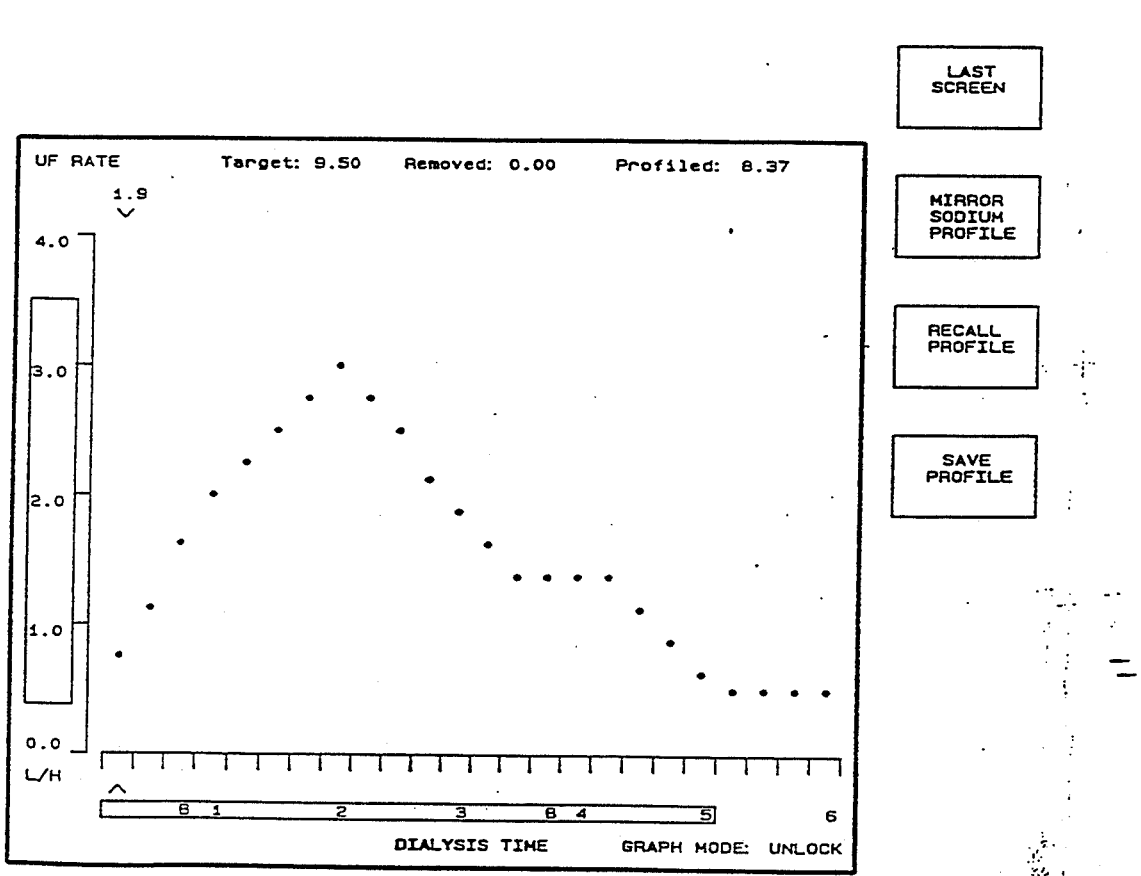

In this picture the operator has touched SAVE PROFILE twice, causing it to indicate SAVE PROFILE #2. The VERIFY button is then touched, storing the current profile in location 2.
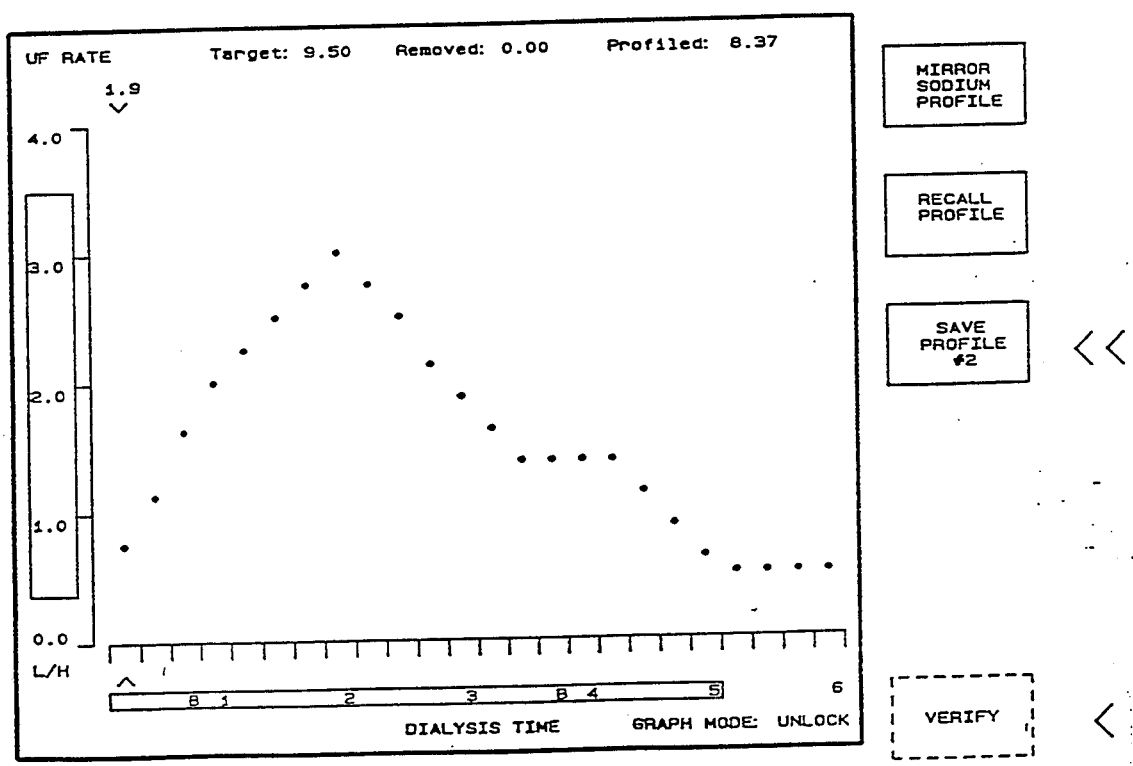

In this picture the operator has touched RECALL PROFILE, which caused the button to change to RECALL PROFILE #1, and caused the VERIFY button to appear. In addition, the profile stored in location #1 was drawn on the graph.

If the RECALL PROFILE button is touched again prior to the VERIFY button timing out, the next stored profile will be displayed and the number on the button will increment (much like the SAVE PROFILE button). If the verify button is allowed to time out, regardless of the number on the RECALL PROFILE button, the graph will go back to the original profile, prior to the first RECALL PROFILE button touch (shown on page 24).

If the VERIFY button is touched, the current profile (indicated on the RECALL PROFILE button) remains on the graph and becomes the active profile.

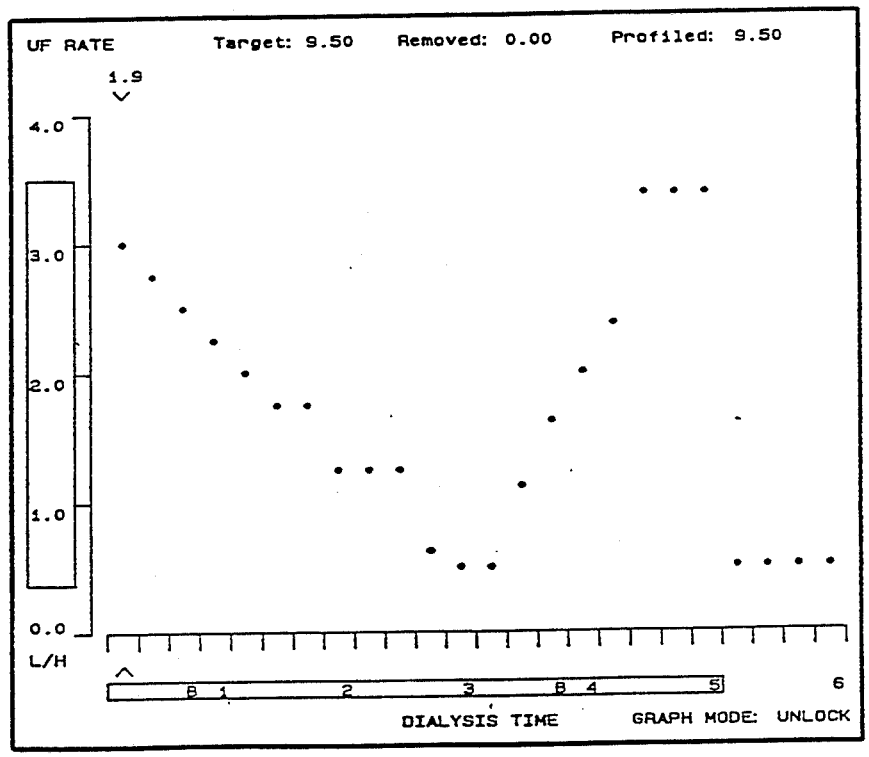

In this picture the operator has touched the MIRROR SODIUM PROFILE button, which causes a profile to appear on the graph which resembles the Sodium profile, and causes the VERIFY button to appear.

The Mirror Sodium feature is similar to Recall Profile, in that an unadjusted profile is made available to the operator.

To determine the mirror profile, the Sodium profile is scaled to the current UF rate limits. The sodium profile illustrated in this picture actually started at the extreme upper left hand corner of the Sodium graph, and extended to the lower right hand corner (the Sodium profile is allowed to exceed the treatment time limit).

The mirrored profile has been scaled to fit within the UF rate limits which caused the upper left corner of the mirror profile to start at UF rate 3.50L. The lower right corner has been truncated, due to the required minimum UF rate beyond the treatment time.

Touching the VERIFY button makes the mirror profile the active profile (like RECALL PROFILE/VERIFY). Allowing the VERIFY button to time out returns the original profile to the graph.

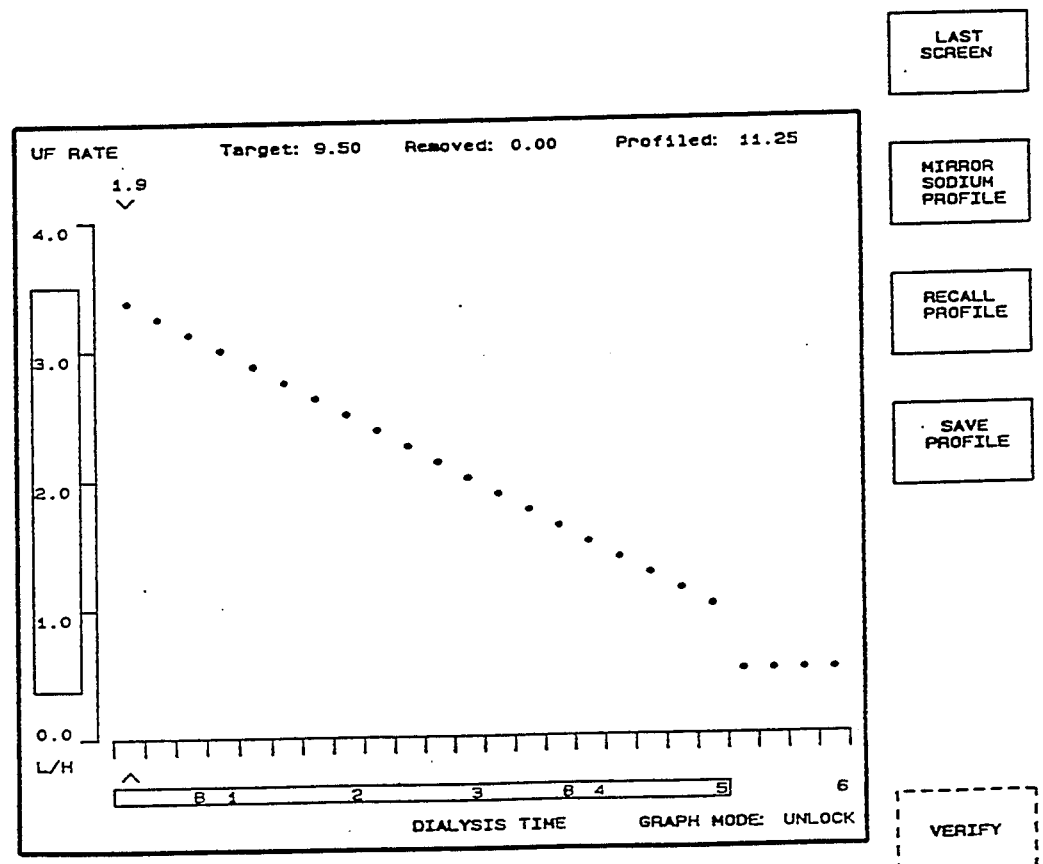

The profile interval defaults to 15 minute segments, and can be changed to 30 or 60 minutes in the calibration program. When the interval is set to 30 or 60 minutes, blips within each segment move concurrently when that segment is touched.

This picture shows both 30 and 60 minute intervals. The dashed box on the left shows the segment area for the 30 minute interval. Any touch within the dashed box will cause both blips to move to that position.

Likewise, the dashed box on the right shows the segment area for a 60 minute interval.

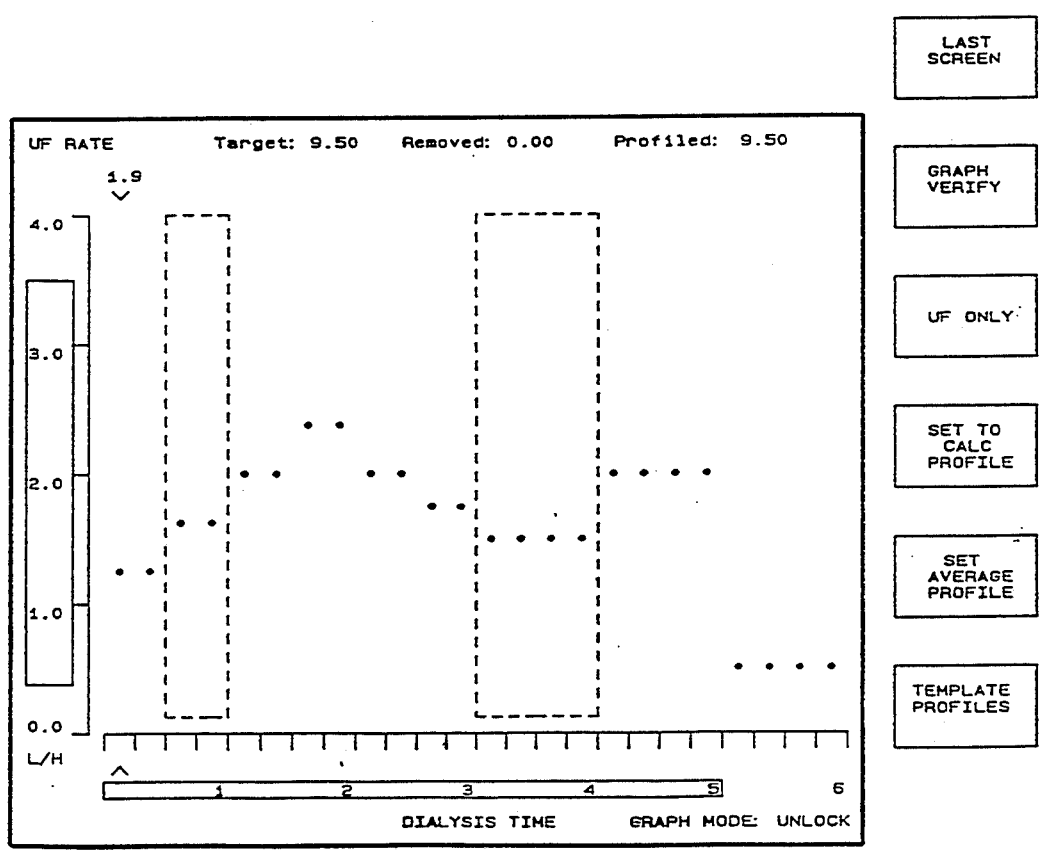

The UF Only time segments are also adjustable in calibration.
This picture shows the same segment areas, with the graph in the UF Only entry mode.
The "B's" for each segment operate concurrently, as do the blips while profiling UF rate.
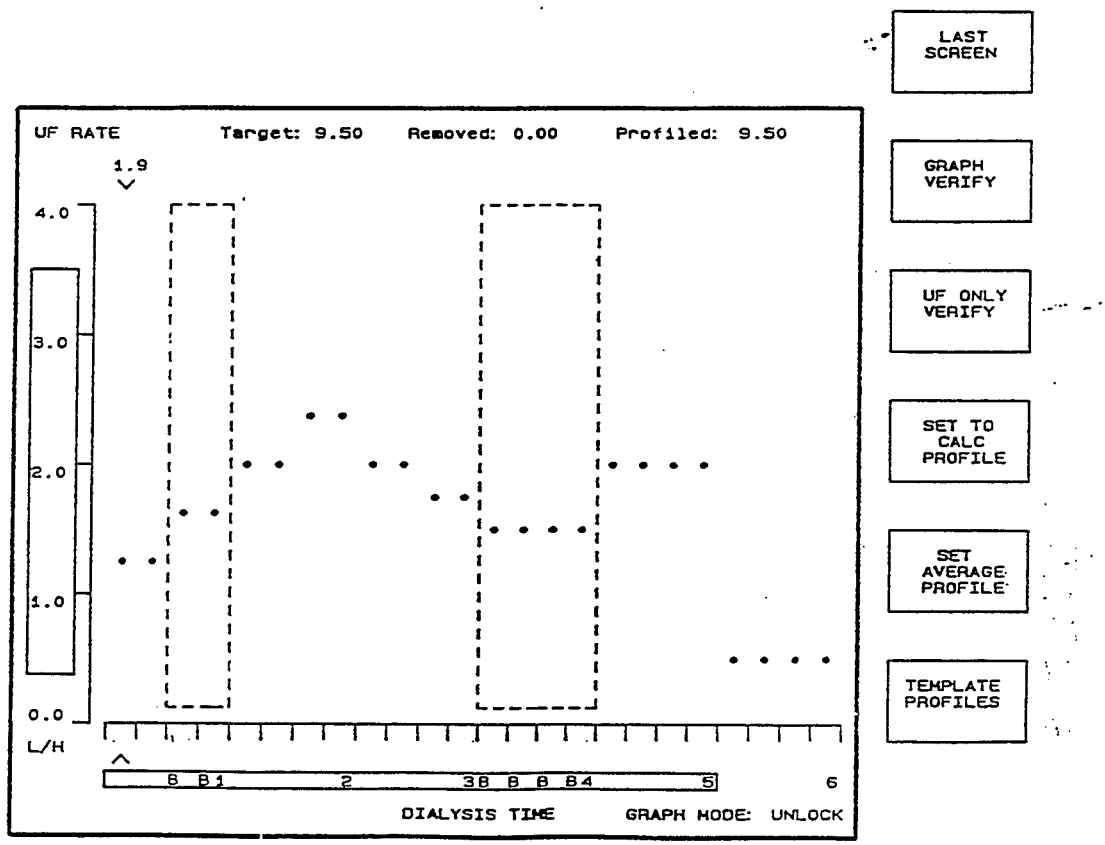

What is claimed is:

1. A method of providing operational instructions to a hemodialysis machine, having a programmable memory and having ultrafiltration capability, so as to enable the machine to perform ultrafiltration of fluid from a patient according to a time-variable ultrafiltration profile, the method comprising:
   (a) entering into the programmable memory a prescribed time for dialysis;
   (b) entering into the programmable memory a target ultrafiltration volume of fluid to be removed from the patient;
   (c) entering into the programmable memory a proposed ultrafiltration profile being representable as a plot of coordinates on an ultrafiltration rate axis and a time axis and defining a profile ultrafiltration volume; and
   (d) shifting the proposed ultrafiltration profile along the ultrafiltration rate axis to the degree necessary to make the profile ultrafiltration volume equal to the target ultrafiltration volume, so as to allow the hemodialysis machine to achieve, while ultrafiltrating the fluid according to the shifted ultrafiltration profile, the entered target ultrafiltration volume within the entered prescribed time.

2. A method of providing operational instructions to a hemodialysis machine having a programmable memory and having ultrafiltration capability so as to enable the machine to perform ultrafiltration of fluid from a patient according to a time-variable ultrafiltration profile, the method comprising:
   (a) providing a user/machine interface configured as a touch screen operably connected to the hemodialysis machine;
   (b) using the touch screen, entering into the programmable memory a prescribed time for dialysis;
   (c) using the touch screen, entering into the programmable memory a target ultrafiltration volume of fluid to be removed from the patient;
   (d) displaying on the touch screen first and second intersecting axes defining a ultrafiltration profile region, the first axis corresponding to ultrafiltration rate, and the second axis corresponding to time;
   (e) touching the touch screen at a plurality of points within the ultrafiltration profile region so as to define a proposed continuous ultrafiltration rate-versus time profile defining a profile ultrafiltration volume; and
   (f) shifting the proposed profile along the first axis to the degree necessary to make the profile ultrafiltration volume equal to the target ultrafiltration volume so as to allow the hemodialysis machine to achieve, while ultrafiltrating the fluid according to the shifted profile, the entered target ultrafiltration volume within the entered prescribed time.

3. A method of providing operational instructions to a hemodialysis machine having a programmable memory and having a capability of ultrafiltrating fluid from a patient according to a time-variable ultrafiltration profile, the method comprising:
   (a) providing a user/machine interface configured as a touch screen operably connected to the hemodialysis machine;
   (b) using the touch screen, entering into the programmable memory a prescribed time for dialysis;
   (c) using the touch screen, entering into the programmable memory a target ultrafiltration volume of fluid to be removed from the patient;
   (d) displaying the target ultrafiltration volume;
   (e) while displaying the target ultrafiltration volume, displaying on the touch screen first and second intersecting axes defining an ultrafiltration profile region, the first axis corresponding to ultrafiltration rate, and the second axis corresponding to time; within which ultrafiltration profile region an ultrafiltration rate-versus-time profile can be displayed which defines a profile ultrafiltration volume;
   (f) providing a display of profile ultrafiltration volume; and
   (g) while observing the displayed target ultrafiltration and profile ultrafiltration volumes, touching the touch screen at a plurality of points within the ultrafiltration profile region so as to define a ultrafiltration rate-versus time profile defining a profile ultrafiltration volume equal to the target ultrafiltration volume.

4. A method of providing operational instructions to a dialysate-producing machine having a user-programmable memory, a capability of changing sodium concentration in the dialysate according to a time-variable sodium profile, and a capability of ultrafiltrating fluid from a patient according to a time-variable ultrafiltration profile, so as to enable the machine to produce dialysate having particular sodium and ultrafiltration characteristics at various times during use of the machine for a dialysis procedure, the method comprising:
   (a) providing a user/machine interface configured as a touch screen operably connected to the dialysate-producing machine;
   (b) programming into the user-programmable memory a desired sodium profile;
   (c) providing on the touch screen an indicium enabling a user of the machine to create an ultrafiltration profile that substantially conforms to the sodium profile;
   (d) using the touch screen, displaying on the touch screen first and second intersecting axes defining a ultrafiltration profile region, the first axis corresponding to ultrafiltration rate, and the second axis corresponding to time; and
   (e) touching the indicium provided in step (c) to cause the touch screen to display within the ultrafiltration profile region an ultrafiltration profile substantially conforming to the sodium profile programmed in step (b).

5. A method of providing operational instructions to a dialysate-producing machine having a memory and a capability of ultrafiltrating fluid from a patient according to a time-variable ultrafiltration profile, so as to enable the machine to produce dialysate having particular ultrafiltration characteristics at various times during use of the machine for a dialysis procedure, the method comprising:
   (a) providing a user/machine interface configured as a touch screen operably connected to the dialysate-producing machine;
   (b) programming into the memory a first ultrafiltration profile;
   (c) providing on the touch screen an indicium enabling a user of the machine to recall the first ultrafiltration profile from the memory;
   (d) using the touch screen, displaying on the touch screen first and second intersecting axes defining a ultrafiltration profile region, the first axis corresponding to ultrafiltration rate, and the second axis corresponding to time; and (e) touching the indicium provided in step (c) to cause the touch screen to display within the ultrafiltration profile region a second ultrafiltration profile substantially conforming to the first ultrafiltration profile.

6. A method of providing operational instructions to a hemodialysis machine equipped with a programmable memory, so as to enable the machine to operate according to an operational parameter that can vary overtime, the method comprising:

(a) entering into the programmable memory a time period;

(b) entering into the programmable memory a target cumulative value corresponding to the operational parameter to be achieved while operating the machine during the time period;

(c) entering into the programmable memory a proposed time-varying profile of the operational parameter to be executed by the machine during the time period, the profile being representable as a plot of coordinates in a region defined by an ordinate of values of the parameter and a time-based abscissa, the plot defining a profile cumulative value of the parameter; and (d) changing the proposed time-varying profile along the ordinate to the degree needed to make the profile cumulative value equal to the target cumulative value, so as to allow the hemodialysis machine to achieve, while operating, the entered target cumulative value within the time period.

7. In an apparatus for performing hemodialysis comprising means for circulating dialysate through a dialysate compartment of a hemodialyzer and means for effecting extracorporeal circulating of blood through a blood compartment of the hemodialyzer, an improvement comprising:

(a) programmable memory means;

(b) means for entering a time period into said memory means;

(c) means for entering into said memory means a target cumulative value of a time-varying parameter to be achieved while operating the apparatus during the time period;

(d) means for entering into said programmable memory means a proposed time-varying profile of the operational parameter to be executed by the apparatus during the time period, the proposed profile being representable as a plot of coordinates in a region defined by an ordinate of values of the parameter and a time-based abscissa, the plot defining a profile cumulative value of the parameter;

(e) means, responsive to the entered time period and entered proposed profile, for comparing the profile cumulative value with the target cumulative value;

(f) means, responsive to said means defined in (e), for changing the proposed profile along the ordinate so that the profile cumulative value is made equal to the target cumulative value;

(g) means for entering the changed profile into said memory means in place of the proposed profile; and (h) means, responsive to said means defined in (g), for causing the apparatus to operate according to the changed shifted profile so as to enable the apparatus to achieve, while operating, the entered target cumulative value within the time period.

* * * * *

UNITED STATES PATENT AND TRADEMARK OFFICE
CERTIFICATE OF CORRECTION

PATENT NO. : 5,326,476
DATED : July 5, 1994
INVENTOR(S) : Grogan et al.

It is certified that error appears in the above-identified patent and that said Letters Patent is hereby corrected as shown below:

Column 12, line 63, "526 The" should be --526.  The--.

Column 25, line 53, "Rh(30)=A·Rr(30)+S" should be --Rh(30) = A·Rr(30) + B--.

Column 25, line 54, "Rh(40)=A·Rr(40)+S" should be --Rh(40) = A·Rr(40) + B--.

Column 26, line 21, "FF 75" should be --ET 75--.

Signed and Sealed this

Twentieth Day of December, 1994

Attest:

BRUCE LEHMAN

*Attesting Officer*   *Commissioner of Patents and Trademarks*